(12) United States Patent
Brooun et al.

(10) Patent No.: US 7,076,372 B1
(45) Date of Patent: Jul. 11, 2006

US007076372B1

(54) CRYSTAL STRUCTURE OF MVAS

(75) Inventors: Alexei Brooun, San Diego, CA (US); David J. Hosfield, San Diego, CA (US); Robert J. Skene, San Diego, CA (US); Leslie W. Tari, San Diego, CA (US); Sheng Ye, Allen, TX (US)

(73) Assignee: Takeda San Diego, Inc., San Diego, CA (US)

(*) Notice: Subject to any disclaimer, the term of this patent is extended or adjusted under 35 U.S.C. 154(b) by 309 days.

(21) Appl. No.: 10/757,963

(22) Filed: Jan. 14, 2004

(51) Int. Cl.
*G01N 33/48* (2006.01)
*G06G 19/00* (2006.01)
(52) U.S. Cl. .......................................... 702/19; 703/11
(58) Field of Classification Search ................. 702/19; 703/11
See application file for complete search history.

*Primary Examiner*—Ardin H. Marschel
*Assistant Examiner*—Anna Skibinsky
(74) *Attorney, Agent, or Firm*—David J. Weitz

(57) ABSTRACT

Provided are structure coordinates relating to MvaS and its various uses.

5 Claims, 137 Drawing Sheets

FIGURE 1

Amino acid sequence for full-length E. faecalis MvaS
with 6 residue polyhistidine C-terminal tag (tag is underlined)
[SEQ. ID No. 1]

MTIGIDKISFFVPPYYIDMTALAEARNVDPGKFHIGIGQDQMAVNPISQDIVTFAANAAE
AILTKEDKEAIDMVIVGTESSIDESKAAAVVLHRLMGIQPFARSFEIKEACYGATAGLQL
AKNHVALHPDKKVLVVAADIAKYGLNSGGEPTQGAGAVAMLVASEPRILALKEDNVMLTQ
DIYDFWRPTGHPYPMVDGPLSNETYIQSFAQVWDEHKKRTGLDFADYDALAFHIPYTKMG
KKALLAKISDQTEAEQERILARYEESIVYSRRVGNLYTGSLYLGLISLLENATTLTAGNQ
IGLFSYGSGAVAEFFTGELVAGYQNHLQKETHLALLDNRTELSIAEYEAMFAETLDTDID
QTLEDELKYSISAINNTVRSYRNKG<u>HHHHHH</u>

FIGURE 1 (cont.)

cDNA sequence encoding MvaS
with 6 residue polyhistidine C-terminal tag (tag is underlined)
[SEQ. ID No. 2]

ATGACAATTGGGATTGATAAAATTAGTTTTTTTGTGCCCCCTTATTATATTGATATGACG
GCACTGGCTGAAGCCAGAAATGTAGACCCTGGAAAATTTCATATTGGTATTGGGCAAGAC
CAAATGGCGGTGAACCCAATCAGCCAAGATATTGTGACATTTGCAGCCAATGCCGCAGAA
GCGATCTTGACCAAAGAAGATAAAGAGGCCATTGATATGGTGATTGTCGGGACTGAGTCC
AGTATCGATGAGTCAAAAGCGGCCGCAGTTGTCTTACATCGTTTAATGGGGATTCAACCT
TTCGCTCGCTCTTTCGAAATCAAGGAAGCTTGTTACGGAGCAACAGCAGGCTTACAGTTA
GCTAAGAATCACGTAGCCTTACATCCAGATAAAAAAGTCTTGGTCGTAGCGGCAGATATT
GCAAAATATGGCTTAAATTCTGGCGGTGAGCCTACACAAGGAGCTGGGGCGGTTGCAATG
TTAGTTGCTAGTGAACCGCGCATTTTGGCTTTAAAAGAGGATAATGTGATGCTGACGCAA
GATATCTATGACTTTTGGCGTCCAACAGGCCACCCGTATCCTATGGTCGATGGTCCTTTG
TCAAACGAAACCTACATCCAATCTTTTGCCCAAGTCTGGGATGAACATAAAAAACGAACC
GGTCTTGATTTTGCAGATTATGATGCTTTAGCGTTCCATATTCCTTACACAAAAATGGGC
AAAAAGCCTTATTAGCAAAAATCTCCGACCAAACTGAAGCAGAACAGGAACGAATTTTA
GCCCGTTATGAAGAAAGTATCGTCTATAGTCGTCGCGTAGGAAACTTGTATACGGGTTCA
CTTTATCTGGGACTCATTTCCCTTTTAGAAAATGCAACGACTTTAACCGCAGGCAATCAA
ATTGGTTTATTCAGTTATGGTTCTGGTGCTGTCGCTGAATTTTTCACTGGTGAATTAGTA
GCTGGTTATCAAAATCATTTACAAAAGAAACTCATTTAGCACTGCTGGATAATCGGACA
GAACTTTCTATCGCTGAATATGAAGCCATGTTTGCAGAAACTTTAGACACAGACATTGAT
CAAACGTTAGAAGATGAATTAAAATATAGTATTTCTGCTATTAATAATACCGTTCGTTCT
TATCGAAACAAAGGGCACCACCACCACCACCACTAG

FIGURE 3

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | THR | A | 2 | 54.202 | 21.266 | 59.185 | 1.00 | 12.76 |
| 3 | CA | THR | A | 2 | 53.298 | 22.012 | 58.259 | 1.00 | 12.73 |
| 5 | CB | THR | A | 2 | 53.265 | 21.336 | 56.877 | 1.00 | 12.92 |
| 7 | OG1 | THR | A | 2 | 52.969 | 19.942 | 57.029 | 1.00 | 13.28 |
| 9 | CG2 | THR | A | 2 | 54.644 | 21.356 | 56.213 | 1.00 | 13.54 |
| 13 | C | THR | A | 2 | 51.881 | 22.071 | 58.815 | 1.00 | 12.42 |
| 14 | O | THR | A | 2 | 51.505 | 21.269 | 59.663 | 1.00 | 12.26 |
| 17 | N | ILE | A | 3 | 51.110 | 23.043 | 58.334 | 1.00 | 12.20 |
| 19 | CA | ILE | A | 3 | 49.699 | 23.198 | 58.678 | 1.00 | 12.13 |
| 21 | CB | ILE | A | 3 | 49.512 | 24.327 | 59.734 | 1.00 | 12.36 |
| 23 | CG1 | ILE | A | 3 | 50.240 | 23.994 | 61.046 | 1.00 | 13.14 |
| 26 | CD1 | ILE | A | 3 | 50.999 | 25.158 | 61.613 | 1.00 | 14.29 |
| 30 | CG2 | ILE | A | 3 | 48.031 | 24.568 | 60.020 | 1.00 | 12.57 |
| 34 | C | ILE | A | 3 | 48.939 | 23.545 | 57.398 | 1.00 | 11.73 |
| 35 | O | ILE | A | 3 | 49.438 | 24.307 | 56.575 | 1.00 | 11.68 |
| 36 | N | GLY | A | 4 | 47.738 | 23.004 | 57.224 | 1.00 | 11.36 |
| 38 | CA | GLY | A | 4 | 46.946 | 23.325 | 56.046 | 1.00 | 10.99 |
| 41 | C | GLY | A | 4 | 45.699 | 22.492 | 55.846 | 1.00 | 10.68 |
| 42 | O | GLY | A | 4 | 45.102 | 22.020 | 56.806 | 1.00 | 10.27 |
| 43 | N | ILE | A | 5 | 45.302 | 22.337 | 54.584 | 1.00 | 10.31 |
| 45 | CA | ILE | A | 5 | 44.117 | 21.575 | 54.219 | 1.00 | 10.15 |
| 47 | CB | ILE | A | 5 | 43.554 | 22.047 | 52.861 | 1.00 | 9.92 |
| 49 | CG1 | ILE | A | 5 | 43.163 | 23.530 | 52.930 | 1.00 | 9.60 |
| 52 | CD1 | ILE | A | 5 | 42.865 | 24.157 | 51.583 | 1.00 | 9.27 |
| 56 | CG2 | ILE | A | 5 | 42.350 | 21.194 | 52.465 | 1.00 | 9.51 |
| 60 | C | ILE | A | 5 | 44.462 | 20.091 | 54.155 | 1.00 | 10.35 |
| 61 | O | ILE | A | 5 | 45.211 | 19.655 | 53.287 | 1.00 | 10.12 |
| 62 | N | ASP | A | 6 | 43.920 | 19.329 | 55.093 | 1.00 | 10.68 |
| 64 | CA | ASP | A | 6 | 44.139 | 17.891 | 55.151 | 1.00 | 11.01 |
| 66 | CB | ASP | A | 6 | 43.964 | 17.398 | 56.584 | 1.00 | 11.02 |
| 69 | CG | ASP | A | 6 | 44.307 | 15.939 | 56.733 | 1.00 | 11.04 |
| 70 | OD1 | ASP | A | 6 | 43.452 | 15.165 | 57.209 | 1.00 | 11.93 |
| 71 | OD2 | ASP | A | 6 | 45.403 | 15.477 | 56.377 | 1.00 | 11.09 |
| 72 | C | ASP | A | 6 | 43.167 | 17.151 | 54.235 | 1.00 | 11.30 |
| 73 | O | ASP | A | 6 | 43.541 | 16.204 | 53.543 | 1.00 | 11.21 |
| 74 | N | LYS | A | 7 | 41.912 | 17.583 | 54.264 | 1.00 | 11.57 |
| 76 | CA | LYS | A | 7 | 40.877 | 17.024 | 53.406 | 1.00 | 11.77 |
| 78 | CB | LYS | A | 7 | 40.084 | 15.959 | 54.161 | 1.00 | 11.90 |
| 81 | CG | LYS | A | 7 | 40.791 | 14.617 | 54.253 | 1.00 | 12.84 |
| 84 | CD | LYS | A | 7 | 39.941 | 13.586 | 54.991 | 1.00 | 13.41 |
| 87 | CE | LYS | A | 7 | 39.932 | 13.830 | 56.487 | 1.00 | 13.31 |
| 90 | NZ | LYS | A | 7 | 39.401 | 12.662 | 57.245 | 1.00 | 12.81 |
| 94 | C | LYS | A | 7 | 39.948 | 18.128 | 52.939 | 1.00 | 11.62 |

FIGURE 3 (Cont.)

| A | B | C | D | E | F | G | H | I | J |
|---|---|---|---|---|---|---|---|---|---|
| 95 | O | LYS | A | 7 | 39.798 | 19.144 | 53.608 | 1.00 | 11.79 |
| 96 | N | ILE | A | 8 | 39.324 | 17.915 | 51.788 | 1.00 | 11.63 |
| 98 | CA | ILE | A | 8 | 38.470 | 18.916 | 51.167 | 1.00 | 11.75 |
| 100 | CB | ILE | A | 8 | 39.336 | 19.982 | 50.442 | 1.00 | 11.87 |
| 102 | CG1 | ILE | A | 8 | 38.459 | 21.110 | 49.887 | 1.00 | 12.41 |
| 105 | CD1 | ILE | A | 8 | 39.237 | 22.314 | 49.392 | 1.00 | 12.56 |
| 109 | CG2 | ILE | A | 8 | 40.174 | 19.347 | 49.328 | 1.00 | 11.90 |
| 113 | C | ILE | A | 8 | 37.475 | 18.250 | 50.208 | 1.00 | 11.79 |
| 114 | O | ILE | A | 8 | 37.833 | 17.350 | 49.439 | 1.00 | 12.04 |
| 115 | N | SER | A | 9 | 36.221 | 18.688 | 50.281 | 1.00 | 11.37 |
| 117 | CA | SER | A | 9 | 35.157 | 18.175 | 49.424 | 1.00 | 11.02 |
| 119 | CB | CSER | A | 9 | 34.493 | 16.938 | 50.041 | 0.35 | 11.08 |
| 120 | CB | BSER | A | 9 | 34.474 | 16.996 | 50.111 | 0.65 | 11.31 |
| 125 | OG | CSER | A | 9 | 33.846 | 16.153 | 49.046 | 0.35 | 10.11 |
| 126 | OG | BSER | A | 9 | 33.959 | 17.399 | 51.375 | 0.65 | 11.90 |
| 129 | C | SER | A | 9 | 34.129 | 19.256 | 49.180 | 1.00 | 10.96 |
| 130 | O | SER | A | 9 | 34.100 | 20.268 | 49.879 | 1.00 | 10.68 |
| 131 | N | PHE | A | 10 | 33.282 | 19.045 | 48.183 | 1.00 | 10.54 |
| 133 | CA | PHE | A | 10 | 32.190 | 19.966 | 47.936 | 1.00 | 10.59 |
| 135 | CB | PHE | A | 10 | 32.477 | 20.855 | 46.715 | 1.00 | 10.51 |
| 138 | CG | PHE | A | 10 | 32.295 | 20.171 | 45.383 | 1.00 | 11.28 |
| 139 | CD1 | PHE | A | 10 | 33.378 | 19.587 | 44.731 | 1.00 | 11.21 |
| 141 | CE1 | PHE | A | 10 | 33.219 | 18.981 | 43.498 | 1.00 | 11.22 |
| 143 | CZ | PHE | A | 10 | 31.971 | 18.947 | 42.892 | 1.00 | 11.52 |
| 145 | CE2 | PHE | A | 10 | 30.887 | 19.531 | 43.521 | 1.00 | 11.70 |
| 147 | CD2 | PHE | A | 10 | 31.052 | 20.149 | 44.758 | 1.00 | 11.87 |
| 149 | C | PHE | A | 10 | 30.870 | 19.224 | 47.799 | 1.00 | 10.41 |
| 150 | O | PHE | A | 10 | 30.838 | 18.022 | 47.522 | 1.00 | 10.43 |
| 151 | N | PHE | A | 11 | 29.792 | 19.956 | 48.042 | 1.00 | 10.09 |
| 153 | CA | PHE | A | 11 | 28.441 | 19.477 | 47.811 | 1.00 | 10.04 |
| 155 | CB | PHE | A | 11 | 27.732 | 19.203 | 49.126 | 1.00 | 10.11 |
| 158 | CG | PHE | A | 11 | 26.362 | 18.629 | 48.953 | 1.00 | 10.84 |
| 159 | CD1 | PHE | A | 11 | 26.194 | 17.278 | 48.696 | 1.00 | 11.42 |
| 161 | CE1 | PHE | A | 11 | 24.920 | 16.739 | 48.525 | 1.00 | 11.03 |
| 163 | CZ | PHE | A | 11 | 23.813 | 17.554 | 48.603 | 1.00 | 10.90 |
| 165 | CE2 | PHE | A | 11 | 23.968 | 18.907 | 48.854 | 1.00 | 11.21 |
| 167 | CD2 | PHE | A | 11 | 25.237 | 19.442 | 49.022 | 1.00 | 10.79 |
| 169 | C | PHE | A | 11 | 27.669 | 20.527 | 47.033 | 1.00 | 9.94 |
| 170 | O | PHE | A | 11 | 27.855 | 21.723 | 47.243 | 1.00 | 9.62 |
| 171 | N | VAL | A | 12 | 26.818 | 20.063 | 46.123 | 1.00 | 9.67 |
| 173 | CA | VAL | A | 12 | 25.876 | 20.919 | 45.411 | 1.00 | 9.73 |
| 175 | CB | VAL | A | 12 | 26.335 | 21.192 | 43.950 | 1.00 | 9.74 |
| 177 | CG1 | VAL | A | 12 | 27.651 | 21.953 | 43.945 | 1.00 | 9.55 |
| 181 | CG2 | VAL | A | 12 | 26.466 | 19.894 | 43.145 | 1.00 | 9.78 |
| 185 | C | VAL | A | 12 | 24.511 | 20.228 | 45.433 | 1.00 | 9.88 |
| 186 | O | VAL | A | 12 | 24.442 | 19.008 | 45.587 | 1.00 | 9.71 |
| 187 | N | PRO | A | 13 | 23.429 | 20.990 | 45.295 | 1.00 | 10.22 |
| 188 | CA | PRO | A | 13 | 22.085 | 20.408 | 45.319 | 1.00 | 10.37 |
| 190 | CB | PRO | A | 13 | 21.176 | 21.637 | 45.234 | 1.00 | 10.35 |
| 193 | CG | PRO | A | 13 | 22.003 | 22.662 | 44.582 | 1.00 | 10.09 |
| 196 | CD | PRO | A | 13 | 23.381 | 22.450 | 45.106 | 1.00 | 10.13 |
| 199 | C | PRO | A | 13 | 21.840 | 19.462 | 44.138 | 1.00 | 10.73 |
| 200 | O | PRO | A | 13 | 22.529 | 19.556 | 43.129 | 1.00 | 10.40 |

FIGURE 3 (Cont.)

| A | B | C | D | E | F | G | H | I | J |
|---|---|---|---|---|---|---|---|---|---|
| 201 | N | PRO | A | 14 | 20.867 | 18.566 | 44.268 | 1.00 | 11.46 |
| 202 | CA | PRO | A | 14 | 20.593 | 17.548 | 43.240 | 1.00 | 11.83 |
| 204 | CB | PRO | A | 14 | 19.724 | 16.531 | 43.991 | 1.00 | 11.99 |
| 207 | CG | PRO | A | 14 | 19.042 | 17.320 | 45.049 | 1.00 | 11.75 |
| 210 | CD | PRO | A | 14 | 19.976 | 18.430 | 45.432 | 1.00 | 11.49 |
| 213 | C | PRO | A | 14 | 19.868 | 18.031 | 41.974 | 1.00 | 12.30 |
| 214 | O | PRO | A | 14 | 19.307 | 17.189 | 41.277 | 1.00 | 12.17 |
| 215 | N | TYR | A | 15 | 19.876 | 19.333 | 41.684 | 1.00 | 12.69 |
| 217 | CA | TYR | A | 15 | 19.283 | 19.862 | 40.454 | 1.00 | 13.05 |
| 219 | CB | TYR | A | 15 | 17.974 | 20.597 | 40.764 | 1.00 | 13.30 |
| 222 | CG | TYR | A | 15 | 16.998 | 19.806 | 41.605 | 1.00 | 14.56 |
| 223 | CD1 | TYR | A | 15 | 16.181 | 18.840 | 41.027 | 1.00 | 16.14 |
| 225 | CE1 | TYR | A | 15 | 15.282 | 18.103 | 41.792 | 1.00 | 17.40 |
| 227 | CZ | TYR | A | 15 | 15.190 | 18.337 | 43.153 | 1.00 | 17.72 |
| 228 | OH | TYR | A | 15 | 14.299 | 17.606 | 43.904 | 1.00 | 18.77 |
| 230 | CE2 | TYR | A | 15 | 15.990 | 19.295 | 43.753 | 1.00 | 17.03 |
| 232 | CD2 | TYR | A | 15 | 16.888 | 20.025 | 42.975 | 1.00 | 16.32 |
| 234 | C | TYR | A | 15 | 20.222 | 20.821 | 39.717 | 1.00 | 12.88 |
| 235 | O | TYR | A | 15 | 21.107 | 21.430 | 40.311 | 1.00 | 12.42 |
| 236 | N | TYR | A | 16 | 20.009 | 20.942 | 38.412 | 1.00 | 12.94 |
| 238 | CA | TYR | A | 16 | 20.636 | 21.986 | 37.607 | 1.00 | 13.10 |
| 240 | CB | TYR | A | 16 | 21.992 | 21.519 | 37.079 | 1.00 | 13.06 |
| 243 | CG | TYR | A | 16 | 21.909 | 20.435 | 36.021 | 1.00 | 13.03 |
| 244 | CD1 | TYR | A | 16 | 21.964 | 20.746 | 34.663 | 1.00 | 12.67 |
| 246 | CE1 | TYR | A | 16 | 21.887 | 19.751 | 33.695 | 1.00 | 12.93 |
| 248 | CZ | TYR | A | 16 | 21.760 | 18.434 | 34.084 | 1.00 | 13.25 |
| 249 | OH | TYR | A | 16 | 21.685 | 17.437 | 33.140 | 1.00 | 14.53 |
| 251 | CE2 | TYR | A | 16 | 21.707 | 18.101 | 35.423 | 1.00 | 13.25 |
| 253 | CD2 | TYR | A | 16 | 21.779 | 19.098 | 36.380 | 1.00 | 12.97 |
| 255 | C | TYR | A | 16 | 19.746 | 22.354 | 36.427 | 1.00 | 13.45 |
| 256 | O | TYR | A | 16 | 18.871 | 21.582 | 36.048 | 1.00 | 13.46 |
| 257 | N | ILE | A | 17 | 19.977 | 23.531 | 35.852 | 1.00 | 13.65 |
| 259 | CA | ILE | A | 17 | 19.398 | 23.887 | 34.558 | 1.00 | 14.00 |
| 261 | CB | ILE | A | 17 | 18.515 | 25.177 | 34.624 | 1.00 | 14.14 |
| 263 | CG1 | ILE | A | 17 | 17.841 | 25.419 | 33.261 | 1.00 | 14.75 |
| 266 | CD1 | ILE | A | 17 | 16.856 | 26.590 | 33.213 | 1.00 | 15.47 |
| 270 | CG2 | ILE | A | 17 | 19.330 | 26.410 | 35.028 | 1.00 | 14.31 |
| 274 | C | ILE | A | 17 | 20.531 | 24.041 | 33.548 | 1.00 | 14.08 |
| 275 | O | ILE | A | 17 | 21.597 | 24.582 | 33.864 | 1.00 | 13.99 |
| 276 | N | ASP | A | 18 | 20.300 | 23.535 | 32.342 | 1.00 | 14.02 |
| 278 | CA | ASP | A | 18 | 21.256 | 23.657 | 31.253 | 1.00 | 14.10 |
| 280 | CB | ASP | A | 18 | 20.886 | 22.694 | 30.127 | 1.00 | 14.36 |
| 283 | CG | ASP | A | 18 | -21.899 | 22.690 | 29.009 | 1.00 | 15.09 |
| 284 | OD1 | ASP | A | 18 | 21.701 | 23.449 | 28.049 | 1.00 | 16.90 |
| 285 | OD2 | ASP | A | 18 | 22.916 | 21.966 | 29.000 | 1.00 | 16.39 |
| 286 | C | ASP | A | 18 | 21.253 | 25.098 | 30.749 | 1.00 | 13.93 |
| 287 | O | ASP | A | 18 | 20.195 | 25.699 | 30.588 | 1.00 | 13.73 |
| 288 | N | MSE | A | 19 | 22.437 | 25.646 | 30.495 | 1.00 | 13.99 |
| 290 | CA | MSE | A | 19 | 22.571 | 27.055 | 30.129 | 1.00 | 14.18 |
| 292 | CB | MSE | A | 19 | 24.009 | 27.533 | 30.356 | 1.00 | 14.41 |
| 295 | CG | MSE | A | 19 | 24.431 | 27.530 | 31.835 | 1.00 | 14.83 |
| 298 | SE | MSE | A | 19 | 23.364 | 28.719 | 32.966 | 1.00 | 16.73 |
| 299 | CE | MSE | A | 19 | 24.021 | 30.366 | 32.299 | 1.00 | 14.28 |

FIGURE 3 (Cont.)

| A | B | C | D | E | F | G | H | I | J |
|---|---|---|---|---|---|---|---|---|---|
| 303 | C | MSE | A | 19 | 22.108 | 27.366 | 28.696 | 1.00 | 14.36 |
| 304 | O | MSE | A | 19 | 21.753 | 28.510 | 28.399 | 1.00 | 14.04 |
| 305 | N | THR | A | 20 | 22.121 | 26.369 | 27.812 | 1.00 | 14.52 |
| 307 | CA | THR | A | 20 | 21.480 | 26.517 | 26.498 | 1.00 | 15.04 |
| 309 | CB | THR | A | 20 | 21.798 | 25.316 | 25.567 | 1.00 | 15.16 |
| 311 | OG1 | THR | A | 20 | 23.183 | 25.341 | 25.202 | 1.00 | 15.54 |
| 313 | CG2 | THR | A | 20 | 21.066 | 25.432 | 24.225 | 1.00 | 15.69 |
| 317 | C | THR | A | 20 | 19.975 | 26.684 | 26.682 | 1.00 | 15.04 |
| 318 | O | THR | A | 20 | 19.362 | 27.542 | 26.051 | 1.00 | 15.18 |
| 319 | N | ALA | A | 21 | 19.386 | 25.885 | 27.568 | 1.00 | 15.34 |
| 321 | CA | ALA | A | 21 | 17.953 | 25.981 | 27.857 | 1.00 | 15.33 |
| 323 | CB | ALA | A | 21 | 17.508 | 24.820 | 28.740 | 1.00 | 15.48 |
| 327 | C | ALA | A | 21 | 17.572 | 27.321 | 28.495 | 1.00 | 15.50 |
| 328 | O | ALA | A | 21 | 16.505 | 27.866 | 28.200 | 1.00 | 15.37 |
| 329 | N | LEU | A | 22 | 18.437 | 27.858 | 29.357 | 1.00 | 15.62 |
| 331 | CA | LEU | A | 22 | 18.184 | 29.161 | 29.975 | 1.00 | 15.90 |
| 333 | CB | LEU | A | 22 | 19.184 | 29.459 | 31.098 | 1.00 | 15.87 |
| 336 | CG | LEU | A | 22 | 18.985 | 30.800 | 31.816 | 1.00 | 15.98 |
| 338 | CD1 | LEU | A | 22 | 17.648 | 30.831 | 32.550 | 1.00 | 16.60 |
| 342 | CD2 | LEU | A | 22 | 20.133 | 31.088 | 32.774 | 1.00 | 16.14 |
| 346 | C | LEU | A | 22 | 18.262 | 30.259 | 28.921 | 1.00 | 16.25 |
| 347 | O | LEU | A | 22 | 17.420 | 31.147 | 28.883 | 1.00 | 15.88 |
| 348 | N | ALA | A | 23 | 19.280 | 30.180 | 28.069 | 1.00 | 16.78 |
| 350 | CA | ALA | A | 23 | 19.480 | 31.147 | 26.991 | 1.00 | 17.28 |
| 352 | CB | ALA | A | 23 | 20.737 | 30.798 | 26.196 | 1.00 | 17.30 |
| 356 | C | ALA | A | 23 | 18.265 | 31.206 | 26.069 | 1.00 | 17.81 |
| 357 | O | ALA | A | 23 | 17.804 | 32.287 | 25.719 | 1.00 | 17.89 |
| 358 | N | GLU | A | 24 | 17.737 | 30.042 | 25.702 | 1.00 | 18.41 |
| 360 | CA | GLU | A | 24 | 16.566 | 29.958 | 24.829 | 1.00 | 19.06 |
| 362 | CB | GLU | A | 24 | 16.231 | 28.494 | 24.513 | 1.00 | 19.40 |
| 365 | CG | GLU | A | 24 | 17.196 | 27.847 | 23.527 | 1.00 | 21.08 |
| 368 | CD | GLU | A | 24 | 17.045 | 26.335 | 23.425 | 1.00 | 23.42 |
| 369 | OE1 | GLU | A | 24 | 17.752 | 25.719 | 22.590 | 1.00 | 24.83 |
| 370 | OE2 | GLU | A | 24 | 16.231 | 25.753 | 24.176 | 1.00 | 25.56 |
| 371 | C | GLU | A | 24 | 15.363 | 30.666 | 25.453 | 1.00 | 19.03 |
| 372 | O | GLU | A | 24 | 14.706 | 31.466 | 24.798 | 1.00 | 19.00 |
| 373 | N | ALA | A | 25 | 15.102 | 30.388 | 26.728 | 1.00 | 19.06 |
| 375 | CA | ALA | A | 25 | 13.996 | 31.015 | 27.452 | 1.00 | 19.10 |
| 377 | CB | ALA | A | 25 | 13.843 | 30.383 | 28.826 | 1.00 | 19.13 |
| 381 | C | ALA | A | 25 | 14.171 | 32.531 | 27.588 | 1.00 | 19.09 |
| 382 | O | ALA | A | 25 | 13.185 | 33.274 | 27.601 | 1.00 | 18.96 |
| 383 | N | ARG | A | 26 | 15.424 | 32.977 | 27.671 | 1.00 | 19.04 |
| 385 | CA | ARG | A | 26 | 15.752 | 34.390 | 27.874 | 1.00 | 19.16 |
| 387 | CB | ARG | A | 26 | 17.009 | 34.514 | 28.744 | 1.00 | 18.89 |
| 390 | CG | ARG | A | 26 | 16.835 | 33.991 | 30.157 | 1.00 | 18.63 |
| 393 | CD | ARG | A | 26 | 16.147 | 34.961 | 31.102 | 1.00 | 18.00 |
| 396 | NE | ARG | A | 26 | 15.882 | 34.328 | 32.393 | 1.00 | 17.40 |
| 398 | CZ | ARG | A | 26 | 14.798 | 33.607 | 32.685 | 1.00 | 16.51 |
| 399 | NH1 | ARG | A | 26 | 14.678 | 33.082 | 33.898 | 1.00 | 16.37 |
| 402 | NH2 | ARG | A | 26 | 13.847 | 33.385 | 31.783 | 1.00 | 15.78 |
| 405 | C | ARG | A | 26 | 15.958 | 35.178 | 26.572 | 1.00 | 19.36 |
| 406 | O | ARG | A | 26 | 16.205 | 36.382 | 26.621 | 1.00 | 19.15 |
| 407 | N | ASN | A | 27 | 15.850 | 34.506 | 25.425 | 1.00 | 19.83 |

FIGURE 3 (Cont.)

| A | B | C | D | E | F | G | H | I | J |
|---|---|---|---|---|---|---|---|---|---|
| 409 | CA | ASN | A | 27 | 16.103 | 35.119 | 24.116 | 1.00 | 20.28 |
| 411 | CB | ASN | A | 27 | 15.046 | 36.180 | 23.789 | 1.00 | 20.64 |
| 414 | CG | ASN | A | 27 | 13.636 | 35.648 | 23.897 | 1.00 | 21.76 |
| 415 | OD1 | ASN | A | 27 | 13.253 | 34.723 | 23.177 | 1.00 | 23.63 |
| 416 | ND2 | ASN | A | 27 | 12.849 | 36.230 | 24.800 | 1.00 | 24.44 |
| 419 | C | ASN | A | 27 | 17.507 | 35.715 | 24.030 | 1.00 | 20.29 |
| 420 | O | ASN | A | 27 | 17.695 | 36.851 | 23.590 | 1.00 | 20.27 |
| 421 | N | VAL | A | 28 | 18.481 | 34.918 | 24.459 | 1.00 | 20.19 |
| 423 | CA | VAL | A | 28 | 19.886 | 35.303 | 24.507 | 1.00 | 20.13 |
| 425 | CB | VAL | A | 28 | 20.348 | 35.416 | 25.986 | 1.00 | 20.20 |
| 427 | CG1 | VAL | A | 28 | 21.867 | 35.474 | 26.113 | 1.00 | 20.44 |
| 431 | CG2 | VAL | A | 28 | 19.715 | 36.633 | 26.636 | 1.00 | 20.75 |
| 435 | C | VAL | A | 28 | 20.698 | 34.244 | 23.764 | 1.00 | 19.93 |
| 436 | O | VAL | A | 28 | 20.304 | 33.078 | 23.719 | 1.00 | 19.72 |
| 437 | N | ASP | A | 29 | 21.817 | 34.648 | 23.168 | 1.00 | 19.84 |
| 439 | CA | ASP | A | 29 | 22.725 | 33.703 | 22.520 | 1.00 | 19.87 |
| 441 | CB | ASP | A | 29 | 23.974 | 34.403 | 21.995 | 1.00 | 20.36 |
| 444 | CG | ASP | A | 29 | 23.691 | 35.280 | 20.833 | 1.00 | 21.87 |
| 445 | OD1 | ASP | A | 29 | 24.360 | 36.317 | 20.693 | 1.00 | 24.76 |
| 446 | OD2 | ASP | A | 29 | 22.803 | 35.026 | 20.006 | 1.00 | 24.37 |
| 447 | C | ASP | A | 29 | 23.201 | 32.693 | 23.533 | 1.00 | 19.28 |
| 448 | O | ASP | A | 29 | 23.692 | 33.092 | 24.587 | -1.00 | 19.38 |
| 449 | N | PRO | A | 30 | 23.071 | 31.401 | 23.237 | 1.00 | 18.47 |
| 450 | CA | PRO | A | 30 | 23.710 | 30.376 | 24.068 | 1.00 | 18.01 |
| 452 | CB | PRO | A | 30 | 23.467 | 29.081 | 23.282 | 1.00 | 18.19 |
| 455 | CG | PRO | A | 30 | 22.258 | 29.351 | 22.464 | 1.00 | 18.39 |
| 458 | CD | PRO | A | 30 | 22.306 | 30.810 | 22.123 | 1.00 | 18.51 |
| 461 | C | PRO | A | 30 | 25.207 | 30.653 | 24.228 | 1.00 | 17.35 |
| 462 | O | PRO | A | 30 | 25.760 | 30.406 | 25.294 | 1.00 | 17.14 |
| 463 | N | GLY | A | 31 | 25.836 | 31.177 | 23.178 | 1.00 | 16.62 |
| 465 | CA | GLY | A | 31 | 27.241 | 31.541 | 23.206 | 1.00 | 16.12 |
| 468 | C | GLY | A | 31 | 27.595 | 32.624 | 24.213 | 1.00 | 15.61 |
| 469 | O | GLY | A | 31 | 28.709 | 32.647 | 24.707 | 1.00 | 15.49 |
| 470 | N | LYS | A | 32 | 26.671 | 33.533 | 24.512 | 1.00 | 15.15 |
| 472 | CA | LYS | A | 32 | 26.907 | 34.509 | 25.577 | 1.00 | 14.66 |
| 474 | CB | LYS | A | 32 | 25.757 | 35.512 | 25.714 | 1.00 | 14.83 |
| 477 | CG | LYS | A | 32 | 25.881 | 36.386 | 26.965 | 1.00 | 15.07 |
| 480 | CD | LYS | A | 32 | 25.019 | 37.630 | 26.928 | 1.00 | 15.92 |
| 483 | CE | LYS | A | 32 | 25.352 | 38.527 | 28.117 | 1.00 | 16.39 |
| 486 | NZ | LYS | A | 32 | 24.485 | 39.730 | 28.225 | 1.00 | 17.58 |
| 490 | C | LYS | A | 32 | 27.122 | 33.794 | 26.913 | 1.00 | 14.25 |
| 491 | O | LYS | A | 32 | 28.016 | 34.152 | 27.679 | 1.00 | 13.74 |
| 492 | N | PHE | A | 33 | 26.298 | 32.789 | 27.187 | 1.00 | 13.77 |
| 494 | CA | PHE | A | 33 | 26.402 | 32.045 | 28.437 | 1.00 | 13.51 |
| 496 | CB | PHE | A | 33 | 25.093 | 31.313 | 28.737 | 1.00 | 13.42 |
| 499 | CG | PHE | A | 33 | 23.943 | 32.224 | 29.113 | 1.00 | 13.19 |
| 500 | CD1 | PHE | A | 33 | 24.128 | 33.589 | 29.342 | 1.00 | 13.57 |
| 502 | CE1 | PHE | A | 33 | 23.058 | 34.404 | 29.686 | 1.00 | 12.97 |
| 504 | CZ | PHE | A | 33 | 21.796 | 33.870 | 29.807 | 1.00 | 13.22 |
| 506 | CE2 | PHE | A | 33 | 21.597 | 32.517 | 29.593 | 1.00 | 13.79 |
| 508 | CD2 | PHE | A | 33 | 22.666 | 31.704 | 29.244 | 1.00 | 13.39 |
| 510 | C | PHE | A | 33 | 27.580 | 31.068 | 28.449 | 1.00 | 13.45 |
| 511 | O | PHE | A | 33 | 28.331 | 31.040 | 29.413 | 1.00 | 13.33 |

FIGURE 3 (Cont.)

| A | B | C | D | E | F | G | H | I | J |
|---|---|---|---|---|---|---|---|---|---|
| 512 | N | HIS | A | 34 | 27.740 | 30.285 | 27.384 | 1.00 | 13.16 |
| 514 | CA | HIS | A | 34 | 28.790 | 29.265 | 27.308 | 1.00 | 13.28 |
| 516 | CB | AHIS | A | 34 | 28.538 | 28.315 | 26.130 | 0.65 | 13.05 |
| 519 | CG | AHIS | A | 34 | 27.365 | 27.403 | 26.318 | 0.65 | 12.62 |
| 520 | ND1 | AHIS | A | 34 | 27.336 | 26.415 | 27.278 | 0.65 | 11.69 |
| 522 | CE1 | AHIS | A | 34 | 26.190 | 25.763 | 27.201 | 0.65 | 11.84 |
| 524 | NE2 | AHIS | A | 34 | 25.473 | 26.293 | 26.227 | 0.65 | 11.89 |
| 526 | CD2 | AHIS | A | 34 | 26.187 | 27.317 | 25.655 | 0.65 | 12.54 |
| 528 | C | HIS | A | 34 | 30.193 | 29.863 | 27.164 | 1.00 | 13.65 |
| 529 | O | HIS | A | 34 | 31.149 | 29.355 | 27.740 | 1.00 | 13.61 |
| 530 | N | ILE | A | 35 | 30.307 | 30.937 | 26.388 | 1.00 | 14.08 |
| 532 | CA | ILE | A | 35 | 31.606 | 31.508 | 26.039 | 1.00 | 14.54 |
| 534 | CB | ILE | A | 35 | 31.719 | 31.687 | 24.506 | 1.00 | 14.87 |
| 536 | CG1 | ILE | A | 35 | 31.696 | 30.316 | 23.815 | 1.00 | 16.02 |
| 539 | CD1 | ILE | A | 35 | 31.304 | 30.368 | 22.354 | 1.00 | 17.50 |
| 543 | CG2 | ILE | A | 35 | 33.000 | 32.454 | 24.143 | 1.00 | 15.59 |
| 547 | C | ILE | A | 35 | 31.847 | 32.834 | 26.746 | 1.00 | 14.23 |
| 548 | O | ILE | A | 35 | 32.871 | 33.010 | 27.391 | 1.00 | 14.42 |
| 549 | N | GLY | A | 36 | 30.909 | 33.764 | 26.606 | 1.00 | 14.01 |
| 551 | CA | GLY | A | 36 | 31.053 | 35.099 | 27.155 | 1.00 | 13.69 |
| 554 | C | GLY | A | 36 | 31.202 | 35.137 | 28.666 | 1.00 | 13.42 |
| 555 | O | GLY | A | 36 | 32.059 | 35.849 | 29.193 | 1.00 | 13.42 |
| 556 | N | ILE | A | 37 | 30.372 | 34.362 | 29.354 | 1.00 | 12.85 |
| 558 | CA | ILE | A | 37 | 30.382 | 34.305 | 30.808 | 1.00 | 12.76 |
| 560 | CB | ILE | A | 37 | 28.936 | 34.356 | 31.348 | 1.00 | 12.91 |
| 562 | CG1 | ILE | A | 37 | 28.347 | 35.751 | 31.086 | 1.00 | 13.62 |
| 565 | CD1 | ILE | A | 37 | 26.855 | 35.841 | 31.283 | 1.00 | 14.41 |
| 569 | CG2 | ILE | A | 37 | 28.891 | 34.047 | 32.835 | 1.00 | 13.07 |
| 573 | C | ILE | A | 37 | 31.142 | 33.059 | 31.265 | 1.00 | 12.16 |
| 574 | O | ILE | A | 37 | 31.944 | 33.134 | 32.187 | 1.00 | 11.96 |
| 575 | N | GLY | A | 38 | 30.884 | 31.925 | 30.614 | 1.00 | 11.77 |
| 577 | CA | GLY | A | 38 | 31.678 | 30.716 | 30.791 | 1.00 | 11.48 |
| 580 | C | GLY | A | 38 | 31.038 | 29.579 | 31.573 | 1.00 | 11.24 |
| 581 | O | GLY | A | 38 | 31.746 | 28.851 | 32.275 | 1.00 | 10.83 |
| 582 | N | GLN | A | 39 | 29.719 | 29.417 | 31.434 | 1.00 | 11.08 |
| 584 | CA | GLN | A | 39 | 28.939 | 28.431 | 32.187 | 1.00 | 11.05 |
| 586 | CB | GLN | A | 39 | 27.922 | 29.132 | 33.096 | 1.00 | 11.03 |
| 589 | CG | GLN | A | 39 | 28.463 | 30.262 | 33.959 | 1.00 | 10.92 |
| 592 | CD | GLN | A | 39 | 29.713 | 29.886 | 34.725 | 1.00 | 11.49 |
| 593 | OE1 | GLN | A | 39 | 30.680 | 30.635 | 34.718 | 1.00 | 12.44 |
| 594 | NE2 | GLN | A | 39 | 29.689 | 28.742 | 35.404 | 1.00 | 10.80 |
| 597 | C | GLN | A | 39 | 28.161 | 27.473 | 31.276 | 1.00 | 11.17 |
| 598 | O | GLN | A | 39 | 27.673 | 27.868 | 30.210 | 1.00 | 11.03 |
| 599 | N | ASP | A | 40 | 28.014 | 26.230 | 31.735 | 1.00 | 11.33 |
| 601 | CA | ASP | A | 40 | 27.286 | 25.180 | 31.006 | 1.00 | 11.34 |
| 603 | CB | ASP | A | 40 | 28.224 | 24.022 | 30.708 | 1.00 | 11.45 |
| 606 | CG | ASP | A | 40 | 29.402 | 24.445 | 29.875 | 1.00 | 11.30 |
| 607 | OD1 | ASP | A | 40 | 30.514 | 23.932 | 30.118 | 1.00 | 11.57 |
| 608 | OD2 | ASP | A | 40 | 29.300 | 25.294 | 28.963 | 1.00 | 11.08 |
| 609 | C | ASP | A | 40 | 26.063 | 24.649 | 31.751 | 1.00 | 11.49 |
| 610 | O | ASP | A | 40 | 25.033 | 24.376 | 31.136 | 1.00 | 11.09 |
| 611 | N | GLN | A | 41 | 26.197 | 24.473 | 33.065 | 1.00 | 11.59 |
| 613 | CA | GLN | A | 41 | 25.106 | 24.023 | 33.927 | 1.00 | 11.82 |

FIGURE 3 (Cont.)

| A | B | C | D | E | F | G | H | I | J |
|---|---|---|---|---|---|---|---|---|---|
| 615 | CB | GLN | A | 41 | 25.240 | 22.520 | 34.241 | 1.00 | 12.05 |
| 618 | CG | GLN | A | 41 | 25.568 | 21.618 | 33.021 | 1.00 | 13.21 |
| 621 | CD | GLN | A | 41 | 25.873 | 20.161 | 33.394 | 1.00 | 14.52 |
| 622 | OE1 | GLN | A | 41 | 26.563 | 19.891 | 34.379 | 1.00 | 13.91 |
| 623 | NE2 | GLN | A | 41 | 25.366 | 19.225 | 32.593 | 1.00 | 16.25 |
| 626 | C | GLN | A | 41 | 25.131 | 24.846 | 35.222 | 1.00 | 11.84 |
| 627 | O | GLN | A | 41 | 26.204 | 25.125 | 35.755 | 1.00 | 11.66 |
| 628 | N | MSE | A | 42 | 23.950 | 25.228 | 35.710 | 1.00 | 11.86 |
| 630 | CA | MSE | A | 42 | 23.792 | 26.025 | 36.929 | 1.00 | 12.11 |
| 632 | CB | MSE | A | 42 | 22.932 | 27.260 | 36.643 | 1.00 | 12.54 |
| 635 | CG | MSE | A | 42 | 22.262 | 27.873 | 37.893 | 1.00 | 14.05 |
| 638 | SE | MSE | A | 42 | 20.813 | 29.094 | 37.490 | 1.00 | 17.99 |
| 639 | CE | MSE | A | 42 | 21.767 | 30.128 | 36.184 | 1.00 | 13.71 |
| 643 | C | MSE | A | 42 | 23.118 | 25.205 | 38.030 | 1.00 | 11.66 |
| 644 | O | MSE | A | 42 | 22.049 | 24.647 | 37.814 | 1.00 | 11.88 |
| 645 | N | ALA | A | 43 | 23.719 | 25.179 | 39.215 | 1.00 | 11.19 |
| 647 | CA | ALA | A | 43 | 23.119 | 24.533 | 40.381 | 1.00 | 10.83 |
| 649 | CB | ALA | A | 43 | 24.126 | 24.455 | 41.516 | 1.00 | 10.95 |
| 653 | C | ALA | A | 43 | 21.876 | 25.300 | 40.833 | 1.00 | 10.69 |
| 654 | O | ALA | A | 43 | 21.878 | 26.532 | 40.867 | 1.00 | 10.31 |
| 655 | N | VAL | A | 44 | 20.822 | 24.558 | 41.162 | 1.00 | 10.31 |
| 657 | CA | VAL | A | 44 | 19.573 | 25.124 | 41.679 | 1.00 | 10.37 |
| 659 | CB | AVAL | A | 44 | 18.457 | 25.128 | 40.607 | 0.65 | 10.06 |
| 661 | CG1 | AVAL | A | 44 | 17.245 | 25.923 | 41.090 | 0.65 | 10.02 |
| 665 | CG2 | AVAL | A | 44 | 18.973 | 25.693 | 39.290 | 0.65 | 10.22 |
| 669 | C | VAL | A | 44 | 19.109 | 24.287 | 42.871 | 1.00 | 10.47 |
| 670 | O | VAL | A | 44 | 19.283 | 23.067 | 42.876 | 1.00 | 10.39 |
| 671 | N | ASN | A | 45 | 18.525 | 24.947 | 43.874 | 1.00 | 10.73 |
| 673 | CA | ASN | A | 45 | 18.023 | 24.271 | 45.075 | 1.00 | 10.88 |
| 675 | CB | ASN | A | 45 | 18.976 | 24.481 | 46.255 | 1.00 | 11.00 |
| 678 | CG | ASN | A | 45 | 19.019 | 25.925 | 46.730 | 1.00 | 11.03 |
| 679 | OD1 | ASN | A | 45 | 19.650 | 26.778 | 46.103 | 1.00 | 12.28 |
| 680 | ND2 | ASN | A | 45 | 18.349 | 26.204 | 47.846 | 1.00 | 10.36 |
| 683 | C | ASN | A | 45 | 16.622 | 24.741 | 45.471 | 1.00 | 10.98 |
| 684 | O | ASN | A | 45 | 16.277 | 25.909 | 45.274 | 1.00 | 10.93 |
| 685 | N | PRO | A | 46 | 15.819 | 23.839 | 46.037 | 1.00 | 11.03 |
| 686 | CA | PRO | A | 46 | 14.504 | 24.216 | 46.561 | 1.00 | 11.13 |
| 688 | CB | PRO | A | 46 | 13.773 | 22.875 | 46.652 | 1.00 | 11.07 |
| 691 | CG | PRO | A | 46 | 14.862 | 21.894 | 46.968 | 1.00 | 11.32 |
| 694 | CD | PRO | A | 46 | 16.086 | 22.402 | 46.229 | 1.00 | 11.02 |
| 697 | C | PRO | A | 46 | 14.625 | 24.859 | 47.940 | 1.00 | 11.19 |
| 698 | O | PRO | A | 46 | 15.711 | 24.844 | 48.540 | 1.00 | 11.08 |
| 699 | N | ILE | A | 47 | 13.512 | 25.398 | 48.434 | 1.00 | 11.09 |
| 701 | CA | ILE | A | 47 | 13.465 | 26.082 | 49.731 | 1.00 | 11.17 |
| 703 | CB | ILE | A | 47 | 12.114 | 26.833 | 49.909 | 1.00 | 11.38 |
| 705 | CG1 | ILE | A | 47 | 10.924 | 25.922 | 49.562 | 1.00 | 12.55 |
| 708 | CD1 | ILE | A | 47 | 9.662 | 26.210 | 50.348 | 1.00 | 13.79 |
| 712 | CG2 | ILE | A | 47 | 12.095 | 28.069 | 49.058 | 1.00 | 12.16 |
| 716 | C | ILE | A | 47 | 13.692 | 25.144 | 50.920 | 1.00 | 10.64 |
| 717 | O | ILE | A | 47 | 13.913 | 25.603 | 52.038 | 1.00 | 10.56 |
| 718 | N | SER | A | 48 | 13.629 | 23.835 | 50.673 | 1.00 | 10.28 |
| 720 | CA | SER | A | 48 | 13.890 | 22.828 | 51.699 | 1.00 | 9.93 |
| 722 | CB | SER | A | 48 | 13.142 | 21.531 | 51.370 | 1.00 | 9.94 |

FIGURE 3 (Cont.)

| A | B | C | D | E | F | G | H | I | J |
|---|---|---|---|---|---|---|---|---|---|
| 725 | OG | SER | A | 48 | 13.407 | 21.104 | 50.045 | 1.00 | 9.71 |
| 727 | C | SER | A | 48 | 15.381 | 22.529 | 51.896 | 1.00 | 9.68 |
| 728 | O | SER | A | 48 | 15.736 | 21.669 | 52.702 | 1.00 | 9.62 |
| 729 | N | GLN | A | 49 | 16.249 | 23.230 | 51.167 | 1.00 | 9.36 |
| 731 | CA | GLN | A | 49 | 17.699 | 23.087 | 51.316 | 1.00 | 8.98 |
| 733 | CB | GLN | A | 49 | 18.290 | 22.411 | 50.078 | 1.00 | 8.84 |
| 736 | CG | GLN | A | 49 | 17.717 | 21.006 | 49.829 | 1.00 | 8.93 |
| 739 | CD | GLN | A | 49 | 18.158 | 20.390 | 48.512 | 1.00 | 8.85 |
| 740 | OE1 | GLN | A | 49 | 19.162 | 20.803 | 47.919 | 1.00 | 8.61 |
| 741 | NE2 | GLN | A | 49 | 17.403 | 19.395 | 48.048 | 1.00 | 8.11 |
| 744 | C | GLN | A | 49 | 18.336 | 24.458 | 51.550 | 1.00 | 8.87 |
| 745 | O | GLN | A | 49 | 18.130 | 25.382 | 50.761 | 1.00 | 8.42 |
| 746 | N | ASP | A | 50 | 19.087 | 24.582 | 52.648 | 1.00 | 8.68 |
| 748 | CA | ASP | A | 50 | 19.737 | 25.835 | 53.030 | 1.00 | 8.68 |
| 750 | CB | ASP | A | 50 | 19.026 | 26.463 | 54.248 | 1.00 | 8.61 |
| 753 | CG | ASP | A | 50 | 19.161 | 25.627 | 55.517 | 1.00 | 9.06 |
| 754 | OD1 | ASP | A | 50 | 18.396 | 25.864 | 56.473 | 1.00 | 9.22 |
| 755 | OD2 | ASP | A | 50 | 19.990 | 24.714 | 55.662 | 1.00 | 8.75 |
| 756 | C | ASP | A | 50 | 21.233 | 25.596 | 53.282 | 1.00 | 8.79 |
| 757 | O | ASP | A | 50 | 21.743 | 24.511 | 52.994 | 1.00 | 8.31 |
| 758 | N | ILE | A | 51 | 21.942 | 26.599 | 53.796 | 1.00 | 8.88 |
| 760 | CA | ILE | A | 51 | 23.389 | 26.471 | 53.992 | 1.00 | 9.16 |
| 762 | CB | ILE | A | 51 | 24.049 | 27.815 | 54.403 | 1.00 | 9.22 |
| 764 | CG1 | ILE | A | 51 | 23.437 | 28.382 | 55.688 | 1.00 | 9.46 |
| 767 | CD1 | ILE | A | 51 | 24.332 | 29.393 | 56.375 | 1.00 | 10.27 |
| 771 | CG2 | ILE | A | 51 | 23.962 | 28.831 | 53.254 | 1.00 | 9.17 |
| 775 | C | ILE | A | 51 | 23.772 | 25.365 | 54.976 | 1.00 | 9.27 |
| 776 | O | ILE | A | 51 | 24.843 | 24.780 | 54.854 | 1.00 | 9.30 |
| 777 | N | VAL | A | 52 | 22.915 | 25.094 | 55.955 | 1.00 | 9.36 |
| 779 | CA | VAL | A | 52 | 23.147 | 23.980 | 56.875 | 1.00 | 9.56 |
| 781 | CB | VAL | A | 52 | 22.164 | 24.013 | 58.072 | 1.00 | 9.60 |
| 783 | CG1 | VAL | A | 52 | 22.227 | 22.726 | 58.887 | 1.00 | 10.02 |
| 787 | CG2 | VAL | A | 52 | 22.451 | 25.216 | 58.957 | 1.00 | 9.30 |
| 791 | C | VAL | A | 52 | 23.069 | 22.641 | 56.125 | 1.00 | 9.53 |
| 792 | O | VAL | A | 52 | 23.895 | 21.762 | 56.339 | 1.00 | 9.54 |
| 793 | N | THR | A | 53 | 22.073 | 22.492 | 55.259 | 1.00 | 9.66 |
| 795 | CA | THR | A | 53 | 21.955 | 21.306 | 54.405 | 1.00 | 9.55 |
| 797 | CB | THR | A | 53 | 20.789 | 21.480 | 53.406 | 1.00 | 9.50 |
| 799 | OG1 | THR | A | 53 | 19.553 | 21.663 | 54.115 | 1.00 | 8.91 |
| 801 | CG2 | THR | A | 53 | 20.580 | 20.212 | 52.565 | 1.00 | 9.74 |
| 805 | C | THR | A | 53 | 23.236 | 21.047 | 53.619 | 1.00 | 9.49 |
| 806 | O | THR | A | 53 | 23.761 | 19.933 | 53.619 | 1.00 | 9.29 |
| 807 | N | PHE | A | 54 | 23.730 | 22.081 | 52.944 | 1.00 | 9.46 |
| 809 | CA | PHE | A | 54 | 24.903 | 21.941 | 52.086 | 1.00 | 9.60 |
| 811 | CB | PHE | A | 54 | 25.073 | 23.180 | 51.196 | 1.00 | 9.77 |
| 814 | CG | PHE | A | 54 | 23.902 | 23.451 | 50.275 | 1.00 | 10.24 |
| 815 | CD1 | PHE | A | 54 | 23.664 | 24.737 | 49.818 | 1.00 | 11.07 |
| 817 | CE1 | PHE | A | 54 | 22.602 | 25.006 | 48.969 | 1.00 | 11.79 |
| 819 | CZ | PHE | A | 54 | 21.764 | 23.983 | 48.567 | 1.00 | 11.82 |
| 821 | CE2 | PHE | A | 54 | 21.987 | 22.695 | 49.008 | 1.00 | 11.72 |
| 823 | CD2 | PHE | A | 54 | 23.051 | 22.429 | 49.856 | 1.00 | 11.25 |
| 825 | C | PHE | A | 54 | 26.167 | 21.703 | 52.907 | 1.00 | 9.52 |
| 826 | O | PHE | A | 54 | 26.993 | 20.870 | 52.545 | 1.00 | 9.43 |

FIGURE 3 (Cont.)

| A | B | C | D | E | F | G | H | I | J |
|---|---|---|---|---|---|---|---|---|---|
| 827 | N | ALA | A | 55 | 26.308 | 22.436 | 54.009 | 1.00 | 9.48 |
| 829 | CA | ALA | A | 55 | 27.489 | 22.343 | 54.863 | 1.00 | 9.61 |
| 831 | CB | ALA | A | 55 | 27.458 | 23.426 | 55.938 | 1.00 | 9.73 |
| 835 | C | ALA | A | 55 | 27.603 | 20.965 | 55.507 | 1.00 | 9.72 |
| 836 | O | ALA | A | 55 | 28.687 | 20.396 | 55.558 | 1.00 | 9.74 |
| 837 | N | ALA | A | 56 | 26.478 | 20.428 | 55.972 | 1.00 | 9.72 |
| 839 | CA | ALA | A | 56 | 26.451 | 19.111 | 56.611 | 1.00 | 9.90 |
| 841 | CB | ALA | A | 56 | 25.085 | 18.849 | 57.223 | 1.00 | 9.91 |
| 845 | C | ALA | A | 56 | 26.809 | 17.999 | 55.617 | 1.00 | 9.86 |
| 846 | O | ALA | A | 56 | 27.559 | 17.089 | 55.946 | 1.00 | 10.08 |
| 847 | N | ASN | A | 57 | 26.282 | 18.084 | 54.402 | 1.00 | 9.75 |
| 849 | CA | ASN | A | 57 | 26.573 | 17.082 | 53.377 | 1.00 | 10.16 |
| 851 | CB | ASN | A | 57 | 25.614 | 17.227 | 52.186 | 1.00 | 9.90 |
| 854 | CG | ASN | A | 57 | 24.273 | 16.544 | 52.432 | 1.00 | 10.88 |
| 855 | OD1 | ASN | A | 57 | 24.200 | 15.315 | 52.494 | 1.00 | 11.08 |
| 856 | ND2 | ASN | A | 57 | 23.208 | 17.339 | 52.591 | 1.00 | 9.43 |
| 859 | C | ASN | A | 57 | 28.042 | 17.128 | 52.931 | 1.00 | 10.26 |
| 860 | O | ASN | A | 57 | 28.675 | 16.086 | 52.753 | 1.00 | 10.39 |
| 861 | N | ALA | A | 58 | 28.592 | 18.332 | 52.804 | 1.00 | 10.35 |
| 863 | CA | ALA | A | 58 | 29.985 | 18.501 | 52.397 | 1.00 | 10.70 |
| 865 | CB | ALA | A | 58 | 30.264 | 19.955 | 52.072 | 1.00 | 10.67 |
| 869 | C | ALA | A | 58 | 30.950 | 17.997 | 53.477 | 1.00 | 10.99 |
| 870 | O | ALA | A | 58 | 31.872 | 17.237 | 53.187 | 1.00 | 10.93 |
| 871 | N | ALA | A | 59 | 30.706 | 18.411 | 54.715 | 1.00 | 11.42 |
| 873 | CA | ALA | A | 59 | 31.533 | 18.040 | 55.859 | 1.00 | 11.86 |
| 875 | CB | ALA | A | 59 | 31.074 | 18.799 | 57.100 | 1.00 | 11.98 |
| 879 | C | ALA | A | 59 | 31.502 | 16.536 | 56.126 | 1.00 | 12.44 |
| 880 | O | ALA | A | 59 | 32.529 | 15.936 | 56.446 | 1.00 | 12.41 |
| 881 | N | GLU | A | 60 | 30.327 | 15.932 | 55.985 | 1.00 | 12.73 |
| 883 | CA | GLU | A | 60 | 30.156 | 14.499 | 56.220 | 1.00 | 13.31 |
| 885 | CB | GLU | A | 60 | 28.690 | 14.110 | 56.046 | 1.00 | 13.48 |
| 888 | CG | GLU | A | 60 | 28.414 | 12.641 | 56.303 | 1.00 | 14.88 |
| 891 | CD | GLU | A | 60 | 26.964 | 12.388 | 56.630 | 1.00 | 15.94 |
| 892 | OE1 | GLU | A | 60 | 26.614 | 12.446 | 57.824 | 1.00 | 16.74 |
| 893 | OE2 | GLU | A | 60 | 26.183 | 12.153 | 55.690 | 1.00 | 16.79 |
| 894 | C | GLU | A | 60 | 31.032 | 13.638 | 55.301 | 1.00 | 13.32 |
| 895 | O | GLU | A | 60 | 31.443 | 12.540 | 55.683 | 1.00 | 13.40 |
| 896 | N | ALA | A | 61 | 31.318 | 14.140 | 54.101 | 1.00 | 13.39 |
| 898 | CA | ALA | A | 61 | 32.189 | 13.448 | 53.148 | 1.00 | 13.61 |
| 900 | CB | ALA | A | 61 | 32.114 | 14.127 | 51.777 | 1.00 | 13.57 |
| 904 | C | ALA | A | 61 | 33.658 | 13.336 | 53.593 | 1.00 | 13.74 |
| 905 | O | ALA | A | 61 | 34.402 | 12.523 | 53.042 | 1.00 | 13.86 |
| 906 | N | ILE | A | 62 | 34.078 | 14.141 | 54.571 | 1.00 | 13.64 |
| 908 | CA | ILE | A | 62 | 35.483 | 14.170 | 54.988 | 1.00 | 13.81 |
| 910 | CB | ILE | A | 62 | 36.138 | 15.528 | 54.611 | 1.00 | 13.73 |
| 912 | CG1 | ILE | A | 62 | 35.407 | 16.704 | 55.272 | 1.00 | 13.83 |
| 915 | CD1 | ILE | A | 62 | 36.198 | 17.998 | 55.266 | 1.00 | 13.82 |
| 919 | CG2 | ILE | A | 62 | 36.173 | 15.701 | 53.090 | 1.00 | 14.19 |
| 923 | C | ILE | A | 62 | 35.754 | 13.868 | 56.470 | 1.00 | 13.93 |
| 924 | O | ILE | A | 62 | 36.914 | 13.738 | 56.848 | 1.00 | 14.43 |
| 925 | N | LEU | A | 63 | 34.722 | 13.756 | 57.307 | 1.00 | 13.93 |
| 927 | CA | LEU | A | 63 | 34.937 | 13.626 | 58.754 | 1.00 | 14.10 |
| 929 | CB | LEU | A | 63 | 33.939 | 14.490 | 59.528 | 1.00 | 14.11 |

FIGURE 3 (Cont.)

| A | B | C | D | E | F | G | H | I | J |
|---|---|---|---|---|---|---|---|---|---|
| 932 | CG | LEU | A | 63 | 34.000 | 16.011 | 59.349 | 1.00 | 14.11 |
| 934 | CD1 | LEU | A | 63 | 33.078 | 16.666 | 60.355 | 1.00 | 14.85 |
| 938 | CD2 | LEU | A | 63 | 35.412 | 16.564 | 59.478 | 1.00 | 13.81 |
| 942 | C | LEU | A | 63 | 34.853 | 12.185 | 59.273 | 1.00 | 14.48 |
| 943 | O | LEU | A | 63 | 33.834 | 11.515 | 59.108 | 1.00 | 14.48 |
| 944 | N | THR | A | 64 | 35.928 | 11.737 | 59.920 | 1.00 | 14.71 |
| 946 | CA | THR | A | 64 | 35.965 | 10.453 | 60.612 | 1.00 | 14.96 |
| 948 | CB | THR | A | 64 | 37.362 | 9.816 | 60.521 | 1.00 | 14.98 |
| 950 | OG1 | THR | A | 64 | 38.322 | 10.652 | 61.184 | 1.00 | 13.73 |
| 952 | CG2 | THR | A | 64 | 37.858 | 9.734 | 59.068 | 1.00 | 15.18 |
| 956 | C | THR | A | 64 | 35.625 | 10.688 | 62.077 | 1.00 | 15.39 |
| 957 | O | THR | A | 64 | 35.547 | 11.830 | 62.524 | 1.00 | 15.05 |
| 958 | N | LYS | A | 65 | 35.455 | 9.607 | 62.828 | 1.00 | 15.85 |
| 960 | CA | LYS | A | 65 | 35.156 | 9.708 | 64.254 | 1.00 | 16.51 |
| 962 | CB | LYS | A | 65 | 34.752 | 8.343 | 64.838 | 1.00 | 16.93 |
| 965 | CG | LYS | A | 65 | 35.879 | 7.432 | 65.303 | 1.00 | 19.15 |
| 968 | CD | LYS | A | 65 | 35.328 | 6.281 | 66.159 | 1.00 | 21.61 |
| 971 | CE | LYS | A | 65 | 35.187 | 6.694 | 67.630 | 1.00 | 23.10 |
| 974 | NZ | LYS | A | 65 | 34.275 | 5.798 | 68.409 | 1.00 | 23.96 |
| 978 | C | LYS | A | 65 | 36.324 | 10.341 | 65.013 | 1.00 | 16.23 |
| 979 | O | LYS | A | 65 | 36.121 | 11.066 | 65.981 | 1.00 | 16.07 |
| 980 | N | GLU | A | 66 | 37.539 | 10.091 | 64.537 | 1.00 | 16.15 |
| 982 | CA | GLU | A | 66 | 38.743 | 10.654 | 65.139 | 1.00 | 16.18 |
| 984 | CB | GLU | A | 66 | 39.998 | 9.974 | 64.577 | 1.00 | 16.57 |
| 987 | CG | GLU | A | 66 | 40.201 | 8.527 | 65.026 | 1.00 | 17.97 |
| 990 | CD | GLU | A | 66 | 39.331 | 7.518 | 64.283 | 1.00 | 20.11 |
| 991 | OE1 | GLU | A | 66 | 38.981 | 6.482 | 64.895 | 1.00 | 21.72 |
| 992 | OE2 | GLU | A | 66 | 38.994 | 7.743 | 63.095 | 1.00 | 20.15 |
| 993 | C | GLU | A | 66 | 38.804 | 12.169 | 64.898 | 1.00 | 15.55 |
| 994 | O | GLU | A | 66 | 39.147 | 12.930 | 65.795 | 1.00 | 15.36 |
| 995 | N | ASP | A | 67 | 38.464 | 12.596 | 63.684 | 1.00 | 15.02 |
| 997 | CA | ASP | A | 67 | 38.398 | 14.021 | 63.358 | 1.00 | 14.45 |
| 999 | CB | ASP | A | 67 | 37.952 | 14.241 | 61.909 | 1.00 | 14.27 |
| 1002 | CG | ASP | A | 67 | 38.970 | 13.761 | 60.892 | 1.00 | 14.31 |
| 1003 | OD1 | ASP | A | 67 | 38.549 | 13.401 | 59.771 | 1.00 | 13.66 |
| 1004 | OD2 | ASP | A | 67 | 40.199 | 13.715 | 61.111 | 1.00 | 13.56 |
| 1005 | C | ASP | A | 67 | 37.423 | 14.738 | 64.290 | 1.00 | 14.17 |
| 1006 | O | ASP | A | 67 | 37.713 | 15.823 | 64.780 | 1.00 | 13.76 |
| 1007 | N | LYS | A | 68 | 36.273 | 14.117 | 64.533 | 1.00 | 14.15 |
| 1009 | CA | LYS | A | 68 | 35.216 | 14.714 | 65.349 | 1.00 | 14.43 |
| 1011 | CB | LYS | A | 68 | 33.941 | 13.858 | 65.289 | 1.00 | 14.38 |
| 1014 | CG | LYS | A | 68 | 33.270 | 13.844 | 63.921 | 1.00 | 14.69 |
| 1017 | CD | LYS | A | 68 | 32.285 | 12.687 | 63.772 | 1.00 | 14.89 |
| 1020 | CE | LYS | A | 68 | 31.688 | 12.645 | 62.372 | 1.00 | 15.19 |
| 1023 | NZ | LYS | A | 68 | 30.360 | 11.982 | 62.339 | 1.00 | 15.93 |
| 1027 | C | LYS | A | 68 | 35.645 | 14.932 | 66.805 | 1.00 | 14.61 |
| 1028 | O | LYS | A | 68 | 35.166 | 15.859 | 67.453 | 1.00 | 14.84 |
| 1029 | N | GLU | A | 69 | 36.539 | 14.089 | 67.318 | 1.00 | 14.70 |
| 1031 | CA | GLU | A | 69 | 37.087 | 14.285 | 68.667 | 1.00 | 14.91 |
| 1033 | CB | GLU | A | 69 | 37.578 | 12.957 | 69.261 | 1.00 | 15.31 |
| 1036 | CG | GLU | A | 69 | 36.508 | 11.886 | 69.435 | 1.00 | 17.18 |
| 1039 | CD | GLU | A | 69 | 35.369 | 12.297 | 70.360 | 1.00 | 19.72 |
| 1040 | OE1 | GLU | A | 69 | 34.204 | 11.955 | 70.050 | 1.00 | 21.65 |

FIGURE 3 (Cont.)

| A | B | C | D | E | F | G | H | I | J |
|---|---|---|---|---|---|---|---|---|---|
| 1041 | OE2 | GLU | A | 69 | 35.627 | 12.956 | 71.391 | 1.00 | 20.78 |
| 1042 | C | GLU | A | 69 | 38.236 | 15.305 | 68.689 | 1.00 | 14.33 |
| 1043 | O | GLU | A | 69 | 38.487 | 15.933 | 69.710 | 1.00 | 14.23 |
| 1044 | N | ALA | A | 70 | 38.937 | 15.459 | 67.569 | 1.00 | 13.75 |
| 1046 | CA | ALA | A | 70 | 40.089 | 16.361 | 67.497 | 1.00 | 13.33 |
| 1048 | CB | ALA | A | 70 | 41.101 | 15.833 | 66.492 | 1.00 | 13.40 |
| 1052 | C | ALA | A | 70 | 39.710 | 17.807 | 67.151 | 1.00 | 12.66 |
| 1053 | O | ALA | A | 70 | 40.496 | 18.724 | 67.391 | 1.00 | 12.47 |
| 1054 | N | ILE | A | 71 | 38.518 | 18.008 | 66.591 | 1.00 | 11.85 |
| 1056 | CA | ILE | A | 71 | 38.064 | 19.344 | 66.211 | 1.00 | 11.47 |
| 1058 | CB | ILE | A | 71 | 36.931 | 19.275 | 65.163 | 1.00 | 11.36 |
| 1060 | CG1 | ILE | A | 71 | 37.465 | 18.779 | 63.817 | 1.00 | 11.45 |
| 1063 | CD1 | ILE | A | 71 | 36.378 | 18.256 | 62.888 | 1.00 | 11.32 |
| 1067 | CG2 | ILE | A | 71 | 36.281 | 20.652 | 64.970 | 1.00 | 11.31 |
| 1071 | C | ILE | A | 71 | 37.579 | 20.107 | 67.442 | 1.00 | 10.92 |
| 1072 | O | ILE | A | 71 | 36.707 | 19.639 | 68.168 | 1.00 | 10.81 |
| 1073 | N | ASP | A | 72 | 38.148 | 21.283 | 67.673 | 1.00 | 10.67 |
| 1075 | CA | ASP | A | 72 | 37.672 | 22.159 | 68.738 | 1.00 | 10.44 |
| 1077 | CB | ASP | A | 72 | 38.694 | 22.224 | 69.880 | 1.00 | 10.61 |
| 1080 | CG | ASP | A | 72 | 39.945 | 23.004 | 69.518 | 1.00 | 10.78 |
| 1081 | OD1 | ASP | A | 72 | 40.183 | 23.276 | 68.321 | 1.00 | 10.77 |
| 1082 | OD2 | ASP | A | 72 | 40.755 | 23.383 | 70.384 | 1.00 | 11.55 |
| 1083 | C | ASP | A | 72 | 37.295 | 23.559 | 68.231 | 1.00 | 10.25 |
| 1084 | O | ASP | A | 72 | 37.127 | 24.479 | 69.024 | 1.00 | 10.14 |
| 1085 | N | MSE | A | 73 | 37.177 | 23.712 | 66.915 | 1.00 | 9.93 |
| 1087 | CA | MSE | A | 73 | 36.603 | 24.918 | 66.321 | 1.00 | 9.92 |
| 1089 | CB | MSE | A | 73 | 37.672 | 25.990 | 66.073 | 1.00 | 10.02 |
| 1092 | CG | MSE | A | 73 | 37.094 | 27.346 | 65.653 | 1.00 | 11.07 |
| 1095 | SE | MSE | A | 73 | 38.335 | 28.847 | 65.896 | 1.00 | 13.87 |
| 1096 | CE | MSE | A | 73 | 39.739 | 28.213 | 64.801 | 1.00 | 12.03 |
| 1100 | C | MSE | A | 73 | 35.880 | 24.579 | 65.022 | 1.00 | 9.47 |
| 1101 | O | MSE | A | 73 | 36.356 | 23.776 | 64.222 | 1.00 | 9.43 |
| 1102 | N | VAL | A | 74 | 34.718 | 25.194 | 64.839 | 1.00 | 9.21 |
| 1104 | CA | VAL | A | 74 | 33.873 | 24.994 | 63.671 | 1.00 | 9.07 |
| 1106 | CB | VAL | A | 74 | 32.604 | 24.184 | 64.030 | 1.00 | 9.03 |
| 1108 | CG1 | VAL | A | 74 | 31.704 | 23.991 | 62.809 | 1.00 | 8.94 |
| 1112 | CG2 | VAL | A | 74 | 32.985 | 22.839 | 64.633 | 1.00 | 9.27 |
| 1116 | C | VAL | A | 74 | 33.476 | 26.378 | 63.151 | 1.00 | 8.82 |
| 1117 | O | VAL | A | 74 | 32.859 | 27.159 | 63.873 | 1.00 | 8.43 |
| 1118 | N | ILE | A | 75 | 33.847 | 26.673 | 61.907 | 1.00 | 8.63 |
| 1120 | CA | ILE | A | 75 | 33.570 | 27.966 | 61.287 | 1.00 | 8.56 |
| 1122 | CB | ILE | A | 75 | 34.886 | 28.698 | 60.947 | 1.00 | 8.55 |
| 1124 | CG1 | ILE | A | 75 | 35.773 | 28.833 | 62.187 | 1.00 | 8.60 |
| 1127 | CD1 | ILE | A | 75 | 37.127 | 29.466 | 61.912 | 1.00 | 8.51 |
| 1131 | CG2 | ILE | A | 75 | 34.594 | 30.077 | 60.346 | 1.00 | 8.56 |
| 1135 | C | ILE | A | 75 | 32.773 | 27.751 | 60.013 | 1.00 | 8.34 |
| 1136 | O | ILE | A | 75 | 33.154 | 26.939 | 59.179 | 1.00 | 8.41 |
| 1137 | N | VAL | A | 76 | 31.667 | 28.471 | 59.869 | 1.00 | 8.30 |
| 1139 | CA | VAL | A | 76 | 30.967 | 28.560 | 58.590 | 1.00 | 8.31 |
| 1141 | CB | VAL | A | 76 | 29.468 | 28.232 | 58.724 | 1.00 | 8.34 |
| 1143 | CG1 | VAL | A | 76 | 28.712 | 28.535 | 57.424 | 1.00 | 8.39 |
| 1147 | CG2 | VAL | A | 76 | 29.282 | 26.776 | 59.111 | 1.00 | 8.97 |
| 1151 | C | VAL | A | 76 | 31.141 | 29.973 | 58.053 | 1.00 | 8.09 |

FIGURE 3 (Cont.)

| A | B | C | D | E | F | G | H | I | J |
|---|---|---|---|---|---|---|---|---|---|
| 1152 | O | VAL | A | 76 | 30.773 | 30.936 | 58.719 | 1.00 | 8.06 |
| 1153 | N | GLY | A | 77 | 31.735 | 30.087 | 56.867 | 1.00 | 8.02 |
| 1155 | CA | GLY | A | 77 | 31.753 | 31.328 | 56.113 | 1.00 | 7.89 |
| 1158 | C | GLY | A | 77 | 30.579 | 31.370 | 55.148 | 1.00 | 7.71 |
| 1159 | O | GLY | A | 77 | 30.398 | 30.463 | 54.332 | 1.00 | 7.60 |
| 1160 | N | THR | A | 78 | 29.777 | 32.421 | 55.242 | 1.00 | 7.48 |
| 1162 | CA | THR | A | 78 | 28.583 | 32.553 | 54.416 | 1.00 | 7.39 |
| 1164 | CB | THR | A | 78 | 27.446 | 31.655 | 54.997 | 1.00 | 7.27 |
| 1166 | OG1 | THR | A | 78 | 26.329 | 31.596 | 54.096 | 1.00 | 6.69 |
| 1168 | CG2 | THR | A | 78 | 26.874 | 32.236 | 56.282 | 1.00 | 7.23 |
| 1172 | C | THR | A | 78 | 28.124 | 34.008 | 54.312 | 1.00 | 7.62 |
| 1173 | O | THR | A | 78 | 28.470 | 34.849 | 55.145 | 1.00 | 8.02 |
| 1174 | N | GLU | A | 79 | 27.376 | 34.289 | 53.254 | 1.00 | 7.72 |
| 1176 | CA | GLU | A | 79 | 26.596 | 35.514 | 53.114 | 1.00 | 7.58 |
| 1178 | CB | GLU | A | 79 | 27.162 | 36.384 | 51.981 | 1.00 | 7.61 |
| 1181 | CG | GLU | A | 79 | 27.153 | 35.719 | 50.614 | 1.00 | 7.60 |
| 1184 | CD | GLU | A | 79 | 27.605 | 36.653 | 49.510 | 1.00 | 7.88 |
| 1185 | OE1 | GLU | A | 79 | 26.772 | 37.432 | 49.009 | 1.00 | 8.45 |
| 1186 | OE2 | GLU | A | 79 | 28.795 | 36.608 | 49.149 | 1.00 | 7.55 |
| 1187 | C | GLU | A | 79 | 25.130 | 35.170 | 52.833 | 1.00 | 7.49 |
| 1188 | O | GLU | A | 79 | 24.377 | 36.019 | 52.374 | 1.00 | 7.22 |
| 1189 | N | SER | A | 80 | 24.740 | 33.923 | 53.112 | 1.00 | 7.54 |
| 1191 | CA | SER | A | 80 | 23.378 | 33.431 | 52.882 | 1.00 | 7.58 |
| 1193 | CB | SER | A | 80 | 23.405 | 32.279 | 51.875 | 1.00 | 7.71 |
| 1196 | OG | SER | A | 80 | 23.947 | 32.697 | 50.639 | 1.00 | 7.17 |
| 1198 | C | SER | A | 80 | 22.756 | 32.949 | 54.193 | 1.00 | 7.76 |
| 1199 | O | SER | A | 80 | 22.122 | 31.889 | 54.248 | 1.00 | 7.40 |
| 1200 | N | SER | A | 81 | 22.933 | 33.738 | 55.249 | 1.00 | 7.78 |
| 1202 | CA | SER | A | 81 | 22.553 | 33.312 | 56.593 | 1.00 | 7.91 |
| 1204 | CB | SER | A | 81 | 23.118 | 34.271 | 57.647 | 1.00 | 7.95 |
| 1207 | OG | SER | A | 81 | 22.560 | 35.566 | 57.524 | 1.00 | 6.84 |
| 1209 | C | SER | A | 81 | 21.039 | 33.192 | 56.761 | 1.00 | 8.38 |
| 1210 | O | SER | A | 81 | 20.271 | 33.825 | 56.043 | 1.00 | 8.26 |
| 1211 | N | ILE | A | 82 | 20.636 | 32.365 | 57.722 | 1.00 | 8.89 |
| 1213 | CA | ILE | A | 82 | 19.230 | 32.152 | 58.070 | 1.00 | 9.25 |
| 1215 | CB | ILE | A | 82 | 18.861 | 30.654 | 57.923 | 1.00 | 9.41 |
| 1217 | CG1 | ILE | A | 82 | 19.725 | 29.776 | 58.839 | 1.00 | 10.65 |
| 1220 | CD1 | ILE | A | 82 | 19.475 | 28.291 | 58.698 | 1.00 | 11.86 |
| 1224 | CG2 | ILE | A | 82 | 19.014 | 30.235 | 56.459 | 1.00 | 10.24 |
| 1228 | C | ILE | A | 82 | 18.892 | 32.662 | 59.468 | 1.00 | 9.16 |
| 1229 | O | ILE | A | 82 | 17.729 | 32.639 | 59.881 | 1.00 | 9.55 |
| 1230 | N | ASP | A | 83 | 19.907 | 33.127 | 60.189 | 1.00 | 8.91 |
| 1232 | CA | ASP | A | 83 | 19.713 | 33.773 | 61.478 | 1.00 | 8.84 |
| 1234 | CB | ASP | A | 83 | 19.922 | 32.767 | 62.617 | 1.00 | 8.51 |
| 1237 | CG | ASP | A | 83 | 19.138 | 33.126 | 63.865 | 1.00 | 8.43 |
| 1238 | OD1 | ASP | A | 83 | 18.029 | 32.587 | 64.073 | 1.00 | 7.70 |
| 1239 | OD2 | ASP | A | 83 | 19.558 | 33.944 | 64.699 | 1.00 | 6.58 |
| 1240 | C | ASP | A | 83 | 20.676 | 34.953 | 61.614 | 1.00 | 8.75 |
| 1241 | O | ASP | A | 83 | 21.805 | 34.910 | 61.115 | 1.00 | 9.10 |
| 1242 | N | GLU | A | 84 | 20.219 | 36.008 | 62.282 | 1.00 | 8.77 |
| 1244 | CA | GLU | A | 84 | 21.024 | 37.213 | 62.496 | 1.00 | 8.82 |
| 1246 | CB | GLU | A | 84 | 20.120 | 38.441 | 62.640 | 1.00 | 8.81 |
| 1249 | CG | GLU | A | 84 | 19.238 | 38.735 | 61.438 | 1.00 | 9.44 |

FIGURE 3 (Cont.)

| A | B | C | D | E | F | G | H | I | J |
|---|---|---|---|---|---|---|---|---|---|
| 1252 | CD | GLU | A | 84 | 20.022 | 39.129 | 60.197 | 1.00 | 9.80 |
| 1253 | OE1 | GLU | A | 84 | 21.181 | 39.586 | 60.331 | 1.00 | 8.70 |
| 1254 | OE2 | GLU | A | 84 | 19.465 | 38.973 | 59.086 | 1.00 | 9.67 |
| 1255 | C | GLU | A | 84 | 21.906 | 37.113 | 63.741 | 1.00 | 8.57 |
| 1256 | O | GLU | A | 84 | 22.822 | 37.920 | 63.916 | 1.00 | 8.58 |
| 1257 | N | SER | A | 85 | 21.608 | 36.146 | 64.609 | 1.00 | 8.36 |
| 1259 | CA | SER | A | 85 | 22.339 | 35.948 | 65.864 | 1.00 | 8.05 |
| 1261 | CB | SER | A | 85 | 21.383 | 36.080 | 67.054 | 1.00 | 8.08 |
| 1264 | OG | SER | A | 85 | 21.993 | 35.694 | 68.274 | 1.00 | 7.24 |
| 1266 | C | SER | A | 85 | 23.034 | 34.589 | 65.924 | 1.00 | 8.01 |
| 1267 | O | SER | A | 85 | 24.230 | 34.520 | 66.163 | 1.00 | 8.24 |
| 1268 | N | LYS | A | 86 | 22.273 | 33.515 | 65.728 | 1.00 | 8.08 |
| 1270 | CA | LYS | A | 86 | 22.772 | 32.150 | 65.913 | 1.00 | 7.68 |
| 1272 | CB | LYS | A | 86 | 21.603 | 31.192 | 66.152 | 1.00 | 7.76 |
| 1275 | CG | LYS | A | 86 | 22.005 | 29.734 | 66.397 | 1.00 | 7.63 |
| 1278 | CD | LYS | A | 86 | 20.839 | 28.937 | 66.967 | 1.00 | 7.97 |
| 1281 | CE | LYS | A | 86 | 21.142 | 27.444 | 67.027 | 1.00 | 8.16 |
| 1284 | NZ | LYS | A | 86 | 20.401 | 26.760 | 68.125 | 1.00 | 8.15 |
| 1288 | C | LYS | A | 86 | 23.583 | 31.684 | 64.707 | 1.00 | 7.48 |
| 1289 | O | LYS | A | 86 | 23.070 | 31.612 | 63.591 | 1.00 | 7.15 |
| 1290 | N | ALA | A | 87 | 24.848 | 31.347 | 64.947 | 1.00 | 7.38 |
| 1292 | CA | ALA | A | 87 | 25.752 | 30.927 | 63.888 | 1.00 | 7.23 |
| 1294 | CB | ALA | A | 87 | 27.168 | 30.802 | 64.420 | 1.00 | 7.23 |
| 1298 | C | ALA | A | 87 | 25.296 | 29.601 | 63.299 | 1.00 | 7.30 |
| 1299 | O | ALA | A | 87 | 24.928 | 28.681 | 64.034 | 1.00 | 6.89 |
| 1300 | N | ALA | A | 88 | 25.315 | 29.521 | 61.968 | 1.00 | 7.54 |
| 1302 | CA | ALA | A | 88 | 25.046 | 28.280 | 61.251 | 1.00 | 7.62 |
| 1304 | CB | ALA | A | 88 | 25.209 | 28.496 | 59.756 | 1.00 | 7.62 |
| 1308 | C | ALA | A | 88 | 25.978 | 27.167 | 61.731 | 1.00 | 7.54 |
| 1309 | O | ALA | A | 88 | 25.605 | 26.003 | 61.729 | 1.00 | 7.60 |
| 1310 | N | ALA | A | 89 | 27.187 | 27.541 | 62.139 | 1.00 | 7.81 |
| 1312 | CA | ALA | A | 89 | 28.183 | 26.593 | 62.642 | 1.00 | 7.82 |
| 1314 | CB | ALA | A | 89 | 29.474 | 27.322 | 62.972 | 1.00 | 7.91 |
| 1318 | C | ALA | A | 89 | 27.712 | 25.800 | 63.861 | 1.00 | 8.06 |
| 1319 | O | ALA | A | 89 | 28.165 | 24.681 | 64.079 | 1.00 | 7.82 |
| 1320 | N | VAL | A | 90 | 26.821 | 26.380 | 64.660 | 1.00 | 8.22 |
| 1322 | CA | VAL | A | 90 | 26.307 | 25.699 | 65.846 | 1.00 | 8.77 |
| 1324 | CB | VAL | A | 90 | 25.449 | 26.638 | 66.736 | 1.00 | 8.77 |
| 1326 | CG1 | VAL | A | 90 | 24.844 | 25.871 | 67.894 | 1.00 | 9.00 |
| 1330 | CG2 | VAL | A | 90 | 26.291 | 27.799 | 67.244 | 1.00 | 8.82 |
| 1334 | C | VAL | A | 90 | 25.487 | 24.472 | 65.459 | 1.00 | 9.04 |
| 1335 | O | VAL | A | 90 | 25.661 | 23.402 | 66.036 | 1.00 | 8.95 |
| 1336 | N | VAL | A | 91 | 24.595 | 24.626 | 64.485 | 1.00 | 9.29 |
| 1338 | CA | VAL | A | 91 | 23.777 | 23.505 | 64.032 | 1.00 | 9.56 |
| 1340 | CB | VAL | A | 91 | 22.641 | 23.954 | 63.095 | 1.00 | 9.78 |
| 1342 | CG1 | VAL | A | 91 | 21.824 | 22.753 | 62.625 | 1.00 | 9.69 |
| 1346 | CG2 | VAL | A | 91 | 21.739 | 24.972 | 63.801 | 1.00 | 10.13 |
| 1350 | C | VAL | A | 91 | 24.658 | 22.465 | 63.338 | 1.00 | 9.53 |
| 1351 | O | VAL | A | 91 | 24.468 | 21.264 | 63.527 | 1.00 | 9.69 |
| 1352 | N | LEU | A | 92 | 25.622 | 22.936 | 62.546 | 1.00 | 9.56 |
| 1354 | CA | LEU | A | 92 | 26.579 | 22.061 | 61.876 | 1.00 | 9.52 |
| 1356 | CB | LEU | A | 92 | 27.537 | 22.876 | 60.993 | 1.00 | 9.63 |
| 1359 | CG | LEU | A | 92 | 28.615 | 22.092 | 60.236 | 1.00 | 9.79 |

FIGURE 3 (Cont.)

| A | B | C | D | E | F | G | H | I | J |
|---|---|---|---|---|---|---|---|---|---|
| 1361 | CD1 | LEU | A | 92 | 27.985 | 21.088 | 59.288 | 1.00 | 9.95 |
| 1365 | CD2 | LEU | A | 92 | 29.537 | 23.039 | 59.479 | 1.00 | 10.31 |
| 1369 | C | LEU | A | 92 | 27.372 | 21.236 | 62.890 | 1.00 | 9.42 |
| 1370 | O | LEU | A | 92 | 27.619 | 20.052 | 62.666 | 1.00 | 9.26 |
| 1371 | N | HIS | A | 93 | 27.751 | 21.861 | 64.004 | 1.00 | 9.42 |
| 1373 | CA | HIS | A | 93 | 28.475 | 21.182 | 65.085 | 1.00 | 9.52 |
| 1375 | CB | HIS | A | 93 | 28.813 | 22.168 | 66.218 | 1.00 | 9.54 |
| 1378 | CG | HIS | A | 93 | 29.417 | 21.525 | 67.433 | 1.00 | 9.46 |
| 1379 | ND1 | HIS | A | 93 | 28.662 | 20.890 | 68.398 | 1.00 | 9.46 |
| 1381 | CE1 | HIS | A | 93 | 29.460 | 20.419 | 69.340 | 1.00 | 9.30 |
| 1383 | NE2 | HIS | A | 93 | 30.703 | 20.741 | 69.031 | 1.00 | 8.60 |
| 1385 | CD2 | HIS | A | 93 | 30.704 | 21.431 | 67.843 | 1.00 | 8.77 |
| 1387 | C | HIS | A | 93 | 27.672 | 19.988 | 65.623 | 1.00 | 9.52 |
| 1388 | O | HIS | A | 93 | 28.234 | 18.914 | 65.831 | 1.00 | 9.62 |
| 1389 | N | ARG | A | 94 | 26.368 | 20.178 | 65.837 | 1.00 | 9.50 |
| 1391 | CA | ARG | A | 94 | 25.491 | 19.098 | 66.312 | 1.00 | 9.69 |
| 1393 | CB | ARG | A | 94 | 24.086 | 19.616 | 66.668 | 1.00 | 9.81 |
| 1396 | CG | ARG | A | 94 | 23.074 | 18.492 | 67.003 | 1.00 | 9.95 |
| 1399 | CD | ARG | A | 94 | 21.692 | 18.955 | 67.454 | 1.00 | 10.32 |
| 1402 | NE | ARG | A | 94 | 20.960 | 19.637 | 66.388 | 1.00 | 10.94 |
| 1404 | CZ | ARG | A | 94 | 20.370 | 19.030 | 65.354 | 1.00 | 11.28 |
| 1405 | NH1 | ARG | A | 94 | 19.745 | 19.754 | 64.435 | 1.00 | 11.42 |
| 1408 | NH2 | ARG | A | 94 | 20.381 | 17.712 | 65.236 | 1.00 | 11.38 |
| 1411 | C | ARG | A | 94 | 25.356 | 17.977 | 65.286 | 1.00 | 9.74 |
| 1412 | O | ARG | A | 94 | 25.508 | 16.809 | 65.625 | 1.00 | 9.71 |
| 1413 | N | LEU | A | 95 | 25.051 | 18.339 | 64.041 | 1.00 | 9.85 |
| 1415 | CA | LEU | A | 95 | 24.798 | 17.355 | 62.989 | 1.00 | 10.10 |
| 1417 | CB | LEU | A | 95 | 24.336 | 18.042 | 61.699 | 1.00 | 9.96 |
| 1420 | CG | LEU | A | 95 | 22.972 | 18.735 | 61.732 | 1.00 | 9.83 |
| 1422 | CD1 | LEU | A | 95 | 22.776 | 19.544 | 60.465 | 1.00 | 10.47 |
| 1426 | CD2 | LEU | A | 95 | 21.847 | 17.734 | 61.901 | 1.00 | 10.58 |
| 1430 | C | LEU | A | 95 | 26.014 | 16.471 | 62.698 | 1.00 | 10.44 |
| 1431 | O | LEU | A | 95 | 25.860 | 15.295 | 62.374 | 1.00 | 10.47 |
| 1432 | N | MSE | A | 96 | 27.214 | 17.033 | 62.821 | 1.00 | 10.89 |
| 1434 | CA | MSE | A | 96 | 28.446 | 16.284 | 62.562 | 1.00 | 11.53 |
| 1436 | CB | MSE | A | 96 | 29.551 | 17.227 | 62.073 | 1.00 | 11.58 |
| 1439 | CG | MSE | A | 96 | 29.253 | 17.880 | 60.735 | 1.00 | 12.76 |
| 1442 | SE | MSE | A | 96 | 29.080 | 16.592 | 59.285 | 1.00 | 15.36 |
| 1443 | CE | MSE | A | 96 | 27.133 | 16.359 | 59.265 | 1.00 | 14.46 |
| 1447 | C | MSE | A | 96 | 28.945 | 15.499 | 63.782 | 1.00 | 11.55 |
| 1448 | O | MSE | A | 96 | 29.945 | 14.798 | 63.688 | 1.00 | 12.05 |
| 1449 | N | GLY | A | 97 | 28.265 | 15.627 | 64.920 | 1.00 | 11.70 |
| 1451 | CA | GLY | A | 97 | 28.626 | 14.905 | 66.131 | 1.00 | 11.68 |
| 1454 | C | GLY | A | 97 | 30.011 | 15.259 | 66.649 | 1.00 | 11.66 |
| 1455 | O | GLY | A | 97 | 30.722 | 14.407 | 67.191 | 1.00 | 11.30 |
| 1456 | N | ILE | A | 98 | 30.403 | 16.517 | 66.465 | 1.00 | 11.46 |
| 1458 | CA | ILE | A | 98 | 31.697 | 16.998 | 66.935 | 1.00 | 11.56 |
| 1460 | CB | ILE | A | 98 | 32.044 | 18.357 | 66.261 | 1.00 | 11.67 |
| 1462 | CG1 | ILE | A | 98 | 32.386 | 18.121 | 64.783 | 1.00 | 12.15 |
| 1465 | CD1 | ILE | A | 98 | 32.076 | 19.290 | 63.891 | 1.00 | 13.07 |
| 1469 | CG2 | ILE | A | 98 | 33.213 | 19.060 | 66.957 | 1.00 | 11.73 |
| 1473 | C | ILE | A | 98 | 31.667 | 17.092 | 68.458 | 1.00 | 11.39 |
| 1474 | O | ILE | A | 98 | 30.633 | 17.401 | 69.047 | 1.00 | 11.30 |

FIGURE 3 (Cont.)

| A | B | C | D | E | F | G | H | I | J |
|---|---|---|---|---|---|---|---|---|---|
| 1475 | N | GLN | A | 99 | 32.800 | 16.795 | 69.088 | 1.00 | 11 46 |
| 1477 | CA | GLN | A | 99 | 32.905 | 16.809 | 70.547 | 1.00 | 11.54 |
| 1479 | CB | GLN | A | 99 | 34.324 | 16.428 | 71.007 | 1.00 | 11.48 |
| 1482 | CG | GLN | A | 99 | 35.434 | 17.381 | 70.554 | 1.00 | 11.36 |
| 1485 | CD | GLN | A | 99 | 35.666 | 18.553 | 71.498 | 1.00 | 11.13 |
| 1486 | OE1 | GLN | A | 99 | 35.422 | 18.453 | 72.704 | 1.00 | 10.05 |
| 1487 | NE2 | GLN | A | 99 | 36.141 | 19.668 | 70.948 | 1.00 | 10.34 |
| 1490 | C | GLN | A | 99 | 32.502 | 18.179 | 71.083 | 1.00 | 11.70 |
| 1491 | O | GLN | A | 99 | 32.718 | 19.201 | 70.412 | 1.00 | 11.69 |
| 1492 | N | PRO | A | 100 | 31.917 | 18.204 | 72.279 | 1.00 | 11.75 |
| 1493 | CA | PRO | A | 100 | 31.247 | 19.408 | 72.786 | 1.00 | 11.77 |
| 1495 | CB | PRO | A | 100 | 30.564 | 18.919 | 74.071 | 1.00 | 11.87 |
| 1498 | CG | PRO | A | 100 | 31.324 | 17.714 | 74.489 | 1.00 | 12.30 |
| 1501 | CD | PRO | A | 100 | 31.840 | 17.084 | 73.236 | 1.00 | 12.01 |
| 1504 | C | PRO | A | 100 | 32.154 | 20.606 | 73.088 | 1.00 | 11.66 |
| 1505 | O | PRO | A | 100 | 31.709 | 21.733 | 72.894 | 1.00 | 11.40 |
| 1506 | N | PHE | A | 101 | 33.374 | 20.379 | 73.568 | 1.00 | 11.39 |
| 1508 | CA | PHE | A | 101 | 34.247 | 21.482 | 73.971 | 1.00 | 11.08 |
| 1510 | CB | PHE | A | 101 | 35.238 | 21.024 | 75.039 | 1.00 | 11.24 |
| 1513 | CG | PHE | A | 101 | 34.570 | 20.585 | 76.308 | 1.00 | 12.06 |
| 1514 | CD1 | PHE | A | 101 | 34.508 | 19.242 | 76.650 | 1.00 | 13.05 |
| 1516 | CE1 | PHE | A | 101 | 33.875 | 18.835 | 77.817 | 1.00 | 13.37 |
| 1518 | CZ | PHE | A | 101 | 33.289 | 19.778 | 78.653 | 1.00 | 13.83 |
| 1520 | CE2 | PHE | A | 101 | 33.339 | 21.118 | 78.319 | 1.00 | 13.49 |
| 1522 | CD2 | PHE | A | 101 | 33.976 | 21.517 | 77.148 | 1.00 | 12.73 |
| 1524 | C | PHE | A | 101 | 34.940 | 22.141 | 72.779 | 1.00 | 10.89 |
| 1525 | O | PHE | A | 101 | 36.146 | 21.994 | 72.559 | 1.00 | 10.48 |
| 1526 | N | ALA | A | 102 | 34.139 | 22.896 | 72.032 | 1.00 | 10.37 |
| 1528 | CA | ALA | A | 102 | 34.557 | 23.531 | 70.799 | 1.00 | 10.37 |
| 1530 | CB | ALA | A | 102 | 34.195 | 22.653 | 69.624 | 1.00 | 10.31 |
| 1534 | C | ALA | A | 102 | 33.849 | 24.873 | 70.678 | 1.00 | 10.19 |
| 1535 | O | ALA | A | 102 | 32.712 | 25.018 | 71.122 | 1.00 | 9.89 |
| 1536 | N | ARG | A | 103 | 34.521 | 25.855 | 70.088 | 1.00 | 10.20 |
| 1538 | CA | ARG | A | 103 | 33.868 | 27.112 | 69.765 | 1.00 | 10.13 |
| 1540 | CB | ARG | A | 103 | 34.794 | 28.306 | 70.010 | 1.00 | 10.35 |
| 1543 | CG | ARG | A | 103 | 35.971 | 28.450 | 69.079 | 1.00 | 10.90 |
| 1546 | CD | ARG | A | 103 | 36.654 | 29.799 | 69.203 | 1.00 | 12.28 |
| 1549 | NE | ARG | A | 103 | 37.413 | 29.913 | 70.453 | 1.00 | 12.82 |
| 1551 | CZ | ARG | A | 103 | 38.734 | 29.763 | 70.561 | 1.00 | 13.92 |
| 1552 | NH1 | ARG | A | 103 | 39.489 | 29.462 | 69.509 | 1.00 | 13.66 |
| 1555 | NH2 | ARG | A | 103 | 39.308 | 29.897 | 71.748 | 1.00 | 14.54 |
| 1558 | C | ARG | A | 103 | 33.368 | 27.056 | 68.326 | 1.00 | 9.80 |
| 1559 | O | ARG | A | 103 | 34.030 | 26.502 | 67.451 | 1.00 | 9.76 |
| 1560 | N | SER | A | 104 | 32.180 | 27.608 | 68.101 | 1.00 | 9.40 |
| 1562 | CA | SER | A | 104 | 31.554 | 27.602 | 66.787 | 1.00 | 9.14 |
| 1564 | CB | SER | A | 104 | 30.402 | 26.595 | 66.754 | 1.00 | 9.08 |
| 1567 | OG | SER | A | 104 | 30.836 | 25.305 | 67.148 | 1.00 | 9.35 |
| 1569 | C | SER | A | 104 | 31.033 | 28.989 | 66.455 | 1.00 | 8.93 |
| 1570 | O | SER | A | 104 | 30.402 | 29.638 | 67.291 | 1.00 | 9.02 |
| 1571 | N | PHE | A | 105 | 31.300 | 29.451 | 65.239 | 1.00 | 8.58 |
| 1573 | CA | PHE | A | 105 | 30.807 | 30.753 | 64.810 | 1.00 | 8.44 |
| 1575 | CB | PHE | A | 105 | 31.632 | 31.886 | 65.446 | 1.00 | 8.51 |
| 1578 | CG | PHE | A | 105 | 33.110 | 31.809 | 65.163 | 1.00 | 8.77 |

FIGURE 3 (Cont.)

| A | B | C | D | E | F | G | H | I | J |
|---|---|---|---|---|---|---|---|---|---|
| 1579 | CD1 | PHE | A | 105 | 33.652 | 32.439 | 64.050 | 1.00 | 9.46 |
| 1581 | CE1 | PHE | A | 105 | 35.016 | 32.376 | 63.793 | 1.00 | 9.83 |
| 1583 | CZ | PHE | A | 105 | 35.850 | 31.680 | 64.657 | 1.00 | 9.82 |
| 1585 | CE2 | PHE | A | 105 | 35.323 | 31.061 | 65.774 | 1.00 | 9.29 |
| 1587 | CD2 | PHE | A | 105 | 33.959 | 31.127 | 66.023 | 1.00 | 9.41 |
| 1589 | C | PHE | A | 105 | 30.737 | 30.899 | 63.289 | 1.00 | 8.37 |
| 1590 | O | PHE | A | 105 | 31.187 | 30.039 | 62.533 | 1.00 | 8.04 |
| 1591 | N | GLU | A | 106 | 30.125 | 31.995 | 62.868 | 1.00 | 8.24 |
| 1593 | CA | GLU | A | 106 | 29.899 | 32.317 | 61.474 | 1.00 | 8.07 |
| 1595 | CB | GLU | A | 106 | 28.412 | 32.627 | 61.281 | 1.00 | 8.20 |
| 1598 | CG | GLU | A | 106 | 27.932 | 32.754 | 59.846 | 1.00 | 8.35 |
| 1601 | CD | GLU | A | 106 | 26.426 | 32.965 | 59.761 | 1.00 | 8.72 |
| 1602 | OE1 | GLU | A | 106 | 25.997 | 34.028 | 59.278 | 1.00 | 8.98 |
| 1603 | OE2 | GLU | A | 106 | 25.666 | 32.070 | 60.185 | 1.00 | 8.37 |
| 1604 | C | GLU | A | 106 | 30.747 | 33.542 | 61.145 | 1.00 | 8.13 |
| 1605 | O | GLU | A | 106 | 30.863 | 34.447 | 61.970 | 1.00 | 8.04 |
| 1606 | N | ILE | A | 107 | 31.364 | 33.550 | 59.966 | 1.00 | 7.95 |
| 1608 | CA | ILE | A | 107 | 32.082 | 34.718 | 59.465 | 1.00 | 8.06 |
| 1610 | CB | ILE | A | 107 | 33.538 | 34.376 | 59.089 | 1.00 | 8.03 |
| 1612 | CG1 | ILE | A | 107 | 34.322 | 33.932 | 60.324 | 1.00 | 7.95 |
| 1615 | CD1 | ILE | A | 107 | 35.773 | 33.575 | 60.051 | 1.00 | 8.07 |
| 1619 | CG2 | ILE | A | 107 | 34.206 | 35.585 | 58.431 | 1.00 | 8.63 |
| 1623 | C | ILE | A | 107 | 31.358 | 35.251 | 58.242 | 1.00 | 8.20 |
| 1624 | O | ILE | A | 107 | 30.989 | 34.487 | 57.351 | 1.00 | 7.98 |
| 1625 | N | LYS | A | 108 | 31.165 | 36.567 | 58.213 | 1.00 | 8.27 |
| 1627 | CA | LYS | A | 108 | 30.539 | 37.257 | 57.102 | 1.00 | 8.05 |
| 1629 | CB | LYS | A | 108 | 29.251 | 37.934 | 57.574 | 1.00 | 8.27 |
| 1632 | CG | LYS | A | 108 | 28.519 | 38.748 | 56.506 | 1.00 | 7.91 |
| 1635 | CD | LYS | A | 108 | 27.625 | 39.815 | 57.123 | 1.00 | 7.62 |
| 1638 | CE | LYS | A | 108 | 26.417 | 39.204 | 57.820 | 1.00 | 7.37 |
| 1641 | NZ | LYS | A | 108 | 25.663 | 40.213 | 58.627 | 1.00 | 6.60 |
| 1645 | C | LYS | A | 108 | 31.482 | 38.314 | 56.537 | 1.00 | 8.22 |
| 1646 | O | LYS | A | 108 | 31.869 | 39.247 | 57.238 | 1.00 | 8.27 |
| 1647 | N | GLU | A | 109 | 31.863 | 38.135 | 55.274 | 1.00 | 7.96 |
| 1649 | CA | GLU | A | 109 | 32.377 | 39.210 | 54.436 | 1.00 | 8.10 |
| 1651 | CB | GLU | A | 109 | 33.819 | 39.604 | 54.810 | 1.00 | 8.20 |
| 1654 | CG | GLU | A | 109 | 34.553 | 40.569 | 53.870 | 1.00 | 8.27 |
| 1657 | CD | GLU | A | 109 | 33.658 | 41.419 | 52.973 | 1.00 | 8.80 |
| 1658 | OE1 | GLU | A | 109 | 33.943 | 41.501 | 51.760 | 1.00 | 8.15 |
| 1659 | OE2 | GLU | A | 109 | 32.687 | 42.021 | 53.466 | 1.00 | 7.88 |
| 1660 | C | GLU | A | 109 | 32.286 | 38.719 | 53.002 | 1.00 | 8.25 |
| 1661 | O | GLU | A | 109 | 33.284 | 38.315 | 52.412 | 1.00 | 8.36 |
| 1662 | N | ALA | A | 110 | 31.062 | 38.699 | 52.476 | 1.00 | 8.30 |
| 1664 | CA | ALA | A | 110 | 30.818 | 38.409 | 51.071 | 1.00 | 8.53 |
| 1666 | CB | ALA | A | 110 | 31.352 | 39.556 | 50.199 | 1.00 | 8.42 |
| 1670 | C | ALA | A | 110 | 31.444 | 37.051 | 50.715 | 1.00 | 8.69 |
| 1671 | O | ALA | A | 110 | 31.274 | 36.092 | 51.474 | 1.00 | 8.51 |
| 1672 | N | CYS | A | 111 | 32.172 | 36.962 | 49.600 | 1.00 | 8.92 |
| 1674 | CA | CYS | A | 111 | 32.778 | 35.694 | 49.172 | 1.00 | 9.35 |
| 1676 | CB | CYS | A | 111 | 32.860 | 35.642 | 47.650 | 1.00 | 9.57 |
| 1679 | SG | CYS | A | 111 | 31.241 | 35.528 | 46.894 | 1.00 | 12.01 |
| 1680 | C | CYS | A | 111 | 34.166 | 35.445 | 49.767 | 1.00 | 8.90 |
| 1681 | O | CYS | A | 111 | 34.855 | 34.504 | 49.368 | 1.00 | 8.75 |

FIGURE 3 (Cont.)

| A | B | C | D | E | F | G | H | I | J |
|---|---|---|---|---|---|---|---|---|---|
| 1682 | N | TYR | A | 112 | 34.562 | 36.289 | 50.715 | 1.00 | 8.51 |
| 1684 | CA | TYR | A | 112 | 35.842 | 36.171 | 51.398 | 1.00 | 8.49 |
| 1686 | CB | TYR | A | 112 | 36.433 | 37.572 | 51.639 | 1.00 | 8.45 |
| 1689 | CG | TYR | A | 112 | 37.714 | 37.558 | 52.438 | 1.00 | 8.23 |
| 1690 | CD1 | TYR | A | 112 | 37.718 | 37.902 | 53.789 | 1.00 | 7.94 |
| 1692 | CE1 | TYR | A | 112 | 38.879 | 37.862 | 54.531 | 1.00 | 7.59 |
| 1694 | CZ | TYR | A | 112 | 40.056 | 37.470 | 53.932 | 1.00 | 7.85 |
| 1695 | OH | TYR | A | 112 | 41.207 | 37.433 | 54.670 | 1.00 | 9.07 |
| 1697 | CE2 | TYR | A | 112 | 40.083 | 37.122 | 52.594 | 1.00 | 7.85 |
| 1699 | CD2 | TYR | A | 112 | 38.911 | 37.162 | 51.857 | 1.00 | 8.16 |
| 1701 | C | TYR | A | 112 | 35.732 | 35.399 | 52.727 | 1.00 | 8.56 |
| 1702 | O | TYR | A | 112 | 36.745 | 34.965 | 53.274 | 1.00 | 8.45 |
| 1703 | N | GLY | A | 113 | 34.510 | 35.212 | 53.225 | 1.00 | 8.46 |
| 1705 | CA | GLY | A | 113 | 34.287 | 34.679 | 54.563 | 1.00 | 8.51 |
| 1708 | C | GLY | A | 113 | 34.959 | 33.366 | 54.926 | 1.00 | 8.48 |
| 1709 | O | GLY | A | 113 | 35.472 | 33.223 | 56.039 | 1.00 | 8.59 |
| 1710 | N | ALA | A | 114 | 34.936 | 32.397 | 54.016 | 1.00 | 8.53 |
| 1712 | CA | ALA | A | 114 | 35.578 | 31.104 | 54.269 | 1.00 | 8.54 |
| 1714 | CB | ALA | A | 114 | 35.145 | 30.077 | 53.250 | 1.00 | 8.62 |
| 1718 | C | ALA | A | 114 | 37.105 | 31.210 | 54.301 | 1.00 | 8.33 |
| 1719 | O | ALA | A | 114 | 37.750 | 30.510 | 55.068 | 1.00 | 8.29 |
| 1720 | N | THR | A | 115 | 37.667 | 32.078 | 53.466 | 1.00 | 8.17 |
| 1722 | CA | THR | A | 115 | 39.105 | 32.345 | 53.464 | 1.00 | 7.94 |
| 1724 | CB | THR | A | 115 | 39.471 | 33.350 | 52.353 | 1.00 | 7.92 |
| 1726 | OG1 | THR | A | 115 | 39.187 | 32.770 | 51.073 | 1.00 | 7.06 |
| 1728 | CG2 | THR | A | 115 | 40.977 | 33.625 | 52.325 | 1.00 | 7.44 |
| 1732 | C | THR | A | 115 | 39.573 | 32.871 | 54.813 | 1.00 | 8.12 |
| 1733 | O | THR | A | 115 | 40.575 | 32.405 | 55.340 | 1.00 | 7.77 |
| 1734 | N | ALA | A | 116 | 38.842 | 33.835 | 55.370 | 1.00 | 8.24 |
| 1736 | CA | ALA | A | 116 | 39.132 | 34.329 | 56.707 | 1.00 | 8.43 |
| 1738 | CB | ALA | A | 116 | 38.110 | 35.374 | 57.119 | 1.00 | 8.68 |
| 1742 | C | ALA | A | 116 | 39.136 | 33.164 | 57.701 | 1.00 | 8.51 |
| 1743 | O | ALA | A | 116 | 40.024 | 33.065 | 58.536 | 1.00 | 8.28 |
| 1744 | N | GLY | A | 117 | 38.154 | 32.272 | 57.587 | 1.00 | 8.58 |
| 1746 | CA | GLY | A | 117 | 38.083 | 31.091 | 58.430 | 1.00 | 9.08 |
| 1749 | C | GLY | A | 117 | 39.288 | 30.171 | 58.283 | 1.00 | 9.55 |
| 1750 | O | GLY | A | 117 | 39.802 | 29.669 | 59.274 | 1.00 | 9.65 |
| 1751 | N | LEU | A | 118 | 39.736 | 29.959 | 57.048 | 1.00 | 10.21 |
| 1753 | CA | LEU | A | 118 | 40.879 | 29.085 | 56.763 | 1.00 | 10.89 |
| 1755 | CB | LEU | A | 118 | 41.087 | 28.956 | 55.251 | 1.00 | 10.87 |
| 1758 | CG | LEU | A | 118 | 42.324 | 28.178 | 54.785 | 1.00 | 10.58 |
| 1760 | CD1 | LEU | A | 118 | 42.271 | 26.743 | 55.281 | 1.00 | 10.27 |
| 1764 | CD2 | LEU | A | 118 | 42.431 | 28.226 | 53.273 | 1.00 | 10.81 |
| 1768 | C | LEU | A | 118 | 42.166 | 29.589 | 57.411 | 1.00 | 11.53 |
| 1769 | O | LEU | A | 118 | 42.910 | 28.808 | 57.993 | 1.00 | 11.49 |
| 1770 | N | GLN | A | 119 | 42.408 | 30.895 | 57.317 | 1.00 | 12.46 |
| 1772 | CA | GLN | A | 119 | 43.637 | 31.504 | 57.827 | 1.00 | 13.02 |
| 1774 | CB | GLN | A | 119 | 43.802 | 32.942 | 57.314 | 1.00 | 13.45 |
| 1777 | CG | GLN | A | 119 | 43.618 | 33.145 | 55.806 | 1.00 | 14.55 |
| 1780 | CD | GLN | A | 119 | 44.550 | 32.315 | 54.948 | 1.00 | 16.06 |
| 1781 | OE1 | GLN | A | 119 | 45.334 | 31.516 | 55.453 | 1.00 | 18.97 |
| 1782 | NE2 | GLN | A | 119 | 44.473 | 32.513 | 53.641 | 1.00 | 18.15 |
| 1785 | C | GLN | A | 119 | 43.658 | 31.514 | 59.344 | 1.00 | 13.14 |

FIGURE 3 (Cont.)

| A | B | C | D | E | F | G | H | I | J |
|---|---|---|---|---|---|---|---|---|---|
| 1786 | O | GLN | A | 119 | 44.692 | 31.275 | 59.957 | 1.00 | 13.12 |
| 1787 | N | LEU | A | 120 | 42.507 | 31.792 | 59.945 | 1.00 | 13.35 |
| 1789 | CA | LEU | A | 120 | 42.375 | 31.796 | 61.396 | 1.00 | 13.65 |
| 1791 | CB | LEU | A | 120 | 41.050 | 32.418 | 61.805 | 1.00 | 14.11 |
| 1794 | CG | LEU | A | 120 | 40.744 | 33.831 | 61.304 | 1.00 | 15.84 |
| 1796 | CD1 | LEU | A | 120 | 41.577 | 34.872 | 62.009 | 1.00 | 17.23 |
| 1800 | CD2 | LEU | A | 120 | 39.253 | 34.089 | 61.477 | 1.00 | 17.37 |
| 1804 | C | LEU | A | 120 | 42.463 | 30.372 | 61.956 | 1.00 | 13.27 |
| 1805 | O | LEU | A | 120 | 42.996 | 30.160 | 63.045 | 1.00 | 12.95 |
| 1806 | N | ALA | A | 121 | 41.942 | 29.405 | 61.203 | 1.00 | 12.70 |
| 1808 | CA | ALA | A | 121 | 42.070 | 27.996 | 61.564 | 1.00 | 12.46 |
| 1810 | CB | ALA | A | 121 | 41.259 | 27.123 | 60.616 | 1.00 | 12.45 |
| 1814 | C | ALA | A | 121 | 43.539 | 27.586 | 61.532 | 1.00 | 12.30 |
| 1815 | O | ALA | A | 121 | 44.004 | 26.867 | 62.411 | 1.00 | 12.02 |
| 1816 | N | LYS | A | 122 | 44.259 | 28.066 | 60.520 | 1.00 | 12.24 |
| 1818 | CA | LYS | A | 122 | 45.688 | 27.811 | 60.369 | 1.00 | 12.39 |
| 1820 | CB | LYS | A | 122 | 46.212 | 28.498 | 59.097 | 1.00 | 12.82 |
| 1823 | CG | LYS | A | 122 | 47.722 | 28.482 | 58.890 | 1.00 | 14.09 |
| 1826 | CD | LYS | A | 122 | 48.135 | 29.357 | 57.696 | 1.00 | 16.44 |
| 1829 | CE | LYS | A | 122 | 48.020 | 30.862 | 58.011 | 1.00 | 18.11 |
| 1832 | NZ | LYS | A | 122 | 48.699 | 31.750 | 57.010 | 1.00 | 19.35 |
| 1836 | C | LYS | A | 122 | 46.444 | 28.298 | 61.604 | 1.00 | 12.07 |
| 1837 | O | LYS | A | 122 | 47.277 | 27.579 | 62.142 | 1.00 | 11.46 |
| 1838 | N | ASN | A | 123 | 46.132 | 29.511 | 62.057 | 1.00 | 11.91 |
| 1840 | CA | ASN | A | 123 | 46.801 | 30.100 | 63.213 | 1.00 | 12.03 |
| 1842 | CB | ASN | A | 123 | 46.379 | 31.558 | 63.407 | 1.00 | 12.06 |
| 1845 | CG | ASN | A | 123 | 46.852 | 32.477 | 62.289 | 1.00 | 13.18 |
| 1846 | OD1 | ASN | A | 123 | 46.371 | 33.604 | 62.175 | 1.00 | 16.00 |
| 1847 | ND2 | ASN | A | 123 | 47.796 | 32.013 | 61.470 | 1.00 | 12.33 |
| 1850 | C | ASN | A | 123 | 46.509 | 29.316 | 64.491 | 1.00 | 11.82 |
| 1851 | O | ASN | A | 123 | 47.395 | 29.121 | 65.317 | 1.00 | 11.85 |
| 1852 | N | HIS | A | 124 | 45.262 | 28.870 | 64.635 | 1.00 | 11.73 |
| 1854 | CA | HIS | A | 124 | 44.811 | 28.096 | 65.793 | 1.00 | 11.68 |
| 1856 | CB | HIS | A | 124 | 43.282 | 27.909 | 65.729 | 1.00 | 11.67 |
| 1859 | CG | HIS | A | 124 | 42.732 | 26.956 | 66.749 | 1.00 | 11.58 |
| 1860 | ND1 | HIS | A | 124 | 42.570 | 27.292 | 68.076 | 1.00 | 12.35 |
| 1862 | CE1 | HIS | A | 124 | 42.064 | 26.263 | 68.731 | 1.00 | 12.28 |
| 1864 | NE2 | HIS | A | 124 | 41.891 | 25.271 | 67.877 | 1.00 | 12.09 |
| 1866 | CD2 | HIS | A | 124 | 42.299 | 25.679 | 66.631 | 1.00 | 11.67 |
| 1868 | C | HIS | A | 124 | 45.540 | 26.744 | 65.884 | 1.00 | 11.74 |
| 1869 | O | HIS | A | 124 | 45.940 | 26.328 | 66.967 | 1.00 | 11.33 |
| 1870 | N | VAL | A | 125 | 45.730 | 26.078 | 64.748 | 1.00 | 11.98 |
| 1872 | CA | VAL | A | 125 | 46.416 | 24.786 | 64.725 | 1.00 | 12.32 |
| 1874 | CB | VAL | A | 125 | 46.173 | 24.014 | 63.407 | 1.00 | 12.42 |
| 1876 | CG1 | VAL | A | 125 | 46.966 | 22.714 | 63.389 | 1.00 | 12.42 |
| 1880 | CG2 | VAL | A | 125 | 44.686 | 23.708 | 63.224 | 1.00 | 12.06 |
| 1884 | C | VAL | A | 125 | 47.916 | 24.981 | 64.970 | 1.00 | 12.81 |
| 1885 | O | VAL | A | 125 | 48.550 | 24.156 | 65.621 | 1.00 | 12.71 |
| 1886 | N | ALA | A | 126 | 48.472 | 26.086 | 64.479 | 1.00 | 13.25 |
| 1888 | CA | ALA | A | 126 | 49.879 | 26.397 | 64.699 | 1.00 | 13.63 |
| 1890 | CB | ALA | A | 126 | 50.257 | 27.723 | 64.026 | 1.00 | 13.69 |
| 1894 | C | ALA | A | 126 | 50.181 | 26.457 | 66.188 | 1.00 | 13.97 |
| 1895 | O | ALA | A | 126 | 51.231 | 26.006 | 66.628 | 1.00 | 13.99 |

FIGURE 3 (Cont.)

| A | B | C | D | E | F | G | H | I | J |
|---|---|---|---|---|---|---|---|---|---|
| 1896 | N | LEU | A | 127 | 49.241 | 27.001 | 66.955 | 1.00 | 14.43 |
| 1898 | CA | LEU | A | 127 | 49.413 | 27.177 | 68.393 | 1.00 | 14.74 |
| 1900 | CB | LEU | A | 127 | 48.655 | 28.420 | 68.860 | 1.00 | 14.90 |
| 1903 | CG | LEU | A | 127 | 49.404 | 29.753 | 68.731 | 1.00 | 15.69 |
| 1905 | CD1 | LEU | A | 127 | 50.073 | 29.920 | 67.391 | 1.00 | 16.52 |
| 1909 | CD2 | LEU | A | 127 | 48.456 | 30.894 | 68.961 | 1.00 | 16.12 |
| 1913 | C | LEU | A | 127 | 48.966 | 25.951 | 69.193 | 1.00 | 14.73 |
| 1914 | O | LEU | A | 127 | 49.373 | 25.777 | 70.338 | 1.00 | 14.56 |
| 1915 | N | HIS | A | 128 | 48.127 | 25.114 | 68.583 | 1.00 | 14.52 |
| 1917 | CA | HIS | A | 128 | 47.609 | 23.898 | 69.208 | 1.00 | 14.43 |
| 1919 | CB | HIS | A | 128 | 46.153 | 24.103 | 69.661 | 1.00 | 14.55 |
| 1922 | CG | HIS | A | 128 | 45.942 | 25.329 | 70.490 | 1.00 | 15.35 |
| 1923 | ND1 | HIS | A | 128 | 46.328 | 25.411 | 71.811 | 1.00 | 16.64 |
| 1925 | CE1 | HIS | A | 128 | 46.030 | 26.609 | 72.281 | 1.00 | 16.80 |
| 1927 | NE2 | HIS | A | 128 | 45.460 | 27.305 | 71.314 | 1.00 | 16.52 |
| 1929 | CD2 | HIS | A | 128 | 45.398 | 26.530 | 70.182 | 1.00 | 16.04 |
| 1931 | C | HIS | A | 128 | 47.689 | 22.772 | 68.171 | 1.00 | 14.17 |
| 1932 | O | HIS | A | 128 | 46.677 | 22.409 | 67.580 | 1.00 | 13.81 |
| 1933 | N | PRO | A | 129 | 48.890 | 22.238 | 67.928 | 1.00 | 14.20 |
| 1934 | CA | PRO | A | 129 | 49.129 | 21.375 | 66.756 | 1.00 | 14.22 |
| 1936 | CB | PRO | A | 129 | 50.654 | 21.151 | 66.761 | 1.00 | 14.34 |
| 1939 | CG | PRO | A | 129 | 51.212 | 21.889 | 67.923 | 1.00 | 14.71 |
| 1942 | CD | PRO | A | 129 | 50.098 | 22.420 | 68.749 | 1.00 | 14.36 |
| 1945 | C | PRO | A | 129 | 48.387 | 20.034 | 66.716 | 1.00 | 14.07 |
| 1946 | O | PRO | A | 129 | 48.372 | 19.413 | 65.654 | 1.00 | 13.54 |
| 1947 | N | ASP | A | 130 | 47.802 | 19.591 | 67.826 | 1.00 | 14.13 |
| 1949 | CA | ASP | A | 130 | 47.031 | 18.345 | 67.843 | 1.00 | 14.53 |
| 1951 | CB | ASP | A | 130 | 47.235 | 17.606 | 69.170 | 1.00 | 14.97 |
| 1954 | CG | ASP | A | 130 | 48.542 | 16.852 | 69.212 | 1.00 | 17.16 |
| 1955 | OD1 | ASP | A | 130 | 49.007 | 16.505 | 70.321 | 1.00 | 19.49 |
| 1956 | OD2 | ASP | A | 130 | 49.178 | 16.564 | 68.173 | 1.00 | 20.73 |
| 1957 | C | ASP | A | 130 | 45.540 | 18.573 | 67.601 | 1.00 | 14.17 |
| 1958 | O | ASP | A | 130 | 44.783 | 17.616 | 67.450 | 1.00 | 14.02 |
| 1959 | N | LYS | A | 131 | 45.123 | 19.834 | 67.570 | 1.00 | 13.78 |
| 1961 | CA | LYS | A | 131 | 43.730 | 20.174 | 67.308 | 1.00 | 13.67 |
| 1963 | CB | LYS | A | 131 | 43.336 | 21.445 | 68.062 | 1.00 | 13.85 |
| 1966 | CG | LYS | A | 131 | 43.532 | 21.369 | 69.571 | 1.00 | 15.14 |
| 1969 | CD | LYS | A | 131 | 42.730 | 20.237 | 70.206 | 1.00 | 16.93 |
| 1972 | CE | LYS | A | 131 | 42.857 | 20.254 | 71.721 | 1.00 | 18.42 |
| 1975 | NZ | LYS | A | 131 | 42.059 | 19.155 | 72.349 | 1.00 | 20.05 |
| 1979 | C | LYS | A | 131 | 43.483 | 20.354 | 65.819 | 1.00 | 13.04 |
| 1980 | O | LYS | A | 131 | 44.406 | 20.611 | 65.047 | 1.00 | 13.33 |
| 1981 | N | LYS | A | 132 | 42.225 | 20.203 | 65.427 | 1.00 | 12.41 |
| 1983 | CA | LYS | A | 132 | 41.801 | 20.403 | 64.049 | 1.00 | 11.95 |
| 1985 | CB | LYS | A | 132 | 41.384 | 19.069 | 63.419 | 1.00 | 11.87 |
| 1988 | CG | LYS | A | 132 | 42.485 | 18.008 | 63.418 | 1.00 | 12.18 |
| 1991 | CD | LYS | A | 132 | 42.055 | 16.738 | 62.684 | 1.00 | 12.64 |
| 1994 | CE | LYS | A | 132 | 43.042 | 15.580 | 62.920 | 1.00 | 13.88 |
| 1997 | NZ | LYS | A | 132 | 42.723 | 14.399 | 62.054 | 1.00 | 14.60 |
| 2001 | C | LYS | A | 132 | 40.649 | 21.411 | 64.014 | 1.00 | 11.55 |
| 2002 | O | LYS | A | 132 | 40.044 | 21.724 | 65.041 | 1.00 | 11.06 |
| 2003 | N | VAL | A | 133 | 40.369 | 21.932 | 62.825 | 1.00 | 11.00 |
| 2005 | CA | VAL | A | 133 | 39.317 | 22.922 | 62.643 | 1.00 | 10.59 |

FIGURE 3 (Cont.)

| A | B | C | D | E | F | G | H | I | J |
|---|---|---|---|---|---|---|---|---|---|
| 2007 | CB | VAL | A | 133 | 39.903 | 24.339 | 62.483 | 1.00 | 10.69 |
| 2009 | CG1 | VAL | A | 133 | 38.787 | 25.383 | 62.357 | 1.00 | 10.86 |
| 2013 | CG2 | VAL | A | 133 | 40.825 | 24.674 | 63.650 | 1.00 | 10.72 |
| 2017 | C | VAL | A | 133 | 38.513 | 22.566 | 61.403 | 1.00 | 10.26 |
| 2018 | O | VAL | A | 133 | 39.086 | 22.259 | 60.361 | 1.00 | 9.85 |
| 2019 | N | LEU | A | 134 | 37.188 | 22.586 | 61.527 | 1.00 | 9.94 |
| 2021 | CA | LEU | A | 134 | 36.303 | 22.427 | 60.380 | 1.00 | 9.68 |
| 2023 | CB | LEU | A | 134 | 35.059 | 21.616 | 60.759 | 1.00 | 9.64 |
| 2026 | CG | LEU | A | 134 | 33.986 | 21.460 | 59.676 | 1.00 | 9.49 |
| 2028 | CD1 | LEU | A | 134 | 34.510 | 20.649 | 58.499 | 1.00 | 9.95 |
| 2032 | CD2 | LEU | A | 134 | 32.735 | 20.827 | 60.246 | 1.00 | 9.09 |
| 2036 | C | LEU | A | 134 | 35.910 | 23.811 | 59.884 | 1.00 | 9.54 |
| 2037 | O | LEU | A | 134 | 35.357 | 24.605 | 60.638 | 1.00 | 9.41 |
| 2038 | N | VAL | A | 135 | 36.232 | 24.097 | 58.625 | 1.00 | 9.38 |
| 2040 | CA | VAL | A | 135 | 35.868 | 25.349 | 57.974 | 1.00 | 9.26 |
| 2042 | CB | VAL | A | 135 | 37.110 | 26.128 | 57.506 | 1.00 | 9.28 |
| 2044 | CG1 | VAL | A | 135 | 36.702 | 27.435 | 56.799 | 1.00 | 9.56 |
| 2048 | CG2 | VAL | A | 135 | 38.032 | 26.420 | 58.683 | 1.00 | 9.40 |
| 2052 | C | VAL | A | 135 | 35.017 | 25.008 | 56.765 | 1.00 | 9.01 |
| 2053 | O | VAL | A | 135 | 35.452 | 24.261 | 55.906 | 1.00 | 9.07 |
| 2054 | N | VAL | A | 136 | 33.805 | 25.547 | 56.705 | 1.00 | 8.85 |
| 2056 | CA | VAL | A | 136 | 32.890 | 25.265 | 55.607 | 1.00 | 8.69 |
| 2058 | CB | VAL | A | 136 | 31.669 | 24.451 | 56.076 | 1.00 | 8.63 |
| 2060 | CG1 | VAL | A | 136 | 30.798 | 24.056 | 54.883 | 1.00 | 8.60 |
| 2064 | CG2 | VAL | A | 136 | 32.105 | 23.216 | 56.856 | 1.00 | 8.66 |
| 2068 | C | VAL | A | 136 | 32.391 | 26.552 | 54.969 | 1.00 | 8.66 |
| 2069 | O | VAL | A | 136 | 31.784 | 27.392 | 55.635 | 1.00 | 9.26 |
| 2070 | N | ALA | A | 137 | 32.669 | 26.706 | 53.679 | 1.00 | 8.40 |
| 2072 | CA | ALA | A | 137 | 32.022 | 27.712 | 52.852 | 1.00 | 8.10 |
| 2074 | CB | ALA | A | 137 | 32.859 | 27.975 | 51.616 | 1.00 | 8.23 |
| 2078 | C | ALA | A | 137 | 30.658 | 27.168 | 52.452 | 1.00 | 7.88 |
| 2079 | O | ALA | A | 137 | 30.564 | 26.045 | 51.974 | 1.00 | 7.70 |
| 2080 | N | ALA | A | 138 | 29.604 | 27.946 | 52.657 | 1.00 | 7.43 |
| 2082 | CA | ALA | A | 138 | 28.262 | 27.537 | 52.251 | 1.00 | 7.40 |
| 2084 | CB | ALA | A | 138 | 27.589 | 26.769 | 53.365 | 1.00 | 7.40 |
| 2088 | C | ALA | A | 138 | 27.432 | 28.760 | 51.859 | 1.00 | 7.37 |
| 2089 | O | ALA | A | 138 | 27.448 | 29.785 | 52.543 | 1.00 | 7.17 |
| 2090 | N | ASP | A | 139 | 26.707 | 28.649 | 50.756 | 1.00 | 7.60 |
| 2092 | CA | ASP | A | 139 | 26.025 | 29.804 | 50.177 | 1.00 | 7.67 |
| 2094 | CB | ASP | A | 139 | 27.048 | 30.772 | 49.559 | 1.00 | 7.67 |
| 2097 | CG | ASP | A | 139 | 27.526 | 31.841 | 50.526 | 1.00 | 7.79 |
| 2098 | OD1 | ASP | A | 139 | 26.684 | 32.509 | 51.159 | 1.00 | 7.08 |
| 2099 | OD2 | ASP | A | 139 | 28.739 | 32.089 | 50.713 | 1.00 | 7.82 |
| 2100 | C | ASP | A | 139 | 25.030 | 29.404 | 49.100 | 1.00 | 7.68 |
| 2101 | O | ASP | A | 139 | 25.143 | 28.342 | 48.480 | 1.00 | 7.56 |
| 2102 | N | ILE | A | 140 | 24.058 | 30.283 | 48.884 | 1.00 | 7.73 |
| 2104 | CA | ILE | A | 140 | 23.115 | 30.187 | 47.781 | 1.00 | 7.89 |
| 2106 | CB | ILE | A | 140 | 21.688 | 29.955 | 48.317 | 1.00 | 7.98 |
| 2108 | CG1 | ILE | A | 140 | 21.574 | 28.567 | 48.953 | 1.00 | 7.66 |
| 2111 | CD1 | ILE | A | 140 | 20.487 | 28.472 | 49.996 | 1.00 | 8.00 |
| 2115 | CG2 | ILE | A | 140 | 20.648 | 30.111 | 47.202 | 1.00 | 7.70 |
| 2119 | C | ILE | A | 140 | 23.184 | 31.508 | 47.020 | 1.00 | 8.26 |
| 2120 | O | ILE | A | 140 | 22.756 | 32.544 | 47.532 | 1.00 | 8.00 |

FIGURE 3 (Cont.)

| A | B | C | D | E | F | G | H | I | J |
|---|---|---|---|---|---|---|---|---|---|
| 2121 | N | ALA | A | 141 | 23.742 | 31.465 | 45.811 | 1.00 | 8.66 |
| 2123 | CA | ALA | A | 141 | 23.851 | 32.641 | 44.950 | 1.00 | 9.05 |
| 2125 | CB | ALA | A | 141 | 25.141 | 32.582 | 44.149 | 1.00 | 8.98 |
| 2129 | C | ALA | A | 141 | 22.646 | 32.783 | 44.020 | 1.00 | 9.34 |
| 2130 | O | ALA | A | 141 | 22.586 | 32.152 | 42.962 | 1.00 | 9.52 |
| 2131 | N | LYS | A | 142 | 21.688 | 33.609 | 44.441 | 1.00 | 9.81 |
| 2133 | CA | LYS | A | 142 | 20.492 | 33.927 | 43.667 | 1.00 | 10.11 |
| 2135 | CB | LYS | A | 142 | 19.244 | 33.435 | 44.404 | 1.00 | 10.11 |
| 2138 | CG | LYS | A | 142 | 19.073 | 31.923 | 44.412 | 1.00 | 10.30 |
| 2141 | CD | LYS | A | 142 | 17.929 | 31.479 | 45.328 | 1.00 | 10.41 |
| 2144 | CE | LYS | A | 142 | 16.563 | 31.579 | 44.646 | 1.00 | 10.11 |
| 2147 | NZ | LYS | A | 142 | 15.512 | 30.779 | 45.356 | 1.00 | 9.92 |
| 2151 | C | LYS | A | 142 | 20.391 | 35.441 | 43.450 | 1.00 | 10.40 |
| 2152 | O | LYS | A | 142 | 20.428 | 36.213 | 44.415 | 1.00 | 10.68 |
| 2153 | N | TYR | A | 143 | 20.262 | 35.851 | 42.187 | 1.00 | 10.40 |
| 2155 | CA | TYR | A | 143 | 20.173 | 37.266 | 41.807 | 1.00 | 10.45 |
| 2157 | CB | TYR | A | 143 | 21.115 | 37.559 | 40.639 | 1.00 | 10.34 |
| 2160 | CG | TYR | A | 143 | 22.571 | 37.658 | 41.025 | 1.00 | 10.19 |
| 2161 | CD1 | TYR | A | 143 | 23.410 | 36.554 | 40.943 | 1.00 | 10.20 |
| 2163 | CE1 | TYR | A | 143 | 24.756 | 36.643 | 41.295 | 1.00 | 9.77 |
| 2165 | CZ | TYR | A | 143 | 25.271 | 37.851 | 41.721 | 1.00 | 10.11 |
| 2166 | OH | TYR | A | 143 | 26.597 | 37.946 | 42.062 | 1.00 | 9.94 |
| 2168 | CE2 | TYR | A | 143 | 24.458 | 38.968 | 41.807 | 1.00 | 10.39 |
| 2170 | CD2 | TYR | A | 143 | 23.116 | 38.867 | 41.459 | 1.00 | 10.62 |
| 2172 | C | TYR | A | 143 | 18.762 | 37.699 | 41.415 | 1.00 | 10.67 |
| 2173 | O | TYR | A | 143 | 18.375 | 38.851 | 41.638 | 1.00 | 10.26 |
| 2174 | N | GLY | A | 144 | 18.019 | 36.784 | 40.797 | 1.00 | 10.86 |
| 2176 | CA | GLY | A | 144 | 16.657 | 37.040 | 40.370 | 1.00 | 11.24 |
| 2179 | C | GLY | A | 144 | 16.453 | 36.603 | 38.931 | 1.00 | 11.57 |
| 2180 | O | GLY | A | 144 | 17.376 | 36.662 | 38.111 | 1.00 | 11.55 |
| 2181 | N | LEU | A | 145 | 15.238 | 36.165 | 38.627 | 1.00 | 11.92 |
| 2183 | CA | LEU | A | 145 | 14.871 | 35.794 | 37.270 | 1.00 | 12.48 |
| 2185 | CB | LEU | A | 145 | 13.484 | 35.149 | 37.248 | 1.00 | 12.67 |
| 2188 | CG | LEU | A | 145 | 13.302 | 33.876 | 38.082 | 1.00 | 13.43 |
| 2190 | CD1 | LEU | A | 145 | 11.839 | 33.450 | 38.066 | 1.00 | 14.02 |
| 2194 | CD2 | LEU | A | 145 | 14.191 | 32.747 | 37.588 | 1.00 | 14.37 |
| 2198 | C | LEU | A | 145 | 14.895 | 37.041 | 36.383 | 1.00 | 12.71 |
| 2199 | O | LEU | A | 145 | 14.393 | 38.094 | 36.774 | 1.00 | 12.20 |
| 2200 | N | ASN | A | 146 | 15.483 | 36.899 | 35.195 | 1.00 | 13.10 |
| 2202 | CA | ASN | A | 146 | 15.672 | 37.994 | 34.243 | 1.00 | 13.64 |
| 2204 | CB | ASN | A | 146 | 14.313 | 38.566 | 33.808 | 1.00 | 14.03 |
| 2207 | CG | ASN | A | 146 | 13.440 | 37.521 | 33.153 | 1.00 | 14.84 |
| 2208 | OD1 | ASN | A | 146 | 13.721 | 37.083 | 32.042 | 1.00 | 16.89 |
| 2209 | ND2 | ASN | A | 146 | 12.391 | 37.095 | 33.847 | 1.00 | 16.12 |
| 2212 | C | ASN | A | 146 | 16.605 | 39.108 | 34.722 | 1.00 | 13.76 |
| 2213 | O | ASN | A | 146 | 16.589 | 40.211 | 34.173 | 1.00 | 14.21 |
| 2214 | N | SER | A | 147 | 17.434 | 38.815 | 35.721 | 1.00 | 13.67 |
| 2216 | CA | SER | A | 147 | 18.389 | 39.787 | 36.242 | 1.00 | 13.63 |
| 2218 | CB | SER | A | 147 | 18.606 | 39.582 | 37.745 | 1.00 | 13.62 |
| 2221 | OG | SER | A | 147 | 19.282 | 38.366 | 38.013 | 1.00 | 13.22 |
| 2223 | C | SER | A | 147 | 19.712 | 39.673 | 35.488 | 1.00 | 13.63 |
| 2224 | O | SER | A | 147 | 19.980 | 38.662 | 34.832 | 1.00 | 13.87 |
| 2225 | N | GLY | A | 148 | 20.533 | 40.716 | 35.575 | 1.00 | 13.52 |

FIGURE 3 (Cont.)

| A | B | C | D | E | F | G | H | I | J |
|---|---|---|---|---|---|---|---|---|---|
| 2227 | CA | GLY | A | 148 | 21.849 | 40.713 | 34.958 | 1.00 | 13.38 |
| 2230 | C | GLY | A | 148 | 22.749 | 39.629 | 35.530 | 1.00 | 13.14 |
| 2231 | O | GLY | A | 148 | 23.518 | 38.999 | 34.801 | 1.00 | 13.57 |
| 2232 | N | GLY | A | 149 | 22.636 | 39.397 | 36.836 | 1.00 | 12.78 |
| 2234 | CA | GLY | A | 149 | 23.474 | 38.432 | 37.528 | 1.00 | 12.37 |
| 2237 | C | GLY | A | 149 | 23.030 | 36.981 | 37.414 | 1.00 | 12.09 |
| 2238 | O | GLY | A | 149 | 23.775 | 36.088 | 37.812 | 1.00 | 11.90 |
| 2239 | N | GLU | A | 150 | 21.839 | 36.744 | 36.862 | 1.00 | 11.62 |
| 2241 | CA | GLU | A | 150 | 21.231 | 35.406 | 36.850 | 1.00 | 11.65 |
| 2243 | CB | GLU | A | 150 | 19.874 | 35.425 | 36.130 | 1.00 | 11.55 |
| 2246 | CG | GLU | A | 150 | 19.063 | 34.146 | 36.312 | 1.00 | 11.84 |
| 2249 | CD | GLU | A | 150 | 17.831 | 34.090 | 35.431 | 1.00 | 12.30 |
| 2250 | OE1 | GLU | A | 150 | 17.666 | 34.968 | 34.556 | 1.00 | 11.88 |
| 2251 | OE2 | GLU | A | 150 | 17.023 | 33.160 | 35.618 | 1.00 | 12.75 |
| 2252 | C | GLU | A | 150 | 22.088 | 34.280 | 36.259 | 1.00 | 11.47 |
| 2253 | O | GLU | A | 150 | 22.097 | 33.178 | 36.811 | 1.00 | 11.26 |
| 2254 | N | PRO | A | 151 | 22.763 | 34.515 | 35.133 | 1.00 | 11.33 |
| 2255 | CA | PRO | A | 151 | 23.605 | 33.472 | 34.526 | 1.00 | 11.30 |
| 2257 | CB | PRO | A | 151 | 24.141 | 34.144 | 33.255 | 1.00 | 11.34 |
| 2260 | CG | PRO | A | 151 | 23.224 | 35.266 | 32.996 | 1.00 | 11.39 |
| 2263 | CD | PRO | A | 151 | 22.765 | 35.748 | 34.325 | 1.00 | 11.43 |
| 2266 | C | PRO | A | 151 | 24.770 | 32.999 | 35.403 | 1.00 | 10.92 |
| 2267 | O | PRO | A | 151 | 25.282 | 31.904 | 35.174 | 1.00 | 11.23 |
| 2268 | N | THR | A | 152 | 25.178 | 33.807 | 36.378 | 1.00 | 10.60 |
| 2270 | CA | THR | A | 152 | 26.276 | 33.456 | 37.282 | 1.00 | 10.18 |
| 2272 | CB | THR | A | 152 | 27.086 | 34.717 | 37.661 | 1.00 | 10.21 |
| 2274 | OG1 | THR | A | 152 | 26.318 | 35.566 | 38.529 | 1.00 | 10.12 |
| 2276 | CG2 | THR | A | 152 | 27.381 | 35.576 | 36.426 | 1.00 | 9.78 |
| 2280 | C | THR | A | 152 | 25.827 | 32.742 | 38.557 | 1.00 | 10.14 |
| 2281 | O | THR | A | 152 | 26.650 | 32.469 | 39.432 | 1.00 | 9.99 |
| 2282 | N | GLN | A | 153 | 24.538 | 32.430 | 38.657 | 1.00 | 9.86 |
| 2284 | CA | GLN | A | 153 | 23.969 | 31.833 | 39.864 | 1.00 | 9.69 |
| 2286 | CB | GLN | A | 153 | 22.441 | 31.772 | 39.758 | 1.00 | 9.87 |
| 2289 | CG | GLN | A | 153 | 21.752 | 33.121 | 39.943 | 1.00 | 9.53 |
| 2292 | CD | GLN | A | 153 | 20.264 | 33.095 | 39.626 | 1.00 | 9.61 |
| 2293 | OE1 | GLN | A | 153 | 19.578 | 34.096 | 39.803 | 1.00 | 10.05 |
| 2294 | NE2 | GLN | A | 153 | 19.764 | 31.956 | 39.163 | 1.00 | 10.14 |
| 2297 | C | GLN | A | 153 | 24.514 | 30.432 | 40.143 | 1.00 | 9.50 |
| 2298 | O | GLN | A | 153 | 25.005 | 29.749 | 39.248 | 1.00 | 9.22 |
| 2299 | N | GLY | A | 154 | 24.412 | 30.025 | 41.403 | 1.00 | 9.32 |
| 2301 | CA | GLY | A | 154 | 24.827 | 28.701 | 41.841 | 1.00 | 9.29 |
| 2304 | C | GLY | A | 154 | 24.465 | 28.458 | 43.298 | 1.00 | 9.23 |
| 2305 | O | GLY | A | 154 | 23.792 | 29.279 | 43.917 | 1.00 | 9.03 |
| 2306 | N | ALA | A | 155 | 24.908 | 27.329 | 43.844 | 1.00 | 9.22 |
| 2308 | CA | ALA | A | 155 | 24.603 | 26.970 | 45.236 | 1.00 | 9.24 |
| 2310 | CB | ALA | A | 155 | 23.108 | 26.732 | 45.419 | 1.00 | 9.26 |
| 2314 | C | ALA | A | 155 | 25.373 | 25.733 | 45.674 | 1.00 | 9.36 |
| 2315 | O | ALA | A | 155 | 25.624 | 24.833 | 44.870 | 1.00 | 9.41 |
| 2316 | N | GLY | A | 156 | 25.723 | 25.683 | 46.958 | 1.00 | 9.14 |
| 2318 | CA | GLY | A | 156 | 26.509 | 24.587 | 47.486 | 1.00 | 9.00 |
| 2321 | C | GLY | A | 156 | 27.404 | 24.960 | 48.649 | 1.00 | 8.94 |
| 2322 | O | GLY | A | 156 | 27.261 | 26.021 | 49.257 | 1.00 | 8.71 |
| 2323 | N | ALA | A | 157 | 28.334 | 24.061 | 48.950 | 1.00 | 8.95 |

FIGURE 3 (Cont.)

| A | B | C | D | E | F | G | H | I | J |
|---|---|---|---|---|---|---|---|---|---|
| 2325 | CA | ALA | A | 157 | 29.261 | 24.218 | 50.058 | 1.00 | 8.73 |
| 2327 | CB | ALA | A | 157 | 28.649 | 23.656 | 51.327 | 1.00 | 9.01 |
| 2331 | C | ALA | A | 157 | 30.583 | 23.515 | 49.760 | 1.00 | 9.11 |
| 2332 | O | ALA | A | 157 | 30.639 | 22.580 | 48.959 | 1.00 | 8.66 |
| 2333 | N | VAL | A | 158 | 31.649 | 23.999 | 50.383 | 1.00 | 9.22 |
| 2335 | CA | VAL | A | 158 | 32.941 | 23.330 | 50.358 | 1.00 | 9.60 |
| 2337 | CB | VAL | A | 158 | 33.978 | 24.108 | 49.521 | 1.00 | 9.65 |
| 2339 | CG1 | VAL | A | 158 | 35.328 | 23.395 | 49.531 | 1.00 | 10.09 |
| 2343 | CG2 | VAL | A | 158 | 33.485 | 24.300 | 48.088 | 1.00 | 10.12 |
| 2347 | C | VAL | A | 158 | 33.429 | 23.233 | 51.796 | 1.00 | 9.65 |
| 2348 | O | VAL | A | 158 | 33.571 | 24.252 | 52.471 | 1.00 | 9.33 |
| 2349 | N | ALA | A | 159 | 33.667 | 22.006 | 52.253 | 1.00 | 9.67 |
| 2351 | CA | ALA | A | 159 | 34.161 | 21.744 | 53.598 | 1.00 | 9.72 |
| 2353 | CB | ALA | A | 159 | 33.394 | 20.591 | 54.223 | 1.00 | 9.65 |
| 2357 | C | ALA | A | 159 | 35.644 | 21.421 | 53.558 | 1.00 | 9.92 |
| 2358 | O | ALA | A | 159 | 36.111 | 20.731 | 52.652 | 1.00 | 9.97 |
| 2359 | N | MSE | A | 160 | 36.366 | 21.912 | 54.561 | 1.00 | 9.85 |
| 2361 | CA | MSE | A | 160 | 37.807 | 21.740 | 54.676 | 1.00 | 10.25 |
| 2363 | CB | MSE | A | 160 | 38.525 | 23.048 | 54.332 | 1.00 | 10.33 |
| 2366 | CG | MSE | A | 160 | 38.599 | 23.355 | 52.855 | 1.00 | 11.81 |
| 2369 | SE | MSE | A | 160 | 39.220 | 25.196 | 52.551 | 1.00 | 16.07 |
| 2370 | CE | MSE | A | 160 | 37.567 | 26.133 | 52.909 | 1.00 | 15.45 |
| 2374 | C | MSE | A | 160 | 38.172 | 21.352 | 56.101 | 1.00 | 9.83 |
| 2375 | O | MSE | A | 160 | 37.702 | 21.970 | 57.052 | 1.00 | 10.11 |
| 2376 | N | LEU | A | 161 | 39.009 | 20.332 | 56.248 | 1.00 | 9.54 |
| 2378 | CA | LEU | A | 161 | 39.587 | 19.997 | 57.541 | 1.00 | 9.30 |
| 2380 | CB | LEU | A | 161 | 39.620 | 18.486 | 57.765 | 1.00 | 9.38 |
| 2383 | CG | LEU | A | 161 | 40.029 | 18.052 | 59.176 | 1.00 | 9.40 |
| 2385 | CD1 | LEU | A | 161 | 38.957 | 18.433 | 60.216 | 1.00 | 9.53 |
| 2389 | CD2 | LEU | A | 161 | 40.317 | 16.565 | 59.210 | 1.00 | 9.63 |
| 2393 | C | LEU | A | 161 | 40.993 | 20.577 | 57.579 | 1.00 | 9.21 |
| 2394 | O | LEU | A | 161 | 41.837 | 20.227 | 56.758 | 1.00 | 8.91 |
| 2395 | N | VAL | A | 162 | 41.220 | 21.492 | 58.514 | 1.00 | 9.26 |
| 2397 | CA | VAL | A | 162 | 42.504 | 22.153 | 58.677 | 1.00 | 9.34 |
| 2399 | CB | VAL | A | 162 | 42.314 | 23.657 | 58.975 | 1.00 | 9.39 |
| 2401 | CG1 | VAL | A | 162 | 43.645 | 24.353 | 59.162 | 1.00 | 9.25 |
| 2405 | CG2 | VAL | A | 162 | 41.514 | 24.328 | 57.849 | 1.00 | 9.48 |
| 2409 | C | VAL | A | 162 | 43.233 | 21.457 | 59.823 | 1.00 | 9.57 |
| 2410 | O | VAL | A | 162 | 42.665 | 21.254 | 60.895 | 1.00 | 9.48 |
| 2411 | N | ALA | A | 163 | 44.488 | 21.087 | 59.594 | 1.00 | 9.96 |
| 2413 | CA | ALA | A | 163 | 45.246 | 20.303 | 60.567 | 1.00 | 10.16 |
| 2415 | CB | ALA | A | 163 | 44.794 | 18.851 | 60.517 | 1.00 | 10.29 |
| 2419 | C | ALA | A | 163 | 46.748 | 20.378 | 60.338 | 1.00 | 10.35 |
| 2420 | O | ALA | A | 163 | 47.214 | 20.822 | 59.287 | 1.00 | 10.41 |
| 2421 | N | SER | A | 164 | 47.496 | 19.943 | 61.347 | 1.00 | 10.54 |
| 2423 | CA | SER | A | 164 | 48.933 | 19.719 | 61.228 | 1.00 | 10.62 |
| 2425 | CB | ASER | A | 164 | 49.551 | 19.436 | 62.602 | 0.65 | 10.46 |
| 2428 | OG | ASER | A | 164 | 49.589 | 20.613 | 63.387 | 0.65 | 10.35 |
| 2430 | C | SER | A | 164 | 49.213 | 18.548 | 60.289 | 1.00 | 10.78 |
| 2431 | O | SER | A | 164 | 48.393 | 17.640 | 60.156 | 1.00 | 10.59 |
| 2432 | N | GLU | A | 165 | 50.382 | 18.576 | 59.655 | 1.00 | 11.10 |
| 2434 | CA | GLU | A | 165 | 50.777 | 17.573 | 58.667 | 1.00 | 11.46 |
| 2436 | CB | GLU | A | 165 | 51.269 | 16.304 | 59.380 | 1.00 | 12.06 |

FIGURE 3 (Cont.)

| A | B | C | D | E | F | G | H | I | J |
|---|---|---|---|---|---|---|---|---|---|
| 2439 | CG | GLU | A | 165 | 52.429 | 16.547 | 60.341 | 1.00 | 13.61 |
| 2442 | CD | GLU | A | 165 | 53.615 | 17.200 | 59.665 | 1.00 | 15.76 |
| 2443 | OE1 | GLU | A | 165 | 54.131 | 16.613 | 58.687 | 1.00 | 18.61 |
| 2444 | OE2 | GLU | A | 165 | 54.023 | 18.305 | 60.095 | 1.00 | 17.31 |
| 2445 | C | GLU | A | 165 | 49.651 | 17.248 | 57.676 | 1.00 | 11.24 |
| 2446 | O | GLU | A | 165 | 49.270 | 16.087 | 57.510 | 1.00 | 10.92 |
| 2447 | N | PRO | A | 166 | 49.127 | 18.271 | 56.999 | 1.00 | 10.93 |
| 2448 | CA | PRO | A | 166 | 47.983 | 18.079 | 56.102 | 1.00 | 10.91 |
| 2450 | CB | PRO | A | 166 | 47.660 | 19.504 | 55.646 | 1.00 | 10.85 |
| 2453 | CG | PRO | A | 166 | 48.971 | 20.202 | 55.723 | 1.00 | 10.89 |
| 2456 | CD | PRO | A | 166 | 49.605 | 19.664 | 56.974 | 1.00 | 10.93 |
| 2459 | C | PRO | A | 166 | 48.367 | 17.209 | 54.913 | 1.00 | 10.94 |
| 2460 | O | PRO | A | 166 | 49.510 | 17.253 | 54.466 | 1.00 | 10.53 |
| 2461 | N | ARG | A | 167 | 47.419 | 16.428 | 54.411 | 1.00 | 11.26 |
| 2463 | CA | ARG | A | 167 | 47.697 | 15.496 | 53.330 | 1.00 | 11.78 |
| 2465 | CB | ARG | A | 167 | 46.844 | 14.233 | 53.491 | 1.00 | 12.00 |
| 2468 | CG | ARG | A | 167 | 47.414 | 13.295 | 54.549 | 1.00 | 13.51 |
| 2471 | CD | ARG | A | 167 | 46.535 | 12.105 | 54.859 | 1.00 | 15.69 |
| 2474 | NE | ARG | A | 167 | 45.383 | 12.474 | 55.681 | 1.00 | 16.29 |
| 2476 | CZ | ARG | A | 167 | 44.367 | 11.660 | 55.957 | 1.00 | 17.66 |
| 2477 | NH1 | ARG | A | 167 | 44.346 | 10.415 | 55.499 | 1.00 | 18.68 |
| 2480 | NH2 | ARG | A | 167 | 43.362 | 12.092 | 56.704 | 1.00 | 18.00 |
| 2483 | C | ARG | A | 167 | 47.540 | 16.100 | 51.928 | 1.00 | 11.71 |
| 2484 | O | ARG | A | 167 | 47.971 | 15.487 | 50.960 | 1.00 | 11.52 |
| 2485 | N | ILE | A | 168 | 46.962 | 17.297 | 51.814 | 1.00 | 11.78 |
| 2487 | CA | ILE | A | 168 | 46.747 | 17.908 | 50.495 | 1.00 | 11.82 |
| 2489 | CB | ILE | A | 168 | 45.243 | 18.166 | 50.239 | 1.00 | 11.94 |
| 2491 | CG1 | ILE | A | 168 | 44.481 | 16.833 | 50.206 | 1.00 | 12.52 |
| 2494 | CD1 | ILE | A | 168 | 42.981 | 16.965 | 50.345 | 1.00 | 12.95 |
| 2498 | CG2 | ILE | A | 168 | 45.040 | 18.912 | 48.913 | 1.00 | 11.64 |
| 2502 | C | ILE | A | 168 | 47.575 | 19.175 | 50.261 | 1.00 | 11.73 |
| 2503 | O | ILE | A | 168 | 48.413 | 19.202 | 49.361 | 1.00 | 11.69 |
| 2504 | N | LEU | A | 169 | 47.335 | 20.217 | 51.052 | 1.00 | 11.78 |
| 2506 | CA | LEU | A | 169 | 47.941 | 21.523 | 50.815 | 1.00 | 11.87 |
| 2508 | CB | LEU | A | 169 | 46.906 | 22.464 | 50.192 | 1.00 | 11.71 |
| 2511 | CG | LEU | A | 169 | 47.416 | 23.762 | 49.559 | 1.00 | 11.64 |
| 2513 | CD1 | LEU | A | 169 | 48.135 | 23.480 | 48.252 | 1.00 | 11.68 |
| 2517 | CD2 | LEU | A | 169 | 46.264 | 24.741 | 49.332 | 1.00 | 11.66 |
| 2521 | C | LEU | A | 169 | 48.503 | 22.137 | 52.099 | 1.00 | 12.17 |
| 2522 | O | LEU | A | 169 | 47.756 | 22.442 | 53.021 | 1.00 | 12.38 |
| 2523 | N | ALA | A | 170 | 49.822 | 22.298 | 52.149 | 1.00 | 12.45 |
| 2525 | CA | ALA | A | 170 | 50.502 | 22.980 | 53.251 | 1.00 | 12.68 |
| 2527 | CB | ALA | A | 170 | 51.923 | 22.447 | 53.391 | 1.00 | 12.67 |
| 2531 | C | ALA | A | 170 | 50.529 | 24.494 | 52.994 | 1.00 | 13.02 |
| 2532 | O | ALA | A | 170 | 51.084 | 24.941 | 51.994 | 1.00 | 13.05 |
| 2533 | N | LEU | A | 171 | 49.933 | 25.273 | 53.892 | 1.00 | 13.30 |
| 2535 | CA | LEU | A | 171 | 49.847 | 26.729 | 53.735 | 1.00 | 13.74 |
| 2537 | CB | LEU | A | 171 | 48.643 | 27.267 | 54.514 | 1.00 | 13.75 |
| 2540 | CG | LEU | A | 171 | 47.285 | 26.676 | 54.126 | 1.00 | 13.45 |
| 2542 | CD1 | LEU | A | 171 | 46.208 | 27.199 | 55.055 | 1.00 | 13.54 |
| 2546 | CD2 | LEU | A | 171 | 46.945 | 26.985 | 52.674 | 1.00 | 13.44 |
| 2550 | C | LEU | A | 171 | 51.117 | 27.485 | 54.161 | 1.00 | 14.39 |
| 2551 | O | LEU | A | 171 | 51.699 | 27.212 | 55.215 | 1.00 | 14.08 |

FIGURE 3 (Cont.)

| A | B | C | D | E | F | G | H | I | J |
|---|---|---|---|---|---|---|---|---|---|
| 2552 | N | LYS | A | 172 | 51.522 | 28.447 | 53.333 | 1.00 | 15.09 |
| 2554 | CA | LYS | A | 172 | 52.697 | 29.283 | 53.588 | 1.00 | 16.02 |
| 2556 | CB | LYS | A | 172 | 53.357 | 29.681 | 52.267 | 1.00 | 16.24 |
| 2559 | CG | LYS | A | 172 | 53.726 | 28.519 | 51.360 | 1.00 | 17.61 |
| 2562 | CD | LYS | A | 172 | 54.865 | 27.687 | 51.925 | 1.00 | 19.43 |
| 2565 | CE | LYS | A | 172 | 55.694 | 27.054 | 50.808 | 1.00 | 20.67 |
| 2568 | NZ | LYS | A | 172 | 56.483 | 25.886 | 51.299 | 1.00 | 20.97 |
| 2572 | C | LYS | A | 172 | 52.308 | 30.548 | 54.362 | 1.00 | 16.28 |
| 2573 | O | LYS | A | 172 | 51.127 | 30.810 | 54.583 | 1.00 | 16.26 |
| 2574 | N | GLU | A | 173 | 53.306 | 31.337 | 54.754 | 1.00 | 16.75 |
| 2576 | CA | GLU | A | 173 | 53.078 | 32.555 | 55.534 | 1.00 | 17.09 |
| 2578 | CB | GLU | A | 173 | 53.994 | 32.566 | 56.771 | 1.00 | 17.42 |
| 2581 | CG | GLU | A | 173 | 53.625 | 31.526 | 57.821 | 1.00 | 18.72 |
| 2584 | CD | GLU | A | 173 | 52.260 | 31.774 | 58.436 | 1.00 | 20.65 |
| 2585 | OE1 | GLU | A | 173 | 51.387 | 30.887 | 58.336 | 1.00 | 22.61 |
| 2586 | OE2 | GLU | A | 173 | 52.056 | 32.861 | 59.013 | 1.00 | 22.84 |
| 2587 | C | GLU | A | 173 | 53.292 | 33.823 | 54.702 | 1.00 | 16.94 |
| 2588 | O | GLU | A | 173 | 53.699 | 34.855 | 55.234 | 1.00 | 17.36 |
| 2589 | N | ASP | A | 174 | 52.982 | 33.754 | 53.410 | 1.00 | 16.40 |
| 2591 | CA | ASP | A | 174 | 53.199 | 34.879 | 52.491 | 1.00 | 16.18 |
| 2593 | CB | ASP | A | 174 | 53.844 | 34.380 | 51.189 | 1.00 | 16.21 |
| 2596 | CG | ASP | A | 174 | 52.908 | 33.516 | 50.350 | 1.00 | 16.32 |
| 2597 | OD1 | ASP | A | 174 | 51.965 | 32.913 | 50.909 | 1.00 | 16.12 |
| 2598 | OD2 | ASP | A | 174 | 53.050 | 33.378 | 49.115 | 1.00 | 16.66 |
| 2599 | C | ASP | A | 174 | 51.917 | 35.675 | 52.189 | 1.00 | 15.69 |
| 2600 | O | ASP | A | 174 | 51.791 | 36.277 | 51.123 | 1.00 | 15.42 |
| 2601 | N | ASN | A | 175 | 51.002 | 35.714 | 53.155 | 1.00 | 15.39 |
| 2603 | CA | ASN | A | 175 | 49.680 | 36.311 | 52.969 | 1.00 | 15.40 |
| 2605 | CB | ASN | A | 175 | 48.796 | 36.082 | 54.208 | 1.00 | 15.65 |
| 2608 | CG | ASN | A | 175 | 48.653 | 34.609 | 54.575 | 1.00 | 16.38 |
| 2609 | OD1 | ASN | A | 175 | 49.614 | 33.970 | 55.013 | 1.00 | 17.33 |
| 2610 | ND2 | ASN | A | 175 | 47.449 | 34.069 | 54.410 | 1.00 | 16.77 |
| 2613 | C | ASN | A | 175 | 49.755 | 37.817 | 52.702 | 1.00 | 14.93 |
| 2614 | O | ASN | A | 175 | 50.455 | 38.539 | 53.411 | 1.00 | 14.79 |
| 2615 | N | VAL | A | 176 | 49.041 | 38.276 | 51.676 | 1.00 | 14.38 |
| 2617 | CA | VAL | A | 176 | 48.820 | 39.704 | 51.444 | 1.00 | 13.96 |
| 2619 | CB | VAL | A | 176 | 49.479 | 40.189 | 50.142 | 1.00 | 13.89 |
| 2621 | CG1 | VAL | A | 176 | 49.216 | 41.686 | 49.933 | 1.00 | 13.89 |
| 2625 | CG2 | VAL | A | 176 | 50.975 | 39.897 | 50.155 | 1.00 | 13.82 |
| 2629 | C | VAL | A | 176 | 47.319 | 39.977 | 51.361 | 1.00 | 13.73 |
| 2630 | O | VAL | A | 176 | 46.641 | 39.458 | 50.484 | 1.00 | 13.61 |
| 2631 | N | MSE | A | 177 | 46.821 | 40.810 | 52.265 | 1.00 | 13.44 |
| 2633 | CA | MSE | A | 177 | 45.400 | 41.126 | 52.355 | 1.00 | 13.57 |
| 2635 | CB | MSE | A | 177 | 44.917 | 40.898 | 53.783 | 1.00 | 14.27 |
| 2638 | CG | MSE | A | 177 | 45.227 | 39.509 | 54.276 | 1.00 | 17.42 |
| 2641 | SE | MSE | A | 177 | 46.866 | 39.452 | 55.287 | 1.00 | 25.32 |
| 2642 | CE | MSE | A | 177 | 46.098 | 40.044 | 56.963 | 1.00 | 20.95 |
| 2646 | C | MSE | A | 177 | 45.135 | 42.562 | 51.950 | 1.00 | 12.52 |
| 2647 | O | MSE | A | 177 | 46.062 | 43.365 | 51.856 | 1.00 | 12.00 |
| 2648 | N | LEU | A | 178 | 43.861 | 42.874 | 51.729 | 1.00 | 11.51 |
| 2650 | CA | LEU | A | 178 | 43.431 | 44.195 | 51.274 | 1.00 | 10.81 |
| 2652 | CB | LEU | A | 178 | 43.549 | 44.293 | 49.754 | 1.00 | 10.73 |
| 2655 | CG | LEU | A | 178 | 43.062 | 45.590 | 49.104 | 1.00 | 10.48 |

FIGURE 3 (Cont.)

| A | B | C | D | E | F | G | H | I | J |
|---|---|---|---|---|---|---|---|---|---|
| 2657 | CD1 | LEU | A | 178 | 43.974 | 46.756 | 49.475 | 1.00 | 10.91 |
| 2661 | CD2 | LEU | A | 178 | 42.976 | 45.428 | 47.595 | 1.00 | 10.18 |
| 2665 | C | LEU | A | 178 | 41.988 | 44.476 | 51.686 | 1.00 | 10.49 |
| 2666 | O | LEU | A | 178 | 41.126 | 43.613 | 51.551 | 1.00 | 10.69 |
| 2667 | N | THR | A | 179 | 41.738 | 45.681 | 52.189 | 1.00 | 9.92 |
| 2669 | CA | THR | A | 179 | 40.386 | 46.157 | 52.463 | 1.00 | 9.76 |
| 2671 | CB | THR | A | 179 | 40.099 | 46.227 | 53.983 | 1.00 | 9.58 |
| 2673 | OG1 | THR | A | 179 | 40.141 | 44.918 | 54.561 | 1.00 | 9.01 |
| 2675 | CG2 | THR | A | 179 | 38.666 | 46.691 | 54.241 | 1.00 | 9.54 |
| 2679 | C | THR | A | 179 | 40.204 | 47.542 | 51.850 | 1.00 | 9.95 |
| 2680 | O | THR | A | 179 | 41.029 | 48.431 | 52.053 | 1.00 | 9.68 |
| 2681 | N | GLN | A | 180 | 39.125 | 47.698 | 51.093 | 1.00 | 10.38 |
| 2683 | CA | GLN | A | 180 | 38.723 | 48.972 | 50.500 | 1.00 | 10.89 |
| 2685 | CB | GLN | A | 180 | 39.103 | 49.022 | 49.019 | 1.00 | 11.29 |
| 2688 | CG | GLN | A | 180 | 40.588 | 49.011 | 48.731 | 1.00 | 13.32 |
| 2691 | CD | GLN | A | 180 | 40.878 | 48.810 | 47.255 | 1.00 | 16.17 |
| 2692 | OE1 | GLN | A | 180 | 40.339 | 47.894 | 46.632 | 1.00 | 19.30 |
| 2693 | NE2 | GLN | A | 180 | 41.726 | 49.659 | 46.695 | 1.00 | 18.52 |
| 2696 | C | GLN | A | 180 | 37.215 | 49.062 | 50.594 | 1.00 | 10.59 |
| 2697 | O | GLN | A | 180 | 36.522 | 48.139 | 50.184 | 1.00 | 10.83 |
| 2698 | N | ASP | A | 181 | 36.695 | 50.166 | 51.110 | 1.00 | 10.21 |
| 2700 | CA | ASP | A | 181 | 35.250 | 50.339 | 51.224 | 1.00 | 10.01 |
| 2702 | CB | ASP | A | 181 | 34.940 | 51.394 | 52.289 | 1.00 | 10.05 |
| 2705 | CG | ASP | A | 181 | 33.456 | 51.509 | 52.606 | 1.00 | 10.32 |
| 2706 | OD1 | ASP | A | 181 | 32.615 | 50.849 | 51.952 | 1.00 | 9.35 |
| 2707 | OD2 | ASP | A | 181 | 33.039 | 52.263 | 53.509 | 1.00 | 10.08 |
| 2708 | C | ASP | A | 181 | 34.657 | 50.727 | 49.862 | 1.00 | 9.83 |
| 2709 | O | ASP | A | 181 | 34.656 | 51.899 | 49.488 | 1.00 | 9.57 |
| 2710 | N | ILE | A | 182 | 34.177 | 49.723 | 49.124 | 1.00 | 9.65 |
| 2712 | CA | ILE | A | 182 | 33.582 | 49.906 | 47.797 | 1.00 | 9.51 |
| 2714 | CB | ILE | A | 182 | 34.546 | 49.379 | 46.698 | 1.00 | 9.85 |
| 2716 | CG1 | ILE | A | 182 | 35.866 | 50.163 | 46.698 | 1.00 | 10.58 |
| 2719 | CD1 | ILE | A | 182 | 37.031 | 49.410 | 46.068 | 1.00 | 11.59 |
| 2723 | CG2 | ILE | A | 182 | 33.889 | 49.454 | 45.311 | 1.00 | 9.86 |
| 2727 | C | ILE | A | 182 | 32.255 | 49.145 | 47.716 | 1.00 | 9.36 |
| 2728 | O | ILE | A | 182 | 32.189 | 47.967 | 48.072 | 1.00 | 9.29 |
| 2729 | N | TYR | A | 183 | 31.206 | 49.810 | 47.235 | 1.00 | 8.98 |
| 2731 | CA | TYR | A | 183 | 29.889 | 49.186 | 47.098 | 1.00 | 8.58 |
| 2733 | CB | TYR | A | 183 | 28.780 | 50.159 | 47.512 | 1.00 | 8.77 |
| 2736 | CG | TYR | A | 183 | 28.601 | 50.230 | 49.009 | 1.00 | 8.16 |
| 2737 | CD1 | TYR | A | 183 | 27.776 | 49.325 | 49.668 | 1.00 | 8.38 |
| 2739 | CE1 | TYR | A | 183 | 27.609 | 49.372 | 51.036 | 1.00 | 8.36 |
| 2741 | CZ | TYR | A | 183 | 28.280 | 50.324 | 51.777 | 1.00 | 8.58 |
| 2742 | OH | TYR | A | 183 | 28.104 | 50.361 | 53.139 | 1.00 | 8.59 |
| 2744 | CE2 | TYR | A | 183 | 29.114 | 51.236 | 51.153 | 1.00 | 8.23 |
| 2746 | CD2 | TYR | A | 183 | 29.276 | 51.181 | 49.771 | 1.00 | 8.47 |
| 2748 | C | TYR | A | 183 | 29.678 | 48.658 | 45.675 | 1.00 | 8.55 |
| 2749 | O | TYR | A | 183 | 28.853 | 49.163 | 44.913 | 1.00 | 8.15 |
| 2750 | N | ASP | A | 184 | 30.456 | 47.635 | 45.335 | 1.00 | 8.32 |
| 2752 | CA | ASP | A | 184 | 30.312 | 46.932 | 44.066 | 1.00 | 8.18 |
| 2754 | CB | ASP | A | 184 | 31.622 | 46.248 | 43.661 | 1.00 | 8.22 |
| 2757 | CG | ASP | A | 184 | 32.101 | 45.209 | 44.673 | 1.00 | 8.18 |
| 2758 | OD1 | ASP | A | 184 | 32.535 | 44.115 | 44.246 | 1.00 | 8.68 |

FIGURE 3 (Cont.)

| A | B | C | D | E | F | G | H | I | J |
|---|---|---|---|---|---|---|---|---|---|
| 2759 | OD2 | ASP | A | 184 | 32.088 | 45.394 | 45.911 | 1.00 | 7.47 |
| 2760 | C | ASP | A | 184 | 29.175 | 45.916 | 44.140 | 1.00 | 8.24 |
| 2761 | O | ASP | A | 184 | 28.450 | 45.707 | 43.168 | 1.00 | 7.84 |
| 2762 | N | PHE | A | 185 | 29.037 | 45.295 | 45.306 | 1.00 | 8.04 |
| 2764 | CA | PHE | A | 185 | 28.040 | 44.267 | 45.542 | 1.00 | 7.89 |
| 2766 | CB | PHE | A | 185 | 28.508 | 42.943 | 44.915 | 1.00 | 7.75 |
| 2769 | CG | PHE | A | 185 | 27.760 | 41.702 | 45.371 | 1.00 | 7.63 |
| 2770 | CD1 | PHE | A | 185 | 27.087 | 40.911 | 44.441 | 1.00 | 7.45 |
| 2772 | CE1 | PHE | A | 185 | 26.432 | 39.750 | 44.830 | 1.00 | 7.90 |
| 2774 | CZ | PHE | A | 185 | 26.444 | 39.357 | 46.156 | 1.00 | 7.91 |
| 2776 | CE2 | PHE | A | 185 | 27.116 | 40.120 | 47.092 | 1.00 | 7.43 |
| 2778 | CD2 | PHE | A | 185 | 27.782 | 41.281 | 46.699 | 1.00 | 7.90 |
| 2780 | C | PHE | A | 185 | 27.843 | 44.191 | 47.054 | 1.00 | 7.70 |
| 2781 | O | PHE | A | 185 | 28.804 | 44.200 | 47.827 | 1.00 | 7.20 |
| 2782 | N | TRP | A | 186 | 26.579 | 44.158 | 47.454 | 1.00 | 7.77 |
| 2784 | CA | TRP | A | 186 | 26.188 | 44.121 | 48.854 | 1.00 | 7.97 |
| 2786 | CB | TRP | A | 186 | 26.418 | 45.494 | 49.511 | 1.00 | 8.09 |
| 2789 | CG | TRP | A | 186 | 25.474 | 46.599 | 49.098 | 1.00 | 8.54 |
| 2790 | CD1 | TRP | A | 186 | 24.474 | 47.130 | 49.855 | 1.00 | 8.87 |
| 2792 | NE1 | TRP | A | 186 | 23.829 | 48.126 | 49.164 | 1.00 | 9.00 |
| 2794 | CE2 | TRP | A | 186 | 24.421 | 48.279 | 47.939 | 1.00 | 8.41 |
| 2795 | CD2 | TRP | A | 186 | 25.464 | 47.332 | 47.857 | 1.00 | 8.64 |
| 2796 | CE3 | TRP | A | 186 | 26.232 | 47.286 | 46.683 | 1.00 | 8.84 |
| 2798 | CZ3 | TRP | A | 186 | 25.930 | 48.162 | 45.647 | 1.00 | 8.24 |
| 2800 | CH2 | TRP | A | 186 | 24.882 | 49.087 | 45.763 | 1.00 | 8.87 |
| 2802 | CZ2 | TRP | A | 186 | 24.117 | 49.159 | 46.897 | 1.00 | 8.83 |
| 2804 | C | TRP | A | 186 | 24.726 | 43.660 | 48.944 | 1.00 | 8.31 |
| 2805 | O | TRP | A | 186 | 24.062 | 43.491 | 47.924 | 1.00 | 7.89 |
| 2806 | N | ARG | A | 187 | 24.240 | 43.411 | 50.153 | 1.00 | 8.44 |
| 2808 | CA | ARG | A | 187 | 22.861 | 42.965 | 50.333 | 1.00 | 8.63 |
| 2810 | CB | ARG | A | 187 | 22.767 | 41.437 | 50.300 | 1.00 | 8.69 |
| 2813 | CG | ARG | A | 187 | 21.335 | 40.924 | 50.245 | 1.00 | 8.68 |
| 2816 | CD | ARG | A | 187 | 21.186 | 39.557 | 49.596 | 1.00 | 9.08 |
| 2819 | NE | ARG | A | 187 | 21.676 | 38.478 | 50.454 | 1.00 | 8.27 |
| 2821 | CZ | ARG | A | 187 | 20.997 | 37.943 | 51.468 | 1.00 | 9.32 |
| 2822 | NH1 | ARG | A | 187 | 19.794 | 38.386 | 51.793 | 1.00 | 9.21 |
| 2825 | NH2 | ARG | A | 187 | 21.534 | 36.954 | 52.172 | 1.00 | 8.40 |
| 2828 | C | ARG | A | 187 | 22.299 | 43.509 | 51.635 | 1.00 | 8.85 |
| 2829 | O | ARG | A | 187 | 22.457 | 42.891 | 52.686 | 1.00 | 8.59 |
| 2830 | N | PRO | A | 188 | 21.648 | 44.670 | 51.567 | 1.00 | 9.08 |
| 2831 | CA | PRO | A | 188 | 21.059 | 45.291 | 52.757 | 1.00 | 9.34 |
| 2833 | CB | PRO | A | 188 | 20.270 | 46.470 | 52.178 | 1.00 | 9.52 |
| 2836 | CG | PRO | A | 188 | 20.973 | 46.799 | 50.913 | 1.00 | 9.37 |
| 2839 | CD | PRO | A | 188 | 21.421 | 45.483 | 50.361 | 1.00 | 9.02 |
| 2842 | C | PRO | A | 188 | 20.113 | 44.346 | 53.479 | 1.00 | 9.61 |
| 2843 | O | PRO | A | 188 | 19.489 | 43.509 | 52.839 | 1.00 | 9.17 |
| 2844 | N | THR | A | 189 | 20.021 | 44.487 | 54.797 | 1.00 | 10.08 |
| 2846 | CA | THR | A | 189 | 19.025 | 43.776 | 55.585 | 1.00 | 10.64 |
| 2848 | CB | THR | A | 189 | 18.966 | 44.364 | 57.002 | 1.00 | 10.72 |
| 2850 | OG1 | THR | A | 189 | 20.264 | 44.306 | 57.609 | 1.00 | 12.49 |
| 2852 | CG2 | THR | A | 189 | 18.091 | 43.515 | 57.917 | 1.00 | 11.72 |
| 2856 | C | THR | A | 189 | 17.663 | 43.923 | 54.911 | 1.00 | 10.69 |
| 2857 | O | THR | A | 189 | 17.269 | 45.029 | 54.564 | 1.00 | 10.20 |

FIGURE 3 (Cont.)

| A | B | C | D | E | F | G | H | I | J |
|---|---|---|---|---|---|---|---|---|---|
| 2858 | N | GLY | A | 190 | 16.976 | 42.805 | 54.693 | 1.00 | 10.96 |
| 2860 | CA | GLY | A | 190 | 15.627 | 42.810 | 54.144 | 1.00 | 11.38 |
| 2863 | C | GLY | A | 190 | 15.556 | 42.650 | 52.632 | 1.00 | 11.71 |
| 2864 | O | GLY | A | 190 | 14.465 | 42.623 | 52.064 | 1.00 | 11.57 |
| 2865 | N | HIS | A | 191 | 16.714 | 42.550 | 51.981 | 1.00 | 11.92 |
| 2867 | CA | HIS | A | 191 | 16.784 | 42.363 | 50.534 | 1.00 | 12.20 |
| 2869 | CB | HIS | A | 191 | 17.903 | 43.220 | 49.927 | 1.00 | 12.31 |
| 2872 | CG | HIS | A | 191 | 17.491 | 44.625 | 49.618 | 1.00 | 12.72 |
| 2873 | ND1 | HIS | A | 191 | 17.645 | 45.186 | 48.368 | 1.00 | 13.27 |
| 2875 | CE1 | HIS | A | 191 | 17.192 | 46.428 | 48.387 | 1.00 | 13.66 |
| 2877 | NE2 | HIS | A | 191 | 16.761 | 46.696 | 49.607 | 1.00 | 12.72 |
| 2879 | CD2 | HIS | A | 191 | 16.937 | 45.585 | 50.396 | 1.00 | 12.96 |
| 2881 | C | HIS | A | 191 | 17.084 | 40.895 | 50.275 | 1.00 | 12.38 |
| 2882 | O | HIS | A | 191 | 18.163 | 40.434 | 50.628 | 1.00 | 12.13 |
| 2883 | N | PRO | A | 192 | 16.151 | 40.148 | 49.686 | 1.00 | 12.83 |
| 2884 | CA | PRO | A | 192 | 16.416 | 38.734 | 49.374 | 1.00 | 12.99 |
| 2886 | CB | PRO | A | 192 | 15.068 | 38.206 | 48.856 | 1.00 | 13.16 |
| 2889 | CG | PRO | A | 192 | 14.215 | 39.396 | 48.583 | 1.00 | 13.46 |
| 2892 | CD | PRO | A | 192 | 14.791 | 40.568 | 49.303 | 1.00 | 12.97 |
| 2895 | C | PRO | A | 192 | 17.534 | 38.524 | 48.339 | 1.00 | 13.12 |
| 2896 | O | PRO | A | 192 | 18.205 | 37.491 | 48.384 | 1.00 | 12.98 |
| 2897 | N | TYR | A | 193 | 17.723 | 39.484 | 47.435 | 1.00 | 13.01 |
| 2899 | CA | TYR | A | 193 | 18.759 | 39.406 | 46.404 | 1.00 | 13.28 |
| 2901 | CB | TYR | A | 193 | 18.133 | 39.481 | 45.009 | 1.00 | 13.73 |
| 2904 | CG | TYR | A | 193 | 16.960 | 38.542 | 44.827 | 1.00 | 15.52 |
| 2905 | CD1 | TYR | A | 193 | 15.660 | 39.031 | 44.679 | 1.00 | 17.56 |
| 2907 | CE1 | TYR | A | 193 | 14.579 | 38.162 | 44.519 | 1.00 | 18.57 |
| 2909 | CZ | TYR | A | 193 | 14.800 | 36.796 | 44.507 | 1.00 | 19.06 |
| 2910 | OH | TYR | A | 193 | 13.746 | 35.921 | 44.351 | 1.00 | 20.91 |
| 2912 | CE2 | TYR | A | 193 | 16.081 | 36.296 | 44.659 | 1.00 | 18.12 |
| 2914 | CD2 | TYR | A | 193 | 17.147 | 37.167 | 44.817 | 1.00 | 16.56 |
| 2916 | C | TYR | A | 193 | 19.776 | 40.532 | 46.580 | 1.00 | 12.67 |
| 2917 | O | TYR | A | 193 | 19.457 | 41.566 | 47.164 | 1.00 | 12.10 |
| 2918 | N | PRO | A | 194 | 20.995 | 40.345 | 46.071 | 1.00 | 12.36 |
| 2919 | CA | PRO | A | 194 | 22.033 | 41.368 | 46.216 | 1.00 | 12.05 |
| 2921 | CB | PRO | A | 194 | 23.314 | 40.667 | 45.730 | 1.00 | 12.21 |
| 2924 | CG | PRO | A | 194 | 22.942 | 39.263 | 45.398 | 1.00 | 12.23 |
| 2927 | CD | PRO | A | 194 | 21.475 | 39.178 | 45.314 | 1.00 | 12.31 |
| 2930 | C | PRO | A | 194 | 21.765 | 42.601 | 45.364 | 1.00 | 11.73 |
| 2931 | O | PRO | A | 194 | 21.135 | 42.507 | 44.309 | 1.00 | 11.51 |
| 2932 | N | MSE | A | 195 | 22.211 | 43.749 | 45.859 | 1.00 | 11.40 |
| 2934 | CA | MSE | A | 195 | 22.414 | 44.935 | 45.039 | 1.00 | 11.37 |
| 2936 | CB | MSE | A | 195 | 22.485 | 46.182 | 45.922 | 1.00 | 11.37 |
| 2939 | CG | MSE | A | 195 | 21.212 | 46.460 | 46.720 | 1.00 | 12.09 |
| 2942 | SE | MSE | A | 195 | 19.752 | 47.017 | 45.570 | 1.00 | 13.97 |
| 2943 | CE | MSE | A | 195 | 20.307 | 48.880 | 45.251 | 1.00 | 14.52 |
| 2947 | C | MSE | A | 195 | 23.744 | 44.737 | 44.329 | 1.00 | 11.09 |
| 2948 | O | MSE | A | 195 | 24.694 | 44.251 | 44.936 | 1.00 | 11.00 |
| 2949 | N | VAL | A | 196 | 23.824 | 45.088 | 43.050 | 1.00 | 10.94 |
| 2951 | CA | VAL | A | 196 | 25.066 | 44.893 | 42.301 | 1.00 | 10.93 |
| 2953 | CB | VAL | A | 196 | 25.182 | 43.445 | 41.716 | 1.00 | 11.01 |
| 2955 | CG1 | VAL | A | 196 | 24.035 | 43.122 | 40.778 | 1.00 | 11.21 |
| 2959 | CG2 | VAL | A | 196 | 26.534 | 43.241 | 41.009 | 1.00 | 10.99 |

FIGURE 3 (Cont.)

| A | B | C | D | E | F | G | H | I | J |
|---|---|---|---|---|---|---|---|---|---|
| 2963 | C | VAL | A | 196 | 25.261 | 45.938 | 41.202 | 1.00 | 11.03 |
| 2964 | O | VAL | A | 196 | 24.341 | 46.267 | 40.456 | 1.00 | 10.75 |
| 2965 | N | ASP | A | 197 | 26.477 | 46.471 | 41.157 | 1.00 | 10.89 |
| 2967 | CA | ASP | A | 197 | 26.969 | 47.275 | 40.055 | 1.00 | 10.78 |
| 2969 | CB | ASP | A | 197 | 27.702 | 48.500 | 40.611 | 1.00 | 10.72 |
| 2972 | CG | ASP | A | 197 | 28.136 | 49.475 | 39.535 | 1.00 | 11.15 |
| 2973 | OD1 | ASP | A | 197 | 28.342 | 49.052 | 38.371 | 1.00 | 10.48 |
| 2974 | OD2 | ASP | A | 197 | 28.322 | 50.690 | 39.778 | 1.00 | 9.78 |
| 2975 | C | ASP | A | 197 | 27.910 | 46.358 | 39.278 | 1.00 | 10.64 |
| 2976 | O | ASP | A | 197 | 29.068 | 46.176 | 39.658 | 1.00 | 10.59 |
| 2977 | N | GLY | A | 198 | 27.395 | 45.759 | 38.208 | 1.00 | 10.37 |
| 2979 | CA | GLY | A | 198 | 28.124 | 44.766 | 37.437 | 1.00 | 10.19 |
| 2982 | C | GLY | A | 198 | 29.495 | 45.234 | 36.987 | 1.00 | 9.97 |
| 2983 | O | GLY | A | 198 | 30.497 | 44.590 | 37.304 | 1.00 | 10.01 |
| 2984 | N | PRO | A | 199 | 29.540 | 46.327 | 36.226 | 1.00 | 9.78 |
| 2985 | CA | PRO | A | 199 | 30.807 | 46.961 | 35.837 | 1.00 | 9.66 |
| 2987 | CB | PRO | A | 199 | 30.349 | 48.278 | 35.211 | 1.00 | 9.64 |
| 2990 | CG | PRO | A | 199 | 29.006 | 47.957 | 34.633 | 1.00 | 9.92 |
| 2993 | CD | PRO | A | 199 | 28.380 | 47.005 | 35.613 | 1.00 | 9.90 |
| 2996 | C | PRO | A | 199 | 31.772 | 47.222 | 36.999 | 1.00 | 9.45 |
| 2997 | O | PRO | A | 199 | 32.940 | 46.862 | 36.892 | 1.00 | 9.31 |
| 2998 | N | LEU | A | 200 | 31.290 | 47.821 | 38.085 | 1.00 | 9.13 |
| 3000 | CA | LEU | A | 200 | 32.141 | 48.134 | 39.235 | 1.00 | 9.24 |
| 3002 | CB | LEU | A | 200 | 31.369 | 48.946 | 40.285 | 1.00 | 9.17 |
| 3005 | CG | LEU | A | 200 | 32.048 | 50.065 | 41.093 | 1.00 | 10.20 |
| 3007 | CD1 | LEU | A | 200 | 31.416 | 50.193 | 42.478 | 1.00 | 9.79 |
| 3011 | CD2 | LEU | A | 200 | 33.556 | 49.964 | 41.198 | 1.00 | 10.61 |
| 3015 | C | LEU | A | 200 | 32.688 | 46.864 | 39.883 | 1.00 | 8.86 |
| 3016 | O | LEU | A | 200 | 33.815 | 46.845 | 40.353 | 1.00 | 8.60 |
| 3017 | N | SER | A | 201 | 31.877 | 45.813 | 39.902 | 1.00 | 8.93 |
| 3019 | CA | SER | A | 201 | 32.258 | 44.553 | 40.520 | 1.00 | 8.99 |
| 3021 | CB | SER | A | 201 | 31.037 | 43.631 | 40.694 | 1.00 | 8.96 |
| 3024 | OG | SER | A | 201 | 30.650 | 43.034 | 39.468 | 1.00 | 8.56 |
| 3026 | C | SER | A | 201 | 33.373 | 43.876 | 39.725 | 1.00 | 8.97 |
| 3027 | O | SER | A | 201 | 34.303 | 43.350 | 40.313 | 1.00 | 8.83 |
| 3028 | N | ASN | A | 202 | 33.282 | 43.907 | 38.397 | 1.00 | 9.21 |
| 3030 | CA | ASN | A | 202 | 34.352 | 43.395 | 37.538 | 1.00 | 9.42 |
| 3032 | CB | ASN | A | 202 | 33.968 | 43.497 | 36.051 | 1.00 | 9.30 |
| 3035 | CG | ASN | A | 202 | 33.023 | 42.391 | 35.591 | 1.00 | 10.15 |
| 3036 | OD1 | ASN | A | 202 | 32.700 | 41.450 | 36.332 | 1.00 | 9.92 |
| 3037 | ND2 | ASN | A | 202 | 32.570 | 42.505 | 34.341 | 1.00 | 11.15 |
| 3040 | C | ASN | A | 202 | 35.649 | 44.170 | 37.768 | 1.00 | 9.26 |
| 3041 | O | ASN | A | 202 | 36.701 | 43.577 | 37.982 | 1.00 | 9.22 |
| 3042 | N | GLU | A | 203 | 35.559 | 45.495 | 37.725 | 1.00 | 9.43 |
| 3044 | CA | GLU | A | 203 | 36.728 | 46.366 | 37.863 | 1.00 | 9.77 |
| 3046 | CB | GLU | A | 203 | 36.338 | 47.838 | 37.641 | 1.00 | 10.17 |
| 3049 | CG | GLU | A | 203 | 37.410 | 48.875 | 37.982 | 1.00 | 11.47 |
| 3052 | CD | GLU | A | 203 | 38.661 | 48.771 | 37.125 | 1.00 | 14.61 |
| 3053 | OE1 | GLU | A | 203 | 38.694 | 47.939 | 36.191 | 1.00 | 16.44 |
| 3054 | OE2 | GLU | A | 203 | 39.624 | 49.534 | 37.386 | 1.00 | 15.76 |
| 3055 | C | GLU | A | 203 | 37.396 | 46.202 | 39.220 | 1.00 | 9.56 |
| 3056 | O | GLU | A | 203 | 38.616 | 46.155 | 39.306 | 1.00 | 9.36 |
| 3057 | N | THR | A | 204 | 36.588 | 46.110 | 40.270 | 1.00 | 9.48 |

FIGURE 3 (Cont.)

| A | B | C | D | E | F | G | H | I | J |
|---|---|---|---|---|---|---|---|---|---|
| 3059 | CA | THR | A | 204 | 37.095 | 46.011 | 41.631 | 1.00 | 9.47 |
| 3061 | CB | THR | A | 204 | 35.959 | 46.249 | 42.661 | 1.00 | 9.32 |
| 3063 | OG1 | THR | A | 204 | 35.328 | 47.516 | 42.416 | 1.00 | 9.28 |
| 3065 | CG2 | THR | A | 204 | 36.519 | 46.389 | 44.078 | 1.00 | 9.49 |
| 3069 | C | THR | A | 204 | 37.761 | 44.655 | 41.864 | 1.00 | 9.32 |
| 3070 | O | THR | A | 204 | 38.759 | 44.578 | 42.568 | 1.00 | 9.44 |
| 3071 | N | TYR | A | 205 | 37.203 | 43.595 | 41.279 | 1.00 | 9.40 |
| 3073 | CA | TYR | A | 205 | 37.811 | 42.263 | 41.335 | 1.00 | 9.27 |
| 3075 | CB | TYR | A | 205 | 36.919 | 41.239 | 40.617 | 1.00 | 9.41 |
| 3078 | CG | TYR | A | 205 | 37.446 | 39.812 | 40.598 | 1.00 | 9.70 |
| 3079 | CD1 | TYR | A | 205 | 38.587 | 39.469 | 39.871 | 1.00 | 10.40 |
| 3081 | CE1 | TYR | A | 205 | 39.058 | 38.167 | 39.845 | 1.00 | 10.53 |
| 3083 | CZ | TYR | A | 205 | 38.383 | 37.183 | 40.543 | 1.00 | 10.43 |
| 3084 | OH | TYR | A | 205 | 38.844 | 35.893 | 40.521 | 1.00 | 8.84 |
| 3086 | CE2 | TYR | A | 205 | 37.251 | 37.491 | 41.264 | 1.00 | 10.24 |
| 3088 | CD2 | TYR | A | 205 | 36.783 | 38.795 | 41.285 | 1.00 | 10.36 |
| 3090 | C | TYR | A | 205 | 39.199 | 42.294 | 40.703 | 1.00 | 9.25 |
| 3091 | O | TYR | A | 205 | 40.171 | 41.865 | 41.319 | 1.00 | 9.10 |
| 3092 | N | ILE | A | 206 | 39.279 | 42.807 | 39.476 | 1.00 | 9.41 |
| 3094 | CA | ILE | A | 206 | 40.538 | 42.873 | 38.735 | 1.00 | 9.74 |
| 3096 | CB | ILE | A | 206 | 40.303 | 43.384 | 37.283 | 1.00 | 9.65 |
| 3098 | CG1 | ILE | A | 206 | 39.559 | 42.322 | 36.467 | 1.00 | 9.87 |
| 3101 | CD1 | ILE | A | 206 | 39.022 | 42.815 | 35.129 | 1.00 | 10.20 |
| 3105 | CG2 | ILE | A | 206 | 41.636 | 43.746 | 36.605 | 1.00 | 9.77 |
| 3109 | C | ILE | A | 206 | 41.577 | 43.736 | 39.454 | 1.00 | 9.91 |
| 3110 | O | ILE | A | 206 | 42.729 | 43.328 | 39.583 | 1.00 | 10.17 |
| 3111 | N | GLN | A | 207 | 41.164 | 44.912 | 39.925 | 1.00 | 10.11 |
| 3113 | CA | GLN | A | 207 | 42.070 | 45.843 | 40.614 | 1.00 | 10.38 |
| 3115 | CB | GLN | A | 207 | 41.412 | 47.214 | 40.806 | 1.00 | 10.74 |
| 3118 | CG | GLN | A | 207 | 41.269 | 48.027 | 39.531 | 1.00 | 11.84 |
| 3121 | CD | GLN | A | 207 | 42.598 | 48.369 | 38.900 | 1.00 | 14.03 |
| 3122 | OE1 | GLN | A | 207 | 42.818 | 48.099 | 37.714 | 1.00 | 15.97 |
| 3123 | NE2 | GLN | A | 207 | 43.488 | 48.964 | 39.681 | 1.00 | 14.52 |
| 3126 | C | GLN | A | 207 | 42.529 | 45.323 | 41.971 | 1.00 | 10.11 |
| 3127 | O | GLN | A | 207 | 43.639 | 45.612 | 42.391 | 1.00 | 10.00 |
| 3128 | N | SER | A | 208 | 41.670 | 44.562 | 42.645 | 1.00 | 9.73 |
| 3130 | CA | SER | A | 208 | 41.999 | 43.965 | 43.933 | 1.00 | 9.46 |
| 3132 | CB | ASER | A | 208 | 40.755 | 43.362 | 44.592 | 0.65 | 9.28 |
| 3135 | OG | ASER | A | 208 | 39.886 | 44.380 | 45.046 | 0.65 | 8.22 |
| 3137 | C | SER | A | 208 | 43.067 | 42.890 | 43.767 | 1.00 | 9.73 |
| 3138 | O | SER | A | 208 | 43.988 | 42.793 | 44.580 | 1.00 | 9.78 |
| 3139 | N | PHE | A | 209 | 42.945 | 42.089 | 42.710 | 1.00 | 9.73 |
| 3141 | CA | PHE | A | 209 | 43.946 | 41.082 | 42.409 | 1.00 | 9.84 |
| 3143 | CB | PHE | A | 209 | 43.503 | 40.147 | 41.284 | 1.00 | 9.83 |
| 3146 | CG | PHE | A | 209 | 44.606 | 39.257 | 40.791 | 1.00 | 10.02 |
| 3147 | CD1 | PHE | A | 209 | 45.152 | 39.431 | 39.525 | 1.00 | 11.34 |
| 3149 | CE1 | PHE | A | 209 | 46.187 | 38.615 | 39.082 | 1.00 | 11.62 |
| 3151 | CZ | PHE | A | 209 | 46.694 | 37.630 | 39.915 | 1.00 | 10.97 |
| 3153 | CE2 | PHE | A | 209 | 46.162 | 37.455 | 41.176 | 1.00 | 11.11 |
| 3155 | CD2 | PHE | A | 209 | 45.129 | 38.272 | 41.614 | 1.00 | 10.26 |
| 3157 | C | PHE | A | 209 | 45.256 | 41.758 | 42.025 | 1.00 | 9.87 |
| 3158 | O | PHE | A | 209 | 46.309 | 41.374 | 42.505 | 1.00 | 9.55 |
| 3159 | N | ALA | A | 210 | 45.178 | 42.770 | 41.167 | 1.00 | 10.37 |

FIGURE 3 (Cont.)

| A | B | C | D | E | F | G | H | I | J |
|---|---|---|---|---|---|---|---|---|---|
| 3161 | CA | ALA | A | 210 | 46.357 | 43.536 | 40.765 | 1.00 | 10.51 |
| 3163 | CB | ALA | A | 210 | 45.963 | 44.676 | 39.822 | 1.00 | 10.55 |
| 3167 | C | ALA | A | 210 | 47.097 | 44.087 | 41.983 | 1.00 | 10.65 |
| 3168 | O | ALA | A | 210 | 48.318 | 44.014 | 42.053 | 1.00 | 10.62 |
| 3169 | N | GLN | A | 211 | 46.353 | 44.613 | 42.951 | 1.00 | 10.88 |
| 3171 | CA | GLN | A | 211 | 46.956 | 45.238 | 44.122 | 1.00 | 11.24 |
| 3173 | CB | GLN | A | 211 | 45.920 | 46.054 | 44.894 | 1.00 | 11.54 |
| 3176 | CG | GLN | A | 211 | 45.614 | 47.389 | 44.244 | 1.00 | 13.00 |
| 3179 | CD | GLN | A | 211 | 44.595 | 48.181 | 45.027 | 1.00 | 15.10 |
| 3180 | OE1 | GLN | A | 211 | 44.936 | 48.823 | 46.019 | 1.00 | 16.17 |
| 3181 | NE2 | GLN | A | 211 | 43.341 | 48.129 | 44.594 | 1.00 | 16.63 |
| 3184 | C | GLN | A | 211 | 47.639 | 44.239 | 45.054 | 1.00 | 11.01 |
| 3185 | O | GLN | A | 211 | 48.768 | 44.469 | 45.477 | 1.00 | 11.06 |
| 3186 | N | VAL | A | 212 | 46.965 | 43.137 | 45.378 | 1.00 | 10.96 |
| 3188 | CA | VAL | A | 212 | 47.553 | 42.138 | 46.277 | 1.00 | 10.91 |
| 3190 | CB | VAL | A | 212 | 46.512 | 41.141 | 46.863 | 1.00 | 10.99 |
| 3192 | CG1 | VAL | A | 212 | 45.459 | 41.884 | 47.697 | 1.00 | 10.77 |
| 3196 | CG2 | VAL | A | 212 | 45.859 | 40.296 | 45.776 | 1.00 | 10.92 |
| 3200 | C | VAL | A | 212 | 48.690 | 41.367 | 45.607 | 1.00 | 10.99 |
| 3201 | O | VAL | A | 212 | 49.643 | 40.973 | 46.276 | 1.00 | 10.71 |
| 3202 | N | TRP | A | 213 | 48.586 | 41.155 | 44.297 | 1.00 | 11.02 |
| 3204 | CA | TRP | A | 213 | 49.644 | 40.494 | 43.539 | 1.00 | 11.32 |
| 3206 | CB | TRP | A | 213 | 49.193 | 40.147 | 42.115 | 1.00 | 11.16 |
| 3209 | CG | TRP | A | 213 | 50.333 | 39.672 | 41.261 | 1.00 | 11.29 |
| 3210 | CD1 | TRP | A | 213 | 51.082 | 40.423 | 40.390 | 1.00 | 11.41 |
| 3212 | NE1 | TRP | A | 213 | 52.056 | 39.646 | 39.811 | 1.00 | 11.34 |
| 3214 | CE2 | TRP | A | 213 | 51.957 | 38.370 | 40.302 | 1.00 | 12.03 |
| 3215 | CD2 | TRP | A | 213 | 50.887 | 38.353 | 41.225 | 1.00 | 11.82 |
| 3216 | CE3 | TRP | A | 213 | 50.580 | 37.148 | 41.872 | 1.00 | 12.27 |
| 3218 | CZ3 | TRP | A | 213 | 51.336 | 36.026 | 41.589 | 1.00 | 12.81 |
| 3220 | CH2 | TRP | A | 213 | 52.393 | 36.076 | 40.667 | 1.00 | 13.39 |
| 3222 | CZ2 | TRP | A | 213 | 52.715 | 37.235 | 40.014 | 1.00 | 12.56 |
| 3224 | C | TRP | A | 213 | 50.896 | 41.367 | 43.474 | 1.00 | 11.61 |
| 3225 | O | TRP | A | 213 | 51.997 | 40.879 | 43.692 | 1.00 | 11.77 |
| 3226 | N | ASP | A | 214 | 50.720 | 42.649 | 43.160 | 1.00 | 11.97 |
| 3228 | CA | ASP | A | 214 | 51.839 | 43.591 | 43.073 | 1.00 | 12.39 |
| 3230 | CB | ASP | A | 214 | 51.360 | 44.985 | 42.655 | 1.00 | 12.46 |
| 3233 | CG | ASP | A | 214 | 51.026 | 45.074 | 41.178 | 1.00 | 12.90 |
| 3234 | OD1 | ASP | A | 214 | 50.358 | 46.055 | 40.788 | 1.00 | 12.70 |
| 3235 | OD2 | ASP | A | 214 | 51.378 | 44.215 | 40.340 | 1.00 | 14.02 |
| 3236 | C | ASP | A | 214 | 52.559 | 43.693 | 44.411 | 1.00 | 12.49 |
| 3237 | O | ASP | A | 214 | 53.787 | 43.699 | 44.461 | 1.00 | 12.48 |
| 3238 | N | GLU | A | 215 | 51.784 | 43.774 | 45.487 | 1.00 | 12.61 |
| 3240 | CA | GLU | A | 215 | 52.342 | 43.863 | 46.830 | 1.00 | 12.87 |
| 3242 | CB | GLU | A | 215 | 51.258 | 44.268 | 47.836 | 1.00 | 12.91 |
| 3245 | CG | GLU | A | 215 | 51.728 | 44.362 | 49.286 | 1.00 | 13.30 |
| 3248 | CD | GLU | A | 215 | 52.781 | 45.435 | 49.520 | 1.00 | 13.66 |
| 3249 | OE1 | GLU | A | 215 | 53.473 | 45.361 | 50.556 | 1.00 | 14.87 |
| 3250 | OE2 | GLU | A | 215 | 52.916 | 46.360 | 48.691 | 1.00 | 13.75 |
| 3251 | C | GLU | A | 215 | 52.995 | 42.544 | 47.246 | 1.00 | 13.03 |
| 3252 | O | GLU | A | 215 | 54.001 | 42.553 | 47.952 | 1.00 | 12.59 |
| 3253 | N | HIS | A | 216 | 52.424 | 41.419 | 46.811 | 1.00 | 13.21 |
| 3255 | CA | HIS | A | 216 | 53.008 | 40.110 | 47.095 | 1.00 | 13.59 |

FIGURE 3 (Cont.)

| A | B | C | D | E | F | G | H | I | J |
|---|---|---|---|---|---|---|---|---|---|
| 3257 | CB | HIS | A | 216 | 52.081 | 38.963 | 46.677 | 1.00 | 13.55 |
| 3260 | CG | HIS | A | 216 | 52.654 | 37.610 | 46.961 | 1.00 | 13.88 |
| 3261 | ND1 | HIS | A | 216 | 53.566 | 36.999 | 46.128 | 1.00 | 13.98 |
| 3263 | CE1 | HIS | A | 216 | 53.912 | 35.831 | 46.640 | 1.00 | 14.60 |
| 3265 | NE2 | HIS | A | 216 | 53.261 | 35.663 | 47.777 | 1.00 | 13.75 |
| 3267 | CD2 | HIS | A | 216 | 52.473 | 36.765 | 48.004 | 1.00 | 14.13 |
| 3269 | C | HIS | A | 216 | 54.359 | 39.947 | 46.404 | 1.00 | 13.90 |
| 3270 | O | HIS | A | 216 | 55.289 | 39.400 | 46.988 | 1.00 | 13.96 |
| 3271 | N | LYS | A | 217 | 54.461 | 40.418 | 45.166 | 1.00 | 14.33 |
| 3273 | CA | LYS | A | 217 | 55.708 | 40.334 | 44.408 | 1.00 | 14.97 |
| 3275 | CB | LYS | A | 217 | 55.477 | 40.707 | 42.936 | 1.00 | 14.97 |
| 3278 | CG | LYS | A | 217 | 56.744 | 40.707 | 42.077 | 1.00 | 16.28 |
| 3281 | CD | LYS | A | 217 | 56.457 | 41.023 | 40.617 | 1.00 | 17.31 |
| 3284 | CE | LYS | A | 217 | 57.757 | 41.163 | 39.828 | 1.00 | 18.89 |
| 3287 | NZ | LYS | A | 217 | 57.523 | 41.578 | 38.410 | 1.00 | 19.34 |
| 3291 | C | LYS | A | 217 | 56.762 | 41.247 | 45.042 | 1.00 | 15.06 |
| 3292 | O | LYS | A | 217 | 57.934 | 40.907 | 45.077 | 1.00 | 14.93 |
| 3293 | N | LYS | A | 218 | 56.331 | 42.398 | 45.551 | 1.00 | 15.32 |
| 3295 | CA | LYS | A | 218 | 57.236 | 43.355 | 46.181 | 1.00 | 15.67 |
| 3297 | CB | LYS | A | 218 | 56.491 | 44.663 | 46.468 | 1.00 | 15.87 |
| 3300 | CG | LYS | A | 218 | 57.303 | 45.726 | 47.187 | 1.00 | 16.86 |
| 3303 | CD | LYS | A | 218 | 56.483 | 46.990 | 47.364 | 1.00 | 17.91 |
| 3306 | CE | LYS | A | 218 | 57.215 | 48.018 | 48.204 | 1.00 | 18.82 |
| 3309 | NZ | LYS | A | 218 | 56.392 | 49.250 | 48.373 | 1.00 | 19.84 |
| 3313 | C | LYS | A | 218 | 57.832 | 42.776 | 47.466 | 1.00 | 15.60 |
| 3314 | O | LYS | A | 218 | 59.023 | 42.932 | 47.728 | 1.00 | 15.45 |
| 3315 | N | ARG | A | 219 | 57.000 | 42.092 | 48.250 | 1.00 | 15.60 |
| 3317 | CA | ARG | A | 219 | 57.422 | 41.522 | 49.526 | 1.00 | 15.67 |
| 3319 | CB | ARG | A | 219 | 56.205 | 41.128 | 50.367 | 1.00 | 15.83 |
| 3322 | CG | ARG | A | 219 | 55.440 | 42.292 | 50.986 | 1.00 | 16.43 |
| 3325 | CD | ARG | A | 219 | 54.271 | 41.840 | 51.854 | 1.00 | 17.43 |
| 3328 | NE | ARG | A | 219 | 53.334 | 42.919 | 52.166 | 1.00 | 18.00 |
| 3330 | CZ | ARG | A | 219 | 52.237 | 42.759 | 52.903 | 1.00 | 18.96 |
| 3331 | NH1 | ARG | A | 219 | 51.434 | 43.792 | 53.133 | 1.00 | 19.57 |
| 3334 | NH2 | ARG | A | 219 | 51.942 | 41.578 | 53.426 | 1.00 | 19.15 |
| 3337 | C | ARG | A | 219 | 58.309 | 40.292 | 49.353 | 1.00 | 15.58 |
| 3338 | O | ARG | A | 219 | 59.292 | 40.137 | 50.073 | 1.00 | 15.47 |
| 3339 | N | THR | A | 220 | 57.960 | 39.426 | 48.400 | 1.00 | 15.33 |
| 3341 | CA | THR | A | 220 | 58.542 | 38.080 | 48.317 | 1.00 | 15.34 |
| 3343 | CB | THR | A | 220 | 57.423 | 37.013 | 48.205 | 1.00 | 15.30 |
| 3345 | OG1 | THR | A | 220 | 56.697 | 37.180 | 46.974 | 1.00 | 15.10 |
| 3347 | CG2 | THR | A | 220 | 56.379 | 37.181 | 49.303 | 1.00 | 15.04 |
| 3351 | C | THR | A | 220 | 59.517 | 37.874 | 47.159 | 1.00 | 15.28 |
| 3352 | O | THR | A | 220 | 60.326 | 36.956 | 47.197 | 1.00 | 15.33 |
| 3353 | N | GLY | A | 221 | 59.419 | 38.703 | 46.125 | 1.00 | 15.22 |
| 3355 | CA | GLY | A | 221 | 60.190 | 38.512 | 44.909 | 1.00 | 15.17 |
| 3358 | C | GLY | A | 221 | 59.580 | 37.505 | 43.941 | 1.00 | 15.09 |
| 3359 | O | GLY | A | 221 | 60.061 | 37.366 | 42.821 | 1.00 | 15.22 |
| 3360 | N | LEU | A | 222 | 58.516 | 36.819 | 44.357 | 1.00 | 14.99 |
| 3362 | CA | LEU | A | 222 | 57.909 | 35.763 | 43.552 | 1.00 | 14.90 |
| 3364 | CB | LEU | A | 222 | 57.062 | 34.838 | 44.426 | 1.00 | 15.08 |
| 3367 | CG | LEU | A | 222 | 57.785 | 34.126 | 45.577 | 1.00 | 15.48 |
| 3369 | CD1 | LEU | A | 222 | 56.775 | 33.475 | 46.511 | 1.00 | 15.64 |

FIGURE 3 (Cont.)

| A | B | C | D | E | F | G | H | I | J |
|---|---|---|---|---|---|---|---|---|---|
| 3373 | CD2 | LEU | A | 222 | 58.783 | 33.094 | 45.048 | 1.00 | 15.97 |
| 3377 | C | LEU | A | 222 | 57.059 | 36.333 | 42.422 | 1.00 | 14.65 |
| 3378 | O | LEU | A | 222 | 56.424 | 37.377 | 42.569 | 1.00 | 14.43 |
| 3379 | N | ASP | A | 223 | 57.054 | 35.623 | 41.298 | 1.00 | 14.37 |
| 3381 | CA | ASP | A | 223 | 56.390 | 36.065 | 40.074 | 1.00 | 14.20 |
| 3383 | CB | ASP | A | 223 | 57.434 | 36.669 | 39.124 | 1.00 | 14.31 |
| 3386 | CG | ASP | A | 223 | 56.868 | 37.759 | 38.230 | 1.00 | 14.36 |
| 3387 | OD1 | ASP | A | 223 | 57.650 | 38.642 | 37.804 | 1.00 | 14.98 |
| 3388 | OD2 | ASP | A | 223 | 55.670 | 37.812 | 37.887 | 1.00 | 13.31 |
| 3389 | C | ASP | A | 223 | 55.668 | 34.867 | 39.440 | 1.00 | 14.10 |
| 3390 | O | ASP | A | 223 | 55.632 | 33.785 | 40.025 | 1.00 | 13.88 |
| 3391 | N | PHE | A | 224 | 55.086 | 35.057 | 38.258 | 1.00 | 14.09 |
| 3393 | CA | PHE | A | 224 | 54.245 | 34.033 | 37.634 | 1.00 | 14.25 |
| 3395 | CB | PHE | A | 224 | 53.601 | 34.584 | 36.360 | 1.00 | 14.36 |
| 3398 | CG | PHE | A | 224 | 52.506 | 35.577 | 36.625 | 1.00 | 14.07 |
| 3399 | CD1 | PHE | A | 224 | 51.260 | 35.149 | 37.050 | 1.00 | 14.25 |
| 3401 | CE1 | PHE | A | 224 | 50.241 | 36.066 | 37.308 | 1.00 | 14.53 |
| 3403 | CZ | PHE | A | 224 | 50.474 | 37.419 | 37.143 | 1.00 | 14.35 |
| 3405 | CE2 | PHE | A | 224 | 51.716 | 37.855 | 36.725 | 1.00 | 14.12 |
| 3407 | CD2 | PHE | A | 224 | 52.728 | 36.936 | 36.473 | 1.00 | 13.93 |
| 3409 | C | PHE | A | 224 | 54.984 | 32.721 | 37.344 | 1.00 | 14.39 |
| 3410 | O | PHE | A | 224 | 54.409 | 31.638 | 37.483 | 1.00 | 14.36 |
| 3411 | N | ALA | A | 225 | 56.261 | 32.824 | 36.981 | 1.00 | 14.50 |
| 3413 | CA | ALA | A | 225 | 57.093 | 31.651 | 36.694 | 1.00 | 14.54 |
| 3415 | CB | ALA | A | 225 | 58.413 | 32.089 | 36.054 | 1.00 | 14.64 |
| 3419 | C | ALA | A | 225 | 57.368 | 30.790 | 37.934 | 1.00 | 14.48 |
| 3420 | O | ALA | A | 225 | 57.740 | 29.623 | 37.811 | 1.00 | 14.52 |
| 3421 | N | ASP | A | 226 | 57.196 | 31.373 | 39.120 | 1.00 | 14.37 |
| 3423 | CA | ASP | A | 226 | 57.389 | 30.660 | 40.385 | 1.00 | 14.29 |
| 3425 | CB | ASP | A | 226 | 57.828 | 31.634 | 41.475 | 1.00 | 14.41 |
| 3428 | CG | ASP | A | 226 | 59.123 | 32.323 | 41.137 | 1.00 | 14.96 |
| 3429 | OD1 | ASP | A | 226 | 59.161 | 33.568 | 41.157 | 1.00 | 15.70 |
| 3430 | OD2 | ASP | A | 226 | 60.153 | 31.695 | 40.824 | 1.00 | 16.10 |
| 3431 | C | ASP | A | 226 | 56.149 | 29.903 | 40.854 | 1.00 | 13.93 |
| 3432 | O | ASP | A | 226 | 56.210 | 29.180 | 41.844 | 1.00 | 14.19 |
| 3433 | N | TYR | A | 227 | 55.032 | 30.068 | 40.149 | 1.00 | 13.69 |
| 3435 | CA | TYR | A | 227 | 53.790 | 29.390 | 40.500 | 1.00 | 13.36 |
| 3437 | CB | TYR | A | 227 | 52.656 | 30.407 | 40.648 | 1.00 | 13.39 |
| 3440 | CG | TYR | A | 227 | 52.747 | 31.099 | 41.974 | 1.00 | 13.55 |
| 3441 | CD1 | TYR | A | 227 | 53.420 | 32.309 | 42.103 | 1.00 | 13.12 |
| 3443 | CE1 | TYR | A | 227 | 53.536 | 32.935 | 43.335 | 1.00 | 12.90 |
| 3445 | CZ | TYR | A | 227 | 52.993 | 32.336 | 44.453 | 1.00 | 13.21 |
| 3446 | OH | TYR | A | 227 | 53.108 | 32.948 | 45.674 | 1.00 | 13.75 |
| 3448 | CE2 | TYR | A | 227 | 52.331 | 31.125 | 44.350 | 1.00 | 13.04 |
| 3450 | CD2 | TYR | A | 227 | 52.224 | 30.509 | 43.120 | 1.00 | 13.32 |
| 3452 | C | TYR | A | 227 | 53.425 | 28.314 | 39.493 | 1.00 | 13.13 |
| 3453 | O | TYR | A | 227 | 53.335 | 28.568 | 38.300 | 1.00 | 12.91 |
| 3454 | N | ASP | A | 228 | 53.232 | 27.101 | 39.993 | 1.00 | 13.02 |
| 3456 | CA | ASP | A | 228 | 52.765 | 25.990 | 39.172 | 1.00 | 12.87 |
| 3458 | CB | ASP | A | 228 | 53.015 | 24.672 | 39.896 | 1.00 | 12.80 |
| 3461 | CG | ASP | A | 228 | 54.480 | 24.437 | 40.149 | 1.00 | 12.93 |
| 3462 | OD1 | ASP | A | 228 | 55.158 | 23.933 | 39.235 | 1.00 | 12.61 |
| 3463 | OD2 | ASP | A | 228 | 55.046 | 24.755 | 41.216 | 1.00 | 12.06 |

FIGURE 3 (Cont.)

| A | B | C | D | E | F | G | H | I | J |
|---|---|---|---|---|---|---|---|---|---|
| 3464 | C | ASP | A | 228 | 51.286 | 26.129 | 38.808 | 1.00 | 12.70 |
| 3465 | O | ASP | A | 228 | 50.850 | 25.590 | 37.797 | 1.00 | 12.73 |
| 3466 | N | ALA | A | 229 | 50.524 | 26.843 | 39.633 | 1.00 | 12.48 |
| 3468 | CA | ALA | A | 229 | 49.138 | 27.186 | 39.306 | 1.00 | 12.41 |
| 3470 | CB | ALA | A | 229 | 48.228 | 25.971 | 39.479 | 1.00 | 12.51 |
| 3474 | C | ALA | A | 229 | 48.619 | 28.351 | 40.144 | 1.00 | 12.35 |
| 3475 | O | ALA | A | 229 | 49.060 | 28.559 | 41.271 | 1.00 | 12.18 |
| 3476 | N | LEU | A | 230 | 47.680 | 29.101 | 39.575 | 1.00 | 12.14 |
| 3478 | CA | LEU | A | 230 | 46.977 | 30.168 | 40.283 | 1.00 | 11.98 |
| 3480 | CB | LEU | A | 230 | 47.277 | 31.527 | 39.662 | 1.00 | 12.06 |
| 3483 | CG | LEU | A | 230 | 48.741 | 31.962 | 39.670 | 1.00 | 13.01 |
| 3485 | CD1 | LEU | A | 230 | 48.899 | 33.282 | 38.919 | 1.00 | 13.82 |
| 3489 | CD2 | LEU | A | 230 | 49.261 | 32.083 | 41.092 | 1.00 | 13.19 |
| 3493 | C | LEU | A | 230 | 45.474 | 29.908 | 40.242 | 1.00 | 11.76 |
| 3494 | O | LEU | A | 230 | 44.875 | 29.869 | 39.167 | 1.00 | 11.90 |
| 3495 | N | ALA | A | 231 | 44.885 | 29.713 | 41.418 | 1.00 | 11.31 |
| 3497 | CA | ALA | A | 231 | 43.450 | 29.529 | 41.571 | 1.00 | 11.20 |
| 3499 | CB | ALA | A | 231 | 43.170 | 28.412 | 42.564 | 1.00 | 11.34 |
| 3503 | C | ALA | A | 231 | 42.812 | 30.837 | 42.040 | 1.00 | 10.96 |
| 3504 | O | ALA | A | 231 | 43.418 | 31.598 | 42.798 | 1.00 | 10.56 |
| 3505 | N | PHE | A | 232 | 41.585 | 31.078 | 41.589 | 1.00 | 10.56 |
| 3507 | CA | PHE | A | 232 | 40.882 | 32.339 | 41.819 | 1.00 | 10.45 |
| 3509 | CB | PHE | A | 232 | 40.748 | 33.098 | 40.499 | 1.00 | 10.47 |
| 3512 | CG | PHE | A | 232 | 42.031 | 33.711 | 40.014 | 1.00 | 10.95 |
| 3513 | CD1 | PHE | A | 232 | 42.241 | 35.078 | 40.112 | 1.00 | 11.25 |
| 3515 | CE1 | PHE | A | 232 | 43.423 | 35.647 | 39.663 | 1.00 | 11.28 |
| 3517 | CZ | PHE | A | 232 | 44.401 | 34.853 | 39.104 | 1.00 | 11.30 |
| 3519 | CE2 | PHE | A | 232 | 44.200 | 33.487 | 38.990 | 1.00 | 11.56 |
| 3521 | CD2 | PHE | A | 232 | 43.020 | 32.923 | 39.443 | 1.00 | 11.38 |
| 3523 | C | PHE | A | 232 | 39.481 | 32.100 | 42.355 | 1.00 | 10.12 |
| 3524 | O | PHE | A | 232 | 38.896 | 31.042 | 42.137 | 1.00 | 9.99 |
| 3525 | N | HIS | A | 233 | 38.927 | 33.098 | 43.035 | 1.00 | 9.62 |
| 3527 | CA | HIS | A | 233 | 37.495 | 33.112 | 43.300 | 1.00 | 9.47 |
| 3529 | CB | HIS | A | 233 | 37.100 | 34.360 | 44.083 | 1.00 | 9.43 |
| 3532 | CG | HIS | A | 233 | 35.625 | 34.597 | 44.130 | 1.00 | 8.75 |
| 3533 | ND1 | HIS | A | 233 | 34.760 | 33.757 | 44.796 | 1.00 | 8.36 |
| 3535 | CE1 | HIS | A | 233 | 33.525 | 34.211 | 44.666 | 1.00 | 8.71 |
| 3537 | NE2 | HIS | A | 233 | 33.559 | 35.314 | 43.939 | 1.00 | 7.38 |
| 3539 | CD2 | HIS | A | 233 | 34.861 | 35.578 | 43.593 | 1.00 | 8.29 |
| 3541 | C | HIS | A | 233 | 36.789 | 33.108 | 41.945 | 1.00 | 9.39 |
| 3542 | O | HIS | A | 233 | 37.109 | 33.932 | 41.088 | 1.00 | 9.26 |
| 3543 | N | ILE | A | 234 | 35.855 | 32.177 | 41.755 | 1.00 | 9.28 |
| 3545 | CA | ILE | A | 234 | 35.147 | 32.020 | 40.479 | 1.00 | 9.30 |
| 3547 | CB | ILE | A | 234 | 35.284 | 30.563 | 39.943 | 1.00 | 9.24 |
| 3549 | CG1 | ILE | A | 234 | 36.753 | 30.144 | 39.827 | 1.00 | 9.72 |
| 3552 | CD1 | ILE | A | 234 | 36.964 | 28.640 | 39.940 | 1.00 | 10.24 |
| 3556 | CG2 | ILE | A | 234 | 34.611 | 30.427 | 38.577 | 1.00 | 9.21 |
| 3560 | C | ILE | A | 234 | 33.663 | 32.393 | 40.590 | 1.00 | 9.26 |
| 3561 | O | ILE | A | 234 | 32.829 | 31.537 | 40.867 | 1.00 | 9.37 |
| 3562 | N | PRO | A | 235 | 33.327 | 33.664 | 40.369 | 1.00 | 9.59 |
| 3563 | CA | PRO | A | 235 | 31.919 | 34.084 | 40.310 | 1.00 | 9.73 |
| 3565 | CB | PRO | A | 235 | 32.002 | 35.610 | 40.389 | 1.00 | 9.66 |
| 3568 | CG | PRO | A | 235 | 33.364 | 35.952 | 39.856 | 1.00 | 9.68 |

FIGURE 3 (Cont.)

| A | B | C | D | E | F | G | H | I | J |
|---|---|---|---|---|---|---|---|---|---|
| 3571 | CD | PRO | A | 235 | 34.251 | 34.794 | 40.161 | 1.00 | 9.55 |
| 3574 | C | PRO | A | 235 | 31.265 | 33.630 | 39.003 | 1.00 | 9.88 |
| 3575 | O | PRO | A | 235 | 30.095 | 33.235 | 38.977 | 1.00 | 9.85 |
| 3576 | N | TYR | A | 236 | 32.039 | 33.741 | 37.929 | 1.00 | 9.97 |
| 3578 | CA | TYR | A | 236 | 31.801 | 33.061 | 36.661 | 1.00 | 10.06 |
| 3580 | CB | TYR | A | 236 | 30.961 | 33.919 | 35.722 | 1.00 | 10.08 |
| 3583 | CG | TYR | A | 236 | 31.461 | 35.328 | 35.472 | 1.00 | 10.32 |
| 3584 | CD1 | TYR | A | 236 | 32.142 | 35.643 | 34.299 | 1.00 | 9.99 |
| 3586 | CE1 | TYR | A | 236 | 32.576 | 36.925 | 34.040 | 1.00 | 10.61 |
| 3588 | CZ | TYR | A | 236 | 32.329 | 37.931 | 34.950 | 1.00 | 11.09 |
| 3589 | OH | TYR | A | 236 | 32.768 | 39.207 | 34.671 | 1.00 | 12.27 |
| 3591 | CE2 | TYR | A | 236 | 31.641 | 37.655 | 36.121 | 1.00 | 10.82 |
| 3593 | CD2 | TYR | A | 236 | 31.201 | 36.357 | 36.372 | 1.00 | 9.99 |
| 3595 | C | TYR | A | 236 | 33.172 | 32.757 | 36.063 | 1.00 | 10.28 |
| 3596 | O | TYR | A | 236 | 34.137 | 33.442 | 36.373 | 1.00 | 10.16 |
| 3597 | N | THR | A | 237 | 33.277 | 31.733 | 35.222 | 1.00 | 10.61 |
| 3599 | CA | THR | A | 237 | 34.596 | 31.175 | 34.915 | 1.00 | 11.06 |
| 3601 | CB | THR | A | 237 | 34.504 | 29.796 | 34.217 | 1.00 | 10.95 |
| 3603 | OG1 | THR | A | 237 | 33.967 | 29.940 | 32.900 | 1.00 | 10.27 |
| 3605 | CG2 | THR | A | 237 | 33.540 | 28.848 | 34.949 | 1.00 | 10.79 |
| 3609 | C | THR | A | 237 | 35.502 | 32.110 | 34.108 | 1.00 | 11.63 |
| 3610 | O | THR | A | 237 | 36.716 | 31.967 | 34.155 | 1.00 | 11.74 |
| 3611 | N | LYS | A | 238 | 34.936 | 33.071 | 33.392 | 1.00 | 12.35 |
| 3613 | CA | LYS | A | 238 | 35.772 | 34.020 | 32.652 | 1.00 | 13.33 |
| 3615 | CB | LYS | A | 238 | 35.032 | 34.596 | 31.437 | 1.00 | 13.80 |
| 3618 | CG | LYS | A | 238 | 35.789 | 34.368 | 30.125 | 1.00 | 16.53 |
| 3621 | CD | LYS | A | 238 | 34.955 | 34.768 | 28.945 | 1.00 | 20.06 |
| 3624 | CE | LYS | A | 238 | 35.652 | 34.483 | 27.627 | 1.00 | 21.44 |
| 3627 | NZ | LYS | A | 238 | 35.079 | 35.333 | 26.539 | 1.00 | 22.72 |
| 3631 | C | LYS | A | 238 | 36.337 | 35.146 | 33.526 | 1.00 | 13.19 |
| 3632 | O | LYS | A | 238 | 37.256 | 35.836 | 33.105 | 1.00 | 13.23 |
| 3633 | N | MSE | A | 239 | 35.803 | 35.332 | 34.734 | 1.00 | 13.14 |
| 3635 | CA | MSE | A | 239 | 36.278 | 36.399 | 35.619 | 1.00 | 13.03 |
| 3637 | CB | MSE | A | 239 | 35.496 | 36.419 | 36.938 | 1.00 | 13.21 |
| 3640 | CG | MSE | A | 239 | 35.845 | 37.601 | 37.838 | 1.00 | 13.27 |
| 3643 | SE | MSE | A | 239 | 35.184 | 39.279 | 37.114 | 1.00 | 14.41 |
| 3644 | CE | MSE | A | 239 | 36.845 | 40.067 | 36.493 | 1.00 | 13.65 |
| 3648 | C | MSE | A | 239 | 37.761 | 36.246 | 35.921 | 1.00 | 13.05 |
| 3649 | O | MSE | A | 239 | 38.540 | 37.188 | 35.744 | 1.00 | 12.46 |
| 3650 | N | GLY | A | 240 | 38.146 | 35.053 | 36.365 | 1.00 | 12.92 |
| 3652 | CA | GLY | A | 240 | 39.526 | 34.775 | 36.703 | 1.00 | 13.08 |
| 3655 | C | GLY | A | 240 | 40.440 | 34.951 | 35.506 | 1.00 | 13.30 |
| 3656 | O | GLY | A | 240 | 41.542 | 35.481 | 35.645 | 1.00 | 12.94 |
| 3657 | N | LYS | A | 241 | 39.976 | 34.520 | 34.333 | 1.00 | 13.29 |
| 3659 | CA | LYS | A | 241 | 40.747 | 34.664 | 33.102 | 1.00 | 13.47 |
| 3661 | CB | LYS | A | 241 | 40.027 | 34.021 | 31.905 | 1.00 | 13.60 |
| 3664 | CG | LYS | A | 241 | 40.945 | 33.808 | 30.703 | 1.00 | 14.20 |
| 3667 | CD | LYS | A | 241 | 40.193 | 33.477 | 29.432 | 1.00 | 14.93 |
| 3670 | CE | LYS | A | 241 | 41.172 | 33.098 | 28.320 | 1.00 | 15.42 |
| 3673 | NZ | LYS | A | 241 | 40.489 | 32.894 | 27.022 | 1.00 | 16.18 |
| 3677 | C | LYS | A | 241 | 41.041 | 36.131 | 32.799 | 1.00 | 13.39 |
| 3678 | O | LYS | A | 241 | 42.151 | 36.464 | 32.412 | 1.00 | 13.26 |
| 3679 | N | LYS | A | 242 | 40.042 | 36.993 | 32.983 | 1.00 | 13.40 |

FIGURE 3 (Cont.)

| A | B | C | D | E | F | G | H | I | J |
|---|---|---|---|---|---|---|---|---|---|
| 3681 | CA | LYS | A | 242 | 40.171 | 38.422 | 32.704 | 1.00 | 13.29 |
| 3683 | CB | LYS | A | 242 | 38.796 | 39.107 | 32.747 | 1.00 | 13.31 |
| 3686 | CG | LYS | A | 242 | 37.896 | 38.729 | 31.573 | 1.00 | 13.37 |
| 3689 | CD | LYS | A | 242 | 36.660 | 39.606 | 31.476 | 1.00 | 14.18 |
| 3692 | CE | LYS | A | 242 | 35.626 | 39.259 | 32.538 | 1.00 | 13.92 |
| 3695 | NZ | LYS | A | 242 | 34.396 | 40.094 | 32.404 | 1.00 | 13.37 |
| 3699 | C | LYS | A | 242 | 41.150 | 39.108 | 33.659 | 1.00 | 13.17 |
| 3700 | O | LYS | A | 242 | 41.895 | 39.990 | 33.247 | 1.00 | 12.84 |
| 3701 | N | ALA | A | 243 | 41.157 | 38.688 | 34.924 | 1.00 | 13.18 |
| 3703 | CA | ALA | A | 243 | 42.105 | 39.206 | 35.913 | 1.00 | 13.08 |
| 3705 | CB | ALA | A | 243 | 41.740 | 38.696 | 37.299 | 1.00 | 13.16 |
| 3709 | C | ALA | A | 243 | 43.540 | 38.802 | 35.561 | 1.00 | 13.25 |
| 3710 | O | ALA | A | 243 | 44.476 | 39.607 | 35.666 | 1.00 | 12.55 |
| 3711 | N | LEU | A | 244 | 43.690 | 37.547 | 35.140 | 1.00 | 13.41 |
| 3713 | CA | LEU | A | 244 | 44.967 | 36.993 | 34.706 | 1.00 | 13.76 |
| 3715 | CB | LEU | A | 244 | 44.807 | 35.513 | 34.314 | 1.00 | 13.88 |
| 3718 | CG | LEU | A | 244 | 45.587 | 34.373 | 34.987 | 1.00 | 13.88 |
| 3720 | CD1 | LEU | A | 244 | 46.371 | 34.771 | 36.220 | 1.00 | 13.13 |
| 3724 | CD2 | LEU | A | 244 | 44.643 | 33.210 | 35.300 | 1.00 | 13.61 |
| 3728 | C | LEU | A | 244 | 45.505 | 37.773 | 33.511 | 1.00 | 14.11 |
| 3729 | O | LEU | A | 244 | 46.652 | 38.202 | 33.521 | 1.00 | 14.01 |
| 3730 | N | LEU | A | 245 | 44.663 | 37.967 | 32.499 | 1.00 | 14.45 |
| 3732 | CA | LEU | A | 245 | 45.059 | 38.666 | 31.276 | 1.00 | 15.05 |
| 3734 | CB | LEU | A | 245 | 43.928 | 38.615 | 30.236 | 1.00 | 15.10 |
| 3737 | CG | LEU | A | 245 | 43.610 | 37.239 | 29.635 | 1.00 | 15.53 |
| 3739 | CD1 | LEU | A | 245 | 42.285 | 37.282 | 28.882 | 1.00 | 16.24 |
| 3743 | CD2 | LEU | A | 245 | 44.719 | 36.764 | 28.715 | 1.00 | 16.38 |
| 3747 | C | LEU | A | 245 | 45.475 | 40.118 | 31.530 | 1.00 | 15.25 |
| 3748 | O | LEU | A | 245 | 46.306 | 40.663 | 30.801 | 1.00 | 15.60 |
| 3749 | N | ALA | A | 246 | 44.915 | 40.737 | 32.567 | 1.00 | 15.37 |
| 3751 | CA | ALA | A | 246 | 45.275 | 42.105 | 32.934 | 1.00 | 15.63 |
| 3753 | CB | ALA | A | 246 | 44.267 | 42.664 | 33.933 | 1.00 | 15.62 |
| 3757 | C | ALA | A | 246 | 46.693 | 42.224 | 33.507 | 1.00 | 15.85 |
| 3758 | O | ALA | A | 246 | 47.270 | 43.311 | 33.484 | 1.00 | 16.08 |
| 3759 | N | LYS | A | 247 | 47.246 | 41.123 | 34.022 | 1.00 | 16.04 |
| 3761 | CA | LYS | A | 247 | 48.539 | 41.154 | 34.721 | 1.00 | 16.29 |
| 3763 | CB | LYS | A | 247 | 48.342 | 40.766 | 36.195 | 1.00 | 16.30 |
| 3766 | CG | LYS | A | 247 | 47.455 | 41.722 | 37.001 | 1.00 | 16.75 |
| 3769 | CD | LYS | A | 247 | 48.035 | 43.135 | 37.112 | 1.00 | 16.67 |
| 3772 | CE | LYS | A | 247 | 49.184 | 43.214 | 38.101 | 1.00 | 16.58 |
| 3775 | NZ | LYS | A | 247 | 49.942 | 44.488 | 37.959 | 1.00 | 15.66 |
| 3779 | C | LYS | A | 247 | 49.668 | 40.292 | 34.141 | 1.00 | 16.26 |
| 3780 | O | LYS | A | 247 | 50.814 | 40.451 | 34.563 | 1.00 | 16.19 |
| 3781 | N | ILE | A | 248 | 49.371 | 39.406 | 33.188 | 1.00 | 16.34 |
| 3783 | CA | ILE | A | 248 | 50.379 | 38.468 | 32.670 | 1.00 | 16.63 |
| 3785 | CB | ILE | A | 248 | 49.831 | 37.009 | 32.605 | 1.00 | 16.58 |
| 3787 | CG1 | ILE | A | 248 | 48.712 | 36.879 | 31.559 | 1.00 | 16.72 |
| 3790 | CD1 | ILE | A | 248 | 48.431 | 35.459 | 31.141 | 1.00 | 17.21 |
| 3794 | CG2 | ILE | A | 248 | 49.391 | 36.534 | 33.987 | 1.00 | 17.19 |
| 3798 | C | ILE | A | 248 | 50.932 | 38.847 | 31.295 | 1.00 | 16.60 |
| 3799 | O | ILE | A | 248 | 51.698 | 38.084 | 30.718 | 1.00 | 16.44 |
| 3800 | N | SER | A | 249 | 50.549 | 40.010 | 30.774 | 1.00 | 16.85 |
| 3802 | CA | SER | A | 249 | 50.911 | 40.395 | 29.407 | 1.00 | 17.16 |

FIGURE 3 (Cont.)

| A | B | C | D | E | F | G | H | I | J |
|---|---|---|---|---|---|---|---|---|---|
| 3804 | CB | SER | A | 249 | 50.099 | 41.617 | 28.959 | 1.00 | 17.16 |
| 3807 | OG | SER | A | 249 | 50.556 | 42.797 | 29.586 | 1.00 | 17.71 |
| 3809 | C | SER | A | 249 | 52.411 | 40.646 | 29.202 | 1.00 | 17.30 |
| 3810 | O | SER | A | 249 | 52.890 | 40.603 | 28.068 | 1.00 | 17.55 |
| 3811 | N | ASP | A | 250 | 53.145 | 40.898 | 30.287 | 1.00 | 17.39 |
| 3813 | CA | ASP | A | 250 | 54.602 | 41.074 | 30.224 | 1.00 | 17.72 |
| 3815 | CB | ASP | A | 250 | 55.070 | 42.078 | 31.292 | 1.00 | 18.24 |
| 3818 | CG | ASP | A | 250 | 54.888 | 43.515 | 30.859 | 1.00 | 19.97 |
| 3819 | OD1 | ASP | A | 250 | 55.265 | 43.843 | 29.712 | 1.00 | 22.70 |
| 3820 | OD2 | ASP | A | 250 | 54.384 | 44.392 | 31.597 | 1.00 | 23.44 |
| 3821 | C | ASP | A | 250 | 55.384 | 39.760 | 30.378 | 1.00 | 17.17 |
| 3822 | O | ASP | A | 250 | 56.616 | 39.760 | 30.329 | 1.00 | 17.01 |
| 3823 | N | GLN | A | 251 | 54.678 | 38.650 | 30.570 | 1.00 | 16.33 |
| 3825 | CA | GLN | A | 251 | 55.313 | 37.335 | 30.632 | 1.00 | 15.93 |
| 3827 | CB | GLN | A | 251 | 54.441 | 36.358 | 31.429 | 1.00 | 15.91 |
| 3830 | CG | GLN | A | 251 | 54.075 | 36.843 | 32.832 | 1.00 | 15.67 |
| 3833 | CD | GLN | A | 251 | 55.299 | 37.163 | 33.667 | 1.00 | 15.80 |
| 3834 | OE1 | GLN | A | 251 | 56.084 | 36.266 | 33.985 | 1.00 | 16.67 |
| 3835 | NE2 | GLN | A | 251 | 55.476 | 38.440 | 34.014 | 1.00 | 13.76 |
| 3838 | C | GLN | A | 251 | 55.570 | 36.774 | 29.229 | 1.00 | 15.67 |
| 3839 | O | GLN | A | 251 | 54.943 | 37.192 | 28.251 | 1.00 | 15.16 |
| 3840 | N | THR | A | 252 | 56.488 | 35.816 | 29.139 | 1.00 | 15.50 |
| 3842 | CA | THR | A | 252 | 56.757 | 35.129 | 27.875 | 1.00 | 15.52 |
| 3844 | CB | THR | A | 252 | 57.905 | 34.103 | 28.015 | 1.00 | 15.54 |
| 3846 | OG1 | THR | A | 252 | 57.499 | 33.029 | 28.874 | 1.00 | 15.27 |
| 3848 | CG2 | THR | A | 252 | 59.146 | 34.715 | 28.708 | 1.00 | 15.65 |
| 3852 | C | THR | A | 252 | 55.490 | 34.408 | 27.432 | 1.00 | 15.60 |
| 3853 | O | THR | A | 252 | 54.635 | 34.095 | 28.260 | 1.00 | 15.29 |
| 3854 | N | GLU | A | 253 | 55.371 | 34.148 | 26.133 | 1.00 | 15.70 |
| 3856 | CA | GLU | A | 253 | 54.202 | 33.457 | 25.595 | 1.00 | 16.04 |
| 3858 | CB | GLU | A | 253 | 54.301 | 33.323 | 24.067 | 1.00 | 16.45 |
| 3861 | CG | GLU | A | 253 | 53.102 | 32.656 | 23.391 | 1.00 | 17.80 |
| 3864 | CD | GLU | A | 253 | 51.777 | 33.372 | 23.631 | 1.00 | 20.25 |
| 3865 | OE1 | GLU | A | 253 | 51.783 | 34.605 | 23.829 | 1.00 | 21.15 |
| 3866 | OE2 | GLU | A | 253 | 50.718 | 32.696 | 23.608 | 1.00 | 21.83 |
| 3867 | C | GLU | A | 253 | 54.016 | 32.084 | 26.244 | 1.00 | 15.83 |
| 3868 | O | GLU | A | 253 | 52.896 | 31.693 | 26.549 | 1.00 | 15.55 |
| 3869 | N | ALA | A | 254 | 55.112 | 31.364 | 26.467 | 1.00 | 15.77 |
| 3871 | CA | ALA | A | 254 | 55.043 | 30.040 | 27.083 | 1.00 | 15.57 |
| 3873 | CB | ALA | A | 254 | 56.411 | 29.371 | 27.075 | 1.00 | 15.79 |
| 3877 | C | ALA | A | 254 | 54.490 | 30.111 | 28.510 | 1.00 | 15.36 |
| 3878 | O | ALA | A | 254 | 53.695 | 29.264 | 28.906 | 1.00 | 15.01 |
| 3879 | N | GLU | A | 255 | 54.908 | 31.122 | 29.268 | 1.00 | 15.15 |
| 3881 | CA | GLU | A | 255 | 54.437 | 31.300 | 30.645 | 1.00 | 15.25 |
| 3883 | CB | GLU | A | 255 | 55.283 | 32.340 | 31.390 | 1.00 | 15.32 |
| 3886 | CG | GLU | A | 255 | 56.695 | 31.867 | 31.725 | 1.00 | 16.46 |
| 3889 | CD | GLU | A | 255 | 56.743 | 30.862 | 32.863 | 1.00 | 17.58 |
| 3890 | OE1 | GLU | A | 255 | 57.834 | 30.298 | 33.103 | 1.00 | 19.28 |
| 3891 | OE2 | GLU | A | 255 | 55.700 | 30.629 | 33.516 | 1.00 | 16.76 |
| 3892 | C | GLU | A | 255 | 52.959 | 31.695 | 30.690 | 1.00 | 14.93 |
| 3893 | O | GLU | A | 255 | 52.225 | 31.224 | 31.548 | 1.00 | 14.65 |
| 3894 | N | GLN | A | 256 | 52.534 | 32.551 | 29.763 | 1.00 | 14.88 |
| 3896 | CA | GLN | A | 256 | 51.129 | 32.946 | 29.655 | 1.00 | 14.90 |

FIGURE 3 (Cont.)

| A | B | C | D | E | F | G | H | I | J |
|---|---|---|---|---|---|---|---|---|---|
| 3898 | CB | GLN | A | 256 | 50.942 | 34.028 | 28.586 | 1.00 | 14.83 |
| 3901 | CG | GLN | A | 256 | 51.620 | 35.355 | 28.913 | 1.00 | 15.28 |
| 3904 | CD | GLN | A | 256 | 51.289 | 36.456 | 27.915 | 1.00 | 15.87 |
| 3905 | OE1 | GLN | A | 256 | 50.140 | 36.608 | 27.510 | 1.00 | 15.04 |
| 3906 | NE2 | GLN | A | 256 | 52.297 | 37.229 | 27.525 | 1.00 | 15.87 |
| 3909 | C | GLN | A | 256 | 50.260 | 31.738 | 29.324 | 1.00 | 14.97 |
| 3910 | O | GLN | A | 256 | 49.212 | 31.537 | 29.932 | 1.00 | 14.79 |
| 3911 | N | GLU | A | 257 | 50.708 | 30.927 | 28.370 | 1.00 | 15.15 |
| 3913 | CA | GLU | A | 257 | 49.942 | 29.762 | 27.928 | 1.00 | 15.48 |
| 3915 | CB | GLU | A | 257 | 50.571 | 29.137 | 26.674 | 1.00 | 15.99 |
| 3918 | CG | GLU | A | 257 | 50.270 | 29.899 | 25.387 | 1.00 | 17.00 |
| 3921 | CD | GLU | A | 257 | 50.813 | 29.213 | 24.140 | 1.00 | 19.41 |
| 3922 | OE1 | GLU | A | 257 | 50.948 | 27.966 | 24.137 | 1.00 | 20.60 |
| 3923 | OE2 | GLU | A | 257 | 51.105 | 29.924 | 23.150 | 1.00 | 20.98 |
| 3924 | C | GLU | A | 257 | 49.829 | 28.717 | 29.040 | 1.00 | 15.24 |
| 3925 | O | GLU | A | 257 | 48.802 | 28.053 | 29.170 | 1.00 | 15.28 |
| 3926 | N | ARG | A | 258 | 50.884 | 28.594 | 29.844 | 1.00 | 14.85 |
| 3928 | CA | ARG | A | 258 | 50.934 | 27.630 | 30.938 | 1.00 | 14.84 |
| 3930 | CB | ARG | A | 258 | 52.374 | 27.485 | 31.443 | 1.00 | 15.05 |
| 3933 | CG | ARG | A | 258 | 52.559 | 26.431 | 32.519 | 1.00 | 15.67 |
| 3936 | CD | ARG | A | 258 | 53.990 | 26.334 | 33.059 | 1.00 | 16.97 |
| 3939 | NE | ARG | A | 258 | 54.412 | 27.534 | 33.790 | 1.00 | 17.01 |
| 3941 | CZ | ARG | A | 258 | 53.990 | 27.877 | 35.006 | 1.00 | 17.70 |
| 3942 | NH1 | ARG | A | 258 | 53.114 | 27.127 | 35.659 | 1.00 | 17.42 |
| 3945 | NH2 | ARG | A | 258 | 54.443 | 28.992 | 35.573 | 1.00 | 17.88 |
| 3948 | C | ARG | A | 258 | 50.022 | 28.040 | 32.098 | 1.00 | 14.45 |
| 3949 | O | ARG | A | 258 | 49.338 | 27.200 | 32.674 | 1.00 | 14.10 |
| 3950 | N | ILE | A | 259 | 50.026 | 29.324 | 32.445 | 1.00 | 14.19 |
| 3952 | CA | ILE | A | 259 | 49.207 | 29.827 | 33.550 | 1.00 | 14.18 |
| 3954 | CB | ILE | A | 259 | 49.653 | 31.258 | 33.962 | 1.00 | 14.35 |
| 3956 | CG1 | ILE | A | 259 | 51.052 | 31.224 | 34.588 | 1.00 | 14.80 |
| 3959 | CD1 | ILE | A | 259 | 51.095 | 30.714 | 36.037 | 1.00 | 15.47 |
| 3963 | CG2 | ILE | A | 259 | 48.656 | 31.888 | 34.937 | 1.00 | 14.33 |
| 3967 | C | ILE | A | 259 | 47.723 | 29.795 | 33.167 | 1.00 | 13.92 |
| 3968 | O | ILE | A | 259 | 46.869 | 29.466 | 33.994 | 1.00 | 13.64 |
| 3969 | N | LEU | A | 260 | 47.430 | 30.113 | 31.907 | 1.00 | 13.67 |
| 3971 | CA | LEU | A | 260 | 46.056 | 30.103 | 31.409 | 1.00 | 13.59 |
| 3973 | CB | LEU | A | 260 | 45.958 | 30.798 | 30.047 | 1.00 | 13.79 |
| 3976 | CG | LEU | A | 260 | 46.109 | 32.320 | 30.056 | 1.00 | 13.94 |
| 3978 | CD1 | LEU | A | 260 | 46.294 | 32.833 | 28.640 | 1.00 | 14.91 |
| 3982 | CD2 | LEU | A | 260 | 44.915 | 32.994 | 30.705 | 1.00 | 14.51 |
| 3986 | C | LEU | A | 260 | 45.509 | 28.683 | 31.312 | 1.00 | 13.40 |
| 3987 | O | LEU | A | 260 | 44.322 | 28.462 | 31.546 | 1.00 | 13.26 |
| 3988 | N | ALA | A | 261 | 46.376 | 27.727 | 30.978 | 1.00 | 13.23 |
| 3990 | CA | ALA | A | 261 | 45.982 | 26.322 | 30.876 | 1.00 | 12.97 |
| 3992 | CB | ALA | A | 261 | 47.083 | 25.498 | 30.200 | 1.00 | 13.22 |
| 3996 | C | ALA | A | 261 | 45.647 | 25.741 | 32.249 | 1.00 | 12.72 |
| 3997 | O | ALA | A | 261 | 44.697 | 24.966 | 32.378 | 1.00 | 12.45 |
| 3998 | N | ARG | A | 262 | 46.426 | 26.109 | 33.267 | 1.00 | 12.25 |
| 4000 | CA | ARG | A | 262 | 46.125 | 25.707 | 34.642 | 1.00 | 11.93 |
| 4002 | CB | ARG | A | 262 | 47.213 | 26.156 | 35.622 | 1.00 | 11.93 |
| 4005 | CG | ARG | A | 262 | 48.566 | 25.499 | 35.424 | 1.00 | 11.69 |
| 4008 | CD | AARG | A | 262 | 48.600 | 23.984 | 35.657 | 0.65 | 11.36 |

FIGURE 3 (Cont.)

| A | B | C | D | E | F | G | H | I | J |
|---|---|---|---|---|---|---|---|---|---|
| 4011 | NE | AARG | A | 262 | 48.132 | 23.231 | 34.491 | 0.65 | 11.38 |
| 4013 | CZ | AARG | A | 262 | 48.768 | 23.159 | 33.320 | 0.65 | 10.48 |
| 4014 | NH1 | AARG | A | 262 | 48.236 | 22.458 | 32.328 | 0.65 | 10.21 |
| 4017 | NH2 | AARG | A | 262 | 49.936 | 23.759 | 33.132 | 0.65 | 10.36 |
| 4020 | C | ARG | A | 262 | 44.791 | 26.291 | 35.084 | 1.00 | 11.78 |
| 4021 | O | ARG | A | 262 | 44.017 | 25.621 | 35.774 | 1.00 | 11.46 |
| 4022 | N | TYR | A | 263 | 44.524 | 27.536 | 34.688 | 1.00 | 11.46 |
| 4024 | CA | TYR | A | 263 | 43.266 | 28.179 | 35.045 | 1.00 | 11.47 |
| 4026 | CB | TYR | A | 263 | 43.215 | 29.652 | 34.609 | 1.00 | 11.44 |
| 4029 | CG | TYR | A | 263 | 41.906 | 30.284 | 35.023 | 1.00 | 11.19 |
| 4030 | CD1 | TYR | A | 263 | 40.896 | 30.507 | 34.097 | 1.00 | 11.41 |
| 4032 | CE1 | TYR | A | 263 | 39.679 | 31.043 | 34.483 | 1.00 | 11.15 |
| 4034 | CZ | TYR | A | 263 | 39.456 | 31.347 | 35.818 | 1.00 | 11.66 |
| 4035 | OH | TYR | A | 263 | 38.250 | 31.880 | 36.216 | 1.00 | 10.68 |
| 4037 | CE2 | TYR | A | 263 | 40.441 | 31.117 | 36.757 | 1.00 | 11.14 |
| 4039 | CD2 | TYR | A | 263 | 41.652 | 30.580 | 36.358 | 1.00 | 11.18 |
| 4041 | C | TYR | A | 263 | 42.066 | 27.409 | 34.476 | 1.00 | 11.45 |
| 4042 | O | TYR | A | 263 | 41.052 | 27.248 | 35.159 | 1.00 | 11.47 |
| 4043 | N | GLU | A | 264 | 42.183 | 26.928 | 33.240 | 1.00 | 11.46 |
| 4045 | CA | GLU | A | 264 | 41.103 | 26.158 | 32.616 | 1.00 | 11.61 |
| 4047 | CB | GLU | A | 264 | 41.455 | 25.778 | 31.173 | 1.00 | 11.89 |
| 4050 | CG | GLU | A | 264 | 41.466 | 26.937 | 30.192 | 1.00 | 12.94 |
| 4053 | CD | GLU | A | 264 | 40.132 | 27.656 | 30.111 | 1.00 | 14.36 |
| 4054 | OE1 | GLU | A | 264 | 40.060 | 28.824 | 30.552 | 1.00 | 15.08 |
| 4055 | OE2 | GLU | A | 264 | 39.157 | 27.051 | 29.616 | 1.00 | 15.17 |
| 4056 | C | GLU | A | 264 | 40.774 | 24.893 | 33.410 | 1.00 | 11.17 |
| 4057 | O | GLU | A | 264 | 39.614 | 24.500 | 33.505 | 1.00 | 11.03 |
| 4058 | N | GLU | A | 265 | 41.799 | 24.254 | 33.966 | 1.00 | 10.85 |
| 4060 | CA | GLU | A | 265 | 41.600 | 23.058 | 34.783 | 1.00 | 10.76 |
| 4062 | CB | GLU | A | 265 | 42.941 | 22.383 | 35.089 | 1.00 | 11.00 |
| 4065 | CG | GLU | A | 265 | 43.543 | 21.657 | 33.892 | 1.00 | 11.57 |
| 4068 | CD | GLU | A | 265 | 45.056 | 21.517 | 33.955 | 1.00 | 12.81 |
| 4069 | OE1 | GLU | A | 265 | 45.678 | 21.993 | 34.924 | 1.00 | 13.87 |
| 4070 | OE2 | GLU | A | 265 | 45.634 | 20.927 | 33.024 | 1.00 | 14.57 |
| 4071 | C | GLU | A | 265 | 40.867 | 23.392 | 36.080 | 1.00 | 10.42 |
| 4072 | O | GLU | A | 265 | 40.078 | 22.587 | 36.574 | 1.00 | 10.42 |
| 4073 | N | SER | A | 266 | 41.124 | 24.587 | 36.611 | 1.00 | 9.97 |
| 4075 | CA | SER | A | 266 | 40.501 | 25.050 | 37.848 | 1.00 | 9.70 |
| 4077 | CB | SER | A | 266 | 41.268 | 26.261 | 38.416 | 1.00 | 9.67 |
| 4080 | OG | SER | A | 266 | 40.864 | 27.483 | 37.816 | 1.00 | 9.01 |
| 4082 | C | SER | A | 266 | 39.012 | 25.382 | 37.685 | 1.00 | 9.58 |
| 4083 | O | SER | A | 266 | 38.284 | 25.399 | 38.667 | 1.00 | 9.63 |
| 4084 | N | ILE | A | 267 | 38.557 | 25.627 | 36.457 | 1.00 | 9.58 |
| 4086 | CA | ILE | A | 267 | 37.149 | 25.982 | 36.216 | 1.00 | 9.53 |
| 4088 | CB | ILE | A | 267 | 37.037 | 27.234 | 35.290 | 1.00 | 9.60 |
| 4090 | CG1 | ILE | A | 267 | 37.700 | 26.985 | 33.929 | 1.00 | 9.97 |
| 4093 | CD1 | ILE | A | 267 | 37.242 | 27.939 | 32.837 | 1.00 | 10.63 |
| 4097 | CG2 | ILE | A | 267 | 37.649 | 28.446 | 35.970 | 1.00 | 9.36 |
| 4101 | C | ILE | A | 267 | 36.266 | 24.842 | 35.681 | 1.00 | 9.32 |
| 4102 | O | ILE | A | 267 | 35.084 | 25.051 | 35.445 | 1.00 | 9.48 |
| 4103 | N | VAL | A | 268 | 36.820 | 23.644 | 35.515 | 1.00 | 9.59 |
| 4105 | CA | VAL | A | 268 | 36.061 | 22.513 | 34.971 | 1.00 | 9.51 |
| 4107 | CB | VAL | A | 268 | 36.902 | 21.213 | 34.945 | 1.00 | 9.57 |

FIGURE 3 (Cont.)

| A | B | C | D | E | F | G | H | I | J |
|---|---|---|---|---|---|---|---|---|---|
| 4109 | CG1 | VAL | A | 268 | 36.040 | 20.005 | 34.544 | 1.00 | 10.02 |
| 4113 | CG2 | VAL | A | 268 | 38.091 | 21.361 | 33.987 | 1.00 | 9.79 |
| 4117 | C | VAL | A | 268 | 34.755 | 22.279 | 35.748 | 1.00 | 9.45 |
| 4118 | O | VAL | A | 268 | 33.679 | 22.215 | 35.148 | 1.00 | 9.60 |
| 4119 | N | TYR | A | 269 | 34.848 | 22.171 | 37.072 | 1.00 | 9.19 |
| 4121 | CA | TYR | A | 269 | 33.670 | 21.926 | 37.907 | 1.00 | 9.07 |
| 4123 | CB | TYR | A | 269 | 34.074 | 21.504 | 39.329 | 1.00 | 9.21 |
| 4126 | CG | TYR | A | 269 | 34.731 | 20.135 | 39.459 | 1.00 | 9.43 |
| 4127 | CD1 | TYR | A | 269 | 35.500 | 19.824 | 40.578 | 1.00 | 10.23 |
| 4129 | CE1 | TYR | A | 269 | 36.105 | 18.576 | 40.717 | 1.00 | 9.75 |
| 4131 | CZ | TYR | A | 269 | 35.938 | 17.621 | 39.732 | 1.00 | 9.77 |
| 4132 | OH | TYR | A | 269 | 36.534 | 16.387 | 39.866 | 1.00 | 9.83 |
| 4134 | CE2 | TYR | A | 269 | 35.178 | 17.902 | 38.614 | 1.00 | 9.59 |
| 4136 | CD2 | TYR | A | 269 | 34.578 | 19.148 | 38.481 | 1.00 | 9.81 |
| 4138 | C | TYR | A | 269 | 32.743 | 23.144 | 37.969 | 1.00 | 9.12 |
| 4139 | O | TYR | A | 269 | 31.517 | 22.996 | 37.951 | 1.00 | 8.85 |
| 4140 | N | SER | A | 270 | 33.327 | 24.341 | 38.029 | 1.00 | 8.95 |
| 4142 | CA | SER | A | 270 | 32.549 | 25.580 | 38.119 | 1.00 | 9.04 |
| 4144 | CB | ASER | A | 270 | 33.463 | 26.800 | 38.285 | 0.65 | 8.83 |
| 4147 | OG | ASER | A | 270 | 33.873 | 26.944 | 39.631 | 0.65 | 8.28 |
| 4149 | C | SER | A | 270 | 31.645 | 25.772 | 36.903 | 1.00 | 9.50 |
| 4150 | O | SER | A | 270 | 30.571 | 26.355 | 37.018 | 1.00 | 9.48 |
| 4151 | N | ARG | A | 271 | 32.073 | 25.269 | 35.746 | 1.00 | 9.75 |
| 4153 | CA | ARG | A | 271 | 31.258 | 25.337 | 34.535 | 1.00 | 10.20 |
| 4155 | CB | ARG | A | 271 | 32.033 | 24.822 | 33.319 | 1.00 | 10.52 |
| 4158 | CG | ARG | A | 271 | 33.219 | 25.682 | 32.902 | 1.00 | 12.04 |
| 4161 | CD | ARG | A | 271 | 33.860 | 25.233 | 31.593 | 1.00 | 14.32 |
| 4164 | NE | ARG | A | 271 | 32.938 | 25.434 | 30.477 | 1.00 | 16.57 |
| 4166 | CZ | ARG | A | 271 | 32.807 | 26.571 | 29.793 | 1.00 | 17.38 |
| 4167 | NH1 | ARG | A | 271 | 33.573 | 27.625 | 30.048 | 1.00 | 18.13 |
| 4170 | NH2 | ARG | A | 271 | 31.905 | 26.645 | 28.826 | 1.00 | 18.27 |
| 4173 | C | ARG | A | 271 | 29.969 | 24.530 | 34.689 | 1.00 | 9.90 |
| 4174 | O | ARG | A | 271 | 29.004 | 24.782 | 33.990 | 1.00 | 9.82 |
| 4175 | N | ARG | A | 272 | 29.969 | 23.553 | 35.593 | 1.00 | 9.79 |
| 4177 | CA | ARG | A | 272 | 28.801 | 22.707 | 35.834 | 1.00 | 9.64 |
| 4179 | CB | ARG | A | 272 | 29.247 | 21.250 | 35.950 | 1.00 | 9.58 |
| 4182 | CG | ARG | A | 272 | 30.072 | 20.753 | 34.776 | 1.00 | 10.52 |
| 4185 | CD | ARG | A | 272 | 30.495 | 19.301 | 34.917 | 1.00 | 11.34 |
| 4188 | NE | ARG | A | 272 | 29.333 | 18.410 | 34.908 | 1.00 | 11.95 |
| 4190 | CZ | ARG | A | 272 | 29.371 | 17.113 | 35.195 | 1.00 | 13.18 |
| 4191 | NH1 | ARG | A | 272 | 30.513 | 16.516 | 35.523 | 1.00 | 13.54 |
| 4194 | NH2 | ARG | A | 272 | 28.252 | 16.402 | 35.148 | 1.00 | 13.69 |
| 4197 | C | ARG | A | 272 | 27.990 | 23.090 | 37.081 | 1.00 | 9.50 |
| 4198 | O | ARG | A | 272 | 26.998 | 22.438 | 37.388 | 1.00 | 9.30 |
| 4199 | N | VAL | A | 273 | 28.386 | 24.156 | 37.774 | 1.00 | 9.32 |
| 4201 | CA | VAL | A | 273 | 27.826 | 24.484 | 39.089 | 1.00 | 9.24 |
| 4203 | CB | VAL | A | 273 | 28.836 | 24.123 | 40.196 | 1.00 | 9.06 |
| 4205 | CG1 | VAL | A | 273 | 28.420 | 24.710 | 41.546 | 1.00 | 9.50 |
| 4209 | CG2 | VAL | A | 273 | 28.980 | 22.606 | 40.291 | 1.00 | 9.79 |
| 4213 | C | VAL | A | 273 | 27.424 | 25.953 | 39.217 | 1.00 | 9.00 |
| 4214 | O | VAL | A | 273 | 26.290 | 26.261 | 39.587 | 1.00 | 8.83 |
| 4215 | N | GLY | A | 274 | 28.365 | 26.849 | 38.936 | 1.00 | 8.89 |
| 4217 | CA | GLY | A | 274 | 28.133 | 28.281 | 39.022 | 1.00 | 8.88 |

FIGURE 3 (Cont.)

| A | B | C | D | E | F | G | H | I | J |
|---|---|---|---|---|---|---|---|---|---|
| 4220 | C | GLY | A | 274 | 28.753 | 28.841 | 40.286 | 1.00 | 8.84 |
| 4221 | O | GLY | A | 274 | 29.564 | 28.175 | 40.930 | 1.00 | 8.79 |
| 4222 | N | ASN | A | 275 | 28.362 | 30.061 | 40.645 | 1.00 | 8.87 |
| 4224 | CA | ASN | A | 275 | 28.916 | 30.746 | 41.812 | 1.00 | 8.85 |
| 4226 | CB | ASN | A | 275 | 28.529 | 32.235 | 41.792 | 1.00 | 8.70 |
| 4229 | CG | ASN | A | 275 | 29.463 | 33.115 | 42.622 | 1.00 | 8.94 |
| 4230 | OD1 | ASN | A | 275 | 30.262 | 32.625 | 43.425 | 1.00 | 8.05 |
| 4231 | ND2 | ASN | A | 275 | 29.361 | 34.437 | 42.424 | 1.00 | 7.58 |
| 4234 | C | ASN | A | 275 | 28.450 | 30.093 | 43.119 | 1.00 | 8.92 |
| 4235 | O | ASN | A | 275 | 27.251 | 29.995 | 43.380 | 1.00 | 8.75 |
| 4236 | N | LEU | A | 276 | 29.414 | 29.644 | 43.921 | 1.00 | 9.21 |
| 4238 | CA | LEU | A | 276 | 29.176 | 29.155 | 45.282 | 1.00 | 9.50 |
| 4240 | CB | LEU | A | 276 | 30.065 | 27.934 | 45.569 | 1.00 | 9.87 |
| 4243 | CG | LEU | A | 276 | 29.846 | 26.664 | 44.750 | 1.00 | 11.31 |
| 4245 | CD1 | LEU | A | 276 | 30.542 | 25.486 | 45.425 | 1.00 | 12.59 |
| 4249 | CD2 | LEU | A | 276 | 28.376 | 26.373 | 44.601 | 1.00 | 12.44 |
| 4253 | C | LEU | A | 276 | 29.486 | 30.233 | 46.325 | 1.00 | 9.08 |
| 4254 | O | LEU | A | 276 | 29.597 | 29.935 | 47.514 | 1.00 | 8.62 |
| 4255 | N | TYR | A | 277 | 29.593 | 31.481 | 45.874 | 1.00 | 8.74 |
| 4257 | CA | TYR | A | 277 | 30.076 | 32.597 | 46.689 | 1.00 | 8.39 |
| 4259 | CB | TYR | A | 277 | 28.962 | 33.122 | 47.617 | 1.00 | 8.37 |
| 4262 | CG | TYR | A | 277 | 27.861 | 33.966 | 46.969 | 1.00 | 8.51 |
| 4263 | CD1 | TYR | A | 277 | 28.043 | 34.605 | 45.739 | 1.00 | 8.90 |
| 4265 | CE1 | TYR | A | 277 | 27.033 | 35.382 | 45.172 | 1.00 | 8.79 |
| 4267 | CZ | TYR | A | 277 | 25.827 | 35.521 | 45.826 | 1.00 | 8.70 |
| 4268 | OH | TYR | A | 277 | 24.829 | 36.282 | 45.262 | 1.00 | 9.50 |
| 4270 | CE2 | TYR | A | 277 | 25.618 | 34.898 | 47.042 | 1.00 | 8.82 |
| 4272 | CD2 | TYR | A | 277 | 26.631 | 34.126 | 47.606 | 1.00 | 8.40 |
| 4274 | C | TYR | A | 277 | 31.363 | 32.254 | 47.474 | 1.00 | 8.10 |
| 4275 | O | TYR | A | 277 | 32.440 | 32.175 | 46.879 | 1.00 | 8.20 |
| 4276 | N | THR | A | 278 | 31.265 | 32.054 | 48.790 | 1.00 | 7.83 |
| 4278 | CA | THR | A | 278 | 32.447 | 31.790 | 49.619 | 1.00 | 7.68 |
| 4280 | CB | THR | A | 278 | 32.081 | 31.570 | 51.110 | 1.00 | 7.53 |
| 4282 | OG1 | THR | A | 278 | 31.009 | 30.624 | 51.226 | 1.00 | 6.29 |
| 4284 | CG2 | THR | A | 278 | 31.566 | 32.858 | 51.771 | 1.00 | 7.58 |
| 4288 | C | THR | A | 278 | 33.214 | 30.568 | 49.135 | 1.00 | 7.95 |
| 4289 | O | THR | A | 278 | 34.437 | 30.517 | 49.241 | 1.00 | 8.42 |
| 4290 | N | GLY | A | 279 | 32.481 | 29.585 | 48.621 | 1.00 | 8.08 |
| 4292 | CA | GLY | A | 279 | 33.049 | 28.320 | 48.204 | 1.00 | 8.20 |
| 4295 | C | GLY | A | 279 | 33.725 | 28.289 | 46.848 | 1.00 | 8.28 |
| 4296 | O | GLY | A | 279 | 34.439 | 27.334 | 46.570 | 1.00 | 8.35 |
| 4297 | N | SER | A | 280 | 33.532 | 29.316 | 46.020 | 1.00 | 8.21 |
| 4299 | CA | SER | A | 280 | 33.980 | 29.271 | 44.623 | 1.00 | 8.21 |
| 4301 | CB | SER | A | 280 | 33.554 | 30.532 | 43.873 | 1.00 | 8.03 |
| 4304 | OG | SER | A | 280 | 32.147 | 30.651 | 43.841 | 1.00 | 8.53 |
| 4306 | C | SER | A | 280 | 35.482 | 29.067 | 44.443 | 1.00 | 8.10 |
| 4307 | O | SER | A | 280 | 35.895 | 28.262 | 43.611 | 1.00 | 7.89 |
| 4308 | N | LEU | A | 281 | 36.288 | 29.812 | 45.200 | 1.00 | 8.23 |
| 4310 | CA | LEU | A | 281 | 37.746 | 29.672 | 45.166 | 1.00 | 8.11 |
| 4312 | CB | LEU | A | 281 | 38.425 | 30.620 | 46.168 | 1.00 | 8.18 |
| 4315 | CG | LEU | A | 281 | 39.923 | 30.393 | 46.441 | 1.00 | 8.38 |
| 4317 | CD1 | LEU | A | 281 | 40.747 | 30.579 | 45.174 | 1.00 | 8.36 |
| 4321 | CD2 | LEU | A | 281 | 40.437 | 31.313 | 47.538 | 1.00 | 8.23 |

FIGURE 3 (Cont.)

| A | B | C | D | E | F | G | H | I | J |
|---|---|---|---|---|---|---|---|---|---|
| 4325 | C | LEU | A | 281 | 38.147 | 28.240 | 45.484 | 1.00 | 8.25 |
| 4326 | O | LEU | A | 281 | 39.031 | 27.676 | 44.843 | 1.00 | 7.91 |
| 4327 | N | TYR | A | 282 | 37.489 | 27.662 | 46.481 | 1.00 | 8.36 |
| 4329 | CA | TYR | A | 282 | 37.851 | 26.337 | 46.972 | 1.00 | 8.55 |
| 4331 | CB | TYR | A | 282 | 37.457 | 26.212 | 48.452 | 1.00 | 8.56 |
| 4334 | CG | TYR | A | 282 | 38.166 | 27.302 | 49.215 | 1.00 | 9.12 |
| 4335 | CD1 | TYR | A | 282 | 39.547 | 27.244 | 49.396 | 1.00 | 9.10 |
| 4337 | CE1 | TYR | A | 282 | 40.231 | 28.258 | 50.029 | 1.00 | 9.11 |
| 4339 | CZ | TYR | A | 282 | 39.548 | 29.372 | 50.473 | 1.00 | 8.49 |
| 4340 | OH | TYR | A | 282 | 40.256 | 30.364 | 51.101 | 1.00 | 9.74 |
| 4342 | CE2 | TYR | A | 282 | 38.176 | 29.479 | 50.287 | 1.00 | 8.84 |
| 4344 | CD2 | TYR | A | 282 | 37.493 | 28.449 | 49.641 | 1.00 | 9.17 |
| 4346 | C | TYR | A | 282 | 37.329 | 25.212 | 46.075 | 1.00 | 8.52 |
| 4347 | O | TYR | A | 282 | 37.946 | 24.157 | 46.000 | 1.00 | 8.50 |
| 4348 | N | LEU | A | 283 | 36.237 | 25.455 | 45.356 | 1.00 | 8.61 |
| 4350 | CA | LEU | A | 283 | 35.784 | 24.528 | 44.324 | 1.00 | 8.58 |
| 4352 | CB | LEU | A | 283 | 34.409 | 24.928 | 43.777 | 1.00 | 8.52 |
| 4355 | CG | LEU | A | 283 | 33.858 | 24.075 | 42.627 | 1.00 | 8.62 |
| 4357 | CD1 | LEU | A | 283 | 33.607 | 22.644 | 43.087 | 1.00 | 8.94 |
| 4361 | CD2 | LEU | A | 283 | 32.573 | 24.690 | 42.056 | 1.00 | 8.73 |
| 4365 | C | LEU | A | 283 | 36.812 | 24.524 | 43.202 | 1.00 | 8.52 |
| 4366 | O | LEU | A | 283 | 37.115 | 23.481 | 42.637 | 1.00 | 8.44 |
| 4367 | N | GLY | A | 284 | 37.355 | 25.698 | 42.896 | 1.00 | 8.64 |
| 4369 | CA | GLY | A | 284 | 38.396 | 25.818 | 41.898 | 1.00 | 8.70 |
| 4372 | C | GLY | A | 284 | 39.663 | 25.077 | 42.282 | 1.00 | 8.71 |
| 4373 | O | GLY | A | 284 | 40.315 | 24.495 | 41.422 | 1.00 | 8.58 |
| 4374 | N | LEU | A | 285 | 40.008 | 25.091 | 43.568 | 1.00 | 8.84 |
| 4376 | CA | LEU | A | 285 | 41.163 | 24.346 | 44.060 | 1.00 | 8.71 |
| 4378 | CB | LEU | A | 285 | 41.435 | 24.656 | 45.535 | 1.00 | 8.87 |
| 4381 | CG | LEU | A | 285 | 42.538 | 23.833 | 46.214 | 1.00 | 8.94 |
| 4383 | CD1 | LEU | A | 285 | 43.886 | 24.050 | 45.535 | 1.00 | 9.39 |
| 4387 | CD2 | LEU | A | 285 | 42.623 | 24.168 | 47.683 | 1.00 | 8.77 |
| 4391 | C | LEU | A | 285 | 40.941 | 22.851 | 43.872 | 1.00 | 8.67 |
| 4392 | O | LEU | A | 285 | 41.832 | 22.147 | 43.404 | 1.00 | 8.45 |
| 4393 | N | ILE | A | 286 | 39.752 | 22.374 | 44.232 | 1.00 | 8.66 |
| 4395 | CA | ILE | A | 286 | 39.410 | 20.958 | 44.072 | 1.00 | 8.64 |
| 4397 | CB | ILE | A | 286 | 37.997 | 20.654 | 44.632 | 1.00 | 8.70 |
| 4399 | CG1 | ILE | A | 286 | 37.943 | 20.852 | 46.148 | 1.00 | 9.02 |
| 4402 | CD1 | ILE | A | 286 | 36.532 | 20.771 | 46.708 | 1.00 | 9.27 |
| 4406 | CG2 | ILE | A | 286 | 37.583 | 19.224 | 44.278 | 1.00 | 9.03 |
| 4410 | C | ILE | A | 286 | 39.444 | 20.570 | 42.594 | 1.00 | 8.40 |
| 4411 | O | ILE | A | 286 | 39.951 | 19.509 | 42.230 | 1.00 | 8.45 |
| 4412 | N | SER | A | 287 | 38.883 | 21.428 | 41.752 | 1.00 | 8.38 |
| 4414 | CA | SER | A | 287 | 38.788 | 21.160 | 40.322 | 1.00 | 8.50 |
| 4416 | CB | SER | A | 287 | 37.970 | 22.245 | 39.621 | 1.00 | 8.63 |
| 4419 | OG | SER | A | 287 | 37.865 | 21.986 | 38.228 | 1.00 | 8.70 |
| 4421 | C | SER | A | 287 | 40.178 | 21.085 | 39.713 | 1.00 | 8.70 |
| 4422 | O | SER | A | 287 | 40.451 | 20.222 | 38.876 | 1.00 | 8.70 |
| 4423 | N | LEU | A | 288 | 41.055 | 21.979 | 40.155 | 1.00 | 8.70 |
| 4425 | CA | LEU | A | 288 | 42.425 | 22.024 | 39.681 | 1.00 | 9.02 |
| 4427 | CB | LEU | A | 288 | 43.173 | 23.189 | 40.334 | 1.00 | 9.08 |
| 4430 | CG | LEU | A | 288 | 44.664 | 23.318 | 40.020 | 1.00 | 9.63 |
| 4432 | CD1 | LEU | A | 288 | 44.880 | 23.628 | 38.541 | 1.00 | 9.47 |

FIGURE 3 (Cont.)

| A | B | C | D | E | F | G | H | I | J |
|---|---|---|---|---|---|---|---|---|---|
| 4436 | CD2 | LEU | A | 288 | 45.284 | 24.389 | 40.904 | 1.00 | 10.42 |
| 4440 | C | LEU | A | 288 | 43.135 | 20.711 | 39.989 | 1.00 | 9.00 |
| 4441 | O | LEU | A | 288 | 43.756 | 20.120 | 39.115 | 1.00 | 8.91 |
| 4442 | N | LEU | A | 289 | 43.031 | 20.254 | 41.232 | 1.00 | 9.02 |
| 4444 | CA | LEU | A | 289 | 43.750 | 19.059 | 41.665 | 1.00 | 9.24 |
| 4446 | CB | LEU | A | 289 | 43.780 | 18.966 | 43.193 | 1.00 | 9.31 |
| 4449 | CG | LEU | A | 289 | 44.371 | 20.182 | 43.921 | 1.00 | 9.40 |
| 4451 | CD1 | LEU | A | 289 | 44.594 | 19.863 | 45.377 | 1.00 | 9.52 |
| 4455 | CD2 | LEU | A | 289 | 45.671 | 20.678 | 43.276 | 1.00 | 9.44 |
| 4459 | C | LEU | A | 289 | 43.166 | 17.785 | 41.071 | 1.00 | 9.34 |
| 4460 | O | LEU | A | 289 | 43.903 | 16.839 | 40.820 | 1.00 | 9.59 |
| 4461 | N | GLU | A | 290 | 41.857 | 17.765 | 40.825 | 1.00 | 9.47 |
| 4463 | CA | GLU | A | 290 | 41.193 | 16.559 | 40.319 | 1.00 | 9.89 |
| 4465 | CB | GLU | A | 290 | 39.779 | 16.424 | 40.910 | 1.00 | 9.82 |
| 4468 | CG | GLU | A | 290 | 39.822 | 15.948 | 42.354 | 1.00 | 9.67 |
| 4471 | CD | GLU | A | 290 | 38.479 | 15.927 | 43.059 | 1.00 | 10.11 |
| 4472 | OE1 | GLU | A | 290 | 37.433 | 16.076 | 42.401 | 1.00 | 9.35 |
| 4473 | OE2 | GLU | A | 290 | 38.478 | 15.756 | 44.299 | 1.00 | 9.95 |
| 4474 | C | GLU | A | 290 | 41.178 | 16.476 | 38.791 | 1.00 | 10.33 |
| 4475 | O | GLU | A | 290 | 40.897 | 15.414 | 38.233 | 1.00 | 10.92 |
| 4476 | N | ASN | A | 291 | 41.521 | 17.572 | 38.115 | 1.00 | 10.64 |
| 4478 | CA | ASN | A | 291 | 41.537 | 17.598 | 36.650 | 1.00 | 11.20 |
| 4480 | CB | ASN | A | 291 | 40.564 | 18.658 | 36.125 | 1.00 | 10.92 |
| 4483 | CG | ASN | A | 291 | 39.116 | 18.277 | 36.353 | 1.00 | 11.08 |
| 4484 | OD1 | ASN | A | 291 | 38.585 | 17.389 | 35.676 | 1.00 | 10.76 |
| 4485 | ND2 | ASN | A | 291 | 38.464 | 18.940 | 37.314 | 1.00 | 9.82 |
| 4488 | C | ASN | A | 291 | 42.924 | 17.789 | 36.022 | 1.00 | 11.68 |
| 4489 | O | ASN | A | 291 | 43.101 | 17.535 | 34.831 | 1.00 | 12.13 |
| 4490 | N | ALA | A | 292 | 43.904 | 18.223 | 36.810 | 1.00 | 12.16 |
| 4492 | CA | ALA | A | 292 | 45.266 | 18.396 | 36.308 | 1.00 | 12.58 |
| 4494 | CB | ALA | A | 292 | 46.092 | 19.220 | 37.277 | 1.00 | 12.39 |
| 4498 | C | ALA | A | 292 | 45.928 | 17.037 | 36.070 | 1.00 | 12.93 |
| 4499 | O | ALA | A | 292 | 45.578 | 16.044 | 36.714 | 1.00 | 13.31 |
| 4500 | N | THR | A | 293 | 46.862 | 16.995 | 35.125 | 1.00 | 13.24 |
| 4502 | CA | THR | A | 293 | 47.683 | 15.806 | 34.898 | 1.00 | 13.57 |
| 4504 | CB | THR | A | 293 | 47.458 | 15.261 | 33.474 | 1.00 | 13.57 |
| 4506 | OG1 | THR | A | 293 | 47.817 | 16.253 | 32.502 | 1.00 | 13.65 |
| 4508 | CG2 | THR | A | 293 | 45.967 | 14.995 | 33.213 | 1.00 | 13.56 |
| 4512 | C | THR | A | 293 | 49.181 | 16.042 | 35.136 | 1.00 | 13.82 |
| 4513 | O | THR | A | 293 | 49.942 | 15.075 | 35.216 | 1.00 | 14.12 |
| 4514 | N | THR | A | 294 | 49.597 | 17.307 | 35.264 | 1.00 | 13.87 |
| 4516 | CA | THR | A | 294 | 51.015 | 17.664 | 35.405 | 1.00 | 13.84 |
| 4518 | CB | THR | A | 294 | 51.447 | 18.646 | 34.290 | 1.00 | 14.00 |
| 4520 | OG1 | THR | A | 294 | 50.733 | 19.879 | 34.416 | 1.00 | 13.79 |
| 4522 | CG2 | THR | A | 294 | 51.068 | 18.131 | 32.905 | 1.00 | 14.47 |
| 4526 | C | THR | A | 294 | 51.382 | 18.275 | 36.767 | 1.00 | 13.69 |
| 4527 | O | THR | A | 294 | 52.557 | 18.566 | 37.014 | 1.00 | 13.89 |
| 4528 | N | LEU | A | 295 | 50.399 | 18.482 | 37.640 | 1.00 | 13.12 |
| 4530 | CA | LEU | A | 295 | 50.688 | 18.908 | 39.005 | 1.00 | 12.78 |
| 4532 | CB | LEU | A | 295 | 49.449 | 19.513 | 39.673 | 1.00 | 12.73 |
| 4535 | CG | LEU | A | 295 | 48.997 | 20.871 | 39.137 | 1.00 | 12.56 |
| 4537 | CD1 | LEU | A | 295 | 50.092 | 21.924 | 39.292 | 1.00 | 12.76 |
| 4541 | CD2 | LEU | A | 295 | 47.723 | 21.316 | 39.835 | 1.00 | 12.97 |

FIGURE 3 (Cont.)

| A | B | C | D | E | F | G | H | I | J |
|---|---|---|---|---|---|---|---|---|---|
| 4545 | C | LEU | A | 295 | 51.214 | 17.728 | 39.825 | 1.00 | 12.71 |
| 4546 | O | LEU | A | 295 | 50.805 | 16.579 | 39.630 | 1.00 | 12.26 |
| 4547 | N | THR | A | 296 | 52.121 | 18.030 | 40.747 | 1.00 | 12.72 |
| 4549 | CA | THR | A | 296 | 52.761 | 17.021 | 41.578 | 1.00 | 12.77 |
| 4551 | CB | THR | A | 296 | 53.936 | 16.365 | 40.799 | 1.00 | 13.01 |
| 4553 | OG1 | THR | A | 296 | 54.442 | 15.242 | 41.528 | 1.00 | 13.56 |
| 4555 | CG2 | THR | A | 296 | 55.137 | 17.304 | 40.674 | 1.00 | 13.30 |
| 4559 | C | THR | A | 296 | 53.234 | 17.621 | 42.902 | 1.00 | 12.58 |
| 4560 | O | THR | A | 296 | 53.312 | 18.843 | 43.049 | 1.00 | 12.37 |
| 4561 | N | ALA | A | 297 | 53.533 | 16.753 | 43.863 | 1.00 | 12.15 |
| 4563 | CA | ALA | A | 297 | 54.014 | 17.173 | 45.181 | 1.00 | 12.17 |
| 4565 | CB | ALA | A | 297 | 54.411 | 15.953 | 46.004 | 1.00 | 12.24 |
| 4569 | C | ALA | A | 297 | 55.192 | 18.137 | 45.074 | 1.00 | 12.03 |
| 4570 | O | ALA | A | 297 | 56.084 | 17.944 | 44.246 | 1.00 | 11.87 |
| 4571 | N | GLY | A | 298 | 55.176 | 19.179 | 45.902 | 1.00 | 11.72 |
| 4573 | CA | GLY | A | 298 | 56.208 | 20.203 | 45.893 | 1.00 | 11.69 |
| 4576 | C | GLY | A | 298 | 55.806 | 21.457 | 45.135 | 1.00 | 11.49 |
| 4577 | O | GLY | A | 298 | 56.389 | 22.521 | 45.352 | 1.00 | 11.72 |
| 4578 | N | ASN | A | 299 | 54.816 | 21.334 | 44.252 | 1.00 | 11.26 |
| 4580 | CA | ASN | A | 299 | 54.354 | 22.449 | 43.422 | 1.00 | 11.14 |
| 4582 | CB | ASN | A | 299 | 53.321 | 21.976 | 42.383 | 1.00 | 10.93 |
| 4585 | CG | ASN | A | 299 | 53.940 | 21.226 | 41.194 | 1.00 | 11.89 |
| 4586 | OD1 | ASN | A | 299 | 53.210 | 20.785 | 40.302 | 1.00 | 12.20 |
| 4587 | ND2 | ASN | A | 299 | 55.267 | 21.084 | 41.170 | 1.00 | 11.78 |
| 4590 | C | ASN | A | 299 | 53.725 | 23.558 | 44.268 | 1.00 | 10.95 |
| 4591 | O | ASN | A | 299 | 53.098 | 23.287 | 45.295 | 1.00 | 10.82 |
| 4592 | N | GLN | A | 300 | 53.893 | 24.801 | 43.820 | 1.00 | 10.62 |
| 4594 | CA | GLN | A | 300 | 53.370 | 25.978 | 44.503 | 1.00 | 10.59 |
| 4596 | CB | GLN | A | 300 | 54.389 | 27.125 | 44.450 | 1.00 | 10.64 |
| 4599 | CG | GLN | A | 300 | 55.800 | 26.744 | 44.912 | 1.00 | 10.75 |
| 4602 | CD | GLN | A | 300 | 55.848 | 26.350 | 46.372 | 1.00 | 10.79 |
| 4603 | OE1 | GLN | A | 300 | 55.566 | 27.168 | 47.250 | 1.00 | 11.66 |
| 4604 | NE2 | GLN | A | 300 | 56.205 | 25.102 | 46.640 | 1.00 | 10.15 |
| 4607 | C | GLN | A | 300 | 52.060 | 26.429 | 43.860 | 1.00 | 10.45 |
| 4608 | O | GLN | A | 300 | 52.006 | 26.662 | 42.655 | 1.00 | 10.12 |
| 4609 | N | ILE | A | 301 | 51.012 | 26.531 | 44.675 | 1.00 | 10.19 |
| 4611 | CA | ILE | A | 301 | 49.695 | 26.983 | 44.244 | 1.00 | 10.27 |
| 4613 | CB | ILE | A | 301 | 48.601 | 25.960 | 44.671 | 1.00 | 10.29 |
| 4615 | CG1 | ILE | A | 301 | 49.012 | 24.522 | 44.319 | 1.00 | 10.32 |
| 4618 | CD1 | ILE | A | 301 | 49.292 | 24.282 | 42.841 | 1.00 | 10.76 |
| 4622 | CG2 | ILE | A | 301 | 47.264 | 26.303 | 44.035 | 1.00 | 10.38 |
| 4626 | C | ILE | A | 301 | 49.404 | 28.335 | 44.882 | 1.00 | 10.08 |
| 4627 | O | ILE | A | 301 | 49.353 | 28.444 | 46.103 | 1.00 | 9.85 |
| 4628 | N | GLY | A | 302 | 49.244 | 29.368 | 44.063 | 1.00 | 9.94 |
| 4630 | CA | GLY | A | 302 | 48.768 | 30.654 | 44.535 | 1.00 | 9.95 |
| 4633 | C | GLY | A | 302 | 47.250 | 30.694 | 44.527 | 1.00 | 9.87 |
| 4634 | O | GLY | A | 302 | 46.619 | 30.141 | 43.634 | 1.00 | 9.95 |
| 4635 | N | LEU | A | 303 | 46.666 | 31.361 | 45.514 | 1.00 | 9.87 |
| 4637 | CA | LEU | A | 303 | 45.217 | 31.467 | 45.639 | 1.00 | 9.75 |
| 4639 | CB | LEU | A | 303 | 44.718 | 30.632 | 46.814 | 1.00 | 10.07 |
| 4642 | CG | LEU | A | 303 | 44.939 | 29.121 | 46.714 | 1.00 | 10.40 |
| 4644 | CD1 | LEU | A | 303 | 46.155 | 28.711 | 47.502 | 1.00 | 11.23 |
| 4648 | CD2 | LEU | A | 303 | 43.718 | 28.365 | 47.206 | 1.00 | 11.26 |

FIGURE 3 (Cont.)

| A | B | C | D | E | F | G | H | I | J |
|---|---|---|---|---|---|---|---|---|---|
| 4652 | C | LEU | A | 303 | 44.815 | 32.916 | 45.852 | 1.00 | 9.66 |
| 4653 | O | LEU | A | 303 | 45.345 | 33.577 | 46.737 | 1.00 | 9.54 |
| 4654 | N | PHE | A | 304 | 43.877 | 33.397 | 45.038 | 1.00 | 9.37 |
| 4656 | CA | PHE | A | 304 | 43.315 | 34.733 | 45.181 | 1.00 | 9.15 |
| 4658 | CB | PHE | A | 304 | 43.346 | 35.488 | 43.852 | 1.00 | 9.07 |
| 4661 | CG | PHE | A | 304 | 42.619 | 36.804 | 43.900 | 1.00 | 8.84 |
| 4662 | CD1 | PHE | A | 304 | 41.452 | 37.000 | 43.176 | 1.00 | 9.28 |
| 4664 | CE1 | PHE | A | 304 | 40.781 | 38.216 | 43.228 | 1.00 | 9.27 |
| 4666 | CZ | PHE | A | 304 | 41.271 | 39.243 | 44.020 | 1.00 | 8.92 |
| 4668 | CE2 | PHE | A | 304 | 42.424 | 39.053 | 44.750 | 1.00 | 9.41 |
| 4670 | CD2 | PHE | A | 304 | 43.090 | 37.835 | 44.693 | 1.00 | 9.35 |
| 4672 | C | PHE | A | 304 | 41.873 | 34.641 | 45.647 | 1.00 | 8.91 |
| 4673 | O | PHE | A | 304 | 41.011 | 34.139 | 44.916 | 1.00 | 8.83 |
| 4674 | N | SER | A | 305 | 41.617 | 35.111 | 46.866 | 1.00 | 8.69 |
| 4676 | CA | SER | A | 305 | 40.268 | 35.189 | 47.405 | 1.00 | 8.71 |
| 4678 | CB | SER | A | 305 | 40.250 | 34.761 | 48.872 | 1.00 | 8.91 |
| 4681 | OG | SER | A | 305 | 38.925 | 34.760 | 49.378 | 1.00 | 8.85 |
| 4683 | C | SER | A | 305 | 39.745 | 36.615 | 47.282 | 1.00 | 8.74 |
| 4684 | O | SER | A | 305 | 40.464 | 37.575 | 47.560 | 1.00 | 8.40 |
| 4685 | N | TYR | A | 306 | 38.495 | 36.746 | 46.854 | 1.00 | 8.84 |
| 4687 | CA | TYR | A | 306 | 37.836 | 38.042 | 46.776 | 1.00 | 8.90 |
| 4689 | CB | TYR | A | 306 | 37.658 | 38.473 | 45.315 | 1.00 | 9.03 |
| 4692 | CG | TYR | A | 306 | 36.989 | 39.829 | 45.150 | 1.00 | 8.97 |
| 4693 | CD1 | TYR | A | 306 | 35.622 | 39.930 | 44.890 | 1.00 | 9.44 |
| 4695 | CE1 | TYR | A | 306 | 35.005 | 41.169 | 44.741 | 1.00 | 9.01 |
| 4697 | CZ | TYR | A | 306 | 35.757 | 42.327 | 44.845 | 1.00 | 9.46 |
| 4698 | OH | TYR | A | 306 | 35.154 | 43.564 | 44.693 | 1.00 | 9.46 |
| 4700 | CE2 | TYR | A | 306 | 37.117 | 42.251 | 45.096 | 1.00 | 9.35 |
| 4702 | CD2 | TYR | A | 306 | 37.725 | 41.008 | 45.248 | 1.00 | 9.15 |
| 4704 | C | TYR | A | 306 | 36.476 | 38.003 | 47.457 | 1.00 | 9.03 |
| 4705 | O | TYR | A | 306 | 35.757 | 37.008 | 47.389 | 1.00 | 8.97 |
| 4706 | N | GLY | A | 307 | 36.139 | 39.113 | 48.103 | 1.00 | 8.79 |
| 4708 | CA | GLY | A | 307 | 34.822 | 39.338 | 48.658 | 1.00 | 8.63 |
| 4711 | C | GLY | A | 307 | 34.418 | 40.763 | 48.335 | 1.00 | 8.73 |
| 4712 | O | GLY | A | 307 | 35.178 | 41.699 | 48.577 | 1.00 | 8.53 |
| 4713 | N | SER | A | 308 | 33.230 | 40.933 | 47.769 | 1.00 | 8.82 |
| 4715 | CA | SER | A | 308 | 32.736 | 42.255 | 47.414 | 1.00 | 8.77 |
| 4717 | CB | SER | A | 308 | 31.406 | 42.145 | 46.676 | 1.00 | 8.84 |
| 4720 | OG | SER | A | 308 | 31.615 | 41.873 | 45.297 | 1.00 | 9.01 |
| 4722 | C | SER | A | 308 | 32.585 | 43.092 | 48.680 | 1.00 | 8.82 |
| 4723 | O | SER | A | 308 | 32.346 | 42.548 | 49.759 | 1.00 | 8.61 |
| 4724 | N | GLY | A | 309 | 32.771 | 44.407 | 48.564 | 1.00 | 8.95 |
| 4726 | CA | GLY | A | 309 | 32.613 | 45.286 | 49.709 | 1.00 | 9.08 |
| 4729 | C | GLY | A | 309 | 33.721 | 46.267 | 50.073 | 1.00 | 9.19 |
| 4730 | O | GLY | A | 309 | 33.384 | 47.328 | 50.599 | 1.00 | 9.59 |
| 4731 | N | ALA | A | 310 | 35.010 | 45.979 | 49.856 | 1.00 | 9.12 |
| 4733 | CA | ALA | A | 310 | 35.550 | 44.743 | 49.295 | 1.00 | 9.06 |
| 4735 | CB | ALA | A | 310 | 35.854 | 44.925 | 47.801 | 1.00 | 9.22 |
| 4739 | C | ALA | A | 310 | 36.828 | 44.338 | 50.028 | 1.00 | 8.95 |
| 4740 | O | ALA | A | 310 | 37.618 | 45.190 | 50.435 | 1.00 | 8.64 |
| 4741 | N | VAL | A | 311 | 37.023 | 43.032 | 50.184 | 1.00 | 8.73 |
| 4743 | CA | VAL | A | 311 | 38.198 | 42.476 | 50.842 | 1.00 | 8.86 |
| 4745 | CB | VAL | A | 311 | 37.814 | 41.884 | 52.209 | 1.00 | 8.75 |

FIGURE 3 (Cont.)

| A | B | C | D | E | F | G | H | I | J |
|---|---|---|---|---|---|---|---|---|---|
| 4747 | CG1 | VAL | A | 311 | 39.012 | 41.211 | 52.890 | 1.00 | 8.70 |
| 4751 | CG2 | VAL | A | 311 | 37.218 | 42.978 | 53.098 | 1.00 | 8.85 |
| 4755 | C | VAL | A | 311 | 38.815 | 41.393 | 49.957 | 1.00 | 8.91 |
| 4756 | O | VAL | A | 311 | 38.101 | 40.587 | 49.380 | 1.00 | 9.22 |
| 4757 | N | ALA | A | 312 | 40.137 | 41.381 | 49.843 | 1.00 | 9.19 |
| 4759 | CA | ALA | A | 312 | 40.828 | 40.345 | 49.078 | 1.00 | 9.12 |
| 4761 | CB | ALA | A | 312 | 41.156 | 40.854 | 47.689 | 1.00 | 9.15 |
| 4765 | C | ALA | A | 312 | 42.095 | 39.864 | 49.773 | 1.00 | 9.28 |
| 4766 | O | ALA | A | 312 | 42.601 | 40.509 | 50.680 | 1.00 | 9.01 |
| 4767 | N | GLU | A | 313 | 42.599 | 38.716 | 49.333 | 1.00 | 9.43 |
| 4769 | CA | GLU | A | 313 | 43.807 | 38.133 | 49.895 | 1.00 | 9.80 |
| 4771 | CB | GLU | A | 313 | 43.487 | 37.380 | 51.187 | 1.00 | 9.88 |
| 4774 | CG | GLU | A | 313 | 44.692 | 36.701 | 51.835 | 1.00 | 11.08 |
| 4777 | CD | GLU | A | 313 | 44.442 | 36.289 | 53.277 | 1.00 | 12.23 |
| 4778 | OE1 | GLU | A | 313 | 43.392 | 36.658 | 53.841 | 1.00 | 14.20 |
| 4779 | OE2 | GLU | A | 313 | 45.304 | 35.602 | 53.855 | 1.00 | 13.22 |
| 4780 | C | GLU | A | 313 | 44.459 | 37.184 | 48.900 | 1.00 | 9.80 |
| 4781 | O | GLU | A | 313 | 43.787 | 36.336 | 48.314 | 1.00 | 9.64 |
| 4782 | N | PHE | A | 314 | 45.762 | 37.347 | 48.701 | 1.00 | 9.72 |
| 4784 | CA | PHE | A | 314 | 46.558 | 36.375 | 47.975 | 1.00 | 9.99 |
| 4786 | CB | PHE | A | 314 | 47.469 | 37.068 | 46.970 | 1.00 | 9.90 |
| 4789 | CG | PHE | A | 314 | 48.222 | 36.117 | 46.093 | 1.00 | 10.55 |
| 4790 | CD1 | PHE | A | 314 | 47.625 | 35.579 | 44.960 | 1.00 | 10.91 |
| 4792 | CE1 | PHE | A | 314 | 48.316 | 34.696 | 44.146 | 1.00 | 11.38 |
| 4794 | CZ | PHE | A | 314 | 49.613 | 34.334 | 44.467 | 1.00 | 11.49 |
| 4796 | CE2 | PHE | A | 314 | 50.215 | 34.853 | 45.593 | 1.00 | 11.30 |
| 4798 | CD2 | PHE | A | 314 | 49.519 | 35.741 | 46.406 | 1.00 | 11.26 |
| 4800 | C | PHE | A | 314 | 47.390 | 35.579 | 48.970 | 1.00 | 10.10 |
| 4801 | O | PHE | A | 314 | 47.962 | 36.144 | 49.897 | 1.00 | 10.31 |
| 4802 | N | PHE | A | 315 | 47.454 | 34.266 | 48.782 | 1.00 | 10.34 |
| 4804 | CA | PHE | A | 315 | 48.241 | 33.399 | 49.655 | 1.00 | 10.44 |
| 4806 | CB | PHE | A | 315 | 47.489 | 33.107 | 50.964 | 1.00 | 10.61 |
| 4809 | CG | PHE | A | 315 | 46.206 | 32.328 | 50.788 | 1.00 | 11.09 |
| 4810 | CD1 | PHE | A | 315 | 46.170 | 30.957 | 51.021 | 1.00 | 10.66 |
| 4812 | CE1 | PHE | A | 315 | 44.985 | 30.238 | 50.870 | 1.00 | 10.90 |
| 4814 | CZ | PHE | A | 315 | 43.823 | 30.891 | 50.494 | 1.00 | 11.17 |
| 4816 | CE2 | PHE | A | 315 | 43.844 | 32.260 | 50.268 | 1.00 | 11.22 |
| 4818 | CD2 | PHE | A | 315 | 45.029 | 32.971 | 50.414 | 1.00 | 11.10 |
| 4820 | C | PHE | A | 315 | 48.629 | 32.113 | 48.935 | 1.00 | 10.60 |
| 4821 | O | PHE | A | 315 | 48.031 | 31.753 | 47.921 | 1.00 | 10.36 |
| 4822 | N | THR | A | 316 | 49.637 | 31.424 | 49.458 | 1.00 | 10.78 |
| 4824 | CA | THR | A | 316 | 50.228 | 30.281 | 48.768 | 1.00 | 11.04 |
| 4826 | CB | THR | A | 316 | 51.713 | 30.574 | 48.453 | 1.00 | 11.21 |
| 4828 | OG1 | THR | A | 316 | 51.809 | 31.721 | 47.596 | 1.00 | 12.11 |
| 4830 | CG2 | THR | A | 316 | 52.347 | 29.450 | 47.630 | 1.00 | 11.83 |
| 4834 | C | THR | A | 316 | 50.111 | 28.994 | 49.578 | 1.00 | 11.02 |
| 4835 | O | THR | A | 316 | 50.136 | 29.013 | 50.807 | 1.00 | 10.73 |
| 4836 | N | GLY | A | 317 | 49.966 | 27.883 | 48.863 | 1.00 | 10.94 |
| 4838 | CA | GLY | A | 317 | 50.042 | 26.551 | 49.429 | 1.00 | 11.14 |
| 4841 | C | GLY | A | 317 | 50.988 | 25.690 | 48.609 | 1.00 | 11.32 |
| 4842 | O | GLY | A | 317 | 51.249 | 25.973 | 47.439 | 1.00 | 11.78 |
| 4843 | N | GLU | A | 318 | 51.518 | 24.643 | 49.227 | 1.00 | 11.12 |
| 4845 | CA | GLU | A | 318 | 52.373 | 23.690 | 48.541 | 1.00 | 11.00 |

FIGURE 3 (Cont.)

| A | B | C | D | E | F | G | H | I | J |
|---|---|---|---|---|---|---|---|---|---|
| 4847 | CB | GLU | A | 318 | 53.732 | 23.594 | 49.240 | 1.00 | 11.07 |
| 4850 | CG | GLU | A | 318 | 54.680 | 22.563 | 48.645 | 1.00 | 11.58 |
| 4853 | CD | GLU | A | 318 | 56.074 | 22.639 | 49.235 | 1.00 | 12.25 |
| 4854 | OE1 | GLU | A | 318 | 56.621 | 21.580 | 49.603 | 1.00 | 13.30 |
| 4855 | OE2 | GLU | A | 318 | 56.622 | 23.755 | 49.332 | 1.00 | 13.49 |
| 4856 | C | GLU | A | 318 | 51.675 | 22.343 | 48.560 | 1.00 | 10.76 |
| 4857 | O | GLU | A | 318 | 51.166 | 21.929 | 49.593 | 1.00 | 10.68 |
| 4858 | N | LEU | A | 319 | 51.638 | 21.667 | 47.417 | 1.00 | 10.71 |
| 4860 | CA | LEU | A | 319 | 51.057 | 20.335 | 47.337 | 1.00 | 10.55 |
| 4862 | CB | LEU | A | 319 | 50.876 | 19.909 | 45.878 | 1.00 | 10.67 |
| 4865 | CG | LEU | A | 319 | 49.841 | 20.737 | 45.110 | 1.00 | 10.56 |
| 4867 | CD1 | LEU | A | 319 | 49.787 | 20.327 | 43.651 | 1.00 | 10.06 |
| 4871 | CD2 | LEU | A | 319 | 48.466 | 20.608 | 45.753 | 1.00 | 10.35 |
| 4875 | C | LEU | A | 319 | 51.929 | 19.334 | 48.094 | 1.00 | 10.59 |
| 4876 | O | LEU | A | 319 | 53.151 | 19.331 | 47.967 | 1.00 | 10.10 |
| 4877 | N | VAL | A | 320 | 51.279 | 18.486 | 48.882 | 1.00 | 10.87 |
| 4879 | CA | VAL | A | 320 | 51.966 | 17.585 | 49.795 | 1.00 | 11.11 |
| 4881 | CB | VAL | A | 320 | 51.151 | 17.410 | 51.091 | 1.00 | 11.10 |
| 4883 | CG1 | VAL | A | 320 | 51.809 | 16.394 | 52.028 | 1.00 | 11.37 |
| 4887 | CG2 | VAL | A | 320 | 50.972 | 18.758 | 51.789 | 1.00 | 10.69 |
| 4891 | C | VAL | A | 320 | 52.178 | 16.236 | 49.117 | 1.00 | 11.41 |
| 4892 | O | VAL | A | 320 | 51.344 | 15.798 | 48.333 | 1.00 | 11.49 |
| 4893 | N | ALA | A | 321 | 53.305 | 15.592 | 49.407 | 1.00 | 11.87 |
| 4895 | CA | ALA | A | 321 | 53.580 | 14.237 | 48.930 | 1.00 | 12.19 |
| 4897 | CB | ALA | A | 321 | 54.849 | 13.685 | 49.596 | 1.00 | 12.50 |
| 4901 | C | ALA | A | 321 | 52.393 | 13.327 | 49.217 | 1.00 | 12.25 |
| 4902 | O | ALA | A | 321 | 51.933 | 13.241 | 50.354 | 1.00 | 12.30 |
| 4903 | N | GLY | A | 322 | 51.870 | 12.694 | 48.173 | 1.00 | 12.42 |
| 4905 | CA | GLY | A | 322 | 50.766 | 11.756 | 48.304 | 1.00 | 12.75 |
| 4908 | C | GLY | A | 322 | 49.367 | 12.357 | 48.244 | 1.00 | 12.86 |
| 4909 | O | GLY | A | 322 | 48.391 | 11.641 | 48.454 | 1.00 | 12.95 |
| 4910 | N | TYR | A | 323 | 49.256 | 13.647 | 47.931 | 1.00 | 13.17 |
| 4912 | CA | TYR | A | 323 | 47.957 | 14.332 | 47.904 | 1.00 | 13.58 |
| 4914 | CB | TYR | A | 323 | 48.117 | 15.836 | 47.607 | 1.00 | 13.42 |
| 4917 | CG | TYR | A | 323 | 48.302 | 16.159 | 46.141 | 1.00 | 13.11 |
| 4918 | CD1 | TYR | A | 323 | 47.208 | 16.460 | 45.332 | 1.00 | 12.63 |
| 4920 | CE1 | TYR | A | 323 | 47.367 | 16.742 | 43.983 | 1.00 | 12.13 |
| 4922 | CZ | TYR | A | 323 | 48.634 | 16.726 | 43.430 | 1.00 | 11.78 |
| 4923 | OH | TYR | A | 323 | 48.800 | 16.999 | 42.102 | 1.00 | 11.57 |
| 4925 | CE2 | TYR | A | 323 | 49.738 | 16.430 | 44.211 | 1.00 | 12.43 |
| 4927 | CD2 | TYR | A | 323 | 49.568 | 16.147 | 45.557 | 1.00 | 12.62 |
| 4929 | C | TYR | A | 323 | 46.987 | 13.707 | 46.901 | 1.00 | 13.96 |
| 4930 | O | TYR | A | 323 | 45.776 | 13.730 | 47.111 | 1.00 | 13.71 |
| 4931 | N | GLN | A | 324 | 47.522 | 13.150 | 45.818 | 1.00 | 14.65 |
| 4933 | CA | GLN | A | 324 | 46.696 | 12.572 | 44.757 | 1.00 | 15.33 |
| 4935 | CB | GLN | A | 324 | 47.553 | 12.220 | 43.533 | 1.00 | 15.41 |
| 4938 | CG | GLN | A | 324 | 48.089 | 13.449 | 42.807 | 1.00 | 15.91 |
| 4941 | CD | GLN | A | 324 | 49.054 | 13.117 | 41.681 | 1.00 | 16.94 |
| 4942 | OE1 | GLN | A | 324 | 49.172 | 11.961 | 41.278 | 1.00 | 17.77 |
| 4943 | NE2 | GLN | A | 324 | 49.751 | 14.131 | 41.175 | 1.00 | 16.22 |
| 4946 | C | GLN | A | 324 | 45.885 | 11.355 | 45.216 | 1.00 | 15.61 |
| 4947 | O | GLN | A | 324 | 44.905 | 10.996 | 44.566 | 1.00 | 15.76 |
| 4948 | N | ASN | A | 325 | 46.293 | 10.739 | 46.328 | 1.00 | 16.19 |

FIGURE 3 (Cont.)

| A | B | C | D | E | F | G | H | I | J |
|---|---|---|---|---|---|---|---|---|---|
| 4950 | CA | ASN | A | 325 | 45.571 | 9.615 | 46.934 | 1.00 | 16.67 |
| 4952 | CB | ASN | A | 325 | 46.559 | 8.674 | 47.635 | 1.00 | 16.92 |
| 4955 | CG | ASN | A | 325 | 47.581 | 8.099 | 46.683 | 1.00 | 18.10 |
| 4956 | OD1 | ASN | A | 325 | 47.227 | 7.576 | 45.630 | 1.00 | 20.28 |
| 4957 | ND2 | ASN | A | 325 | 48.860 | 8.199 | 47.043 | 1.00 | 19.45 |
| 4960 | C | ASN | A | 325 | 44.493 | 10.020 | 47.938 | 1.00 | 16.69 |
| 4961 | O | ASN | A | 325 | 43.843 | 9.153 | 48.520 | 1.00 | 17.30 |
| 4962 | N | HIS | A | 326 | 44.305 | 11.322 | 48.146 | 1.00 | 16.56 |
| 4964 | CA | HIS | A | 326 | 43.376 | 11.831 | 49.156 | 1.00 | 16.43 |
| 4966 | CB | HIS | A | 326 | 44.167 | 12.425 | 50.329 | 1.00 | 16.47 |
| 4969 | CG | HIS | A | 326 | 45.027 | 11.416 | 51.024 | 1.00 | 16.56 |
| 4970 | ND1 | HIS | A | 326 | 44.500 | 10.357 | 51.731 | 1.00 | 16.47 |
| 4972 | CE1 | HIS | A | 326 | 45.484 | 9.613 | 52.204 | 1.00 | 16.81 |
| 4974 | NE2 | HIS | A | 326 | 46.630 | 10.150 | 51.824 | 1.00 | 16.63 |
| 4976 | CD2 | HIS | A | 326 | 46.371 | 11.275 | 51.079 | 1.00 | 16.51 |
| 4978 | C | HIS | A | 326 | 42.374 | 12.837 | 48.579 | 1.00 | 16.15 |
| 4979 | O | HIS | A | 326 | 41.856 | 13.700 | 49.289 | 1.00 | 16.06 |
| 4980 | N | LEU | A | 327 | 42.098 | 12.702 | 47.285 | 1.00 | 15.84 |
| 4982 | CA | LEU | A | 327 | 41.060 | 13.478 | 46.620 | 1.00 | 15.79 |
| 4984 | CB | LEU | A | 327 | 41.540 | 13.922 | 45.235 | 1.00 | 15.93 |
| 4987 | CG | LEU | A | 327 | 42.870 | 14.688 | 45.239 | 1.00 | 15.85 |
| 4989 | CD1 | LEU | A | 327 | 43.378 | 14.920 | 43.823 | 1.00 | 15.79 |
| 4993 | CD2 | LEU | A | 327 | 42.715 | 16.003 | 45.979 | 1.00 | 16.33 |
| 4997 | C | LEU | A | 327 | 39.795 | 12.626 | 46.527 | 1.00 | 15.74 |
| 4998 | O | LEU | A | 327 | 39.796 | 11.457 | 46.927 | 1.00 | 15.54 |
| 4999 | N | GLN | A | 328 | 38.716 | 13.216 | 46.022 | 1.00 | 15.56 |
| 5001 | CA | GLN | A | 328 | 37.436 | 12.514 | 45.902 | 1.00 | 15.73 |
| 5003 | CB | GLN | A | 328 | 36.463 | 13.000 | 46.987 | 1.00 | 16.18 |
| 5006 | CG | GLN | A | 328 | 37.015 | 12.901 | 48.420 | 1.00 | 18.86 |
| 5009 | CD | GLN | A | 328 | 35.951 | 12.605 | 49.474 | 1.00 | 21.97 |
| 5010 | OE1 | GLN | A | 328 | 36.269 | 12.511 | 50.658 | 1.00 | 25.17 |
| 5011 | NE2 | GLN | A | 328 | 34.697 | 12.456 | 49.050 | 1.00 | 23.76 |
| 5014 | C | GLN | A | 328 | 36.815 | 12.698 | 44.517 | 1.00 | 14.70 |
| 5015 | O | GLN | A | 328 | 35.640 | 13.033 | 44.401 | 1.00 | 14.70 |
| 5016 | N | LYS | A | 329 | 37.605 | 12.464 | 43.470 | 1.00 | 13.86 |
| 5018 | CA | LYS | A | 329 | 37.144 | 12.676 | 42.099 | 1.00 | 13.08 |
| 5020 | CB | LYS | A | 329 | 38.252 | 12.377 | 41.083 | 1.00 | 12.96 |
| 5023 | CG | LYS | A | 329 | 37.872 | 12.727 | 39.643 | 1.00 | 12.63 |
| 5026 | CD | LYS | A | 329 | 39.080 | 12.714 | 38.717 | 1.00 | 12.37 |
| 5029 | CE | LYS | A | 329 | 38.741 | 13.292 | 37.356 | 1.00 | 12.53 |
| 5032 | NZ | LYS | A | 329 | 39.913 | 13.304 | 36.429 | 1.00 | 11.95 |
| 5036 | C | LYS | A | 329 | 35.895 | 11.870 | 41.746 | 1.00 | 12.64 |
| 5037 | O | LYS | A | 329 | 34.955 | 12.419 | 41.183 | 1.00 | 12.22 |
| 5038 | N | GLU | A | 330 | 35.884 | 10.578 | 42.065 | 1.00 | 12.20 |
| 5040 | CA | GLU | A | 330 | 34.758 | 9.723 | 41.685 | 1.00 | 12.11 |
| 5042 | CB | GLU | A | 330 | 35.009 | 8.249 | 42.020 | 1.00 | 12.12 |
| 5045 | CG | GLU | A | 330 | 33.962 | 7.331 | 41.390 | 1.00 | 12.23 |
| 5048 | CD | GLU | A | 330 | 34.160 | 5.858 | 41.695 | 1.00 | 12.23 |
| 5049 | OE1 | GLU | A | 330 | 35.275 | 5.449 | 42.071 | 1.00 | 12.41 |
| 5050 | OE2 | GLU | A | 330 | 33.182 | 5.106 | 41.546 | 1.00 | 12.10 |
| 5051 | C | GLU | A | 330 | 33.476 | 10.188 | 42.365 | 1.00 | 11.99 |
| 5052 | O | GLU | A | 330 | 32.433 | 10.280 | 41.731 | 1.00 | 11.67 |
| 5053 | N | THR | A | 331 | 33.571 | 10.471 | 43.658 | 1.00 | 11.91 |

FIGURE 3 (Cont.)

| A | B | C | D | E | F | G | H | I | J |
|---|---|---|---|---|---|---|---|---|---|
| 5055 | CA | THR | A | 331 | 32.446 | 10.987 | 44.435 | 1.00 | 12.09 |
| 5057 | CB | THR | A | 331 | 32.885 | 11.195 | 45.892 | 1.00 | 12.18 |
| 5059 | OG1 | THR | A | 331 | 33.103 | 9.919 | 46.511 | 1.00 | 12.75 |
| 5061 | CG2 | THR | A | 331 | 31.784 | 11.840 | 46.732 | 1.00 | 12.84 |
| 5065 | C | THR | A | 331 | 31.911 | 12.295 | 43.852 | 1.00 | 12.00 |
| 5066 | O | THR | A | 331 | 30.700 | 12.499 | 43.796 | 1.00 | 11.65 |
| 5067 | N | HIS | A | 332 | 32.817 | 13.169 | 43.412 | 1.00 | 11.95 |
| 5069 | CA | HIS | A | 332 | 32.439 | 14.480 | 42.893 | 1.00 | 11.91 |
| 5071 | CB | HIS | A | 332 | 33.659 | 15.406 | 42.820 | 1.00 | 11.96 |
| 5074 | CG | HIS | A | 332 | 34.186 | 15.812 | 44.161 | 1.00 | 12.02 |
| 5075 | ND1 | HIS | A | 332 | 35.512 | 16.113 | 44.381 | 1.00 | 12.79 |
| 5077 | CE1 | HIS | A | 332 | 35.684 | 16.431 | 45.653 | 1.00 | 13.18 |
| 5079 | NE2 | HIS | A | 332 | 34.516 | 16.350 | 46.265 | 1.00 | 12.44 |
| 5081 | CD2 | HIS | A | 332 | 33.563 | 15.962 | 45.354 | 1.00 | 12.47 |
| 5083 | C | HIS | A | 332 | 31.774 | 14.374 | 41.525 | 1.00 | 11.96 |
| 5084 | O | HIS | A | 332 | 30.790 | 15.057 | 41.259 | 1.00 | 11.84 |
| 5085 | N | LEU | A | 333 | 32.310 | 13.519 | 40.659 | 1.00 | 11.95 |
| 5087 | CA | LEU | A | 333 | 31.718 | 13.303 | 39.342 | 1.00 | 12.15 |
| 5089 | CB | LEU | A | 333 | 32.637 | 12.448 | 38.466 | 1.00 | 12.35 |
| 5092 | CG | LEU | A | 333 | 33.967 | 13.098 | 38.068 | 1.00 | 13.14 |
| 5094 | CD1 | LEU | A | 333 | 34.859 | 12.082 | 37.367 | 1.00 | 14.23 |
| 5098 | CD2 | LEU | A | 333 | 33.744 | 14.320 | 37.181 | 1.00 | 13.58 |
| 5102 | C | LEU | A | 333 | 30.346 | 12.647 | 39.486 | 1.00 | 12.02 |
| 5103 | O | LEU | A | 333 | 29.421 | 12.981 | 38.759 | 1.00 | 11.47 |
| 5104 | N | ALA | A | 334 | 30.227 | 11.729 | 40.441 | 1.00 | 11.95 |
| 5106 | CA | ALA | A | 334 | 28.955 | 11.080 | 40.751 | 1.00 | 12.28 |
| 5108 | CB | ALA | A | 334 | 29.153 | 10.009 | 41.810 | 1.00 | 12.24 |
| 5112 | C | ALA | A | 334 | 27.935 | 12.109 | 41.223 | 1.00 | 12.38 |
| 5113 | O | ALA | A | 334 | 26.781 | 12.079 | 40.816 | 1.00 | 12.29 |
| 5114 | N | LEU | A | 335 | 28.385 | 13.033 | 42.062 | 1.00 | 12.77 |
| 5116 | CA | LEU | A | 335 | 27.534 | 14.091 | 42.593 | 1.00 | 13.03 |
| 5118 | CB | LEU | A | 335 | 28.335 | 14.955 | 43.565 | 1.00 | 13.25 |
| 5121 | CG | LEU | A | 335 | 27.595 | 16.070 | 44.298 | 1.00 | 14.25 |
| 5123 | CD1 | LEU | A | 335 | 26.607 | 15.492 | 45.290 | 1.00 | 15.18 |
| 5127 | CD2 | LEU | A | 335 | 28.613 | 16.963 | 44.986 | 1.00 | 15.82 |
| 5131 | C | LEU | A | 335 | 26.957 | 14.956 | 41.474 | 1.00 | 12.87 |
| 5132 | O | LEU | A | 335 | 25.765 | 15.247 | 41.468 | 1.00 | 12.92 |
| 5133 | N | LEU | A | 336 | 27.804 | 15.350 | 40.528 | 1.00 | 12.77 |
| 5135 | CA | LEU | A | 336 | 27.387 | 16.205 | 39.416 | 1.00 | 12.81 |
| 5137 | CB | LEU | A | 336 | 28.611 | 16.822 | 38.728 | 1.00 | 12.79 |
| 5140 | CG | LEU | A | 336 | 29.490 | 17.731 | 39.592 | 1.00 | 13.01 |
| 5142 | CD1 | LEU | A | 336 | 30.814 | 18.013 | 38.897 | 1.00 | 13.56 |
| 5146 | CD2 | LEU | A | 336 | 28.776 | 19.034 | 39.940 | 1.00 | 13.15 |
| 5150 | C | LEU | A | 336 | 26.537 | 15.441 | 38.391 | 1.00 | 12.88 |
| 5151 | O | LEU | A | 336 | 25.557 | 15.973 | 37.880 | 1.00 | 12.68 |
| 5152 | N | ASP | A | 337 | 26.901 | 14.187 | 38.123 | 1.00 | 13.04 |
| 5154 | CA | ASP | A | 337 | 26.225 | 13.362 | 37.116 | 1.00 | 13.25 |
| 5156 | CB | ASP | A | 337 | 27.050 | 12.099 | 36.810 | 1.00 | 13.42 |
| 5159 | CG | ASP | A | 337 | 28.269 | 12.379 | 35.946 | 1.00 | 14.32 |
| 5160 | OD1 | ASP | A | 337 | 28.263 | 13.374 | 35.194 | 1.00 | 16.21 |
| 5161 | OD2 | ASP | A | 337 | 29.278 | 11.642 | 35.941 | 1.00 | 15.33 |
| 5162 | C | ASP | A | 337 | 24.821 | 12.926 | 37.532 | 1.00 | 13.22 |
| 5163 | O | ASP | A | 337 | 23.925 | 12.840 | 36.697 | 1.00 | 12.93 |

FIGURE 3 (Cont.)

| A | B | C | D | E | F | G | H | I | J |
|---|---|---|---|---|---|---|---|---|---|
| 5164 | N | ASN | A | 338 | 24.632 | 12.645 | 38.819 | 1.00 | 13.37 |
| 5166 | CA | ASN | A | 338 | 23.364 | 12.102 | 39.312 | 1.00 | 13.64 |
| 5168 | CB | ASN | A | 338 | 23.609 | 11.224 | 40.548 | 1.00 | 13.85 |
| 5171 | CG | ASN | A | 338 | 24.323 | 9.922 | 40.201 | 1.00 | 14.54 |
| 5172 | OD1 | ASN | A | 338 | 25.233 | 9.487 | 40.910 | 1.00 | 16.43 |
| 5173 | ND2 | ASN | A | 338 | 23.918 | 9.302 | 39.099 | 1.00 | 14.86 |
| 5176 | C | ASN | A | 338 | 22.298 | 13.169 | 39.589 | 1.00 | 13.50 |
| 5177 | O | ASN | A | 338 | 21.219 | 12.861 | 40.105 | 1.00 | 13.84 |
| 5178 | N | ARG | A | 339 | 22.584 | 14.413 | 39.212 | 1.00 | 13.19 |
| 5180 | CA | ARG | A | 339 | 21.616 | 15.491 | 39.348 | 1.00 | 12.90 |
| 5182 | CB | ARG | A | 339 | 22.294 | 16.855 | 39.205 | 1.00 | 12.58 |
| 5185 | CG | ARG | A | 339 | 23.347 | 17.141 | 40.272 | 1.00 | 12.17 |
| 5188 | CD | ARG | A | 339 | 24.052 | 18.483 | 40.111 | 1.00 | 11.56 |
| 5191 | NE | ARG | A | 339 | 24.788 | 18.577 | 38.847 | 1.00 | 10.52 |
| 5193 | CZ | ARG | A | 339 | 25.338 | 19.688 | 38.371 | 1.00 | 10.16 |
| 5194 | NH1 | ARG | A | 339 | 25.246 | 20.831 | 39.037 | 1.00 | 9.64 |
| 5197 | NH2 | ARG | A | 339 | 25.978 | 19.655 | 37.210 | 1.00 | 10.28 |
| 5200 | C | ARG | A | 339 | 20.513 | 15.357 | 38.306 | 1.00 | 13.10 |
| 5201 | O | ARG | A | 339 | 20.714 | 14.764 | 37.246 | 1.00 | 12.95 |
| 5202 | N | THR | A | 340 | 19.356 | 15.925 | 38.633 | 1.00 | 13.21 |
| 5204 | CA | THR | A | 340 | 18.201 | 15.974 | 37.753 | 1.00 | 13.55 |
| 5206 | CB | THR | A | 340 | 16.915 | 15.816 | 38.585 | 1.00 | 13.57 |
| 5208 | OG1 | THR | A | 340 | 16.940 | 14.564 | 39.281 | 1.00 | 13.66 |
| 5210 | CG2 | THR | A | 340 | 15.671 | 15.733 | 37.691 | 1.00 | 14.07 |
| 5214 | C | THR | A | 340 | 18.173 | 17.311 | 37.023 | 1.00 | 13.84 |
| 5215 | O | THR | A | 340 | 18.227 | 18.371 | 37.654 | 1.00 | 13.89 |
| 5216 | N | GLU | A | 341 | 18.084 | 17.260 | 35.697 | 1.00 | 14.08 |
| 5218 | CA | GLU | A | 341 | 17.932 | 18.460 | 34.891 | 1.00 | 14.42 |
| 5220 | CB | GLU | A | 341 | 18.218 | 18.172 | 33.419 | 1.00 | 14.68 |
| 5223 | CG | GLU | A | 341 | 18.241 | 19.431 | 32.562 | 1.00 | 15.06 |
| 5226 | CD | GLU | A | 341 | 18.585 | 19.167 | 31.110 | 1.00 | 16.30 |
| 5227 | OE1 | GLU | A | 341 | 18.652 | 20.149 | 30.345 | 1.00 | 18.47 |
| 5228 | OE2 | GLU | A | 341 | 18.784 | 17.994 | 30.730 | 1.00 | 17.71 |
| 5229 | C | GLU | A | 341 | 16.520 | 19.018 | 35.018 | 1.00 | 14.64 |
| 5230 | O | GLU | A | 341 | 15.540 | 18.284 | 34.878 | 1.00 | 14.46 |
| 5231 | N | LEU | A | 342 | 16.435 | 20.325 | 35.257 | 1.00 | 14.72 |
| 5233 | CA | LEU | A | 342 | 15.169 | 21.037 | 35.315 | 1.00 | 14.92 |
| 5235 | CB | LEU | A | 342 | 15.204 | 22.113 | 36.409 | 1.00 | 15.14 |
| 5238 | CG | LEU | A | 342 | 15.439 | 21.660 | 37.854 | 1.00 | 15.76 |
| 5240 | CD1 | LEU | A | 342 | 15.562 | 22.870 | 38.763 | 1.00 | 16.15 |
| 5244 | CD2 | LEU | A | 342 | 14.333 | 20.734 | 38.340 | 1.00 | 16.53 |
| 5248 | C | LEU | A | 342 | 14.897 | 21.716 | 33.978 | 1.00 | 14.85 |
| 5249 | O | LEU | A | 342 | 15.806 | 22.250 | 33.349 | 1.00 | 14.61 |
| 5250 | N | SER | A | 343 | 13.636 | 21.694 | 33.552 | 1.00 | 14.71 |
| 5252 | CA | SER | A | 343 | 13.176 | 22.534 | 32.458 | 1.00 | 14.55 |
| 5254 | CB | SER | A | 343 | 11.771 | 22.112 | 32.027 | 1.00 | 14.63 |
| 5257 | OG | SER | A | 343 | 10.819 | 22.501 | 33.002 | 1.00 | 13.80 |
| 5259 | C | SER | A | 343 | 13.146 | 23.970 | 32.961 | 1.00 | 14.64 |
| 5260 | O | SER | A | 343 | 13.220 | 24.196 | 34.162 | 1.00 | 14.05 |
| 5261 | N | ILE | A | 344 | 13.026 | 24.936 | 32.053 | 1.00 | 14.98 |
| 5263 | CA | ILE | A | 344 | 12.940 | 26.343 | 32.447 | 1.00 | 15.27 |
| 5265 | CB | ILE | A | 344 | 12.850 | 27.295 | 31.210 | 1.00 | 15.60 |
| 5267 | CG1 | ILE | A | 344 | 12.845 | 28.764 | 31.650 | 1.00 | 15.91 |

FIGURE 3 (Cont.)

| A | B | C | D | E | F | G | H | I | J |
|---|---|---|---|---|---|---|---|---|---|
| 5270 | CD1 | ILE | A | 344 | 14.197 | 29.297 | 32.043 | 1.00 | 16.15 |
| 5274 | CG2 | ILE | A | 344 | 11.597 | 27.020 | 30.363 | 1.00 | 16.26 |
| 5278 | C | ILE | A | 344 | 11.766 | 26.567 | 33.398 | 1.00 | 15.22 |
| 5279 | O | ILE | A | 344 | 11.903 | 27.281 | 34.392 | 1.00 | 15.26 |
| 5280 | N | ALA | A | 345 | 10.626 | 25.948 | 33.108 | 1.00 | 14.85 |
| 5282 | CA | ALA | A | 345 | 9.433 | 26.132 | 33.932 | 1.00 | 14.73 |
| 5284 | CB | ALA | A | 345 | 8.218 | 25.497 | 33.262 | 1.00 | 14.93 |
| 5288 | C | ALA | A | 345 | 9.636 | 25.558 | 35.338 | 1.00 | 14.48 |
| 5289 | O | ALA | A | 345 | 9.194 | 26.148 | 36.323 | 1.00 | 14.31 |
| 5290 | N | GLU | A | 346 | 10.307 | 24.413 | 35.422 | 1.00 | 14.15 |
| 5292 | CA | GLU | A | 346 | 10.624 | 23.786 | 36.707 | 1.00 | 14.02 |
| 5294 | CB | GLU | A | 346 | 11.146 | 22.363 | 36.496 | 1.00 | 13.95 |
| 5297 | CG | GLU | A | 346 | 10.062 | 21.362 | 36.117 | 1.00 | 14.71 |
| 5300 | CD | GLU | A | 346 | 10.605 | 20.037 | 35.605 | 1.00 | 15.06 |
| 5301 | OE1 | GLU | A | 346 | 9.819 | 19.069 | 35.512 | 1.00 | 16.85 |
| 5302 | OE2 | GLU | A | 346 | 11.806 | 19.950 | 35.289 | 1.00 | 13.70 |
| 5303 | C | GLU | A | 346 | 11.642 | 24.615 | 37.504 | 1.00 | 13.65 |
| 5304 | O | GLU | A | 346 | 11.509 | 24.767 | 38.715 | 1.00 | 13.64 |
| 5305 | N | TYR | A | 347 | 12.646 | 25.149 | 36.816 | 1.00 | 13.27 |
| 5307 | CA | TYR | A | 347 | 13.638 | 26.042 | 37.426 | 1.00 | 13.05 |
| 5309 | CB | TYR | A | 347 | 14.718 | 26.426 | 36.403 | 1.00 | 12.89 |
| 5312 | CG | TYR | A | 347 | 15.455 | 27.726 | 36.686 | 1.00 | 13.10 |
| 5313 | CD1 | TYR | A | 347 | 15.277 | 28.843 | 35.871 | 1.00 | 13.64 |
| 5315 | CE1 | TYR | A | 347 | 15.958 | 30.036 | 36.120 | 1.00 | 13.73 |
| 5317 | CZ | TYR | A | 347 | 16.827 | 30.119 | 37.191 | 1.00 | 13.43 |
| 5318 | OH | TYR | A | 347 | 17.505 | 31.297 | 37.437 | 1.00 | 13.87 |
| 5320 | CE2 | TYR | A | 347 | 17.021 | 29.025 | 38.011 | 1.00 | 13.24 |
| 5322 | CD2 | TYR | A | 347 | 16.338 | 27.834 | 37.754 | 1.00 | 12.87 |
| 5324 | C | TYR | A | 347 | 12.976 | 27.294 | 37.999 | 1.00 | 13.02 |
| 5325 | O | TYR | A | 347 | 13.245 | 27.673 | 39.134 | 1.00 | 12.68 |
| 5326 | N | GLU | A | 348 | 12.097 | 27.919 | 37.219 | 1.00 | 13.09 |
| 5328 | CA | GLU | A | 348 | 11.475 | 29.176 | 37.623 | 1.00 | 13.46 |
| 5330 | CB | GLU | A | 348 | 10.756 | 29.839 | 36.436 | 1.00 | 13.51 |
| 5333 | CG | GLU | A | 348 | 11.722 | 30.349 | 35.368 | 1.00 | 14.34 |
| 5336 | CD | GLU | A | 348 | 11.114 | 31.371 | 34.418 | 1.00 | 15.48 |
| 5337 | OE1 | GLU | A | 348 | 9.910 | 31.274 | 34.106 | 1.00 | 16.56 |
| 5338 | OE2 | GLU | A | 348 | 11.853 | 32.272 | 33.974 | 1.00 | 15.67 |
| 5339 | C | GLU | A | 348 | 10.534 | 28.981 | 38.815 | 1.00 | 13.52 |
| 5340 | O | GLU | A | 348 | 10.436 | 29.855 | 39.670 | 1.00 | 13.44 |
| 5341 | N | ALA | A | 349 | 9.863 | 27.833 | 38.880 | 1.00 | 13.86 |
| 5343 | CA | ALA | A | 349 | 8.988 | 27.520 | 40.012 | 1.00 | 14.18 |
| 5345 | CB | ALA | A | 349 | 8.127 | 26.300 | 39.707 | 1.00 | 14.18 |
| 5349 | C | ALA | A | 349 | 9.814 | 27.294 | 41.282 | 1.00 | 14.24 |
| 5350 | O | ALA | A | 349 | 9.505 | 27.849 | 42.341 | 1.00 | 14.45 |
| 5351 | N | MSE | A | 350 | 10.871 | 26.494 | 41.166 | 1.00 | 14.32 |
| 5353 | CA | MSE | A | 350 | 11.759 | 26.214 | 42.295 | 1.00 | 14.50 |
| 5355 | CB | MSE | A | 350 | 12.809 | 25.168 | 41.906 | 1.00 | 14.42 |
| 5358 | CG | MSE | A | 350 | 13.668 | 24.690 | 43.076 | 1.00 | 14.25 |
| 5361 | SE | MSE | A | 350 | 14.904 | 23.272 | 42.580 | 1.00 | 14.19 |
| 5362 | CE | MSE | A | 350 | 13.645 | 21.797 | 42.383 | 1.00 | 14.41 |
| 5366 | C | MSE | A | 350 | 12.454 | 27.486 | 42.790 | 1.00 | 14.59 |
| 5367 | O | MSE | A | 350 | 12.580 | 27.708 | 43.991 | 1.00 | 14.60 |
| 5368 | N | PHE | A | 351 | 12.883 | 28.323 | 41.856 | 1.00 | 14.91 |

FIGURE 3 (Cont.)

| A | B | C | D | E | F | G | H | I | J |
|---|---|---|---|---|---|---|---|---|---|
| 5370 | CA | PHE | A | 351 | 13.594 | 29.555 | 42.182 | 1.00 | 15.21 |
| 5372 | CB | PHE | A | 351 | 14.116 | 30.215 | 40.896 | 1.00 | 15.04 |
| 5375 | CG | PHE | A | 351 | 14.958 | 31.436 | 41.137 | 1.00 | 14.10 |
| 5376 | CD1 | PHE | A | 351 | 14.368 | 32.661 | 41.423 | 1.00 | 13.66 |
| 5378 | CE1 | PHE | A | 351 | 15.141 | 33.782 | 41.648 | 1.00 | 13.50 |
| 5380 | CZ | PHE | A | 351 | 16.523 | 33.694 | 41.579 | 1.00 | 13.30 |
| 5382 | CE2 | PHE | A | 351 | 17.120 | 32.486 | 41.293 | 1.00 | 13.49 |
| 5384 | CD2 | PHE | A | 351 | 16.342 | 31.363 | 41.071 | 1.00 | 13.51 |
| 5386 | C | PHE | A | 351 | 12.694 | 30.533 | 42.930 | 1.00 | 15.78 |
| 5387 | O | PHE | A | 351 | 13.110 | 31.138 | 43.918 | 1.00 | 16.13 |
| 5388 | N | ALA | A | 352 | 11.462 | 30.678 | 42.454 | 1.00 | 16.47 |
| 5390 | CA | ALA | A | 352 | 10.562 | 31.729 | 42.929 | 1.00 | 17.03 |
| 5392 | CB | ALA | A | 352 | 9.472 | 31.993 | 41.896 | 1.00 | 17.21 |
| 5396 | C | ALA | A | 352 | 9.934 | 31.404 | 44.286 | 1.00 | 17.53 |
| 5397 | O | ALA | A | 352 | 9.524 | 32.308 | 45.012 | 1.00 | 17.43 |
| 5398 | N | GLU | A | 353 | 9.878 | 30.118 | 44.629 | 1.00 | 18.01 |
| 5400 | CA | GLU | A | 353 | 9.221 | 29.681 | 45.857 | 1.00 | 18.57 |
| 5402 | CB | GLU | A | 353 | 9.292 | 28.157 | 46.004 | 1.00 | 18.73 |
| 5405 | CG | GLU | A | 353 | 8.269 | 27.580 | 46.974 | 1.00 | 19.70 |
| 5408 | CD | GLU | A | 353 | 8.309 | 26.062 | 47.054 | 1.00 | 20.97 |
| 5409 | OE1 | GLU | A | 353 | 7.481 | 25.492 | 47.795 | 1.00 | 23.03 |
| 5410 | OE2 | GLU | A | 353 | 9.171 | 25.433 | 46.395 | 1.00 | 20.91 |
| 5411 | C | GLU | A | 353 | 9.834 | 30.364 | 47.076 | 1.00 | 18.59 |
| 5412 | O | GLU | A | 353 | 11.056 | 30.440 | 47.218 | 1.00 | 18.77 |
| 5413 | N | THR | A | 354 | 8.969 | 30.889 | 47.934 | 1.00 | 18.65 |
| 5415 | CA | THR | A | 354 | 9.393 | 31.526 | 49.171 | 1.00 | 18.59 |
| 5417 | CB | ATHR | A | 354 | 8.729 | 32.908 | 49.340 | 0.65 | 18.54 |
| 5419 | OG1 | ATHR | A | 354 | 7.318 | 32.807 | 49.117 | 0.65 | 18.59 |
| 5421 | CG2 | ATHR | A | 354 | 9.206 | 33.874 | 48.270 | 0.65 | 18.76 |
| 5425 | C | THR | A | 354 | 9.030 | 30.631 | 50.340 | 1.00 | 18.54 |
| 5426 | O | THR | A | 354 | 8.105 | 29.817 | 50.259 | 1.00 | 18.83 |
| 5427 | N | LEU | A | 355 | 9.795 | 30.768 | 51.413 | 1.00 | 18.42 |
| 5429 | CA | LEU | A | 355 | 9.529 | 30.068 | 52.655 | 1.00 | 18.38 |
| 5431 | CB | LEU | A | 355 | 10.738 | 29.231 | 53.072 | 1.00 | 18.30 |
| 5434 | CG | LEU | A | 355 | 10.609 | 28.468 | 54.396 | 1.00 | 18.64 |
| 5436 | CD1 | LEU | A | 355 | 9.409 | 27.526 | 54.379 | 1.00 | 18.61 |
| 5440 | CD2 | LEU | A | 355 | 11.888 | 27.707 | 54.680 | 1.00 | 18.77 |
| 5444 | C | LEU | A | 355 | 9.231 | 31.123 | 53.705 | 1.00 | 17.93 |
| 5445 | O | LEU | A | 355 | 10.080 | 31.958 | 54.002 | 1.00 | 17.93 |
| 5446 | N | ASP | A | 356 | 8.007 | 31.099 | 54.221 | 1.00 | 17.67 |
| 5448 | CA | ASP | A | 356 | 7.603 | 31.937 | 55.342 | 1.00 | 17.33 |
| 5450 | CB | ASP | A | 356 | 6.134 | 32.339 | 55.197 | 1.00 | 17.51 |
| 5453 | CG | ASP | A | 356 | 5.705 | 33.391 | 56.207 | 1.00 | 17.64 |
| 5454 | OD1 | ASP | A | 356 | 6.474 | 33.697 | 57.144 | 1.00 | 17.26 |
| 5455 | OD2 | ASP | A | 356 | 4.604 | 33.967 | 56.136 | 1.00 | 18.45 |
| 5456 | C | ASP | A | 356 | 7.823 | 31.150 | 56.636 | 1.00 | 16.92 |
| 5457 | O | ASP | A | 356 | 7.016 | 30.296 | 56.996 | 1.00 | 16.46 |
| 5458 | N | THR | A | 357 | 8.921 | 31.453 | 57.325 | 1.00 | 16.68 |
| 5460 | CA | THR | A | 357 | 9.314 | 30.732 | 58.539 | 1.00 | 16.73 |
| 5462 | CB | THR | A | 357 | 10.809 | 30.971 | 58.868 | 1.00 | 16.81 |
| 5464 | OG1 | THR | A | 357 | 11.066 | 32.372 | 58.977 | 1.00 | 17.70 |
| 5466 | CG2 | THR | A | 357 | 11.719 | 30.510 | 57.725 | 1.00 | 17.29 |
| 5470 | C | THR | A | 357 | 8.462 | 31.079 | 59.763 | 1.00 | 16.35 |

FIGURE 3 (Cont.)

| A | B | C | D | E | F | G | H | I | J |
|---|---|---|---|---|---|---|---|---|---|
| 5471 | O | THR | A | 357 | 8.589 | 30.435 | 60.802 | 1.00 | 16.08 |
| 5472 | N | ASP | A | 358 | 7.611 | 32.096 | 59.646 | 1.00 | 16.13 |
| 5474 | CA | ASP | A | 358 | 6.614 | 32.398 | 60.676 | 1.00 | 16.27 |
| 5476 | CB | ASP | A | 358 | 6.080 | 33.824 | 60.512 | 1.00 | 16.34 |
| 5479 | CG | ASP | A | 358 | 7.090 | 34.877 | 60.915 | 1.00 | 16.62 |
| 5480 | OD1 | ASP | A | 358 | 8.037 | 34.558 | 61.666 | 1.00 | 17.57 |
| 5481 | OD2 | ASP | A | 358 | 7.004 | 36.058 | 60.537 | 1.00 | 17.02 |
| 5482 | C | ASP | A | 358 | 5.437 | 31.421 | 60.662 | 1.00 | 16.16 |
| 5483 | O | ASP | A | 358 | 4.621 | 31.431 | 61.580 | 1.00 | 16.17 |
| 5484 | N | ILE | A | 359 | 5.351 | 30.595 | 59.620 | 1.00 | 16.11 |
| 5486 | CA | ILE | A | 359 | 4.297 | 29.593 | 59.489 | 1.00 | 16.26 |
| 5488 | CB | ILE | A | 359 | 3.732 | 29.572 | 58.045 | 1.00 | 16.55 |
| 5490 | CG1 | ILE | A | 359 | 3.285 | 30.971 | 57.601 | 1.00 | 17.22 |
| 5493 | CD1 | ILE | A | 359 | 2.109 | 31.539 | 58.375 | 1.00 | 18.42 |
| 5497 | CG2 | ILE | A | 359 | 2.574 | 28.561 | 57.929 | 1.00 | 16.87 |
| 5501 | C | ILE | A | 359 | 4.847 | 28.219 | 59.830 | 1.00 | 15.89 |
| 5502 | O | ILE | A | 359 | 5.779 | 27.742 | 59.187 | 1.00 | 15.72 |
| 5503 | N | ASP | A | 360 | 4.267 | 27.589 | 60.845 | 1.00 | 15.65 |
| 5505 | CA | ASP | A | 360 | 4.597 | 26.214 | 61.190 | 1.00 | 15.51 |
| 5507 | CB | ASP | A | 360 | 3.920 | 25.800 | 62.498 | 1.00 | 15.42 |
| 5510 | CG | ASP | A | 360 | 4.374 | 26.640 | 63.673 | 1.00 | 15.22 |
| 5511 | OD1 | ASP | A | 360 | 3.644 | 26.709 | 64.677 | 1.00 | 14.30 |
| 5512 | OD2 | ASP | A | 360 | 5.446 | 27.281 | 63.671 | 1.00 | 14.41 |
| 5513 | C | ASP | A | 360 | 4.179 | 25.294 | 60.054 | 1.00 | 15.39 |
| 5514 | O | ASP | A | 360 | 3.063 | 25.380 | 59.554 | 1.00 | 15.44 |
| 5515 | N | GLN | A | 361 | 5.098 | 24.429 | 59.643 | 1.00 | 15.26 |
| 5517 | CA | GLN | A | 361 | 4.896 | 23.568 | 58.484 | 1.00 | 15.11 |
| 5519 | CB | GLN | A | 361 | 4.911 | 24.400 | 57.196 | 1.00 | 15.34 |
| 5522 | CG | GLN | A | 361 | 6.217 | 25.165 | 56.961 | 1.00 | 15.68 |
| 5525 | CD | GLN | A | 361 | 6.119 | 26.161 | 55.817 | 1.00 | 16.76 |
| 5526 | OE1 | GLN | A | 361 | 5.988 | 25.768 | 54.661 | 1.00 | 16.89 |
| 5527 | NE2 | GLN | A | 361 | 6.190 | 27.449 | 56.136 | 1.00 | 17.13 |
| 5530 | C | GLN | A | 361 | 5.975 | 22.500 | 58.393 | 1.00 | 14.90 |
| 5531 | O | GLN | A | 361 | 7.018 | 22.587 | 59.037 | 1.00 | 14.23 |
| 5532 | N | THR | A | 362 | 5.716 | 21.506 | 57.557 | 1.00 | 14.83 |
| 5534 | CA | THR | A | 362 | 6.671 | 20.453 | 57.262 | 1.00 | 15.17 |
| 5536 | CB | THR | A | 362 | 6.036 | 19.085 | 57.557 | 1.00 | 15.31 |
| 5538 | OG1 | THR | A | 362 | 5.428 | 19.100 | 58.860 | 1.00 | 15.89 |
| 5540 | CG2 | THR | A | 362 | 7.099 | 18.001 | 57.648 | 1.00 | 15.70 |
| 5544 | C | THR | A | 362 | 7.045 | 20.540 | 55.789 | 1.00 | 15.03 |
| 5545 | O | THR | A | 362 | 6.169 | 20.636 | 54.934 | 1.00 | 15.06 |
| 5546 | N | LEU | A | 363 | 8.342 | 20.518 | 55.500 | 1.00 | 14.98 |
| 5548 | CA | LEU | A | 363 | 8.831 | 20.495 | 54.126 | 1.00 | 15.07 |
| 5550 | CB | BLEU | A | 363 | 10.037 | 21.426 | 53.950 | 0.35 | 15.14 |
| 5551 | CB | ALEU | A | 363 | 10.030 | 21.433 | 53.957 | 0.65 | 15.12 |
| 5556 | CG | BLEU | A | 363 | 9.823 | 22.946 | 54.005 | 0.35 | 15.70 |
| 5557 | CG | ALEU | A | 363 | 9.744 | 22.938 | 53.973 | 0.65 | 15.75 |
| 5560 | CD1 | BLEU | A | 363 | 8.571 | 23.374 | 53.246 | 0.35 | 15.88 |
| 5561 | CD1 | ALEU | A | 363 | 9.140 | 23.378 | 55.299 | 0.65 | 16.69 |
| 5568 | CD2 | BLEU | A | 363 | 9.770 | 23.444 | 55.442 | 0.35 | 16.27 |
| 5569 | CD2 | ALEU | A | 363 | 11.016 | 23.720 | 53.674 | 0.65 | 15.48 |
| 5576 | C | LEU | A | 363 | 9.235 | 19.064 | 53.819 | 1.00 | 14.86 |
| 5577 | O | LEU | A | 363 | 9.811 | 18.394 | 54.675 | 1.00 | 14.87 |

FIGURE 3 (Cont.)

| A | B | C | D | E | F | G | H | I | J |
|---|---|---|---|---|---|---|---|---|---|
| 5578 | N | GLU | A | 364 | 8.921 | 18.600 | 52.612 | 1.00 | 14.49 |
| 5580 | CA | GLU | A | 364 | 9.267 | 17.250 | 52.170 | 1.00 | 14.45 |
| 5582 | CB | GLU | A | 364 | 8.042 | 16.537 | 51.573 | 1.00 | 14.64 |
| 5585 | CG | GLU | A | 364 | 8.334 | 15.346 | 50.655 | 1.00 | 15.61 |
| 5588 | CD | GLU | A | 364 | 9.295 | 14.309 | 51.232 | 1.00 | 17.24 |
| 5589 | OE1 | GLU | A | 364 | 9.482 | 14.229 | 52.475 | 1.00 | 17.33 |
| 5590 | OE2 | GLU | A | 364 | 9.871 | 13.551 | 50.422 | 1.00 | 17.72 |
| 5591 | C | GLU | A | 364 | 10.405 | 17.321 | 51.162 | 1.00 | 13.90 |
| 5592 | O | GLU | A | 364 | 10.347 | 18.067 | 50.187 | 1.00 | 13.79 |
| 5593 | N | ASP | A | 365 | 11.441 | 16.535 | 51.419 | 1.00 | 13.54 |
| 5595 | CA | ASP | A | 365 | 12.632 | 16.501 | 50.581 | 1.00 | 13.42 |
| 5597 | CB | ASP | A | 365 | 13.518 | 17.715 | 50.893 | 1.00 | 13.35 |
| 5600 | CG | ASP | A | 365 | 14.550 | 17.999 | 49.807 | 1.00 | 13.84 |
| 5601 | OD1 | ASP | A | 365 | 15.117 | 17.045 | 49.239 | 1.00 | 13.44 |
| 5602 | OD2 | ASP | A | 365 | 14.863 | 19.157 | 49.461 | 1.00 | 13.26 |
| 5603 | C | ASP | A | 365 | 13.367 | 15.187 | 50.849 | 1.00 | 13.21 |
| 5604 | O | ASP | A | 365 | 13.516 | 14.779 | 52.001 | 1.00 | 12.99 |
| 5605 | N | GLU | A | 366 | 13.816 | 14.526 | 49.784 | 1.00 | 13.11 |
| 5607 | CA | GLU | A | 366 | 14.494 | 13.233 | 49.887 | 1.00 | 13.06 |
| 5609 | CB | GLU | A | 366 | 14.522 | 12.539 | 48.514 | 1.00 | 13.38 |
| 5612 | CG | AGLU | A | 366 | 13.154 | 12.149 | 47.966 | 0.65 | 13.53 |
| 5615 | CD | AGLU | A | 366 | 13.237 | 11.143 | 46.825 | 0.65 | 14.22 |
| 5616 | OE1 | AGLU | A | 366 | 12.245 | 10.417 | 46.599 | 0.65 | 14.91 |
| 5617 | OE2 | AGLU | A | 366 | 14.292 | 11.064 | 46.158 | 0.65 | 14.08 |
| 5618 | C | GLU | A | 366 | 15.929 | 13.353 | 50.403 | 1.00 | 12.99 |
| 5619 | O | GLU | A | 366 | 16.506 | 12.372 | 50.870 | 1.00 | 12.92 |
| 5620 | N | LEU | A | 367 | 16.509 | 14.547 | 50.310 | 1.00 | 12.76 |
| 5622 | CA | LEU | A | 367 | 17.924 | 14.741 | 50.618 | 1.00 | 12.46 |
| 5624 | CB | LEU | A | 367 | 18.417 | 16.074 | 50.041 | 1.00 | 12.48 |
| 5627 | CG | LEU | A | 367 | 19.920 | 16.360 | 50.154 | 1.00 | 12.94 |
| 5629 | CD1 | LEU | A | 367 | 20.740 | 15.404 | 49.296 | 1.00 | 14.22 |
| 5633 | CD2 | LEU | A | 367 | 20.221 | 17.801 | 49.781 | 1.00 | 12.50 |
| 5637 | C | LEU | A | 367 | 18.202 | 14.702 | 52.116 | 1.00 | 12.25 |
| 5638 | O | LEU | A | 367 | 17.457 | 15.271 | 52.917 | 1.00 | 12.00 |
| 5639 | N | LYS | A | 368 | 19.289 | 14.031 | 52.479 | 1.00 | 11.83 |
| 5641 | CA | LYS | A | 368 | 19.790 | 14.040 | 53.845 | 1.00 | 11.73 |
| 5643 | CB | LYS | A | 368 | 21.010 | 13.120 | 53.972 | 1.00 | 11.82 |
| 5646 | CG | LYS | A | 368 | 21.418 | 12.780 | 55.403 | 1.00 | 12.46 |
| 5649 | CD | LYS | A | 368 | 22.741 | 12.019 | 55.413 | 1.00 | 13.39 |
| 5652 | CE | LYS | A | 368 | 22.925 | 11.207 | 56.682 | 1.00 | 14.11 |
| 5655 | NZ | LYS | A | 368 | 24.215 | 10.465 | 56.682 | 1.00 | 14.32 |
| 5659 | C | LYS | A | 368 | 20.152 | 15.478 | 54.240 | 1.00 | 11.19 |
| 5660 | O | LYS | A | 368 | 20.703 | 16.239 | 53.439 | 1.00 | 10.84 |
| 5661 | N | TYR | A | 369 | 19.798 | 15.834 | 55.471 | 1.00 | 10.91 |
| 5663 | CA | TYR | A | 369 | 20.042 | 17.157 | 56.049 | 1.00 | 10.67 |
| 5665 | CB | TYR | A | 369 | 21.541 | 17.486 | 56.060 | 1.00 | 10.69 |
| 5668 | CG | TYR | A | 369 | 22.389 | 16.472 | 56.798 | 1.00 | 11.38 |
| 5669 | CD1 | TYR | A | 369 | 23.471 | 15.859 | 56.177 | 1.00 | 12.19 |
| 5671 | CE1 | TYR | A | 369 | 24.256 | 14.930 | 56.852 | 1.00 | 13.08 |
| 5673 | CZ | TYR | A | 369 | 23.958 | 14.604 | 58.165 | 1.00 | 13.09 |
| 5674 | OH | TYR | A | 369 | 24.733 | 13.690 | 58.829 | 1.00 | 14.74 |
| 5676 | CE2 | TYR | A | 369 | 22.889 | 15.196 | 58.808 | 1.00 | 13.03 |
| 5678 | CD2 | TYR | A | 369 | 22.110 | 16.128 | 58.123 | 1.00 | 12.38 |

FIGURE 3 (Cont.)

| A | B | C | D | E | F | G | H | I | J |
|---|---|---|---|---|---|---|---|---|---|
| 5680 | C | TYR | A | 369 | 19.239 | 18.297 | 55.407 | 1.00 | 10.49 |
| 5681 | O | TYR | A | 369 | 19.521 | 19.472 | 55.667 | 1.00 | 10.34 |
| 5682 | N | SER | A | 370 | 18.235 | 17.958 | 54.597 | 1.00 | 9.93 |
| 5684 | CA | SER | A | 370 | 17.258 | 18.939 | 54.136 | 1.00 | 10.02 |
| 5686 | CB | SER | A | 370 | 16.434 | 18.395 | 52.963 | 1.00 | 9.93 |
| 5689 | OG | SER | A | 370 | 15.825 | 17.156 | 53.296 | 1.00 | 10.17 |
| 5691 | C | SER | A | 370 | 16.327 | 19.320 | 55.286 | 1.00 | 9.92 |
| 5692 | O | SER | A | 370 | 16.237 | 18.612 | 56.286 | 1.00 | 9.97 |
| 5693 | N | ILE | A | 371 | 15.627 | 20.436 | 55.136 | 1.00 | 10.13 |
| 5695 | CA | ILE | A | 371 | 14.715 | 20.913 | 56.165 | 1.00 | 10.20 |
| 5697 | CB | ILE | A | 371 | 14.286 | 22.372 | 55.894 | 1.00 | 10.24 |
| 5699 | CG1 | ILE | A | 371 | 15.496 | 23.311 | 55.868 | 1.00 | 10.27 |
| 5702 | CD1 | ILE | A | 371 | 15.233 | 24.609 | 55.107 | 1.00 | 10.40 |
| 5706 | CG2 | ILE | A | 371 | 13.297 | 22.848 | 56.964 | 1.00 | 9.83 |
| 5710 | C | ILE | A | 371 | 13.476 | 20.022 | 56.212 | 1.00 | 10.36 |
| 5711 | O | ILE | A | 371 | 12.886 | 19.721 | 55.169 | 1.00 | 10.09 |
| 5712 | N | SER | A | 372 | 13.107 | 19.600 | 57.422 | 1.00 | 10.60 |
| 5714 | CA | SER | A | 372 | 11.821 | 18.963 | 57.688 | 1.00 | 11.05 |
| 5716 | CB | SER | A | 372 | 11.994 | 17.690 | 58.529 | 1.00 | 11.11 |
| 5719 | OG | SER | A | 372 | 12.698 | 17.956 | 59.726 | 1.00 | 9.90 |
| 5721 | C | SER | A | 372 | 10.894 | 19.972 | 58.381 | 1.00 | 11.52 |
| 5722 | O | SER | A | 372 | 10.160 | 20.678 | 57.716 | 1.00 | 12.46 |
| 5723 | N | ALA | A | 373 | 10.946 | 20.081 | 59.704 | 1.00 | 11.97 |
| 5725 | CA | ALA | A | 373 | 10.030 | 20.968 | 60.421 | 1.00 | 11.70 |
| 5727 | CB | ALA | A | 373 | 9.876 | 20.505 | 61.859 | 1.00 | 11.92 |
| 5731 | C | ALA | A | 373 | 10.481 | 22.431 | 60.395 | 1.00 | 11.76 |
| 5732 | O | ALA | A | 373 | 11.673 | 22.721 | 60.404 | 1.00 | 11.09 |
| 5733 | N | ILE | A | 374 | 9.507 | 23.335 | 60.311 | 1.00 | 11.77 |
| 5735 | CA | ILE | A | 374 | 9.649 | 24.710 | 60.782 | 1.00 | 12.11 |
| 5737 | CB | ILE | A | 374 | 9.333 | 25.751 | 59.687 | 1.00 | 12.41 |
| 5739 | CG1 | ILE | A | 374 | 10.153 | 25.492 | 58.420 | 1.00 | 13.61 |
| 5742 | CD1 | ILE | A | 374 | 11.641 | 25.634 | 58.607 | 1.00 | 14.48 |
| 5746 | CG2 | ILE | A | 374 | 9.597 | 27.167 | 60.214 | 1.00 | 12.27 |
| 5750 | C | ILE | A | 374 | 8.649 | 24.841 | 61.922 | 1.00 | 11.96 |
| 5751 | O | ILE | A | 374 | 7.449 | 24.635 | 61.727 | 1.00 | 11.50 |
| 5752 | N | ASN | A | 375 | 9.145 | 25.157 | 63.112 | 1.00 | 11.72 |
| 5754 | CA | ASN | A | 375 | 8.316 | 25.217 | 64.304 | 1.00 | 11.69 |
| 5756 | CB | ASN | A | 375 | 8.426 | 23.907 | 65.098 | 1.00 | 11.66 |
| 5759 | CG | ASN | A | 375 | 7.452 | 23.845 | 66.274 | 1.00 | 12.59 |
| 5760 | OD1 | ASN | A | 375 | 7.663 | 23.104 | 67.233 | 1.00 | 14.92 |
| 5761 | ND2 | ASN | A | 375 | 6.380 | 24.614 | 66.195 | 1.00 | 13.50 |
| 5764 | C | ASN | A | 375 | 8.753 | 26.388 | 65.166 | 1.00 | 11.38 |
| 5765 | O | ASN | A | 375 | 9.876 | 26.406 | 65.669 | 1.00 | 11.16 |
| 5766 | N | ASN | A | 376 | 7.859 | 27.352 | 65.345 | 1.00 | 11.20 |
| 5768 | CA | ASN | A | 376 | 8.185 | 28.592 | 66.037 | 1.00 | 11.21 |
| 5770 | CB | ASN | A | 376 | 8.319 | 28.332 | 67.543 | 1.00 | 11.11 |
| 5773 | CG | ASN | A | 376 | 8.185 | 29.597 | 68.373 | 1.00 | 11.35 |
| 5774 | OD1 | ASN | A | 376 | 7.387 | 30.484 | 68.058 | 1.00 | 10.26 |
| 5775 | ND2 | ASN | A | 376 | 8.971 | 29.686 | 69.441 | 1.00 | 11.55 |
| 5778 | C | ASN | A | 376 | 9.455 | 29.232 | 65.453 | 1.00 | 11.05 |
| 5779 | O | ASN | A | 376 | 10.330 | 29.684 | 66.189 | 1.00 | 10.77 |
| 5780 | N | THR | A | 377 | 9.524 | 29.246 | 64.117 | 1.00 | 10.89 |
| 5782 | CA | THR | A | 377 | 10.668 | 29.735 | 63.318 | 1.00 | 10.98 |

FIGURE 3 (Cont.)

| A | B | C | D | E | F | G | H | I | J |
|---|---|---|---|---|---|---|---|---|---|
| 5784 | CB | THR | A | 377 | 11.077 | 31.200 | 63.674 | 1.00 | 10.89 |
| 5786 | OG1 | THR | A | 377 | 11.735 | 31.236 | 64.946 | 1.00 | 10.33 |
| 5788 | CG2 | THR | A | 377 | 9.859 | 32.111 | 63.832 | 1.00 | 11.01 |
| 5792 | C | THR | A | 377 | 11.916 | 28.840 | 63.316 | 1.00 | 10.94 |
| 5793 | O | THR | A | 377 | 12.841 | 29.086 | 62.543 | 1.00 | 10.97 |
| 5794 | N | VAL | A | 378 | 11.944 | 27.807 | 64.153 | 1.00 | 11.19 |
| 5796 | CA | VAL | A | 378 | 13.105 | 26.927 | 64.250 | 1.00 | 11.25 |
| 5798 | CB | VAL | A | 378 | 13.203 | 26.264 | 65.640 | 1.00 | 11.31 |
| 5800 | CG1 | VAL | A | 378 | 14.437 | 25.358 | 65.726 | 1.00 | 11.42 |
| 5804 | CG2 | VAL | A | 378 | 13.226 | 27.323 | 66.735 | 1.00 | 11.87 |
| 5808 | C | VAL | A | 378 | 13.066 | 25.834 | 63.188 | 1.00 | 11.32 |
| 5809 | O | VAL | A | 378 | 12.068 | 25.126 | 63.043 | 1.00 | 11.24 |
| 5810 | N | ARG | A | 379 | 14.174 | 25.685 | 62.468 | 1.00 | 11.42 |
| 5812 | CA | ARG | A | 379 | 14.314 | 24.646 | 61.462 | 1.00 | 11.70 |
| 5814 | CB | ARG | A | 379 | 15.297 | 25.081 | 60.372 | 1.00 | 11.87 |
| 5817 | CG | ARG | A | 379 | 14.855 | 26.293 | 59.564 | 1.00 | 12.48 |
| 5820 | CD | ARG | A | 379 | 15.988 | 26.961 | 58.799 | 1.00 | 13.13 |
| 5823 | NE | ARG | A | 379 | 15.572 | 28.253 | 58.248 | 1.00 | 13.12 |
| 5825 | CZ | ARG | A | 379 | 15.731 | 28.646 | 56.983 | 1.00 | 12.53 |
| 5826 | NH1 | ARG | A | 379 | 16.342 | 27.885 | 56.084 | 1.00 | 12.53 |
| 5829 | NH2 | ARG | A | 379 | 15.290 | 29.844 | 56.618 | 1.00 | 12.90 |
| 5832 | C | ARG | A | 379 | 14.822 | 23.358 | 62.104 | 1.00 | 11.69 |
| 5833 | O | ARG | A | 379 | 15.712 | 23.385 | 62.960 | 1.00 | 11.39 |
| 5834 | N | SER | A | 380 | 14.239 | 22.238 | 61.692 | 1.00 | 11.60 |
| 5836 | CA | SER | A | 380 | 14.797 | 20.927 | 61.955 | 1.00 | 11.82 |
| 5838 | CB | SER | A | 380 | 13.747 | 20.015 | 62.581 | 1.00 | 11.99 |
| 5841 | OG | SER | A | 380 | 13.304 | 20.542 | 63.814 | 1.00 | 12.10 |
| 5843 | C | SER | A | 380 | 15.284 | 20.347 | 60.635 | 1.00 | 11.85 |
| 5844 | O | SER | A | 380 | 14.803 | 20.730 | 59.572 | 1.00 | 11.84 |
| 5845 | N | TYR | A | 381 | 16.244 | 19.435 | 60.720 | 1.00 | 11.95 |
| 5847 | CA | TYR | A | 381 | 16.850 | 18.797 | 59.557 | 1.00 | 12.18 |
| 5849 | CB | TYR | A | 381 | 18.313 | 19.235 | 59.429 | 1.00 | 12.11 |
| 5852 | CG | TYR | A | 381 | 18.447 | 20.729 | 59.282 | 1.00 | 10.28 |
| 5853 | CD1 | TYR | A | 381 | 18.402 | 21.325 | 58.033 | 1.00 | 9.25 |
| 5855 | CE1 | TYR | A | 381 | 18.498 | 22.699 | 57.886 | 1.00 | 8.92 |
| 5857 | CZ | TYR | A | 381 | 18.630 | 23.497 | 59.005 | 1.00 | 8.09 |
| 5858 | OH | TYR | A | 381 | 18.718 | 24.852 | 58.854 | 1.00 | 7.57 |
| 5860 | CE2 | TYR | A | 381 | 18.668 | 22.934 | 60.265 | 1.00 | 8.75 |
| 5862 | CD2 | TYR | A | 381 | 18.570 | 21.549 | 60.398 | 1.00 | 9.56 |
| 5864 | C | TYR | A | 381 | 16.755 | 17.278 | 59.688 | 1.00 | 12.78 |
| 5865 | O | TYR | A | 381 | 17.047 | 16.718 | 60.748 | 1.00 | 12.72 |
| 5866 | N | ARG | A | 382 | 16.328 | 16.611 | 58.621 | 1.00 | 13.67 |
| 5868 | CA | ARG | A | 382 | 16.218 | 15.152 | 58.648 | 1.00 | 14.36 |
| 5870 | CB | ARG | A | 382 | 15.333 | 14.605 | 57.507 | 1.00 | 14.27 |
| 5873 | CG | ARG | A | 382 | 15.536 | 15.214 | 56.133 | 1.00 | 13.64 |
| 5876 | CD | ARG | A | 382 | 14.693 | 14.563 | 55.036 | 1.00 | 13.08 |
| 5879 | NE | ARG | A | 382 | 13.254 | 14.715 | 55.266 | 1.00 | 11.85 |
| 5881 | CZ | ARG | A | 382 | 12.553 | 15.828 | 55.060 | 1.00 | 11.18 |
| 5882 | NH1 | ARG | A | 382 | 11.252 | 15.838 | 55.316 | 1.00 | 11.19 |
| 5885 | NH2 | ARG | A | 382 | 13.127 | 16.931 | 54.600 | 1.00 | 10.55 |
| 5888 | C | ARG | A | 382 | 17.614 | 14.519 | 58.667 | 1.00 | 15.14 |
| 5889 | O | ARG | A | 382 | 18.498 | 14.918 | 57.914 | 1.00 | 15.32 |
| 5890 | N | ASN | A | 383 | 17.803 | 13.555 | 59.564 | 1.00 | 16.08 |

FIGURE 3 (Cont.)

| A | B | C | D | E | F | G | H | I | J |
|---|---|---|---|---|---|---|---|---|---|
| 5892 | CA | ASN | A | 383 | 19.102 | 12.918 | 59.794 | 1.00 | 16.97 |
| 5894 | CB | AASN | A | 383 | 19.156 | 12.301 | 61.202 | 0.65 | 16.85 |
| 5897 | CG | AASN | A | 383 | 19.078 | 13.343 | 62.307 | 0.65 | 17.39 |
| 5898 | OD1 | AASN | A | 383 | 18.410 | 13.138 | 63.322 | 0.65 | 18.43 |
| 5899 | ND2 | AASN | A | 383 | 19.767 | 14.461 | 62.120 | 0.65 | 17.07 |
| 5902 | C | ASN | A | 383 | 19.428 | 11.837 | 58.769 | 1.00 | 17.67 |
| 5903 | O | ASN | A | 383 | 20.563 | 11.355 | 58.711 | 1.00 | 17.96 |
| 5904 | N | ALA | A | 384 | 18.430 | 11.440 | 57.985 | 1.00 | 18.47 |
| 5906 | CA | ALA | A | 384 | 18.634 | 10.473 | 56.909 | 1.00 | 18.93 |
| 5908 | CB | ALA | A | 384 | 18.130 | 9.090 | 57.336 | 1.00 | 19.18 |
| 5912 | C | ALA | A | 384 | 17.924 | 10.921 | 55.642 | 1.00 | 19.23 |
| 5913 | O | ALA | A | 384 | 16.879 | 11.566 | 55.699 | 1.00 | 19.29 |
| 5914 | N | GLY | A | 385 | 18.501 | 10.582 | 54.496 | 1.00 | 19.64 |
| 5916 | CA | GLY | A | 385 | 17.799 | 10.700 | 53.233 | 1.00 | 20.00 |
| 5919 | C | GLY | A | 385 | 16.771 | 9.587 | 53.115 | 1.00 | 20.41 |
| 5920 | O | GLY | A | 385 | 16.734 | 8.670 | 53.939 | 1.00 | 20.69 |
| 5921 | N | HIS | A | 386 | 15.926 | 9.674 | 52.096 | 1.00 | 20.83 |
| 5923 | CA | HIS | A | 386 | 14.971 | 8.611 | 51.796 | 1.00 | 21.17 |
| 5925 | CB | HIS | A | 386 | 13.735 | 8.715 | 52.705 | 1.00 | 21.06 |
| 5928 | CG | HIS | A | 386 | 12.963 | 9.992 | 52.544 | 1.00 | 20.61 |
| 5929 | ND1 | HIS | A | 386 | 13.073 | 11.045 | 53.427 | 1.00 | 20.63 |
| 5931 | CE1 | HIS | A | 386 | 12.276 | 12.027 | 53.044 | 1.00 | 19.49 |
| 5933 | NE2 | HIS | A | 386 | 11.650 | 11.647 | 51.945 | 1.00 | 19.98 |
| 5935 | CD2 | HIS | A | 386 | 12.058 | 10.377 | 51.613 | 1.00 | 20.28 |
| 5937 | C | HIS | A | 386 | 14.553 | 8.620 | 50.328 | 1.00 | 21.64 |
| 5938 | O | HIS | A | 386 | 14.799 | 9.583 | 49.602 | 1.00 | 21.80 |
| 5939 | N | ALA | A | 387 | 13.948 | 7.518 | 49.902 | 1.00 | 22.16 |
| 5941 | CA | ALA | A | 387 | 13.315 | 7.411 | 48.591 | 1.00 | 22.56 |
| 5943 | CB | ALA | A | 387 | 14.329 | 6.994 | 47.540 | 1.00 | 22.65 |
| 5947 | C | ALA | A | 387 | 12.204 | 6.373 | 48.725 | 1.00 | 22.96 |
| 5948 | O | ALA | A | 387 | 12.481 | 5.174 | 48.824 | 1.00 | 23.38 |
| 5949 | N | ALA | A | 388 | 10.954 | 6.839 | 48.744 | 1.00 | 23.23 |
| 5951 | CA | ALA | A | 388 | 9.829 | 6.021 | 49.210 | 1.00 | 23.31 |
| 5953 | CB | ALA | A | 388 | 8.609 | 6.911 | 49.495 | 1.00 | 23.34 |
| 5957 | C | ALA | A | 388 | 9.449 | 4.890 | 48.249 | 1.00 | 23.62 |
| 5958 | O | ALA | A | 388 | 9.783 | 4.930 | 47.058 | 1.00 | 24.07 |
| 5959 | N | THR | B | 2 | 54.358 | 38.490 | 75.937 | 1.00 | 11.97 |
| 5961 | CA | THR | B | 2 | 52.902 | 38.329 | 76.203 | 1.00 | 12.11 |
| 5963 | CB | THR | B | 2 | 52.503 | 39.021 | 77.518 | 1.00 | 12.22 |
| 5965 | OG1 | THR | B | 2 | 52.909 | 40.395 | 77.491 | 1.00 | 12.34 |
| 5967 | CG2 | THR | B | 2 | 53.253 | 38.421 | 78.709 | 1.00 | 13.31 |
| 5971 | C | THR | B | 2 | 52.089 | 38.913 | 75.061 | 1.00 | 11.80 |
| 5972 | O | THR | B | 2 | 52.613 | 39.663 | 74.238 | 1.00 | 11.83 |
| 5975 | N | ILE | B | 3 | 50.813 | 38.539 | 75.013 | 1.00 | 11.52 |
| 5977 | CA | ILE | B | 3 | 49.856 | 39.041 | 74.022 | 1.00 | 11.38 |
| 5979 | CB | ILE | B | 3 | 49.672 | 38.032 | 72.868 | 1.00 | 11.66 |
| 5981 | CG1 | ILE | B | 3 | 51.000 | 37.716 | 72.174 | 1.00 | 12.99 |
| 5984 | CD1 | ILE | B | 3 | 51.015 | 36.354 | 71.556 | 1.00 | 14.40 |
| 5988 | CG2 | ILE | B | 3 | 48.670 | 38.565 | 71.844 | 1.00 | 12.11 |
| 5992 | C | ILE | B | 3 | 48.506 | 39.234 | 74.689 | 1.00 | 10.74 |
| 5993 | O | ILE | B | 3 | 48.089 | 38.401 | 75.489 | 1.00 | 10.37 |
| 5994 | N | GLY | B | 4 | 47.807 | 40.310 | 74.343 | 1.00 | 10.22 |
| 5996 | CA | GLY | B | 4 | 46.466 | 40.515 | 74.859 | 1.00 | 10.00 |

FIGURE 3 (Cont.)

| A | B | C | D | E | F | G | H | I | J |
|---|---|---|---|---|---|---|---|---|---|
| 5999 | C | GLY | B | 4 | 45.862 | 41.875 | 74.579 | 1.00 | 9.71 |
| 6000 | O | GLY | B | 4 | 46.128 | 42.486 | 73.544 | 1.00 | 9.39 |
| 6001 | N | ILE | B | 5 | 45.017 | 42.324 | 75.503 | 1.00 | 9.42 |
| 6003 | CA | ILE | B | 5 | 44.315 | 43.589 | 75.373 | 1.00 | 9.31 |
| 6005 | CB | ILE | B | 5 | 43.039 | 43.603 | 76.249 | 1.00 | 9.46 |
| 6007 | CG1 | ILE | B | 5 | 42.068 | 42.504 | 75.785 | 1.00 | 9.81 |
| 6010 | CD1 | ILE | B | 5 | 40.958 | 42.173 | 76.784 | 1.00 | 10.10 |
| 6014 | CG2 | ILE | B | 5 | 42.354 | 44.963 | 76.167 | 1.00 | 9.61 |
| 6018 | C | ILE | B | 5 | 45.261 | 44.730 | 75.735 | 1.00 | 9.06 |
| 6019 | O | ILE | B | 5 | 45.571 | 44.958 | 76.901 | 1.00 | 8.73 |
| 6020 | N | ASP | B | 6 | 45.739 | 45.416 | 74.707 | 1.00 | 8.88 |
| 6022 | CA | ASP | B | 6 | 46.635 | 46.551 | 74.866 | 1.00 | 8.82 |
| 6024 | CB | ASP | B | 6 | 47.421 | 46.772 | 73.574 | 1.00 | 8.72 |
| 6027 | CG | ASP | B | 6 | 48.464 | 47.851 | 73.709 | 1.00 | 9.13 |
| 6028 | OD1 | ASP | B | 6 | 48.569 | 48.693 | 72.792 | 1.00 | 10.02 |
| 6029 | OD2 | ASP | B | 6 | 49.217 | 47.938 | 74.699 | 1.00 | 8.01 |
| 6030 | C | ASP | B | 6 | 45.856 | 47.817 | 75.230 | 1.00 | 8.64 |
| 6031 | O | ASP | B | 6 | 46.280 | 48.594 | 76.082 | 1.00 | 8.63 |
| 6032 | N | LYS | B | 7 | 44.730 | 48.022 | 74.555 | 1.00 | 8.52 |
| 6034 | CA | LYS | B | 7 | 43.843 | 49.150 | 74.828 | 1.00 | 8.56 |
| 6036 | CB | LYS | B | 7 | 44.014 | 50.252 | 73.779 | 1.00 | 8.57 |
| 6039 | CG | LYS | B | 7 | 45.424 | 50.767 | 73.601 | 1.00 | 8.68 |
| 6042 | CD | LYS | B | 7 | 45.459 | 51.789 | 72.481 | 1.00 | 8.18 |
| 6045 | CE | LYS | B | 7 | 46.854 | 52.317 | 72.231 | 1.00 | 7.72 |
| 6048 | NZ | LYS | B | 7 | 46.811 | 53.444 | 71.253 | 1.00 | 7.10 |
| 6052 | C | LYS | B | 7 | 42.400 | 48.688 | 74.806 | 1.00 | 8.49 |
| 6053 | O | LYS | B | 7 | 42.063 | 47.709 | 74.144 | 1.00 | 8.34 |
| 6054 | N | ILE | B | 8 | 41.550 | 49.400 | 75.533 | 1.00 | 8.42 |
| 6056 | CA | ILE | B | 8 | 40.128 | 49.108 | 75.568 | 1.00 | 8.31 |
| 6058 | CB | ILE | B | 8 | 39.829 | 47.934 | 76.536 | 1.00 | 8.48 |
| 6060 | CG1 | ILE | B | 8 | 38.365 | 47.500 | 76.417 | 1.00 | 8.68 |
| 6063 | CD1 | ILE | B | 8 | 38.032 | 46.195 | 77.148 | 1.00 | 9.29 |
| 6067 | CG2 | ILE | B | 8 | 40.190 | 48.301 | 77.980 | 1.00 | 8.89 |
| 6071 | C | ILE | B | 8 | 39.334 | 50.359 | 75.941 | 1.00 | 8.15 |
| 6072 | O | ILE | B | 8 | 39.769 | 51.170 | 76.759 | 1.00 | 8.02 |
| 6073 | N | SER | B | 9 | 38.178 | 50.509 | 75.303 | 1.00 | 7.95 |
| 6075 | CA | SER | B | 9 | 37.270 | 51.626 | 75.547 | 1.00 | 7.81 |
| 6077 | CB | ASER | B | 9 | 37.628 | 52.800 | 74.644 | 0.65 | 7.88 |
| 6080 | OG | ASER | B | 9 | 37.584 | 52.403 | 73.279 | 0.65 | 8.76 |
| 6082 | C | SER | B | 9 | 35.840 | 51.193 | 75.250 | 1.00 | 7.48 |
| 6083 | O | SER | B | 9 | 35.611 | 50.126 | 74.683 | 1.00 | 7.14 |
| 6084 | N | PHE | B | 10 | 34.878 | 52.014 | 75.644 | 1.00 | 7.33 |
| 6086 | CA | PHE | B | 10 | 33.505 | 51.794 | 75.212 | 1.00 | 7.53 |
| 6088 | CB | PHE | B | 10 | 32.712 | 50.997 | 76.261 | 1.00 | 7.38 |
| 6091 | CG | PHE | B | 10 | 32.279 | 51.799 | 77.456 | 1.00 | 7.52 |
| 6092 | CD1 | PHE | B | 10 | 33.105 | 51.923 | 78.565 | 1.00 | 7.28 |
| 6094 | CE1 | PHE | B | 10 | 32.701 | 52.644 | 79.676 | 1.00 | 7.36 |
| 6096 | CZ | PHE | B | 10 | 31.459 | 53.243 | 79.698 | 1.00 | 7.81 |
| 6098 | CE2 | PHE | B | 10 | 30.612 | 53.114 | 78.608 | 1.00 | 7.86 |
| 6100 | CD2 | PHE | B | 10 | 31.023 | 52.392 | 77.493 | 1.00 | 8.08 |
| 6102 | C | PHE | B | 10 | 32.801 | 53.085 | 74.826 | 1.00 | 7.53 |
| 6103 | O | PHE | B | 10 | 33.248 | 54.184 | 75.149 | 1.00 | 7.64 |
| 6104 | N | PHE | B | 11 | 31.713 | 52.921 | 74.089 | 1.00 | 7.82 |

FIGURE 3 (Cont.)

| A | B | C | D | E | F | G | H | I | J |
|---|---|---|---|---|---|---|---|---|---|
| 6106 | CA | PHE | B | 11 | 30.830 | 54.013 | 73.730 | 1.00 | 7.90 |
| 6108 | CB | PHE | B | 11 | 31.062 | 54.452 | 72.282 | 1.00 | 8.05 |
| 6111 | CG | PHE | B | 11 | 30.176 | 55.590 | 71.851 | 1.00 | 8.85 |
| 6112 | CD1 | PHE | B | 11 | 30.498 | 56.900 | 72.184 | 1.00 | 10.21 |
| 6114 | CE1 | PHE | B | 11 | 29.678 | 57.954 | 71.799 | 1.00 | 10.00 |
| 6116 | CZ | PHE | B | 11 | 28.518 | 57.700 | 71.087 | 1.00 | 10.09 |
| 6118 | CE2 | PHE | B | 11 | 28.181 | 56.396 | 70.758 | 1.00 | 10.00 |
| 6120 | CD2 | PHE | B | 11 | 29.005 | 55.349 | 71.142 | 1.00 | 9.45 |
| 6122 | C | PHE | B | 11 | 29.391 | 53.546 | 73.903 | 1.00 | 7.88 |
| 6123 | O | PHE | B | 11 | 29.044 | 52.415 | 73.572 | 1.00 | 7.64 |
| 6124 | N | VAL | B | 12 | 28.559 | 54.424 | 74.439 | 1.00 | 7.67 |
| 6126 | CA | VAL | B | 12 | 27.122 | 54.190 | 74.476 | 1.00 | 7.66 |
| 6128 | CB | VAL | B | 12 | 26.623 | 53.899 | 75.910 | 1.00 | 7.44 |
| 6130 | CG1 | VAL | B | 12 | 27.199 | 52.585 | 76.409 | 1.00 | 7.66 |
| 6134 | CG2 | VAL | B | 12 | 26.974 | 55.035 | 76.870 | 1.00 | 7.50 |
| 6138 | C | VAL | B | 12 | 26.438 | 55.420 | 73.894 | 1.00 | 7.74 |
| 6139 | O | VAL | B | 12 | 27.006 | 56.512 | 73.931 | 1.00 | 7.70 |
| 6140 | N | PRO | B | 13 | 25.234 | 55.258 | 73.345 | -1.00 | 8.04 |
| 6141 | CA | PRO | B | 13 | 24.516 | 56.398 | 72.766 | 1.00 | 8.23 |
| 6143 | CB | PRO | B | 13 | 23.212 | 55.779 | 72.250 | 1.00 | 8.12 |
| 6146 | CG | PRO | B | 13 | 23.084 | 54.477 | 72.956 | 1.00 | 8.19 |
| 6149 | CD | PRO | B | 13 | 24.474 | 54.004 | 73.218 | 1.00 | 7.96 |
| 6152 | C | PRO | B | 13 | 24.236 | 57.505 | 73.793 | 1.00 | 8.35 |
| 6153 | O | PRO | B | 13 | 24.266 | 57.249 | 75.002 | 1.00 | 8.43 |
| 6154 | N | PRO | B | 14 | 23.991 | 58.723 | 73.320 | 1.00 | 8.55 |
| 6155 | CA | PRO | B | 14 | 23.799 | 59.870 | 74.218 | 1.00 | 8.72 |
| 6157 | CB | PRO | B | 14 | 24.046 | 61.080 | 73.297 | 1.00 | 8.86 |
| 6160 | CG | PRO | B | 14 | 23.756 | 60.602 | 71.920 | 1.00 | 8.88 |
| 6163 | CD | PRO | B | 14 | 23.923 | 59.113 | 71.899 | 1.00 | 8.58 |
| 6166 | C | PRO | B | 14 | 22.420 | 59.958 | 74.882 | 1.00 | 8.78 |
| 6167 | O | PRO | B | 14 | 22.063 | 61.045 | 75.316 | 1.00 | 9.11 |
| 6168 | N | TYR | B | 15 | 21.674 | 58.856 | 74.967 | 1.00 | 8.86 |
| 6170 | CA | TYR | B | 15 | 20.357 | 58.848 | 75.608 | 1.00 | 8.89 |
| 6172 | CB | TYR | B | 15 | 19.237 | 58.854 | 74.552 | 1.00 | 9.12 |
| 6175 | CG | TYR | B | 15 | 19.435 | 59.870 | 73.455 | 1.00 | 10.12 |
| 6176 | CD1 | TYR | B | 15 | 19.161 | 61.213 | 73.675 | 1.00 | 11.31 |
| 6178 | CE1 | TYR | B | 15 | 19.359 | 62.162 | 72.681 | 1.00 | 12.15 |
| 6180 | CZ | TYR | B | 15 | 19.834 | 61.772 | 71.447 | 1.00 | 12.28 |
| 6181 | OH | TYR | B | 15 | 20.022 | 62.721 | 70.464 | 1.00 | 12.56 |
| 6183 | CE2 | TYR | B | 15 | 20.120 | 60.437 | 71.199 | 1.00 | 11.49 |
| 6185 | CD2 | TYR | B | 15 | 19.919 | 59.493 | 72.204 | 1.00 | 11.10 |
| 6187 | C | TYR | B | 15 | 20.172 | 57.636 | 76.517 | 1.00 | 8.63 |
| 6188 | O | TYR | B | 15 | 20.785 | 56.590 | 76.314 | 1.00 | 8.71 |
| 6189 | N | TYR | B | 16 | 19.320 | 57.790 | 77.522 | 1.00 | 8.11 |
| 6191 | CA | TYR | B | 16 | 18.926 | 56.675 | 78.373 | 1.00 | 7.89 |
| 6193 | CB | TYR | B | 16 | 19.940 | 56.481 | 79.511 | 1.00 | 7.84 |
| 6196 | CG | TYR | B | 16 | 19.954 | 57.597 | 80.542 | 1.00 | 7.55 |
| 6197 | CD1 | TYR | B | 16 | 19.266 | 57.471 | 81.746 | 1.00 | 7.48 |
| 6199 | CE1 | TYR | B | 16 | 19.276 | 58.493 | 82.693 | 1.00 | 7.33 |
| 6201 | CZ | TYR | B | 16 | 19.986 | 59.649 | 82.441 | 1.00 | 7.17 |
| 6202 | OH | TYR | B | 16 | 20.005 | 60.663 | 83.373 | 1.00 | 6.75 |
| 6204 | CE2 | TYR | B | 16 | 20.679 | 59.794 | 81.253 | 1.00 | 7.64 |
| 6206 | CD2 | TYR | B | 16 | 20.663 | 58.770 | 80.315 | 1.00 | 7.44 |

FIGURE 3 (Cont.)

| A | B | C | D | E | F | G | H | I | J |
|---|---|---|---|---|---|---|---|---|---|
| 6208 | C | TYR | B | 16 | 17.532 | 56.897 | 78.946 | 1.00 | 7.76 |
| 6209 | O | TYR | B | 16 | 17.000 | 57.997 | 78.871 | 1.00 | 7.36 |
| 6210 | N | ILE | B | 17 | 16.938 | 55.849 | 79.503 | 1.00 | 7.79 |
| 6212 | CA | ILE | B | 17 | 15.757 | 56.012 | 80.340 | 1.00 | 7.84 |
| 6214 | CB | ILE | B | 17 | 14.510 | 55.273 | 79.776 | 1.00 | 7.99 |
| 6216 | CG1 | ILE | B | 17 | 14.793 | 53.789 | 79.517 | 1.00 | 7.93 |
| 6219 | CD1 | ILE | B | 17 | 13.543 | 52.982 | 79.254 | 1.00 | 8.24 |
| 6223 | CG2 | ILE | B | 17 | 14.013 | 55.947 | 78.506 | 1.00 | 7.85 |
| 6227 | C | ILE | B | 17 | 16.060 | 55.533 | 81.745 | 1.00 | 8.17 |
| 6228 | O | ILE | B | 17 | 16.910 | 54.663 | 81.957 | 1.00 | 8.10 |
| 6229 | N | ASP | B | 18 | 15.350 | 56.117 | 82.698 | 1.00 | 8.20 |
| 6231 | CA | ASP | B | 18 | 15.410 | 55.714 | 84.090 | 1.00 | 8.49 |
| 6233 | CB | ASP | B | 18 | 14.943 | 56.870 | 84.968 | 1.00 | 8.42 |
| 6236 | CG | ASP | B | 18 | 14.947 | 56.519 | 86.431 | 1.00 | 8.88 |
| 6237 | OD1 | ASP | B | 18 | 13.911 | 56.026 | 86.907 | 1.00 | 8.51 |
| 6238 | OD2 | ASP | B | 18 | 15.935 | 56.691 | 87.174 | 1.00 | 8.45 |
| 6239 | C | ASP | B | 18 | 14.513 | 54.492 | 84.284 | 1.00 | 8.59 |
| 6240 | O | ASP | B | 18 | 13.387 | 54.470 | 83.801 | 1.00 | 8.47 |
| 6241 | N | MSE | B | 19 | 15.005 | 53.486 | 85.001 | 1.00 | 9.04 |
| 6243 | CA | MSE | B | 19 | 14.304 | 52.202 | 85.095 | 1.00 | 9.46 |
| 6245 | CB | MSE | B | 19 | 15.270 | 51.072 | 85.471 | 1.00 | 9.51 |
| 6248 | CG | MSE | B | 19 | 16.269 | 50.745 | 84.370 | 1.00 | 10.48 |
| 6251 | SE | MSE | B | 19 | 15.462 | 50.056 | 82.750 | 1.00 | 12.23 |
| 6252 | CE | MSE | B | 19 | 14.963 | 48.288 | 83.376 | 1.00 | 11.07 |
| 6256 | C | MSE | B | 19 | 13.124 | 52.234 | 86.055 | 1.00 | 9.55 |
| 6257 | O | MSE | B | 19 | 12.196 | 51.445 | 85.904 | 1.00 | 9.59 |
| 6258 | N | THR | B | 20 | 13.155 | 53.122 | 87.045 | 1.00 | 9.67 |
| 6260 | CA | THR | B | 20 | 11.965 | 53.372 | 87.865 | 1.00 | 10.06 |
| 6262 | CB | THR | B | 20 | 12.257 | 54.357 | 89.018 | 1.00 | 10.21 |
| 6264 | OG1 | THR | B | 20 | 12.942 | 53.675 | 90.063 | 1.00 | 11.41 |
| 6266 | CG2 | THR | B | 20 | 10.970 | 54.830 | 89.706 | 1.00 | 10.83 |
| 6270 | C | THR | B | 20 | 10.849 | 53.923 | 86.992 | 1.00 | 9.83 |
| 6271 | O | THR | B | 20 | 9.705 | 53.511 | 87.122 | 1.00 | 9.82 |
| 6272 | N | ALA | B | 21 | 11.194 | 54.847 | 86.101 | 1.00 | 9.81 |
| 6274 | CA | ALA | B | 21 | 10.219 | 55.443 | 85.196 | 1.00 | 9.87 |
| 6276 | CB | ALA | B | 21 | 10.837 | 56.595 | 84.421 | 1.00 | 9.90 |
| 6280 | C | ALA | B | 21 | 9.644 | 54.397 | 84.242 | 1.00 | 9.88 |
| 6281 | O | ALA | B | 21 | 8.459 | 54.438 | 83.938 | 1.00 | 9.92 |
| 6282 | N | LEU | B | 22 | 10.468 | 53.455 | 83.784 | 1.00 | 9.90 |
| 6284 | CA | LEU | B | 22 | 9.968 | 52.381 | 82.927 | 1.00 | 10.02 |
| 6286 | CB | LEU | B | 22 | 11.098 | 51.513 | 82.359 | 1.00 | 9.81 |
| 6289 | CG | LEU | B | 22 | 10.619 | 50.459 | 81.342 | 1.00 | 9.32 |
| 6291 | CD1 | LEU | B | 22 | 10.072 | 51.120 | 80.085 | 1.00 | 8.62 |
| 6295 | CD2 | LEU | B | 22 | 11.723 | 49.460 | 80.989 | 1.00 | 8.55 |
| 6299 | C | LEU | B | 22 | 8.993 | 51.506 | 83.704 | 1.00 | 10.37 |
| 6300 | O | LEU | B | 22 | 7.937 | 51.161 | 83.192 | 1.00 | 10.52 |
| 6301 | N | ALA | B | 23 | 9.355 | 51.154 | 84.935 | 1.00 | 10.74 |
| 6303 | CA | ALA | B | 23 | 8.506 | 50.332 | 85.791 | 1.00 | 11.16 |
| 6305 | CB | ALA | B | 23 | 9.191 | 50.074 | 87.130 | 1.00 | 11.15 |
| 6309 | C | ALA | B | 23 | 7.146 | 50.990 | 86.006 | 1.00 | 11.59 |
| 6310 | O | ALA | B | 23 | 6.111 | 50.334 | 85.908 | 1.00 | 11.65 |
| 6311 | N | GLU | B | 24 | 7.160 | 52.290 | 86.271 | 1.00 | 12.27 |
| 6313 | CA | GLU | B | 24 | 5.939 | 53.060 | 86.498 | 1.00 | 13.20 |

FIGURE 3 (Cont.)

| A | B | C | D | E | F | G | H | I | J |
|---|---|---|---|---|---|---|---|---|---|
| 6315 | CB | GLU | B | 24 | 6.284 | 54.497 | 86.914 | 1.00 | 13.42 |
| 6318 | CG | GLU | B | 24 | 6.883 | 54.580 | 88.315 | 1.00 | 15.95 |
| 6321 | CD | GLU | B | 24 | 7.415 | 55.958 | 88.692 | 1.00 | 18.51 |
| 6322 | OE1 | GLU | B | 24 | 7.059 | 56.436 | 89.788 | 1.00 | 21.38 |
| 6323 | OE2 | GLU | B | 24 | 8.207 | 56.558 | 87.925 | 1.00 | 19.65 |
| 6324 | C | GLU | B | 24 | 5.036 | 53.045 | 85.262 | 1.00 | 13.23 |
| 6325 | O | GLU | B | 24 | 3.828 | 52.852 | 85.377 | 1.00 | 13.34 |
| 6326 | N | ALA | B | 25 | 5.634 | 53.216 | 84.085 | 1.00 | 13.44 |
| 6328 | CA | ALA | B | 25 | 4.892 | 53.205 | 82.821 | 1.00 | 13.59 |
| 6330 | CB | ALA | B | 25 | 5.781 | 53.698 | 81.684 | 1.00 | 13.63 |
| 6334 | C | ALA | B | 25 | 4.349 | 51.816 | 82.492 | 1.00 | 13.79 |
| 6335 | O | ALA | B | 25 | 3.272 | 51.687 | 81.905 | 1.00 | 13.63 |
| 6336 | N | ARG | B | 26 | 5.090 | 50.785 | 82.895 | 1.00 | 13.92 |
| 6338 | CA | ARG | B | 26 | 4.747 | 49.400 | 82.583 | 1.00 | 14.23 |
| 6340 | CB | ARG | B | 26 | 6.028 | 48.582 | 82.394 | 1.00 | 14.26 |
| 6343 | CG | ARG | B | 26 | 6.818 | 48.960 | 81.159 | 1.00 | 14.12 |
| 6346 | CD | ARG | B | 26 | 6.261 | 48.381 | 79.870 | 1.00 | 13.76 |
| 6349 | NE | ARG | B | 26 | 6.948 | 48.934 | 78.704 | 1.00 | 12.68 |
| 6351 | CZ | ARG | B | 26 | 6.620 | 50.067 | 78.086 | 1.00 | 13.15 |
| 6352 | NH1 | ARG | B | 26 | 7.330 | 50.453 | 77.036 | 1.00 | 12.91 |
| 6355 | NH2 | ARG | B | 26 | 5.612 | 50.829 | 78.509 | 1.00 | 12.84 |
| 6358 | C | ARG | B | 26 | 3.881 | 48.735 | 83.655 | 1.00 | 14.61 |
| 6359 | O | ARG | B | 26 | 3.555 | 47.555 | 83.536 | 1.00 | 14.48 |
| 6360 | N | ASN | B | 27 | 3.515 | 49.483 | 84.697 | 1.00 | 15.05 |
| 6362 | CA | ASN | B | 27 | 2.734 | 48.944 | 85.814 | 1.00 | 15.63 |
| 6364 | CB | ASN | B | 27 | 1.288 | 48.638 | 85.382 | 1.00 | 15.92 |
| 6367 | CG | ASN | B | 27 | 0.474 | 49.902 | 85.105 | 1.00 | 17.74 |
| 6368 | OD1 | ASN | B | 27 | 0.580 | 50.901 | 85.822 | 1.00 | 19.96 |
| 6369 | ND2 | ASN | B | 27 | -0.359 | 49.851 | 84.073 | 1.00 | 20.56 |
| 6372 | C | ASN | B | 27 | 3.392 | 47.713 | 86.450 | 1.00 | 15.59 |
| 6373 | O | ASN | B | 27 | 2.729 | 46.722 | 86.770 | 1.00 | 15.31 |
| 6374 | N | VAL | B | 28 | 4.708 | 47.781 | 86.614 | 1.00 | 15.63 |
| 6376 | CA | VAL | B | 28 | 5.440 | 46.773 | 87.366 | 1.00 | 15.59 |
| 6378 | CB | VAL | B | 28 | 6.421 | 45.948 | 86.468 | 1.00 | 15.89 |
| 6380 | CG1 | VAL | B | 28 | 5.920 | 45.858 | 85.022 | 1.00 | 16.07 |
| 6384 | CG2 | VAL | B | 28 | 7.837 | 46.486 | 86.511 | 1.00 | 16.02 |
| 6388 | C | VAL | B | 28 | 6.162 | 47.423 | 88.550 | 1.00 | 15.44 |
| 6389 | O | VAL | B | 28 | 6.508 | 48.602 | 88.519 | 1.00 | 15.06 |
| 6390 | N | ASP | B | 29 | 6.344 | 46.628 | 89.598 | 1.00 | 15.37 |
| 6392 | CA | ASP | B | 29 | 7.125 | 46.990 | 90.778 | 1.00 | 15.46 |
| 6394 | CB | ASP | B | 29 | 7.243 | 45.750 | 91.674 | 1.00 | 15.86 |
| 6397 | CG | ASP | B | 29 | 7.440 | 46.088 | 93.128 | 1.00 | 17.63 |
| 6398 | OD1 | ASP | B | 29 | 8.276 | 46.962 | 93.437 | 1.00 | 19.48 |
| 6399 | OD2 | ASP | B | 29 | 6.809 | 45.508 | 94.038 | 1.00 | 20.82 |
| 6400 | C | ASP | B | 29 | 8.532 | 47.477 | 90.393 | 1.00 | 14.68 |
| 6401 | O | ASP | B | 29 | 9.284 | 46.725 | 89.775 | 1.00 | 14.52 |
| 6402 | N | PRO | B | 30 | 8.891 | 48.716 | 90.737 | 1.00 | 13.88 |
| 6403 | CA | PRO | B | 30 | 10.261 | 49.209 | 90.513 | 1.00 | 13.41 |
| 6405 | CB | PRO | B | 30 | 10.274 | 50.549 | 91.254 | 1.00 | 13.40 |
| 6408 | CG | PRO | B | 30 | 8.859 | 51.004 | 91.202 | 1.00 | 13.77 |
| 6411 | CD | PRO | B | 30 | 8.034 | 49.757 | 91.337 | 1.00 | 14.11 |
| 6414 | C | PRO | B | 30 | 11.342 | 48.274 | 91.065 | 1.00 | 12.95 |

FIGURE 3 (Cont.)

| A | B | C | D | E | F | G | H | I | J |
|---|---|---|---|---|---|---|---|---|---|
| 6415 | O | PRO | B | 30 | 12.424 | 48.168 | 90.487 | 1.00 | 12.69 |
| 6416 | N | GLY | B | 31 | 11.042 | 47.612 | 92.176 | 1.00 | 12.39 |
| 6418 | CA | GLY | B | 31 | 11.903 | 46.585 | 92.732 | 1.00 | 12.09 |
| 6421 | C | GLY | B | 31 | 12.256 | 45.436 | 91.797 | 1.00 | 11.76 |
| 6422 | O | GLY | B | 31 | 13.355 | 44.900 | 91.871 | 1.00 | 11.54 |
| 6423 | N | LYS | B | 32 | 11.330 | 45.034 | 90.934 | 1.00 | 11.49 |
| 6425 | CA | LYS | B | 32 | 11.625 | 44.015 | 89.921 | 1.00 | 11.51 |
| 6427 | CB | LYS | B | 32 | 10.413 | 43.752 | 89.020 | 1.00 | 11.58 |
| 6430 | CG | LYS | B | 32 | 10.696 | 42.735 | 87.918 | 1.00 | 12.00 |
| 6433 | CD | LYS | B | 32 | 9.430 | 42.254 | 87.231 | 1.00 | 12.94 |
| 6436 | CE | LYS | B | 32 | 9.750 | 41.096 | 86.288 | 1.00 | 13.25 |
| 6439 | NZ | LYS | B | 32 | 8.601 | 40.734 | 85.416 | 1.00 | 13.34 |
| 6443 | C | LYS | B | 32 | 12.831 | 44.387 | 89.050 | 1.00 | 11.32 |
| 6444 | O | LYS | B | 32 | 13.665 | 43.542 | 88.752 | 1.00 | 10.69 |
| 6445 | N | PHE | B | 33 | 12.904 | 45.644 | 88.632 | 1.00 | 11.40 |
| 6447 | CA | PHE | B | 33 | 14.000 | 46.103 | 87.786 | 1.00 | 11.57 |
| 6449 | CB | PHE | B | 33 | 13.574 | 47.334 | 86.975 | 1.00 | 11.68 |
| 6452 | CG | PHE | B | 33 | 12.482 | 47.066 | 85.954 | 1.00 | 11.23 |
| 6453 | CD1 | PHE | B | 33 | 12.030 | 45.772 | 85.676 | 1.00 | 11.28 |
| 6455 | CE1 | PHE | B | 33 | 11.035 | 45.555 | 84.731 | 1.00 | 10.87 |
| 6457 | CZ | PHE | B | 33 | 10.474 | 46.624 | 84.052 | 1.00 | 10.60 |
| 6459 | CE2 | PHE | B | 33 | 10.908 | 47.911 | 84.319 | 1.00 | 11.10 |
| 6461 | CD2 | PHE | B | 33 | 11.903 | 48.127 | 85.265 | 1.00 | 11.53 |
| 6463 | C | PHE | B | 33 | 15.259 | 46.395 | 88.608 | 1.00 | 11.99 |
| 6464 | O | PHE | B | 33 | 16.356 | 45.999 | 88.223 | 1.00 | 11.67 |
| 6465 | N | HIS | B | 34 | 15.095 | 47.043 | 89.756 | 1.00 | 12.14 |
| 6467 | CA | HIS | B | 34 | 16.233 | 47.505 | 90.556 | 1.00 | 12.63 |
| 6469 | CB BHIS | B | 34 | 15.725 | 48.534 | 91.576 | 0.35 | 12.50 |
| 6470 | CB AHIS | B | 34 | 15.821 | 48.620 | 91.514 | 0.65 | 12.74 |
| 6475 | CG BHIS | B | 34 | 16.804 | 49.212 | 92.361 | 0.35 | 12.42 |
| 6476 | CG AHIS | B | 34 | 15.697 | 49.944 | 90.835 | 0.65 | 13.74 |
| 6477 | ND1BHIS | B | 34 | 16.967 | 49.027 | 93.716 | 0.35 | 12.36 |
| 6478 | ND1AHIS | B | 34 | 14.564 | 50.722 | 90.908 | 0.65 | 14.45 |
| 6481 | CE1BHIS | B | 34 | 17.982 | 49.758 | 94.140 | 0.35 | 12.26 |
| 6482 | CE1AHIS | B | 34 | 14.743 | 51.815 | 90.190 | 0.65 | 15.15 |
| 6485 | NE2BHIS | B | 34 | 18.479 | 50.416 | 93.108 | 0.35 | 12.76 |
| 6486 | NE2AHIS | B | 34 | 15.939 | 51.765 | 89.637 | 0.65 | 15.08 |
| 6489 | CD2BHIS | B | 34 | 17.756 | 50.096 | 91.986 | 0.35 | 12.36 |
| 6490 | CD2AHIS | B | 34 | 16.554 | 50.602 | 90.020 | 0.65 | 13.99 |
| 6493 | C | HIS | B | 34 | 16.971 | 46.379 | 91.280 | 1.00 | 12.66 |
| 6494 | O | HIS | B | 34 | 18.198 | 46.399 | 91.350 | 1.00 | 12.36 |
| 6495 | N | ILE | B | 35 | 16.227 | 45.400 | 91.788 | 1.00 | 12.80 |
| 6497 | CA | ILE | B | 35 | 16.808 | 44.250 | 92.481 | 1.00 | 13.30 |
| 6499 | CB | ILE | B | 35 | 16.161 | 44.080 | 93.876 | 1.00 | 13.38 |
| 6501 | CG1 | ILE | B | 35 | 16.474 | 45.304 | 94.751 | 1.00 | 14.39 |
| 6504 | CD1 | ILE | B | 35 | 15.730 | 45.359 | 96.096 | 1.00 | 15.65 |
| 6508 | CG2 | ILE | B | 35 | 16.651 | 42.794 | 94.548 | 1.00 | 14.03 |
| 6512 | C | ILE | B | 35 | 16.682 | 42.955 | 91.667 | 1.00 | 13.23 |
| 6513 | O | ILE | B | 35 | 17.653 | 42.220 | 91.526 | 1.00 | 13.45 |
| 6514 | N | GLY | B | 36 | 15.492 | 42.676 | 91.140 | 1.00 | 13.20 |
| 6516 | CA | GLY | B | 36 | 15.232 | 41.418 | 90.454 | 1.00 | 13.18 |
| 6519 | C | GLY | B | 36 | 16.115 | 41.193 | 89.242 | 1.00 | 13.27 |

FIGURE 3 (Cont.)

| A | B | C | D | E | F | G | H | I | J |
|---|---|---|---|---|---|---|---|---|---|
| 6520 | O | GLY | B | 36 | 16.674 | 40.115 | 89.064 | 1.00 | 13.07 |
| 6521 | N | ILE | B | 37 | 16.252 | 42.231 | 88.425 | 1.00 | 13.44 |
| 6523 | CA | ILE | B | 37 | 17.077 | 42.190 | 87.220 | 1.00 | 13.85 |
| 6525 | CB | ILE | B | 37 | 16.247 | 42.747 | 86.033 | 1.00 | 14.28 |
| 6527 | CG1 | ILE | B | 37 | 15.123 | 41.760 | 85.695 | 1.00 | 15.96 |
| 6530 | CD1 | ILE | B | 37 | 13.940 | 42.399 | 84.989 | 1.00 | 17.56 |
| 6534 | CG2 | ILE | B | 37 | 17.087 | 42.978 | 84.796 | 1.00 | 15.32 |
| 6538 | C | ILE | B | 37 | 18.393 | 42.951 | 87.461 | 1.00 | 13.29 |
| 6539 | O | ILE | B | 37 | 19.441 | 42.554 | 86.960 | 1.00 | 13.28 |
| 6540 | N | GLY | B | 38 | 18.338 | 44.017 | 88.260 | 1.00 | 12.52 |
| 6542 | CA | GLY | B | 38 | 19.523 | 44.768 | 88.648 | 1.00 | 11.90 |
| 6545 | C | GLY | B | 38 | 19.921 | 45.898 | 87.711 | 1.00 | 11.34 |
| 6546 | O | GLY | B | 38 | 21.105 | 46.093 | 87.452 | 1.00 | 11.12 |
| 6547 | N | GLN | B | 39 | 18.941 | 46.658 | 87.226 | 1.00 | 10.97 |
| 6549 | CA | GLN | B | 39 | 19.182 | 47.751 | 86.287 | 1.00 | 10.82 |
| 6551 | CB | GLN | B | 39 | 18.564 | 47.420 | 84.930 | 1.00 | 10.92 |
| 6554 | CG | GLN | B | 39 | 19.050 | 46.128 | 84.303 | 1.00 | 11.21 |
| 6557 | CD | GLN | B | 39 | 20.552 | 46.072 | 84.101 | 1.00 | 11.92 |
| 6558 | OE1 | GLN | B | 39 | 21.165 | 45.047 | 84.360 | 1.00 | 14.41 |
| 6559 | NE2 | GLN | B | 39 | 21.141 | 47.161 | 83.628 | 1.00 | 11.68 |
| 6562 | C | GLN | B | 39 | 18.608 | 49.077 | 86.780 | 1.00 | 10.71 |
| 6563 | O | GLN | B | 39 | 17.505 | 49.119 | 87.333 | 1.00 | 10.50 |
| 6564 | N | ASP | B | 40 | 19.365 | 50.150 | 86.546 | 1.00 | 10.36 |
| 6566 | CA | ASP | B | 40 | 19.015 | 51.505 | 86.965 | 1.00 | 10.24 |
| 6568 | CB | ASP | B | 40 | 20.145 | 52.103 | 87.805 | 1.00 | 10.33 |
| 6571 | CG | ASP | B | 40 | 20.395 | 51.330 | 89.079 | 1.00 | 10.61 |
| 6572 | OD1 | ASP | B | 40 | 21.547 | 51.294 | 89.549 | 1.00 | 10.78 |
| 6573 | OD2 | ASP | B | 40 | 19.492 | 50.732 | 89.680 | 1.00 | 9.84 |
| 6574 | C | ASP | B | 40 | 18.739 | 52.440 | 85.788 | 1.00 | 9.86 |
| 6575 | O | ASP | B | 40 | 17.826 | 53.254 | 85.854 | 1.00 | 9.83 |
| 6576 | N | GLN | B | 41 | 19.547 | 52.346 | 84.734 | 1.00 | 9.64 |
| 6578 | CA | GLN | B | 41 | 19.365 | 53.147 | 83.515 | 1.00 | 9.47 |
| 6580 | CB | GLN | B | 41 | 20.274 | 54.385 | 83.532 | 1.00 | 9.36 |
| 6583 | CG | GLN | B | 41 | 20.121 | 55.274 | 84.767 | 1.00 | 9.47 |
| 6586 | CD | GLN | B | 41 | 21.235 | 56.301 | 84.916 | 1.00 | 9.49 |
| 6587 | OE1 | GLN | B | 41 | 22.358 | 56.077 | 84.468 | 1.00 | 9.00 |
| 6588 | NE2 | GLN | B | 41 | 20.926 | 57.419 | 85.560 | 1.00 | 8.91 |
| 6591 | C | GLN | B | 41 | 19.662 | 52.304 | 82.266 | 1.00 | 9.36 |
| 6592 | O | GLN | B | 41 | 20.595 | 51.493 | 82.269 | 1.00 | 9.52 |
| 6593 | N | MSE | B | 42 | 18.868 | 52.501 | 81.212 | 1.00 | 9.19 |
| 6595 | CA | MSE | B | 42 | 18.996 | 51.752 | 79.954 | 1.00 | 8.73 |
| 6597 | CB | MSE | B | 42 | 17.665 | 51.075 | 79.593 | 1.00 | 8.52 |
| 6600 | CG | MSE | B | 42 | 17.507 | 50.691 | 78.114 | 0.65 | 7.15 |
| 6603 | SE | MSE | B | 42 | 15.656 | 50.495 | 77.556 | 0.65 | 5.04 |
| 6604 | CE | MSE | B | 42 | 15.129 | 49.260 | 78.919 | 0.65 | 3.30 |
| 6608 | C | MSE | B | 42 | 19.406 | 52.675 | 78.810 | 1.00 | 9.03 |
| 6609 | O | MSE | B | 42 | 18.738 | 53.670 | 78.540 | 1.00 | 8.87 |
| 6610 | N | ALA | B | 43 | 20.488 | 52.314 | 78.126 | 1.00 | 9.15 |
| 6612 | CA | ALA | B | 43 | 20.929 | 53.001 | 76.914 | 1.00 | 9.35 |
| 6614 | CB | ALA | B | 43 | 22.295 | 52.478 | 76.489 | 1.00 | 9.28 |
| 6618 | C | ALA | B | 43 | 19.926 | 52.814 | 75.776 | 1.00 | 9.74 |
| 6619 | O | ALA | B | 43 | 19.431 | 51.710 | 75.549 | 1.00 | 9.76 |

FIGURE 3 (Cont.)

| A | B | C | D | E | F | G | H | I | J |
|---|---|---|---|---|---|---|---|---|---|
| 6620 | N | VAL | B | 44 | 19.630 | 53.905 | 75.073 | 1.00 | 9.98 |
| 6622 | CA | VAL | B | 44 | 18.722 | 53.895 | 73.927 | 1.00 | 10.30 |
| 6624 | CB | VAL | B | 44 | 17.299 | 54.355 | 74.336 | 1.00 | 10.48 |
| 6626 | CG1 | VAL | B | 44 | 16.358 | 54.402 | 73.126 | 1.00 | 11.30 |
| 6630 | CG2 | VAL | B | 44 | 16.732 | 53.413 | 75.391 | 1.00 | 10.90 |
| 6634 | C | VAL | B | 44 | 19.294 | 54.799 | 72.833 | 1.00 | 10.31 |
| 6635 | O | VAL | B | 44 | 20.013 | 55.758 | 73.124 | 1.00 | 10.12 |
| 6636 | N | ASN | B | 45 | 18.997 | 54.472 | 71.577 | 1.00 | 10.43 |
| 6638 | CA | ASN | B | 45 | 19.539 | 55.210 | 70.438 | 1.00 | 10.61 |
| 6640 | CB | ASN | B | 45 | 20.759 | 54.490 | 69.853 | 1.00 | 10.51 |
| 6643 | CG | ASN | B | 45 | 20.416 | 53.141 | 69.252 | 1.00 | 10.59 |
| 6644 | OD1 | ASN | B | 45 | 20.312 | 52.146 | 69.966 | 1.00 | 10.53 |
| 6645 | ND2 | ASN | B | 45 | 20.231 | 53.103 | 67.932 | 1.00 | 9.40 |
| 6648 | C | ASN | B | 45 | 18.511 | 55.456 | 69.340 | 1.00 | 10.98 |
| 6649 | O | ASN | B | 45 | 17.579 | 54.663 | 69.152 | 1.00 | 10.53 |
| 6650 | N | PRO | B | 46 | 18.688 | 56.550 | 68.603 | 1.00 | 11.26 |
| 6651 | CA | PRO | B | 46 | 17.811 | 56.844 | 67.476 | 1.00 | 11.44 |
| 6653 | CB | PRO | B | 46 | 18.060 | 58.333 | 67.225 | 1.00 | 11.44 |
| 6656 | CG | PRO | B | 46 | 19.470 | 58.531 | 67.610 | 1.00 | 11.39 |
| 6659 | CD | PRO | B | 46 | 19.721 | 57.588 | 68.764 | 1.00 | 11.19 |
| 6662 | C | PRO | B | 46 | 18.222 | 56.017 | 66.275 | 1.00 | 11.68 |
| 6663 | O | PRO | B | 46 | 19.304 | 55.422 | 66.251 | 1.00 | 11.73 |
| 6664 | N | ILE | B | 47 | 17.365 | 56.018 | 65.269 | 1.00 | 11.77 |
| 6666 | CA | ILE | B | 47 | 17.554 | 55.208 | 64.081 | 1.00 | 12.10 |
| 6668 | CB | ILE | B | 47 | 16.203 | 55.128 | 63.321 | 1.00 | 12.50 |
| 6670 | CG1 | ILE | B | 47 | 16.154 | 53.885 | 62.437 | 1.00 | 14.50 |
| 6673 | CD1 | ILE | B | 47 | 15.948 | 52.573 | 63.186 | 1.00 | 15.85 |
| 6677 | CG2 | ILE | B | 47 | 15.935 | 56.415 | 62.519 | 1.00 | 13.10 |
| 6681 | C | ILE | B | 47 | 18.706 | 55.746 | 63.206 | 1.00 | 11.34 |
| 6682 | O | ILE | B | 47 | 19.190 | 55.068 | 62.303 | 1.00 | 11.58 |
| 6683 | N | SER | B | 48 | 19.148 | 56.965 | 63.503 | 1.00 | 10.49 |
| 6685 | CA | SER | B | 48 | 20.323 | 57.558 | 62.876 | 1.00 | 9.76 |
| 6687 | CB | SER | B | 48 | 20.254 | 59.080 | 63.034 | 1.00 | 9.85 |
| 6690 | OG | SER | B | 48 | 20.140 | 59.435 | 64.399 | 1.00 | 8.56 |
| 6692 | C | SER | B | 48 | 21.668 | 57.050 | 63.426 | 1.00 | 9.36 |
| 6693 | O | SER | B | 48 | 22.719 | 57.534 | 63.023 | 1.00 | 9.52 |
| 6694 | N | GLN | B | 49 | 21.638 | 56.085 | 64.338 | 1.00 | 8.82 |
| 6696 | CA | GLN | B | 49 | 22.850 | 55.514 | 64.925 | 1.00 | 8.17 |
| 6698 | CB | GLN | B | 49 | 22.983 | 55.959 | 66.384 | 1.00 | 8.26 |
| 6701 | CG | GLN | B | 49 | 23.162 | 57.473 | 66.547 | 1.00 | 7.72 |
| 6704 | CD | GLN | B | 49 | 23.127 | 57.937 | 67.996 | 1.00 | 8.24 |
| 6705 | OE1 | GLN | B | 49 | 23.383 | 57.156 | 68.918 | 1.00 | 6.37 |
| 6706 | NE2 | GLN | B | 49 | 22.804 | 59.215 | 68.201 | 1.00 | 8.63 |
| 6709 | C | GLN | B | 49 | 22.793 | 53.991 | 64.831 | 1.00 | 8.00 |
| 6710 | O | GLN | B | 49 | 21.829 | 53.377 | 65.281 | 1.00 | 7.70 |
| 6711 | N | ASP | B | 50 | 23.814 | 53.391 | 64.223 | 1.00 | 7.86 |
| 6713 | CA | ASP | B | 50 | 23.882 | 51.939 | 64.043 | 1.00 | 7.79 |
| 6715 | CB | ASP | B | 50 | 23.682 | 51.580 | 62.558 | 1.00 | 7.84 |
| 6718 | CG | ASP | B | 50 | 24.803 | 52.085 | 61.667 | 1.00 | 7.80 |
| 6719 | OD1 | ASP | B | 50 | 24.616 | 52.112 | 60.426 | 1.00 | 8.06 |
| 6720 | OD2 | ASP | B | 50 | 25.899 | 52.480 | 62.108 | 1.00 | 6.46 |
| 6721 | C | ASP | B | 50 | 25.200 | 51.387 | 64.604 | 1.00 | 7.72 |

FIGURE 3 (Cont.)

| A | B | C | D | E | F | G | H | I | J |
|---|---|---|---|---|---|---|---|---|---|
| 6722 | O | ASP | B | 50 | 25.930 | 52.106 | 65.283 | 1.00 | 7.78 |
| 6723 | N | ILE | B | 51 | 25.508 | 50.123 | 64.324 | 1.00 | 7.46 |
| 6725 | CA | ILE | B | 51 | 26.715 | 49.507 | 64.876 | 1.00 | 7.43 |
| 6727 | CB | ILE | B | 51 | 26.766 | 47.983 | 64.626 | 1.00 | 7.67 |
| 6729 | CG1 | ILE | B | 51 | 26.566 | 47.642 | 63.142 | 1.00 | 7.53 |
| 6732 | CD1 | ILE | B | 51 | 27.045 | 46.271 | 62.792 | 1.00 | 8.04 |
| 6736 | CG2 | ILE | B | 51 | 25.743 | 47.263 | 65.505 | 1.00 | 7.52 |
| 6740 | C | ILE | B | 51 | 28.000 | 50.174 | 64.391 | 1.00 | 7.20 |
| 6741 | O | ILE | B | 51 | 28.976 | 50.207 | 65.129 | 1.00 | 6.95 |
| 6742 | N | VAL | B | 52 | 27.993 | 50.712 | 63.170 | 1.00 | 7.05 |
| 6744 | CA | VAL | B | 52 | 29.133 | 51.476 | 62.650 | 1.00 | 7.13 |
| 6746 | CB | VAL | B | 52 | 28.971 | 51.846 | 61.146 | 1.00 | 7.10 |
| 6748 | CG1 | VAL | B | 52 | 30.128 | 52.734 | 60.676 | 1.00 | 7.56 |
| 6752 | CG2 | VAL | B | 52 | 28.893 | 50.590 | 60.289 | 1.00 | 7.18 |
| 6756 | C | VAL | B | 52 | 29.344 | 52.754 | 63.462 | 1.00 | 6.97 |
| 6757 | O | VAL | B | 52 | 30.466 | 53.085 | 63.820 | 1.00 | 7.05 |
| 6758 | N | THR | B | 53 | 28.266 | 53.470 | 63.750 | 1.00 | 7.20 |
| 6760 | CA | THR | B | 53 | 28.332 | 54.653 | 64.609 | 1.00 | 7.34 |
| 6762 | CB | THR | B | 53 | 26.914 | 55.181 | 64.912 | 1.00 | 7.40 |
| 6764 | OG1 | THR | B | 53 | 26.206 | 55.437 | 63.688 | 1.00 | 7.94 |
| 6766 | CG2 | THR | B | 53 | 26.979 | 56.532 | 65.614 | 1.00 | 7.28 |
| 6770 | C | THR | B | 53 | 29.035 | 54.359 | 65.934 | 1.00 | 7.35 |
| 6771 | O | THR | B | 53 | 29.962 | 55.062 | 66.325 | 1.00 | 7.11 |
| 6772 | N | PHE | B | 54 | 28.582 | 53.317 | 66.617 | 1.00 | 7.48 |
| 6774 | CA | PHE | B | 54 | 29.117 | 52.972 | 67.929 | 1.00 | 7.73 |
| 6776 | CB | PHE | B | 54 | 28.218 | 51.942 | 68.624 | 1.00 | 7.88 |
| 6779 | CG | PHE | B | 54 | 26.790 | 52.403 | 68.821 | 1.00 | 9.16 |
| 6780 | CD1 | PHE | B | 54 | 25.773 | 51.474 | 68.965 | 1.00 | 10.57 |
| 6782 | CE1 | PHE | B | 54 | 24.462 | 51.884 | 69.152 | 1.00 | 11.25 |
| 6784 | CZ | PHE | B | 54 | 24.155 | 53.229 | 69.191 | 1.00 | 11.34 |
| 6786 | CE2 | PHE | B | 54 | 25.155 | 54.166 | 69.052 | 1.00 | 11.04 |
| 6788 | CD2 | PHE | B | 54 | 26.463 | 53.757 | 68.866 | 1.00 | 9.97 |
| 6790 | C | PHE | B | 54 | 30.545 | 52.455 | 67.835 | 1.00 | 7.63 |
| 6791 | O | PHE | B | 54 | 31.387 | 52.820 | 68.650 | 1.00 | 7.58 |
| 6792 | N | ALA | B | 55 | 30.815 | 51.615 | 66.839 | 1.00 | 7.64 |
| 6794 | CA | ALA | B | 55 | 32.141 | 51.032 | 66.651 | 1.00 | 7.62 |
| 6796 | CB | ALA | B | 55 | 32.110 | 49.992 | 65.552 | 1.00 | 7.58 |
| 6800 | C | ALA | B | 55 | 33.184 | 52.098 | 66.333 | 1.00 | 7.66 |
| 6801 | O | ALA | B | 55 | 34.303 | 52.045 | 66.841 | 1.00 | 7.81 |
| 6802 | N | ALA | B | 56 | 32.813 | 53.064 | 65.497 | 1.00 | 7.59 |
| 6804 | CA | ALA | B | 56 | 33.728 | 54.135 | 65.101 | 1.00 | 7.91 |
| 6806 | CB | ALA | B | 56 | 33.148 | 54.929 | 63.936 | 1.00 | 7.75 |
| 6810 | C | ALA | B | 56 | 34.038 | 55.062 | 66.274 | 1.00 | 7.94 |
| 6811 | O | ALA | B | 56 | 35.176 | 55.482 | 66.450 | 1.00 | 7.82 |
| 6812 | N | ASN | B | 57 | 33.019 | 55.379 | 67.071 | 1.00 | 8.07 |
| 6814 | CA | ASN | B | 57 | 33.197 | 56.225 | 68.251 | 1.00 | 8.28 |
| 6816 | CB | ASN | B | 57 | 31.840 | 56.693 | 68.805 | 1.00 | 8.08 |
| 6819 | CG | ASN | B | 57 | 31.311 | 57.929 | 68.083 | 1.00 | 8.68 |
| 6820 | OD1 | ASN | B | 57 | 31.813 | 59.033 | 68.282 | 1.00 | 9.61 |
| 6821 | ND2 | ASN | B | 57 | 30.298 | 57.744 | 67.242 | 1.00 | 7.87 |
| 6824 | C | ASN | B | 57 | 34.033 | 55.527 | 69.336 | 1.00 | 8.28 |
| 6825 | O | ASN | B | 57 | 34.891 | 56.148 | 69.948 | 1.00 | 8.32 |

FIGURE 3 (Cont.)

| A | B | C | D | E | F | G | H | I | J |
|---|---|---|---|---|---|---|---|---|---|
| 6826 | N | ALA | B | 58 | 33.817 | 54.233 | 69.541 | 1.00 | 8.45 |
| 6828 | CA | ALA | B | 58 | 34.586 | 53.478 | 70.535 | 1.00 | 8.58 |
| 6830 | CB | ALA | B | 58 | 33.991 | 52.095 | 70.739 | 1.00 | 8.59 |
| 6834 | C | ALA | B | 58 | 36.054 | 53.365 | 70.146 | 1.00 | 8.74 |
| 6835 | O | ALA | B | 58 | 36.940 | 53.600 | 70.970 | 1.00 | 8.79 |
| 6836 | N | ALA | B | 59 | 36.299 | 52.994 | 68.892 | 1.00 | 8.94 |
| 6838 | CA | ALA | B | 59 | 37.651 | 52.820 | 68.374 | 1.00 | 9.30 |
| 6840 | CB | ALA | B | 59 | 37.612 | 52.155 | 67.003 | 1.00 | 9.25 |
| 6844 | C | ALA | B | 59 | 38.429 | 54.138 | 68.299 | 1.00 | 9.81 |
| 6845 | O | ALA | B | 59 | 39.644 | 54.146 | 68.475 | 1.00 | 9.51 |
| 6846 | N | GLU | B | 60 | 37.733 | 55.243 | 68.038 | 1.00 | 10.12 |
| 6848 | CA | GLU | B | 60 | 38.372 | 56.562 | 68.000 | 1.00 | 10.75 |
| 6850 | CB | GLU | B | 60 | 37.358 | 57.655 | 67.646 | 1.00 | 11.06 |
| 6853 | CG | GLU | B | 60 | 37.936 | 59.059 | 67.660 | 1.00 | 13.54 |
| 6856 | CD | GLU | B | 60 | 37.158 | 60.021 | 66.789 | 1.00 | 16.66 |
| 6857 | OE1 | GLU | B | 60 | 37.106 | 59.812 | 65.559 | 1.00 | 20.20 |
| 6858 | OE2 | GLU | B | 60 | 36.604 | 60.987 | 67.335 | 1.00 | 19.85 |
| 6859 | C | GLU | B | 60 | 39.037 | 56.891 | 69.337 | 1.00 | 10.37 |
| 6860 | O | GLU | B | 60 | 40.063 | 57.567 | 69.373 | 1.00 | 10.72 |
| 6861 | N | ALA | B | 61 | 38.446 | 56.409 | 70.428 | 1.00 | 10.12 |
| 6863 | CA | ALA | B | 61 | 38.985 | 56.632 | 71.769 | 1.00 | 9.80 |
| 6865 | CB | ALA | B | 61 | 38.041 | 56.048 | 72.823 | 1.00 | 9.92 |
| 6869 | C | ALA | B | 61 | 40.403 | 56.079 | 71.975 | 1.00 | 9.50 |
| 6870 | O | ALA | B | 61 | 41.159 | 56.628 | 72.772 | 1.00 | 9.14 |
| 6871 | N | ILE | B | 62 | 40.757 | 55.005 | 71.265 | 1.00 | 9.13 |
| 6873 | CA | ILE | B | 62 | 42.021 | 54.292 | 71.515 | 1.00 | 9.12 |
| 6875 | CB | ILE | B | 62 | 41.749 | 52.800 | 71.895 | 1.00 | 9.15 |
| 6877 | CG1 | ILE | B | 62 | 40.879 | 52.102 | 70.850 | 1.00 | 8.64 |
| 6880 | CD1 | ILE | B | 62 | 40.883 | 50.590 | 70.971 | 1.00 | 8.95 |
| 6884 | CG2 | ILE | B | 62 | 41.100 | 52.702 | 73.271 | 1.00 | 9.62 |
| 6888 | C | ILE | B | 62 | 43.068 | 54.348 | 70.394 | 1.00 | 9.06 |
| 6889 | O | ILE | B | 62 | 44.258 | 54.198 | 70.668 | 1.00 | 8.87 |
| 6890 | N | LEU | B | 63 | 42.645 | 54.564 | 69.149 | 1.00 | 9.05 |
| 6892 | CA | LEU | B | 63 | 43.545 | 54.391 | 68.006 | 1.00 | 9.20 |
| 6894 | CB | LEU | B | 63 | 42.762 | 53.983 | 66.757 | 1.00 | 9.45 |
| 6897 | CG | LEU | B | 63 | 42.059 | 52.626 | 66.818 | 1.00 | 9.71 |
| 6899 | CD1 | LEU | B | 63 | 41.365 | 52.349 | 65.498 | 1.00 | 10.99 |
| 6903 | CD2 | LEU | B | 63 | 43.037 | 51.510 | 67.160 | 1.00 | 10.12 |
| 6907 | C | LEU | B | 63 | 44.393 | 55.622 | 67.694 | 1.00 | 9.23 |
| 6908 | O | LEU | B | 63 | 43.895 | 56.746 | 67.659 | 1.00 | 8.67 |
| 6909 | N | THR | B | 64 | 45.680 | 55.374 | 67.457 | 1.00 | 9.40 |
| 6911 | CA | THR | B | 64 | 46.633 | 56.391 | 67.032 | 1.00 | 9.49 |
| 6913 | CB | THR | B | 64 | 47.903 | 56.317 | 67.890 | 1.00 | 9.46 |
| 6915 | OG1 | THR | B | 64 | 48.564 | 55.055 | 67.696 | 1.00 | 8.48 |
| 6917 | CG2 | THR | B | 64 | 47.559 | 56.357 | 69.376 | 1.00 | 9.16 |
| 6921 | C | THR | B | 64 | 47.002 | 56.171 | 65.578 | 1.00 | 10.16 |
| 6922 | O | THR | B | 64 | 46.655 | 55.147 | 64.997 | 1.00 | 9.62 |
| 6923 | N | LYS | B | 65 | 47.706 | 57.139 | 64.995 | 1.00 | 10.80 |
| 6925 | CA | LYS | B | 65 | 48.255 | 56.999 | 63.645 | 1.00 | 11.52 |
| 6927 | CB | LYS | B | 65 | 49.017 | 58.272 | 63.237 | 1.00 | 11.99 |
| 6930 | CG | LYS | B | 65 | 49.892 | 58.125 | 61.995 | 1.00 | 14.05 |
| 6933 | CD | LYS | B | 65 | 50.177 | 59.465 | 61.323 | 1.00 | 16.38 |

FIGURE 3 (Cont.)

| A | B | C | D | E | F | G | H | I | J |
|---|---|---|---|---|---|---|---|---|---|
| 6936 | CE | LYS | B | 65 | 50.752 | 59.262 | 59.927 | 1.00 | 17.78 |
| 6939 | NZ | LYS | B | 65 | 51.451 | 60.487 | 59.448 | 1.00 | 18.55 |
| 6943 | C | LYS | B | 65 | 49.152 | 55.764 | 63.513 | 1.00 | 11.70 |
| 6944 | O | LYS | B | 65 | 49.089 | 55.060 | 62.505 | 1.00 | 11.54 |
| 6945 | N | GLU | B | 66 | 49.981 | 55.490 | 64.518 | 1.00 | 11.90 |
| 6947 | CA | GLU | B | 66 | 50.873 | 54.334 | 64.427 | 1.00 | 12.04 |
| 6949 | CB | GLU | B | 66 | 52.118 | 54.478 | 65.312 | 1.00 | 12.65 |
| 6952 | CG | GLU | B | 66 | 51.901 | 54.506 | 66.807 | 1.00 | 13.77 |
| 6955 | CD | GLU | B | 66 | 53.181 | 54.844 | 67.571 | 1.00 | 15.02 |
| 6956 | OE1 | GLU | B | 66 | 54.245 | 55.036 | 66.932 | 1.00 | 16.61 |
| 6957 | OE2 | GLU | B | 66 | 53.123 | 54.915 | 68.813 | 1.00 | 12.38 |
| 6958 | C | GLU | B | 66 | 50.140 | 53.003 | 64.643 | 1.00 | 11.57 |
| 6959 | O | GLU | B | 66 | 50.526 | 52.005 | 64.046 | 1.00 | 11.19 |
| 6960 | N | ASP | B | 67 | 49.074 | 52.991 | 65.446 | 1.00 | 11.03 |
| 6962 | CA | ASP | B | 67 | 48.189 | 51.821 | 65.521 | 1.00 | 10.75 |
| 6964 | CB | ASP | B | 67 | 47.003 | 52.057 | 66.462 | 1.00 | 10.68 |
| 6967 | CG | ASP | B | 67 | 47.395 | 52.090 | 67.925 | 1.00 | 9.95 |
| 6968 | OD1 | ASP | B | 67 | 46.614 | 52.653 | 68.718 | 1.00 | 9.21 |
| 6969 | OD2 | ASP | B | 67 | 48.436 | 51.579 | 68.379 | 1.00 | 9.31 |
| 6970 | C | ASP | B | 67 | 47.620 | 51.536 | 64.134 | 1.00 | 10.87 |
| 6971 | O | ASP | B | 67 | 47.593 | 50.398 | 63.679 | 1.00 | 10.55 |
| 6972 | N | LYS | B | 68 | 47.169 | 52.591 | 63.467 | 1.00 | 10.91 |
| 6974 | CA | LYS | B | 68 | 46.520 | 52.462 | 62.170 | 1.00 | 11.29 |
| 6976 | CB | LYS | B | 68 | 45.951 | 53.808 | 61.715 | 1.00 | 11.12 |
| 6979 | CG | LYS | B | 68 | 44.736 | 54.236 | 62.533 | 1.00 | 11.60 |
| 6982 | CD | LYS | B | 68 | 44.515 | 55.732 | 62.508 | 1.00 | 11.28 |
| 6985 | CE | LYS | B | 68 | 43.460 | 56.147 | 63.516 | 1.00 | 11.97 |
| 6988 | NZ | LYS | B | 68 | 42.820 | 57.437 | 63.132 | 1.00 | 12.27 |
| 6992 | C | LYS | B | 68 | 47.466 | 51.876 | 61.125 | 1.00 | 11.42 |
| 6993 | O | LYS | B | 68 | 47.019 | 51.165 | 60.234 | 1.00 | 11.64 |
| 6994 | N | GLU | B | 69 | 48.764 | 52.142 | 61.265 | 1.00 | 11.69 |
| 6996 | CA | GLU | B | 69 | 49.783 | 51.571 | 60.374 | 1.00 | 12.26 |
| 6998 | CB | GLU | B | 69 | 51.052 | 52.434 | 60.379 | 1.00 | 12.71 |
| 7001 | CG | GLU | B | 69 | 50.918 | 53.749 | 59.627 | 1.00 | 15.37 |
| 7004 | CD | GLU | B | 69 | 50.417 | 53.568 | 58.203 | 1.00 | 19.14 |
| 7005 | OE1 | GLU | B | 69 | 50.856 | 52.605 | 57.523 | 1.00 | 21.31 |
| 7006 | OE2 | GLU | B | 69 | 49.575 | 54.386 | 57.768 | 1.00 | 22.20 |
| 7007 | C | GLU | B | 69 | 50.163 | 50.122 | 60.690 | 1.00 | 11.77 |
| 7008 | O | GLU | B | 69 | 50.610 | 49.397 | 59.801 | 1.00 | 11.80 |
| 7009 | N | ALA | B | 70 | 50.004 | 49.709 | 61.946 | 1.00 | 11.28 |
| 7011 | CA | ALA | B | 70 | 50.369 | 48.356 | 62.377 | 1.00 | 10.71 |
| 7013 | CB | ALA | B | 70 | 51.005 | 48.404 | 63.760 | 1.00 | 10.67 |
| 7017 | C | ALA | B | 70 | 49.204 | 47.365 | 62.379 | 1.00 | 10.29 |
| 7018 | O | ALA | B | 70 | 49.430 | 46.159 | 62.490 | 1.00 | 9.99 |
| 7019 | N | ILE | B | 71 | 47.971 | 47.859 | 62.262 | 1.00 | 9.85 |
| 7021 | CA | ILE | B | 71 | 46.798 | 46.990 | 62.276 | 1.00 | 9.48 |
| 7023 | CB | ILE | B | 71 | 45.514 | 47.769 | 62.661 | 1.00 | 9.43 |
| 7025 | CG1 | ILE | B | 71 | 45.498 | 48.082 | 64.157 | 1.00 | 9.33 |
| 7028 | CD1 | ILE | B | 71 | 44.579 | 49.237 | 64.519 | 1.00 | 9.50 |
| 7032 | CG2 | ILE | B | 71 | 44.260 | 46.969 | 62.297 | 1.00 | 9.37 |
| 7036 | C | ILE | B | 71 | 46.633 | 46.361 | 60.900 | 1.00 | 9.23 |
| 7037 | O | ILE | B | 71 | 46.501 | 47.073 | 59.904 | 1.00 | 8.76 |

FIGURE 3 (Cont.)

| A | B | C | D | E | F | G | H | I | J |
|---|---|---|---|---|---|---|---|---|---|
| 7038 | N | ASP | B | 72 | 46.637 | 45.031 | 60.850 | 1.00 | 9.13 |
| 7040 | CA | ASP | B | 72 | 46.412 | 44.312 | 59.596 | 1.00 | 9.13 |
| 7042 | CB | ASP | B | 72 | 47.695 | 43.601 | 59.140 | 1.00 | 9.36 |
| 7045 | CG | ASP | B | 72 | 48.089 | 42.436 | 60.026 | 1.00 | 9.51 |
| 7046 | OD1 | ASP | B | 72 | 47.560 | 42.284 | 61.153 | 1.00 | 9.46 |
| 7047 | OD2 | ASP | B | 72 | 48.949 | 41.611 | 59.654 | 1.00 | 9.56 |
| 7048 | C | ASP | B | 72 | 45.204 | 43.364 | 59.645 | 1.00 | 9.04 |
| 7049 | O | ASP | B | 72 | 45.012 | 42.539 | 58.745 | 1.00 | 9.02 |
| 7050 | N | MSE | B | 73 | 44.386 | 43.494 | 60.686 | 1.00 | 8.74 |
| 7052 | CA | MSE | B | 73 | 43.102 | 42.801 | 60.753 | 1.00 | 8.69 |
| 7054 | CB | MSE | B | 73 | 43.274 | 41.387 | 61.322 | 1.00 | 8.97 |
| 7057 | CG | MSE | B | 73 | 41.991 | 40.569 | 61.321 | 1.00 | 9.32 |
| 7060 | SE | MSE | B | 73 | 42.277 | 38.638 | 61.433 | 1.00 | 12.78 |
| 7061 | CE | MSE | B | 73 | 43.198 | 38.553 | 63.112 | 1.00 | 10.88 |
| 7065 | C | MSE | B | 73 | 42.093 | 43.592 | 61.593 | 1.00 | 8.36 |
| 7066 | O | MSE | B | 73 | 42.423 | 44.082 | 62.669 | 1.00 | 8.05 |
| 7067 | N | VAL | B | 74 | 40.872 | 43.718 | 61.074 | 1.00 | 8.04 |
| 7069 | CA | VAL | B | 74 | 39.783 | 44.439 | 61.729 | 1.00 | 7.80 |
| 7071 | CB | VAL | B | 74 | 39.376 | 45.701 | 60.930 | 1.00 | 7.72 |
| 7073 | CG1 | VAL | B | 74 | 38.256 | 46.456 | 61.640 | 1.00 | 7.53 |
| 7077 | CG2 | VAL | B | 74 | 40.582 | 46.616 | 60.703 | 1.00 | 8.12 |
| 7081 | C | VAL | B | 74 | 38.583 | 43.498 | 61.825 | 1.00 | 7.58 |
| 7082 | O | VAL | B | 74 | 38.098 | 43.015 | 60.810 | 1.00 | 7.50 |
| 7083 | N | ILE | B | 75 | 38.123 | 43.231 | 63.043 | 1.00 | 7.40 |
| 7085 | CA | ILE | B | 75 | 37.015 | 42.312 | 63.280 | 1.00 | 7.30 |
| 7087 | CB | ILE | B | 75 | 37.483 | 41.084 | 64.105 | 1.00 | 7.47 |
| 7089 | CG1 | ILE | B | 75 | 38.602 | 40.332 | 63.377 | 1.00 | 7.67 |
| 7092 | CD1 | ILE | B | 75 | 39.306 | 39.292 | 64.241 | 1.00 | 7.71 |
| 7096 | CG2 | ILE | B | 75 | 36.322 | 40.129 | 64.364 | 1.00 | 7.66 |
| 7100 | C | ILE | B | 75 | 35.920 | 43.052 | 64.029 | 1.00 | 7.19 |
| 7101 | O | ILE | B | 75 | 36.193 | 43.734 | 65.014 | 1.00 | 7.34 |
| 7102 | N | VAL | B | 76 | 34.686 | 42.921 | 63.559 | 1.00 | 6.98 |
| 7104 | CA | VAL | B | 76 | 33.527 | 43.381 | 64.311 | 1.00 | 6.66 |
| 7106 | CB | VAL | B | 76 | 32.674 | 44.372 | 63.496 | 1.00 | 6.65 |
| 7108 | CG1 | VAL | B | 76 | 31.329 | 44.646 | 64.187 | 1.00 | 6.47 |
| 7112 | CG2 | VAL | B | 76 | 33.435 | 45.667 | 63.291 | 1.00 | 6.68 |
| 7116 | C | VAL | B | 76 | 32.701 | 42.164 | 64.706 | 1.00 | 6.55 |
| 7117 | O | VAL | B | 76 | 32.293 | 41.383 | 63.852 | 1.00 | 6.27 |
| 7118 | N | GLY | B | 77 | 32.488 | 41.996 | 66.006 | 1.00 | 6.51 |
| 7120 | CA | GLY | B | 77 | 31.551 | 41.017 | 66.524 | 1.00 | 6.42 |
| 7123 | C | GLY | B | 77 | 30.212 | 41.697 | 66.728 | 1.00 | 6.39 |
| 7124 | O | GLY | B | 77 | 30.134 | 42.738 | 67.370 | 1.00 | 6.20 |
| 7125 | N | THR | B | 78 | 29.161 | 41.108 | 66.175 | 1.00 | 6.22 |
| 7127 | CA | THR | B | 78 | 27.832 | 41.696 | 66.239 | 1.00 | 6.26 |
| 7129 | CB | THR | B | 78 | 27.747 | 42.926 | 65.281 | 1.00 | 6.20 |
| 7131 | OG1 | THR | B | 78 | 26.546 | 43.666 | 65.529 | 1.00 | 5.52 |
| 7133 | CG2 | THR | B | 78 | 27.643 | 42.502 | 63.810 | 1.00 | 6.26 |
| 7137 | C | THR | B | 78 | 26.739 | 40.680 | 65.903 | 1.00 | 6.54 |
| 7138 | O | THR | B | 78 | 26.990 | 39.658 | 65.268 | 1.00 | 6.66 |
| 7139 | N | GLU | B | 79 | 25.537 | 40.971 | 66.380 | 1.00 | 6.93 |
| 7141 | CA | GLU | B | 79 | 24.313 | 40.309 | 65.953 | 1.00 | 7.29 |
| 7143 | CB | GLU | B | 79 | 23.780 | 39.427 | 67.084 | 1.00 | 7.52 |

FIGURE 3 (Cont.)

| A | B | C | D | E | F | G | H | I | J |
|---|---|---|---|---|---|---|---|---|---|
| 7146 | CG | GLU | B | 79 | 23.394 | 40.183 | 68.346 | 1.00 | 8.01 |
| 7149 | CD | GLU | B | 79 | 22.711 | 39.293 | 69.360 | 1.00 | 8.61 |
| 7150 | OE1 | GLU | B | 79 | 21.488 | 39.072 | 69.227 | 1.00 | 8.33 |
| 7151 | OE2 | GLU | B | 79 | 23.402 | 38.815 | 70.281 | 1.00 | 8.46 |
| 7152 | C | GLU | B | 79 | 23.262 | 41.352 | 65.542 | 1.00 | 7.45 |
| 7153 | O | GLU | B | 79 | 22.073 | 41.048 | 65.466 | 1.00 | 7.53 |
| 7154 | N | SER | B | 80 | 23.714 | 42.579 | 65.280 | 1.00 | 7.57 |
| 7156 | CA | SER | B | 80 | 22.840 | 43.699 | 64.918 | 1.00 | 7.59 |
| 7158 | CB | SER | B | 80 | 22.947 | 44.810 | 65.970 | 1.00 | 7.65 |
| 7161 | OG | SER | B | 80 | 22.736 | 44.312 | 67.282 | 1.00 | 6.95 |
| 7163 | C | SER | B | 80 | 23.251 | 44.234 | 63.546 | 1.00 | 7.69 |
| 7164 | O | SER | B | 80 | 23.329 | 45.447 | 63.333 | 1.00 | 7.98 |
| 7165 | N | SER | B | 81 | 23.516 | 43.319 | 62.616 | 1.00 | 7.72 |
| 7167 | CA | SER | B | 81 | 24.106 | 43.680 | 61.329 | 1.00 | 7.69 |
| 7169 | CB | SER | B | 81 | 24.596 | 42.431 | 60.587 | 1.00 | 7.79 |
| 7172 | OG | SER | B | 81 | 23.518 | 41.597 | 60.200 | 1.00 | 7.75 |
| 7174 | C | SER | B | 81 | 23.146 | 44.481 | 60.448 | 1.00 | 7.61 |
| 7175 | O | SER | B | 81 | 21.927 | 44.420 | 60.616 | 1.00 | 7.37 |
| 7176 | N | ILE | B | 82 | 23.726 | 45.233 | 59.517 | 1.00 | 7.65 |
| 7178 | CA | ILE | B | 82 | 22.985 | 46.088 | 58.587 | 1.00 | 7.88 |
| 7180 | CB | ILE | B | 82 | 23.421 | 47.566 | 58.763 | 1.00 | 8.13 |
| 7182 | CG1 | ILE | B | 82 | 24.941 | 47.719 | 58.610 | 1.00 | 8.23 |
| 7185 | CD1 | ILE | B | 82 | 25.434 | 49.157 | 58.651 | 1.00 | 8.96 |
| 7189 | CG2 | ILE | B | 82 | 22.962 | 48.077 | 60.128 | 1.00 | 8.71 |
| 7193 | C | ILE | B | 82 | 23.155 | 45.641 | 57.128 | 1.00 | 7.77 |
| 7194 | O | ILE | B | 82 | 22.549 | 46.207 | 56.219 | 1.00 | 7.67 |
| 7195 | N | ASP | B | 83 | 23.978 | 44.619 | 56.916 | 1.00 | 7.50 |
| 7197 | CA | ASP | B | 83 | 24.133 | 43.995 | 55.608 | 1.00 | 7.47 |
| 7199 | CB | ASP | B | 83 | 25.313 | 44.627 | 54.870 | 1.00 | 7.26 |
| 7202 | CG | ASP | B | 83 | 25.189 | 44.525 | 53.366 | 1.00 | 7.04 |
| 7203 | OD1 | ASP | B | 83 | 24.704 | 45.487 | 52.738 | 1.00 | 6.29 |
| 7204 | OD2 | ASP | B | 83 | 25.564 | 43.525 | 52.721 | 1.00 | 6.05 |
| 7205 | C | ASP | B | 83 | 24.355 | 42.493 | 55.789 | 1.00 | 7.40 |
| 7206 | O | ASP | B | 83 | 25.004 | 42.074 | 56.745 | 1.00 | 7.38 |
| 7207 | N | GLU | B | 84 | 23.819 | 41.699 | 54.863 | 1.00 | 7.39 |
| 7209 | CA | GLU | B | 84 | 23.950 | 40.240 | 54.891 | 1.00 | 7.52 |
| 7211 | CB | GLU | B | 84 | 22.767 | 39.589 | 54.165 | 1.00 | 7.49 |
| 7214 | CG | GLU | B | 84 | 21.406 | 39.921 | 54.753 | 1.00 | 7.77 |
| 7217 | CD | GLU | B | 84 | 21.231 | 39.412 | 56.171 | 1.00 | 8.17 |
| 7218 | OE1 | GLU | B | 84 | 21.969 | 38.483 | 56.576 | 1.00 | 7.42 |
| 7219 | OE2 | GLU | B | 84 | 20.352 | 39.950 | 56.880 | 1.00 | 8.27 |
| 7220 | C | GLU | B | 84 | 25.249 | 39.733 | 54.261 | 1.00 | 7.54 |
| 7221 | O | GLU | B | 84 | 25.604 | 38.567 | 54.436 | 1.00 | 7.76 |
| 7222 | N | SER | B | 85 | 25.945 | 40.610 | 53.535 | 1.00 | 7.44 |
| 7224 | CA | SER | B | 85 | 27.158 | 40.254 | 52.802 | 1.00 | 7.23 |
| 7226 | CB | SER | B | 85 | 26.921 | 40.453 | 51.302 | 1.00 | 7.35 |
| 7229 | OG | SER | B | 85 | 28.117 | 40.312 | 50.556 | 1.00 | 7.16 |
| 7231 | C | SER | B | 85 | 28.358 | 41.090 | 53.249 | 1.00 | 7.19 |
| 7232 | O | SER | B | 85 | 29.393 | 40.548 | 53.634 | 1.00 | 6.98 |
| 7233 | N | LYS | B | 86 | 28.216 | 42.410 | 53.185 | 1.00 | 7.33 |
| 7235 | CA | LYS | B | 86 | 29.306 | 43.330 | 53.493 | 1.00 | 7.58 |
| 7237 | CB | LYS | B | 86 | 29.030 | 44.702 | 52.869 | 1.00 | 7.63 |

FIGURE 3 (Cont.)

| A | B | C | D | E | F | G | H | I | J |
|---|---|---|---|---|---|---|---|---|---|
| 7240 | CG | LYS | B | 86 | 30.161 | 45.703 | 53.028 | 1.00 | 7.94 |
| 7243 | CD | LYS | B | 86 | 30.028 | 46.824 | 52.002 | 1.00 | 8.85 |
| 7246 | CE | LYS | B | 86 | 30.906 | 48.013 | 52.345 | 1.00 | 8.51 |
| 7249 | NZ | LYS | B | 86 | 31.205 | 48.818 | 51.136 | 1.00 | 8.73 |
| 7253 | C | LYS | B | 86 | 29.501 | 43.475 | 54.995 | 1.00 | 7.50 |
| 7254 | O | LYS | B | 86 | 28.592 | 43.906 | 55.708 | 1.00 | 7.54 |
| 7255 | N | ALA | B | 87 | 30.695 | 43.117 | 55.461 | 1.00 | 7.29 |
| 7257 | CA | ALA | B | 87 | 31.050 | 43.202 | 56.874 | 1.00 | 7.22 |
| 7259 | CB | ALA | B | 87 | 32.415 | 42.579 | 57.102 | 1.00 | 7.03 |
| 7263 | C | ALA | B | 87 | 31.063 | 44.650 | 57.340 | 1.00 | 7.15 |
| 7264 | O | ALA | B | 87 | 31.601 | 45.514 | 56.657 | 1.00 | 6.99 |
| 7265 | N | ALA | B | 88 | 30.493 | 44.907 | 58.514 | 1.00 | 7.30 |
| 7267 | CA | ALA | B | 88 | 30.564 | 46.232 | 59.130 | 1.00 | 7.23 |
| 7269 | CB | ALA | B | 88 | 29.831 | 46.232 | 60.465 | 1.00 | 7.30 |
| 7273 | C | ALA | B | 88 | 32.018 | 46.670 | 59.328 | 1.00 | 7.18 |
| 7274 | O | ALA | B | 88 | 32.315 | 47.864 | 59.318 | 1.00 | 7.50 |
| 7275 | N | ALA | B | 89 | 32.917 | 45.701 | 59.506 | 1.00 | 6.97 |
| 7277 | CA | ALA | B | 89 | 34.344 | 45.968 | 59.696 | 1.00 | 6.83 |
| 7279 | CB | ALA | B | 89 | 35.089 | 44.663 | 59.981 | 1.00 | 6.97 |
| 7283 | C | ALA | B | 89 | 34.998 | 46.691 | 58.516 | 1.00 | 6.89 |
| 7284 | O | ALA | B | 89 | 35.982 | 47.398 | 58.698 | 1.00 | 6.86 |
| 7285 | N | VAL | B | 90 | 34.468 | 46.486 | 57.312 | 1.00 | 7.09 |
| 7287 | CA | VAL | B | 90 | 34.972 | 47.157 | 56.117 | 1.00 | 7.12 |
| 7289 | CB | VAL | B | 90 | 34.313 | 46.611 | 54.838 | 1.00 | 7.21 |
| 7291 | CG1 | VAL | B | 90 | 34.705 | 47.461 | 53.627 | 1.00 | 7.23 |
| 7295 | CG2 | VAL | B | 90 | 34.704 | 45.144 | 54.623 | 1.00 | 7.18 |
| 7299 | C | VAL | B | 90 | 34.752 | 48.667 | 56.205 | 1.00 | 7.21 |
| 7300 | O | VAL | B | 90 | 35.662 | 49.449 | 55.922 | 1.00 | 7.09 |
| 7301 | N | VAL | B | 91 | 33.549 | 49.070 | 56.603 | 1.00 | 7.34 |
| 7303 | CA | VAL | B | 91 | 33.249 | 50.490 | 56.781 | 1.00 | 7.42 |
| 7305 | CB | VAL | B | 91 | 31.741 | 50.737 | 57.004 | 1.00 | 7.45 |
| 7307 | CG1 | VAL | B | 91 | 31.463 | 52.234 | 57.152 | 1.00 | 7.31 |
| 7311 | CG2 | VAL | B | 91 | 30.937 | 50.151 | 55.856 | 1.00 | 7.57 |
| 7315 | C | VAL | B | 91 | 34.059 | 51.068 | 57.949 | 1.00 | 7.42 |
| 7316 | O | VAL | B | 91 | 34.577 | 52.175 | 57.861 | 1.00 | 7.48 |
| 7317 | N | LEU | B | 92 | 34.175 | 50.312 | 59.035 | 1.00 | 7.65 |
| 7319 | CA | LEU | B | 92 | 35.010 | 50.719 | 60.168 | 1.00 | 7.86 |
| 7321 | CB | LEU | B | 92 | 34.925 | 49.686 | 61.288 | 1.00 | 8.01 |
| 7324 | CG | LEU | B | 92 | 35.699 | 49.963 | 62.575 | 1.00 | 8.20 |
| 7326 | CD1 | LEU | B | 92 | 35.213 | 51.243 | 63.237 | 1.00 | 8.64 |
| 7330 | CD2 | LEU | B | 92 | 35.561 | 48.783 | 63.519 | 1.00 | 8.52 |
| 7334 | C | LEU | B | 92 | 36.475 | 50.936 | 59.754 | 1.00 | 7.96 |
| 7335 | O | LEU | B | 92 | 37.108 | 51.897 | 60.181 | 1.00 | 7.93 |
| 7336 | N | HIS | B | 93 | 36.998 | 50.042 | 58.922 | 1.00 | 8.02 |
| 7338 | CA | HIS | B | 93 | 38.373 | 50.129 | 58.434 | 1.00 | 8.16 |
| 7340 | CB | HIS | B | 93 | 38.669 | 48.947 | 57.501 | 1.00 | 8.37 |
| 7343 | CG | HIS | B | 93 | 40.000 | 49.023 | 56.817 | 1.00 | 8.87 |
| 7344 | ND1 | HIS | B | 93 | 40.201 | 49.743 | 55.659 | 1.00 | 9.04 |
| 7346 | CE1 | HIS | B | 93 | 41.463 | 49.628 | 55.285 | 1.00 | 8.95 |
| 7348 | NE2 | HIS | B | 93 | 42.088 | 48.857 | 56.157 | 1.00 | 8.12 |
| 7350 | CD2 | HIS | B | 93 | 41.194 | 48.461 | 57.123 | 1.00 | 8.80 |
| 7352 | C | HIS | B | 93 | 38.613 | 51.468 | 57.721 | 1.00 | 8.22 |

FIGURE 3 (Cont.)

| A | B | C | D | E | F | G | H | I | J |
|---|---|---|---|---|---|---|---|---|---|
| 7353 | O | HIS | B | 93 | 39.650 | 52.103 | 57.915 | 1.00 | 8.01 |
| 7354 | N | ARG | B | 94 | 37.649 | 51.895 | 56.910 | 1.00 | 8.13 |
| 7356 | CA | ARG | B | 94 | 37.728 | 53.190 | 56.232 | 1.00 | 8.47 |
| 7358 | CB | ARG | B | 94 | 36.595 | 53.345 | 55.213 | 1.00 | 8.47 |
| 7361 | CG | ARG | B | 94 | 36.543 | 54.729 | 54.545 | 1.00 | 9.24 |
| 7364 | CD | ARG | B | 94 | 35.476 | 54.863 | 53.479 | 1.00 | 9.63 |
| 7367 | NE | ARG | B | 94 | 34.130 | 54.799 | 54.053 | 1.00 | 10.38 |
| 7369 | CZ | ARG | B | 94 | 33.479 | 55.833 | 54.590 | 1.00 | 10.84 |
| 7370 | NH1 | ARG | B | 94 | 32.257 | 55.658 | 55.079 | 1.00 | 10.90 |
| 7373 | NH2 | ARG | B | 94 | 34.040 | 57.031 | 54.667 | 1.00 | 11.11 |
| 7376 | C | ARG | B | 94 | 37.673 | 54.346 | 57.230 | 1.00 | 8.41 |
| 7377 | O | ARG | B | 94 | 38.537 | 55.221 | 57.223 | 1.00 | 8.30 |
| 7378 | N | LEU | B | 95 | 36.655 | 54.348 | 58.083 | 1.00 | 8.54 |
| 7380 | CA | LEU | B | 95 | 36.425 | 55.465 | 58.999 | 1.00 | 8.56 |
| 7382 | CB | LEU | B | 95 | 35.132 | 55.266 | 59.799 | 1.00 | 8.44 |
| 7385 | CG | LEU | B | 95 | 33.814 | 55.350 | 59.015 | 1.00 | 8.26 |
| 7387 | CD1 | LEU | B | 95 | 32.641 | 54.912 | 59.897 | 1.00 | 8.69 |
| 7391 | CD2 | LEU | B | 95 | 33.564 | 56.751 | 58.449 | 1.00 | 7.70 |
| 7395 | C | LEU | B | 95 | 37.609 | 55.688 | 59.938 | 1.00 | 8.76 |
| 7396 | O | LEU | B | 95 | 37.937 | 56.828 | 60.249 | 1.00 | 8.37 |
| 7397 | N | MSE | B | 96 | 38.257 | 54.601 | 60.363 | 1.00 | 9.13 |
| 7399 | CA | MSE | B | 96 | 39.412 | 54.671 | 61.265 | 1.00 | 9.46 |
| 7401 | CB | MSE | B | 96 | 39.512 | 53.384 | 62.094 | 1.00 | 9.75 |
| 7404 | CG | MSE | B | 96 | 38.376 | 53.196 | 63.075 | 1.00 | 11.12 |
| 7407 | SE | MSE | B | 96 | 38.299 | 54.659 | 64.353 | 1.00 | 14.97 |
| 7408 | CE | MSE | B | 96 | 36.822 | 55.632 | 63.579 | 1.00 | 13.42 |
| 7412 | C | MSE | B | 96 | 40.744 | 54.909 | 60.534 | 1.00 | 9.47 |
| 7413 | O | MSE | B | 96 | 41.792 | 54.993 | 61.170 | 1.00 | 9.50 |
| 7414 | N | GLY | B | 97 | 40.705 | 54.993 | 59.208 | 1.00 | 9.45 |
| 7416 | CA | GLY | B | 97 | 41.880 | 55.292 | 58.406 | 1.00 | 9.56 |
| 7419 | C | GLY | B | 97 | 42.985 | 54.260 | 58.558 | 1.00 | 9.64 |
| 7420 | O | GLY | B | 97 | 44.164 | 54.601 | 58.532 | 1.00 | 9.32 |
| 7421 | N | ILE | B | 98 | 42.603 | 52.998 | 58.728 | 1.00 | 9.83 |
| 7423 | CA | ILE | B | 98 | 43.573 | 51.917 | 58.889 | 1.00 | 10.10 |
| 7425 | CB | ILE | B | 98 | 42.876 | 50.652 | 59.483 | 1.00 | 10.24 |
| 7427 | CG1 | ILE | B | 98 | 42.530 | 50.906 | 60.955 | 1.00 | 11.02 |
| 7430 | CD1 | ILE | B | 98 | 41.459 | 50.005 | 61.506 | 1.00 | 12.13 |
| 7434 | CG2 | ILE | B | 98 | 43.757 | 49.405 | 59.357 | 1.00 | 10.28 |
| 7438 | C | ILE | B | 98 | 44.244 | 51.648 | 57.540 | 1.00 | 9.95 |
| 7439 | O | ILE | B | 98 | 43.622 | 51.809 | 56.491 | 1.00 | 9.62 |
| 7440 | N | GLN | B | 99 | 45.520 | 51.266 | 57.579 | 1.00 | 9.89 |
| 7442 | CA | GLN | B | 99 | 46.296 | 51.007 | 56.368 | 1.00 | 9.77 |
| 7444 | CB | GLN | B | 99 | 47.745 | 50.621 | 56.715 | 1.00 | 9.84 |
| 7447 | CG | GLN | B | 99 | 47.909 | 49.322 | 57.513 | 1.00 | 8.98 |
| 7450 | CD | GLN | B | 99 | 47.972 | 48.074 | 56.646 | 1.00 | 8.98 |
| 7451 | OE1 | GLN | B | 99 | 48.396 | 48.128 | 55.493 | 1.00 | 7.76 |
| 7452 | NE2 | GLN | B | 99 | 47.544 | 46.945 | 57.204 | 1.00 | 7.65 |
| 7455 | C | GLN | B | 99 | 45.623 | 49.925 | 55.516 | 1.00 | 9.97 |
| 7456 | O | GLN | B | 99 | 44.970 | 49.026 | 56.053 | 1.00 | 9.88 |
| 7457 | N | PRO | B | 100 | 45.773 | 50.016 | 54.195 | 1.00 | 10.26 |
| 7458 | CA | PRO | B | 100 | 44.968 | 49.207 | 53.269 | 1.00 | 10.30 |
| 7460 | CB | PRO | B | 100 | 45.339 | 49.768 | 51.888 | 1.00 | 10.35 |

FIGURE 3 (Cont.)

| A | B | C | D | E | F | G | H | I | J |
|---|---|---|---|---|---|---|---|---|---|
| 7463 | CG | PRO | B | 100 | 46.666 | 50.418 | 52.061 | 1.00 | 10.88 |
| 7466 | CD | PRO | B | 100 | 46.716 | 50.899 | 53.482 | 1.00 | 10.51 |
| 7469 | C | PRO | B | 100 | 45.210 | 47.695 | 53.310 | 1.00 | 10.33 |
| 7470 | O | PRO | B | 100 | 44.263 | 46.954 | 53.071 | 1.00 | 10.56 |
| 7471 | N | PHE | B | 101 | 46.432 | 47.250 | 53.581 | 1.00 | 10.02 |
| 7473 | CA | PHE | B | 101 | 46.763 | 45.828 | 53.496 | 1.00 | 10.15 |
| 7475 | CB | PHE | B | 101 | 48.242 | 45.634 | 53.143 | 1.00 | 10.26 |
| 7478 | CG | PHE | B | 101 | 48.622 | 46.221 | 51.805 | 1.00 | 11.29 |
| 7479 | CD1 | PHE | B | 101 | 49.511 | 47.285 | 51.720 | 1.00 | 12.63 |
| 7481 | CE1 | PHE | B | 101 | 49.857 | 47.834 | 50.477 | 1.00 | 12.90 |
| 7483 | CZ | PHE | B | 101 | 49.305 | 47.320 | 49.316 | 1.00 | 13.04 |
| 7485 | CE2 | PHE | B | 101 | 48.413 | 46.260 | 49.387 | 1.00 | 12.62 |
| 7487 | CD2 | PHE | B | 101 | 48.074 | 45.718 | 50.629 | 1.00 | 12.53 |
| 7489 | C | PHE | B | 101 | 46.369 | 45.073 | 54.770 | 1.00 | 9.98 |
| 7490 | O | PHE | B | 101 | 47.212 | 44.663 | 55.567 | 1.00 | 9.84 |
| 7491 | N | ALA | B | 102 | 45.059 | 44.911 | 54.928 | 1.00 | 9.66 |
| 7493 | CA | ALA | B | 102 | 44.451 | 44.293 | 56.094 | 1.00 | 9.85 |
| 7495 | CB | ALA | B | 102 | 44.036 | 45.361 | 57.088 | 1.00 | 9.95 |
| 7499 | C | ALA | B | 102 | 43.229 | 43.487 | 55.667 | 1.00 | 9.77 |
| 7500 | O | ALA | B | 102 | 42.588 | 43.815 | 54.666 | 1.00 | 9.43 |
| 7501 | N | ARG | B | 103 | 42.907 | 42.437 | 56.421 | 1.00 | 9.85 |
| 7503 | CA | ARG | B | 103 | 41.651 | 41.725 | 56.218 | 1.00 | 9.82 |
| 7505 | CB | ARG | B | 103 | 41.834 | 40.207 | 56.295 | 1.00 | 10.02 |
| 7508 | CG | ARG | B | 103 | 42.108 | 39.629 | 57.661 | 1.00 | 10.75 |
| 7511 | CD | ARG | B | 103 | 42.048 | 38.113 | 57.678 | 1.00 | 12.03 |
| 7514 | NE | ARG | B | 103 | 43.157 | 37.487 | 56.955 | 1.00 | 11.32 |
| 7516 | CZ | ARG | B | 103 | 44.288 | 37.050 | 57.512 | 1.00 | 12.65 |
| 7517 | NH1 | ARG | B | 103 | 44.513 | 37.182 | 58.815 | 1.00 | 13.47 |
| 7520 | NH2 | ARG | B | 103 | 45.219 | 36.485 | 56.754 | 1.00 | 11.84 |
| 7523 | C | ARG | B | 103 | 40.615 | 42.216 | 57.218 | 1.00 | 9.66 |
| 7524 | O | ARG | B | 103 | 40.935 | 42.489 | 58.377 | 1.00 | 9.72 |
| 7525 | N | SER | B | 104 | 39.378 | 42.338 | 56.750 | 1.00 | 9.01 |
| 7527 | CA | SER | B | 104 | 38.287 | 42.864 | 57.557 | 1.00 | 8.81 |
| 7529 | CB | SER | B | 104 | 37.948 | 44.297 | 57.132 | 1.00 | 8.73 |
| 7532 | OG | SER | B | 104 | 39.081 | 45.146 | 57.238 | 1.00 | 8.12 |
| 7534 | C | SER | B | 104 | 37.067 | 41.965 | 57.411 | 1.00 | 8.56 |
| 7535 | O | SER | B | 104 | 36.683 | 41.601 | 56.299 | 1.00 | 8.59 |
| 7536 | N | PHE | B | 105 | 36.478 | 41.582 | 58.536 | 1.00 | 8.30 |
| 7538 | CA | PHE | B | 105 | 35.272 | 40.761 | 58.516 | 1.00 | 8.28 |
| 7540 | CB | PHE | B | 105 | 35.610 | 39.294 | 58.225 | 1.00 | 8.17 |
| 7543 | CG | PHE | B | 105 | 36.596 | 38.695 | 59.183 | 1.00 | 8.22 |
| 7544 | CD1 | PHE | B | 105 | 37.960 | 38.767 | 58.925 | 1.00 | 8.53 |
| 7546 | CE1 | PHE | B | 105 | 38.876 | 38.214 | 59.803 | 1.00 | 9.11 |
| 7548 | CZ | PHE | B | 105 | 38.435 | 37.577 | 60.953 | 1.00 | 8.87 |
| 7550 | CE2 | PHE | B | 105 | 37.079 | 37.502 | 61.223 | 1.00 | 8.82 |
| 7552 | CD2 | PHE | B | 105 | 36.165 | 38.060 | 60.340 | 1.00 | 8.70 |
| 7554 | C | PHE | B | 105 | 34.482 | 40.857 | 59.806 | 1.00 | 8.33 |
| 7555 | O | PHE | B | 105 | 34.955 | 41.379 | 60.815 | 1.00 | 8.29 |
| 7556 | N | GLU | B | 106 | 33.270 | 40.322 | 59.732 | 1.00 | 8.40 |
| 7558 | CA | GLU | B | 106 | 32.288 | 40.335 | 60.796 | 1.00 | 8.41 |
| 7560 | CB | GLU | B | 106 | 30.952 | 40.773 | 60.183 | 1.00 | 8.56 |
| 7563 | CG | GLU | B | 106 | 29.839 | 41.160 | 61.133 | 1.00 | 8.46 |

FIGURE 3 (Cont.)

| A | B | C | D | E | F | G | H | I | J |
|---|---|---|---|---|---|---|---|---|---|
| 7566 | CD | GLU | B | 106 | 28.616 | 41.666 | 60.388 | 1.00 | 7.62 |
| 7567 | OE1 | GLU | B | 106 | 27.572 | 40.981 | 60.424 | 1.00 | 6.66 |
| 7568 | OE2 | GLU | B | 106 | 28.701 | 42.742 | 59.749 | 1.00 | 6.42 |
| 7569 | C | GLU | B | 106 | 32.191 | 38.911 | 61.333 | 1.00 | 8.49 |
| 7570 | O | GLU | B | 106 | 32.226 | 37.953 | 60.550 | 1.00 | 8.68 |
| 7571 | N | ILE | B | 107 | 32.107 | 38.767 | 62.656 | 1.00 | 8.33 |
| 7573 | CA | ILE | B | 107 | 31.844 | 37.479 | 63.288 | 1.00 | 8.42 |
| 7575 | CB | ILE | B | 107 | 32.900 | 37.153 | 64.365 | 1.00 | 8.22 |
| 7577 | CG1 | ILE | B | 107 | 34.269 | 36.975 | 63.711 | 1.00 | 8.66 |
| 7580 | CD1 | ILE | B | 107 | 35.397 | 36.642 | 64.670 | 1.00 | 8.64 |
| 7584 | CG2 | ILE | B | 107 | 32.503 | 35.887 | 65.135 | 1.00 | 8.53 |
| 7588 | C | ILE | B | 107 | 30.452 | 37.493 | 63.905 | 1.00 | 8.27 |
| 7589 | O | ILE | B | 107 | 30.074 | 38.452 | 64.586 | 1.00 | 7.94 |
| 7590 | N | LYS | B | 108 | 29.702 | 36.421 | 63.669 | 1.00 | 8.10 |
| 7592 | CA | LYS | B | 108 | 28.368 | 36.267 | 64.222 | 1.00 | 8.22 |
| 7594 | CB | LYS | B | 108 | 27.325 | 36.269 | 63.110 | 1.00 | 8.28 |
| 7597 | CG | LYS | B | 108 | 25.881 | 36.111 | 63.596 | 1.00 | 8.67 |
| 7600 | CD | LYS | B | 108 | 24.973 | 35.558 | 62.499 | 1.00 | 9.61 |
| 7603 | CE | LYS | B | 108 | 24.857 | 36.503 | 61.322 | 1.00 | 9.93 |
| 7606 | NZ | LYS | B | 108 | 24.135 | 35.872 | 60.183 | 1.00 | 10.41 |
| 7610 | C | LYS | B | 108 | 28.251 | 34.971 | 65.009 | 1.00 | 8.13 |
| 7611 | O | LYS | B | 108 | 28.425 | 33.883 | 64.464 | 1.00 | 8.15 |
| 7612 | N | GLU | B | 109 | 27.973 | 35.116 | 66.298 | 1.00 | 8.03 |
| 7614 | CA | GLU | B | 109 | 27.443 | 34.045 | 67.127 | 1.00 | 8.05 |
| 7616 | CB | GLU | B | 109 | 28.492 | 32.964 | 67.406 | 1.00 | 8.00 |
| 7619 | CG | GLU | B | 109 | 28.143 | 31.898 | 68.448 | 1.00 | 8.09 |
| 7622 | CD | GLU | B | 109 | 26.661 | 31.724 | 68.729 | 1.00 | 8.51 |
| 7623 | OE1 | GLU | B | 109 | 26.301 | 31.645 | 69.920 | 1.00 | 9.51 |
| 7624 | OE2 | GLU | B | 109 | 25.861 | 31.644 | 67.779 | 1.00 | 7.95 |
| 7625 | C | GLU | B | 109 | 26.956 | 34.716 | 68.401 | 1.00 | 8.06 |
| 7626 | O | GLU | B | 109 | 27.618 | 34.676 | 69.434 | 1.00 | 7.89 |
| 7627 | N | ALA | B | 110 | 25.820 | 35.396 | 68.279 | 1.00 | 8.12 |
| 7629 | CA | ALA | B | 110 | 25.128 | 35.979 | 69.412 | 1.00 | 8.29 |
| 7631 | CB | ALA | B | 110 | 24.523 | 34.858 | 70.277 | 1.00 | 8.28 |
| 7635 | C | ALA | B | 110 | 26.076 | 36.889 | 70.209 | 1.00 | 8.41 |
| 7636 | O | ALA | B | 110 | 26.827 | 37.666 | 69.617 | 1.00 | 8.54 |
| 7637 | N | CYS | B | 111 | 26.063 | 36.785 | 71.534 | 1.00 | 8.54 |
| 7639 | CA | CYS | B | 111 | 26.910 | 37.626 | 72.382 | 1.00 | 8.88 |
| 7641 | CB | CYS | B | 111 | 26.256 | 37.794 | 73.745 | 1.00 | 8.84 |
| 7644 | SG | CYS | B | 111 | 24.812 | 38.846 | 73.647 | 1.00 | 11.06 |
| 7645 | C | CYS | B | 111 | 28.335 | 37.104 | 72.555 | 1.00 | 8.69 |
| 7646 | O | CYS | B | 111 | 29.104 | 37.654 | 73.345 | 1.00 | 8.74 |
| 7647 | N | TYR | B | 112 | 28.678 | 36.056 | 71.807 | 1.00 | 8.59 |
| 7649 | CA | TYR | B | 112 | 30.005 | 35.449 | 71.825 | 1.00 | 8.67 |
| 7651 | CB | TYR | B | 112 | 29.871 | 33.915 | 71.746 | 1.00 | 8.58 |
| 7654 | CG | TYR | B | 112 | 31.196 | 33.209 | 71.649 | 1.00 | 9.19 |
| 7655 | CD1 | TYR | B | 112 | 31.666 | 32.726 | 70.427 | 1.00 | 9.60 |
| 7657 | CE1 | TYR | B | 112 | 32.898 | 32.095 | 70.335 | 1.00 | 10.32 |
| 7659 | CZ | TYR | B | 112 | 33.672 | 31.958 | 71.465 | 1.00 | 10.38 |
| 7660 | OH | TYR | B | 112 | 34.889 | 31.349 | 71.387 | 1.00 | 12.93 |
| 7662 | CE2 | TYR | B | 112 | 33.232 | 32.439 | 72.682 | 1.00 | 10.52 |
| 7664 | CD2 | TYR | B | 112 | 32.003 | 33.062 | 72.766 | 1.00 | 9.66 |

FIGURE 3 (Cont.)

| A | B | C | D | E | F | G | H | I | J |
|---|---|---|---|---|---|---|---|---|---|
| 7666 | C | TYR | B | 112 | 30.930 | 35.963 | 70.707 | 1.00 | 8.60 |
| 7667 | O | TYR | B | 112 | 32.141 | 35.782 | 70.783 | 1.00 | 8.62 |
| 7668 | N | GLY | B | 113 | 30.372 | 36.636 | 69.701 | 1.00 | 8.82 |
| 7670 | CA | GLY | B | 113 | 31.113 | 37.018 | 68.505 | 1.00 | 8.74 |
| 7673 | C | GLY | B | 113 | 32.401 | 37.811 | 68.684 | 1.00 | 8.96 |
| 7674 | O | GLY | B | 113 | 33.387 | 37.552 | 67.991 | 1.00 | 8.72 |
| 7675 | N | ALA | B | 114 | 32.398 | 38.796 | 69.577 | 1.00 | 8.93 |
| 7677 | CA | ALA | B | 114 | 33.611 | 39.585 | 69.832 | 1.00 | 8.87 |
| 7679 | CB | ALA | B | 114 | 33.285 | 40.851 | 70.598 | 1.00 | 8.96 |
| 7683 | C | ALA | B | 114 | 34.680 | 38.776 | 70.569 | 1.00 | 8.89 |
| 7684 | O | ALA | B | 114 | 35.869 | 38.987 | 70.352 | 1.00 | 8.80 |
| 7685 | N | THR | B | 115 | 34.256 | 37.862 | 71.441 | 1.00 | 8.83 |
| 7687 | CA | THR | B | 115 | 35.175 | 36.944 | 72.111 | 1.00 | 8.79 |
| 7689 | CB | THR | B | 115 | 34.432 | 36.058 | 73.133 | 1.00 | 8.81 |
| 7691 | OG1 | THR | B | 115 | 33.857 | 36.874 | 74.163 | 1.00 | 8.88 |
| 7693 | CG2 | THR | B | 115 | 35.407 | 35.143 | 73.879 | 1.00 | 8.57 |
| 7697 | C | THR | B | 115 | 35.907 | 36.059 | 71.108 | 1.00 | 8.94 |
| 7698 | O | THR | B | 115 | 37.111 | 35.855 | 71.232 | 1.00 | 9.11 |
| 7699 | N | ALA | B | 116 | 35.179 | 35.527 | 70.130 | 1.00 | 9.08 |
| 7701 | CA | ALA | B | 116 | 35.782 | 34.768 | 69.035 | 1.00 | 9.15 |
| 7703 | CB | ALA | B | 116 | 34.716 | 34.345 | 68.036 | 1.00 | 9.32 |
| 7707 | C | ALA | B | 116 | 36.852 | 35.610 | 68.343 | 1.00 | 9.11 |
| 7708 | O | ALA | B | 116 | 37.966 | 35.144 | 68.117 | 1.00 | 8.61 |
| 7709 | N | GLY | B | 117 | 36.500 | 36.854 | 68.024 | 1.00 | 9.01 |
| 7711 | CA | GLY | B | 117 | 37.431 | 37.818 | 67.464 | 1.00 | 9.22 |
| 7714 | C | GLY | B | 117 | 38.663 | 38.047 | 68.325 | 1.00 | 9.47 |
| 7715 | O | GLY | B | 117 | 39.777 | 38.102 | 67.809 | 1.00 | 9.25 |
| 7716 | N | LEU | B | 118 | 38.471 | 38.168 | 69.637 | 1.00 | 9.82 |
| 7718 | CA | LEU | B | 118 | 39.585 | 38.410 | 70.560 | 1.00 | 10.30 |
| 7720 | CB | LEU | B | 118 | 39.072 | 38.638 | 71.987 | 1.00 | 10.13 |
| 7723 | CG | LEU | B | 118 | 40.123 | 38.803 | 73.095 | 1.00 | 10.25 |
| 7725 | CD1 | LEU | B | 118 | 41.049 | 39.983 | 72.811 | 1.00 | 9.79 |
| 7729 | CD2 | LEU | B | 118 | 39.441 | 38.970 | 74.444 | 1.00 | 10.10 |
| 7733 | C | LEU | B | 118 | 40.586 | 37.249 | 70.544 | 1.00 | 10.80 |
| 7734 | O | LEU | B | 118 | 41.793 | 37.473 | 70.486 | 1.00 | 10.33 |
| 7735 | N | GLN | B | 119 | 40.078 | 36.019 | 70.581 | 1.00 | 11.80 |
| 7737 | CA | GLN | B | 119 | 40.937 | 34.833 | 70.635 | 1.00 | 12.63 |
| 7739 | CB | GLN | B | 119 | 40.147 | 33.564 | 70.998 | 1.00 | 12.89 |
| 7742 | CG | GLN | B | 119 | 39.185 | 33.659 | 72.193 | 1.00 | 14.42 |
| 7745 | CD | GLN | B | 119 | 39.807 | 34.168 | 73.483 | 1.00 | 16.62 |
| 7746 | OE1 | GLN | B | 119 | 40.944 | 34.635 | 73.503 | 1.00 | 19.22 |
| 7747 | NE2 | GLN | B | 119 | 39.054 | 34.067 | 74.574 | 1.00 | 18.23 |
| 7750 | C | GLN | B | 119 | 41.658 | 34.613 | 69.312 | 1.00 | 12.81 |
| 7751 | O | GLN | B | 119 | 42.818 | 34.213 | 69.298 | 1.00 | 13.12 |
| 7752 | N | LEU | B | 120 | 40.969 | 34.864 | 68.204 | 1.00 | 13.02 |
| 7754 | CA | LEU | B | 120 | 41.572 | 34.728 | 66.884 | 1.00 | 13.42 |
| 7756 | CB | LEU | B | 120 | 40.523 | 34.870 | 65.780 | 1.00 | 13.74 |
| 7759 | CG | LEU | B | 120 | 39.333 | 33.903 | 65.756 | 1.00 | 15.83 |
| 7761 | CD1 | LEU | B | 120 | 39.710 | 32.527 | 65.253 | 1.00 | 17.40 |
| 7765 | CD2 | LEU | B | 120 | 38.212 | 34.496 | 64.907 | 1.00 | 17.31 |
| 7769 | C | LEU | B | 120 | 42.639 | 35.804 | 66.703 | 1.00 | 12.90 |
| 7770 | O | LEU | B | 120 | 43.673 | 35.559 | 66.088 | 1.00 | 12.94 |

FIGURE 3 (Cont.)

| A | B | C | D | E | F | G | H | I | J |
|---|---|---|---|---|---|---|---|---|---|
| 7771 | N | ALA | B | 121 | 42.372 | 36.993 | 67.239 | 1.00 | 12.34 |
| 7773 | CA | ALA | B | 121 | 43.309 | 38.111 | 67.168 | 1.00 | 12.05 |
| 7775 | CB | ALA | B | 121 | 42.672 | 39.383 | 67.718 | 1.00 | 11.75 |
| 7779 | C | ALA | B | 121 | 44.574 | 37.770 | 67.945 | 1.00 | 12.04 |
| 7780 | O | ALA | B | 121 | 45.682 | 38.039 | 67.490 | 1.00 | 11.38 |
| 7781 | N | LYS | B | 122 | 44.389 | 37.159 | 69.111 | 1.00 | 12.10 |
| 7783 | CA | LYS | B | 122 | 45.493 | 36.725 | 69.959 | 1.00 | 12.49 |
| 7785 | CB | LYS | B | 122 | 44.941 | 36.030 | 71.215 | 1.00 | 12.72 |
| 7788 | CG | LYS | B | 122 | 45.986 | 35.456 | 72.165 | 1.00 | 14.03 |
| 7791 | CD | LYS | B | 122 | 45.341 | 34.606 | 73.267 | 1.00 | 15.97 |
| 7794 | CE | LYS | B | 122 | 44.654 | 33.353 | 72.721 | 1.00 | 17.50 |
| 7797 | NZ | LYS | B | 122 | 44.366 | 32.349 | 73.795 | 1.00 | 19.15 |
| 7801 | C | LYS | B | 122 | 46.434 | 35.794 | 69.191 | 1.00 | 12.39 |
| 7802 | O | LYS | B | 122 | 47.650 | 35.985 | 69.223 | 1.00 | 12.34 |
| 7803 | N | ASN | B | 123 | 45.872 | 34.805 | 68.497 | 1.00 | 12.25 |
| 7805 | CA | ASN | B | 123 | 46.668 | 33.841 | 67.732 | 1.00 | 12.44 |
| 7807 | CB | ASN | B | 123 | 45.787 | 32.725 | 67.150 | 1.00 | 12.60 |
| 7810 | CG | ASN | B | 123 | 45.086 | 31.887 | 68.205 | 1.00 | 13.06 |
| 7811 | OD1 | ASN | B | 123 | 44.120 | 31.198 | 67.894 | 1.00 | 14.34 |
| 7812 | ND2 | ASN | B | 123 | 45.565 | 31.932 | 69.442 | 1.00 | 13.08 |
| 7815 | C | ASN | B | 123 | 47.417 | 34.506 | 66.572 | 1.00 | 12.48 |
| 7816 | O | ASN | B | 123 | 48.557 | 34.140 | 66.264 | 1.00 | 12.27 |
| 7817 | N | HIS | B | 124 | 46.758 | 35.471 | 65.928 | 1.00 | 12.26 |
| 7819 | CA | HIS | B | 124 | 47.327 | 36.198 | 64.804 | 1.00 | 12.30 |
| 7821 | CB | HIS | B | 124 | 46.276 | 37.135 | 64.170 | 1.00 | 12.36 |
| 7824 | CG | HIS | B | 124 | 46.834 | 38.055 | 63.126 | 1.00 | 12.26 |
| 7825 | ND1 | HIS | B | 124 | 47.222 | 37.619 | 61.878 | 1.00 | 12.36 |
| 7827 | CE1 | HIS | B | 124 | 47.682 | 38.641 | 61.179 | 1.00 | 12.09 |
| 7829 | NE2 | HIS | B | 124 | 47.595 | 39.728 | 61.925 | 1.00 | 12.22 |
| 7831 | CD2 | HIS | B | 124 | 47.071 | 39.388 | 63.148 | 1.00 | 12.11 |
| 7833 | C | HIS | B | 124 | 48.558 | 36.984 | 65.258 | 1.00 | 12.58 |
| 7834 | O | HIS | B | 124 | 49.609 | 36.919 | 64.616 | 1.00 | 12.12 |
| 7835 | N | VAL | B | 125 | 48.431 | 37.701 | 66.375 | 1.00 | 12.77 |
| 7837 | CA | VAL | B | 125 | 49.540 | 38.490 | 66.912 | 1.00 | 13.43 |
| 7839 | CB | VAL | B | 125 | 49.072 | 39.485 | 68.005 | 1.00 | 13.44 |
| 7841 | CG1 | VAL | B | 125 | 50.270 | 40.245 | 68.598 | 1.00 | 13.41 |
| 7845 | CG2 | VAL | B | 125 | 48.049 | 40.479 | 67.435 | 1.00 | 12.56 |
| 7849 | C | VAL | B | 125 | 50.664 | 37.585 | 67.447 | 1.00 | 14.14 |
| 7850 | O | VAL | B | 125 | 51.837 | 37.950 | 67.389 | 1.00 | 14.26 |
| 7851 | N | ALA | B | 126 | 50.313 | 36.400 | 67.937 | 1.00 | 14.90 |
| 7853 | CA | ALA | B | 126 | 51.312 | 35.424 | 68.381 | 1.00 | 15.70 |
| 7855 | CB | ALA | B | 126 | 50.633 | 34.190 | 68.985 | 1.00 | 15.74 |
| 7859 | C | ALA | B | 126 | 52.245 | 35.009 | 67.247 | 1.00 | 16.23 |
| 7860 | O | ALA | B | 126 | 53.449 | 34.860 | 67.455 | 1.00 | 16.73 |
| 7861 | N | LEU | B | 127 | 51.685 | 34.839 | 66.052 | 1.00 | 16.80 |
| 7863 | CA | LEU | B | 127 | 52.455 | 34.424 | 64.880 | 1.00 | 17.31 |
| 7865 | CB | LEU | B | 127 | 51.575 | 33.608 | 63.918 | 1.00 | 17.53 |
| 7868 | CG | LEU | B | 127 | 51.382 | 32.088 | 64.114 | 1.00 | 18.75 |
| 7870 | CD1 | LEU | B | 127 | 52.421 | 31.431 | 65.039 | 1.00 | 19.77 |
| 7874 | CD2 | LEU | B | 127 | 49.984 | 31.765 | 64.603 | 1.00 | 19.36 |
| 7878 | C | LEU | B | 127 | 53.066 | 35.620 | 64.138 | 1.00 | 17.22 |
| 7879 | O | LEU | B | 127 | 53.945 | 35.439 | 63.299 | 1.00 | 17.45 |

FIGURE 3 (Cont.)

| A | B | C | D | E | F | G | H | I | J |
|---|---|---|---|---|---|---|---|---|---|
| 7880 | N | HIS | B | 128 | 52.589 | 36.829 | 64.441 | 1.00 | 17.01 |
| 7882 | CA | HIS | B | 128 | 53.073 | 38.065 | 63.820 | 1.00 | 16.68 |
| 7884 | CB | HIS | B | 128 | 52.142 | 38.500 | 62.677 | 1.00 | 16.85 |
| 7887 | CG | HIS | B | 128 | 51.862 | 37.431 | 61.663 | 1.00 | 17.36 |
| 7888 | ND1 | HIS | B | 128 | 52.743 | 37.113 | 60.651 | 1.00 | 17.93 |
| 7890 | CE1 | HIS | B | 128 | 52.230 | 36.146 | 59.912 | 1.00 | 18.58 |
| 7892 | NE2 | HIS | B | 128 | 51.044 | 35.831 | 60.402 | 1.00 | 17.74 |
| 7894 | CD2 | HIS | B | 128 | 50.789 | 36.622 | 61.495 | 1.00 | 17.62 |
| 7896 | C | HIS | B | 128 | 53.128 | 39.170 | 64.886 | 1.00 | 16.40 |
| 7897 | O | HIS | B | 128 | 52.307 | 40.085 | 64.874 | 1.00 | 16.07 |
| 7898 | N | PRO | B | 129 | 54.086 | 39.085 | 65.811 | 1.00 | 16.20 |
| 7899 | CA | PRO | B | 129 | 54.069 | 39.916 | 67.025 | 1.00 | 16.09 |
| 7901 | CB | PRO | B | 129 | 55.163 | 39.286 | 67.900 | 1.00 | 16.24 |
| 7904 | CG | PRO | B | 129 | 56.065 | 38.589 | 66.961 | 1.00 | 16.45 |
| 7907 | CD | PRO | B | 129 | 55.254 | 38.190 | 65.770 | 1.00 | 16.35 |
| 7910 | C | PRO | B | 129 | 54.306 | 41.416 | 66.827 | 1.00 | 15.87 |
| 7911 | O | PRO | B | 129 | 54.107 | 42.168 | 67.782 | 1.00 | 15.87 |
| 7912 | N | ASP | B | 130 | 54.710 | 41.841 | 65.633 | 1.00 | 15.34 |
| 7914 | CA | ASP | B | 130 | 54.811 | 43.270 | 65.313 | 1.00 | 15.42 |
| 7916 | CB | ASP | B | 130 | 55.965 | 43.526 | 64.326 | 1.00 | 15.88 |
| 7919 | CG | ASP | B | 130 | 55.772 | 42.831 | 62.980 | 1.00 | 17.58 |
| 7920 | OD1 | ASP | B | 130 | 56.308 | 43.341 | 61.969 | 1.00 | 20.91 |
| 7921 | OD2 | ASP | B | 130 | 55.125 | 41.769 | 62.833 | 1.00 | 20.55 |
| 7922 | C | ASP | B | 130 | 53.495 | 43.884 | 64.781 | 1.00 | 14.64 |
| 7923 | O | ASP | B | 130 | 53.411 | 45.093 | 64.564 | 1.00 | 14.32 |
| 7924 | N | LYS | B | 131 | 52.477 | 43.054 | 64.580 | 1.00 | 13.73 |
| 7926 | CA | LYS | B | 131 | 51.191 | 43.511 | 64.066 | 1.00 | 13.21 |
| 7928 | CB | LYS | B | 131 | 50.695 | 42.564 | 62.968 | 1.00 | 13.53 |
| 7931 | CG | LYS | B | 131 | 51.658 | 42.392 | 61.795 | 1.00 | 14.63 |
| 7934 | CD | LYS | B | 131 | 51.913 | 43.713 | 61.079 | 1.00 | 16.47 |
| 7937 | CE | LYS | B | 131 | 52.663 | 43.516 | 59.780 | 1.00 | 18.03 |
| 7940 | NZ | LYS | B | 131 | 52.937 | 44.831 | 59.113 | 1.00 | 19.37 |
| 7944 | C | LYS | B | 131 | 50.147 | 43.615 | 65.178 | 1.00 | 12.34 |
| 7945 | O | LYS | B | 131 | 50.301 | 43.031 | 66.256 | 1.00 | 11.80 |
| 7946 | N | LYS | B | 132 | 49.083 | 44.361 | 64.895 | 1.00 | 11.49 |
| 7948 | CA | LYS | B | 132 | 47.995 | 44.579 | 65.842 | 1.00 | 11.10 |
| 7950 | CB | LYS | B | 132 | 48.015 | 46.020 | 66.363 | 1.00 | 10.95 |
| 7953 | CG | LYS | B | 132 | 49.374 | 46.483 | 66.884 | 1.00 | 11.28 |
| 7956 | CD | LYS | B | 132 | 49.303 | 47.891 | 67.471 | 1.00 | 11.09 |
| 7959 | CE | LYS | B | 132 | 50.689 | 48.501 | 67.651 | 1.00 | 11.33 |
| 7962 | NZ | LYS | B | 132 | 50.657 | 49.803 | 68.384 | 1.00 | 11.67 |
| 7966 | C | LYS | B | 132 | 46.645 | 44.283 | 65.188 | 1.00 | 10.70 |
| 7967 | O | LYS | B | 132 | 46.523 | 44.266 | 63.965 | 1.00 | 10.35 |
| 7968 | N | VAL | B | 133 | 45.637 | 44.041 | 66.018 | 1.00 | 10.17 |
| 7970 | CA | VAL | B | 133 | 44.296 | 43.746 | 65.542 | 1.00 | 9.79 |
| 7972 | CB | VAL | B | 133 | 43.926 | 42.269 | 65.786 | 1.00 | 9.67 |
| 7974 | CG1 | VAL | B | 133 | 42.547 | 41.952 | 65.215 | 1.00 | 9.58 |
| 7978 | CG2 | VAL | B | 133 | 44.976 | 41.351 | 65.183 | 1.00 | 9.63 |
| 7982 | C | VAL | B | 133 | 43.290 | 44.621 | 66.269 | 1.00 | 9.60 |
| 7983 | O | VAL | B | 133 | 43.346 | 44.757 | 67.487 | 1.00 | 9.85 |
| 7984 | N | LEU | B | 134 | 42.376 | 45.221 | 65.515 | 1.00 | 9.11 |
| 7986 | CA | LEU | B | 134 | 41.251 | 45.934 | 66.099 | 1.00 | 8.74 |

FIGURE 3 (Cont.)

| A | B | C | D | E | F | G | H | I | J |
|---|---|---|---|---|---|---|---|---|---|
| 7988 | CB | LEU | B | 134 | 40.865 | 47.133 | 65.232 | 1.00 | 8.86 |
| 7991 | CG | LEU | B | 134 | 39.605 | 47.893 | 65.655 | 1.00 | 8.70 |
| 7993 | CD1 | LEU | B | 134 | 39.760 | 48.449 | 67.060 | 1.00 | 9.48 |
| 7997 | CD2 | LEU | B | 134 | 39.303 | 48.999 | 64.662 | 1.00 | 9.46 |
| 8001 | C | LEU | B | 134 | 40.078 | 44.968 | 66.200 | 1.00 | 8.50 |
| 8002 | O | LEU | B | 134 | 39.638 | 44.430 | 65.193 | 1.00 | 8.27 |
| 8003 | N | VAL | B | 135 | 39.595 | 44.738 | 67.416 | 1.00 | 8.22 |
| 8005 | CA | VAL | B | 135 | 38.417 | 43.911 | 67.652 | 1.00 | 8.36 |
| 8007 | CB | VAL | B | 135 | 38.745 | 42.703 | 68.551 | 1.00 | 8.37 |
| 8009 | CG1 | VAL | B | 135 | 37.491 | 41.861 | 68.818 | 1.00 | 8.54 |
| 8013 | CG2 | VAL | B | 135 | 39.856 | 41.860 | 67.927 | 1.00 | 8.48 |
| 8017 | C | VAL | B | 135 | 37.359 | 44.772 | 68.329 | 1.00 | 8.17 |
| 8018 | O | VAL | B | 135 | 37.590 | 45.297 | 69.410 | 1.00 | 8.27 |
| 8019 | N | VAL | B | 136 | 36.198 | 44.905 | 67.695 | 1.00 | 8.09 |
| 8021 | CA | VAL | B | 136 | 35.125 | 45.731 | 68.222 | 1.00 | 7.93 |
| 8023 | CB | VAL | B | 136 | 34.880 | 46.973 | 67.334 | 1.00 | 7.88 |
| 8025 | CG1 | VAL | B | 136 | 33.836 | 47.879 | 67.967 | 1.00 | 8.08 |
| 8029 | CG2 | VAL | B | 136 | 36.183 | 47.739 | 67.114 | 1.00 | 7.70 |
| 8033 | C | VAL | B | 136 | 33.827 | 44.943 | 68.360 | 1.00 | 7.83 |
| 8034 | O | VAL | B | 136 | 33.331 | 44.371 | 67.393 | 1.00 | 7.80 |
| 8035 | N | ALA | B | 137 | 33.319 | 44.890 | 69.588 | 1.00 | 7.75 |
| 8037 | CA | ALA | B | 137 | 31.964 | 44.458 | 69.882 | 1.00 | 7.86 |
| 8039 | CB | ALA | B | 137 | 31.871 | 44.001 | 71.325 | 1.00 | 7.93 |
| 8043 | C | ALA | B | 137 | 31.038 | 45.649 | 69.654 | 1.00 | 7.97 |
| 8044 | O | ALA | B | 137 | 31.302 | 46.732 | 70.153 | 1.00 | 8.11 |
| 8045 | N | ALA | B | 138 | 29.968 | 45.449 | 68.895 | 1.00 | 7.73 |
| 8047 | CA | ALA | B | 138 | 29.015 | 46.515 | 68.598 | 1.00 | 7.67 |
| 8049 | CB | ALA | B | 138 | 29.446 | 47.285 | 67.359 | 1.00 | 7.78 |
| 8053 | C | ALA | B | 138 | 27.634 | 45.916 | 68.400 | 1.00 | 7.68 |
| 8054 | O | ALA | B | 138 | 27.470 | 44.967 | 67.641 | 1.00 | 7.88 |
| 8055 | N | ASP | B | 139 | 26.641 | 46.461 | 69.095 | 1.00 | 7.64 |
| 8057 | CA | ASP | B | 139 | 25.299 | 45.890 | 69.068 | 1.00 | 7.54 |
| 8059 | CB | ASP | B | 139 | 25.247 | 44.597 | 69.896 | 1.00 | 7.44 |
| 8062 | CG | ASP | B | 139 | 25.578 | 43.352 | 69.082 | 1.00 | 7.51 |
| 8063 | OD1 | ASP | B | 139 | 24.936 | 43.119 | 68.031 | 1.00 | 6.08 |
| 8064 | OD2 | ASP | B | 139 | 26.468 | 42.547 | 69.423 | 1.00 | 6.25 |
| 8065 | C | ASP | B | 139 | 24.253 | 46.860 | 69.600 | 1.00 | 7.50 |
| 8066 | O | ASP | B | 139 | 24.557 | 47.804 | 70.332 | 1.00 | 7.14 |
| 8067 | N | ILE | B | 140 | 23.015 | 46.606 | 69.200 | 1.00 | 7.60 |
| 8069 | CA | ILE | B | 140 | 21.848 | 47.328 | 69.680 | 1.00 | 7.83 |
| 8071 | CB | ILE | B | 140 | 21.235 | 48.168 | 68.543 | 1.00 | 7.89 |
| 8073 | CG1 | ILE | B | 140 | 22.179 | 49.309 | 68.155 | 1.00 | 8.01 |
| 8076 | CD1 | ILE | B | 140 | 22.021 | 49.766 | 66.722 | 1.00 | 8.36 |
| 8080 | CG2 | ILE | B | 140 | 19.875 | 48.735 | 68.950 | 1.00 | 8.22 |
| 8084 | C | ILE | B | 140 | 20.871 | 46.260 | 70.153 | 1.00 | 7.95 |
| 8085 | O | ILE | B | 140 | 20.359 | 45.483 | 69.346 | 1.00 | 7.95 |
| 8086 | N | ALA | B | 141 | 20.653 | 46.196 | 71.462 | 1.00 | 8.00 |
| 8088 | CA | ALA | B | 141 | 19.764 | 45.194 | 72.057 | 1.00 | 8.17 |
| 8090 | CB | ALA | B | 141 | 20.332 | 44.703 | 73.381 | 1.00 | 8.32 |
| 8094 | C | ALA | B | 141 | 18.356 | 45.745 | 72.254 | 1.00 | 8.33 |
| 8095 | O | ALA | B | 141 | 18.084 | 46.445 | 73.236 | 1.00 | 8.23 |
| 8096 | N | LYS | B | 142 | 17.478 | 45.433 | 71.301 | 1.00 | 8.58 |

FIGURE 3 (Cont.)

| A | B | C | D | E | F | G | H | I | J |
|---|---|---|---|---|---|---|---|---|---|
| 8098 | CA | LYS | B | 142 | 16.060 | 45.803 | 71.352 | 1.00 | 8.81 |
| 8100 | CB | LYS | B | 142 | 15.728 | 46.766 | 70.206 | 1.00 | 8.77 |
| 8103 | CG | LYS | B | 142 | 16.444 | 48.102 | 70.284 | 1.00 | 8.96 |
| 8106 | CD | LYS | B | 142 | 16.297 | 48.917 | 68.995 | 1.00 | 9.53 |
| 8109 | CE | LYS | B | 142 | 14.880 | 49.443 | 68.792 | 1.00 | 9.66 |
| 8112 | NZ | LYS | B | 142 | 14.829 | 50.591 | 67.824 | 1.00 | 9.14 |
| 8116 | C | LYS | B | 142 | 15.185 | 44.554 | 71.243 | 1.00 | 8.84 |
| 8117 | O | LYS | B | 142 | 15.345 | 43.766 | 70.317 | 1.00 | 8.63 |
| 8118 | N | TYR | B | 143 | 14.276 | 44.383 | 72.204 | 1.00 | 9.18 |
| 8120 | CA | TYR | B | 143 | 13.365 | 43.237 | 72.270 | 1.00 | 9.43 |
| 8122 | CB | TYR | B | 143 | 13.354 | 42.659 | 73.688 | 1.00 | 9.55 |
| 8125 | CG | TYR | B | 143 | 14.573 | 41.839 | 74.047 | 1.00 | 9.30 |
| 8126 | CD1 | TYR | B | 143 | 15.687 | 42.433 | 74.639 | 1.00 | 9.59 |
| 8128 | CE1 | TYR | B | 143 | 16.808 | 41.681 | 74.980 | 1.00 | 9.01 |
| 8130 | CZ | TYR | B | 143 | 16.819 | 40.318 | 74.734 | 1.00 | 8.66 |
| 8131 | OH | TYR | B | 143 | 17.925 | 39.573 | 75.073 | 1.00 | 8.51 |
| 8133 | CE2 | TYR | B | 143 | 15.726 | 39.704 | 74.153 | 1.00 | 8.87 |
| 8135 | CD2 | TYR | B | 143 | 14.608 | 40.466 | 73.812 | 1.00 | 8.96 |
| 8137 | C | TYR | B | 143 | 11.931 | 43.600 | 71.884 | 1.00 | 9.83 |
| 8138 | O | TYR | B | 143 | 11.194 | 42.758 | 71.365 | 1.00 | 10.11 |
| 8139 | N | GLY | B | 144 | 11.532 | 44.839 | 72.170 | 1.00 | 10.33 |
| 8141 | CA | GLY | B | 144 | 10.205 | 45.333 | 71.843 | 1.00 | 10.47 |
| 8144 | C | GLY | B | 144 | 9.529 | 45.982 | 73.036 | 1.00 | 10.78 |
| 8145 | O | GLY | B | 144 | 9.742 | 45.570 | 74.172 | 1.00 | 10.58 |
| 8146 | N | LEU | B | 145 | 8.724 | 47.007 | 72.774 | 1.00 | 11.32 |
| 8148 | CA | LEU | B | 145 | 7.933 | 47.661 | 73.811 | 1.00 | 11.74 |
| 8150 | CB | LEU | B | 145 | 7.177 | 48.865 | 73.238 | 1.00 | 11.94 |
| 8153 | CG | LEU | B | 145 | 8.017 | 49.960 | 72.572 | 1.00 | 12.14 |
| 8155 | CD1 | LEU | B | 145 | 7.117 | 51.050 | 72.011 | 1.00 | 12.72 |
| 8159 | CD2 | LEU | B | 145 | 9.033 | 50.538 | 73.542 | 1.00 | 12.06 |
| 8163 | C | LEU | B | 145 | 6.941 | 46.652 | 74.389 | 1.00 | 12.01 |
| 8164 | O | LEU | B | 145 | 6.276 | 45.946 | 73.637 | 1.00 | 11.59 |
| 8165 | N | ASN | B | 146 | 6.863 | 46.595 | 75.721 | 1.00 | 12.51 |
| 8167 | CA | ASN | B | 146 | 6.017 | 45.636 | 76.452 | 1.00 | 12.94 |
| 8169 | CB | ASN | B | 146 | 4.542 | 45.831 | 76.082 | 1.00 | 13.33 |
| 8172 | CG | ASN | B | 146 | 4.098 | 47.264 | 76.252 | 1.00 | 14.31 |
| 8173 | OD1 | ASN | B | 146 | 3.888 | 47.987 | 75.276 | 1.00 | 16.27 |
| 8174 | ND2 | ASN | B | 146 | 3.983 | 47.693 | 77.499 | 1.00 | 16.21 |
| 8177 | C | ASN | B | 146 | 6.411 | 44.160 | 76.318 | 1.00 | 13.06 |
| 8178 | O | ASN | B | 146 | 5.645 | 43.274 | 76.699 | 1.00 | 13.05 |
| 8179 | N | SER | B | 147 | 7.616 | 43.900 | 75.811 | 1.00 | 13.04 |
| 8181 | CA | SER | B | 147 | 8.113 | 42.533 | 75.659 | 1.00 | 12.90 |
| 8183 | CB | SER | B | 147 | 9.121 | 42.455 | 74.509 | 1.00 | 12.89 |
| 8186 | OG | SER | B | 147 | 10.333 | 43.115 | 74.850 | 1.00 | 12.61 |
| 8188 | C | SER | B | 147 | 8.771 | 42.071 | 76.951 | 1.00 | 12.53 |
| 8189 | O | SER | B | 147 | 9.125 | 42.885 | 77.800 | 1.00 | 12.93 |
| 8190 | N | GLY | B | 148 | 8.943 | 40.760 | 77.090 | 1.00 | 12.38 |
| 8192 | CA | GLY | B | 148 | 9.605 | 40.188 | 78.249 | 1.00 | 11.89 |
| 8195 | C | GLY | B | 148 | 11.045 | 40.655 | 78.391 | 1.00 | 11.37 |
| 8196 | O | GLY | B | 148 | 11.514 | 40.909 | 79.501 | 1.00 | 11.34 |
| 8197 | N | GLY | B | 149 | 11.740 | 40.789 | 77.265 | 1.00 | 10.90 |
| 8199 | CA | GLY | B | 149 | 13.153 | 41.135 | 77.266 | 1.00 | 10.49 |

FIGURE 3 (Cont.)

| A | B | C | D | E | F | G | H | I | J |
|---|---|---|---|---|---|---|---|---|---|
| 8202 | C | GLY | B | 149 | 13.443 | 42.623 | 77.388 | 1.00 | 10.06 |
| 8203 | O | GLY | B | 149 | 14.593 | 43.007 | 77.601 | 1.00 | 9.72 |
| 8204 | N | GLU | B | 150 | 12.407 | 43.454 | 77.263 | 1.00 | 9.69 |
| 8206 | CA | GLU | B | 150 | 12.567 | 44.918 | 77.223 | 1.00 | 9.53 |
| 8208 | CB | GLU | B | 150 | 11.204 | 45.622 | 77.183 | 1.00 | 9.34 |
| 8211 | CG | GLU | B | 150 | 11.290 | 47.087 | 76.783 | 1.00 | 9.48 |
| 8214 | CD | GLU | B | 150 | 10.016 | 47.863 | 77.052 | 1.00 | 10.62 |
| 8215 | OE1 | GLU | B | 150 | 9.052 | 47.279 | 77.590 | 1.00 | 10.58 |
| 8216 | OE2 | GLU | B | 150 | 9.986 | 49.064 | 76.724 | 1.00 | 9.89 |
| 8217 | C | GLU | B | 150 | 13.413 | 45.532 | 78.347 | 1.00 | 9.25 |
| 8218 | O | GLU | B | 150 | 14.248 | 46.391 | 78.066 | 1.00 | 9.16 |
| 8219 | N | PRO | B | 151 | 13.194 | 45.131 | 79.605 | 1.00 | 9.25 |
| 8220 | CA | PRO | B | 151 | 13.958 | 45.693 | 80.730 | 1.00 | 9.23 |
| 8222 | CB | PRO | B | 151 | 13.405 | 44.937 | 81.942 | 1.00 | 9.45 |
| 8225 | CG | PRO | B | 151 | 12.075 | 44.446 | 81.513 | 1.00 | 9.61 |
| 8228 | CD | PRO | B | 151 | 12.211 | 44.135 | 80.066 | 1.00 | 8.94 |
| 8231 | C | PRO | B | 151 | 15.477 | 45.493 | 80.649 | 1.00 | 9.19 |
| 8232 | O | PRO | B | 151 | 16.214 | 46.273 | 81.261 | 1.00 | 9.22 |
| 8233 | N | THR | B | 152 | 15.921 | 44.468 | 79.921 | 1.00 | 8.82 |
| 8235 | CA | THR | B | 152 | 17.344 | 44.152 | 79.785 | 1.00 | 8.61 |
| 8237 | CB | THR | B | 152 | 17.555 | 42.621 | 79.694 | 1.00 | 8.63 |
| 8239 | OG1 | THR | B | 152 | 17.028 | 42.128 | 78.453 | 1.00 | 8.95 |
| 8241 | CG2 | THR | B | 152 | 16.763 | 41.886 | 80.764 | 1.00 | 8.67 |
| 8245 | C | THR | B | 152 | 17.997 | 44.796 | 78.567 | 1.00 | 8.36 |
| 8246 | O | THR | B | 152 | 19.147 | 44.491 | 78.257 | 1.00 | 8.40 |
| 8247 | N | GLN | B | 153 | 17.276 | 45.681 | 77.883 | 1.00 | 7.85 |
| 8249 | CA | GLN | B | 153 | 17.777 | 46.322 | 76.666 | 1.00 | 7.65 |
| 8251 | CB | GLN | B | 153 | 16.664 | 47.139 | 75.993 | 1.00 | 7.68 |
| 8254 | CG | GLN | B | 153 | 15.611 | 46.288 | 75.283 | 1.00 | 7.72 |
| 8257 | CD | GLN | B | 153 | 14.399 | 47.081 | 74.788 | 1.00 | 7.97 |
| 8258 | OE1 | GLN | B | 153 | 13.551 | 46.527 | 74.101 | 1.00 | 9.28 |
| 8259 | NE2 | GLN | B | 153 | 14.316 | 48.364 | 75.134 | 1.00 | 8.06 |
| 8262 | C | GLN | B | 153 | 18.986 | 47.222 | 76.931 | 1.00 | 7.38 |
| 8263 | O | GLN | B | 153 | 19.236 | 47.641 | 78.055 | 1.00 | 7.46 |
| 8264 | N | GLY | B | 154 | 19.726 | 47.507 | 75.869 | 1.00 | 7.38 |
| 8266 | CA | GLY | B | 154 | 20.889 | 48.375 | 75.923 | 1.00 | 7.46 |
| 8269 | C | GLY | B | 154 | 21.444 | 48.585 | 74.529 | 1.00 | 7.64 |
| 8270 | O | GLY | B | 154 | 20.883 | 48.087 | 73.566 | 1.00 | 7.33 |
| 8271 | N | ALA | B | 155 | 22.549 | 49.316 | 74.427 | 1.00 | 7.89 |
| 8273 | CA | ALA | B | 155 | 23.181 | 49.601 | 73.140 | 1.00 | 7.90 |
| 8275 | CB | ALA | B | 155 | 22.317 | 50.560 | 72.322 | 1.00 | 8.10 |
| 8279 | C | ALA | B | 155 | 24.570 | 50.204 | 73.343 | 1.00 | 7.98 |
| 8280 | O | ALA | B | 155 | 24.806 | 50.918 | 74.317 | 1.00 | 8.15 |
| 8281 | N | GLY | B | 156 | 25.481 | 49.917 | 72.416 | 1.00 | 7.63 |
| 8283 | CA | GLY | B | 156 | 26.831 | 50.447 | 72.481 | 1.00 | 7.64 |
| 8286 | C | GLY | B | 156 | 27.875 | 49.576 | 71.811 | 1.00 | 7.52 |
| 8287 | O | GLY | B | 156 | 27.554 | 48.639 | 71.086 | 1.00 | 7.33 |
| 8288 | N | ALA | B | 157 | 29.138 | 49.907 | 72.062 | 1.00 | 7.42 |
| 8290 | CA | ALA | B | 157 | 30.268 | 49.175 | 71.507 | 1.00 | 7.45 |
| 8292 | CB | ALA | B | 157 | 30.686 | 49.783 | 70.163 | 1.00 | 7.48 |
| 8296 | C | ALA | B | 157 | 31.449 | 49.174 | 72.475 | 1.00 | 7.41 |
| 8297 | O | ALA | B | 157 | 31.610 | 50.089 | 73.273 | 1.00 | 7.56 |

FIGURE 3 (Cont.)

| A | B | C | D | E | F | G | H | I | J |
|---|---|---|---|---|---|---|---|---|---|
| 8298 | N | VAL | B | 158 | 32.252 | 48.123 | 72.414 | 1.00 | 7.38 |
| 8300 | CA | VAL | B | 158 | 33.511 | 48.054 | 73.139 | 1.00 | 7.44 |
| 8302 | CB | VAL | B | 158 | 33.476 | 46.939 | 74.204 | 1.00 | 7.44 |
| 8304 | CG1 | VAL | B | 158 | 34.813 | 46.818 | 74.919 | 1.00 | 7.73 |
| 8308 | CG2 | VAL | B | 158 | 32.357 | 47.203 | 75.207 | 1.00 | 7.87 |
| 8312 | C | VAL | B | 158 | 34.615 | 47.787 | 72.118 | 1.00 | 7.43 |
| 8313 | O | VAL | B | 158 | 34.581 | 46.776 | 71.420 | 1.00 | 7.72 |
| 8314 | N | ALA | B | 159 | 35.576 | 48.701 | 72.023 | 1.00 | 7.54 |
| 8316 | CA | ALA | B | 159 | 36.707 | 48.559 | 71.112 | 1.00 | 7.67 |
| 8318 | CB | ALA | B | 159 | 36.985 | 49.877 | 70.416 | 1.00 | 7.65 |
| 8322 | C | ALA | B | 159 | 37.949 | 48.082 | 71.860 | 1.00 | 7.94 |
| 8323 | O | ALA | B | 159 | 38.237 | 48.548 | 72.961 | 1.00 | 7.80 |
| 8324 | N | MSE | B | 160 | 38.689 | 47.163 | 71.245 | 1.00 | 8.28 |
| 8326 | CA | MSE | B | 160 | 39.903 | 46.602 | 71.838 | 1.00 | 8.72 |
| 8328 | CB | MSE | B | 160 | 39.640 | 45.185 | 72.359 | 1.00 | 8.94 |
| 8331 | CG | MSE | B | 160 | 38.753 | 45.121 | 73.593 | 1.00 | 10.14 |
| 8334 | SE | MSE | B | 160 | 38.329 | 43.270 | 74.135 | 1.00 | 11.99 |
| 8335 | CE | MSE | B | 160 | 36.877 | 42.945 | 72.912 | 1.00 | 11.36 |
| 8339 | C | MSE | B | 160 | 41.023 | 46.559 | 70.811 | 1.00 | 8.80 |
| 8340 | O | MSE | B | 160 | 40.801 | 46.196 | 69.658 | 1.00 | 8.95 |
| 8341 | N | LEU | B | 161 | 42.225 | 46.932 | 71.230 | 1.00 | 8.66 |
| 8343 | CA | LEU | B | 161 | 43.415 | 46.767 | 70.414 | 1.00 | 8.46 |
| 8345 | CB | LEU | B | 161 | 44.276 | 48.033 | 70.436 | 1.00 | 8.45 |
| 8348 | CG | LEU | B | 161 | 45.492 | 48.027 | 69.504 | 1.00 | 8.58 |
| 8350 | CD1 | LEU | B | 161 | 45.073 | 48.003 | 68.032 | 1.00 | 8.89 |
| 8354 | CD2 | LEU | B | 161 | 46.386 | 49.231 | 69.791 | 1.00 | 8.77 |
| 8358 | C | LEU | B | 161 | 44.192 | 45.591 | 70.980 | 1.00 | 8.40 |
| 8359 | O | LEU | B | 161 | 44.561 | 45.598 | 72.152 | 1.00 | 8.28 |
| 8360 | N | VAL | B | 162 | 44.422 | 44.585 | 70.144 | 1.00 | 8.18 |
| 8362 | CA | VAL | B | 162 | 45.144 | 43.384 | 70.537 | 1.00 | 8.30 |
| 8364 | CB | VAL | B | 162 | 44.472 | 42.113 | 69.978 | 1.00 | 8.27 |
| 8366 | CG1 | VAL | B | 162 | 45.188 | 40.860 | 70.475 | 1.00 | 8.59 |
| 8370 | CG2 | VAL | B | 162 | 42.990 | 42.076 | 70.363 | 1.00 | 8.38 |
| 8374 | C | VAL | B | 162 | 46.559 | 43.511 | 69.994 | 1.00 | 8.38 |
| 8375 | O | VAL | B | 162 | 46.750 | 43.809 | 68.819 | 1.00 | 7.75 |
| 8376 | N | ALA | B | 163 | 47.544 | 43.302 | 70.861 | 1.00 | 8.59 |
| 8378 | CA | ALA | B | 163 | 48.946 | 43.478 | 70.502 | 1.00 | 8.99 |
| 8380 | CB | ALA | B | 163 | 49.297 | 44.958 | 70.504 | 1.00 | 9.16 |
| 8384 | C | ALA | B | 163 | 49.865 | 42.718 | 71.452 | 1.00 | 9.45 |
| 8385 | O | ALA | B | 163 | 49.431 | 42.246 | 72.505 | 1.00 | 9.76 |
| 8386 | N | SER | B | 164 | 51.131 | 42.594 | 71.064 | 1.00 | 9.94 |
| 8388 | CA | SER | B | 164 | 52.172 | 42.063 | 71.943 | 1.00 | 10.28 |
| 8390 | CB | CSER | B | 164 | 53.437 | 41.709 | 71.150 | 0.35 | 10.32 |
| 8391 | CB | BSER | B | 164 | 53.450 | 41.741 | 71.159 | 0.65 | 10.38 |
| 8396 | OG | CSER | B | 164 | 53.903 | 42.811 | 70.387 | 0.35 | 9.93 |
| 8397 | OG | BSER | B | 164 | 53.186 | 40.902 | 70.050 | 0.65 | 10.21 |
| 8400 | C | SER | B | 164 | 52.493 | 43.082 | 73.030 | 1.00 | 10.76 |
| 8401 | O | SER | B | 164 | 52.307 | 44.287 | 72.836 | 1.00 | 10.77 |
| 8402 | N | GLU | B | 165 | 52.999 | 42.585 | 74.160 | 1.00 | 11.20 |
| 8404 | CA | GLU | B | 165 | 53.299 | 43.405 | 75.329 | 1.00 | 11.54 |
| 8406 | CB | GLU | B | 165 | 54.626 | 44.150 | 75.115 | 1.00 | 12.16 |
| 8409 | CG | GLU | B | 165 | 55.805 | 43.232 | 74.796 | 1.00 | 13.93 |

FIGURE 3 (Cont.)

| A | B | C | D | E | F | G | H | I | J |
|---|---|---|---|---|---|---|---|---|---|
| 8412 | CD | GLU | B | 165 | 55.915 | 42.063 | 75.765 | 1.00 | 17.09 |
| 8413 | OE1 | GLU | B | 165 | 55.936 | 42.317 | 76.992 | 1.00 | 19.30 |
| 8414 | OE2 | GLU | B | 165 | 55.953 | 40.894 | 75.308 | 1.00 | 18.56 |
| 8415 | C | GLU | B | 165 | 52.153 | 44.369 | 75.657 | 1.00 | 11.24 |
| 8416 | O | GLU | B | 165 | 52.359 | 45.583 | 75.776 | 1.00 | 10.79 |
| 8417 | N | PRO | B | 166 | 50.947 | 43.822 | 75.831 | 1.00 | 10.89 |
| 8418 | CA | PRO | B | 166 | 49.754 | 44.651 | 76.021 | 1.00 | 10.95 |
| 8420 | CB | PRO | B | 166 | 48.621 | 43.625 | 76.077 | 1.00 | 10.82 |
| 8423 | CG | PRO | B | 166 | 49.274 | 42.380 | 76.556 | 1.00 | 11.03 |
| 8426 | CD | PRO | B | 166 | 50.626 | 42.385 | 75.909 | 1.00 | 10.81 |
| 8429 | C | PRO | B | 166 | 49.837 | 45.433 | 77.326 | 1.00 | 10.98 |
| 8430 | O | PRO | B | 166 | 50.400 | 44.935 | 78.287 | 1.00 | 10.75 |
| 8431 | N | ARG | B | 167 | 49.281 | 46.637 | 77.346 | 1.00 | 10.96 |
| 8433 | CA | ARG | B | 167 | 49.399 | 47.517 | 78.499 | 1.00 | 11.18 |
| 8435 | CB | ARG | B | 167 | 49.287 | 48.987 | 78.055 | 1.00 | 11.45 |
| 8438 | CG | ARG | B | 167 | 50.581 | 49.534 | 77.448 | 1.00 | 12.90 |
| 8441 | CD | ARG | B | 167 | 50.424 | 50.860 | 76.698 | 1.00 | 14.86 |
| 8444 | NE | ARG | B | 167 | 50.259 | 50.666 | 75.260 | 1.00 | 16.79 |
| 8446 | CZ | ARG | B | 167 | 49.959 | 51.629 | 74.382 | 1.00 | 16.60 |
| 8447 | NH1 | ARG | B | 167 | 49.795 | 52.899 | 74.763 | 1.00 | 15.61 |
| 8450 | NH2 | ARG | B | 167 | 49.834 | 51.313 | 73.102 | 1.00 | 16.08 |
| 8453 | C | ARG | B | 167 | 48.387 | 47.212 | 79.614 | 1.00 | 10.98 |
| 8454 | O | ARG | B | 167 | 48.569 | 47.691 | 80.732 | 1.00 | 10.91 |
| 8455 | N | ILE | B | 168 | 47.350 | 46.415 | 79.326 | 1.00 | 10.68 |
| 8457 | CA | ILE | B | 168 | 46.294 | 46.132 | 80.311 | 1.00 | 10.64 |
| 8459 | CB | ILE | B | 168 | 44.918 | 46.639 | 79.812 | 1.00 | 10.76 |
| 8461 | CG1 | ILE | B | 168 | 44.967 | 48.153 | 79.587 | 1.00 | 11.06 |
| 8464 | CD1 | ILE | B | 168 | 43.772 | 48.700 | 78.863 | 1.00 | 12.01 |
| 8468 | CG2 | ILE | B | 168 | 43.821 | 46.294 | 80.822 | 1.00 | 10.75 |
| 8472 | C | ILE | B | 168 | 46.196 | 44.660 | 80.725 | 1.00 | 10.54 |
| 8473 | O | ILE | B | 168 | 46.397 | 44.339 | 81.893 | 1.00 | 10.43 |
| 8474 | N | LEU | B | 169 | 45.879 | 43.776 | 79.781 | 1.00 | 10.23 |
| 8476 | CA | LEU | B | 169 | 45.569 | 42.387 | 80.114 | 1.00 | 10.23 |
| 8478 | CB | LEU | B | 169 | 44.049 | 42.171 | 80.091 | 1.00 | 9.99 |
| 8481 | CG | LEU | B | 169 | 43.525 | 40.930 | 80.825 | 1.00 | 9.91 |
| 8483 | CD1 | LEU | B | 169 | 43.568 | 41.129 | 82.329 | 1.00 | 9.70 |
| 8487 | CD2 | LEU | B | 169 | 42.111 | 40.586 | 80.373 | 1.00 | 9.88 |
| 8491 | C | LEU | B | 169 | 46.267 | 41.388 | 79.188 | 1.00 | 10.33 |
| 8492 | O | LEU | B | 169 | 45.963 | 41.317 | 78.000 | 1.00 | 10.25 |
| 8493 | N | ALA | B | 170 | 47.212 | 40.631 | 79.745 | 1.00 | 10.57 |
| 8495 | CA | ALA | B | 170 | 47.868 | 39.536 | 79.033 | 1.00 | 10.87 |
| 8497 | CB | ALA | B | 170 | 49.232 | 39.250 | 79.647 | 1.00 | 10.89 |
| 8501 | C | ALA | B | 170 | 47.001 | 38.282 | 79.088 | 1.00 | 11.28 |
| 8502 | O | ALA | B | 170 | 46.656 | 37.815 | 80.167 | 1.00 | 11.30 |
| 8503 | N | LEU | B | 171 | 46.661 | 37.732 | 77.929 | 1.00 | 11.66 |
| 8505 | CA | LEU | B | 171 | 45.806 | 36.551 | 77.859 | 1.00 | 12.24 |
| 8507 | CB | LEU | B | 171 | 45.013 | 36.558 | 76.549 | 1.00 | 12.25 |
| 8510 | CG | LEU | B | 171 | 44.106 | 37.782 | 76.348 | 1.00 | 11.63 |
| 8512 | CD1 | LEU | B | 171 | 43.544 | 37.831 | 74.935 | 1.00 | 11.53 |
| 8516 | CD2 | LEU | B | 171 | 42.976 | 37.799 | 77.376 | 1.00 | 11.69 |
| 8520 | C | LEU | B | 171 | 46.624 | 35.255 | 77.989 | 1.00 | 13.05 |
| 8521 | O | LEU | B | 171 | 47.708 | 35.132 | 77.419 | 1.00 | 12.95 |

FIGURE 3 (Cont.)

| A | B | C | D | E | F | G | H | I | J |
|---|---|---|---|---|---|---|---|---|---|
| 8522 | N | LYS | B | 172 | 46.085 | 34.306 | 78.750 | 1.00 | 13.99 |
| 8524 | CA | LYS | B | 172 | 46.695 | 32.995 | 78.964 | 1.00 | 15.08 |
| 8526 | CB | LYS | B | 172 | 46.414 | 32.507 | 80.390 | 1.00 | 15.29 |
| 8529 | CG | LYS | B | 172 | 46.804 | 33.482 | 81.491 | 1.00 | 16.94 |
| 8532 | CD | LYS | B | 172 | 48.292 | 33.424 | 81.797 | 1.00 | 19.62 |
| 8535 | CE | LYS | B | 172 | 48.628 | 34.075 | 83.138 | 1.00 | 20.83 |
| 8538 | NZ | LYS | B | 172 | 48.827 | 33.064 | 84.226 | 1.00 | 22.61 |
| 8542 | C | LYS | B | 172 | 46.119 | 31.992 | 77.964 | 1.00 | 15.35 |
| 8543 | O | LYS | B | 172 | 45.169 | 32.308 | 77.247 | 1.00 | 15.43 |
| 8544 | N | GLU | B | 173 | 46.689 | 30.788 | 77.932 | 1.00 | 15.73 |
| 8546 | CA | GLU | B | 173 | 46.270 | 29.738 | 76.996 | 1.00 | 16.26 |
| 8548 | CB | GLU | B | 173 | 47.486 | 29.150 | 76.266 | 1.00 | 16.67 |
| 8551 | CG | GLU | B | 173 | 48.240 | 30.136 | 75.385 | 1.00 | 18.61 |
| 8554 | CD | GLU | B | 173 | 47.443 | 30.585 | 74.169 | 1.00 | 21.34 |
| 8555 | OE1 | GLU | B | 173 | 47.262 | 29.774 | 73.234 | 1.00 | 23.06 |
| 8556 | OE2 | GLU | B | 173 | 47.003 | 31.756 | 74.138 | 1.00 | 23.86 |
| 8557 | C | GLU | B | 173 | 45.520 | 28.621 | 77.724 | 1.00 | 15.94 |
| 8558 | O | GLU | B | 173 | 45.843 | 27.440 | 77.574 | 1.00 | 16.49 |
| 8559 | N | ASP | B | 174 | 44.513 | 29.002 | 78.500 | 1.00 | 15.24 |
| 8561 | CA | ASP | B | 174 | 43.759 | 28.057 | 79.322 | 1.00 | 14.89 |
| 8563 | CB | ASP | B | 174 | 43.894 | 28.427 | 80.811 | 1.00 | 14.66 |
| 8566 | CG | ASP | B | 174 | 43.178 | 29.725 | 81.175 | 1.00 | 14.76 |
| 8567 | OD1 | ASP | B | 174 | 43.044 | 30.622 | 80.303 | 1.00 | 13.61 |
| 8568 | OD2 | ASP | B | 174 | 42.717 | 29.931 | 82.321 | 1.00 | 13.29 |
| 8569 | C | ASP | B | 174 | 42.289 | 27.996 | 78.893 | 1.00 | 14.59 |
| 8570 | O | ASP | B | 174 | 41.416 | 27.633 | 79.682 | 1.00 | 14.62 |
| 8571 | N | ASN | B | 175 | 42.040 | 28.316 | 77.623 | 1.00 | 14.44 |
| 8573 | CA | ASN | B | 175 | 40.680 | 28.481 | 77.100 | 1.00 | 14.16 |
| 8575 | CB | ASN | B | 175 | 40.701 | 28.987 | 75.646 | 1.00 | 14.33 |
| 8578 | CG | ASN | B | 175 | 41.486 | 30.294 | 75.475 | 1.00 | 15.12 |
| 8579 | OD1 | ASN | B | 175 | 42.713 | 30.322 | 75.635 | 1.00 | 16.74 |
| 8580 | ND2 | ASN | B | 175 | 40.782 | 31.375 | 75.137 | 1.00 | 14.01 |
| 8583 | C | ASN | B | 175 | 39.910 | 27.164 | 77.155 | 1.00 | 13.87 |
| 8584 | O | ASN | B | 175 | 40.426 | 26.124 | 76.744 | 1.00 | 13.49 |
| 8585 | N | VAL | B | 176 | 38.692 | 27.217 | 77.692 | 1.00 | 13.21 |
| 8587 | CA | VAL | B | 176 | 37.743 | 26.118 | 77.617 | 1.00 | 12.91 |
| 8589 | CB | VAL | B | 176 | 37.371 | 25.559 | 78.999 | 1.00 | 13.03 |
| 8591 | CG1 | VAL | B | 176 | 36.224 | 24.543 | 78.877 | 1.00 | 13.31 |
| 8595 | CG2 | VAL | B | 176 | 38.580 | 24.931 | 79.657 | 1.00 | 13.59 |
| 8599 | C | VAL | B | 176 | 36.481 | 26.637 | 76.959 | 1.00 | 12.50 |
| 8600 | O | VAL | B | 176 | 35.832 | 27.546 | 77.467 | 1.00 | 12.27 |
| 8601 | N | MET | B | 177 | 36.127 | 26.033 | 75.837 | 1.00 | 12.05 |
| 8603 | CA | MET | B | 177 | 34.972 | 26.462 | 75.061 | 1.00 | 11.83 |
| 8605 | CB | MET | B | 177 | 35.411 | 26.923 | 73.677 | 1.00 | 11.77 |
| 8608 | CG | MET | B | 177 | 36.527 | 26.103 | 73.097 | 1.00 | 11.89 |
| 8611 | SD | MET | B | 177 | 38.183 | 26.790 | 73.399 | 1.00 | 8.57 |
| 8612 | CE | MET | B | 177 | 38.703 | 26.682 | 71.741 | 1.00 | 10.96 |
| 8616 | C | MET | B | 177 | 33.956 | 25.329 | 74.962 | 1.00 | 11.70 |
| 8617 | O | MET | B | 177 | 34.264 | 24.175 | 75.256 | 1.00 | 11.25 |
| 8618 | N | LEU | B | 178 | 32.748 | 25.678 | 74.534 | 1.00 | 11.42 |
| 8620 | CA | LEU | B | 178 | 31.619 | 24.765 | 74.547 | 1.00 | 11.25 |
| 8622 | CB | LEU | B | 178 | 30.981 | 24.756 | 75.939 | 1.00 | 11.37 |

FIGURE 3 (Cont.)

| A | B | C | D | E | F | G | H | I | J |
|---|---|---|---|---|---|---|---|---|---|
| 8625 | CG | LEU | B | 178 | 29.700 | 23.939 | 76.129 | 1.00 | 12.09 |
| 8627 | CD1 | LEU | B | 178 | 29.983 | 22.459 | 75.939 | 1.00 | 12.70 |
| 8631 | CD2 | LEU | B | 178 | 29.091 | 24.203 | 77.499 | 1.00 | 12.56 |
| 8635 | C | LEU | B | 178 | 30.590 | 25.197 | 73.504 | 1.00 | 10.91 |
| 8636 | O | LEU | B | 178 | 30.248 | 26.368 | 73.419 | 1.00 | 10.41 |
| 8637 | N | THR | B | 179 | 30.111 | 24.240 | 72.715 | 1.00 | 10.56 |
| 8639 | CA | THR | B | 179 | 29.021 | 24.461 | 71.770 | 1.00 | 10.66 |
| 8641 | CB | THR | B | 179 | 29.521 | 24.294 | 70.315 | 1.00 | 10.50 |
| 8643 | OG1 | THR | B | 179 | 30.467 | 25.322 | 69.994 | 1.00 | 10.71 |
| 8645 | CG2 | THR | B | 179 | 28.385 | 24.506 | 69.323 | 1.00 | 10.71 |
| 8649 | C | THR | B | 179 | 27.911 | 23.445 | 72.034 | 1.00 | 10.76 |
| 8650 | O | THR | B | 179 | 28.168 | 22.247 | 72.078 | 1.00 | 10.27 |
| 8651 | N | GLN | B | 180 | 26.689 | 23.936 | 72.217 | 1.00 | 11.16 |
| 8653 | CA | GLN | B | 180 | 25.488 | 23.103 | 72.284 | 1.00 | 11.76 |
| 8655 | CB | GLN | B | 180 | 24.957 | 23.018 | 73.711 | 1.00 | 11.95 |
| 8658 | CG | GLN | B | 180 | 25.932 | 22.527 | 74.745 | 1.00 | 13.46 |
| 8661 | CD | GLN | B | 180 | 25.410 | 22.765 | 76.145 | 1.00 | 15.16 |
| 8662 | OE1 | GLN | B | 180 | 25.704 | 23.793 | 76.752 | 1.00 | 17.63 |
| 8663 | NE2 | GLN | B | 180 | 24.614 | 21.831 | 76.650 | 1.00 | 16.39 |
| 8666 | C | GLN | B | 180 | 24.408 | 23.745 | 71.432 | 1.00 | 11.70 |
| 8667 | O | GLN | B | 180 | 24.218 | 24.947 | 71.502 | 1.00 | 12.41 |
| 8668 | N | ASP | B | 181 | 23.680 | 22.950 | 70.660 | 1.00 | 11.52 |
| 8670 | CA | ASP | B | 181 | 22.600 | 23.464 | 69.824 | 1.00 | 11.31 |
| 8672 | CB | ASP | B | 181 | 22.404 | 22.543 | 68.622 | 1.00 | 11.40 |
| 8675 | CG | ASP | B | 181 | 21.445 | 23.106 | 67.594 | 1.00 | 11.56 |
| 8676 | OD1 | ASP | B | 181 | 20.798 | 24.147 | 67.853 | 1.00 | 10.88 |
| 8677 | OD2 | ASP | B | 181 | 21.280 | 22.555 | 66.487 | 1.00 | 12.11 |
| 8678 | C | ASP | B | 181 | 21.308 | 23.583 | 70.635 | 1.00 | 11.19 |
| 8679 | O | ASP | B | 181 | 20.555 | 22.616 | 70.778 | 1.00 | 10.91 |
| 8680 | N | ILE | B | 182 | 21.076 | 24.779 | 71.174 | 1.00 | 10.93 |
| 8682 | CA | ILE | B | 182 | 19.920 | 25.074 | 72.016 | 1.00 | 10.73 |
| 8684 | CB | ILE | B | 182 | 20.363 | 25.193 | 73.489 | 1.00 | 10.94 |
| 8686 | CG1 | ILE | B | 182 | 20.862 | 23.844 | 74.021 | 1.00 | 11.42 |
| 8689 | CD1 | ILE | B | 182 | 21.734 | 23.973 | 75.259 | 1.00 | 12.34 |
| 8693 | CG2 | ILE | B | 182 | 19.220 | 25.719 | 74.364 | 1.00 | 11.11 |
| 8697 | C | ILE | B | 182 | 19.275 | 26.392 | 71.582 | 1.00 | 10.45 |
| 8698 | O | ILE | B | 182 | 19.967 | 27.407 | 71.442 | 1.00 | 10.34 |
| 8699 | N | TYR | B | 183 | 17.955 | 26.379 | 71.408 | 1.00 | 9.81 |
| 8701 | CA | TYR | B | 183 | 17.212 | 27.562 | 70.964 | 1.00 | 9.51 |
| 8703 | CB | TYR | B | 183 | 16.141 | 27.172 | 69.938 | 1.00 | 9.43 |
| 8706 | CG | TYR | B | 183 | 16.708 | 27.045 | 68.539 | 1.00 | 8.81 |
| 8707 | CD1 | TYR | B | 183 | 16.838 | 28.159 | 67.723 | 1.00 | 7.75 |
| 8709 | CE1 | TYR | B | 183 | 17.367 | 28.060 | 66.441 | 1.00 | 7.71 |
| 8711 | CZ | TYR | B | 183 | 17.784 | 26.833 | 65.966 | 1.00 | 7.80 |
| 8712 | OH | TYR | B | 183 | 18.310 | 26.745 | 64.697 | 1.00 | 7.51 |
| 8714 | CE2 | TYR | B | 183 | 17.671 | 25.703 | 66.759 | 1.00 | 8.21 |
| 8716 | CD2 | TYR | B | 183 | 17.137 | 25.813 | 68.042 | 1.00 | 8.40 |
| 8718 | C | TYR | B | 183 | 16.633 | 28.349 | 72.144 | 1.00 | 9.13 |
| 8719 | O | TYR | B | 183 | 15.418 | 28.438 | 72.338 | 1.00 | 8.73 |
| 8720 | N | ASP | B | 184 | 17.539 | 28.928 | 72.924 | 1.00 | 8.82 |
| 8722 | CA | ASP | B | 184 | 17.172 | 29.790 | 74.041 | 1.00 | 8.64 |
| 8724 | CB | ASP | B | 184 | 18.255 | 29.771 | 75.131 | 1.00 | 8.83 |

FIGURE 3 (Cont.)

| A | B | C | D | E | F | G | H | I | J |
|---|---|---|---|---|---|---|---|---|---|
| 8727 | CG | ASP | B | 184 | 19.589 | 30.358 | 74.671 | 1.00 | 8.74 |
| 8728 | OD1 | ASP | B | 184 | 20.207 | 31.130 | 75.445 | 1.00 | 9.11 |
| 8729 | OD2 | ASP | B | 184 | 20.107 | 30.097 | 73.565 | 1.00 | 7.83 |
| 8730 | C | ASP | B | 184 | 16.881 | 31.216 | 73.567 | 1.00 | 8.74 |
| 8731 | O | ASP | B | 184 | 15.977 | 31.883 | 74.077 | 1.00 | 8.78 |
| 8732 | N | PHE | B | 185 | 17.647 | 31.664 | 72.581 | 1.00 | 8.37 |
| 8734 | CA | PHE | B | 185 | 17.526 | 33.006 | 72.025 | 1.00 | 8.42 |
| 8736 | CB | PHE | B | 185 | 18.216 | 34.025 | 72.954 | 1.00 | 8.49 |
| 8739 | CG | PHE | B | 185 | 18.548 | 35.370 | 72.324 | 1.00 | 8.38 |
| 8740 | CD1 | PHE | B | 185 | 18.014 | 36.540 | 72.858 | 1.00 | 8.75 |
| 8742 | CE1 | PHE | B | 185 | 18.327 | 37.785 | 72.317 | 1.00 | 8.58 |
| 8744 | CZ | PHE | B | 185 | 19.202 | 37.875 | 71.243 | 1.00 | 8.36 |
| 8746 | CE2 | PHE | B | 185 | 19.751 | 36.727 | 70.712 | 1.00 | 7.46 |
| 8748 | CD2 | PHE | B | 185 | 19.440 | 35.482 | 71.262 | 1.00 | 7.98 |
| 8750 | C | PHE | B | 185 | 18.131 | 32.944 | 70.627 | 1.00 | 8.34 |
| 8751 | O | PHE | B | 185 | 19.178 | 32.325 | 70.407 | 1.00 | 8.33 |
| 8752 | N | TRP | B | 186 | 17.432 | 33.550 | 69.682 | 1.00 | 8.38 |
| 8754 | CA | TRP | B | 186 | 17.865 | 33.602 | 68.297 | 1.00 | 8.40 |
| 8756 | CB | TRP | B | 186 | 17.690 | 32.235 | 67.623 | 1.00 | 8.43 |
| 8759 | CG | TRP | B | 186 | 16.263 | 31.801 | 67.389 | 1.00 | 8.00 |
| 8760 | CD1 | TRP | B | 186 | 15.629 | 31.740 | 66.191 | 1.00 | 8.14 |
| 8762 | NE1 | TRP | B | 186 | 14.345 | 31.279 | 66.350 | 1.00 | 7.86 |
| 8764 | CE2 | TRP | B | 186 | 14.126 | 31.020 | 67.676 | 1.00 | 7.75 |
| 8765 | CD2 | TRP | B | 186 | 15.316 | 31.331 | 68.364 | 1.00 | 7.70 |
| 8766 | CE3 | TRP | B | 186 | 15.348 | 31.147 | 69.755 | 1.00 | 7.21 |
| 8768 | CZ3 | TRP | B | 186 | 14.207 | 30.683 | 70.396 | 1.00 | 7.64 |
| 8770 | CH2 | TRP | B | 186 | 13.045 | 30.380 | 69.678 | 1.00 | 7.63 |
| 8772 | CZ2 | TRP | B | 186 | 12.982 | 30.547 | 68.322 | 1.00 | 7.78 |
| 8774 | C | TRP | B | 186 | 17.067 | 34.691 | 67.589 | 1.00 | 8.47 |
| 8775 | O | TRP | B | 186 | 16.179 | 35.286 | 68.179 | 1.00 | 8.45 |
| 8776 | N | ARG | B | 187 | 17.404 | 34.985 | 66.342 | 1.00 | 8.48 |
| 8778 | CA | ARG | B | 187 | 16.679 | 36.006 | 65.591 | 1.00 | 8.58 |
| 8780 | CB | ARG | B | 187 | 17.307 | 37.390 | 65.792 | 1.00 | 8.52 |
| 8783 | CG | ARG | B | 187 | 16.472 | 38.518 | 65.199 | 1.00 | 8.34 |
| 8786 | CD | ARG | B | 187 | 16.677 | 39.869 | 65.858 | 1.00 | 8.54 |
| 8789 | NE | ARG | B | 187 | 17.964 | 40.470 | 65.516 | 1.00 | 7.93 |
| 8791 | CZ | ARG | B | 187 | 18.245 | 41.054 | 64.352 | 1.00 | 9.02 |
| 8792 | NH1 | ARG | B | 187 | 17.339 | 41.136 | 63.393 | 1.00 | 9.12 |
| 8795 | NH2 | ARG | B | 187 | 19.446 | 41.577 | 64.149 | 1.00 | 8.63 |
| 8798 | C | ARG | B | 187 | 16.633 | 35.646 | 64.113 | 1.00 | 8.78 |
| 8799 | O | ARG | B | 187 | 17.540 | 35.993 | 63.366 | 1.00 | 8.58 |
| 8800 | N | PRO | B | 188 | 15.573 | 34.957 | 63.688 | 1.00 | 9.19 |
| 8801 | CA | PRO | B | 188 | 15.460 | 34.522 | 62.294 | 1.00 | 9.40 |
| 8803 | CB | PRO | B | 188 | 14.075 | 33.862 | 62.230 | 1.00 | 9.46 |
| 8806 | CG | PRO | B | 188 | 13.726 | 33.526 | 63.625 | 1.00 | 9.61 |
| 8809 | CD | PRO | B | 188 | 14.397 | 34.562 | 64.486 | 1.00 | 9.35 |
| 8812 | C | PRO | B | 188 | 15.524 | 35.704 | 61.341 | 1.00 | 9.56 |
| 8813 | O | PRO | B | 188 | 15.115 | 36.810 | 61.704 | 1.00 | 9.65 |
| 8814 | N | THR | B | 189 | 16.036 | 35.465 | 60.140 | 1.00 | 9.76 |
| 8816 | CA | THR | B | 189 | 16.058 | 36.476 | 59.087 | 1.00 | 9.94 |
| 8818 | CB | THR | B | 189 | 16.457 | 35.830 | 57.744 | 1.00 | 9.93 |
| 8820 | OG1 | THR | B | 189 | 17.705 | 35.144 | 57.886 | 1.00 | 10.67 |

FIGURE 3 (Cont.)

| A | B | C | D | E | F | G | H | I | J |
|---|---|---|---|---|---|---|---|---|---|
| 8822 | CG2 | THR | B | 189 | 16.741 | 36.885 | 56.686 | 1.00 | 10.40 |
| 8826 | C | THR | B | 189 | 14.672 | 37.080 | 58.963 | 1.00 | 9.79 |
| 8827 | O | THR | B | 189 | 13.688 | 36.353 | 58.872 | 1.00 | 9.52 |
| 8828 | N | GLY | B | 190 | 14.597 | 38.408 | 58.994 | 1.00 | 9.95 |
| 8830 | CA | GLY | B | 190 | 13.344 | 39.117 | 58.810 | 1.00 | 10.15 |
| 8833 | C | GLY | B | 190 | 12.628 | 39.500 | 60.095 | 1.00 | 10.36 |
| 8834 | O | GLY | B | 190 | 11.618 | 40.190 | 60.043 | 1.00 | 10.54 |
| 8835 | N | HIS | B | 191 | 13.138 | 39.050 | 61.241 | 1.00 | 10.44 |
| 8837 | CA | HIS | B | 191 | 12.617 | 39.458 | 62.543 | 1.00 | 10.52 |
| 8839 | CB | HIS | B | 191 | 12.689 | 38.304 | 63.547 | 1.00 | 10.55 |
| 8842 | CG | HIS | B | 191 | 11.533 | 37.359 | 63.462 | 1.00 | 11.04 |
| 8843 | ND1 | HIS | B | 191 | 10.761 | 37.030 | 64.555 | 1.00 | 12.34 |
| 8845 | CE1 | HIS | B | 191 | 9.814 | 36.187 | 64.183 | 1.00 | 12.73 |
| 8847 | NE2 | HIS | B | 191 | 9.947 | 35.954 | 62.890 | 1.00 | 12.17 |
| 8849 | CD2 | HIS | B | 191 | 11.014 | 36.677 | 62.415 | 1.00 | 11.49 |
| 8851 | C | HIS | B | 191 | 13.460 | 40.624 | 63.057 | 1.00 | 10.51 |
| 8852 | O | HIS | B | 191 | 14.652 | 40.446 | 63.270 | 1.00 | 9.95 |
| 8853 | N | PRO | B | 192 | 12.868 | 41.806 | 63.249 | 1.00 | 10.76 |
| 8854 | CA | PRO | B | 192 | 13.615 | 42.939 | 63.817 | 1.00 | 10.88 |
| 8856 | CB | PRO | B | 192 | 12.620 | 44.108 | 63.730 | 1.00 | 11.03 |
| 8859 | CG | PRO | B | 192 | 11.286 | 43.484 | 63.617 | 1.00 | 11.25 |
| 8862 | CD | PRO | B | 192 | 11.477 | 42.170 | 62.925 | 1.00 | 11.00 |
| 8865 | C | PRO | B | 192 | 14.068 | 42.718 | 65.265 | 1.00 | 10.79 |
| 8866 | O | PRO | B | 192 | 15.092 | 43.280 | 65.651 | 1.00 | 10.64 |
| 8867 | N | TYR | B | 193 | 13.327 | 41.917 | 66.033 | 1.00 | 10.86 |
| 8869 | CA | TYR | B | 193 | 13.650 | 41.634 | 67.439 | 1.00 | 11.09 |
| 8871 | CB | TYR | B | 193 | 12.509 | 42.086 | 68.356 | 1.00 | 11.46 |
| 8874 | CG | TYR | B | 193 | 11.981 | 43.469 | 68.061 | 1.00 | 13.13 |
| 8875 | CD1 | TYR | B | 193 | 10.676 | 43.659 | 67.611 | 1.00 | 14.74 |
| 8877 | CE1 | TYR | B | 193 | 10.186 | 44.937 | 67.339 | 1.00 | 16.26 |
| 8879 | CZ | TYR | B | 193 | 11.008 | 46.037 | 67.517 | 1.00 | 16.72 |
| 8880 | OH | TYR | B | 193 | 10.534 | 47.300 | 67.252 | 1.00 | 17.61 |
| 8882 | CE2 | TYR | B | 193 | 12.306 | 45.873 | 67.965 | 1.00 | 16.67 |
| 8884 | CD2 | TYR | B | 193 | 12.786 | 44.588 | 68.233 | 1.00 | 15.72 |
| 8886 | C | TYR | B | 193 | 13.892 | 40.140 | 67.658 | 1.00 | 10.71 |
| 8887 | O | TYR | B | 193 | 13.401 | 39.313 | 66.886 | 1.00 | 10.63 |
| 8888 | N | PRO | B | 194 | 14.633 | 39.784 | 68.706 | 1.00 | 10.34 |
| 8889 | CA | PRO | B | 194 | 14.917 | 38.373 | 68.978 | 1.00 | 10.19 |
| 8891 | CB | PRO | B | 194 | 15.898 | 38.426 | 70.158 | 1.00 | 10.18 |
| 8894 | CG | PRO | B | 194 | 16.396 | 39.824 | 70.207 | 1.00 | 10.24 |
| 8897 | CD | PRO | B | 194 | 15.277 | 40.664 | 69.699 | 1.00 | 10.35 |
| 8900 | C | PRO | B | 194 | 13.684 | 37.549 | 69.365 | 1.00 | 10.14 |
| 8901 | O | PRO | B | 194 | 12.703 | 38.076 | 69.895 | 1.00 | 9.72 |
| 8902 | N | MSE | B | 195 | 13.750 | 36.261 | 69.050 | 1.00 | 10.14 |
| 8904 | CA | MSE | B | 195 | 12.901 | 35.249 | 69.653 | 1.00 | 10.49 |
| 8906 | CB | MSE | B | 195 | 12.738 | 34.058 | 68.707 | 1.00 | 10.74 |
| 8909 | CG | MSE | B | 195 | 12.073 | 34.392 | 67.384 | 1.00 | 11.07 |
| 8912 | SE | MSE | B | 195 | 10.177 | 34.760 | 67.603 | 1.00 | 13.09 |
| 8913 | CE | MSE | B | 195 | 9.544 | 32.978 | 67.987 | 1.00 | 12.65 |
| 8917 | C | MSE | B | 195 | 13.628 | 34.798 | 70.909 | 1.00 | 10.58 |
| 8918 | O | MSE | B | 195 | 14.829 | 34.538 | 70.868 | 1.00 | 10.57 |
| 8919 | N | VAL | B | 196 | 12.913 | 34.701 | 72.021 | 1.00 | 10.39 |

FIGURE 3 (Cont.)

| A | B | C | D | E | F | G | H | I | J |
|---|---|---|---|---|---|---|---|---|---|
| 8921 | CA | VAL | B | 196 | 13.537 | 34.328 | 73.282 | 1.00 | 10.26 |
| 8923 | CB | VAL | B | 196 | 14.055 | 35.582 | 74.049 | 1.00 | 10.35 |
| 8925 | CG1 | VAL | B | 196 | 12.913 | 36.531 | 74.417 | 1.00 | 10.25 |
| 8929 | CG2 | VAL | B | 196 | 14.856 | 35.177 | 75.287 | 1.00 | 10.28 |
| 8933 | C | VAL | B | 196 | 12.608 | 33.475 | 74.150 | 1.00 | 10.31 |
| 8934 | O | VAL | B | 196 | 11.414 | 33.747 | 74.289 | 1.00 | 10.04 |
| 8935 | N | ASP | B | 197 | 13.176 | 32.397 | 74.671 | 1.00 | 10.15 |
| 8937 | CA | ASP | B | 197 | 12.594 | 31.640 | 75.759 | 1.00 | 10.09 |
| 8939 | CB | ASP | B | 197 | 12.816 | 30.152 | 75.505 | 1.00 | 10.19 |
| 8942 | CG | ASP | B | 197 | 12.154 | 29.271 | 76.542 | 1.00 | 10.28 |
| 8943 | OD1 | ASP | B | 197 | 12.057 | 29.679 | 77.717 | 1.00 | 10.15 |
| 8944 | OD2 | ASP | B | 197 | 11.710 | 28.143 | 76.263 | 1.00 | 10.51 |
| 8945 | C | ASP | B | 197 | 13.315 | 32.109 | 77.020 | 1.00 | 10.20 |
| 8946 | O | ASP | B | 197 | 14.418 | 31.649 | 77.314 | 1.00 | 9.95 |
| 8947 | N | GLY | B | 198 | 12.693 | 33.032 | 77.752 | 1.00 | 9.99 |
| 8949 | CA | GLY | B | 198 | 13.282 | 33.627 | 78.942 | 1.00 | 10.14 |
| 8952 | C | GLY | B | 198 | 13.901 | 32.648 | 79.933 | 1.00 | 10.20 |
| 8953 | O | GLY | B | 198 | 15.113 | 32.688 | 80.149 | 1.00 | 9.77 |
| 8954 | N | PRO | B | 199 | 13.086 | 31.791 | 80.552 | 1.00 | 10.11 |
| 8955 | CA | PRO | B | 199 | 13.603 | 30.768 | 81.473 | 1.00 | 10.10 |
| 8957 | CB | PRO | B | 199 | 12.358 | 29.937 | 81.818 | 1.00 | 10.28 |
| 8960 | CG | PRO | B | 199 | 11.213 | 30.908 | 81.662 | 1.00 | 10.47 |
| 8963 | CD | PRO | B | 199 | 11.612 | 31.772 | 80.475 | 1.00 | 10.38 |
| 8966 | C | PRO | B | 199 | 14.715 | 29.886 | 80.891 | 1.00 | 10.07 |
| 8967 | O | PRO | B | 199 | 15.674 | 29.596 | 81.603 | 1.00 | 9.92 |
| 8968 | N | LEU | B | 200 | 14.600 | 29.476 | 79.630 | 1.00 | 9.92 |
| 8970 | CA | LEU | B | 200 | 15.614 | 28.620 | 79.016 | 1.00 | 9.83 |
| 8972 | CB | LEU | B | 200 | 15.137 | 28.075 | 77.668 | 1.00 | 9.79 |
| 8975 | CG | LEU | B | 200 | 16.108 | 27.145 | 76.928 | 1.00 | 9.73 |
| 8977 | CD1 | LEU | B | 200 | 15.502 | 26.702 | 75.621 | 1.00 | 9.92 |
| 8981 | CD2 | LEU | B | 200 | 16.486 | 25.932 | 77.781 | 1.00 | 10.51 |
| 8985 | C | LEU | B | 200 | 16.941 | 29.354 | 78.831 | 1.00 | 9.83 |
| 8986 | O | LEU | B | 200 | 18.003 | 28.759 | 78.982 | 1.00 | 9.84 |
| 8987 | N | SER | B | 201 | 16.878 | 30.639 | 78.493 | 1.00 | 9.86 |
| 8989 | CA | SER | B | 201 | 18.083 | 31.440 | 78.313 | 1.00 | 10.06 |
| 8991 | CB | SER | B | 201 | 17.742 | 32.808 | 77.702 | 1.00 | 9.89 |
| 8994 | OG | SER | B | 201 | 17.047 | 33.645 | 78.613 | 1.00 | 9.75 |
| 8996 | C | SER | B | 201 | 18.827 | 31.577 | 79.638 | 1.00 | 10.33 |
| 8997 | O | SER | B | 201 | 20.050 | 31.449 | 79.682 | 1.00 | 10.35 |
| 8998 | N | ASN | B | 202 | 18.084 | 31.812 | 80.717 | 1.00 | 10.88 |
| 9000 | CA | ASN | B | 202 | 18.664 | 31.897 | 82.058 | 1.00 | 11.24 |
| 9002 | CB | ASN | B | 202 | 17.584 | 32.229 | 83.097 | 1.00 | 11.29 |
| 9005 | CG | ASN | B | 202 | 17.182 | 33.697 | 83.088 | 1.00 | 11.75 |
| 9006 | OD1 | ASN | B | 202 | 17.863 | 34.550 | 82.507 | 1.00 | 12.97 |
| 9007 | ND2 | ASN | B | 202 | 16.067 | 33.999 | 83.743 | 1.00 | 11.90 |
| 9010 | C | ASN | B | 202 | 19.357 | 30.596 | 82.451 | 1.00 | 11.46 |
| 9011 | O | ASN | B | 202 | 20.502 | 30.596 | 82.901 | 1.00 | 11.23 |
| 9012 | N | GLU | B | 203 | 18.650 | 29.490 | 82.267 | 1.00 | 11.84 |
| 9014 | CA | GLU | B | 203 | 19.162 | 28.181 | 82.636 | 1.00 | 12.22 |
| 9016 | CB | GLU | B | 203 | 18.064 | 27.132 | 82.516 | 1.00 | 12.86 |
| 9019 | CG | GLU | B | 203 | 18.513 | 25.722 | 82.854 | 1.00 | 15.31 |
| 9022 | CD | GLU | B | 203 | 17.407 | 24.718 | 82.650 | 1.00 | 18.80 |

FIGURE 3 (Cont.)

| A | B | C | D | E | F | G | H | I | J |
|---|---|---|---|---|---|---|---|---|---|
| 9023 | OE1 | GLU | B | 203 | 17.148 | 24.351 | 81.481 | 1.00 | 21.49 |
| 9024 | OE2 | GLU | B | 203 | 16.798 | 24.305 | 83.659 | 1.00 | 22.29 |
| 9025 | C | GLU | B | 203 | 20.351 | 27.776 | 81.778 | 1.00 | 11.66 |
| 9026 | O | GLU | B | 203 | 21.295 | 27.191 | 82.291 | 1.00 | 11.26 |
| 9027 | N | THR | B | 204 | 20.304 | 28.084 | 80.482 | 1.00 | 10.99 |
| 9029 | CA | THR | B | 204 | 21.374 | 27.689 | 79.564 | 1.00 | 10.84 |
| 9031 | CB | THR | B | 204 | 20.956 | 27.898 | 78.089 | 1.00 | 10.85 |
| 9033 | OG1 | THR | B | 204 | 19.755 | 27.165 | 77.812 | 1.00 | 10.56 |
| 9035 | CG2 | THR | B | 204 | 21.978 | 27.294 | 77.139 | 1.00 | 10.68 |
| 9039 | C | THR | B | 204 | 22.648 | 28.469 | 79.878 | 1.00 | 10.59 |
| 9040 | O | THR | B | 204 | 23.742 | 27.923 | 79.815 | 1.00 | 10.43 |
| 9041 | N | TYR | B | 205 | 22.490 | 29.742 | 80.229 | 1.00 | 10.47 |
| 9043 | CA | TYR | B | 205 | 23.596 | 30.573 | 80.706 | 1.00 | 10.60 |
| 9045 | CB | TYR | B | 205 | 23.079 | 31.983 | 81.033 | 1.00 | 10.44 |
| 9048 | CG | TYR | B | 205 | 24.126 | 32.991 | 81.492 | 1.00 | 10.65 |
| 9049 | CD1 | TYR | B | 205 | 24.762 | 32.861 | 82.725 | 1.00 | 9.88 |
| 9051 | CE1 | TYR | B | 205 | 25.700 | 33.787 | 83.154 | 1.00 | 10.12 |
| 9053 | CZ | TYR | B | 205 | 26.004 | 34.870 | 82.360 | 1.00 | 10.48 |
| 9054 | OH | TYR | B | 205 | 26.933 | 35.793 | 82.786 | 1.00 | 9.44 |
| 9056 | CE2 | TYR | B | 205 | 25.379 | 35.037 | 81.141 | 1.00 | 10.98 |
| 9058 | CD2 | TYR | B | 205 | 24.442 | 34.102 | 80.712 | 1.00 | 10.82 |
| 9060 | C | TYR | B | 205 | 24.247 | 29.942 | 81.943 | 1.00 | 10.76 |
| 9061 | O | TYR | B | 205 | 25.458 | 29.751 | 81.981 | 1.00 | 10.45 |
| 9062 | N | ILE | B | 206 | 23.431 | 29.635 | 82.950 | 1.00 | 11.19 |
| 9064 | CA | ILE | B | 206 | 23.925 | 29.092 | 84.219 | 1.00 | 11.73 |
| 9066 | CB | ILE | B | 206 | 22.773 | 28.940 | 85.246 | 1.00 | 11.97 |
| 9068 | CG1 | ILE | B | 206 | 22.347 | 30.320 | 85.743 | 1.00 | 12.38 |
| 9071 | CD1 | ILE | B | 206 | 21.041 | 30.331 | 86.502 | 1.00 | 13.48 |
| 9075 | CG2 | ILE | B | 206 | 23.200 | 28.078 | 86.447 | 1.00 | 12.40 |
| 9079 | C | ILE | B | 206 | 24.638 | 27.765 | 84.008 | 1.00 | 11.82 |
| 9080 | O | ILE | B | 206 | 25.745 | 27.569 | 84.507 | 1.00 | 11.94 |
| 9081 | N | GLN | B | 207 | 24.007 | 26.868 | 83.256 | 1.00 | 11.84 |
| 9083 | CA | GLN | B | 207 | 24.556 | 25.537 | 83.025 | 1.00 | 12.03 |
| 9085 | CB | GLN | B | 207 | 23.484 | 24.607 | 82.456 | 1.00 | 12.52 |
| 9088 | CG | GLN | B | 207 | 22.394 | 24.285 | 83.478 | 1.00 | 14.35 |
| 9091 | CD | GLN | B | 207 | 21.295 | 23.395 | 82.932 | 1.00 | 17.08 |
| 9092 | OE1 | GLN | B | 207 | 21.329 | 22.994 | 81.766 | 1.00 | 19.51 |
| 9093 | NE2 | GLN | B | 207 | 20.318 | 23.073 | 83.780 | 1.00 | 17.97 |
| 9096 | C | GLN | B | 207 | 25.783 | 25.576 | 82.122 | 1.00 | 11.30 |
| 9097 | O | GLN | B | 207 | 26.663 | 24.735 | 82.245 | 1.00 | 10.77 |
| 9098 | N | SER | B | 208 | 25.848 | 26.562 | 81.231 | 1.00 | 10.63 |
| 9100 | CA | SER | B | 208 | 26.998 | 26.708 | 80.350 | 1.00 | 10.21 |
| 9102 | CB | ASER | B | 208 | 26.710 | 27.681 | 79.204 | 0.65 | 9.93 |
| 9105 | OG | ASER | B | 208 | 25.793 | 27.110 | 78.294 | 0.65 | 9.20 |
| 9107 | C | SER | B | 208 | 28.206 | 27.165 | 81.155 | 1.00 | 10.16 |
| 9108 | O | SER | B | 208 | 29.296 | 26.638 | 80.978 | 1.00 | 9.71 |
| 9109 | N | PHE | B | 209 | 28.007 | 28.134 | 82.046 | 1.00 | 10.49 |
| 9111 | CA | PHE | B | 209 | 29.072 | 28.565 | 82.946 | 1.00 | 10.78 |
| 9113 | CB | PHE | B | 209 | 28.636 | 29.724 | 83.843 | 1.00 | 10.84 |
| 9116 | CG | PHE | B | 209 | 29.625 | 30.031 | 84.928 | 1.00 | 11.05 |
| 9117 | CD1 | PHE | B | 209 | 29.313 | 29.811 | 86.262 | 1.00 | 11.55 |
| 9119 | CE1 | PHE | B | 209 | 30.247 | 30.071 | 87.260 | 1.00 | 11.85 |

FIGURE 3 (Cont.)

| A | B | C | D | E | F | G | H | I | J |
|---|---|---|---|---|---|---|---|---|---|
| 9121 | CZ | PHE | B | 209 | 31.507 | 30.545 | 86.926 | 1.00 | 11.34 |
| 9123 | CE2 | PHE | B | 209 | 31.831 | 30.756 | 85.598 | 1.00 | 11.62 |
| 9125 | CD2 | PHE | B | 209 | 30.892 | 30.495 | 84.606 | 1.00 | 11.03 |
| 9127 | C | PHE | B | 209 | 29.541 | 27.403 | 83.815 | 1.00 | 11.02 |
| 9128 | O | PHE | B | 209 | 30.733 | 27.159 | 83.934 | 1.00 | 10.70 |
| 9129 | N | ALA | B | 210 | 28.592 | 26.686 | 84.411 | 1.00 | 11.43 |
| 9131 | CA | ALA | B | 210 | 28.900 | 25.519 | 85.236 | 1.00 | 11.46 |
| 9133 | CB | ALA | B | 210 | 27.609 | 24.859 | 85.733 | 1.00 | 11.48 |
| 9137 | C | ALA | B | 210 | 29.751 | 24.500 | 84.480 | 1.00 | 11.49 |
| 9138 | O | ALA | B | 210 | 30.680 | 23.928 | 85.038 | 1.00 | 11.30 |
| 9139 | N | GLN | B | 211 | 29.430 | 24.287 | 83.207 | 1.00 | 11.73 |
| 9141 | CA | GLN | B | 211 | 30.103 | 23.273 | 82.392 | 1.00 | 11.75 |
| 9143 | CB | GLN | B | 211 | 29.298 | 22.982 | 81.117 | 1.00 | 12.08 |
| 9146 | CG | GLN | B | 211 | 28.138 | 22.018 | 81.324 | 1.00 | 13.53 |
| 9149 | CD | GLN | B | 211 | 27.330 | 21.794 | 80.053 | 1.00 | 15.53 |
| 9150 | OE1 | GLN | B | 211 | 27.745 | 21.030 | 79.182 | 1.00 | 16.93 |
| 9151 | NE2 | GLN | B | 211 | 26.179 | 22.454 | 79.949 | 1.00 | 17.13 |
| 9154 | C | GLN | B | 211 | 31.538 | 23.681 | 82.033 | 1.00 | 11.37 |
| 9155 | O | GLN | B | 211 | 32.463 | 22.885 | 82.196 | 1.00 | 10.85 |
| 9156 | N | VAL | B | 212 | 31.718 | 24.905 | 81.535 | 1.00 | 11.01 |
| 9158 | CA | VAL | B | 212 | 33.060 | 25.403 | 81.202 | 1.00 | 11.02 |
| 9160 | CB | VAL | B | 212 | 33.056 | 26.684 | 80.305 | 1.00 | 11.00 |
| 9162 | CG1 | VAL | B | 212 | 32.430 | 26.391 | 78.944 | 1.00 | 11.04 |
| 9166 | CG2 | VAL | B | 212 | 32.363 | 27.860 | 80.996 | 1.00 | 11.14 |
| 9170 | C | VAL | B | 212 | 33.913 | 25.656 | 82.444 | 1.00 | 10.89 |
| 9171 | O | VAL | B | 212 | 35.118 | 25.433 | 82.407 | 1.00 | 10.90 |
| 9172 | N | TRP | B | 213 | 33.300 | 26.117 | 83.533 | 1.00 | 10.70 |
| 9174 | CA | TRP | B | 213 | 34.015 | 26.274 | 84.798 | 1.00 | 10.74 |
| 9176 | CB | TRP | B | 213 | 33.140 | 26.914 | 85.887 | 1.00 | 10.73 |
| 9179 | CG | TRP | B | 213 | 33.807 | 26.876 | 87.231 | 1.00 | 10.43 |
| 9180 | CD1 | TRP | B | 213 | 33.551 | 26.002 | 88.256 | 1.00 | 10.48 |
| 9182 | NE1 | TRP | B | 213 | 34.388 | 26.257 | 89.316 | 1.00 | 9.70 |
| 9184 | CE2 | TRP | B | 213 | 35.207 | 27.309 | 88.996 | 1.00 | 10.64 |
| 9185 | CD2 | TRP | B | 213 | 34.871 | 27.721 | 87.686 | 1.00 | 10.61 |
| 9186 | CE3 | TRP | B | 213 | 35.578 | 28.792 | 87.122 | 1.00 | 10.97 |
| 9188 | CZ3 | TRP | B | 213 | 36.575 | 29.407 | 87.867 | 1.00 | 10.75 |
| 9190 | CH2 | TRP | B | 213 | 36.880 | 28.976 | 89.166 | 1.00 | 10.94 |
| 9192 | CZ2 | TRP | B | 213 | 36.209 | 27.932 | 89.747 | 1.00 | 10.64 |
| 9194 | C | TRP | B | 213 | 34.530 | 24.923 | 85.295 | 1.00 | 10.84 |
| 9195 | O | TRP | B | 213 | 35.706 | 24.788 | 85.610 | 1.00 | 10.48 |
| 9196 | N | ASP | B | 214 | 33.638 | 23.938 | 85.366 | 1.00 | 11.22 |
| 9198 | CA | ASP | B | 214 | 33.980 | 22.604 | 85.873 | 1.00 | 11.47 |
| 9200 | CB | ASP | B | 214 | 32.761 | 21.677 | 85.874 | 1.00 | 11.54 |
| 9203 | CG | ASP | B | 214 | 31.807 | 21.953 | 87.019 | 1.00 | 12.06 |
| 9204 | OD1 | ASP | B | 214 | 30.670 | 21.438 | 86.970 | 1.00 | 12.44 |
| 9205 | OD2 | ASP | B | 214 | 32.093 | 22.667 | 87.998 | 1.00 | 13.30 |
| 9206 | C | ASP | B | 214 | 35.081 | 21.955 | 85.044 | 1.00 | 11.41 |
| 9207 | O | ASP | B | 214 | 35.990 | 21.357 | 85.595 | 1.00 | 11.27 |
| 9208 | N | GLU | B | 215 | 34.982 | 22.074 | 83.722 | 1.00 | 11.45 |
| 9210 | CA | GLU | B | 215 | 35.971 | 21.509 | 82.814 | 1.00 | 11.61 |
| 9212 | CB | GLU | B | 215 | 35.457 | 21.545 | 81.370 | 1.00 | 11.65 |
| 9215 | CG | GLU | B | 215 | 36.429 | 21.019 | 80.319 | 1.00 | 11.36 |

FIGURE 3 (Cont.)

| A | B | C | D | E | F | G | H | I | J |
|---|---|---|---|---|---|---|---|---|---|
| 9218 | CD | GLU | B | 215 | 36.727 | 19.531 | 80.456 | 1.00 | 11.18 |
| 9219 | OE1 | GLU | B | 215 | 37.751 | 19.077 | 79.910 | 1.00 | 11.70 |
| 9220 | OE2 | GLU | B | 215 | 35.949 | 18.811 | 81.097 | 1.00 | 10.36 |
| 9221 | C | GLU | B | 215 | 37.297 | 22.258 | 82.924 | 1.00 | 11.95 |
| 9222 | O | GLU | B | 215 | 38.360 | 21.648 | 82.832 | 1.00 | 12.01 |
| 9223 | N | HIS | B | 216 | 37.227 | 23.573 | 83.119 | 1.00 | 12.30 |
| 9225 | CA | HIS | B | 216 | 38.416 | 24.402 | 83.310 | 1.00 | 12.71 |
| 9227 | CB | HIS | B | 216 | 38.047 | 25.895 | 83.357 | 1.00 | 12.59 |
| 9230 | CG | HIS | B | 216 | 39.231 | 26.807 | 83.477 | 1.00 | 12.79 |
| 9231 | ND1 | HIS | B | 216 | 39.852 | 27.066 | 84.678 | 1.00 | 12.83 |
| 9233 | CE1 | HIS | B | 216 | 40.865 | 27.891 | 84.480 | 1.00 | 13.09 |
| 9235 | NE2 | HIS | B | 216 | 40.919 | 28.183 | 83.193 | 1.00 | 12.89 |
| 9237 | CD2 | HIS | B | 216 | 39.907 | 27.519 | 82.543 | 1.00 | 13.40 |
| 9239 | C | HIS | B | 216 | 39.149 | 24.003 | 84.589 | 1.00 | 12.95 |
| 9240 | O | HIS | B | 216 | 40.370 | 23.879 | 84.589 | 1.00 | 12.95 |
| 9241 | N | LYS | B | 217 | 38.395 | 23.805 | 85.668 | 1.00 | 13.35 |
| 9243 | CA | LYS | B | 217 | 38.960 | 23.412 | 86.962 | 1.00 | 13.93 |
| 9245 | CB | LYS | B | 217 | 37.885 | 23.487 | 88.061 | 1.00 | 14.05 |
| 9248 | CG | LYS | B | 217 | 38.318 | 22.954 | 89.427 | 1.00 | 14.68 |
| 9251 | CD | LYS | B | 217 | 37.337 | 23.336 | 90.540 | 1.00 | 16.39 |
| 9254 | CE | LYS | B | 217 | 36.056 | 22.518 | 90.495 | 1.00 | 17.54 |
| 9257 | NZ | LYS | B | 217 | 35.481 | 22.303 | 91.856 | 1.00 | 19.01 |
| 9261 | C | LYS | B | 217 | 39.540 | 22.000 | 86.866 | 1.00 | 14.16 |
| 9262 | O | LYS | B | 217 | 40.619 | 21.724 | 87.378 | 1.00 | 14.11 |
| 9263 | N | LYS | B | 218 | 38.814 | 21.121 | 86.187 | 1.00 | 14.66 |
| 9265 | CA | LYS | B | 218 | 39.253 | 19.752 | 85.929 | 1.00 | 15.16 |
| 9267 | CB | LYS | B | 218 | 38.184 | 19.041 | 85.091 | 1.00 | 15.50 |
| 9270 | CG | LYS | B | 218 | 38.453 | 17.593 | 84.732 | 1.00 | 16.41 |
| 9273 | CD | LYS | B | 218 | 37.209 | 16.998 | 84.084 | 1.00 | 18.09 |
| 9276 | CE | LYS | B | 218 | 37.437 | 15.568 | 83.648 | 1.00 | 19.19 |
| 9279 | NZ | LYS | B | 218 | 38.339 | 15.500 | 82.479 | 1.00 | 20.49 |
| 9283 | C | LYS | B | 218 | 40.616 | 19.705 | 85.229 | 1.00 | 15.21 |
| 9284 | O | LYS | B | 218 | 41.469 | 18.887 | 85.582 | 1.00 | 15.77 |
| 9285 | N | ARG | B | 219 | 40.828 | 20.606 | 84.269 | 1.00 | 15.02 |
| 9287 | CA | ARG | B | 219 | 42.048 | 20.627 | 83.455 | 1.00 | 14.88 |
| 9289 | CB | ARG | B | 219 | 41.786 | 21.341 | 82.120 | 1.00 | 15.16 |
| 9292 | CG | ARG | B | 219 | 40.966 | 20.572 | 81.082 | 1.00 | 15.82 |
| 9295 | CD | ARG | B | 219 | 40.768 | 21.374 | 79.787 | 1.00 | 16.72 |
| 9298 | NE | ARG | B | 219 | 39.757 | 20.810 | 78.892 | 1.00 | 17.91 |
| 9300 | CZ | ARG | B | 219 | 39.388 | 21.361 | 77.728 | 1.00 | 18.69 |
| 9301 | NH1 | ARG | B | 219 | 38.454 | 20.776 | 76.987 | 1.00 | 19.32 |
| 9304 | NH2 | ARG | B | 219 | 39.956 | 22.481 | 77.289 | 1.00 | 18.71 |
| 9307 | C | ARG | B | 219 | 43.248 | 21.319 | 84.124 | 1.00 | 14.55 |
| 9308 | O | ARG | B | 219 | 44.387 | 20.889 | 83.946 | 1.00 | 14.82 |
| 9309 | N | THR | B | 220 | 42.987 | 22.394 | 84.868 | 1.00 | 13.83 |
| 9311 | CA | THR | B | 220 | 44.032 | 23.312 | 85.348 | 1.00 | 13.14 |
| 9313 | CB | THR | B | 220 | 43.661 | 24.773 | 84.998 | 1.00 | 13.19 |
| 9315 | OG1 | THR | B | 220 | 42.459 | 25.158 | 85.684 | 1.00 | 12.44 |
| 9317 | CG2 | THR | B | 220 | 43.329 | 24.940 | 83.509 | 1.00 | 13.21 |
| 9321 | C | THR | B | 220 | 44.296 | 23.251 | 86.856 | 1.00 | 12.67 |
| 9322 | O | THR | B | 220 | 45.337 | 23.696 | 87.316 | 1.00 | 12.48 |
| 9323 | N | GLY | B | 221 | 43.339 | 22.734 | 87.620 | 1.00 | 12.42 |

FIGURE 3 (Cont.)

| A | B | C | D | E | F | G | H | I | J |
|---|---|---|---|---|---|---|---|---|---|
| 9325 | CA | GLY | B | 221 | 43.407 | 22.752 | 89.071 | 1.00 | 12.41 |
| 9328 | C | GLY | B | 221 | 43.177 | 24.117 | 89.707 | 1.00 | 12.24 |
| 9329 | O | GLY | B | 221 | 43.396 | 24.277 | 90.906 | 1.00 | 11.95 |
| 9330 | N | LEU | B | 222 | 42.727 | 25.091 | 88.917 | 1.00 | 12.05 |
| 9332 | CA | LEU | B | 222 | 42.446 | 26.435 | 89.419 | 1.00 | 12.30 |
| 9334 | CB | LEU | B | 222 | 42.670 | 27.481 | 88.324 | 1.00 | 12.36 |
| 9337 | CG | LEU | B | 222 | 44.091 | 27.519 | 87.756 | 1.00 | 13.59 |
| 9339 | CD1 | LEU | B | 222 | 44.129 | 28.289 | 86.436 | 1.00 | 14.04 |
| 9343 | CD2 | LEU | B | 222 | 45.071 | 28.113 | 88.771 | 1.00 | 14.36 |
| 9347 | C | LEU | B | 222 | 41.012 | 26.498 | 89.911 | 1.00 | 12.13 |
| 9348 | O | LEU | B | 222 | 40.094 | 26.087 | 89.200 | 1.00 | 11.85 |
| 9349 | N | ASP | B | 223 | 40.833 | 26.994 | 91.135 | 1.00 | 12.02 |
| 9351 | CA | ASP | B | 223 | 39.519 | 27.138 | 91.754 | 1.00 | 12.14 |
| 9353 | CB | ASP | B | 223 | 39.471 | 26.342 | 93.068 | 1.00 | 11.93 |
| 9356 | CG | ASP | B | 223 | 38.082 | 25.790 | 93.384 | 1.00 | 11.97 |
| 9357 | OD1 | ASP | B | 223 | 37.987 | 24.833 | 94.183 | 1.00 | 11.89 |
| 9358 | OD2 | ASP | B | 223 | 37.031 | 26.247 | 92.899 | 1.00 | 10.32 |
| 9359 | C | ASP | B | 223 | 39.239 | 28.631 | 91.984 | 1.00 | 12.32 |
| 9360 | O | ASP | B | 223 | 40.058 | 29.477 | 91.634 | 1.00 | 12.25 |
| 9361 | N | PHE | B | 224 | 38.086 | 28.948 | 92.569 | 1.00 | 12.69 |
| 9363 | CA | PHE | B | 224 | 37.647 | 30.336 | 92.745 | 1.00 | 13.02 |
| 9365 | CB | PHE | B | 224 | 36.286 | 30.373 | 93.443 | 1.00 | 13.24 |
| 9368 | CG | PHE | B | 224 | 35.153 | 29.902 | 92.577 | 1.00 | 13.94 |
| 9369 | CD1 | PHE | B | 224 | 34.698 | 30.690 | 91.531 | 1.00 | 14.51 |
| 9371 | CE1 | PHE | B | 224 | 33.655 | 30.263 | 90.720 | 1.00 | 15.63 |
| 9373 | CZ | PHE | B | 224 | 33.058 | 29.032 | 90.951 | 1.00 | 15.40 |
| 9375 | CE2 | PHE | B | 224 | 33.507 | 28.234 | 91.993 | 1.00 | 15.09 |
| 9377 | CD2 | PHE | B | 224 | 34.551 | 28.670 | 92.800 | 1.00 | 14.33 |
| 9379 | C | PHE | B | 224 | 38.646 | 31.202 | 93.512 | 1.00 | 13.10 |
| 9380 | O | PHE | B | 224 | 38.813 | 32.376 | 93.201 | 1.00 | 13.05 |
| 9381 | N | ALA | B | 225 | 39.319 | 30.610 | 94.494 | 1.00 | 13.22 |
| 9383 | CA | ALA | B | 225 | 40.250 | 31.336 | 95.360 | 1.00 | 13.27 |
| 9385 | CB | ALA | B | 225 | 40.488 | 30.553 | 96.640 | 1.00 | 13.53 |
| 9389 | C | ALA | B | 225 | 41.584 | 31.649 | 94.678 | 1.00 | 13.23 |
| 9390 | O | ALA | B | 225 | 42.364 | 32.459 | 95.184 | 1.00 | 13.13 |
| 9391 | N | ASP | B | 226 | 41.849 | 30.999 | 93.546 | 1.00 | 12.84 |
| 9393 | CA | ASP | B | 226 | 42.994 | 31.335 | 92.701 | 1.00 | 12.64 |
| 9395 | CB | ASP | B | 226 | 43.405 | 30.119 | 91.872 | 1.00 | 12.88 |
| 9398 | CG | ASP | B | 226 | 43.757 | 28.935 | 92.738 | 1.00 | 13.26 |
| 9399 | OD1 | ASP | B | 226 | 43.252 | 27.830 | 92.485 | 1.00 | 13.56 |
| 9400 | OD2 | ASP | B | 226 | 44.516 | 29.029 | 93.715 | 1.00 | 13.82 |
| 9401 | C | ASP | B | 226 | 42.721 | 32.520 | 91.772 | 1.00 | 12.31 |
| 9402 | O | ASP | B | 226 | 43.640 | 33.031 | 91.136 | 1.00 | 12.04 |
| 9403 | N | TYR | B | 227 | 41.459 | 32.937 | 91.688 | 1.00 | 11.92 |
| 9405 | CA | TYR | B | 227 | 41.071 | 34.098 | 90.898 | 1.00 | 11.80 |
| 9407 | CB | TYR | B | 227 | 39.820 | 33.787 | 90.073 | 1.00 | 11.60 |
| 9410 | CG | TYR | B | 227 | 40.164 | 32.964 | 88.860 | 1.00 | 11.30 |
| 9411 | CD1 | TYR | B | 227 | 40.058 | 31.571 | 88.879 | 1.00 | 10.87 |
| 9413 | CE1 | TYR | B | 227 | 40.400 | 30.815 | 87.763 | 1.00 | 10.94 |
| 9415 | CZ | TYR | B | 227 | 40.872 | 31.460 | 86.628 | 1.00 | 10.42 |
| 9416 | OH | TYR | B | 227 | 41.227 | 30.747 | 85.511 | 1.00 | 10.39 |
| 9418 | CE2 | TYR | B | 227 | 40.998 | 32.834 | 86.602 | 1.00 | 10.76 |

FIGURE 3 (Cont.)

| A | B | C | D | E | F | G | H | I | J |
|---|---|---|---|---|---|---|---|---|---|
| 9420 | CD2 | TYR | B | 227 | 40.647 | 33.575 | 87.709 | 1.00 | 10.43 |
| 9422 | C | TYR | B | 227 | 40.840 | 35.309 | 91.788 | 1.00 | 11.87 |
| 9423 | O | TYR | B | 227 | 40.184 | 35.219 | 92.820 | 1.00 | 11.61 |
| 9424 | N | ASP | B | 228 | 41.407 | 36.437 | 91.381 | 1.00 | 12.06 |
| 9426 | CA | ASP | B | 228 | 41.164 | 37.703 | 92.055 | 1.00 | 12.40 |
| 9428 | CB | ASP | B | 228 | 42.321 | 38.657 | 91.787 | 1.00 | 12.45 |
| 9431 | CG | ASP | B | 228 | 43.646 | 38.081 | 92.245 | 1.00 | 13.07 |
| 9432 | OD1 | ASP | B | 228 | 43.906 | 38.090 | 93.465 | 1.00 | 13.16 |
| 9433 | OD2 | ASP | B | 228 | 44.472 | 37.569 | 91.465 | 1.00 | 12.77 |
| 9434 | C | ASP | B | 228 | 39.831 | 38.301 | 91.617 | 1.00 | 12.35 |
| 9435 | O | ASP | B | 228 | 39.200 | 39.038 | 92.366 | 1.00 | 12.19 |
| 9436 | N | ALA | B | 229 | 39.398 | 37.976 | 90.402 | 1.00 | 12.37 |
| 9438 | CA | ALA | B | 229 | 38.078 | 38.388 | 89.935 | 1.00 | 12.31 |
| 9440 | CB | ALA | B | 229 | 38.113 | 39.839 | 89.468 | 1.00 | 12.24 |
| 9444 | C | ALA | B | 229 | 37.570 | 37.491 | 88.818 | 1.00 | 12.51 |
| 9445 | O | ALA | B | 229 | 38.354 | 36.891 | 88.088 | 1.00 | 12.16 |
| 9446 | N | LEU | B | 230 | 36.247 | 37.402 | 88.711 | 1.00 | 12.87 |
| 9448 | CA | LEU | B | 230 | 35.575 | 36.737 | 87.597 | 1.00 | 13.18 |
| 9450 | CB | LEU | B | 230 | 34.811 | 35.496 | 88.070 | 1.00 | 13.40 |
| 9453 | CG | LEU | B | 230 | 35.655 | 34.314 | 88.566 | 1.00 | 14.93 |
| 9455 | CD1 | LEU | B | 230 | 34.751 | 33.150 | 88.953 | 1.00 | 16.11 |
| 9459 | CD2 | LEU | B | 230 | 36.668 | 33.873 | 87.525 | 1.00 | 15.46 |
| 9463 | C | LEU | B | 230 | 34.606 | 37.728 | 86.965 | 1.00 | 12.98 |
| 9464 | O | LEU | B | 230 | 33.681 | 38.209 | 87.628 | 1.00 | 13.35 |
| 9465 | N | ALA | B | 231 | 34.845 | 38.052 | 85.697 | 1.00 | 12.47 |
| 9467 | CA | ALA | B | 231 | 33.966 | 38.908 | 84.912 | 1.00 | 11.96 |
| 9469 | CB | ALA | B | 231 | 34.775 | 39.866 | 84.082 | 1.00 | 12.13 |
| 9473 | C | ALA | B | 231 | 33.099 | 38.037 | 84.013 | 1.00 | 11.63 |
| 9474 | O | ALA | B | 231 | 33.562 | 37.032 | 83.472 | 1.00 | 11.43 |
| 9475 | N | PHE | B | 232 | 31.847 | 38.444 | 83.856 | 1.00 | 10.96 |
| 9477 | CA | PHE | B | 232 | 30.842 | 37.671 | 83.145 | 1.00 | 10.45 |
| 9479 | CB | PHE | B | 232 | 29.731 | 37.250 | 84.109 | 1.00 | 10.39 |
| 9482 | CG | PHE | B | 232 | 30.135 | 36.181 | 85.087 | 1.00 | 10.02 |
| 9483 | CD1 | PHE | B | 232 | 29.734 | 34.864 | 84.897 | 1.00 | 10.15 |
| 9485 | CE1 | PHE | B | 232 | 30.090 | 33.873 | 85.801 | 1.00 | 10.15 |
| 9487 | CZ | PHE | B | 232 | 30.842 | 34.192 | 86.911 | 1.00 | 9.24 |
| 9489 | CE2 | PHE | B | 232 | 31.244 | 35.501 | 87.121 | 1.00 | 10.42 |
| 9491 | CD2 | PHE | B | 232 | 30.879 | 36.497 | 86.210 | 1.00 | 9.64 |
| 9493 | C | PHE | B | 232 | 30.207 | 38.510 | 82.057 | 1.00 | 10.11 |
| 9494 | O | PHE | B | 232 | 30.177 | 39.740 | 82.137 | 1.00 | 9.51 |
| 9495 | N | HIS | B | 233 | 29.676 | 37.826 | 81.052 | 1.00 | 9.65 |
| 9497 | CA | HIS | B | 233 | 28.726 | 38.423 | 80.133 | 1.00 | 9.55 |
| 9499 | CB | HIS | B | 233 | 28.221 | 37.365 | 79.159 | 1.00 | 9.43 |
| 9502 | CG | HIS | B | 233 | 27.075 | 37.816 | 78.317 | 1.00 | 9.44 |
| 9503 | ND1 | HIS | B | 233 | 27.225 | 38.709 | 77.281 | 1.00 | 9.43 |
| 9505 | CE1 | HIS | B | 233 | 26.050 | 38.923 | 76.718 | 1.00 | 10.27 |
| 9507 | NE2 | HIS | B | 233 | 25.142 | 38.207 | 77.356 | 1.00 | 9.92 |
| 9509 | CD2 | HIS | B | 233 | 25.757 | 37.508 | 78.363 | 1.00 | 9.87 |
| 9511 | C | HIS | B | 233 | 27.564 | 38.966 | 80.961 | 1.00 | 9.54 |
| 9512 | O | HIS | B | 233 | 27.012 | 38.251 | 81.796 | 1.00 | 9.46 |
| 9513 | N | ILE | B | 234 | 27.226 | 40.237 | 80.752 | 1.00 | 9.46 |
| 9515 | CA | ILE | B | 234 | 26.168 | 40.901 | 81.517 | 1.00 | 9.58 |

FIGURE 3 (Cont.)

| A | B | C | D | E | F | G | H | I | J |
|---|---|---|---|---|---|---|---|---|---|
| 9517 | CB | ILE | B | 234 | 26.711 | 42.167 | 82.238 | 1.00 | 9.69 |
| 9519 | CG1 | ILE | B | 234 | 27.935 | 41.832 | 83.093 | 1.00 | 10.53 |
| 9522 | CD1 | ILE | B | 234 | 28.853 | 43.025 | 83.350 | 1.00 | 11.26 |
| 9526 | CG2 | ILE | B | 234 | 25.629 | 42.780 | 83.134 | 1.00 | 9.85 |
| 9530 | C | ILE | B | 234 | 24.970 | 41.270 | 80.626 | 1.00 | 9.38 |
| 9531 | O | ILE | B | 234 | 24.897 | 42.384 | 80.103 | 1.00 | 9.22 |
| 9532 | N | PRO | B | 235 | 24.023 | 40.347 | 80.467 | 1.00 | 9.19 |
| 9533 | CA | PRO | B | 235 | 22.780 | 40.647 | 79.746 | 1.00 | 9.31 |
| 9535 | CB | PRO | B | 235 | 22.176 | 39.265 | 79.498 | 1.00 | 9.11 |
| 9538 | CG | PRO | B | 235 | 22.689 | 38.414 | 80.622 | 1.00 | 9.23 |
| 9541 | CD | PRO | B | 235 | 24.036 | 38.967 | 80.989 | 1.00 | 9.32 |
| 9544 | C | PRO | B | 235 | 21.870 | 41.477 | 80.637 | 1.00 | 9.27 |
| 9545 | O | PRO | B | 235 | 21.117 | 42.339 | 80.195 | 1.00 | 9.40 |
| 9546 | N | TYR | B | 236 | 21.927 | 41.135 | 81.912 | 1.00 | 9.51 |
| 9548 | CA | TYR | B | 236 | 21.474 | 41.979 | 82.986 | 1.00 | 9.69 |
| 9550 | CB | TYR | B | 236 | 19.975 | 41.835 | 83.239 | 1.00 | 9.64 |
| 9553 | CG | TYR | B | 236 | 19.480 | 40.433 | 83.509 | 1.00 | 9.86 |
| 9554 | CD1 | TYR | B | 236 | 19.296 | 39.979 | 84.812 | 1.00 | 9.65 |
| 9556 | CE1 | TYR | B | 236 | 18.822 | 38.703 | 85.068 | 1.00 | 10.77 |
| 9558 | CZ | TYR | B | 236 | 18.510 | 37.864 | 84.015 | 1.00 | 10.56 |
| 9559 | OH | TYR | B | 236 | 18.035 | 36.599 | 84.276 | 1.00 | 12.52 |
| 9561 | CE2 | TYR | B | 236 | 18.673 | 38.294 | 82.711 | 1.00 | 10.29 |
| 9563 | CD2 | TYR | B | 236 | 19.149 | 39.578 | 82.465 | 1.00 | 10.48 |
| 9565 | C | TYR | B | 236 | 22.296 | 41.606 | 84.206 | 1.00 | 9.87 |
| 9566 | O | TYR | B | 236 | 22.907 | 40.543 | 84.290 | 1.00 | 9.76 |
| 9567 | N | THR | B | 237 | 22.286 | 42.505 | 85.161 | 1.00 | 10.01 |
| 9569 | CA | THR | B | 237 | 23.284 | 42.547 | 86.200 | 1.00 | 10.41 |
| 9571 | CB | THR | B | 237 | 23.126 | 43.941 | 86.863 | 1.00 | 10.73 |
| 9573 | OG1 | THR | B | 237 | 24.192 | 44.811 | 86.445 | 1.00 | 12.28 |
| 9575 | CG2 | THR | B | 237 | 23.168 | 43.901 | 88.323 | 1.00 | 10.41 |
| 9579 | C | THR | B | 237 | 23.183 | 41.345 | 87.169 | 1.00 | 10.48 |
| 9580 | O | THR | B | 237 | 24.196 | 40.837 | 87.656 | 1.00 | 10.20 |
| 9581 | N | LYS | B | 238 | 21.969 | 40.859 | 87.402 | 1.00 | 10.60 |
| 9583 | CA | LYS | B | 238 | 21.768 | 39.712 | 88.284 | 1.00 | 11.06 |
| 9585 | CB | LYS | B | 238 | 20.328 | 39.688 | 88.815 | 1.00 | 11.36 |
| 9588 | CG | LYS | B | 238 | 20.075 | 40.664 | 89.953 | 1.00 | 12.65 |
| 9591 | CD | LYS | B | 238 | 20.697 | 40.181 | 91.264 | 1.00 | 14.34 |
| 9594 | CE | LYS | B | 238 | 20.327 | 41.074 | 92.454 | 1.00 | 15.41 |
| 9597 | NZ | LYS | B | 238 | 20.268 | 42.537 | 92.119 | 1.00 | 16.16 |
| 9601 | C | LYS | B | 238 | 22.103 | 38.367 | 87.631 | 1.00 | 11.04 |
| 9602 | O | LYS | B | 238 | 22.213 | 37.364 | 88.329 | 1.00 | 10.95 |
| 9603 | N | MSE | B | 239 | 22.260 | 38.334 | 86.308 | 1.00 | 11.06 |
| 9605 | CA | MSE | B | 239 | 22.489 | 37.072 | 85.599 | 1.00 | 11.30 |
| 9607 | CB | MSE | B | 239 | 22.501 | 37.288 | 84.080 | 1.00 | 11.48 |
| 9610 | CG | MSE | B | 239 | 22.619 | 35.995 | 83.280 | 1.00 | 11.86 |
| 9613 | SE | MSE | B | 239 | 21.003 | 34.920 | 83.420 | 1.00 | 13.22 |
| 9614 | CE | MSE | B | 239 | 21.628 | 33.500 | 84.587 | 1.00 | 13.65 |
| 9618 | C | MSE | B | 239 | 23.789 | 36.400 | 86.026 | 1.00 | 11.42 |
| 9619 | O | MSE | B | 239 | 23.797 | 35.227 | 86.406 | 1.00 | 11.28 |
| 9620 | N | GLY | B | 240 | 24.884 | 37.148 | 85.957 | 1.00 | 11.70 |
| 9622 | CA | GLY | B | 240 | 26.185 | 36.640 | 86.342 | 1.00 | 11.90 |
| 9625 | C | GLY | B | 240 | 26.202 | 36.261 | 87.809 | 1.00 | 12.32 |

FIGURE 3 (Cont.)

| A | B | C | D | E | F | G | H | I | J |
|---|---|---|---|---|---|---|---|---|---|
| 9626 | O | GLY | B | 240 | 26.809 | 35.258 | 88.182 | 1.00 | 12.10 |
| 9627 | N | LYS | B | 241 | 25.526 | 37.054 | 88.638 | 1.00 | 12.67 |
| 9629 | CA | LYS | B | 241 | 25.439 | 36.755 | 90.064 | 1.00 | 13.33 |
| 9631 | CB | LYS | B | 241 | 24.703 | 37.855 | 90.838 | 1.00 | 13.49 |
| 9634 | CG | LYS | B | 241 | 24.996 | 37.802 | 92.328 | 1.00 | 14.46 |
| 9637 | CD | LYS | B | 241 | 24.093 | 38.700 | 93.136 | 1.00 | 15.93 |
| 9640 | CE | LYS | B | 241 | 24.395 | 38.583 | 94.621 | 1.00 | 16.69 |
| 9643 | NZ | LYS | B | 241 | 23.324 | 39.191 | 95.457 | 1.00 | 17.43 |
| 9647 | C | LYS | B | 241 | 24.762 | 35.412 | 90.317 | 1.00 | 13.31 |
| 9648 | O | LYS | B | 241 | 25.223 | 34.648 | 91.153 | 1.00 | 13.59 |
| 9649 | N | LYS | B | 242 | 23.685 | 35.125 | 89.595 | 1.00 | 13.43 |
| 9651 | CA | LYS | B | 242 | 22.974 | 33.851 | 89.734 | 1.00 | 13.58 |
| 9653 | CB | LYS | B | 242 | 21.699 | 33.844 | 88.885 | 1.00 | 13.58 |
| 9656 | CG | LYS | B | 242 | 20.546 | 34.641 | 89.490 | 1.00 | 13.46 |
| 9659 | CD | LYS | B | 242 | 19.260 | 34.464 | 88.697 | 1.00 | 13.68 |
| 9662 | CE | LYS | B | 242 | 19.318 | 35.149 | 87.339 | 1.00 | 13.49 |
| 9665 | NZ | LYS | B | 242 | 18.020 | 35.052 | 86.623 | 1.00 | 12.97 |
| 9669 | C | LYS | B | 242 | 23.852 | 32.660 | 89.348 | 1.00 | 13.76 |
| 9670 | O | LYS | B | 242 | 23.845 | 31.634 | 90.029 | 1.00 | 13.68 |
| 9671 | N | ALA | B | 243 | 24.599 | 32.797 | 88.255 | 1.00 | 13.88 |
| 9673 | CA | ALA | B | 243 | 25.510 | 31.749 | 87.795 | 1.00 | 14.31 |
| 9675 | CB | ALA | B | 243 | 26.128 | 32.139 | 86.454 | 1.00 | 14.25 |
| 9679 | C | ALA | B | 243 | 26.608 | 31.505 | 88.829 | 1.00 | 14.55 |
| 9680 | O | ALA | B | 243 | 26.975 | 30.362 | 89.113 | 1.00 | 14.25 |
| 9681 | N | LEU | B | 244 | 27.104 | 32.600 | 89.395 | 1.00 | 15.17 |
| 9683 | CA | LEU | B | 244 | 28.164 | 32.575 | 90.396 | 1.00 | 15.68 |
| 9685 | CB | LEU | B | 244 | 28.638 | 34.010 | 90.678 | 1.00 | 15.95 |
| 9688 | CG | LEU | B | 244 | 30.040 | 34.265 | 91.227 | 1.00 | 16.54 |
| 9690 | CD1 | LEU | B | 244 | 31.084 | 33.413 | 90.532 | 1.00 | 16.65 |
| 9694 | CD2 | LEU | B | 244 | 30.368 | 35.751 | 91.089 | 1.00 | 17.30 |
| 9698 | C | LEU | B | 244 | 27.669 | 31.907 | 91.679 | 1.00 | 15.97 |
| 9699 | O | LEU | B | 244 | 28.309 | 30.994 | 92.189 | 1.00 | 16.02 |
| 9700 | N | LEU | B | 245 | 26.514 | 32.353 | 92.173 | 1.00 | 16.37 |
| 9702 | CA | LEU | B | 245 | 25.910 | 31.817 | 93.396 | 1.00 | 16.67 |
| 9704 | CB | LEU | B | 245 | 24.583 | 32.527 | 93.701 | 1.00 | 16.81 |
| 9707 | CG | LEU | B | 245 | 24.663 | 33.950 | 94.269 | 1.00 | 17.19 |
| 9709 | CD1 | LEU | B | 245 | 23.293 | 34.612 | 94.197 | 1.00 | 17.78 |
| 9713 | CD2 | LEU | B | 245 | 25.187 | 33.960 | 95.702 | 1.00 | 16.92 |
| 9717 | C | LEU | B | 245 | 25.667 | 30.309 | 93.322 | 1.00 | 16.87 |
| 9718 | O | LEU | B | 245 | 25.772 | 29.611 | 94.329 | 1.00 | 16.98 |
| 9719 | N | ALA | B | 246 | 25.356 | 29.811 | 92.128 | 1.00 | 16.87 |
| 9721 | CA | ALA | B | 246 | 25.081 | 28.390 | 91.933 | 1.00 | 16.98 |
| 9723 | CB | ALA | B | 246 | 24.443 | 28.163 | 90.568 | 1.00 | 17.00 |
| 9727 | C | ALA | B | 246 | 26.326 | 27.507 | 92.087 | 1.00 | 17.08 |
| 9728 | O | ALA | B | 246 | 26.197 | 26.299 | 92.285 | 1.00 | 17.26 |
| 9729 | N | LYS | B | 247 | 27.517 | 28.104 | 91.993 | 1.00 | 17.02 |
| 9731 | CA | LYS | B | 247 | 28.778 | 27.357 | 92.017 | 1.00 | 17.11 |
| 9733 | CB | LYS | B | 247 | 29.562 | 27.634 | 90.725 | 1.00 | 17.29 |
| 9736 | CG | LYS | B | 247 | 28.890 | 27.154 | 89.446 | 1.00 | 17.21 |
| 9739 | CD | LYS | B | 247 | 28.682 | 25.640 | 89.405 | 1.00 | 17.61 |
| 9742 | CE | LYS | B | 247 | 29.958 | 24.884 | 89.068 | 1.00 | 18.09 |
| 9745 | NZ | LYS | B | 247 | 29.822 | 23.424 | 89.351 | 1.00 | 17.65 |

FIGURE 3 (Cont.)

| A | B | C | D | E | F | G | H | I | J |
|---|---|---|---|---|---|---|---|---|---|
| 9749 | C | LYS | B | 247 | 29.707 | 27.616 | 93.213 | 1.00 | 17.17 |
| 9750 | O | LYS | B | 247 | 30.620 | 26.830 | 93.442 | 1.00 | 17.01 |
| 9751 | N | ILE | B | 248 | 29.490 | 28.695 | 93.967 | 1.00 | 17.30 |
| 9753 | CA | ILE | B | 248 | 30.420 | 29.083 | 95.040 | 1.00 | 17.63 |
| 9755 | CB | ILE | B | 248 | 30.757 | 30.604 | 94.963 | 1.00 | 17.44 |
| 9757 | CG1 | ILE | B | 248 | 29.527 | 31.464 | 95.300 | 1.00 | 17.33 |
| 9760 | CD1 | ILE | B | 248 | 29.787 | 32.965 | 95.291 | 1.00 | 17.80 |
| 9764 | CG2 | ILE | B | 248 | 31.338 | 30.946 | 93.598 | 1.00 | 17.61 |
| 9768 | C | ILE | B | 248 | 29.942 | 28.736 | 96.456 | 1.00 | 18.10 |
| 9769 | O | ILE | B | 248 | 30.551 | 29.172 | 97.432 | 1.00 | 17.86 |
| 9770 | N | SER | B | 249 | 28.867 | 27.960 | 96.569 | 1.00 | 18.95 |
| 9772 | CA | SER | B | 249 | 28.274 | 27.649 | 97.874 | 1.00 | 19.77 |
| 9774 | CB | SER | B | 249 | 26.889 | 27.016 | 97.703 | 1.00 | 19.89 |
| 9777 | OG | SER | B | 249 | 26.989 | 25.664 | 97.292 | 1.00 | 20.20 |
| 9779 | C | SER | B | 249 | 29.152 | 26.747 | 98.751 | 1.00 | 20.41 |
| 9780 | O | SER | B | 249 | 28.993 | 26.741 | 99.971 | 1.00 | 20.61 |
| 9781 | N | ASP | B | 250 | 30.062 | 25.987 | 98.136 | 1.00 | 21.13 |
| 9783 | CA | ASP | B | 250 | 31.032 | 25.172 | 98.889 | 1.00 | 21.79 |
| 9785 | CB | ASP | B | 250 | 31.341 | 23.834 | 98.177 | 1.00 | 22.12 |
| 9788 | CG | ASP | B | 250 | 31.828 | 23.997 | 96.733 | 1.00 | 23.96 |
| 9789 | OD1 | ASP | B | 250 | 32.225 | 25.113 | 96.317 | 1.00 | 26.33 |
| 9790 | OD2 | ASP | B | 250 | 31.849 | 23.030 | 95.934 | 1.00 | 26.36 |
| 9791 | C | ASP | B | 250 | 32.329 | 25.914 | 99.267 | 1.00 | 21.67 |
| 9792 | O | ASP | B | 250 | 33.219 | 25.335 | 99.890 | 1.00 | 21.87 |
| 9793 | N | GLN | B | 251 | 32.416 | 27.196 | 98.913 | 1.00 | 21.36 |
| 9795 | CA | GLN | B | 251 | 33.553 | 28.039 | 99.276 | 1.00 | 21.05 |
| 9797 | CB | GLN | B | 251 | 33.710 | 29.179 | 98.266 | 1.00 | 21.07 |
| 9800 | CG | GLN | B | 251 | 33.864 | 28.718 | 96.821 | 1.00 | 20.67 |
| 9803 | CD | GLN | B | 251 | 35.131 | 27.922 | 96.603 | 1.00 | 19.66 |
| 9804 | OE1 | GLN | B | 251 | 36.223 | 28.398 | 96.905 | 1.00 | 19.19 |
| 9805 | NE2 | GLN | B | 251 | 34.991 | 26.707 | 96.088 | 1.00 | 19.49 |
| 9808 | C | GLN | B | 251 | 33.354 | 28.631 | 100.664 | 1.00 | 21.04 |
| 9809 | O | GLN | B | 251 | 32.227 | 28.721 | 101.144 | 1.00 | 20.86 |
| 9810 | N | THR | B | 252 | 34.446 | 29.059 | 101.295 | 1.00 | 21.07 |
| 9812 | CA | THR | B | 252 | 34.368 | 29.679 | 102.618 | 1.00 | 21.21 |
| 9814 | CB | THR | B | 252 | 35.770 | 29.980 | 103.212 | 1.00 | 21.24 |
| 9816 | OG1 | THR | B | 252 | 36.452 | 30.948 | 102.406 | 1.00 | 20.75 |
| 9818 | CG2 | THR | B | 252 | 36.687 | 28.742 | 103.190 | 1.00 | 21.40 |
| 9822 | C | THR | B | 252 | 33.572 | 30.975 | 102.522 | 1.00 | 21.63 |
| 9823 | O | THR | B | 252 | 33.418 | 31.541 | 101.436 | 1.00 | 21.21 |
| 9824 | N | GLU | B | 253 | 33.072 | 31.438 | 103.661 | 1.00 | 21.89 |
| 9826 | CA | GLU | B | 253 | 32.294 | 32.666 | 103.705 | 1.00 | 22.40 |
| 9828 | CB | GLU | B | 253 | 31.747 | 32.911 | 105.118 | 1.00 | 22.87 |
| 9831 | CG | GLU | B | 253 | 30.769 | 34.079 | 105.227 | 1.00 | 24.62 |
| 9834 | CD | GLU | B | 253 | 29.602 | 33.978 | 104.255 | 1.00 | 26.67 |
| 9835 | OE1 | GLU | B | 253 | 29.070 | 32.860 | 104.069 | 1.00 | 28.15 |
| 9836 | OE2 | GLU | B | 253 | 29.220 | 35.020 | 103.673 | 1.00 | 28.42 |
| 9837 | C | GLU | B | 253 | 33.129 | 33.857 | 103.243 | 1.00 | 22.09 |
| 9838 | O | GLU | B | 253 | 32.623 | 34.728 | 102.538 | 1.00 | 22.02 |
| 9839 | N | ALA | B | 254 | 34.401 | 33.887 | 103.637 | 1.00 | 21.61 |
| 9841 | CA | ALA | B | 254 | 35.306 | 34.961 | 103.245 | 1.00 | 21.48 |
| 9843 | CB | ALA | B | 254 | 36.631 | 34.842 | 103.988 | 1.00 | 21.61 |

FIGURE 3 (Cont.)

| A | B | C | D | E | F | G | H | I | J |
|---|---|---|---|---|---|---|---|---|---|
| 9847 | C | ALA | B | 254 | 35.542 | 34.976 | 101.733 | 1.00 | 21.28 |
| 9848 | O | ALA | B | 254 | 35.599 | 36.042 | 101.125 | 1.00 | 21.21 |
| 9849 | N | GLU | B | 255 | 35.670 | 33.792 | 101.136 | 1.00 | 20.97 |
| 9851 | CA | GLU | B | 255 | 35.878 | 33.667 | 99.692 | 1.00 | 20.88 |
| 9853 | CB | GLU | B | 255 | 36.275 | 32.224 | 99.328 | 1.00 | 20.75 |
| 9856 | CG | GLU | B | 255 | 36.326 | 31.907 | 97.835 | 1.00 | 20.76 |
| 9859 | CD | GLU | B | 255 | 37.194 | 32.866 | 97.039 | 1.00 | 20.55 |
| 9860 | OE1 | GLU | B | 255 | 38.149 | 33.435 | 97.609 | 1.00 | 19.77 |
| 9861 | OE2 | GLU | B | 255 | 36.920 | 33.047 | 95.834 | 1.00 | 20.80 |
| 9862 | C | GLU | B | 255 | 34.633 | 34.098 | 98.909 | 1.00 | 20.78 |
| 9863 | O | GLU | B | 255 | 34.742 | 34.801 | 97.909 | 1.00 | 20.30 |
| 9864 | N | GLN | B | 256 | 33.461 | 33.669 | 99.370 | 1.00 | 20.90 |
| 9866 | CA | GLN | B | 256 | 32.192 | 34.043 | 98.750 | 1.00 | 21.09 |
| 9868 | CB | GLN | B | 256 | 31.015 | 33.369 | 99.466 | 1.00 | 21.04 |
| 9871 | CG | GLN | B | 256 | 30.895 | 31.871 | 99.214 | 1.00 | 20.92 |
| 9874 | CD | GLN | B | 256 | 29.707 | 31.247 | 99.935 | 1.00 | 21.13 |
| 9875 | OE1 | GLN | B | 256 | 28.607 | 31.797 | 99.920 | 1.00 | 20.92 |
| 9876 | NE2 | GLN | B | 256 | 29.928 | 30.098 | 100.567 | 1.00 | 21.13 |
| 9879 | C | GLN | B | 256 | 32.009 | 35.559 | 98.769 | 1.00 | 21.39 |
| 9880 | O | GLN | B | 256 | 31.587 | 36.143 | 97.777 | 1.00 | 21.13 |
| 9881 | N | GLU | B | 257 | 32.348 | 36.190 | 99.894 | 1.00 | 21.79 |
| 9883 | CA | GLU | B | 257 | 32.199 | 37.639 | 100.053 | 1.00 | 22.32 |
| 9885 | CB | GLU | B | 257 | 32.441 | 38.062 | 101.512 | 1.00 | 22.67 |
| 9888 | CG | GLU | B | 257 | 31.194 | 37.986 | 102.387 | 1.00 | 24.60 |
| 9891 | CD | GLU | B | 257 | 31.497 | 38.057 | 103.877 | 1.00 | 27.02 |
| 9892 | OE1 | GLU | B | 257 | 32.475 | 38.734 | 104.264 | 1.00 | 28.68 |
| 9893 | OE2 | GLU | B | 257 | 30.747 | 37.439 | 104.663 | 1.00 | 29.07 |
| 9894 | C | GLU | B | 257 | 33.134 | 38.413 | 99.120 | 1.00 | 22.09 |
| 9895 | O | GLU | B | 257 | 32.752 | 39.442 | 98.571 | 1.00 | 21.87 |
| 9896 | N | ARG | B | 258 | 34.350 | 37.904 | 98.945 | 1.00 | 22.01 |
| 9898 | CA | ARG | B | 258 | 35.373 | 38.561 | 98.135 | 1.00 | 22.01 |
| 9900 | CB | ARG | B | 258 | 36.723 | 37.883 | 98.368 | 1.00 | 22.56 |
| 9903 | CG | ARG | B | 258 | 37.885 | 38.547 | 97.664 | 1.00 | 24.90 |
| 9906 | CD | ARG | B | 258 | 39.253 | 38.114 | 98.181 | 1.00 | 27.91 |
| 9909 | NE | ARG | B | 258 | 39.582 | 36.725 | 97.846 | 1.00 | 30.58 |
| 9911 | CZ | ARG | B | 258 | 39.872 | 36.275 | 96.622 | 1.00 | 32.32 |
| 9912 | NH1 | ARG | B | 258 | 39.865 | 37.088 | 95.568 | 1.00 | 33.66 |
| 9915 | NH2 | ARG | B | 258 | 40.165 | 34.992 | 96.447 | 1.00 | 33.62 |
| 9918 | C | ARG | B | 258 | 35.031 | 38.518 | 96.647 | 1.00 | 21.16 |
| 9919 | O | ARG | B | 258 | 35.134 | 39.520 | 95.943 | 1.00 | 20.98 |
| 9920 | N | ILE | B | 259 | 34.616 | 37.346 | 96.184 | 1.00 | 20.20 |
| 9922 | CA | ILE | B | 259 | 34.328 | 37.124 | 94.773 | 1.00 | 19.47 |
| 9924 | CB | ILE | B | 259 | 34.337 | 35.588 | 94.478 | 1.00 | 19.65 |
| 9926 | CG1 | ILE | B | 259 | 34.949 | 35.294 | 93.099 | 1.00 | 20.75 |
| 9929 | CD1 | ILE | B | 259 | 33.988 | 35.356 | 91.967 | 1.00 | 21.88 |
| 9933 | CG2 | ILE | B | 259 | 32.950 | 34.966 | 94.670 | 1.00 | 19.57 |
| 9937 | C | ILE | B | 259 | 33.013 | 37.815 | 94.374 | 1.00 | 18.39 |
| 9938 | O | ILE | B | 259 | 32.876 | 38.295 | 93.252 | 1.00 | 18.01 |
| 9939 | N | LEU | B | 260 | 32.069 | 37.885 | 95.311 | 1.00 | 17.19 |
| 9941 | CA | LEU | B | 260 | 30.824 | 38.620 | 95.107 | 1.00 | 16.57 |
| 9943 | CB | LEU | B | 260 | 29.790 | 38.264 | 96.180 | 1.00 | 16.55 |
| 9946 | CG | LEU | B | 260 | 29.098 | 36.910 | 96.006 | 1.00 | 16.74 |

FIGURE 3 (Cont.)

| A | B | C | D | E | F | G | H | I | J |
|---|---|---|---|---|---|---|---|---|---|
| 9948 | CD1 | LEU | B | 260 | 28.268 | 36.577 | 97.235 | 1.00 | 16.89 |
| 9952 | CD2 | LEU | B | 260 | 28.228 | 36.890 | 94.750 | 1.00 | 16.61 |
| 9956 | C | LEU | B | 260 | 31.056 | 40.129 | 95.094 | 1.00 | 15.92 |
| 9957 | O | LEU | B | 260 | 30.385 | 40.845 | 94.360 | 1.00 | 15.43 |
| 9958 | N | ALA | B | 261 | 32.004 | 40.605 | 95.902 | 1.00 | 15.12 |
| 9960 | CA | ALA | B | 261 | 32.334 | 42.028 | 95.954 | 1.00 | 14.57 |
| 9962 | CB | ALA | B | 261 | 33.229 | 42.326 | 97.144 | 1.00 | 14.69 |
| 9966 | C | ALA | B | 261 | 33.013 | 42.465 | 94.664 | 1.00 | 14.22 |
| 9967 | O | ALA | B | 261 | 32.779 | 43.568 | 94.169 | 1.00 | 13.99 |
| 9968 | N | ARG | B | 262 | 33.858 | 41.594 | 94.120 | 1.00 | 13.59 |
| 9970 | CA | ARG | B | 262 | 34.502 | 41.863 | 92.844 | 1.00 | 13.34 |
| 9972 | CB | ARG | B | 262 | 35.649 | 40.877 | 92.587 | 1.00 | 13.63 |
| 9975 | CG | ARG | B | 262 | 36.893 | 41.164 | 93.437 | 1.00 | 14.81 |
| 9978 | CD | ARG | B | 262 | 37.809 | 42.212 | 92.837 | 1.00 | 16.51 |
| 9981 | NE | ARG | B | 262 | 38.608 | 42.922 | 93.839 | 1.00 | 17.95 |
| 9983 | CZ | ARG | B | 262 | 39.720 | 42.449 | 94.406 | 1.00 | 19.42 |
| 9984 | NH1 | ARG | B | 262 | 40.370 | 43.186 | 95.299 | 1.00 | 19.80 |
| 9987 | NH2 | ARG | B | 262 | 40.186 | 41.244 | 94.100 | 1.00 | 19.98 |
| 9990 | C | ARG | B | 262 | 33.471 | 41.829 | 91.716 | 1.00 | 12.56 |
| 9991 | O | ARG | B | 262 | 33.590 | 42.584 | 90.755 | 1.00 | 12.44 |
| 9992 | N | TYR | B | 263 | 32.448 | 40.984 | 91.841 | 1.00 | 11.71 |
| 9994 | CA | TYR | B | 263 | 31.390 | 40.945 | 90.833 | 1.00 | 11.23 |
| 9996 | CB | TYR | B | 263 | 30.447 | 39.743 | 91.010 | 1.00 | 11.19 |
| 9999 | CG | TYR | B | 263 | 29.384 | 39.722 | 89.930 | 1.00 | 10.32 |
| 10000 | CD1 | TYR | B | 263 | 28.101 | 40.208 | 90.178 | 1.00 | 10.00 |
| 10002 | CE1 | TYR | B | 263 | 27.133 | 40.224 | 89.180 | 1.00 | 9.69 |
| 10004 | CZ | TYR | B | 263 | 27.448 | 39.766 | 87.911 | 1.00 | 9.66 |
| 10005 | OH | TYR | B | 263 | 26.488 | 39.785 | 86.922 | 1.00 | 9.51 |
| 10007 | CE2 | TYR | B | 263 | 28.718 | 39.293 | 87.635 | 1.00 | 10.00 |
| 10009 | CD2 | TYR | B | 263 | 29.682 | 39.279 | 88.643 | 1.00 | 9.45 |
| 10011 | C | TYR | B | 263 | 30.594 | 42.260 | 90.833 | 1.00 | 11.02 |
| 10012 | O | TYR | B | 263 | 30.283 | 42.793 | 89.770 | 1.00 | 10.51 |
| 10013 | N | GLU | B | 264 | 30.284 | 42.788 | 92.017 | 1.00 | 10.83 |
| 10015 | CA | GLU | B | 264 | 29.582 | 44.075 | 92.122 | 1.00 | 11.08 |
| 10017 | CB | GLU | B | 264 | 29.341 | 44.461 | 93.586 | 1.00 | 10.98 |
| 10020 | CG | GLU | B | 264 | 28.317 | 43.593 | 94.290 | 1.00 | 12.06 |
| 10023 | CD | GLU | B | 264 | 26.958 | 43.640 | 93.620 | 1.00 | 13.73 |
| 10024 | OE1 | GLU | B | 264 | 26.511 | 42.597 | 93.091 | 1.00 | 15.53 |
| 10025 | OE2 | GLU | B | 264 | 26.347 | 44.722 | 93.619 | 1.00 | 14.46 |
| 10026 | C | GLU | B | 264 | 30.337 | 45.199 | 91.411 | 1.00 | 10.96 |
| 10027 | O | GLU | B | 264 | 29.731 | 46.036 | 90.743 | 1.00 | 10.79 |
| 10028 | N | GLU | B | 265 | 31.657 | 45.206 | 91.564 | 1.00 | 10.79 |
| 10030 | CA | GLU | B | 265 | 32.516 | 46.176 | 90.893 | 1.00 | 10.77 |
| 10032 | CB | GLU | B | 265 | 33.968 | 46.003 | 91.358 | 1.00 | 10.86 |
| 10035 | CG | GLU | B | 265 | 34.229 | 46.561 | 92.753 | 1.00 | 11.45 |
| 10038 | CD | GLU | B | 265 | 35.343 | 45.854 | 93.513 | 1.00 | 12.76 |
| 10039 | OE1 | GLU | B | 265 | 36.118 | 45.086 | 92.907 | 1.00 | 12.62 |
| 10040 | OE2 | GLU | B | 265 | 35.446 | 46.076 | 94.740 | 1.00 | 13.93 |
| 10041 | C | GLU | B | 265 | 32.408 | 46.045 | 89.365 | 1.00 | 10.27 |
| 10042 | O | GLU | B | 265 | 32.420 | 47.046 | 88.650 | 1.00 | 10.26 |
| 10043 | N | SER | B | 266 | 32.280 | 44.810 | 88.881 | 1.00 | 9.89 |
| 10045 | CA | SER | B | 266 | 32.172 | 44.535 | 87.446 | 1.00 | 9.59 |

FIGURE 3 (Cont.)

| A | B | C | D | E | F | G | H | I | J |
|---|---|---|---|---|---|---|---|---|---|
| 10047 | CB | SER | B | 266 | 32.372 | 43.037 | 87.162 | 1.00 | 9.78 |
| 10050 | OG | SER | B | 266 | 31.176 | 42.300 | 87.361 | 1.00 | 8.72 |
| 10052 | C | SER | B | 266 | 30.853 | 44.996 | 86.805 | 1.00 | 9.37 |
| 10053 | O | SER | B | 266 | 30.792 | 45.150 | 85.588 | 1.00 | 9.16 |
| 10054 | N | ILE | B | 267 | 29.810 | 45.203 | 87.606 | 1.00 | 9.35 |
| 10056 | CA | ILE | B | 267 | 28.484 | 45.555 | 87.070 | 1.00 | 9.40 |
| 10058 | CB | ILE | B | 267 | 27.391 | 44.633 | 87.658 | 1.00 | 9.40 |
| 10060 | CG1 | ILE | B | 267 | 27.391 | 44.700 | 89.190 | 1.00 | 9.84 |
| 10063 | CD1 | ILE | B | 267 | 26.089 | 44.326 | 89.820 | 1.00 | 10.39 |
| 10067 | CG2 | ILE | B | 267 | 27.593 | 43.206 | 87.178 | 1.00 | 9.93 |
| 10071 | C | ILE | B | 267 | 28.089 | 47.021 | 87.269 | 1.00 | 9.15 |
| 10072 | O | ILE | B | 267 | 26.990 | 47.416 | 86.884 | 1.00 | 8.98 |
| 10073 | N | VAL | B | 268 | 28.980 | 47.825 | 87.845 | 1.00 | 8.94 |
| 10075 | CA | VAL | B | 268 | 28.699 | 49.245 | 88.099 | 1.00 | 8.61 |
| 10077 | CB | VAL | B | 268 | 29.942 | 49.967 | 88.689 | 1.00 | 8.55 |
| 10079 | CG1 | VAL | B | 268 | 29.786 | 51.487 | 88.651 | 1.00 | 8.86 |
| 10083 | CG2 | VAL | B | 268 | 30.199 | 49.494 | 90.119 | 1.00 | 8.39 |
| 10087 | C | VAL | B | 268 | 28.212 | 49.970 | 86.841 | 1.00 | 8.43 |
| 10088 | O | VAL | B | 268 | 27.147 | 50.603 | 86.849 | 1.00 | 8.13 |
| 10089 | N | TYR | B | 269 | 28.985 | 49.874 | 85.765 | 1.00 | 8.14 |
| 10091 | CA | TYR | B | 269 | 28.632 | 50.546 | 84.522 | 1.00 | 8.09 |
| 10093 | CB | TYR | B | 269 | 29.823 | 50.581 | 83.552 | 1.00 | 8.14 |
| 10096 | CG | TYR | B | 269 | 31.034 | 51.385 | 84.020 | 1.00 | 7.97 |
| 10097 | CD1 | TYR | B | 269 | 32.282 | 51.169 | 83.448 | 1.00 | 7.97 |
| 10099 | CE1 | TYR | B | 269 | 33.392 | 51.876 | 83.853 | 1.00 | 8.69 |
| 10101 | CZ | TYR | B | 269 | 33.276 | 52.829 | 84.845 | 1.00 | 8.98 |
| 10102 | OH | TYR | B | 269 | 34.392 | 53.530 | 85.236 | 1.00 | 10.02 |
| 10104 | CE2 | TYR | B | 269 | 32.054 | 53.068 | 85.442 | 1.00 | 9.30 |
| 10106 | CD2 | TYR | B | 269 | 30.938 | 52.347 | 85.031 | 1.00 | 8.73 |
| 10108 | C | TYR | B | 269 | 27.416 | 49.902 | 83.849 | 1.00 | 8.11 |
| 10109 | O | TYR | B | 269 | 26.576 | 50.606 | 83.295 | 1.00 | 8.12 |
| 10110 | N | SER | B | 270 | 27.312 | 48.577 | 83.915 | 1.00 | 8.07 |
| 10112 | CA | SER | B | 270 | 26.209 | 47.859 | 83.273 | 1.00 | 8.44 |
| 10114 | CB | SER | B | 270 | 26.425 | 46.341 | 83.334 | 1.00 | 8.39 |
| 10117 | OG | SER | B | 270 | 27.394 | 45.930 | 82.382 | 1.00 | 8.03 |
| 10119 | C | SER | B | 270 | 24.850 | 48.225 | 83.880 | 1.00 | 8.66 |
| 10120 | O | SER | B | 270 | 23.845 | 48.223 | 83.178 | 1.00 | 8.79 |
| 10121 | N | ARG | B | 271 | 24.823 | 48.562 | 85.168 | 1.00 | 8.99 |
| 10123 | CA | ARG | B | 271 | 23.591 | 49.019 | 85.821 | 1.00 | 9.35 |
| 10125 | CB | ARG | B | 271 | 23.836 | 49.327 | 87.298 | 1.00 | 9.52 |
| 10128 | CG | ARG | B | 271 | 24.149 | 48.118 | 88.171 | 1.00 | 11.24 |
| 10131 | CD | ARG | B | 271 | 24.166 | 48.446 | 89.658 | 1.00 | 13.36 |
| 10134 | NE | ARG | B | 271 | 22.805 | 48.693 | 90.112 | 1.00 | 15.53 |
| 10136 | CZ | ARG | B | 271 | 21.969 | 47.752 | 90.547 | 1.00 | 17.08 |
| 10137 | NH1 | ARG | B | 271 | 22.356 | 46.484 | 90.651 | 1.00 | 17.91 |
| 10140 | NH2 | ARG | B | 271 | 20.735 | 48.088 | 90.899 | 1.00 | 17.29 |
| 10143 | C | ARG | B | 271 | 23.037 | 50.278 | 85.147 | 1.00 | 9.25 |
| 10144 | O | ARG | B | 271 | 21.842 | 50.548 | 85.220 | 1.00 | 9.14 |
| 10145 | N | ARG | B | 272 | 23.911 | 51.051 | 84.511 | 1.00 | 8.96 |
| 10147 | CA | ARG | B | 272 | 23.513 | 52.292 | 83.854 | 1.00 | 8.93 |
| 10149 | CB | ARG | B | 272 | 24.462 | 53.403 | 84.290 | 1.00 | 9.05 |
| 10152 | CG | ARG | B | 272 | 24.433 | 53.652 | 85.792 | 1.00 | 9.52 |

FIGURE 3 (Cont.)

| A | B | C | D | E | F | G | H | I | J |
|---|---|---|---|---|---|---|---|---|---|
| 10155 | CD | ARG | B | 272 | 25.421 | 54.698 | 86.264 | 1.00 | 9.84 |
| 10158 | NE | ARG | B | 272 | 25.143 | 56.012 | 85.695 | 1.00 | 10.08 |
| 10160 | CZ | ARG | B | 272 | 25.962 | 57.055 | 85.750 | 1.00 | 11.39 |
| 10161 | NH1 | ARG | B | 272 | 27.146 | 56.964 | 86.344 | 1.00 | 11.86 |
| 10164 | NH2 | ARG | B | 272 | 25.596 | 58.203 | 85.199 | 1.00 | 12.40 |
| 10167 | C | ARG | B | 272 | 23.445 | 52.219 | 82.319 | 1.00 | 8.99 |
| 10168 | O | ARG | B | 272 | 23.198 | 53.235 | 81.668 | 1.00 | 8.85 |
| 10169 | N | VAL | B | 273 | 23.617 | 51.025 | 81.750 | 1.00 | 8.97 |
| 10171 | CA | VAL | B | 273 | 23.668 | 50.844 | 80.294 | 1.00 | 9.03 |
| 10173 | CB | VAL | B | 273 | 25.114 | 50.512 | 79.828 | 1.00 | 8.94 |
| 10175 | CG1 | VAL | B | 273 | 25.151 | 50.162 | 78.344 | 1.00 | 8.98 |
| 10179 | CG2 | VAL | B | 273 | 26.054 | 51.684 | 80.121 | 1.00 | 9.31 |
| 10183 | C | VAL | B | 273 | 22.717 | 49.754 | 79.790 | 1.00 | 8.97 |
| 10184 | O | VAL | B | 273 | 21.940 | 49.982 | 78.858 | 1.00 | 8.92 |
| 10185 | N | GLY | B | 274 | 22.803 | 48.567 | 80.381 | 1.00 | 8.83 |
| 10187 | CA | GLY | B | 274 | 22.027 | 47.419 | 79.940 | 1.00 | 8.59 |
| 10190 | C | GLY | B | 274 | 22.853 | 46.502 | 79.056 | 1.00 | 8.48 |
| 10191 | O | GLY | B | 274 | 24.071 | 46.645 | 78.980 | 1.00 | 8.26 |
| 10192 | N | ASN | B | 275 | 22.183 | 45.577 | 78.373 | 1.00 | 8.39 |
| 10194 | CA | ASN | B | 275 | 22.846 | 44.590 | 77.511 | 1.00 | 8.59 |
| 10196 | CB | ASN | B | 275 | 21.861 | 43.471 | 77.127 | 1.00 | 8.23 |
| 10199 | CG | ASN | B | 275 | 22.550 | 42.186 | 76.684 | 1.00 | 8.43 |
| 10200 | OD1 | ASN | B | 275 | 23.770 | 42.131 | 76.525 | 1.00 | 7.88 |
| 10201 | ND2 | ASN | B | 275 | 21.754 | 41.133 | 76.487 | 1.00 | 8.29 |
| 10204 | C | ASN | B | 275 | 23.426 | 45.230 | 76.245 | 1.00 | 8.62 |
| 10205 | O | ASN | B | 275 | 22.688 | 45.783 | 75.435 | 1.00 | 8.42 |
| 10206 | N | LEU | B | 276 | 24.754 | 45.171 | 76.114 | 1.00 | 8.77 |
| 10208 | CA | LEU | B | 276 | 25.479 | 45.549 | 74.896 | 1.00 | 9.11 |
| 10210 | CB | LEU | B | 276 | 26.873 | 46.095 | 75.252 | 1.00 | 9.72 |
| 10213 | CG | LEU | B | 276 | 27.002 | 47.380 | 76.045 | 1.00 | 11.32 |
| 10215 | CD1 | LEU | B | 276 | 28.398 | 47.965 | 75.830 | 1.00 | 12.55 |
| 10219 | CD2 | LEU | B | 276 | 25.945 | 48.352 | 75.608 | 1.00 | 12.60 |
| 10223 | C | LEU | B | 276 | 25.710 | 44.357 | 73.976 | 1.00 | 8.49 |
| 10224 | O | LEU | B | 276 | 26.508 | 44.440 | 73.040 | 1.00 | 8.12 |
| 10225 | N | TYR | B | 277 | 25.013 | 43.260 | 74.251 | 1.00 | 7.99 |
| 10227 | CA | TYR | B | 277 | 25.235 | 41.972 | 73.601 | 1.00 | 7.67 |
| 10229 | CB | TYR | B | 277 | 24.610 | 41.951 | 72.198 | 1.00 | 7.72 |
| 10232 | CG | TYR | B | 277 | 23.090 | 41.839 | 72.114 | 1.00 | 7.87 |
| 10233 | CD1 | TYR | B | 277 | 22.320 | 41.283 | 73.145 | 1.00 | 8.24 |
| 10235 | CE1 | TYR | B | 277 | 20.932 | 41.172 | 73.026 | 1.00 | 8.21 |
| 10237 | CZ | TYR | B | 277 | 20.307 | 41.610 | 71.870 | 1.00 | 8.56 |
| 10238 | OH | TYR | B | 277 | 18.937 | 41.518 | 71.724 | 1.00 | 6.72 |
| 10240 | CE2 | TYR | B | 277 | 21.056 | 42.160 | 70.844 | 1.00 | 8.41 |
| 10242 | CD2 | TYR | B | 277 | 22.427 | 42.266 | 70.970 | 1.00 | 8.52 |
| 10244 | C | TYR | B | 277 | 26.721 | 41.549 | 73.595 | 1.00 | 7.35 |
| 10245 | O | TYR | B | 277 | 27.254 | 41.223 | 74.655 | 1.00 | 7.21 |
| 10246 | N | THR | B | 278 | 27.384 | 41.553 | 72.430 | 1.00 | 7.14 |
| 10248 | CA | THR | B | 278 | 28.789 | 41.117 | 72.327 | 1.00 | 6.90 |
| 10250 | CB | THR | B | 278 | 29.330 | 41.256 | 70.873 | 1.00 | 6.98 |
| 10252 | OG1 | THR | B | 278 | 29.004 | 42.546 | 70.338 | 1.00 | 6.34 |
| 10254 | CG2 | THR | B | 278 | 28.664 | 40.261 | 69.912 | 1.00 | 7.04 |
| 10258 | C | THR | B | 278 | 29.733 | 41.877 | 73.274 | 1.00 | 6.89 |

FIGURE 3 (Cont.)

| A | B | C | D | E | F | G | H | I | J |
|---|---|---|---|---|---|---|---|---|---|
| 10259 | O | THR | B | 278 | 30.746 | 41.336 | 73.726 | 1.00 | 6.77 |
| 10260 | N | GLY | B | 279 | 29.405 | 43.131 | 73.559 | 1.00 | 6.64 |
| 10262 | CA | GLY | B | 279 | 30.263 | 43.984 | 74.356 | 1.00 | 6.77 |
| 10265 | C | GLY | B | 279 | 30.092 | 43.870 | 75.860 | 1.00 | 6.78 |
| 10266 | O | GLY | B | 279 | 30.931 | 44.380 | 76.595 | 1.00 | 6.90 |
| 10267 | N | SER | B | 280 | 29.026 | 43.210 | 76.311 | 1.00 | 6.47 |
| 10269 | CA | SER | B | 280 | 28.626 | 43.214 | 77.722 | 1.00 | 6.52 |
| 10271 | CB | ASER | B | 280 | 27.362 | 42.384 | 77.931 | 0.65 | 6.09 |
| 10274 | OG | ASER | B | 280 | 26.265 | 42.968 | 77.270 | 0.65 | 5.89 |
| 10276 | C | SER | B | 280 | 29.707 | 42.707 | 78.659 | 1.00 | 6.62 |
| 10277 | O | SER | B | 280 | 29.973 | 43.331 | 79.679 | 1.00 | 6.68 |
| 10278 | N | LEU | B | 281 | 30.314 | 41.571 | 78.312 | 1.00 | 6.80 |
| 10280 | CA | LEU | B | 281 | 31.413 | 41.002 | 79.094 | 1.00 | 6.89 |
| 10282 | CB | LEU | B | 281 | 31.925 | 39.707 | 78.447 | 1.00 | 6.53 |
| 10285 | CG | LEU | B | 281 | 33.285 | 39.170 | 78.900 | 1.00 | 6.97 |
| 10287 | CD1 | LEU | B | 281 | 33.266 | 38.767 | 80.378 | 1.00 | 7.07 |
| 10291 | CD2 | LEU | B | 281 | 33.722 | 38.000 | 78.027 | 1.00 | 6.76 |
| 10295 | C | LEU | B | 281 | 32.558 | 42.000 | 79.237 | 1.00 | 7.09 |
| 10296 | O | LEU | B | 281 | 33.117 | 42.165 | 80.316 | 1.00 | 7.44 |
| 10297 | N | TYR | B | 282 | 32.887 | 42.668 | 78.139 | 1.00 | 7.32 |
| 10299 | CA | TYR | B | 282 | 34.042 | 43.555 | 78.082 | 1.00 | 7.53 |
| 10301 | CB | TYR | B | 282 | 34.533 | 43.668 | 76.625 | 1.00 | 7.57 |
| 10304 | CG | TYR | B | 282 | 34.897 | 42.284 | 76.138 | 1.00 | 7.84 |
| 10305 | CD1 | TYR | B | 282 | 36.072 | 41.683 | 76.560 | 1.00 | 8.20 |
| 10307 | CE1 | TYR | B | 282 | 36.397 | 40.395 | 76.185 | 1.00 | 8.15 |
| 10309 | CZ | TYR | B | 282 | 35.532 | 39.674 | 75.400 | 1.00 | 7.98 |
| 10310 | OH | TYR | B | 282 | 35.883 | 38.396 | 75.043 | 1.00 | 7.96 |
| 10312 | CE2 | TYR | B | 282 | 34.334 | 40.233 | 74.981 | 1.00 | 8.19 |
| 10314 | CD2 | TYR | B | 282 | 34.016 | 41.532 | 75.364 | 1.00 | 7.52 |
| 10316 | C | TYR | B | 282 | 33.790 | 44.900 | 78.769 | 1.00 | 7.76 |
| 10317 | O | TYR | B | 282 | 34.713 | 45.475 | 79.329 | 1.00 | 7.67 |
| 10318 | N | LEU | B | 283 | 32.544 | 45.367 | 78.768 | 1.00 | 8.08 |
| 10320 | CA | LEU | B | 283 | 32.149 | 46.505 | 79.594 | 1.00 | 8.42 |
| 10322 | CB | LEU | B | 283 | 30.690 | 46.900 | 79.332 | 1.00 | 8.33 |
| 10325 | CG | LEU | B | 283 | 30.133 | 48.062 | 80.162 | 1.00 | 8.65 |
| 10327 | CD1 | LEU | B | 283 | 30.934 | 49.341 | 79.924 | 1.00 | 8.35 |
| 10331 | CD2 | LEU | B | 283 | 28.662 | 48.275 | 79.856 | 1.00 | 8.88 |
| 10335 | C | LEU | B | 283 | 32.337 | 46.141 | 81.059 | 1.00 | 8.46 |
| 10336 | O | LEU | B | 283 | 32.785 | 46.961 | 81.851 | 1.00 | 8.58 |
| 10337 | N | GLY | B | 284 | 32.004 | 44.901 | 81.406 | 1.00 | 8.54 |
| 10339 | CA | GLY | B | 284 | 32.200 | 44.393 | 82.751 | 1.00 | 8.48 |
| 10342 | C | GLY | B | 284 | 33.658 | 44.335 | 83.165 | 1.00 | 8.46 |
| 10343 | O | GLY | B | 284 | 33.972 | 44.572 | 84.327 | 1.00 | 8.35 |
| 10344 | N | LEU | B | 285 | 34.549 | 44.031 | 82.219 | 1.00 | 8.57 |
| 10346 | CA | LEU | B | 285 | 35.983 | 44.055 | 82.473 | 1.00 | 8.42 |
| 10348 | CB | LEU | B | 285 | 36.762 | 43.508 | 81.273 | 1.00 | 8.56 |
| 10351 | CG | LEU | B | 285 | 38.289 | 43.529 | 81.396 | 1.00 | 8.82 |
| 10353 | CD1 | LEU | B | 285 | 38.758 | 42.636 | 82.540 | 1.00 | 9.33 |
| 10357 | CD2 | LEU | B | 285 | 38.942 | 43.113 | 80.083 | 1.00 | 9.48 |
| 10361 | C | LEU | B | 285 | 36.435 | 45.483 | 82.785 | 1.00 | 8.41 |
| 10362 | O | LEU | B | 285 | 37.106 | 45.715 | 83.781 | 1.00 | 8.20 |
| 10363 | N | ILE | B | 286 | 36.043 | 46.430 | 81.938 | 1.00 | 8.29 |

FIGURE 3 (Cont.)

| A | B | C | D | E | F | G | H | I | J |
|---|---|---|---|---|---|---|---|---|---|
| 10365 | CA | ILE | B | 286 | 36.368 | 47.838 | 82.144 | 1.00 | 8.16 |
| 10367 | CB | ILE | B | 286 | 35.761 | 48.726 | 81.033 | 1.00 | 8.31 |
| 10369 | CG1 | ILE | B | 286 | 36.370 | 48.400 | 79.660 | 1.00 | 8.20 |
| 10372 | CD1 | ILE | B | 286 | 35.552 | 48.935 | 78.509 | 1.00 | 8.61 |
| 10376 | CG2 | ILE | B | 286 | 36.001 | 50.198 | 81.348 | 1.00 | 8.39 |
| 10380 | C | ILE | B | 286 | 35.854 | 48.309 | 83.497 | 1.00 | 8.02 |
| 10381 | O | ILE | B | 286 | 36.585 | 48.948 | 84.244 | 1.00 | 7.82 |
| 10382 | N | SER | B | 287 | 34.594 | 47.991 | 83.799 | 1.00 | 7.92 |
| 10384 | CA | SER | B | 287 | 33.946 | 48.417 | 85.042 | 1.00 | 7.98 |
| 10386 | CB | SER | B | 287 | 32.468 | 48.000 | 85.042 | 1.00 | 8.18 |
| 10389 | OG | SER | B | 287 | 31.825 | 48.328 | 86.260 | 1.00 | 7.81 |
| 10391 | C | SER | B | 287 | 34.676 | 47.834 | 86.254 | 1.00 | 8.22 |
| 10392 | O | SER | B | 287 | 34.918 | 48.530 | 87.241 | 1.00 | 8.13 |
| 10393 | N | LEU | B | 288 | 35.045 | 46.561 | 86.161 | 1.00 | 8.50 |
| 10395 | CA | LEU | B | 288 | 35.794 | 45.889 | 87.217 | 1.00 | 8.70 |
| 10397 | CB | LEU | B | 288 | 36.064 | 44.434 | 86.839 | 1.00 | 8.79 |
| 10400 | CG | LEU | B | 288 | 37.069 | 43.665 | 87.703 | 1.00 | 8.95 |
| 10402 | CD1 | LEU | B | 288 | 36.578 | 43.543 | 89.152 | 1.00 | 9.30 |
| 10406 | CD2 | LEU | B | 288 | 37.306 | 42.296 | 87.097 | 1.00 | 9.59 |
| 10410 | C | LEU | B | 288 | 37.118 | 46.595 | 87.509 | 1.00 | 8.83 |
| 10411 | O | LEU | B | 288 | 37.412 | 46.918 | 88.650 | 1.00 | 8.65 |
| 10412 | N | LEU | B | 289 | 37.913 | 46.831 | 86.475 | 1.00 | 9.21 |
| 10414 | CA | LEU | B | 289 | 39.248 | 47.393 | 86.665 | 1.00 | 9.57 |
| 10416 | CB | LEU | B | 289 | 40.062 | 47.313 | 85.365 | 1.00 | 9.80 |
| 10419 | CG | LEU | B | 289 | 40.217 | 45.921 | 84.732 | 1.00 | 10.65 |
| 10421 | CD1 | LEU | B | 289 | 41.241 | 45.956 | 83.614 | 1.00 | 11.22 |
| 10425 | CD2 | LEU | B | 289 | 40.581 | 44.848 | 85.753 | 1.00 | 12.01 |
| 10429 | C | LEU | B | 289 | 39.174 | 48.832 | 87.170 | 1.00 | 9.64 |
| 10430 | O | LEU | B | 289 | 40.038 | 49.276 | 87.924 | 1.00 | 9.61 |
| 10431 | N | GLU | B | 290 | 38.120 | 49.549 | 86.789 | 1.00 | 9.90 |
| 10433 | CA | GLU | B | 290 | 38.005 | 50.967 | 87.131 | 1.00 | 10.24 |
| 10435 | CB | GLU | B | 290 | 37.312 | 51.734 | 85.999 | 1.00 | 10.18 |
| 10438 | CG | GLU | B | 290 | 38.204 | 51.826 | 84.771 | 1.00 | 10.50 |
| 10441 | CD | GLU | B | 290 | 37.605 | 52.576 | 83.598 | 1.00 | 10.02 |
| 10442 | OE1 | GLU | B | 290 | 36.447 | 53.035 | 83.670 | 1.00 | 10.43 |
| 10443 | OE2 | GLU | B | 290 | 38.319 | 52.708 | 82.587 | 1.00 | 9.76 |
| 10444 | C | GLU | B | 290 | 37.328 | 51.213 | 88.479 | 1.00 | 10.55 |
| 10445 | O | GLU | B | 290 | 37.486 | 52.284 | 89.055 | 1.00 | 10.75 |
| 10446 | N | ASN | B | 291 | 36.610 | 50.218 | 89.000 | 1.00 | 10.94 |
| 10448 | CA | ASN | B | 291 | 35.886 | 50.374 | 90.263 | 1.00 | 11.16 |
| 10450 | CB | ASN | B | 291 | 34.412 | 50.006 | 90.081 | 1.00 | 11.20 |
| 10453 | CG | ASN | B | 291 | 33.670 | 51.036 | 89.266 | 1.00 | 10.60 |
| 10454 | OD1 | ASN | B | 291 | 33.220 | 52.048 | 89.797 | 1.00 | 9.38 |
| 10455 | ND2 | ASN | B | 291 | 33.577 | 50.807 | 87.960 | 1.00 | 10.53 |
| 10458 | C | ASN | B | 291 | 36.482 | 49.609 | 91.433 | 1.00 | 11.63 |
| 10459 | O | ASN | B | 291 | 36.191 | 49.922 | 92.582 | 1.00 | 11.63 |
| 10460 | N | ALA | B | 292 | 37.311 | 48.612 | 91.142 | 1.00 | 12.10 |
| 10462 | CA | ALA | B | 292 | 38.069 | 47.911 | 92.176 | 1.00 | 12.58 |
| 10464 | CB | ALA | B | 292 | 38.734 | 46.679 | 91.587 | 1.00 | 12.69 |
| 10468 | C | ALA | B | 292 | 39.118 | 48.863 | 92.756 | 1.00 | 12.97 |
| 10469 | O | ALA | B | 292 | 39.579 | 49.783 | 92.066 | 1.00 | 12.80 |
| 10470 | N | THR | B | 293 | 39.477 | 48.658 | 94.022 | 1.00 | 13.42 |

FIGURE 3 (Cont.)

| A | B | C | D | E | F | G | H | I | J |
|---|---|---|---|---|---|---|---|---|---|
| 10472 | CA | THR | B | 293 | 40.509 | 49.478 | 94.670 | 1.00 | 13.76 |
| 10474 | CB | THR | B | 293 | 39.960 | 50.179 | 95.933 | 1.00 | 14.00 |
| 10476 | OG1 | THR | B | 293 | 39.536 | 49.215 | 96.905 | 1.00 | 14.81 |
| 10478 | CG2 | THR | B | 293 | 38.694 | 50.974 | 95.618 | 1.00 | 14.63 |
| 10482 | C | THR | B | 293 | 41.794 | 48.716 | 95.015 | 1.00 | 13.65 |
| 10483 | O | THR | B | 293 | 42.852 | 49.336 | 95.135 | 1.00 | 13.76 |
| 10484 | N | THR | B | 294 | 41.719 | 47.392 | 95.168 | 1.00 | 13.30 |
| 10486 | CA | THR | B | 294 | 42.903 | 46.608 | 95.557 | 1.00 | 13.11 |
| 10488 | CB | THR | B | 294 | 42.713 | 45.960 | 96.950 | 1.00 | 13.20 |
| 10490 | OG1 | THR | B | 294 | 41.591 | 45.073 | 96.939 | 1.00 | 13.10 |
| 10492 | CG2 | THR | B | 294 | 42.367 | 47.009 | 98.014 | 1.00 | 13.37 |
| 10496 | C | THR | B | 294 | 43.338 | 45.542 | 94.541 | 1.00 | 12.72 |
| 10497 | O | THR | B | 294 | 44.201 | 44.718 | 94.842 | 1.00 | 12.37 |
| 10498 | N | LEU | B | 295 | 42.761 | 45.554 | 93.342 | 1.00 | 12.34 |
| 10500 | CA | LEU | B | 295 | 43.333 | 44.773 | 92.248 | 1.00 | 12.08 |
| 10502 | CB | LEU | B | 295 | 42.425 | 44.766 | 91.017 | 1.00 | 12.04 |
| 10505 | CG | LEU | B | 295 | 41.205 | 43.845 | 91.065 | 1.00 | 11.36 |
| 10507 | CD1 | LEU | B | 295 | 41.609 | 42.373 | 91.222 | 1.00 | 11.10 |
| 10511 | CD2 | LEU | B | 295 | 40.357 | 44.041 | 89.813 | 1.00 | 10.64 |
| 10515 | C | LEU | B | 295 | 44.685 | 45.381 | 91.896 | 1.00 | 12.01 |
| 10516 | O | LEU | B | 295 | 44.883 | 46.587 | 92.026 | 1.00 | 12.07 |
| 10517 | N | THR | B | 296 | 45.612 | 44.539 | 91.459 | 1.00 | 11.99 |
| 10519 | CA | THR | B | 296 | 46.975 | 44.972 | 91.168 | 1.00 | 12.09 |
| 10521 | CB | THR | B | 296 | 47.798 | 45.016 | 92.486 | 1.00 | 12.22 |
| 10523 | OG1 | THR | B | 296 | 49.059 | 45.662 | 92.269 | 1.00 | 13.26 |
| 10525 | CG2 | THR | B | 296 | 48.160 | 43.616 | 92.969 | 1.00 | 12.63 |
| 10529 | C | THR | B | 296 | 47.634 | 44.065 | 90.121 | 1.00 | 11.68 |
| 10530 | O | THR | B | 296 | 47.114 | 43.000 | 89.793 | 1.00 | 11.32 |
| 10531 | N | ALA | B | 297 | 48.776 | 44.499 | 89.599 | 1.00 | 11.44 |
| 10533 | CA | ALA | B | 297 | 49.486 | 43.753 | 88.565 | 1.00 | 11.31 |
| 10535 | CB | ALA | B | 297 | 50.763 | 44.485 | 88.166 | 1.00 | 11.53 |
| 10539 | C | ALA | B | 297 | 49.808 | 42.349 | 89.066 | 1.00 | 10.99 |
| 10540 | O | ALA | B | 297 | 50.191 | 42.173 | 90.220 | 1.00 | 10.96 |
| 10541 | N | GLY | B | 298 | 49.622 | 41.356 | 88.202 | 1.00 | 10.70 |
| 10543 | CA | GLY | B | 298 | 49.882 | 39.970 | 88.540 | 1.00 | 10.67 |
| 10546 | C | GLY | B | 298 | 48.617 | 39.213 | 88.906 | 1.00 | 10.46 |
| 10547 | O | GLY | B | 298 | 48.615 | 37.979 | 88.920 | 1.00 | 10.49 |
| 10548 | N | ASN | B | 299 | 47.537 | 39.940 | 89.190 | 1.00 | 10.09 |
| 10550 | CA | ASN | B | 299 | 46.267 | 39.312 | 89.540 | 1.00 | 9.92 |
| 10552 | CB | ASN | B | 299 | 45.272 | 40.345 | 90.074 | 1.00 | 9.81 |
| 10555 | CG | ASN | B | 299 | 45.612 | 40.832 | 91.480 | 1.00 | 9.81 |
| 10556 | OD1 | ASN | B | 299 | 44.929 | 41.699 | 92.013 | 1.00 | 8.40 |
| 10557 | ND2 | ASN | B | 299 | 46.661 | 40.277 | 92.081 | 1.00 | 9.67 |
| 10560 | C | ASN | B | 299 | 45.656 | 38.588 | 88.346 | 1.00 | 9.90 |
| 10561 | O | ASN | B | 299 | 45.878 | 38.968 | 87.196 | 1.00 | 9.78 |
| 10562 | N | GLN | B | 300 | 44.881 | 37.549 | 88.637 | 1.00 | 9.93 |
| 10564 | CA | GLN | B | 300 | 44.281 | 36.697 | 87.628 | 1.00 | 10.14 |
| 10566 | CB | GLN | B | 300 | 44.487 | 35.224 | 87.994 | 1.00 | 10.33 |
| 10569 | CG | GLN | B | 300 | 45.942 | 34.839 | 88.297 | 1.00 | 11.22 |
| 10572 | CD | GLN | B | 300 | 46.828 | 34.902 | 87.069 | 1.00 | 11.91 |
| 10573 | OE1 | GLN | B | 300 | 46.589 | 34.192 | 86.097 | 1.00 | 12.61 |
| 10574 | NE2 | GLN | B | 300 | 47.850 | 35.755 | 87.107 | 1.00 | 12.60 |

FIGURE 3 (Cont.)

| A | B | C | D | E | F | G | H | I | J |
|---|---|---|---|---|---|---|---|---|---|
| 10577 | C | GLN | B | 300 | 42.791 | 37.001 | 87.520 | 1.00 | 10.07 |
| 10578 | O | GLN | B | 300 | 42.064 | 36.949 | 88.509 | 1.00 | 10.00 |
| 10579 | N | ILE | B | 301 | 42.351 | 37.324 | 86.307 | 1.00 | 9.95 |
| 10581 | CA | ILE | B | 301 | 40.956 | 37.618 | 86.013 | 1.00 | 9.82 |
| 10583 | CB | ILE | B | 301 | 40.844 | 38.971 | 85.264 | 1.00 | 9.96 |
| 10585 | CG1 | ILE | B | 301 | 41.716 | 40.058 | 85.918 | 1.00 | 10.31 |
| 10588 | CD1 | ILE | B | 301 | 41.265 | 40.496 | 87.301 | 1.00 | 11.11 |
| 10592 | CG2 | ILE | B | 301 | 39.393 | 39.413 | 85.162 | 1.00 | 10.03 |
| 10596 | C | ILE | B | 301 | 40.392 | 36.509 | 85.128 | 1.00 | 9.59 |
| 10597 | O | ILE | B | 301 | 40.918 | 36.259 | 84.046 | 1.00 | 9.25 |
| 10598 | N | GLY | B | 302 | 39.330 | 35.848 | 85.583 | 1.00 | 9.40 |
| 10600 | CA | GLY | B | 302 | 38.606 | 34.887 | 84.769 | 1.00 | 9.46 |
| 10603 | C | GLY | B | 302 | 37.485 | 35.575 | 84.011 | 1.00 | 9.41 |
| 10604 | O | GLY | B | 302 | 36.825 | 36.464 | 84.546 | 1.00 | 9.85 |
| 10605 | N | LEU | B | 303 | 37.276 | 35.167 | 82.766 | 1.00 | 9.07 |
| 10607 | CA | LEU | B | 303 | 36.279 | 35.774 | 81.901 | 1.00 | 8.95 |
| 10609 | CB | LEU | B | 303 | 36.949 | 36.514 | 80.739 | 1.00 | 9.50 |
| 10612 | CG | LEU | B | 303 | 37.663 | 37.825 | 81.091 | 1.00 | 10.11 |
| 10614 | CD1 | LEU | B | 303 | 39.134 | 37.574 | 81.356 | 1.00 | 10.34 |
| 10618 | CD2 | LEU | B | 303 | 37.481 | 38.870 | 79.984 | 1.00 | 10.86 |
| 10622 | C | LEU | B | 303 | 35.370 | 34.686 | 81.360 | 1.00 | 8.57 |
| 10623 | O | LEU | B | 303 | 35.839 | 33.721 | 80.754 | 1.00 | 8.55 |
| 10624 | N | PHE | B | 304 | 34.073 | 34.836 | 81.593 | 1.00 | 8.08 |
| 10626 | CA | PHE | B | 304 | 33.085 | 33.936 | 81.030 | 1.00 | 7.82 |
| 10628 | CB | PHE | B | 304 | 32.115 | 33.445 | 82.100 | 1.00 | 7.60 |
| 10631 | CG | PHE | B | 304 | 30.958 | 32.681 | 81.542 | 1.00 | 7.28 |
| 10632 | CD1 | PHE | B | 304 | 29.673 | 33.208 | 81.574 | 1.00 | 7.17 |
| 10634 | CE1 | PHE | B | 304 | 28.604 | 32.495 | 81.046 | 1.00 | 6.96 |
| 10636 | CZ | PHE | B | 304 | 28.821 | 31.255 | 80.460 | 1.00 | 6.67 |
| 10638 | CE2 | PHE | B | 304 | 30.099 | 30.730 | 80.416 | 1.00 | 6.91 |
| 10640 | CD2 | PHE | B | 304 | 31.158 | 31.441 | 80.949 | 1.00 | 6.85 |
| 10642 | C | PHE | B | 304 | 32.309 | 34.654 | 79.931 | 1.00 | 7.77 |
| 10643 | O | PHE | B | 304 | 31.554 | 35.585 | 80.207 | 1.00 | 7.58 |
| 10644 | N | SER | B | 305 | 32.506 | 34.215 | 78.690 | 1.00 | 7.71 |
| 10646 | CA | SER | B | 305 | 31.731 | 34.698 | 77.553 | 1.00 | 7.63 |
| 10648 | CB | SER | B | 305 | 32.635 | 34.891 | 76.342 | 1.00 | 7.57 |
| 10651 | OG | SER | B | 305 | 31.920 | 35.487 | 75.273 | 1.00 | 7.26 |
| 10653 | C | SER | B | 305 | 30.616 | 33.713 | 77.209 | 1.00 | 7.72 |
| 10654 | O | SER | B | 305 | 30.833 | 32.505 | 77.170 | 1.00 | 7.62 |
| 10655 | N | TYR | B | 306 | 29.419 | 34.242 | 76.990 | 1.00 | 7.94 |
| 10657 | CA | TYR | B | 306 | 28.277 | 33.448 | 76.564 | 1.00 | 8.04 |
| 10659 | CB | TYR | B | 306 | 27.218 | 33.380 | 77.674 | 1.00 | 7.99 |
| 10662 | CG | TYR | B | 306 | 26.006 | 32.532 | 77.322 | 1.00 | 8.04 |
| 10663 | CD1 | TYR | B | 306 | 24.823 | 33.122 | 76.876 | 1.00 | 8.05 |
| 10665 | CE1 | TYR | B | 306 | 23.708 | 32.354 | 76.545 | 1.00 | 7.08 |
| 10667 | CZ | TYR | B | 306 | 23.766 | 30.979 | 76.664 | 1.00 | 7.96 |
| 10668 | OH | TYR | B | 306 | 22.662 | 30.222 | 76.337 | 1.00 | 7.85 |
| 10670 | CE2 | TYR | B | 306 | 24.932 | 30.364 | 77.099 | 1.00 | 8.28 |
| 10672 | CD2 | TYR | B | 306 | 26.045 | 31.144 | 77.426 | 1.00 | 8.41 |
| 10674 | C | TYR | B | 306 | 27.660 | 34.070 | 75.325 | 1.00 | 8.18 |
| 10675 | O | TYR | B | 306 | 27.620 | 35.289 | 75.181 | 1.00 | 8.43 |
| 10676 | N | GLY | B | 307 | 27.178 | 33.210 | 74.440 | 1.00 | 7.95 |

FIGURE 3 (Cont.)

| A | B | C | D | E | F | G | H | I | J |
|---|---|---|---|---|---|---|---|---|---|
| 10678 | CA | GLY | B | 307 | 26.350 | 33.606 | 73.322 | 1.00 | 7.95 |
| 10681 | C | GLY | B | 307 | 25.236 | 32.584 | 73.197 | 1.00 | 7.86 |
| 10682 | O | GLY | B | 307 | 25.502 | 31.383 | 73.185 | 1.00 | 7.81 |
| 10683 | N | SER | B | 308 | 23.992 | 33.046 | 73.122 | 1.00 | 7.74 |
| 10685 | CA | SER | B | 308 | 22.845 | 32.157 | 72.942 | 1.00 | 7.75 |
| 10687 | CB | SER | B | 308 | 21.541 | 32.959 | 72.952 | 1.00 | 7.91 |
| 10690 | OG | SER | B | 308 | 21.143 | 33.290 | 74.272 | 1.00 | 6.86 |
| 10692 | C | SER | B | 308 | 22.964 | 31.360 | 71.637 | 1.00 | 8.10 |
| 10693 | O | SER | B | 308 | 23.571 | 31.825 | 70.666 | 1.00 | 8.23 |
| 10694 | N | GLY | B | 309 | 22.408 | 30.151 | 71.619 | 1.00 | 8.33 |
| 10696 | CA | GLY | B | 309 | 22.468 | 29.313 | 70.435 | 1.00 | 8.54 |
| 10699 | C | GLY | B | 309 | 22.934 | 27.873 | 70.600 | 1.00 | 8.72 |
| 10700 | O | GLY | B | 309 | 22.453 | 27.026 | 69.848 | 1.00 | 9.10 |
| 10701 | N | ALA | B | 310 | 23.860 | 27.550 | 71.507 | 1.00 | 8.68 |
| 10703 | CA | ALA | B | 310 | 24.628 | 28.475 | 72.342 | 1.00 | 8.65 |
| 10705 | CB | ALA | B | 310 | 24.087 | 28.460 | 73.762 | 1.00 | 8.78 |
| 10709 | C | ALA | B | 310 | 26.116 | 28.105 | 72.356 | 1.00 | 8.73 |
| 10710 | O | ALA | B | 310 | 26.478 | 26.927 | 72.255 | 1.00 | 8.36 |
| 10711 | N | VAL | B | 311 | 26.969 | 29.121 | 72.471 | 1.00 | 8.77 |
| 10713 | CA | VAL | B | 311 | 28.414 | 28.945 | 72.582 | 1.00 | 9.03 |
| 10715 | CB | VAL | B | 311 | 29.128 | 29.463 | 71.312 | 1.00 | 9.32 |
| 10717 | CG1 | VAL | B | 311 | 30.653 | 29.311 | 71.426 | 1.00 | 9.40 |
| 10721 | CG2 | VAL | B | 311 | 28.607 | 28.729 | 70.083 | 1.00 | 9.55 |
| 10725 | C | VAL | B | 311 | 28.932 | 29.687 | 73.815 | 1.00 | 9.21 |
| 10726 | O | VAL | B | 311 | 28.533 | 30.822 | 74.082 | 1.00 | 9.22 |
| 10727 | N | ALA | B | 312 | 29.810 | 29.044 | 74.577 | 1.00 | 9.04 |
| 10729 | CA | ALA | B | 312 | 30.395 | 29.665 | 75.759 | 1.00 | 9.26 |
| 10731 | CB | ALA | B | 312 | 29.721 | 29.137 | 77.019 | 1.00 | 9.15 |
| 10735 | C | ALA | B | 312 | 31.896 | 29.426 | 75.821 | 1.00 | 9.44 |
| 10736 | O | ALA | B | 312 | 32.413 | 28.501 | 75.197 | 1.00 | 9.47 |
| 10737 | N | GLU | B | 313 | 32.589 | 30.262 | 76.586 | 1.00 | 9.49 |
| 10739 | CA | GLU | B | 313 | 34.022 | 30.122 | 76.776 | 1.00 | 9.77 |
| 10741 | CB | GLU | B | 313 | 34.781 | 30.776 | 75.617 | 1.00 | 9.90 |
| 10744 | CG | GLU | B | 313 | 36.283 | 30.503 | 75.623 | 1.00 | 11.38 |
| 10747 | CD | GLU | B | 313 | 36.969 | 30.864 | 74.311 | 1.00 | 12.61 |
| 10748 | OE1 | GLU | B | 313 | 36.280 | 31.010 | 73.281 | 1.00 | 15.57 |
| 10749 | OE2 | GLU | B | 313 | 38.206 | 30.993 | 74.305 | 1.00 | 13.36 |
| 10750 | C | GLU | B | 313 | 34.472 | 30.723 | 78.108 | 1.00 | 9.75 |
| 10751 | O | GLU | B | 313 | 33.991 | 31.778 | 78.516 | 1.00 | 9.60 |
| 10752 | N | PHE | B | 314 | 35.373 | 30.022 | 78.790 | 1.00 | 9.50 |
| 10754 | CA | PHE | B | 314 | 36.051 | 30.548 | 79.966 | 1.00 | 9.43 |
| 10756 | CB | PHE | B | 314 | 35.821 | 29.649 | 81.181 | 1.00 | 9.53 |
| 10759 | CG | PHE | B | 314 | 36.267 | 30.262 | 82.479 | 1.00 | 9.86 |
| 10760 | CD1 | PHE | B | 314 | 35.409 | 31.063 | 83.216 | 1.00 | 10.20 |
| 10762 | CE1 | PHE | B | 314 | 35.825 | 31.640 | 84.415 | 1.00 | 10.63 |
| 10764 | CZ | PHE | B | 314 | 37.101 | 31.417 | 84.883 | 1.00 | 10.35 |
| 10766 | CE2 | PHE | B | 314 | 37.969 | 30.625 | 84.162 | 1.00 | 11.01 |
| 10768 | CD2 | PHE | B | 314 | 37.550 | 30.050 | 82.957 | 1.00 | 11.06 |
| 10770 | C | PHE | B | 314 | 37.540 | 30.655 | 79.655 | 1.00 | 9.36 |
| 10771 | O | PHE | B | 314 | 38.144 | 29.717 | 79.141 | 1.00 | 8.56 |
| 10772 | N | PHE | B | 315 | 38.121 | 31.811 | 79.950 | 1.00 | 9.48 |
| 10774 | CA | PHE | B | 315 | 39.539 | 32.053 | 79.712 | 1.00 | 9.75 |

FIGURE 3 (Cont.)

| A | B | C | D | E | F | G | H | I | J |
|---|---|---|---|---|---|---|---|---|---|
| 10776 | CB | PHE | B | 315 | 39.775 | 32.527 | 78.270 | 1.00 | 9.70 |
| 10779 | CG | PHE | B | 315 | 39.054 | 33.808 | 77.919 | 1.00 | 10.09 |
| 10780 | CD1 | PHE | B | 315 | 39.736 | 35.019 | 77.886 | 1.00 | 10.68 |
| 10782 | CE1 | PHE | B | 315 | 39.078 | 36.201 | 77.564 | 1.00 | 10.85 |
| 10784 | CZ | PHE | B | 315 | 37.720 | 36.180 | 77.264 | 1.00 | 10.84 |
| 10786 | CE2 | PHE | B | 315 | 37.030 | 34.982 | 77.287 | 1.00 | 10.85 |
| 10788 | CD2 | PHE | B | 315 | 37.698 | 33.799 | 77.617 | 1.00 | 10.37 |
| 10790 | C | PHE | B | 315 | 40.077 | 33.075 | 80.707 | 1.00 | 9.92 |
| 10791 | O | PHE | B | 315 | 39.316 | 33.781 | 81.363 | 1.00 | 10.02 |
| 10792 | N | THR | B | 316 | 41.396 | 33.154 | 80.810 | 1.00 | 10.03 |
| 10794 | CA | THR | B | 316 | 42.028 | 33.930 | 81.862 | 1.00 | 10.28 |
| 10796 | CB | THR | B | 316 | 42.806 | 32.985 | 82.794 | 1.00 | 10.46 |
| 10798 | OG1 | THR | B | 316 | 41.881 | 32.095 | 83.435 | 1.00 | 10.48 |
| 10800 | CG2 | THR | B | 316 | 43.449 | 33.745 | 83.948 | 1.00 | 10.51 |
| 10804 | C | THR | B | 316 | 42.949 | 34.992 | 81.297 | 1.00 | 10.32 |
| 10805 | O | THR | B | 316 | 43.600 | 34.780 | 80.282 | 1.00 | 10.55 |
| 10806 | N | GLY | B | 317 | 42.977 | 36.144 | 81.957 | 1.00 | 10.33 |
| 10808 | CA | GLY | B | 317 | 43.947 | 37.183 | 81.672 | 1.00 | 10.25 |
| 10811 | C | GLY | B | 317 | 44.677 | 37.578 | 82.939 | 1.00 | 10.08 |
| 10812 | O | GLY | B | 317 | 44.163 | 37.395 | 84.041 | 1.00 | 10.03 |
| 10813 | N | GLU | B | 318 | 45.887 | 38.104 | 82.785 | 1.00 | 9.99 |
| 10815 | CA | GLU | B | 318 | 46.665 | 38.606 | 83.906 | 1.00 | 9.90 |
| 10817 | CB | GLU | B | 318 | 48.042 | 37.938 | 83.953 | 1.00 | 9.90 |
| 10820 | CG | GLU | B | 318 | 48.883 | 38.381 | 85.143 | 1.00 | 9.97 |
| 10823 | CD | GLU | B | 318 | 50.151 | 37.568 | 85.310 | 1.00 | 10.49 |
| 10824 | OE1 | GLU | B | 318 | 51.235 | 38.183 | 85.426 | 1.00 | 10.14 |
| 10825 | OE2 | GLU | B | 318 | 50.056 | 36.325 | 85.323 | 1.00 | 10.10 |
| 10826 | C | GLU | B | 318 | 46.826 | 40.113 | 83.766 | 1.00 | 9.85 |
| 10827 | O | GLU | B | 318 | 47.167 | 40.594 | 82.698 | 1.00 | 9.86 |
| 10828 | N | LEU | B | 319 | 46.587 | 40.855 | 84.843 | 1.00 | 9.99 |
| 10830 | CA | LEU | B | 319 | 46.809 | 42.299 | 84.830 | 1.00 | 10.27 |
| 10832 | CB | LEU | B | 319 | 46.222 | 42.955 | 86.084 | 1.00 | 10.12 |
| 10835 | CG | LEU | B | 319 | 44.691 | 42.947 | 86.168 | 1.00 | 10.48 |
| 10837 | CD1 | LEU | B | 319 | 44.217 | 43.417 | 87.548 | 1.00 | 10.28 |
| 10841 | CD2 | LEU | B | 319 | 44.074 | 43.794 | 85.066 | 1.00 | 10.29 |
| 10845 | C | LEU | B | 319 | 48.309 | 42.616 | 84.698 | 1.00 | 10.41 |
| 10846 | O | LEU | B | 319 | 49.139 | 42.070 | 85.419 | 1.00 | 10.27 |
| 10847 | N | VAL | B | 320 | 48.631 | 43.505 | 83.768 | 1.00 | 10.75 |
| 10849 | CA | VAL | B | 320 | 50.007 | 43.828 | 83.408 | 1.00 | 11.23 |
| 10851 | CB | VAL | B | 320 | 50.082 | 44.223 | 81.911 | 1.00 | 11.47 |
| 10853 | CG1 | VAL | B | 320 | 51.453 | 44.782 | 81.534 | 1.00 | 12.40 |
| 10857 | CG2 | VAL | B | 320 | 49.731 | 43.014 | 81.039 | 1.00 | 11.82 |
| 10861 | C | VAL | B | 320 | 50.503 | 44.974 | 84.284 | 1.00 | 11.28 |
| 10862 | O | VAL | B | 320 | 49.720 | 45.830 | 84.683 | 1.00 | 11.34 |
| 10863 | N | ALA | B | 321 | 51.800 | 44.989 | 84.578 | 1.00 | 11.28 |
| 10865 | CA | ALA | B | 321 | 52.406 | 46.086 | 85.331 | 1.00 | 11.21 |
| 10867 | CB | ALA | B | 321 | 53.906 | 45.863 | 85.476 | 1.00 | 11.40 |
| 10871 | C | ALA | B | 321 | 52.126 | 47.427 | 84.652 | 1.00 | 11.10 |
| 10872 | O | ALA | B | 321 | 52.298 | 47.570 | 83.443 | 1.00 | 10.84 |
| 10873 | N | GLY | B | 322 | 51.667 | 48.399 | 85.437 | 1.00 | 11.32 |
| 10875 | CA | GLY | B | 322 | 51.389 | 49.731 | 84.935 | 1.00 | 11.26 |
| 10878 | C | GLY | B | 322 | 49.987 | 49.917 | 84.387 | 1.00 | 11.39 |

FIGURE 3 (Cont.)

| A | B | C | D | E | F | G | H | I | J |
|---|---|---|---|---|---|---|---|---|---|
| 10879 | O | GLY | B | 322 | 49.644 | 51.027 | 83.993 | 1.00 | 11.41 |
| 10880 | N | TYR | B | 323 | 49.172 | 48.858 | 84.381 | 1.00 | 11.50 |
| 10882 | CA | TYR | B | 323 | 47.818 | 48.913 | 83.802 | 1.00 | 11.55 |
| 10884 | CB | TYR | B | 323 | 47.088 | 47.560 | 83.931 | 1.00 | 11.46 |
| 10887 | CG | TYR | B | 323 | 46.376 | 47.353 | 85.256 | 1.00 | 11.15 |
| 10888 | CD1 | TYR | B | 323 | 45.025 | 47.673 | 85.405 | 1.00 | 10.98 |
| 10890 | CE1 | TYR | B | 323 | 44.372 | 47.501 | 86.629 | 1.00 | 10.95 |
| 10892 | CZ | TYR | B | 323 | 45.071 | 46.999 | 87.711 | 1.00 | 10.34 |
| 10893 | OH | TYR | B | 323 | 44.448 | 46.820 | 88.924 | 1.00 | 9.24 |
| 10895 | CE2 | TYR | B | 323 | 46.411 | 46.678 | 87.584 | 1.00 | 10.56 |
| 10897 | CD2 | TYR | B | 323 | 47.056 | 46.861 | 86.363 | 1.00 | 10.56 |
| 10899 | C | TYR | B | 323 | 46.947 | 50.012 | 84.405 | 1.00 | 11.80 |
| 10900 | O | TYR | B | 323 | 46.089 | 50.566 | 83.714 | 1.00 | 11.82 |
| 10901 | N | GLN | B | 324 | 47.154 | 50.306 | 85.687 | 1.00 | 12.05 |
| 10903 | CA | GLN | B | 324 | 46.369 | 51.319 | 86.399 | 1.00 | 12.67 |
| 10905 | CB | GLN | B | 324 | 46.698 | 51.311 | 87.901 | 1.00 | 12.71 |
| 10908 | CG | GLN | B | 324 | 46.159 | 50.075 | 88.632 | 1.00 | 12.91 |
| 10911 | CD | GLN | B | 324 | 46.549 | 49.995 | 90.108 | 1.00 | 13.52 |
| 10912 | OE1 | GLN | B | 324 | 47.270 | 50.856 | 90.621 | 1.00 | 13.51 |
| 10913 | NE2 | GLN | B | 324 | 46.074 | 48.951 | 90.789 | 1.00 | 11.56 |
| 10916 | C | GLN | B | 324 | 46.539 | 52.730 | 85.827 | 1.00 | 13.12 |
| 10917 | O | GLN | B | 324 | 45.626 | 53.548 | 85.931 | 1.00 | 12.98 |
| 10918 | N | ASN | B | 325 | 47.696 | 53.012 | 85.230 | 1.00 | 13.76 |
| 10920 | CA | ASN | B | 325 | 47.920 | 54.287 | 84.530 | 1.00 | 14.65 |
| 10922 | CB | ASN | B | 325 | 49.406 | 54.465 | 84.187 | 1.00 | 14.60 |
| 10925 | CG | ASN | B | 325 | 50.270 | 54.692 | 85.414 | 1.00 | 14.64 |
| 10926 | OD1 | ASN | B | 325 | 49.832 | 55.299 | 86.386 | 1.00 | 14.06 |
| 10927 | ND2 | ASN | B | 325 | 51.510 | 54.210 | 85.365 | 1.00 | 13.91 |
| 10930 | C | ASN | B | 325 | 47.105 | 54.440 | 83.239 | 1.00 | 15.39 |
| 10931 | O | ASN | B | 325 | 47.009 | 55.537 | 82.693 | 1.00 | 15.58 |
| 10932 | N | HIS | B | 326 | 46.542 | 53.343 | 82.742 | 1.00 | 16.27 |
| 10934 | CA | HIS | B | 326 | 45.810 | 53.350 | 81.478 | 1.00 | 17.13 |
| 10936 | CB | HIS | B | 326 | 46.309 | 52.213 | 80.599 | 1.00 | 17.21 |
| 10939 | CG | HIS | B | 326 | 47.773 | 52.286 | 80.319 | 1.00 | 17.01 |
| 10940 | ND1 | HIS | B | 326 | 48.292 | 53.019 | 79.276 | 1.00 | 17.40 |
| 10942 | CE1 | HIS | B | 326 | 49.607 | 52.913 | 79.280 | 1.00 | 18.32 |
| 10944 | NE2 | HIS | B | 326 | 49.961 | 52.149 | 80.298 | 1.00 | 18.38 |
| 10946 | CD2 | HIS | B | 326 | 48.830 | 51.750 | 80.967 | 1.00 | 17.77 |
| 10948 | C | HIS | B | 326 | 44.309 | 53.237 | 81.672 | 1.00 | 17.92 |
| 10949 | O | HIS | B | 326 | 43.569 | 53.056 | 80.705 | 1.00 | 18.15 |
| 10950 | N | LEU | B | 327 | 43.868 | 53.346 | 82.923 | 1.00 | 18.77 |
| 10952 | CA | LEU | B | 327 | 42.450 | 53.329 | 83.246 | 1.00 | 19.23 |
| 10954 | CB | LEU | B | 327 | 42.229 | 52.907 | 84.699 | 1.00 | 19.36 |
| 10957 | CG | LEU | B | 327 | 42.715 | 51.503 | 85.058 | 1.00 | 19.44 |
| 10959 | CD1 | LEU | B | 327 | 42.460 | 51.236 | 86.529 | 1.00 | 20.03 |
| 10963 | CD2 | LEU | B | 327 | 42.059 | 50.436 | 84.181 | 1.00 | 19.68 |
| 10967 | C | LEU | B | 327 | 41.869 | 54.711 | 83.016 | 1.00 | 19.68 |
| 10968 | O | LEU | B | 327 | 42.586 | 55.714 | 83.054 | 1.00 | 19.85 |
| 10969 | N | GLN | B | 328 | 40.558 | 54.753 | 82.805 | 1.00 | 19.92 |
| 10971 | CA | GLN | B | 328 | 39.881 | 55.956 | 82.342 | 1.00 | 20.27 |
| 10973 | CB | GLN | B | 328 | 39.688 | 55.875 | 80.825 | 1.00 | 20.63 |
| 10976 | CG | GLN | B | 328 | 40.814 | 56.464 | 79.991 | 1.00 | 22.15 |

FIGURE 3 (Cont.)

| A | B | C | D | E | F | G | H | I | J |
|---|---|---|---|---|---|---|---|---|---|
| 10979 | CD | GLN | B | 328 | 40.374 | 56.764 | 78.562 | 1.00 | 24.10 |
| 10980 | OE1 | GLN | B | 328 | 39.263 | 56.392 | 78.157 | 1.00 | 25.37 |
| 10981 | NE2 | GLN | B | 328 | 41.241 | 57.433 | 77.793 | 1.00 | 23.77 |
| 10984 | C | GLN | B | 328 | 38.526 | 56.116 | 83.022 | 1.00 | 20.05 |
| 10985 | O | GLN | B | 328 | 37.524 | 56.368 | 82.354 | 1.00 | 19.77 |
| 10986 | N | LYS | B | 329 | 38.502 | 55.976 | 84.347 | 1.00 | 19.72 |
| 10988 | CA | LYS | B | 329 | 37.259 | 56.072 | 85.115 | 1.00 | 19.68 |
| 10990 | CB | LYS | B | 329 | 37.530 | 55.899 | 86.611 | 1.00 | 19.77 |
| 10993 | CG | LYS | B | 329 | 36.277 | 55.639 | 87.435 | 1.00 | 20.23 |
| 10996 | CD | LYS | B | 329 | 36.519 | 55.913 | 88.906 | 1.00 | 21.51 |
| 10999 | CE | LYS | B | 329 | 35.656 | 55.039 | 89.781 | 1.00 | 22.41 |
| 11002 | NZ | LYS | B | 329 | 36.072 | 55.129 | 91.205 | 1.00 | 23.61 |
| 11006 | C | LYS | B | 329 | 36.533 | 57.397 | 84.892 | 1.00 | 19.63 |
| 11007 | O | LYS | B | 329 | 35.317 | 57.418 | 84.701 | 1.00 | 19.12 |
| 11008 | N | GLU | B | 330 | 37.285 | 58.494 | 84.933 | 1.00 | 19.55 |
| 11010 | CA | GLU | B | 330 | 36.713 | 59.833 | 84.794 | 1.00 | 19.83 |
| 11012 | CB | GLU | B | 330 | 37.780 | 60.893 | 85.100 | 1.00 | 20.28 |
| 11015 | CG | GLU | B | 330 | 37.474 | 62.303 | 84.616 | 1.00 | 22.37 |
| 11018 | CD | GLU | B | 330 | 38.633 | 63.250 | 84.862 | 1.00 | 24.86 |
| 11019 | OE1 | GLU | B | 330 | 39.109 | 63.308 | 86.017 | 1.00 | 27.03 |
| 11020 | OE2 | GLU | B | 330 | 39.081 | 63.919 | 83.899 | 1.00 | 27.23 |
| 11021 | C | GLU | B | 330 | 36.105 | 60.044 | 83.407 | 1.00 | 19.11 |
| 11022 | O | GLU | B | 330 | 35.031 | 60.613 | 83.285 | 1.00 | 19.45 |
| 11023 | N | THR | B | 331 | 36.795 | 59.579 | 82.370 | 1.00 | 18.47 |
| 11025 | CA | THR | B | 331 | 36.300 | 59.685 | 81.000 | 1.00 | 18.03 |
| 11027 | CB | THR | B | 331 | 37.352 | 59.158 | 80.009 | 1.00 | 18.07 |
| 11029 | OG1 | THR | B | 331 | 38.534 | 59.969 | 80.075 | 1.00 | 18.47 |
| 11031 | CG2 | THR | B | 331 | 36.884 | 59.303 | 78.569 | 1.00 | 18.27 |
| 11035 | C | THR | B | 331 | 34.992 | 58.905 | 80.841 | 1.00 | 17.47 |
| 11036 | O | THR | B | 331 | 34.076 | 59.349 | 80.156 | 1.00 | 17.18 |
| 11037 | N | HIS | B | 332 | 34.909 | 57.756 | 81.500 | 1.00 | 16.75 |
| 11039 | CA | HIS | B | 332 | 33.762 | 56.869 | 81.360 | 1.00 | 16.28 |
| 11041 | CB | HIS | B | 332 | 34.164 | 55.452 | 81.760 | 1.00 | 16.09 |
| 11044 | CG | HIS | B | 332 | 35.111 | 54.817 | 80.789 | 1.00 | 14.98 |
| 11045 | ND1 | HIS | B | 332 | 35.833 | 53.683 | 81.080 | 1.00 | 13.68 |
| 11047 | CE1 | HIS | B | 332 | 36.566 | 53.348 | 80.033 | 1.00 | 14.64 |
| 11049 | NE2 | HIS | B | 332 | 36.359 | 54.235 | 79.077 | 1.00 | 14.91 |
| 11051 | CD2 | HIS | B | 332 | 35.457 | 55.168 | 79.526 | 1.00 | 15.06 |
| 11053 | C | HIS | B | 332 | 32.537 | 57.362 | 82.129 | 1.00 | 16.07 |
| 11054 | O | HIS | B | 332 | 31.429 | 57.333 | 81.604 | 1.00 | 15.85 |
| 11055 | N | LEU | B | 333 | 32.734 | 57.843 | 83.350 | 1.00 | 15.90 |
| 11057 | CA | LEU | B | 333 | 31.632 | 58.410 | 84.120 | 1.00 | 16.07 |
| 11059 | CB | LEU | B | 333 | 32.043 | 58.675 | 85.571 | 1.00 | 16.27 |
| 11062 | CG | LEU | B | 333 | 32.150 | 57.447 | 86.484 | 1.00 | 16.83 |
| 11064 | CD1 | LEU | B | 333 | 32.671 | 57.863 | 87.856 | 1.00 | 17.10 |
| 11068 | CD2 | LEU | B | 333 | 30.817 | 56.732 | 86.617 | 1.00 | 16.94 |
| 11072 | C | LEU | B | 333 | 31.099 | 59.698 | 83.472 | 1.00 | 15.92 |
| 11073 | O | LEU | B | 333 | 29.910 | 59.982 | 83.559 | 1.00 | 15.74 |
| 11074 | N | ALA | B | 334 | 31.979 | 60.456 | 82.819 | 1.00 | 15.69 |
| 11076 | CA | ALA | B | 334 | 31.588 | 61.652 | 82.072 | 1.00 | 15.54 |
| 11078 | CB | ALA | B | 334 | 32.822 | 62.429 | 81.612 | 1.00 | 15.66 |
| 11082 | C | ALA | B | 334 | 30.722 | 61.291 | 80.865 | 1.00 | 15.16 |

FIGURE 3 (Cont.)

| A | B | C | D | E | F | G | H | I | J |
|---|---|---|---|---|---|---|---|---|---|
| 11083 | O | ALA | B | 334 | 29.765 | 61.988 | 80.560 | 1.00 | 14.91 |
| 11084 | N | LEU | B | 335 | 31.067 | 60.208 | 80.180 | 1.00 | 14.79 |
| 11086 | CA | LEU | B | 335 | 30.277 | 59.733 | 79.047 | 1.00 | 14.69 |
| 11088 | CB | LEU | B | 335 | 30.939 | 58.515 | 78.408 | 1.00 | 14.76 |
| 11091 | CG | LEU | B | 335 | 30.201 | 57.857 | 77.243 | 1.00 | 15.26 |
| 11093 | CD1 | LEU | B | 335 | 30.196 | 58.771 | 76.030 | 1.00 | 15.87 |
| 11097 | CD2 | LEU | B | 335 | 30.849 | 56.519 | 76.922 | 1.00 | 15.88 |
| 11101 | C | LEU | B | 335 | 28.858 | 59.372 | 79.483 | 1.00 | 14.40 |
| 11102 | O | LEU | B | 335 | 27.894 | 59.698 | 78.795 | 1.00 | 14.15 |
| 11103 | N | LEU | B | 336 | 28.741 | 58.707 | 80.631 | 1.00 | 14.05 |
| 11105 | CA | LEU | B | 336 | 27.443 | 58.288 | 81.149 | 1.00 | 14.11 |
| 11107 | CB | LEU | B | 336 | 27.619 | 57.245 | 82.257 | 1.00 | 14.12 |
| 11110 | CG | LEU | B | 336 | 28.312 | 55.948 | 81.818 | 1.00 | 14.19 |
| 11112 | CD1 | LEU | B | 336 | 28.616 | 55.070 | 83.030 | 1.00 | 14.30 |
| 11116 | CD2 | LEU | B | 336 | 27.466 | 55.188 | 80.792 | 1.00 | 14.15 |
| 11120 | C | LEU | B | 336 | 26.648 | 59.488 | 81.655 | 1.00 | 14.14 |
| 11121 | O | LEU | B | 336 | 25.460 | 59.630 | 81.347 | 1.00 | 13.93 |
| 11122 | N | ASP | B | 337 | 27.316 | 60.367 | 82.399 | 1.00 | 14.27 |
| 11124 | CA | ASP | B | 337 | 26.667 | 61.532 | 83.010 | 1.00 | 14.58 |
| 11126 | CB | ASP | B | 337 | 27.629 | 62.238 | 83.983 | 1.00 | 15.00 |
| 11129 | CG | ASP | B | 337 | 27.795 | 61.494 | 85.295 | 1.00 | 15.71 |
| 11130 | OD1 | ASP | B | 337 | 28.893 | 61.558 | 85.884 | 1.00 | 17.33 |
| 11131 | OD2 | ASP | B | 337 | 26.883 | 60.835 | 85.828 | 1.00 | 17.68 |
| 11132 | C | ASP | B | 337 | 26.164 | 62.545 | 81.978 | 1.00 | 14.37 |
| 11133 | O | ASP | B | 337 | 25.165 | 63.218 | 82.206 | 1.00 | 14.11 |
| 11134 | N | ASN | B | 338 | 26.854 | 62.642 | 80.845 | 1.00 | 14.23 |
| 11136 | CA | ASN | B | 338 | 26.540 | 63.651 | 79.835 | 1.00 | 14.33 |
| 11138 | CB | ASN | B | 338 | 27.790 | 63.996 | 79.015 | 1.00 | 14.85 |
| 11141 | CG | ASN | B | 338 | 28.759 | 64.909 | 79.772 | 1.00 | 17.05 |
| 11142 | OD1 | ASN | B | 338 | 28.359 | 65.659 | 80.670 | 1.00 | 20.29 |
| 11143 | ND2 | ASN | B | 338 | 30.037 | 64.852 | 79.404 | 1.00 | 19.22 |
| 11146 | C | ASN | B | 338 | 25.384 | 63.254 | 78.910 | 1.00 | 13.44 |
| 11147 | O | ASN | B | 338 | 24.949 | 64.054 | 78.082 | 1.00 | 13.44 |
| 11148 | N | ARG | B | 339 | 24.876 | 62.034 | 79.065 | 1.00 | 12.30 |
| 11150 | CA | ARG | B | 339 | 23.697 | 61.594 | 78.323 | 1.00 | 11.61 |
| 11152 | CB | ARG | B | 339 | 23.446 | 60.097 | 78.523 | 1.00 | 11.32 |
| 11155 | CG | ARG | B | 339 | 24.606 | 59.192 | 78.137 | 1.00 | 10.86 |
| 11158 | CD | ARG | B | 339 | 24.343 | 57.721 | 78.393 | 1.00 | 10.19 |
| 11161 | NE | ARG | B | 339 | 24.177 | 57.436 | 79.815 | 1.00 | 8.74 |
| 11163 | CZ | ARG | B | 339 | 23.827 | 56.253 | 80.315 | 1.00 | 7.48 |
| 11164 | NH1 | ARG | B | 339 | 23.598 | 55.220 | 79.517 | 1.00 | 5.57 |
| 11167 | NH2 | ARG | B | 339 | 23.698 | 56.113 | 81.630 | 1.00 | 7.50 |
| 11170 | C | ARG | B | 339 | 22.447 | 62.347 | 78.761 | 1.00 | 11.24 |
| 11171 | O | ARG | B | 339 | 22.357 | 62.831 | 79.890 | 1.00 | 11.15 |
| 11172 | N | THR | B | 340 | 21.481 | 62.418 | 77.855 | 1.00 | 10.68 |
| 11174 | CA | THR | B | 340 | 20.192 | 63.034 | 78.120 | 1.00 | 10.42 |
| 11176 | CB | THR | B | 340 | 19.749 | 63.841 | 76.903 | 1.00 | 10.52 |
| 11178 | OG1 | THR | B | 340 | 20.736 | 64.836 | 76.611 | 1.00 | 9.95 |
| 11180 | CG2 | THR | B | 340 | 18.467 | 64.627 | 77.197 | 1.00 | 11.00 |
| 11184 | C | THR | B | 340 | 19.165 | 61.957 | 78.420 | 1.00 | 10.01 |
| 11185 | O | THR | B | 340 | 18.967 | 61.041 | 77.628 | 1.00 | 9.79 |
| 11186 | N | GLU | B | 341 | 18.523 | 62.065 | 79.574 | 1.00 | 9.45 |

FIGURE 3 (Cont.)

| A | B | C | D | E | F | G | H | I | J |
|---|---|---|---|---|---|---|---|---|---|
| 11188 | CA  | GLU | B | 341 | 17.428 | 61.176 | 79.916 | 1.00 | 9.20 |
| 11190 | CB  | GLU | B | 341 | 17.063 | 61.324 | 81.389 | 1.00 | 9.01 |
| 11193 | CG  | GLU | B | 341 | 16.157 | 60.226 | 81.919 | 1.00 | 9.16 |
| 11196 | CD  | GLU | B | 341 | 15.612 | 60.550 | 83.295 | 1.00 | 9.02 |
| 11197 | OE1 | GLU | B | 341 | 14.546 | 60.006 | 83.655 | 1.00 | 9.03 |
| 11198 | OE2 | GLU | B | 341 | 16.233 | 61.374 | 83.998 | 1.00 | 7.47 |
| 11199 | C   | GLU | B | 341 | 16.217 | 61.497 | 79.047 | 1.00 | 8.95 |
| 11200 | O   | GLU | B | 341 | 15.935 | 62.668 | 78.762 | 1.00 | 8.22 |
| 11201 | N   | LEU | B | 342 | 15.513 | 60.446 | 78.635 | 1.00 | 8.86 |
| 11203 | CA  | LEU | B | 342 | 14.274 | 60.568 | 77.881 | 1.00 | 8.98 |
| 11205 | CB  | LEU | B | 342 | 14.300 | 59.667 | 76.641 | 1.00 | 8.94 |
| 11208 | CG  | LEU | B | 342 | 15.437 | 59.828 | 75.623 | 1.00 | 8.96 |
| 11210 | CD1 | LEU | B | 342 | 15.405 | 58.693 | 74.617 | 1.00 | 8.88 |
| 11214 | CD2 | LEU | B | 342 | 15.364 | 61.165 | 74.908 | 1.00 | 8.66 |
| 11218 | C   | LEU | B | 342 | 13.125 | 60.132 | 78.781 | 1.00 | 8.98 |
| 11219 | O   | LEU | B | 342 | 13.287 | 59.244 | 79.627 | 1.00 | 9.12 |
| 11220 | N   | SER | B | 343 | 11.964 | 60.754 | 78.603 | 1.00 | 9.16 |
| 11222 | CA  | SER | B | 343 | 10.744 | 60.270 | 79.235 | 1.00 | 9.05 |
| 11224 | CB  | SER | B | 343 | 9.618  | 61.288 | 79.106 | 1.00 | 9.13 |
| 11227 | OG  | SER | B | 343 | 9.175  | 61.380 | 77.770 | 1.00 | 8.54 |
| 11229 | C   | SER | B | 343 | 10.367 | 58.977 | 78.528 | 1.00 | 9.18 |
| 11230 | O   | SER | B | 343 | 10.869 | 58.696 | 77.438 | 1.00 | 9.00 |
| 11231 | N   | ILE | B | 344 | 9.489  | 58.189 | 79.129 | 1.00 | 9.29 |
| 11233 | CA  | ILE | B | 344 | 9.124  | 56.917 | 78.522 | 1.00 | 9.73 |
| 11235 | CB  | ILE | B | 344 | 8.264  | 56.053 | 79.468 | 1.00 | 9.81 |
| 11237 | CG1 | ILE | B | 344 | 9.051  | 55.708 | 80.741 | 1.00 | 10.18 |
| 11240 | CD1 | ILE | B | 344 | 10.390 | 54.979 | 80.502 | 1.00 | 10.70 |
| 11244 | CG2 | ILE | B | 344 | 7.801  | 54.767 | 78.760 | 1.00 | 10.09 |
| 11248 | C   | ILE | B | 344 | 8.441  | 57.156 | 77.176 | 1.00 | 9.76 |
| 11249 | O   | ILE | B | 344 | 8.692  | 56.423 | 76.237 | 1.00 | 9.79 |
| 11250 | N   | ALA | B | 345 | 7.618  | 58.199 | 77.072 | 1.00 | 9.86 |
| 11252 | CA  | ALA | B | 345 | 6.952  | 58.521 | 75.810 | 1.00 | 9.91 |
| 11254 | CB  | ALA | B | 345 | 5.944  | 59.643 | 76.001 | 1.00 | 10.10 |
| 11258 | C   | ALA | B | 345 | 7.966  | 58.893 | 74.725 | 1.00 | 10.00 |
| 11259 | O   | ALA | B | 345 | 7.839  | 58.457 | 73.578 | 1.00 | 9.82 |
| 11260 | N   | GLU | B | 346 | 8.968  | 59.689 | 75.090 | 1.00 | 10.02 |
| 11262 | CA  | GLU | B | 346 | 10.037 | 60.058 | 74.158 | 1.00 | 10.20 |
| 11264 | CB  | GLU | B | 346 | 10.998 | 61.062 | 74.798 | 1.00 | 10.37 |
| 11267 | CG  | GLU | B | 346 | 10.446 | 62.476 | 74.897 | 1.00 | 11.02 |
| 11270 | CD  | GLU | B | 346 | 11.320 | 63.407 | 75.725 | 1.00 | 12.36 |
| 11271 | OE1 | GLU | B | 346 | 11.062 | 64.631 | 75.709 | 1.00 | 12.10 |
| 11272 | OE2 | GLU | B | 346 | 12.263 | 62.925 | 76.393 | 1.00 | 12.68 |
| 11273 | C   | GLU | B | 346 | 10.800 | 58.809 | 73.723 | 1.00 | 10.06 |
| 11274 | O   | GLU | B | 346 | 11.132 | 58.650 | 72.556 | 1.00 | 10.08 |
| 11275 | N   | TYR | B | 347 | 11.050 | 57.919 | 74.677 | 1.00 | 9.82 |
| 11277 | CA  | TYR | B | 347 | 11.751 | 56.665 | 74.423 | 1.00 | 9.70 |
| 11279 | CB  | TYR | B | 347 | 12.035 | 55.951 | 75.749 | 1.00 | 9.72 |
| 11282 | CG  | TYR | B | 347 | 12.048 | 54.436 | 75.705 | 1.00 | 9.50 |
| 11283 | CD1 | TYR | B | 347 | 10.987 | 53.694 | 76.212 | 1.00 | 8.99 |
| 11285 | CE1 | TYR | B | 347 | 11.007 | 52.307 | 76.194 | 1.00 | 8.24 |
| 11287 | CZ  | TYR | B | 347 | 12.108 | 51.649 | 75.681 | 1.00 | 8.67 |
| 11288 | OH  | TYR | B | 347 | 12.142 | 50.276 | 75.660 | 1.00 | 7.76 |

FIGURE 3 (Cont.)

| A | B | C | D | E | F | G | H | I | J |
|---|---|---|---|---|---|---|---|---|---|
| 11290 | CE2 | TYR | B | 347 | 13.179 | 52.364 | 75.184 | 1.00 | 8.99 |
| 11292 | CD2 | TYR | B | 347 | 13.145 | 53.749 | 75.207 | 1.00 | 9.88 |
| 11294 | C | TYR | B | 347 | 10.959 | 55.764 | 73.483 | 1.00 | 9.76 |
| 11295 | O | TYR | B | 347 | 11.526 | 55.183 | 72.572 | 1.00 | 8.87 |
| 11296 | N | GLU | B | 348 | 9.651 | 55.664 | 73.699 | 1.00 | 10.00 |
| 11298 | CA | GLU | B | 348 | 8.802 | 54.808 | 72.874 | 1.00 | 10.55 |
| 11300 | CB | GLU | B | 348 | 7.389 | 54.718 | 73.454 | 1.00 | 10.69 |
| 11303 | CG | GLU | B | 348 | 7.311 | 53.871 | 74.711 | 1.00 | 11.67 |
| 11306 | CD | GLU | B | 348 | 5.889 | 53.552 | 75.132 | 1.00 | 13.62 |
| 11307 | OE1 | GLU | B | 348 | 4.951 | 54.276 | 74.730 | 1.00 | 15.63 |
| 11308 | OE2 | GLU | B | 348 | 5.710 | 52.570 | 75.870 | 1.00 | 13.66 |
| 11309 | C | GLU | B | 348 | 8.759 | 55.285 | 71.424 | 1.00 | 10.83 |
| 11310 | O | GLU | B | 348 | 8.742 | 54.470 | 70.509 | 1.00 | 10.67 |
| 11311 | N | ALA | B | 349 | 8.764 | 56.602 | 71.228 | 1.00 | 11.02 |
| 11313 | CA | ALA | B | 349 | 8.812 | 57.193 | 69.893 | 1.00 | 11.40 |
| 11315 | CB | ALA | B | 349 | 8.563 | 58.698 | 69.972 | 1.00 | 11.42 |
| 11319 | C | ALA | B | 349 | 10.154 | 56.910 | 69.209 | 1.00 | 11.57 |
| 11320 | O | ALA | B | 349 | 10.190 | 56.495 | 68.053 | 1.00 | 11.54 |
| 11321 | N | MSE | B | 350 | 11.252 | 57.129 | 69.927 | 1.00 | 11.95 |
| 11323 | CA | MSE | B | 350 | 12.587 | 56.821 | 69.409 | 1.00 | 12.09 |
| 11325 | CB | MSE | B | 350 | 13.663 | 57.217 | 70.423 | 1.00 | 12.03 |
| 11328 | CG | MSE | B | 350 | 15.085 | 57.087 | 69.900 | 1.00 | 12.10 |
| 11331 | SE | MSE | B | 350 | 16.436 | 57.770 | 71.113 | 1.00 | 13.04 |
| 11332 | CE | MSE | B | 350 | 16.184 | 59.696 | 70.854 | 1.00 | 12.21 |
| 11336 | C | MSE | B | 350 | 12.720 | 55.332 | 69.071 | 1.00 | 12.20 |
| 11337 | O | MSE | B | 350 | 13.240 | 54.976 | 68.017 | 1.00 | 12.36 |
| 11338 | N | PHE | B | 351 | 12.230 | 54.483 | 69.972 | 1.00 | 12.37 |
| 11340 | CA | PHE | B | 351 | 12.328 | 53.029 | 69.852 | 1.00 | 12.49 |
| 11342 | CB | PHE | B | 351 | 11.750 | 52.362 | 71.108 | 1.00 | 12.28 |
| 11345 | CG | PHE | B | 351 | 11.927 | 50.868 | 71.140 | 1.00 | 12.01 |
| 11346 | CD1 | PHE | B | 351 | 11.057 | 50.031 | 70.447 | 1.00 | 11.28 |
| 11348 | CE1 | PHE | B | 351 | 11.227 | 48.654 | 70.468 | 1.00 | 11.12 |
| 11350 | CZ | PHE | B | 351 | 12.262 | 48.099 | 71.185 | 1.00 | 11.10 |
| 11352 | CE2 | PHE | B | 351 | 13.131 | 48.915 | 71.887 | 1.00 | 11.90 |
| 11354 | CD2 | PHE | B | 351 | 12.960 | 50.297 | 71.864 | 1.00 | 11.87 |
| 11356 | C | PHE | B | 351 | 11.597 | 52.484 | 68.627 | 1.00 | 13.09 |
| 11357 | O | PHE | B | 351 | 12.132 | 51.645 | 67.898 | 1.00 | 13.05 |
| 11358 | N | ALA | B | 352 | 10.369 | 52.955 | 68.425 | 1.00 | 13.62 |
| 11360 | CA | ALA | B | 352 | 9.491 | 52.445 | 67.378 | 1.00 | 14.47 |
| 11362 | CB | ALA | B | 352 | 8.042 | 52.830 | 67.671 | 1.00 | 14.45 |
| 11366 | C | ALA | B | 352 | 9.881 | 52.936 | 65.991 | 1.00 | 15.20 |
| 11367 | O | ALA | B | 352 | 9.490 | 52.329 | 64.995 | 1.00 | 15.48 |
| 11368 | N | GLU | B | 353 | 10.639 | 54.029 | 65.919 | 1.00 | 16.19 |
| 11370 | CA | GLU | B | 353 | 11.013 | 54.606 | 64.631 | 1.00 | 17.09 |
| 11372 | CB | GLU | B | 353 | 11.842 | 55.884 | 64.801 | 1.00 | 17.36 |
| 11375 | CG | GLU | B | 353 | 11.970 | 56.698 | 63.518 | 1.00 | 18.49 |
| 11378 | CD | GLU | B | 353 | 12.588 | 58.072 | 63.725 | 1.00 | 20.21 |
| 11379 | OE1 | GLU | B | 353 | 12.501 | 58.903 | 62.792 | 1.00 | 22.36 |
| 11380 | OE2 | GLU | B | 353 | 13.165 | 58.328 | 64.804 | 1.00 | 20.88 |
| 11381 | C | GLU | B | 353 | 11.779 | 53.588 | 63.790 | 1.00 | 17.43 |
| 11382 | O | GLU | B | 353 | 12.602 | 52.827 | 64.302 | 1.00 | 16.88 |
| 11383 | N | THR | B | 354 | 11.470 | 53.580 | 62.498 | 1.00 | 18.19 |

FIGURE 3 (Cont.)

| A | B | C | D | E | F | G | H | I | J |
|---|---|---|---|---|---|---|---|---|---|
| 11385 | CA | THR | B | 354 | 12.065 | 52.665 | 61.539 | 1.00 | 18.88 |
| 11387 | CB | THR | B | 354 | 10.977 | 51.765 | 60.911 | 1.00 | 19.26 |
| 11389 | OG1 | THR | B | 354 | 9.926 | 52.573 | 60.359 | 1.00 | 19.89 |
| 11391 | CG2 | THR | B | 354 | 10.280 | 50.919 | 61.978 | 1.00 | 19.66 |
| 11395 | C | THR | B | 354 | 12.778 | 53.463 | 60.451 | 1.00 | 19.00 |
| 11396 | O | THR | B | 354 | 12.411 | 54.601 | 60.154 | 1.00 | 19.34 |
| 11397 | N | LEU | B | 355 | 13.825 | 52.867 | 59.897 | 1.00 | 19.13 |
| 11399 | CA | LEU | B | 355 | 14.575 | 53.444 | 58.791 | 1.00 | 19.02 |
| 11401 | CB | LEU | B | 355 | 16.074 | 53.456 | 59.112 | 1.00 | 19.22 |
| 11404 | CG | LEU | B | 355 | 17.057 | 53.885 | 58.021 | 1.00 | 19.75 |
| 11406 | CD1 | LEU | B | 355 | 16.872 | 55.348 | 57.709 | 1.00 | 20.55 |
| 11410 | CD2 | LEU | B | 355 | 18.491 | 53.610 | 58.458 | 1.00 | 20.02 |
| 11414 | C | LEU | B | 355 | 14.300 | 52.576 | 57.577 | 1.00 | 18.55 |
| 11415 | O | LEU | B | 355 | 14.691 | 51.407 | 57.545 | 1.00 | 18.57 |
| 11416 | N | ASP | B | 356 | 13.588 | 53.140 | 56.606 | 1.00 | 17.99 |
| 11418 | CA | ASP | B | 356 | 13.376 | 52.480 | 55.332 | 1.00 | 17.65 |
| 11420 | CB | ASP | B | 356 | 12.046 | 52.917 | 54.707 | 1.00 | 17.85 |
| 11423 | CG | ASP | B | 356 | 11.619 | 52.024 | 53.544 | 1.00 | 18.42 |
| 11424 | OD1 | ASP | B | 356 | 12.467 | 51.283 | 52.999 | 1.00 | 17.69 |
| 11425 | OD2 | ASP | B | 356 | 10.446 | 51.992 | 53.106 | 1.00 | 20.33 |
| 11426 | C | ASP | B | 356 | 14.554 | 52.836 | 54.428 | 1.00 | 17.05 |
| 11427 | O | ASP | B | 356 | 14.610 | 53.931 | 53.864 | 1.00 | 16.95 |
| 11428 | N | THR | B | 357 | 15.494 | 51.900 | 54.305 | 1.00 | 16.42 |
| 11430 | CA | THR | B | 357 | 16.702 | 52.101 | 53.503 | 1.00 | 15.93 |
| 11432 | CB | THR | B | 357 | 17.798 | 51.080 | 53.887 | 1.00 | 15.93 |
| 11434 | OG1 | THR | B | 357 | 17.286 | 49.740 | 53.810 | 1.00 | 15.83 |
| 11436 | CG2 | THR | B | 357 | 18.214 | 51.249 | 55.336 | 1.00 | 16.00 |
| 11440 | C | THR | B | 357 | 16.456 | 52.046 | 51.989 | 1.00 | 15.54 |
| 11441 | O | THR | B | 357 | 17.355 | 52.345 | 51.217 | 1.00 | 14.91 |
| 11442 | N | ASP | B | 358 | 15.252 | 51.660 | 51.572 | 1.00 | 15.35 |
| 11444 | CA | ASP | B | 358 | 14.860 | 51.737 | 50.161 | 1.00 | 15.59 |
| 11446 | CB | ASP | B | 358 | 13.758 | 50.716 | 49.850 | 1.00 | 15.74 |
| 11449 | CG | ASP | B | 358 | 14.283 | 49.292 | 49.785 | 1.00 | 16.61 |
| 11450 | OD1 | ASP | B | 358 | 15.506 | 49.108 | 49.563 | 1.00 | 17.22 |
| 11451 | OD2 | ASP | B | 358 | 13.549 | 48.296 | 49.949 | 1.00 | 17.15 |
| 11452 | C | ASP | B | 358 | 14.409 | 53.145 | 49.744 | 1.00 | 15.48 |
| 11453 | O | ASP | B | 358 | 14.120 | 53.379 | 48.569 | 1.00 | 15.12 |
| 11454 | N | ILE | B | 359 | 14.370 | 54.071 | 50.703 | 1.00 | 15.32 |
| 11456 | CA | ILE | B | 359 | 14.000 | 55.462 | 50.455 | 1.00 | 15.41 |
| 11458 | CB | ILE | B | 359 | 12.851 | 55.890 | 51.401 | 1.00 | 15.60 |
| 11460 | CG1 | ILE | B | 359 | 11.617 | 55.017 | 51.141 | 1.00 | 16.35 |
| 11463 | CD1 | ILE | B | 359 | 10.384 | 55.403 | 51.938 | 1.00 | 17.78 |
| 11467 | CG2 | ILE | B | 359 | 12.521 | 57.390 | 51.214 | 1.00 | 15.96 |
| 11471 | C | ILE | B | 359 | 15.212 | 56.365 | 50.650 | 1.00 | 14.95 |
| 11472 | O | ILE | B | 359 | 15.777 | 56.430 | 51.745 | 1.00 | 14.64 |
| 11473 | N | ASP | B | 360 | 15.607 | 57.050 | 49.581 | 1.00 | 14.56 |
| 11475 | CA | ASP | B | 360 | 16.681 | 58.035 | 49.639 | 1.00 | 14.42 |
| 11477 | CB | ASP | B | 360 | 17.019 | 58.554 | 48.239 | 1.00 | 14.36 |
| 11480 | CG | ASP | B | 360 | 17.728 | 57.516 | 47.379 | 1.00 | 14.74 |
| 11481 | OD1 | ASP | B | 360 | 17.999 | 57.811 | 46.195 | 1.00 | 14.42 |
| 11482 | OD2 | ASP | B | 360 | 18.055 | 56.383 | 47.795 | 1.00 | 14.37 |
| 11483 | C | ASP | B | 360 | 16.276 | 59.196 | 50.553 | 1.00 | 14.32 |

FIGURE 3 (Cont.)

| A | B | C | D | E | F | G | H | I | J |
|---|---|---|---|---|---|---|---|---|---|
| 11484 | O | ASP | B | 360 | 15.209 | 59.788 | 50.387 | 1.00 | 13.96 |
| 11485 | N | GLN | B | 361 | 17.134 | 59.509 | 51.517 | 1.00 | 14.17 |
| 11487 | CA | GLN | B | 361 | 16.824 | 60.506 | 52.540 | 1.00 | 14.32 |
| 11489 | CB | GLN | B | 361 | 15.877 | 59.896 | 53.581 | 1.00 | 14.41 |
| 11492 | CG | GLN | B | 361 | 16.436 | 58.642 | 54.279 | 1.00 | 15.13 |
| 11495 | CD | GLN | B | 361 | 15.370 | 57.832 | 55.008 | 1.00 | 16.45 |
| 11496 | OE1 | GLN | B | 361 | 14.836 | 58.274 | 56.025 | 1.00 | 17.74 |
| 11497 | NE2 | GLN | B | 361 | 15.065 | 56.649 | 54.492 | 1.00 | 17.76 |
| 11500 | C | GLN | B | 361 | 18.079 | 61.010 | 53.243 | 1.00 | 14.13 |
| 11501 | O | GLN | B | 361 | 19.140 | 60.384 | 53.175 | 1.00 | 14.32 |
| 11502 | N | THR | B | 362 | 17.945 | 62.146 | 53.921 | 1.00 | 13.74 |
| 11504 | CA | THR | B | 362 | 18.947 | 62.622 | 54.864 | 1.00 | 13.49 |
| 11506 | CB | THR | B | 362 | 19.278 | 64.110 | 54.630 | 1.00 | 13.57 |
| 11508 | OG1 | THR | B | 362 | 18.088 | 64.900 | 54.742 | 1.00 | 13.40 |
| 11510 | CG2 | THR | B | 362 | 19.763 | 64.353 | 53.198 | 1.00 | 13.84 |
| 11514 | C | THR | B | 362 | 18.423 | 62.429 | 56.283 | 1.00 | 13.44 |
| 11515 | O | THR | B | 362 | 17.210 | 62.468 | 56.526 | 1.00 | 13.00 |
| 11516 | N | LEU | B | 363 | 19.351 | 62.205 | 57.208 | 1.00 | 13.20 |
| 11518 | CA | LEU | B | 363 | 19.050 | 62.092 | 58.626 | 1.00 | 13.20 |
| 11520 | CB | LEU | B | 363 | 19.522 | 60.741 | 59.162 | 1.00 | 13.16 |
| 11523 | CG | ALEU | B | 363 | 18.766 | 59.500 | 58.666 | 0.65 | 12.86 |
| 11525 | CD1 | ALEU | B | 363 | 19.211 | 59.086 | 57.262 | 0.65 | 12.75 |
| 11529 | CD2 | ALEU | B | 363 | 18.942 | 58.339 | 59.639 | 0.65 | 12.75 |
| 11533 | C | LEU | B | 363 | 19.756 | 63.232 | 59.350 | 1.00 | 13.39 |
| 11534 | O | LEU | B | 363 | 20.832 | 63.666 | 58.931 | 1.00 | 13.20 |
| 11535 | N | GLU | B | 364 | 19.136 | 63.719 | 60.421 | 1.00 | 13.53 |
| 11537 | CA | GLU | B | 364 | 19.674 | 64.823 | 61.207 | 1.00 | 13.88 |
| 11539 | CB | GLU | B | 364 | 18.611 | 65.912 | 61.371 | 1.00 | 14.21 |
| 11542 | CG | GLU | B | 364 | 19.117 | 67.169 | 62.056 | 1.00 | 14.98 |
| 11545 | CD | GLU | B | 364 | 18.143 | 68.332 | 61.957 | 1.00 | 16.33 |
| 11546 | OE1 | GLU | B | 364 | 16.919 | 68.101 | 61.794 | 1.00 | 15.82 |
| 11547 | OE2 | GLU | B | 364 | 18.615 | 69.484 | 62.046 | 1.00 | 16.94 |
| 11548 | C | GLU | B | 364 | 20.111 | 64.296 | 62.573 | 1.00 | 13.74 |
| 11549 | O | GLU | B | 364 | 19.288 | 63.818 | 63.351 | 1.00 | 13.49 |
| 11550 | N | ASP | B | 365 | 21.411 | 64.377 | 62.843 | 1.00 | 13.35 |
| 11552 | CA | ASP | B | 365 | 21.987 | 63.891 | 64.093 | 1.00 | 13.46 |
| 11554 | CB | ASP | B | 365 | 22.141 | 62.363 | 64.039 | 1.00 | 13.29 |
| 11557 | CG | ASP | B | 365 | 22.368 | 61.732 | 65.409 | 1.00 | 13.47 |
| 11558 | OD1 | ASP | B | 365 | 22.897 | 62.400 | 66.320 | 1.00 | 12.97 |
| 11559 | OD2 | ASP | B | 365 | 22.050 | 60.552 | 65.668 | 1.00 | 13.18 |
| 11560 | C | ASP | B | 365 | 23.347 | 64.554 | 64.284 | 1.00 | 13.53 |
| 11561 | O | ASP | B | 365 | 24.183 | 64.522 | 63.384 | 1.00 | 13.41 |
| 11562 | N | GLU | B | 366 | 23.577 | 65.136 | 65.456 | 1.00 | 13.68 |
| 11564 | CA | GLU | B | 366 | 24.826 | 65.860 | 65.709 | 1.00 | 14.09 |
| 11566 | CB | GLU | B | 366 | 24.602 | 66.926 | 66.793 | 1.00 | 14.74 |
| 11569 | CG | GLU | B | 366 | 23.671 | 68.058 | 66.354 | 1.00 | 17.25 |
| 11572 | CD | GLU | B | 366 | 23.964 | 68.554 | 64.940 | 1.00 | 20.82 |
| 11573 | OE1 | GLU | B | 366 | 25.076 | 69.085 | 64.710 | 1.00 | 23.21 |
| 11574 | OE2 | GLU | B | 366 | 23.089 | 68.398 | 64.051 | 1.00 | 23.46 |
| 11575 | C | GLU | B | 366 | 26.012 | 64.953 | 66.078 | 1.00 | 13.37 |
| 11576 | O | GLU | B | 366 | 27.162 | 65.401 | 66.071 | 1.00 | 13.09 |
| 11577 | N | LEU | B | 367 | 25.737 | 63.684 | 66.380 | 1.00 | 12.58 |

FIGURE 3 (Cont.)

| A | B | C | D | E | F | G | H | I | J |
|---|---|---|---|---|---|---|---|---|---|
| 11579 | CA | LEU | B | 367 | 26.779 | 62.749 | 66.800 | 1.00 | 12.06 |
| 11581 | CB | LEU | B | 367 | 26.152 | 61.463 | 67.353 | 1.00 | 12.12 |
| 11584 | CG | LEU | B | 367 | 27.113 | 60.407 | 67.915 | 1.00 | 12.42 |
| 11586 | CD1 | LEU | B | 367 | 27.876 | 60.948 | 69.112 | 1.00 | 13.19 |
| 11590 | CD2 | LEU | B | 367 | 26.360 | 59.133 | 68.290 | 1.00 | 12.59 |
| 11594 | C | LEU | B | 367 | 27.718 | 62.405 | 65.646 | 1.00 | 11.46 |
| 11595 | O | LEU | B | 367 | 27.271 | 62.093 | 64.547 | 1.00 | 11.04 |
| 11596 | N | LYS | B | 368 | 29.022 | 62.456 | 65.904 | 1.00 | 10.93 |
| 11598 | CA | LYS | B | 368 | 30.010 | 62.027 | 64.921 | 1.00 | 10.70 |
| 11600 | CB | LYS | B | 368 | 31.431 | 62.236 | 65.443 | 1.00 | 10.71 |
| 11603 | CG | LYS | B | 368 | 32.509 | 62.197 | 64.370 | 1.00 | 11.24 |
| 11606 | CD | LYS | B | 368 | 33.875 | 62.468 | 64.994 | 1.00 | 11.42 |
| 11609 | CE | LYS | B | 368 | 34.974 | 62.497 | 63.966 | 1.00 | 11.16 |
| 11612 | NZ | LYS | B | 368 | 36.316 | 62.456 | 64.603 | 1.00 | 11.46 |
| 11616 | C | LYS | B | 368 | 29.787 | 60.553 | 64.588 | 1.00 | 10.25 |
| 11617 | O | LYS | B | 368 | 29.490 | 59.750 | 65.471 | 1.00 | 9.62 |
| 11618 | N | TYR | B | 369 | 29.904 | 60.229 | 63.302 | 1.00 | 10.05 |
| 11620 | CA | TYR | B | 369 | 29.729 | 58.868 | 62.774 | 1.00 | 10.10 |
| 11622 | CB | TYR | B | 369 | 30.653 | 57.859 | 63.477 | 1.00 | 10.21 |
| 11625 | CG | TYR | B | 369 | 32.125 | 58.219 | 63.420 | 1.00 | 10.85 |
| 11626 | CD1 | TYR | B | 369 | 32.889 | 58.307 | 64.585 | 1.00 | 11.50 |
| 11628 | CE1 | TYR | B | 369 | 34.234 | 58.632 | 64.537 | 1.00 | 11.51 |
| 11630 | CZ | TYR | B | 369 | 34.834 | 58.873 | 63.321 | 1.00 | 11.71 |
| 11631 | OH | TYR | B | 369 | 36.169 | 59.198 | 63.274 | 1.00 | 13.04 |
| 11633 | CE2 | TYR | B | 369 | 34.103 | 58.793 | 62.152 | 1.00 | 11.79 |
| 11635 | CD2 | TYR | B | 369 | 32.756 | 58.461 | 62.206 | 1.00 | 11.05 |
| 11637 | C | TYR | B | 369 | 28.279 | 58.359 | 62.777 | 1.00 | 9.87 |
| 11638 | O | TYR | B | 369 | 28.037 | 57.183 | 62.489 | 1.00 | 9.44 |
| 11639 | N | SER | B | 370 | 27.319 | 59.233 | 63.079 | 1.00 | 9.72 |
| 11641 | CA | SER | B | 370 | 25.908 | 58.910 | 62.876 | 1.00 | 9.85 |
| 11643 | CB | SER | B | 370 | 24.989 | 59.905 | 63.602 | 1.00 | 9.99 |
| 11646 | OG | SER | B | 370 | 25.220 | 61.238 | 63.201 | 1.00 | 9.45 |
| 11648 | C | SER | B | 370 | 25.602 | 58.893 | 61.385 | 1.00 | 10.03 |
| 11649 | O | SER | B | 370 | 26.346 | 59.456 | 60.579 | 1.00 | 10.10 |
| 11650 | N | ILE | B | 371 | 24.510 | 58.235 | 61.021 | 1.00 | 10.28 |
| 11652 | CA | ILE | B | 371 | 24.082 | 58.155 | 59.629 | 1.00 | 10.27 |
| 11654 | CB | ILE | B | 371 | 22.924 | 57.137 | 59.454 | 1.00 | 10.13 |
| 11656 | CG1 | ILE | B | 371 | 23.315 | 55.755 | 59.980 | 1.00 | 9.89 |
| 11659 | CD1 | ILE | B | 371 | 22.140 | 54.883 | 60.313 | 1.00 | 9.38 |
| 11663 | CG2 | ILE | B | 371 | 22.528 | 57.026 | 57.982 | 1.00 | 10.55 |
| 11667 | C | ILE | B | 371 | 23.622 | 59.537 | 59.179 | 1.00 | 10.40 |
| 11668 | O | ILE | B | 371 | 22.709 | 60.109 | 59.777 | 1.00 | 10.47 |
| 11669 | N | SER | B | 372 | 24.269 | 60.057 | 58.138 | 1.00 | 10.37 |
| 11671 | CA | SER | B | 372 | 23.928 | 61.340 | 57.521 | 1.00 | 10.72 |
| 11673 | CB | SER | B | 372 | 25.210 | 62.047 | 57.063 | 1.00 | 10.69 |
| 11676 | OG | SER | B | 372 | 25.960 | 61.220 | 56.189 | 1.00 | 10.82 |
| 11678 | C | SER | B | 372 | 22.969 | 61.209 | 56.323 | 1.00 | 10.91 |
| 11679 | O | SER | B | 372 | 22.193 | 62.126 | 56.048 | 1.00 | 11.12 |
| 11680 | N | ALA | B | 373 | 23.032 | 60.089 | 55.607 | 1.00 | 10.97 |
| 11682 | CA | ALA | B | 373 | 22.185 | 59.881 | 54.427 | 1.00 | 11.30 |
| 11684 | CB | ALA | B | 373 | 22.717 | 60.710 | 53.244 | 1.00 | 11.23 |
| 11688 | C | ALA | B | 373 | 22.054 | 58.415 | 54.004 | 1.00 | 11.59 |

FIGURE 3 (Cont.)

| A | B | C | D | E | F | G | H | I | J |
|---|---|---|---|---|---|---|---|---|---|
| 11689 | O | ALA | B | 373 | 22.896 | 57.581 | 54.339 | 1.00 | 11.84 |
| 11690 | N | ILE | B | 374 | 20.975 | 58.123 | 53.281 | 1.00 | 11.72 |
| 11692 | CA | ILE | B | 374 | 20.789 | 56.872 | 52.550 | 1.00 | 11.93 |
| 11694 | CB | ILE | B | 374 | 19.510 | 56.130 | 53.019 | 1.00 | 12.18 |
| 11696 | CG1 | ILE | B | 374 | 19.485 | 55.945 | 54.543 | 1.00 | 12.53 |
| 11699 | CD1 | ILE | B | 374 | 20.529 | 55.009 | 55.087 | 1.00 | 13.42 |
| 11703 | CG2 | ILE | B | 374 | 19.375 | 54.788 | 52.295 | 1.00 | 12.25 |
| 11707 | C | ILE | B | 374 | 20.645 | 57.214 | 51.065 | 1.00 | 11.83 |
| 11708 | O | ILE | B | 374 | 19.832 | 58.063 | 50.704 | 1.00 | 11.77 |
| 11709 | N | ASN | B | 375 | 21.446 | 56.569 | 50.218 | 1.00 | 11.82 |
| 11711 | CA | ASN | B | 375 | 21.369 | 56.721 | 48.761 | 1.00 | 11.71 |
| 11713 | CB | ASN | B | 375 | 22.489 | 57.613 | 48.232 | 1.00 | 11.99 |
| 11716 | CG | ASN | B | 375 | 22.465 | 58.996 | 48.817 | 1.00 | 13.40 |
| 11717 | OD1 | ASN | B | 375 | 23.199 | 59.292 | 49.765 | 1.00 | 16.17 |
| 11718 | ND2 | ASN | B | 375 | 21.633 | 59.865 | 48.251 | 1.00 | 14.40 |
| 11721 | C | ASN | B | 375 | 21.516 | 55.357 | 48.108 | 1.00 | 11.32 |
| 11722 | O | ASN | B | 375 | 22.553 | 54.718 | 48.251 | 1.00 | 10.98 |
| 11723 | N | ASN | B | 376 | 20.493 | 54.924 | 47.377 | 1.00 | 10.94 |
| 11725 | CA | ASN | B | 376 | 20.491 | 53.610 | 46.744 | 1.00 | 10.89 |
| 11727 | CB | ASN | B | 376 | 21.491 | 53.608 | 45.581 | 1.00 | 10.79 |
| 11730 | CG | ASN | B | 376 | 21.255 | 52.471 | 44.605 | 1.00 | 10.95 |
| 11731 | OD1 | ASN | B | 376 | 20.116 | 52.089 | 44.338 | 1.00 | 10.69 |
| 11732 | ND2 | ASN | B | 376 | 22.337 | 51.917 | 44.079 | 1.00 | 9.65 |
| 11735 | C | ASN | B | 376 | 20.791 | 52.480 | 47.749 | 1.00 | 10.66 |
| 11736 | O | ASN | B | 376 | 21.508 | 51.533 | 47.433 | 1.00 | 10.56 |
| 11737 | N | THR | B | 377 | 20.226 | 52.621 | 48.953 | 1.00 | 10.48 |
| 11739 | CA | THR | B | 377 | 20.414 | 51.732 | 50.121 | 1.00 | 10.44 |
| 11741 | CB | THR | B | 377 | 20.190 | 50.230 | 49.796 | 1.00 | 10.42 |
| 11743 | OG1 | THR | B | 377 | 21.307 | 49.708 | 49.062 | 1.00 | 9.67 |
| 11745 | CG2 | THR | B | 377 | 18.961 | 50.000 | 48.910 | 1.00 | 10.33 |
| 11749 | C | THR | B | 377 | 21.737 | 51.875 | 50.889 | 1.00 | 10.57 |
| 11750 | O | THR | B | 377 | 21.884 | 51.291 | 51.964 | 1.00 | 10.34 |
| 11751 | N | VAL | B | 378 | 22.677 | 52.649 | 50.353 | 1.00 | 10.71 |
| 11753 | CA | VAL | B | 378 | 23.988 | 52.829 | 50.967 | 1.00 | 11.00 |
| 11755 | CB | VAL | B | 378 | 25.051 | 53.187 | 49.909 | 1.00 | 11.03 |
| 11757 | CG1 | VAL | B | 378 | 26.416 | 53.423 | 50.562 | 1.00 | 11.00 |
| 11761 | CG2 | VAL | B | 378 | 25.139 | 52.080 | 48.851 | 1.00 | 11.52 |
| 11765 | C | VAL | B | 378 | 23.967 | 53.920 | 52.040 | 1.00 | 11.06 |
| 11766 | O | VAL | B | 378 | 23.514 | 55.033 | 51.792 | 1.00 | 11.30 |
| 11767 | N | ARG | B | 379 | 24.477 | 53.589 | 53.222 | 1.00 | 11.19 |
| 11769 | CA | ARG | B | 379 | 24.560 | 54.527 | 54.334 | 1.00 | 11.40 |
| 11771 | CB | ARG | B | 379 | 24.609 | 53.779 | 55.669 | 1.00 | 11.23 |
| 11774 | CG | ARG | B | 379 | 23.323 | 53.073 | 56.039 | 1.00 | 11.32 |
| 11777 | CD | ARG | B | 379 | 23.515 | 51.907 | 56.980 | 1.00 | 11.16 |
| 11780 | NE | ARG | B | 379 | 22.319 | 51.068 | 57.081 | 1.00 | 10.96 |
| 11782 | CZ | ARG | B | 379 | 21.563 | 50.924 | 58.174 | 1.00 | 11.65 |
| 11783 | NH1 | ARG | B | 379 | 21.852 | 51.560 | 59.304 | 1.00 | 11.54 |
| 11786 | NH2 | ARG | B | 379 | 20.504 | 50.125 | 58.140 | 1.00 | 11.82 |
| 11789 | C | ARG | B | 379 | 25.807 | 55.392 | 54.215 | 1.00 | 11.75 |
| 11790 | O | ARG | B | 379 | 26.894 | 54.888 | 53.925 | 1.00 | 11.88 |
| 11791 | N | SER | B | 380 | 25.636 | 56.690 | 54.434 | 1.00 | 11.98 |
| 11793 | CA | SER | B | 380 | 26.748 | 57.615 | 54.605 | 1.00 | 12.68 |

FIGURE 3 (Cont.)

| A | B | C | D | E | F | G | H | I | J |
|---|---|---|---|---|---|---|---|---|---|
| 11795 | CB | SER | B | 380 | 26.558 | 58.861 | 53.740 | 1.00 | 12.84 |
| 11798 | OG | SER | B | 380 | 26.702 | 58.548 | 52.369 | 1.00 | 13.53 |
| 11800 | C | SER | B | 380 | 26.800 | 58.007 | 56.076 | 1.00 | 13.02 |
| 11801 | O | SER | B | 380 | 25.762 | 58.087 | 56.735 | 1.00 | 13.05 |
| 11802 | N | TYR | B | 381 | 28.007 | 58.229 | 56.587 | 1.00 | 13.54 |
| 11804 | CA | TYR | B | 381 | 28.214 | 58.643 | 57.970 | 1.00 | 14.00 |
| 11806 | CB | TYR | B | 381 | 29.032 | 57.583 | 58.715 | 1.00 | 13.66 |
| 11809 | CG | TYR | B | 381 | 28.379 | 56.219 | 58.691 | 1.00 | 12.45 |
| 11810 | CD1 | TYR | B | 381 | 27.465 | 55.850 | 59.669 | 1.00 | 11.45 |
| 11812 | CE1 | TYR | B | 381 | 26.853 | 54.609 | 59.650 | 1.00 | 10.51 |
| 11814 | CZ | TYR | B | 381 | 27.140 | 53.719 | 58.634 | 1.00 | 9.82 |
| 11815 | OH | TYR | B | 381 | 26.522 | 52.493 | 58.617 | 1.00 | 8.76 |
| 11817 | CE2 | TYR | B | 381 | 28.040 | 54.059 | 57.642 | 1.00 | 10.75 |
| 11819 | CD2 | TYR | B | 381 | 28.653 | 55.308 | 57.672 | 1.00 | 11.09 |
| 11821 | C | TYR | B | 381 | 28.921 | 59.998 | 57.996 | 1.00 | 15.25 |
| 11822 | O | TYR | B | 381 | 29.795 | 60.261 | 57.169 | 1.00 | 14.80 |
| 11823 | N | ARG | B | 382 | 28.554 | 60.856 | 58.942 | 1.00 | 16.86 |
| 11825 | CA | ARG | B | 382 | 29.159 | 62.188 | 59.008 | 1.00 | 18.63 |
| 11827 | CB | ARG | B | 382 | 28.236 | 63.223 | 59.664 | 1.00 | 18.86 |
| 11830 | CG | ARG | B | 382 | 27.522 | 62.776 | 60.917 | 1.00 | 19.83 |
| 11833 | CD | ARG | B | 382 | 26.739 | 63.892 | 61.600 | 1.00 | 21.14 |
| 11836 | NE | ARG | B | 382 | 25.698 | 64.481 | 60.752 | 1.00 | 21.52 |
| 11838 | CZ | ARG | B | 382 | 24.529 | 63.908 | 60.433 | 1.00 | 22.44 |
| 11839 | NH1 | ARG | B | 382 | 23.669 | 64.566 | 59.660 | 1.00 | 21.88 |
| 11842 | NH2 | ARG | B | 382 | 24.201 | 62.691 | 60.876 | 1.00 | 21.78 |
| 11845 | C | ARG | B | 382 | 30.516 | 62.129 | 59.707 | 1.00 | 19.76 |
| 11846 | O | ARG | B | 382 | 30.681 | 61.431 | 60.705 | 1.00 | 19.63 |
| 11847 | N | ASN | B | 383 | 31.480 | 62.859 | 59.151 | 1.00 | 21.37 |
| 11849 | CA | ASN | B | 383 | 32.865 | 62.851 | 59.624 | 1.00 | 22.70 |
| 11851 | CB | ASN | B | 383 | 33.830 | 63.068 | 58.448 | 1.00 | 23.01 |
| 11854 | CG | ASN | B | 383 | 33.830 | 61.910 | 57.472 | 1.00 | 24.08 |
| 11855 | OD1 | ASN | B | 383 | 34.305 | 60.816 | 57.787 | 1.00 | 25.76 |
| 11856 | ND2 | ASN | B | 383 | 33.291 | 62.140 | 56.280 | 1.00 | 25.55 |
| 11859 | C | ASN | B | 383 | 33.147 | 63.910 | 60.685 | 1.00 | 23.37 |
| 11860 | O | ASN | B | 383 | 34.212 | 63.891 | 61.293 | 1.00 | 23.83 |
| 11861 | N | ALA | B | 384 | 32.211 | 64.837 | 60.884 | 1.00 | 24.20 |
| 11863 | CA | ALA | B | 384 | 32.358 | 65.910 | 61.869 | 1.00 | 24.72 |
| 11865 | CB | ALA | B | 384 | 32.183 | 67.269 | 61.196 | 1.00 | 24.93 |
| 11869 | C | ALA | B | 384 | 31.350 | 65.744 | 63.003 | 1.00 | 24.96 |
| 11870 | O | ALA | B | 384 | 30.169 | 65.479 | 62.761 | 1.00 | 25.48 |
| 11871 | O20 | hmg | X | 1 | 31.868 | 38.489 | 46.772 | 1.00 | 15.99 |
| 11872 | C26 | hmg | X | 1 | 30.626 | 38.392 | 46.633 | 1.00 | 15.92 |
| 11873 | O19 | hmg | X | 1 | 29.883 | 38.193 | 47.613 | 1.00 | 18.35 |
| 11874 | C25 | hmg | X | 1 | 29.940 | 38.529 | 45.287 | 1.00 | 14.18 |
| 11877 | C23 | hmg | X | 1 | 30.762 | 38.109 | 44.064 | 1.00 | 13.23 |
| 11878 | C24 | hmg | X | 1 | 29.898 | 38.350 | 42.827 | 1.00 | 12.51 |
| 11882 | O18 | hmg | X | 1 | 31.037 | 36.709 | 44.114 | 1.00 | 12.37 |
| 11884 | C22 | hmg | X | 1 | 32.091 | 38.869 | 44.040 | 1.00 | 11.82 |
| 11887 | C21 | hmg | X | 1 | 32.696 | 39.018 | 42.669 | 1.00 | 11.05 |
| 11888 | O16 | hmg | X | 1 | 33.313 | 38.085 | 42.190 | 1.00 | 9.37 |
| 11889 | S1 | hmg | X | 1 | 32.545 | 40.457 | 41.827 | 1.00 | 10.73 |
| 11890 | C20 | hmg | X | 1 | 33.185 | 40.192 | 40.201 | 1.00 | 9.89 |

FIGURE 3 (Cont.)

| A | B | C | D | E | F | G | H | I | J |
|---|---|---|---|---|---|---|---|---|---|
| 11893 | C19 | hmg | X | 1 | 32.189 | 39.424 | 39.338 | 1.00 | 10.32 |
| 11896 | N7 | hmg | X | 1 | 30.871 | 40.030 | 39.359 | 1.00 | 9.93 |
| 11898 | C18 | hmg | X | 1 | 29.736 | 39.331 | 39.344 | 1.00 | 10.11 |
| 11899 | O15 | hmg | X | 1 | 29.695 | 38.111 | 39.243 | 1.00 | 9.92 |
| 11900 | C17 | hmg | X | 1 | 28.484 | 40.167 | 39.503 | 1.00 | 10.48 |
| 11903 | C16 | hmg | X | 1 | 27.223 | 39.436 | 39.053 | 1.00 | 11.03 |
| 11906 | N6 | hmg | X | 1 | 27.148 | 39.324 | 37.610 | 1.00 | 12.15 |
| 11908 | C15 | hmg | X | 1 | 26.796 | 40.345 | 36.823 | 1.00 | 13.34 |
| 11909 | O14 | hmg | X | 1 | 26.531 | 41.458 | 37.250 | 1.00 | 12.82 |
| 11910 | C14 | hmg | X | 1 | 26.684 | 40.090 | 35.342 | 1.00 | 14.71 |
| 11912 | O13 | hmg | X | 1 | 26.319 | 38.734 | 35.126 | 1.00 | 15.28 |
| 11914 | C11 | hmg | X | 1 | 27.965 | 40.423 | 34.562 | 1.00 | 16.13 |
| 11915 | C12 | hmg | X | 1 | 29.089 | 39.441 | 34.879 | 1.00 | 16.05 |
| 11919 | C13 | hmg | X | 1 | 28.411 | 41.857 | 34.869 | 1.00 | 16.20 |
| 11923 | C10 | hmg | X | 1 | 27.618 | 40.346 | 33.076 | 1.00 | 17.27 |
| 11926 | O12 | hmg | X | 1 | 26.622 | 41.318 | 32.760 | 1.00 | 18.86 |
| 11927 | P3 | hmg | X | 1 | 26.208 | 41.601 | 31.233 | 1.00 | 19.72 |
| 11928 | O21 | hmg | X | 1 | 25.807 | 40.292 | 30.612 | 1.00 | 20.64 |
| 11929 | O11 | hmg | X | 1 | 25.254 | 42.767 | 31.204 | 1.00 | 20.68 |
| 11930 | O10 | hmg | X | 1 | 27.604 | 42.121 | 30.626 | 1.00 | 23.32 |
| 11931 | P2 | hmg | X | 1 | 28.155 | 41.680 | 29.184 | 1.00 | 24.56 |
| 11932 | O8 | hmg | X | 1 | 26.996 | 41.798 | 28.224 | 1.00 | 25.81 |
| 11933 | O9 | hmg | X | 1 | 29.401 | 42.483 | 28.926 | 1.00 | 25.22 |
| 11934 | O7 | hmg | X | 1 | 28.543 | 40.122 | 29.493 | 1.00 | 26.01 |
| 11935 | C9 | hmg | X | 1 | 29.867 | 39.564 | 29.368 | 1.00 | 25.84 |
| 11938 | C8 | hmg | X | 1 | 30.039 | 39.551 | 27.861 | 1.00 | 26.40 |
| 11940 | O6 | hmg | X | 1 | 29.639 | 38.328 | 27.221 | 1.00 | 25.32 |
| 11941 | C2 | hmg | X | 1 | 30.272 | 38.248 | 25.940 | 1.00 | 25.49 |
| 11943 | C27 | hmg | X | 1 | 31.124 | 39.492 | 25.870 | 1.00 | 26.22 |
| 11945 | O5 | hmg | X | 1 | 31.762 | 40.050 | 24.736 | 1.00 | 26.95 |
| 11947 | C1 | hmg | X | 1 | 31.191 | 40.120 | 27.146 | 1.00 | 26.45 |
| 11949 | O4 | hmg | X | 1 | 32.557 | 40.136 | 27.378 | 1.00 | 27.24 |
| 11950 | P1 | hmg | X | 1 | 33.564 | 40.594 | 28.544 | 1.00 | 27.29 |
| 11951 | O3 | hmg | X | 1 | 33.667 | 42.084 | 28.324 | 1.00 | 28.06 |
| 11952 | O2 | hmg | X | 1 | 32.960 | 40.186 | 29.868 | 1.00 | 26.87 |
| 11953 | O1 | hmg | X | 1 | 34.799 | 39.816 | 28.164 | 1.00 | 26.70 |
| 11954 | N1 | hmg | X | 1 | 29.209 | 38.073 | 24.946 | 1.00 | 24.42 |
| 11955 | C3 | hmg | X | 1 | 29.154 | 37.087 | 24.086 | 1.00 | 23.85 |
| 11956 | N5 | hmg | X | 1 | 30.113 | 36.034 | 23.879 | 1.00 | 23.94 |
| 11957 | C6 | hmg | X | 1 | 29.866 | 35.127 | 22.916 | 1.00 | 24.50 |
| 11959 | N2 | hmg | X | 1 | 28.758 | 35.189 | 22.148 | 1.00 | 24.47 |
| 11960 | C4 | hmg | X | 1 | 27.955 | 37.205 | 23.300 | 1.00 | 24.15 |
| 11961 | N4 | hmg | X | 1 | 27.311 | 38.289 | 23.759 | 1.00 | 24.47 |
| 11962 | C7 | hmg | X | 1 | 28.084 | 38.801 | 24.771 | 1.00 | 24.37 |
| 11964 | C5 | hmg | X | 1 | 27.811 | 36.149 | 22.277 | 1.00 | 24.50 |
| 11965 | N3 | hmg | X | 1 | 26.727 | 36.171 | 21.488 | 1.00 | 24.92 |
| 11968 | O20 | hmg | C | 2 | 23.707 | 35.925 | 73.506 | 1.00 | 10.15 |
| 11969 | C26 | hmg | C | 2 | 22.774 | 36.641 | 73.076 | 1.00 | 11.05 |
| 11970 | O19 | hmg | C | 2 | 22.782 | 37.084 | 71.910 | 1.00 | 13.42 |
| 11971 | C25 | hmg | C | 2 | 21.562 | 36.997 | 73.912 | 1.00 | 10.04 |
| 11974 | C23 | hmg | C | 2 | 21.775 | 37.152 | 75.420 | 1.00 | 9.18 |
| 11975 | C24 | hmg | C | 2 | 20.404 | 37.467 | 76.009 | 1.00 | 9.46 |

FIGURE 3 (Cont.)

| A | B | C | D | E | F | G | H | I | J |
|---|---|---|---|---|---|---|---|---|---|
| 11979 | O18 | hmg | C | 2 | 22.634 | 38.262 | 75.711 | 1.00 | 9.55 |
| 11981 | C22 | hmg | C | 2 | 22.392 | 35.881 | 76.006 | 1.00 | 8.43 |
| 11984 | C21 | hmg | C | 2 | 22.075 | 35.682 | 77.465 | 1.00 | 8.13 |
| 11985 | O16 | hmg | C | 2 | 22.686 | 36.321 | 78.307 | 1.00 | 7.08 |
| 11986 | S1 | hmg | C | 2 | 20.905 | 34.583 | 77.929 | 1.00 | 8.74 |
| 11987 | C20 | hmg | C | 2 | 20.632 | 34.802 | 79.666 | 1.00 | 8.25 |
| 11990 | C19 | hmg | C | 2 | 19.904 | 36.111 | 79.956 | 1.00 | 8.97 |
| 11993 | N7 | hmg | C | 2 | 18.666 | 36.203 | 79.208 | 1.00 | 9.40 |
| 11995 | C18 | hmg | C | 2 | 18.153 | 37.348 | 78.760 | 1.00 | 10.53 |
| 11996 | O15 | hmg | C | 2 | 18.631 | 38.450 | 79.004 | 1.00 | 10.76 |
| 11997 | C17 | hmg | C | 2 | 16.940 | 37.177 | 77.871 | 1.00 | 10.92 |
| 12000 | C16 | hmg | C | 2 | 16.104 | 38.447 | 77.748 | 1.00 | 10.64 |
| 12003 | N6 | hmg | C | 2 | 15.371 | 38.763 | 78.958 | 1.00 | 11.19 |
| 12005 | C15 | hmg | C | 2 | 14.282 | 38.084 | 79.326 | 1.00 | 10.99 |
| 12006 | O14 | hmg | C | 2 | 13.863 | 37.130 | 78.694 | 1.00 | 10.16 |
| 12007 | C14 | hmg | C | 2 | 13.532 | 38.542 | 80.548 | 1.00 | 11.79 |
| 12009 | O13 | hmg | C | 2 | 13.727 | 39.934 | 80.792 | 1.00 | 10.64 |
| 12011 | C11 | hmg | C | 2 | 13.915 | 37.742 | 81.804 | 1.00 | 13.34 |
| 12012 | C12 | hmg | C | 2 | 15.333 | 38.081 | 82.272 | 1.00 | 12.94 |
| 12016 | C13 | hmg | C | 2 | 13.775 | 36.242 | 81.543 | 1.00 | 12.79 |
| 12020 | C10 | hmg | C | 2 | 12.918 | 38.124 | 82.893 | 1.00 | 14.51 |
| 12023 | O12 | hmg | C | 2 | 11.594 | 37.770 | 82.471 | 1.00 | 17.05 |
| 12024 | P3 | hmg | C | 2 | 10.375 | 37.838 | 83.521 | 1.00 | 17.65 |
| 12025 | O21 | hmg | C | 2 | 10.254 | 39.262 | 83.967 | 1.00 | 17.96 |
| 12026 | O11 | hmg | C | 2 | 9.195 | 37.088 | 82.968 | 1.00 | 18.32 |
| 12027 | O10 | hmg | C | 2 | 11.005 | 36.885 | 84.644 | 1.00 | 20.11 |
| 12028 | P2 | hmg | C | 2 | 10.826 | 37.019 | 86.230 | 1.00 | 19.88 |
| 12029 | O8 | hmg | C | 2 | 9.422 | 37.460 | 86.553 | 1.00 | 20.92 |
| 12030 | O9 | hmg | C | 2 | 11.321 | 35.693 | 86.735 | 1.00 | 21.45 |
| 12031 | O7 | hmg | C | 2 | 11.935 | 38.176 | 86.495 | 1.00 | 21.21 |
| 12032 | C9 | hmg | C | 2 | 13.226 | 37.926 | 87.091 | 1.00 | 20.86 |
| 12035 | C8 | hmg | C | 2 | 12.818 | 38.049 | 88.539 | 1.00 | 20.88 |
| 12037 | O6 | hmg | C | 2 | 12.864 | 39.320 | 89.172 | 1.00 | 19.87 |
| 12038 | C2 | hmg | C | 2 | 12.673 | 39.054 | 90.564 | 1.00 | 19.41 |
| 12040 | C27 | hmg | C | 2 | 12.633 | 37.556 | 90.706 | 1.00 | 20.36 |
| 12042 | O5 | hmg | C | 2 | 12.200 | 36.783 | 91.809 | 1.00 | 20.14 |
| 12044 | C1 | hmg | C | 2 | 13.042 | 36.967 | 89.487 | 1.00 | 20.50 |
| 12046 | O4 | hmg | C | 2 | 14.247 | 36.404 | 89.829 | 1.00 | 20.31 |
| 12047 | P1 | hmg | C | 2 | 15.173 | 35.228 | 89.274 | 1.00 | 21.14 |
| 12048 | O3 | hmg | C | 2 | 15.739 | 35.754 | 87.971 | 1.00 | 21.13 |
| 12049 | O2 | hmg | C | 2 | 16.202 | 35.149 | 90.368 | 1.00 | 21.23 |
| 12050 | O1 | hmg | C | 2 | 14.259 | 34.033 | 89.164 | 1.00 | 20.10 |
| 12051 | N1 | hmg | C | 2 | 11.460 | 39.798 | 90.890 | 1.00 | 18.09 |
| 12052 | C3 | hmg | C | 2 | 11.445 | 40.736 | 91.787 | 1.00 | 16.85 |
| 12053 | N5 | hmg | C | 2 | 12.546 | 41.120 | 92.627 | 1.00 | 16.04 |
| 12054 | C6 | hmg | C | 2 | 12.324 | 42.088 | 93.516 | 1.00 | 16.36 |
| 12056 | N2 | hmg | C | 2 | 11.121 | 42.682 | 93.619 | 1.00 | 15.98 |
| 12057 | C4 | hmg | C | 2 | 10.133 | 41.324 | 91.853 | 1.00 | 16.34 |
| 12058 | N4 | hmg | C | 2 | 9.399 | 40.690 | 90.923 | 1.00 | 17.10 |
| 12059 | C7 | hmg | C | 2 | 10.225 | 39.769 | 90.329 | 1.00 | 17.27 |
| 12061 | C5 | hmg | C | 2 | 10.026 | 42.379 | 92.880 | 1.00 | 16.77 |
| 12062 | N3 | hmg | C | 2 | 8.864 | 43.034 | 93.075 | 1.00 | 17.55 |

FIGURE 3 (Cont.)

| A | B | C | D | E | F | G | H | I | J |
|---|---|---|---|---|---|---|---|---|---|
| 12065 | OW0 | HOH | X | 3 | 38.424 | 46.015 | 96.138 | 1.00 | 10.91 |
| 12068 | OW0 | HOH | X | 5 | 23.251 | 55.339 | 76.560 | 1.00 | 4.08 |
| 12071 | OW0 | HOH | X | 8 | 8.607 | 58.942 | 82.102 | 1.00 | 8.82 |
| 12074 | OW0 | HOH | X | 9 | 28.153 | 37.875 | 67.300 | 1.00 | 6.53 |
| 12077 | OW0 | HOH | X | 10 | 29.857 | 37.117 | 75.955 | 1.00 | 6.04 |
| 12080 | OW0 | HOH | X | 12 | 18.714 | 47.130 | 80.539 | 1.00 | 5.61 |
| 12083 | OW0 | HOH | X | 13 | 22.167 | 29.796 | 61.737 | 1.00 | 5.44 |
| 12086 | OW0 | HOH | X | 14 | 35.886 | 24.893 | 39.446 | 1.00 | 5.82 |
| 12089 | OW0 | HOH | X | 15 | 31.134 | 29.774 | 37.855 | 1.00 | 11.32 |
| 12092 | OW0 | HOH | X | 16 | 18.207 | 57.905 | 86.339 | 1.00 | 13.38 |
| 12095 | OW0 | HOH | X | 17 | 19.197 | 26.203 | 61.374 | 1.00 | 10.08 |
| 12098 | OW0 | HOH | X | 18 | 32.294 | 28.739 | 40.816 | 1.00 | 8.00 |
| 12101 | OW0 | HOH | X | 19 | 40.758 | 59.928 | 70.661 | 1.00 | 5.94 |
| 12104 | OW0 | HOH | X | 20 | 27.102 | 27.680 | 35.812 | 1.00 | 7.78 |
| 12107 | OW0 | HOH | X | 22 | 13.260 | 29.188 | 46.179 | 1.00 | 9.93 |
| 12110 | OW0 | HOH | X | 23 | 25.961 | 44.934 | 80.308 | 1.00 | 4.83 |
| 12113 | OW0 | HOH | X | 24 | 17.574 | 22.600 | 31.472 | 1.00 | 11.37 |
| 12116 | OW0 | HOH | X | 25 | 31.119 | 35.560 | 54.121 | 1.00 | 6.56 |
| 12119 | OW0 | HOH | X | 26 | 49.629 | 52.391 | 70.506 | 1.00 | 7.54 |
| 12122 | OW0 | HOH | X | 27 | 18.136 | 24.543 | 63.420 | 1.00 | 8.23 |
| 12125 | OW0 | HOH | X | 28 | 45.770 | 51.153 | 77.296 | 1.00 | 7.32 |
| 12128 | OW0 | HOH | X | 29 | 20.232 | 44.769 | 81.353 | 1.00 | 9.18 |
| 12131 | OW0 | HOH | X | 30 | 10.646 | 25.324 | 67.959 | 1.00 | 9.42 |
| 12134 | OW0 | HOH | X | 31 | 21.576 | 33.121 | 69.085 | 1.00 | 4.38 |
| 12137 | OW0 | HOH | X | 32 | 23.620 | 21.384 | 41.494 | 1.00 | 9.96 |
| 12140 | OW0 | HOH | X | 33 | 23.199 | 48.315 | 63.532 | 1.00 | 8.16 |
| 12143 | OW0 | HOH | X | 34 | 13.305 | 58.192 | 82.153 | 1.00 | 8.26 |
| 12146 | OW0 | HOH | X | 35 | 28.352 | 52.691 | 54.390 | 1.00 | 8.76 |
| 12149 | OW0 | HOH | X | 37 | 16.373 | 27.720 | 62.787 | 1.00 | 9.42 |
| 12152 | OW0 | HOH | X | 38 | 18.128 | 42.902 | 69.553 | 1.00 | 9.00 |
| 12155 | OW0 | HOH | X | 39 | 27.041 | 59.275 | 74.181 | 1.00 | 10.46 |
| 12158 | OW0 | HOH | X | 40 | 45.418 | 31.732 | 86.234 | 1.00 | 12.59 |
| 12161 | OW0 | HOH | X | 41 | 49.530 | 47.467 | 89.556 | 1.00 | 12.58 |
| 12164 | OW0 | HOH | X | 42 | 27.323 | 50.916 | 56.489 | 1.00 | 9.07 |
| 12167 | OW0 | HOH | X | 43 | 31.421 | 38.816 | 72.462 | 1.00 | 5.42 |
| 12170 | OW0 | HOH | X | 44 | 11.707 | 25.714 | 45.953 | 1.00 | 10.55 |
| 12173 | OW0 | HOH | X | 47 | 8.842 | 65.271 | 74.374 | 1.00 | 8.31 |
| 12176 | OW0 | HOH | X | 48 | 10.604 | 40.418 | 65.647 | 1.00 | 14.02 |
| 12179 | OW0 | HOH | X | 50 | 41.412 | 53.142 | 55.819 | 1.00 | 10.46 |
| 12182 | OW0 | HOH | X | 51 | 38.606 | 26.839 | 87.079 | 1.00 | 8.76 |
| 12185 | OW0 | HOH | X | 52 | 42.630 | 48.242 | 91.920 | 1.00 | 8.51 |
| 12188 | OW0 | HOH | X | 53 | 30.872 | 53.521 | 53.638 | 1.00 | 7.68 |
| 12191 | OW0 | HOH | X | 55 | 8.230 | 45.101 | 79.110 | 1.00 | 8.72 |
| 12194 | OW0 | HOH | X | 56 | 40.466 | 29.216 | 39.727 | 1.00 | 10.68 |
| 12197 | OW0 | HOH | X | 60 | 31.984 | 45.645 | 95.661 | 1.00 | 8.86 |
| 12200 | OW0 | HOH | X | 61 | 22.439 | 35.778 | 46.479 | 1.00 | 10.36 |
| 12203 | OW0 | HOH | X | 62 | 46.801 | 29.437 | 36.733 | 1.00 | 12.66 |
| 12206 | OW0 | HOH | X | 64 | 20.665 | 48.925 | 63.292 | 1.00 | 14.68 |
| 12209 | OW0 | HOH | X | 65 | 46.804 | 17.179 | 40.622 | 1.00 | 9.71 |
| 12212 | OW0 | HOH | X | 66 | 20.703 | 48.056 | 55.668 | 1.00 | 12.67 |
| 12215 | OW0 | HOH | X | 67 | 20.977 | 34.620 | 19.495 | 1.00 | 85.42 |
| 12218 | OW0 | HOH | X | 68 | 41.058 | 9.513 | 57.018 | 1.00 | 21.38 |

FIGURE 3 (Cont.)

| A | B | C | D | E | F | G | H | I | J |
|---|---|---|---|---|---|---|---|---|---|
| 12221 | OW0 | HOH | X | 69 | 29.544 | 46.730 | 83.884 | 1.00 | 7.67 |
| 12224 | OW0 | HOH | X | 70 | 53.708 | 37.543 | 43.427 | 1.00 | 12.84 |
| 12227 | OW0 | HOH | X | 71 | 18.522 | 43.932 | 46.172 | 1.00 | 11.07 |
| 12230 | OW0 | HOH | X | 72 | 23.482 | 52.940 | 88.958 | 1.00 | 10.46 |
| 12233 | OW0 | HOH | X | 73 | 16.985 | 53.110 | 66.824 | 1.00 | 8.48 |
| 12236 | OW0 | HOH | X | 74 | 43.483 | 58.490 | 60.558 | 1.00 | 12.33 |
| 12239 | OW0 | HOH | X | 75 | 28.947 | 31.305 | 37.415 | 1.00 | 9.97 |
| 12242 | OW0 | HOH | X | 76 | 14.239 | 53.156 | 66.409 | 1.00 | 8.05 |
| 12245 | OW0 | HOH | X | 77 | 23.165 | 16.499 | 45.164 | 1.00 | 7.44 |
| 12248 | OW0 | HOH | X | 78 | 10.025 | 22.809 | 40.120 | 1.00 | 13.26 |
| 12251 | OW0 | HOH | X | 80 | 27.963 | 46.174 | 57.087 | 1.00 | 7.67 |
| 12254 | OW0 | HOH | X | 81 | 11.021 | 38.002 | 66.975 | 1.00 | 15.55 |
| 12257 | OW0 | HOH | X | 82 | 51.837 | 43.690 | 68.342 | 1.00 | 10.61 |
| 12260 | OW0 | HOH | X | 85 | 1.727 | 54.318 | 84.323 | 1.00 | 19.85 |
| 12263 | OW0 | HOH | X | 86 | 22.017 | 55.208 | 87.937 | 1.00 | 16.95 |
| 12266 | OW0 | HOH | X | 87 | 11.197 | 59.757 | 83.177 | 1.00 | 10.32 |
| 12269 | OW0 | HOH | X | 88 | 26.701 | 44.673 | 59.173 | 1.00 | 13.23 |
| 12272 | OW0 | HOH | X | 89 | 17.203 | 18.725 | 63.349 | 1.00 | 16.94 |
| 12275 | OW0 | HOH | X | 91 | 17.234 | 27.909 | 51.270 | 1.00 | 11.35 |
| 12278 | OW0 | HOH | X | 92 | 40.319 | 10.753 | 43.477 | 1.00 | 11.18 |
| 12281 | OW0 | HOH | X | 93 | 24.671 | 46.144 | 37.034 | 1.00 | 14.85 |
| 12284 | OW0 | HOH | X | 94 | 50.497 | 39.564 | 59.626 | 1.00 | 15.99 |
| 12287 | OW0 | HOH | X | 95 | 28.485 | 11.280 | 44.890 | 1.00 | 13.03 |
| 12290 | OW0 | HOH | X | 96 | 26.076 | 29.955 | 36.770 | 1.00 | 14.67 |
| 12293 | OW0 | HOH | X | 97 | 48.833 | 42.005 | 54.263 | 1.00 | 18.09 |
| 12296 | OW0 | HOH | X | 98 | 49.499 | 49.343 | 87.677 | 1.00 | 9.66 |
| 12299 | OW0 | HOH | X | 99 | 49.711 | 46.937 | 45.448 | 1.00 | 11.20 |
| 12302 | OW0 | HOH | X | 100 | 17.034 | 30.213 | 63.021 | 1.00 | 15.07 |
| 12305 | OW0 | HOH | X | 101 | 39.683 | 15.310 | 34.487 | 1.00 | 13.75 |
| 12308 | OW0 | HOH | X | 102 | 44.335 | 11.635 | 41.805 | 1.00 | 13.31 |
| 12311 | OW0 | HOH | X | 103 | 7.317 | 27.909 | 36.212 | 1.00 | 11.34 |
| 12314 | OW0 | HOH | X | 104 | 14.704 | 56.815 | 66.265 | 1.00 | 8.90 |
| 12317 | OW0 | HOH | X | 105 | 30.994 | 21.544 | 31.303 | 1.00 | 12.47 |
| 12320 | OW0 | HOH | X | 106 | 19.105 | 28.070 | 43.772 | 1.00 | 10.04 |
| 12323 | OW0 | HOH | X | 107 | 16.387 | 23.911 | 71.997 | 1.00 | 11.90 |
| 12326 | OW0 | HOH | X | 108 | 48.313 | 16.191 | 38.471 | 1.00 | 12.69 |
| 12329 | OW0 | HOH | X | 109 | 25.622 | 39.494 | 84.415 | 1.00 | 24.88 |
| 12332 | OW0 | HOH | X | 110 | 50.581 | 54.685 | 69.555 | 1.00 | 8.32 |
| 12335 | OW0 | HOH | X | 112 | 53.769 | 12.589 | 45.674 | 1.00 | 18.44 |
| 12338 | OW0 | HOH | X | 113 | 7.739 | 47.306 | 69.980 | 1.00 | 10.75 |
| 12341 | OW0 | HOH | X | 118 | 24.718 | 48.774 | 36.583 | 1.00 | 34.55 |
| 12344 | OW0 | HOH | X | 119 | 7.420 | 57.013 | 83.641 | 1.00 | 8.77 |
| 12347 | OW0 | HOH | X | 120 | 19.006 | 22.639 | 65.181 | 1.00 | 10.40 |
| 12350 | OW0 | HOH | X | 121 | 22.850 | 31.469 | 59.584 | 1.00 | 9.47 |
| 12353 | OW0 | HOH | X | 123 | 27.592 | 19.750 | 72.231 | 1.00 | 11.90 |
| 12356 | OW0 | HOH | X | 125 | 29.354 | 39.792 | 76.111 | 1.00 | 8.32 |
| 12359 | OW0 | HOH | X | 126 | 16.312 | 16.791 | 46.836 | 1.00 | 10.25 |
| 12362 | OW0 | HOH | X | 127 | 36.004 | 9.585 | 45.288 | 1.00 | 9.94 |
| 12365 | OW0 | HOH | X | 128 | 46.313 | 19.045 | 63.863 | 1.00 | 11.02 |
| 12368 | OW0 | HOH | X | 129 | 18.034 | 51.502 | 71.454 | 1.00 | 9.13 |
| 12371 | OW0 | HOH | X | 130 | 20.505 | 42.254 | 61.270 | 1.00 | 11.65 |
| 12374 | OW0 | HOH | X | 131 | 22.608 | 62.182 | 68.933 | 1.00 | 15.02 |

FIGURE 3 (Cont.)

| A | B | C | D | E | F | G | H | I | J |
|---|---|---|---|---|---|---|---|---|---|
| 12377 | OW0 | HOH | X | 134 | 14.312 | 64.302 | 77.403 | 1.00 | 7.67 |
| 12380 | OW0 | HOH | X | 135 | 11.028 | 39.535 | 74.451 | 1.00 | 19.43 |
| 12383 | OW0 | HOH | X | 136 | 14.223 | 26.650 | 27.585 | 1.00 | 12.87 |
| 12386 | OW0 | HOH | X | 137 | 43.057 | 31.784 | 65.159 | 1.00 | 11.35 |
| 12389 | OW0 | HOH | X | 138 | 58.106 | 28.609 | 35.191 | 1.00 | 14.89 |
| 12392 | OW0 | HOH | X | 139 | 23.212 | 58.740 | 83.180 | 1.00 | 10.87 |
| 12395 | OW0 | HOH | X | 140 | 38.561 | 27.948 | 95.698 | 1.00 | 10.41 |
| 12398 | OW0 | HOH | X | 141 | 45.194 | 30.542 | 83.718 | 1.00 | 14.50 |
| 12401 | OW0 | HOH | X | 142 | 41.728 | 58.102 | 67.430 | 1.00 | 10.85 |
| 12404 | OW0 | HOH | X | 144 | 37.008 | 49.713 | 42.286 | 1.00 | 12.61 |
| 12407 | OW0 | HOH | X | 145 | 26.901 | 50.339 | 36.521 | 1.00 | 7.56 |
| 12410 | OW0 | HOH | X | 146 | 50.276 | 48.399 | 70.764 | 1.00 | 18.66 |
| 12413 | OW0 | HOH | X | 147 | 53.455 | 26.850 | 27.856 | 1.00 | 16.15 |
| 12416 | OW0 | HOH | X | 148 | 18.143 | 14.600 | 34.283 | 1.00 | 22.79 |
| 12419 | OW0 | HOH | X | 150 | 23.128 | 44.982 | 82.122 | 1.00 | 18.72 |
| 12422 | OW0 | HOH | X | 151 | 16.326 | 28.490 | 43.994 | 1.00 | 8.79 |
| 12425 | OW0 | HOH | X | 152 | 19.740 | 48.939 | 82.310 | 1.00 | 9.93 |
| 12428 | OW0 | HOH | X | 153 | 4.832 | 45.171 | 81.797 | 1.00 | 20.26 |
| 12431 | OW0 | HOH | X | 154 | 44.638 | 59.170 | 64.359 | 1.00 | 18.50 |
| 12434 | OW0 | HOH | X | 156 | 16.284 | 41.917 | 46.650 | 1.00 | 12.36 |
| 12437 | OW0 | HOH | X | 157 | 27.192 | 60.806 | 76.452 | 1.00 | 13.73 |
| 12440 | OW0 | HOH | X | 158 | 30.835 | 6.332 | 40.927 | 1.00 | 16.00 |
| 12443 | OW0 | HOH | X | 159 | 21.876 | 51.233 | 92.307 | 1.00 | 23.93 |
| 12446 | OW0 | HOH | X | 160 | 43.013 | 51.452 | 76.998 | 1.00 | 8.07 |
| 12449 | OW0 | HOH | X | 161 | 18.775 | 36.954 | 33.092 | 1.00 | 14.54 |
| 12452 | OW0 | HOH | X | 162 | 15.236 | 31.821 | 59.143 | 1.00 | 12.63 |
| 12455 | OW0 | HOH | X | 164 | 18.617 | 51.118 | 66.094 | 1.00 | 10.12 |
| 12458 | OW0 | HOH | X | 166 | 49.374 | 13.222 | 51.347 | 1.00 | 9.60 |
| 12461 | OW0 | HOH | X | 167 | 49.931 | 36.538 | 77.121 | 1.00 | 10.30 |
| 12464 | OW0 | HOH | X | 168 | 2.809 | 51.944 | 87.715 | 1.00 | 15.56 |
| 12467 | OW0 | HOH | X | 169 | 53.597 | 61.143 | 61.047 | 1.00 | 15.24 |
| 12470 | OW0 | HOH | X | 171 | 44.069 | 33.976 | 64.052 | 1.00 | 10.69 |
| 12473 | OW0 | HOH | X | 172 | 52.540 | 24.738 | 56.320 | 1.00 | 12.53 |
| 12476 | OW0 | HOH | X | 173 | 39.216 | 31.924 | 103.001 | 1.00 | 22.82 |
| 12479 | OW0 | HOH | X | 174 | 19.667 | 24.480 | 78.285 | 1.00 | 16.66 |
| 12482 | O | HOH | X | 175 | 24.755 | 54.772 | 46.478 | 1.00 | 14.47 |
| 12485 | O | HOH | X | 176 | 24.979 | 52.683 | 44.876 | 1.00 | 11.41 |
| 12488 | O | HOH | X | 177 | 27.462 | 51.379 | 44.522 | 1.00 | 12.37 |
| 12491 | O | HOH | X | 178 | 29.011 | 53.276 | 45.703 | 1.00 | 22.84 |
| 12494 | O | HOH | X | 179 | 26.403 | 56.744 | 48.957 | 1.00 | 20.79 |
| 12497 | O | HOH | X | 180 | 35.465 | 61.181 | 42.400 | 1.00 | 13.93 |
| 12500 | O | HOH | X | 181 | 35.452 | 58.415 | 42.353 | 1.00 | 20.51 |
| 12503 | O | HOH | X | 182 | 32.776 | 57.084 | 42.854 | 1.00 | 24.59 |
| 12506 | O | HOH | X | 183 | 31.113 | 63.894 | 43.390 | 1.00 | 20.49 |
| 12509 | O | HOH | X | 184 | 32.114 | 65.989 | 45.232 | 1.00 | 23.59 |
| 12512 | O | HOH | X | 185 | 33.229 | 70.197 | 44.488 | 1.00 | 11.83 |
| 12515 | O | HOH | X | 186 | 26.349 | 69.956 | 44.469 | 1.00 | 12.36 |
| 12518 | O | HOH | X | 187 | 25.968 | 69.575 | 47.056 | 1.00 | 22.01 |
| 12521 | O | HOH | X | 188 | 30.000 | 70.650 | 47.360 | 1.00 | 19.57 |
| 12524 | O | HOH | X | 189 | 24.858 | 64.738 | 46.936 | 1.00 | 20.71 |
| 12527 | O | HOH | X | 190 | 24.236 | 37.355 | 49.741 | 1.00 | 17.95 |
| 12530 | O | HOH | X | 191 | 22.865 | 34.718 | 49.470 | 1.00 | 17.44 |

FIGURE 3 (Cont.)

| A | B | C | D | E | F | G | H | I | J |
|---|---|---|---|---|---|---|---|---|---|
| 12533 | O | HOH | X | 192 | 55.875 | 37.887 | 52.950 | 1.00 | 24.93 |
| 12536 | O | HOH | X | 193 | 55.055 | 31.546 | 49.094 | 1.00 | 17.24 |
| 12539 | O | HOH | X | 194 | 56.005 | 29.887 | 46.941 | 1.00 | 19.43 |
| 12542 | O | HOH | X | 195 | 56.288 | 28.168 | 31.339 | 1.00 | 17.94 |
| 12545 | O | HOH | X | 196 | 57.575 | 35.180 | 31.963 | 1.00 | 11.21 |
| 12548 | O | HOH | X | 197 | 59.355 | 31.084 | 29.185 | 1.00 | 17.13 |
| 12551 | O | HOH | X | 198 | 57.931 | 32.043 | 25.167 | 1.00 | 12.98 |
| 12554 | O | HOH | X | 199 | 58.125 | 34.690 | 24.527 | 1.00 | 24.77 |
| 12557 | O | HOH | X | 200 | 56.681 | 34.627 | 21.202 | 1.00 | 13.50 |
| 12560 | O | HOH | X | 201 | 17.778 | 44.310 | 43.692 | 1.00 | 20.65 |
| 12563 | O | HOH | X | 202 | 16.269 | 40.538 | 41.405 | 1.00 | 17.69 |
| 12566 | O | HOH | X | 203 | 13.079 | 36.714 | 40.768 | 1.00 | 13.52 |
| 12569 | O | HOH | X | 204 | 17.634 | 32.074 | 86.662 | 1.00 | 17.50 |
| 12572 | O | HOH | X | 205 | 11.621 | 26.838 | 74.001 | 1.00 | 27.56 |
| 12575 | O | HOH | X | 206 | 13.067 | 27.428 | 71.840 | 1.00 | 11.46 |
| 12578 | O | HOH | X | 207 | 10.848 | 27.375 | 70.113 | 1.00 | 21.23 |
| 12581 | O | HOH | X | 208 | 5.740 | 43.597 | 89.229 | 1.00 | 22.03 |
| 12584 | O | HOH | X | 209 | 39.732 | 28.662 | 42.301 | 1.00 | 29.18 |
| 12587 | O | HOH | X | 210 | 19.393 | 46.253 | 59.822 | 1.00 | 21.96 |
| 12590 | O | HOH | X | 211 | 18.101 | 47.600 | 55.300 | 1.00 | 17.10 |
| 12593 | O | HOH | X | 212 | 16.143 | 49.623 | 58.989 | 1.00 | 21.68 |
| 12596 | O | HOH | X | 213 | 7.455 | 38.767 | 75.293 | 1.00 | 23.21 |
| 12599 | O | HOH | X | 214 | 9.895 | 37.361 | 75.847 | 1.00 | 20.38 |
| 12602 | O | HOH | X | 215 | 11.175 | 37.040 | 78.126 | 1.00 | 14.50 |
| 12605 | O | HOH | X | 216 | 9.007 | 38.082 | 68.602 | 1.00 | 21.88 |
| 12608 | O | HOH | X | 217 | 11.732 | 39.968 | 71.693 | 1.00 | 10.91 |
| 12611 | O | HOH | X | 218 | 9.728 | 33.470 | 77.480 | 1.00 | 13.86 |
| 12614 | O | HOH | X | 219 | 10.037 | 28.690 | 79.135 | 1.00 | 17.57 |
| 12617 | O | HOH | X | 220 | 20.339 | 40.116 | 67.297 | 1.00 | 17.59 |
| 12620 | O | HOH | X | 221 | 20.091 | 43.126 | 67.388 | 1.00 | 18.87 |
| 12623 | O | HOH | X | 222 | 27.995 | 36.212 | 40.563 | 1.00 | 8.23 |
| 12626 | O | HOH | X | 223 | 5.037 | 18.451 | 53.748 | 1.00 | 20.55 |
| 12629 | O | HOH | X | 224 | 7.871 | 14.917 | 54.622 | 1.00 | 21.87 |
| 12632 | O | HOH | X | 225 | 6.090 | 13.077 | 53.204 | 1.00 | 18.43 |
| 12635 | O | HOH | X | 226 | 6.842 | 11.579 | 51.072 | 1.00 | 19.50 |
| 12638 | O | HOH | X | 227 | 6.694 | 20.091 | 61.060 | 1.00 | 25.26 |
| 12641 | O | HOH | X | 228 | 6.116 | 22.445 | 62.342 | 1.00 | 15.47 |
| 12644 | O | HOH | X | 229 | 3.431 | 22.218 | 61.416 | 1.00 | 23.60 |
| 12647 | O | HOH | X | 230 | 2.936 | 21.420 | 56.473 | 1.00 | 13.56 |
| 12650 | O | HOH | X | 231 | 1.345 | 23.314 | 62.597 | 1.00 | 21.70 |
| 12653 | O | HOH | X | 232 | 20.854 | 12.085 | 50.599 | 1.00 | 16.66 |
| 12656 | O | HOH | X | 233 | 22.967 | 14.270 | 46.618 | 1.00 | 20.55 |
| 12659 | O | HOH | X | 234 | 20.297 | 13.469 | 45.850 | 1.00 | 15.82 |
| 12662 | O | HOH | X | 235 | 17.819 | 14.121 | 46.590 | 1.00 | 25.66 |
| 12665 | O | HOH | X | 236 | 24.675 | 12.693 | 48.148 | 1.00 | 32.57 |
| 12668 | O | HOH | X | 237 | 23.905 | 12.556 | 44.212 | 1.00 | 21.44 |
| 12671 | O | HOH | X | 238 | 25.984 | 10.843 | 43.868 | 1.00 | 18.00 |
| 12674 | O | HOH | X | 239 | 21.872 | 10.445 | 43.853 | 1.00 | 31.66 |
| 12677 | O | HOH | X | 240 | 42.344 | 10.274 | 45.421 | 1.00 | 20.25 |
| 12680 | O | HOH | X | 241 | 38.163 | 8.970 | 43.542 | 1.00 | 16.98 |
| 12683 | O | HOH | X | 242 | 7.689 | 45.214 | 81.716 | 1.00 | 11.77 |
| 12686 | O | HOH | X | 243 | 8.997 | 43.305 | 83.201 | 1.00 | 15.34 |

FIGURE 3 (Cont.)

| A | B | C | D | E | F | G | H | I | J |
|---|---|---|---|---|---|---|---|---|---|
| 12689 | O | HOH | X | 244 | 17.118 | 54.258 | 88.389 | 1.00 | 27.91 |
| 12692 | O | HOH | X | 245 | 15.185 | 56.757 | 89.749 | 1.00 | 36.24 |
| 12695 | O | HOH | X | 246 | 29.876 | 11.951 | 67.175 | 1.00 | 21.22 |
| 12698 | O | HOH | X | 247 | 27.277 | 11.882 | 61.263 | 1.00 | 35.35 |
| 12701 | O | HOH | X | 248 | 31.389 | 11.807 | 58.176 | 1.00 | 20.07 |
| 12704 | O | HOH | X | 249 | 37.938 | 10.860 | 55.565 | 1.00 | 22.84 |
| 12707 | O | HOH | X | 250 | 34.793 | 10.010 | 56.141 | 1.00 | 25.66 |
| 12710 | O | HOH | X | 251 | 24.825 | 10.789 | 52.260 | 1.00 | 31.45 |
| 12713 | O | HOH | X | 252 | 28.151 | 13.670 | 51.691 | 1.00 | 18.08 |
| 12716 | O | HOH | X | 253 | 29.430 | 13.503 | 48.812 | 1.00 | 24.06 |
| 12719 | O | HOH | X | 254 | 12.748 | 32.216 | 53.697 | 1.00 | 25.41 |
| 12722 | O | HOH | X | 255 | 14.006 | 30.573 | 51.911 | 1.00 | 31.83 |
| 12725 | O | HOH | X | 256 | 14.884 | 28.000 | 52.679 | 1.00 | 20.24 |
| 12728 | O | HOH | X | 257 | 15.339 | 27.778 | 47.143 | 1.00 | 14.28 |
| 12731 | O | HOH | X | 258 | 15.571 | 31.486 | 48.111 | 1.00 | 21.83 |
| 12734 | O | HOH | X | 259 | 13.483 | 24.227 | 29.165 | 1.00 | 16.64 |
| 12737 | O | HOH | X | 260 | 37.334 | 41.126 | 28.388 | 1.00 | 32.43 |
| 12740 | O | HOH | X | 261 | 41.224 | 41.496 | 31.259 | 1.00 | 16.82 |
| 12743 | O | HOH | X | 262 | 55.320 | 44.552 | 42.643 | 1.00 | 15.92 |
| 12746 | O | HOH | X | 263 | 53.948 | 43.823 | 39.700 | 1.00 | 19.01 |
| 12749 | O | HOH | X | 264 | 52.132 | 47.502 | 46.431 | 1.00 | 16.47 |
| 12752 | O | HOH | X | 265 | 53.920 | 48.726 | 49.602 | 1.00 | 23.81 |
| 12755 | O | HOH | X | 266 | 55.907 | 46.381 | 51.001 | 1.00 | 23.25 |
| 12758 | O | HOH | X | 267 | 47.976 | 46.511 | 37.562 | 1.00 | 28.41 |
| 12761 | O | HOH | X | 268 | 37.795 | 23.464 | 74.898 | 1.00 | 18.96 |
| 12764 | O | HOH | X | 269 | 40.481 | 22.726 | 72.967 | 1.00 | 25.27 |
| 12767 | O | HOH | X | 270 | 51.470 | 17.307 | 70.892 | 1.00 | 30.35 |
| 12770 | O | HOH | X | 271 | 39.737 | 15.262 | 50.259 | 1.00 | 18.58 |
| 12773 | O | HOH | X | 272 | 43.912 | 15.519 | 59.886 | 1.00 | 24.46 |
| 12776 | O | HOH | X | 273 | 46.651 | 16.342 | 63.985 | 1.00 | 21.78 |
| 12779 | O | HOH | X | 274 | 45.106 | 15.419 | 66.003 | 1.00 | 23.01 |
| 12782 | O | HOH | X | 275 | 41.888 | 14.117 | 69.558 | 1.00 | 24.05 |
| 12785 | O | HOH | X | 276 | 40.912 | 12.292 | 67.638 | 1.00 | 17.83 |
| 12788 | O | HOH | X | 277 | 33.822 | 11.006 | 67.513 | 1.00 | 18.51 |
| 12791 | O | HOH | X | 278 | 50.556 | 12.442 | 45.084 | 1.00 | 13.89 |
| 12794 | O | HOH | X | 279 | 49.512 | 8.691 | 50.082 | 1.00 | 27.01 |
| 12797 | O | HOH | X | 280 | 49.349 | 10.516 | 52.038 | 1.00 | 23.77 |
| 12800 | O | HOH | X | 281 | 46.879 | 8.584 | 55.188 | 1.00 | 21.84 |
| 12803 | O | HOH | X | 282 | 35.899 | 42.525 | 32.875 | 1.00 | 19.60 |
| 12806 | O | HOH | X | 283 | 31.401 | 41.362 | 32.155 | 1.00 | 18.32 |
| 12809 | O | HOH | X | 284 | 23.611 | 38.853 | 32.115 | 1.00 | 17.00 |
| 12812 | O | HOH | X | 285 | 22.116 | 37.635 | 30.066 | 1.00 | 21.60 |
| 12815 | O | HOH | X | 286 | 19.630 | 36.740 | 30.533 | 1.00 | 17.38 |
| 12818 | O | HOH | X | 287 | 17.733 | 38.081 | 29.111 | 1.00 | 24.87 |
| 12821 | O | HOH | X | 288 | 15.158 | 38.582 | 30.365 | 1.00 | 21.75 |
| 12824 | O | HOH | X | 289 | 21.952 | 39.174 | 28.007 | 1.00 | 31.47 |
| 12827 | O | HOH | X | 290 | 21.847 | 39.259 | 25.176 | 1.00 | 24.78 |
| 12830 | O | HOH | X | 291 | 22.590 | 37.714 | 22.899 | 1.00 | 21.69 |
| 12833 | O | HOH | X | 292 | 18.700 | 31.297 | 22.487 | 1.00 | 19.45 |
| 12836 | O | HOH | X | 293 | 14.691 | 28.374 | 21.492 | 1.00 | 37.20 |
| 12839 | O | HOH | X | 294 | 19.811 | 26.767 | 21.127 | 1.00 | 29.13 |
| 12842 | O | HOH | X | 295 | 19.461 | 40.228 | 18.306 | 1.00 | 15.58 |

FIGURE 3 (Cont.)

| A | B | C | D | E | F | G | H | I | J |
|---|---|---|---|---|---|---|---|---|---|
| 12845 | O | HOH | X | 296 | 53.757 | 46.767 | 62.397 | 1.00 | 24.50 |
| 12848 | O | HOH | X | 297 | 53.847 | 49.252 | 61.562 | 1.00 | 27.75 |
| 12851 | O | HOH | X | 298 | 53.025 | 51.368 | 63.486 | 1.00 | 12.86 |
| 12854 | O | HOH | X | 299 | 54.081 | 52.743 | 69.926 | 1.00 | 15.78 |
| 12857 | O | HOH | X | 300 | 55.971 | 50.155 | 72.085 | 1.00 | 30.97 |
| 12860 | O | HOH | X | 301 | 57.259 | 53.959 | 68.699 | 1.00 | 29.61 |
| 12863 | O | HOH | X | 302 | 45.259 | 56.746 | 59.234 | 1.00 | 18.17 |
| 12866 | O | HOH | X | 303 | 48.099 | 55.948 | 60.118 | 1.00 | 20.59 |
| 12869 | O | HOH | X | 304 | 28.107 | 17.450 | 68.352 | 1.00 | 13.92 |
| 12872 | O | HOH | X | 305 | 21.426 | 15.480 | 67.000 | 1.00 | 24.46 |
| 12875 | O | HOH | X | 306 | 24.704 | 19.923 | 70.054 | 1.00 | 22.84 |
| 12878 | O | HOH | X | 307 | 16.803 | 22.717 | 74.616 | 1.00 | 25.93 |
| 12881 | O | HOH | X | 308 | 18.460 | 22.664 | 76.692 | 1.00 | 20.75 |
| 12884 | O | HOH | X | 309 | 26.027 | 21.825 | 68.652 | 1.00 | 13.28 |
| 12887 | O | HOH | X | 310 | 31.822 | 20.284 | 82.401 | 1.00 | 15.61 |
| 12890 | O | HOH | X | 311 | 34.019 | 18.610 | 82.738 | 1.00 | 18.36 |
| 12893 | O | HOH | X | 312 | 39.344 | 17.074 | 80.869 | 1.00 | 20.70 |
| 12896 | O | HOH | X | 313 | 27.432 | 25.734 | 94.654 | 1.00 | 31.09 |
| 12899 | O | HOH | X | 314 | 26.414 | 27.986 | 87.227 | 1.00 | 22.40 |
| 12902 | O | HOH | X | 315 | 24.954 | 25.448 | 88.249 | 1.00 | 24.87 |
| 12905 | O | HOH | X | 316 | 24.325 | 23.866 | 86.217 | 1.00 | 30.14 |
| 12908 | O | HOH | X | 317 | 29.587 | 22.071 | 91.620 | 1.00 | 33.57 |
| 12911 | O | HOH | X | 318 | 30.980 | 24.379 | 92.105 | 1.00 | 29.46 |
| 12914 | O | HOH | X | 319 | 14.731 | 35.754 | 85.338 | 1.00 | 23.23 |
| 12917 | O | HOH | X | 320 | 12.364 | 33.893 | 84.405 | 1.00 | 31.62 |
| 12920 | O | HOH | X | 321 | 14.417 | 31.878 | 84.905 | 1.00 | 25.48 |
| 12923 | O | HOH | X | 322 | 23.284 | 41.523 | 94.438 | 1.00 | 25.80 |
| 12926 | O | HOH | X | 323 | 29.007 | 42.318 | 97.631 | 1.00 | 17.04 |
| 12929 | O | HOH | X | 324 | 27.723 | 40.249 | 94.113 | 1.00 | 21.17 |
| 12932 | O | HOH | X | 325 | 26.887 | 41.076 | 96.388 | 1.00 | 25.45 |
| 12935 | O | HOH | X | 326 | 28.438 | 39.009 | 99.971 | 1.00 | 22.94 |
| 12938 | O | HOH | X | 327 | 30.486 | 40.540 | 99.099 | 1.00 | 19.65 |
| 12941 | O | HOH | X | 328 | 28.496 | 48.427 | 94.049 | 1.00 | 21.62 |
| 12944 | O | HOH | X | 329 | 27.553 | 47.561 | 91.585 | 1.00 | 23.53 |
| 12947 | O | HOH | X | 330 | 32.296 | 54.435 | 89.240 | 1.00 | 18.76 |
| 12950 | O | HOH | X | 331 | 29.701 | 55.028 | 90.167 | 1.00 | 14.15 |
| 12953 | O | HOH | X | 332 | 27.507 | 54.570 | 88.708 | 1.00 | 18.39 |
| 12956 | O | HOH | X | 333 | 26.192 | 52.157 | 88.738 | 1.00 | 12.85 |
| 12959 | O | HOH | X | 334 | 31.773 | 51.995 | 92.467 | 1.00 | 24.07 |
| 12962 | O | HOH | X | 335 | 33.640 | 56.155 | 91.898 | 1.00 | 35.79 |
| 12965 | O | HOH | X | 336 | 29.383 | 53.094 | 92.184 | 1.00 | 31.80 |
| 12968 | O | HOH | X | 337 | 41.297 | 46.407 | 101.493 | 1.00 | 16.85 |
| 12971 | O | HOH | X | 338 | 39.054 | 47.121 | 99.839 | 1.00 | 25.81 |
| 12974 | O | HOH | X | 339 | 43.154 | 48.533 | 101.599 | 1.00 | 19.90 |
| 12977 | O | HOH | X | 340 | 5.500 | 58.089 | 72.276 | 1.00 | 8.90 |
| 12980 | O | HOH | X | 341 | 6.875 | 63.597 | 74.790 | 1.00 | 12.03 |
| 12983 | O | HOH | X | 342 | 4.929 | 65.692 | 72.097 | 1.00 | 38.25 |
| 12986 | O | HOH | X | 343 | 5.626 | 60.056 | 67.977 | 1.00 | 15.05 |
| 12989 | O | HOH | X | 344 | 8.303 | 56.605 | 66.193 | 1.00 | 16.70 |
| 12992 | O | HOH | X | 345 | -2.884 | 57.735 | 80.711 | 1.00 | 16.41 |
| 12995 | O | HOH | X | 346 | -4.177 | 55.723 | 81.677 | 1.00 | 13.40 |
| 12998 | O | HOH | X | 347 | -5.925 | 58.170 | 77.409 | 1.00 | 17.94 |

FIGURE 3 (Cont.)

| A | B | C | D | E | F | G | H | I | J |
|---|---|---|---|---|---|---|---|---|---|
| 13001 | O | HOH | X | 348 | -10.014 | 55.560 | 79.627 | 1.00 | 19.31 |
| 13004 | O | HOH | X | 349 | 7.762 | 58.248 | 85.951 | 1.00 | 21.03 |
| 13007 | O | HOH | X | 350 | 6.209 | 61.419 | 85.241 | 1.00 | 16.16 |
| 13010 | O | HOH | X | 351 | 5.408 | 59.664 | 87.032 | 1.00 | 30.08 |
| 13013 | O | HOH | X | 352 | 13.192 | 50.137 | 88.827 | 1.00 | 27.97 |
| 13016 | O | HOH | X | 353 | 19.027 | 40.519 | 77.372 | 1.00 | 8.11 |
| 13019 | O | HOH | X | 354 | 49.087 | 30.538 | 52.830 | 1.00 | 17.93 |
| 13022 | O | HOH | X | 355 | 47.478 | 31.069 | 54.724 | 1.00 | 35.94 |
| 13025 | O | HOH | X | 356 | 49.981 | 30.266 | 60.977 | 1.00 | 24.32 |
| 13028 | O | HOH | X | 357 | 55.493 | 19.161 | 49.511 | 1.00 | 17.79 |
| 13031 | O | HOH | X | 358 | 55.388 | 17.015 | 51.125 | 1.00 | 19.34 |
| 13034 | O | HOH | X | 359 | 53.941 | 22.671 | 61.547 | 1.00 | 20.83 |
| 13037 | O | HOH | X | 360 | 51.986 | 21.902 | 63.319 | 1.00 | 25.50 |
| 13040 | O | HOH | X | 361 | 52.901 | 24.443 | 65.252 | 1.00 | 23.10 |
| 13043 | O | HOH | X | 362 | 47.408 | 20.768 | 70.780 | 1.00 | 24.47 |
| 13046 | O | HOH | X | 363 | 45.542 | 22.482 | 73.294 | 1.00 | 31.27 |
| 13049 | O | HOH | X | 364 | 42.981 | 25.939 | 75.651 | 1.00 | 27.14 |
| 13052 | O | HOH | X | 365 | 47.297 | 40.701 | 94.829 | 1.00 | 20.58 |
| 13055 | O | HOH | X | 366 | 43.675 | 31.763 | 88.313 | 1.00 | 20.66 |
| 13058 | O | HOH | X | 367 | 45.418 | 35.010 | 91.974 | 1.00 | 20.60 |
| 13061 | O | HOH | X | 368 | 46.497 | 27.385 | 93.574 | 1.00 | 14.46 |
| 13064 | O | HOH | X | 369 | 48.922 | 28.965 | 94.260 | 1.00 | 20.08 |
| 13067 | O | HOH | X | 370 | 45.913 | 31.040 | 94.657 | 1.00 | 28.35 |
| 13070 | O | HOH | X | 371 | 22.247 | 45.971 | 38.845 | 1.00 | 23.72 |
| 13073 | O | HOH | X | 372 | 21.204 | 45.452 | 41.489 | 1.00 | 19.50 |
| 13076 | O | HOH | X | 373 | 27.207 | 48.158 | 55.433 | 1.00 | 21.48 |
| 13079 | O | HOH | X | 374 | 24.882 | 48.062 | 53.589 | 1.00 | 17.59 |
| 13082 | O | HOH | X | 375 | 25.252 | 50.715 | 53.634 | 1.00 | 11.81 |
| 13085 | O | HOH | X | 376 | 19.961 | 61.130 | 50.349 | 1.00 | 20.01 |
| 13088 | O | HOH | X | 377 | 10.761 | 65.286 | 59.048 | 1.00 | 40.59 |
| 13091 | O | HOH | X | 378 | 17.961 | 62.676 | 49.988 | 1.00 | 25.56 |
| 13094 | O | HOH | X | 379 | 15.342 | 63.547 | 53.248 | 1.00 | 18.81 |
| 13097 | O | HOH | X | 380 | 14.325 | 66.690 | 50.023 | 1.00 | 21.09 |
| 13100 | O | HOH | X | 381 | 14.499 | 69.131 | 51.220 | 1.00 | 37.41 |
| 13103 | O | HOH | X | 382 | 20.362 | 58.939 | 45.873 | 1.00 | 26.90 |
| 13106 | O | HOH | X | 383 | 19.800 | 61.904 | 45.998 | 1.00 | 31.62 |
| 13109 | O | HOH | X | 384 | 17.880 | 65.600 | 57.263 | 1.00 | 18.70 |
| 13112 | O | HOH | X | 385 | 16.728 | 64.337 | 39.667 | 1.00 | 13.00 |
| 13115 | O | HOH | X | 386 | 16.223 | 59.605 | 45.082 | 1.00 | 25.78 |
| 13118 | O | HOH | X | 387 | 14.189 | 56.822 | 46.793 | 1.00 | 23.52 |
| 13121 | O | HOH | X | 388 | 13.594 | 59.907 | 48.301 | 1.00 | 27.64 |
| 13124 | O | HOH | X | 389 | 16.763 | 53.016 | 46.768 | 1.00 | 22.02 |
| 13127 | O | HOH | X | 390 | 17.665 | 54.085 | 49.162 | 1.00 | 14.60 |
| 13130 | O | HOH | X | 391 | 19.053 | 55.899 | 44.598 | 1.00 | 20.55 |
| 13133 | O | HOH | X | 392 | 43.866 | 23.316 | 30.312 | 1.00 | 21.04 |
| 13136 | O | HOH | X | 393 | 41.373 | 21.824 | 31.171 | 1.00 | 24.00 |
| 13139 | O | HOH | X | 394 | 40.976 | 19.564 | 32.272 | 1.00 | 25.58 |
| 13142 | O | HOH | X | 395 | 39.255 | 22.629 | 30.002 | 1.00 | 26.43 |
| 13145 | O | HOH | X | 396 | 43.971 | 18.647 | 32.602 | 1.00 | 30.42 |
| 13148 | O | HOH | X | 397 | 35.939 | 16.411 | 35.220 | 1.00 | 14.57 |
| 13151 | O | HOH | X | 398 | 25.361 | 17.252 | 35.431 | 1.00 | 9.94 |
| 13154 | O | HOH | X | 399 | 26.768 | 18.578 | 74.723 | 1.00 | 20.37 |

FIGURE 3 (Cont.)

| A | B | C | D | E | F | G | H | I | J |
|---|---|---|---|---|---|---|---|---|---|
| 13157 | O | HOH | X | 400 | 37.081 | 28.754 | 99.468 | 1.00 | 18.08 |
| 13160 | O | HOH | X | 401 | 39.299 | 30.235 | 100.333 | 1.00 | 33.34 |
| 13163 | O | HOH | X | 402 | 38.086 | 34.906 | 94.487 | 1.00 | 35.56 |
| 13166 | O | HOH | X | 403 | 34.173 | 38.259 | 90.722 | 1.00 | 13.01 |
| 13169 | O | HOH | X | 404 | 30.792 | 40.748 | 85.282 | 1.00 | 13.76 |
| 13172 | O | HOH | X | 405 | 48.556 | 33.288 | 75.704 | 1.00 | 27.62 |
| 13175 | O | HOH | X | 406 | 47.764 | 32.794 | 71.259 | 1.00 | 18.90 |
| 13178 | O | HOH | X | 407 | 53.326 | 31.949 | 70.529 | 1.00 | 30.45 |
| 13181 | O | HOH | X | 408 | 35.510 | 32.479 | 51.024 | 1.00 | 7.19 |
| 13184 | O | HOH | X | 409 | 36.943 | 34.247 | 47.574 | 1.00 | 8.51 |
| 13187 | O | HOH | X | 410 | 35.377 | 32.126 | 46.876 | 1.00 | 5.55 |
| 13190 | O | HOH | X | 411 | 29.437 | 42.669 | 49.946 | 1.00 | 6.94 |
| 13193 | O | HOH | X | 412 | 26.463 | 39.530 | 62.409 | 1.00 | 8.61 |
| 13196 | O | HOH | X | 413 | 23.875 | 40.113 | 62.595 | 1.00 | 8.81 |
| 13199 | O | HOH | X | 414 | 23.355 | 38.555 | 59.001 | 1.00 | 7.41 |
| 13202 | O | HOH | X | 415 | 20.633 | 36.302 | 55.089 | 1.00 | 11.50 |
| 13205 | O | HOH | X | 416 | 24.583 | 36.286 | 55.828 | 1.00 | 11.52 |
| 13208 | O | HOH | X | 417 | 26.706 | 35.543 | 57.299 | 1.00 | 8.12 |
| 13211 | O | HOH | X | 418 | 18.333 | 37.785 | 54.184 | 1.00 | 20.35 |
| 13214 | O | HOH | X | 419 | 20.772 | 29.575 | 53.661 | 1.00 | 10.11 |
| 13217 | O | HOH | X | 420 | 18.315 | 29.949 | 52.639 | 1.00 | 17.01 |
| 13220 | O | HOH | X | 421 | 17.202 | 28.889 | 48.827 | 1.00 | 10.77 |
| 13223 | O | HOH | X | 422 | 24.798 | 57.374 | 51.059 | 1.00 | 10.20 |
| 13226 | O | HOH | X | 423 | 8.702 | 42.173 | 70.339 | 1.00 | 24.94 |
| 13229 | O | HOH | X | 424 | 7.253 | 44.942 | 69.014 | 1.00 | 19.53 |
| 13232 | O | HOH | X | 425 | 8.227 | 49.360 | 68.337 | 1.00 | 18.47 |
| 13235 | O | HOH | X | 426 | 12.217 | 49.061 | 66.748 | 1.00 | 19.81 |
| 13238 | O | HOH | X | 427 | 16.551 | 44.873 | 64.042 | 1.00 | 20.15 |
| 13241 | O | HOH | X | 428 | 15.817 | 49.587 | 65.433 | 1.00 | 19.52 |
| 13244 | O | HOH | X | 429 | 18.410 | 46.149 | 67.202 | 1.00 | 26.92 |
| 13247 | O | HOH | X | 430 | 20.146 | 51.767 | 64.197 | 1.00 | 25.26 |
| 13250 | O | HOH | X | 431 | 19.359 | 52.508 | 61.742 | 1.00 | 24.78 |
| 13253 | O | HOH | X | 432 | 15.030 | 60.723 | 57.139 | 1.00 | 19.57 |
| 13256 | O | HOH | X | 433 | 4.817 | 50.769 | 89.133 | 1.00 | 15.28 |
| 13259 | O | HOH | X | 434 | 11.907 | 22.681 | 64.300 | 1.00 | 13.09 |
| 13262 | O | HOH | X | 435 | 12.032 | 23.024 | 67.077 | 1.00 | 19.39 |
| 13265 | O | HOH | X | 436 | 10.050 | 21.369 | 67.429 | 1.00 | 23.70 |
| 13268 | O | HOH | X | 437 | 12.750 | 18.583 | 65.522 | 1.00 | 25.02 |
| 13271 | O | HOH | X | 438 | 14.617 | 22.209 | 67.576 | 1.00 | 21.11 |
| 13274 | O | HOH | X | 439 | 16.121 | 21.911 | 65.430 | 1.00 | 14.75 |
| 13277 | O | HOH | X | 440 | 16.013 | 19.249 | 65.564 | 1.00 | 25.78 |
| 13280 | O | HOH | X | 441 | 12.826 | 15.595 | 61.077 | 1.00 | 18.47 |
| 13283 | O | HOH | X | 442 | 13.850 | 19.610 | 68.358 | 1.00 | 29.96 |
| 13286 | O | HOH | X | 443 | 45.065 | 30.009 | 71.586 | 1.00 | 23.21 |
| 13289 | O | HOH | X | 444 | 49.416 | 27.426 | 72.720 | 1.00 | 24.73 |
| 13292 | O | HOH | X | 445 | 51.651 | 40.791 | 85.344 | 1.00 | 20.44 |
| 13295 | O | HOH | X | 446 | 56.174 | 37.189 | 77.532 | 1.00 | 33.26 |
| 13298 | O | HOH | X | 447 | 53.393 | 42.572 | 83.764 | 1.00 | 15.79 |
| 13301 | O | HOH | X | 448 | 50.894 | 48.723 | 81.385 | 1.00 | 8.20 |
| 13304 | O | HOH | X | 449 | 52.163 | 51.286 | 81.016 | 1.00 | 25.40 |
| 13307 | O | HOH | X | 450 | 54.393 | 46.882 | 81.953 | 1.00 | 31.73 |
| 13310 | O | HOH | X | 451 | 53.693 | 46.898 | 77.730 | 1.00 | 29.70 |

FIGURE 3 (Cont.)

| A | B | C | D | E | F | G | H | I | J |
|---|---|---|---|---|---|---|---|---|---|
| 13313 | O | HOH | X | 452 | 21.627 | 41.245 | 39.048 | 1.00 | 16.54 |
| 13316 | O | HOH | X | 453 | 16.987 | 40.328 | 58.483 | 1.00 | 24.90 |
| 13319 | O | HOH | X | 454 | 22.149 | 43.484 | 37.745 | 1.00 | 23.19 |
| 13322 | O | HOH | X | 455 | 19.349 | 43.366 | 36.713 | 1.00 | 29.42 |
| 13325 | O | HOH | X | 456 | 21.851 | 44.904 | 33.285 | 1.00 | 32.85 |
| 13328 | O | HOH | X | 457 | 14.763 | 39.091 | 52.663 | 1.00 | 23.00 |
| 13331 | O | HOH | X | 458 | 12.565 | 41.532 | 55.794 | 1.00 | 24.86 |
| 13334 | O | HOH | X | 459 | 14.587 | 42.736 | 57.649 | 1.00 | 22.57 |
| 13337 | O | HOH | X | 460 | 14.635 | 49.015 | 55.320 | 1.00 | 25.40 |
| 13340 | O | HOH | X | 461 | 17.743 | 42.308 | 60.772 | 1.00 | 23.60 |
| 13343 | O | HOH | X | 462 | 14.136 | 39.330 | 55.219 | 1.00 | 27.56 |
| 13346 | O | HOH | X | 463 | 13.610 | 36.778 | 55.422 | 1.00 | 38.60 |
| 13349 | O | HOH | X | 464 | 13.241 | 34.166 | 55.656 | 1.00 | 30.81 |
| 13352 | O | HOH | X | 465 | 13.653 | 33.641 | 58.222 | 1.00 | 24.59 |
| 13355 | O | HOH | X | 466 | 11.052 | 36.056 | 59.115 | 1.00 | 24.92 |
| 13358 | O | HOH | X | 467 | 8.638 | 39.731 | 61.330 | 1.00 | 30.60 |
| 13361 | O | HOH | X | 468 | 13.708 | 29.666 | 60.039 | 1.00 | 22.42 |
| 13364 | O | HOH | X | 469 | 18.344 | 37.662 | 91.022 | 1.00 | 28.31 |
| 13367 | O | HOH | X | 470 | 17.627 | 37.703 | 88.360 | 1.00 | 23.87 |
| 13370 | O | HOH | X | 471 | 22.581 | 43.114 | 90.894 | 1.00 | 20.24 |
| 13373 | O | HOH | X | 472 | 21.787 | 30.931 | 91.396 | 1.00 | 18.65 |
| 13376 | O | HOH | X | 473 | 18.713 | 28.872 | 92.977 | 1.00 | 32.82 |
| 13379 | O | HOH | X | 474 | 22.273 | 29.414 | 93.999 | 1.00 | 27.75 |
| 13382 | O | HOH | X | 475 | 26.002 | 30.630 | 96.979 | 1.00 | 24.07 |
| 13385 | O | HOH | X | 476 | 27.258 | 32.757 | 98.114 | 1.00 | 28.08 |
| 13388 | O | HOH | X | 477 | 30.014 | 44.816 | 97.444 | 1.00 | 16.92 |
| 13391 | O | HOH | X | 478 | 15.911 | 52.518 | 70.059 | 1.00 | 11.43 |
| 13394 | O | HOH | X | 479 | 18.244 | 50.023 | 73.495 | 1.00 | 12.08 |
| 13397 | O | HOH | X | 480 | 46.942 | 39.940 | 28.387 | 1.00 | 27.79 |
| 13400 | O | HOH | X | 481 | 49.601 | 42.760 | 32.126 | 1.00 | 21.03 |
| 13403 | O | HOH | X | 482 | 41.317 | 47.091 | 35.248 | 1.00 | 29.34 |
| 13406 | O | HOH | X | 483 | 35.975 | 51.978 | 43.568 | 1.00 | 22.00 |
| 13409 | O | HOH | X | 484 | 31.504 | 52.682 | 46.494 | 1.00 | 14.97 |
| 13412 | O | HOH | X | 485 | 26.979 | 26.083 | 75.207 | 1.00 | 30.74 |
| 13415 | O | HOH | X | 486 | 46.763 | 35.441 | 60.103 | 1.00 | 17.85 |
| 13418 | O | HOH | X | 487 | 51.024 | 35.379 | 57.107 | 1.00 | 29.28 |
| 13421 | O | HOH | X | 488 | 57.413 | 33.980 | 49.905 | 1.00 | 30.63 |
| 13424 | O | HOH | X | 489 | 57.424 | 35.520 | 36.073 | 1.00 | 12.13 |
| 13427 | O | HOH | X | 490 | 60.248 | 35.561 | 36.195 | 1.00 | 25.63 |
| 13430 | O | HOH | X | 491 | 57.804 | 39.324 | 35.239 | 1.00 | 24.61 |
| 13433 | O | HOH | X | 492 | 53.358 | 36.717 | 23.959 | 1.00 | 25.99 |
| 13436 | O | HOH | X | 493 | 55.320 | 37.740 | 25.527 | 1.00 | 21.74 |
| 13439 | O | HOH | X | 494 | 46.690 | 35.384 | 25.641 | 1.00 | 26.54 |
| 13442 | O | HOH | X | 495 | 47.631 | 26.123 | 25.356 | 1.00 | 18.30 |
| 13445 | O | HOH | X | 496 | 47.036 | 28.020 | 27.265 | 1.00 | 14.94 |
| 13448 | O | HOH | X | 497 | 44.452 | 27.382 | 27.723 | 1.00 | 22.88 |
| 13451 | O | HOH | X | 498 | 22.675 | 64.741 | 56.316 | 1.00 | 14.76 |
| 13454 | O | HOH | X | 499 | 20.302 | 66.617 | 57.360 | 1.00 | 31.53 |
| 13457 | O | HOH | X | 500 | 19.055 | 66.083 | 72.327 | 1.00 | 25.86 |
| 13460 | O | HOH | X | 501 | 16.790 | 64.632 | 73.423 | 1.00 | 28.26 |
| 13463 | O | HOH | X | 502 | 15.743 | 63.356 | 71.407 | 1.00 | 27.95 |
| 13466 | O | HOH | X | 503 | 20.680 | 70.403 | 71.730 | 1.00 | 47.23 |

FIGURE 3 (Cont.)

| A | B | C | D | E | F | G | H | I | J |
|---|---|---|---|---|---|---|---|---|---|
| 13469 | O | HOH | X | 504 | 16.988 | 75.350 | 58.359 | 1.00 | 24.53 |
| 13472 | O | HOH | X | 505 | 17.567 | 71.729 | 61.679 | 1.00 | 13.72 |
| 13475 | O | HOH | X | 506 | 19.567 | 73.569 | 60.956 | 1.00 | 27.61 |
| 13478 | O | HOH | X | 507 | 20.314 | 76.024 | 61.801 | 1.00 | 36.01 |
| 13481 | O | HOH | X | 508 | 18.825 | 77.930 | 62.565 | 1.00 | 24.53 |
| 13484 | O | HOH | X | 509 | 6.533 | 41.760 | 90.903 | 1.00 | 29.00 |
| 13487 | O | HOH | X | 510 | 26.070 | 41.219 | 25.871 | 1.00 | 36.27 |
| 13490 | O | HOH | X | 511 | 10.045 | 41.256 | 81.814 | 1.00 | 24.00 |
| 13493 | O | HOH | X | 512 | 7.317 | 40.616 | 81.247 | 1.00 | 23.74 |
| 13496 | O | HOH | X | 513 | 6.931 | 42.438 | 84.787 | 1.00 | 25.43 |
| 13499 | O | HOH | X | 514 | 5.196 | 42.322 | 86.856 | 1.00 | 24.68 |
| 13502 | O | HOH | X | 515 | 3.579 | 45.863 | 79.410 | 1.00 | 26.22 |
| 13505 | O | HOH | X | 516 | 2.949 | 49.709 | 79.123 | 1.00 | 19.81 |
| 13508 | O | HOH | X | 517 | 3.787 | 50.983 | 75.264 | 1.00 | 20.59 |
| 13511 | O | HOH | X | 518 | 3.543 | 47.726 | 72.803 | 1.00 | 23.74 |
| 13514 | O | HOH | X | 519 | 15.301 | 29.140 | 84.208 | 1.00 | 18.79 |
| 13517 | O | HOH | X | 520 | 17.711 | 29.466 | 85.365 | 1.00 | 27.73 |
| 13520 | O | HOH | X | 521 | 18.184 | 31.284 | 89.201 | 1.00 | 32.32 |
| 13523 | O | HOH | X | 522 | 22.534 | 25.366 | 89.272 | 1.00 | 26.37 |
| 13526 | O | HOH | X | 523 | 20.096 | 33.514 | 92.954 | 1.00 | 29.11 |
| 13529 | O | HOH | X | 524 | 20.910 | 37.959 | 94.854 | 1.00 | 25.95 |
| 13532 | O | HOH | X | 525 | 20.631 | 36.346 | 92.769 | 1.00 | 26.92 |
| 13535 | O | HOH | X | 526 | 35.247 | 7.081 | 61.117 | 1.00 | 22.65 |
| 13538 | O | HOH | X | 527 | 32.414 | 9.481 | 60.755 | 1.00 | 30.25 |
| 13541 | O | HOH | X | 528 | 37.184 | 11.554 | 53.025 | 1.00 | 26.37 |
| 13544 | O | HOH | X | 529 | 41.789 | 11.189 | 52.874 | 1.00 | 20.67 |
| 13547 | O | HOH | X | 530 | 30.631 | 11.131 | 50.004 | 1.00 | 27.43 |
| 13550 | O | HOH | X | 531 | 33.049 | 10.802 | 50.629 | 1.00 | 30.29 |
| 13553 | O | HOH | X | 532 | 29.255 | 11.253 | 52.355 | 1.00 | 28.94 |
| 13556 | O | HOH | X | 533 | 29.100 | 8.815 | 45.737 | 1.00 | 24.92 |
| 13559 | O | HOH | X | 534 | 26.027 | 8.035 | 44.373 | 1.00 | 29.78 |
| 13562 | O | HOH | X | 535 | 30.897 | 7.578 | 43.939 | 1.00 | 29.33 |
| 13565 | O | HOH | X | 536 | 37.728 | 6.345 | 42.827 | 1.00 | 14.73 |
| 13568 | O | HOH | X | 537 | 41.632 | 8.110 | 46.570 | 1.00 | 33.75 |
| 13571 | O | HOH | X | 538 | 41.698 | 11.516 | 41.300 | 1.00 | 21.02 |
| 13574 | O | HOH | X | 539 | 44.336 | 14.941 | 38.940 | 1.00 | 16.97 |
| 13577 | O | HOH | X | 540 | 42.609 | 12.928 | 37.519 | 1.00 | 17.06 |
| 13580 | O | HOH | X | 541 | 47.827 | 19.539 | 33.922 | 1.00 | 18.67 |
| 13583 | O | HOH | X | 542 | 47.911 | 13.575 | 38.010 | 1.00 | 24.47 |
| 13586 | O | HOH | X | 543 | 45.906 | 13.098 | 40.136 | 1.00 | 22.40 |
| 13589 | O | HOH | X | 544 | 52.109 | 18.020 | 55.188 | 1.00 | 24.04 |
| 13592 | O | HOH | X | 545 | 55.179 | 25.152 | 55.761 | 1.00 | 24.94 |
| 13595 | O | HOH | X | 546 | 56.959 | 31.832 | 51.120 | 1.00 | 25.64 |
| 13598 | O | HOH | X | 547 | 56.362 | 29.809 | 54.608 | 1.00 | 33.37 |
| 13601 | O | HOH | X | 548 | 57.400 | 17.263 | 47.859 | 1.00 | 25.72 |
| 13604 | O | HOH | X | 549 | 57.831 | 14.739 | 47.458 | 1.00 | 31.24 |
| 13607 | O | HOH | X | 550 | 56.437 | 12.739 | 46.424 | 1.00 | 29.72 |
| 13610 | O | HOH | X | 551 | 54.403 | 18.534 | 53.681 | 1.00 | 27.18 |
| 13613 | O | HOH | X | 552 | 57.682 | 22.052 | 42.446 | 1.00 | 20.44 |
| 13616 | O | HOH | X | 553 | 58.658 | 24.548 | 43.826 | 1.00 | 31.62 |
| 13619 | O | HOH | X | 554 | 57.399 | 25.802 | 41.808 | 1.00 | 28.72 |
| 13622 | O | HOH | X | 555 | 54.007 | 21.789 | 37.840 | 1.00 | 24.27 |

FIGURE 3 (Cont.)

| A | B | C | D | E | F | G | H | I | J |
|---|---|---|---|---|---|---|---|---|---|
| 13625 | O | HOH | X | 556 | 56.596 | 20.111 | 38.620 | 1.00 | 20.53 |
| 13628 | O | HOH | X | 557 | 57.632 | 23.143 | 39.131 | 1.00 | 25.41 |
| 13631 | O | HOH | X | 558 | 18.243 | 43.236 | 39.008 | 1.00 | 26.13 |
| 13634 | O | HOH | X | 559 | 24.641 | 43.230 | 36.310 | 1.00 | 25.39 |
| 13637 | O | HOH | X | 560 | 13.730 | 39.160 | 41.227 | 1.00 | 23.76 |
| 13640 | O | HOH | X | 561 | 20.298 | 40.795 | 41.981 | 1.00 | 21.27 |
| 13643 | O | HOH | X | 562 | 17.457 | 35.372 | 50.204 | 1.00 | 25.59 |
| 13646 | O | HOH | X | 563 | 20.274 | 33.501 | 48.130 | 1.00 | 25.82 |
| 13649 | O | HOH | X | 564 | 10.550 | 41.183 | 57.569 | 1.00 | 24.95 |
| 13652 | O | HOH | X | 565 | 12.027 | 42.780 | 53.580 | 1.00 | 25.57 |
| 13655 | O | HOH | X | 566 | 29.273 | 62.525 | 76.025 | 1.00 | 28.32 |
| 13658 | O | HOH | X | 567 | 31.523 | 62.817 | 77.548 | 1.00 | 23.35 |
| 13661 | O | HOH | X | 568 | 28.037 | 65.816 | 76.174 | 1.00 | 44.37 |
| 13664 | O | HOH | X | 569 | 26.024 | 67.463 | 73.989 | 1.00 | 32.45 |
| 13667 | O | HOH | X | 570 | 22.825 | 64.097 | 74.794 | 1.00 | 23.85 |
| 13670 | O | HOH | X | 571 | 33.726 | 60.717 | 77.777 | 1.00 | 19.54 |
| 13673 | O | HOH | X | 572 | 34.132 | 58.822 | 75.636 | 1.00 | 20.81 |
| 13676 | O | HOH | X | 573 | 32.823 | 59.240 | 73.388 | 1.00 | 24.12 |
| 13679 | O | HOH | X | 574 | 34.883 | 63.146 | 73.236 | 1.00 | 30.07 |
| 13682 | O | HOH | X | 575 | 37.087 | 59.423 | 72.313 | 1.00 | 15.26 |
| 13685 | O | HOH | X | 576 | 35.192 | 58.550 | 70.774 | 1.00 | 14.97 |
| 13688 | O | HOH | X | 577 | 38.578 | 62.134 | 71.345 | 1.00 | 32.41 |
| 13691 | O | HOH | X | 578 | 38.114 | 62.536 | 62.639 | 1.00 | 26.81 |
| 13694 | O | HOH | X | 579 | 32.528 | 59.391 | 56.055 | 1.00 | 20.50 |
| 13697 | O | HOH | X | 580 | 30.284 | 57.924 | 54.722 | 1.00 | 15.46 |
| 13700 | O | HOH | X | 581 | 28.987 | 55.664 | 52.074 | 1.00 | 22.70 |
| 13703 | O | HOH | X | 582 | 31.827 | 53.786 | 49.233 | 1.00 | 28.26 |
| 13706 | O | HOH | X | 583 | 33.242 | 56.818 | 51.215 | 1.00 | 30.26 |
| 13709 | O | HOH | X | 584 | 36.848 | 58.226 | 54.239 | 1.00 | 18.40 |
| 13712 | O | HOH | X | 585 | 38.920 | 57.075 | 52.962 | 1.00 | 24.63 |
| 13715 | O | HOH | X | 586 | 36.910 | 59.041 | 59.557 | 1.00 | 27.64 |
| 13718 | O | HOH | X | 587 | 41.852 | 50.848 | 51.930 | 1.00 | 15.74 |
| 13721 | O | HOH | X | 588 | 43.187 | 51.974 | 49.865 | 1.00 | 20.39 |
| 13724 | O | HOH | X | 589 | 39.459 | 49.063 | 43.187 | 1.00 | 21.99 |
| 13727 | O | HOH | X | 590 | 37.795 | 53.875 | 41.221 | 1.00 | 25.50 |
| 13730 | O | HOH | X | 591 | 36.851 | 51.385 | 40.128 | 1.00 | 19.60 |
| 13733 | O | HOH | X | 592 | 15.376 | 22.121 | 29.461 | 1.00 | 31.95 |
| 13736 | O | HOH | X | 593 | 14.159 | 19.849 | 30.357 | 1.00 | 25.96 |
| 13739 | O | HOH | X | 594 | 19.395 | 19.901 | 27.944 | 1.00 | 26.28 |
| 13742 | O | HOH | X | 595 | 18.615 | 15.389 | 31.606 | 1.00 | 29.09 |
| 13745 | O | HOH | X | 596 | 27.195 | 20.904 | 28.842 | 1.00 | 28.97 |
| 13748 | O | HOH | X | 597 | 28.706 | 20.088 | 31.297 | 1.00 | 18.65 |
| 13751 | O | HOH | X | 598 | 33.444 | 17.738 | 35.200 | 1.00 | 20.45 |
| 13754 | O | HOH | X | 599 | 35.543 | 22.055 | 31.006 | 1.00 | 22.18 |
| 13757 | O | HOH | X | 600 | 50.236 | 25.728 | 25.352 | 1.00 | 29.75 |
| 13760 | O | HOH | X | 601 | 51.165 | 25.730 | 28.109 | 1.00 | 28.95 |
| 13763 | O | HOH | X | 602 | 26.932 | 13.082 | 63.595 | 1.00 | 35.63 |
| 13766 | O | HOH | X | 603 | 25.128 | 15.308 | 67.695 | 1.00 | 24.94 |
| 13769 | O | HOH | X | 604 | 15.168 | 12.763 | 61.107 | 1.00 | 31.87 |
| 13772 | O | HOH | X | 605 | 23.198 | 8.108 | 55.420 | 1.00 | 32.28 |
| 13775 | O | HOH | X | 606 | 20.895 | 8.535 | 54.145 | 1.00 | 22.97 |
| 13778 | O | HOH | X | 607 | 21.333 | 9.475 | 51.696 | 1.00 | 31.53 |

FIGURE 3 (Cont.)

| A | B | C | D | E | F | G | H | I | J |
|---|---|---|---|---|---|---|---|---|---|
| 13781 | O | HOH | X | 608 | 18.933 | 8.076 | 50.294 | 1.00 | 33.50 |
| 13784 | O | HOH | X | 609 | 18.584 | 16.462 | 63.163 | 1.00 | 17.32 |
| 13787 | O | HOH | X | 610 | 20.001 | 36.335 | 58.384 | 1.00 | 21.91 |
| 13790 | O | HOH | X | 611 | 20.036 | 28.642 | 62.602 | 1.00 | 17.90 |
| 13793 | O | HOH | X | 612 | 38.068 | 50.390 | 54.033 | 1.00 | 18.22 |
| 13796 | O | HOH | X | 613 | 35.406 | 55.414 | 46.895 | 1.00 | 33.60 |
| 13799 | O | HOH | X | 614 | 24.310 | 49.686 | 41.940 | 1.00 | 23.51 |
| 13802 | O | HOH | X | 615 | 44.933 | 12.419 | 59.663 | 1.00 | 28.60 |
| 13805 | O | HOH | X | 616 | 41.939 | 12.624 | 59.432 | 1.00 | 19.58 |
| 13808 | O | HOH | X | 617 | 43.476 | 12.033 | 63.268 | 1.00 | 32.73 |
| 13811 | O | HOH | X | 618 | 23.570 | 14.888 | 42.898 | 1.00 | 9.87 |
| 13814 | O | HOH | X | 619 | 27.745 | 12.466 | 47.203 | 1.00 | 29.35 |
| 13817 | O | HOH | X | 620 | 27.285 | 14.335 | 49.343 | 1.00 | 42.70 |
| 13820 | O | HOH | X | 621 | 26.162 | 13.002 | 53.175 | 1.00 | 25.31 |
| 13823 | O | HOH | X | 622 | 6.642 | 29.713 | 38.074 | 1.00 | 22.86 |
| 13826 | O | HOH | X | 623 | 6.951 | 28.764 | 42.710 | 1.00 | 20.71 |
| 13829 | O | HOH | X | 624 | 4.344 | 26.298 | 39.561 | 1.00 | 30.96 |
| 13832 | O | HOH | X | 625 | 5.574 | 23.617 | 40.784 | 1.00 | 24.72 |
| 13835 | O | HOH | X | 626 | 9.316 | 24.364 | 30.469 | 1.00 | 26.00 |
| 13838 | O | HOH | X | 627 | 8.556 | 21.508 | 32.474 | 1.00 | 22.36 |
| 13841 | O | HOH | X | 628 | 6.713 | 21.927 | 34.377 | 1.00 | 23.08 |
| 13844 | O | HOH | X | 629 | 6.989 | 23.579 | 36.560 | 1.00 | 27.01 |
| 13847 | O | HOH | X | 630 | 12.792 | 35.494 | 29.817 | 1.00 | 27.97 |
| 13850 | O | HOH | X | 631 | 10.838 | 34.619 | 33.520 | 1.00 | 21.30 |
| 13853 | O | HOH | X | 632 | 5.252 | 23.475 | 53.594 | 1.00 | 29.61 |
| 13856 | O | HOH | X | 633 | 7.509 | 20.576 | 50.768 | 1.00 | 21.42 |
| 13859 | O | HOH | X | 634 | 10.822 | 21.133 | 49.094 | 1.00 | 32.71 |
| 13862 | O | HOH | X | 635 | 9.217 | 14.371 | 56.897 | 1.00 | 18.50 |
| 13865 | O | HOH | X | 636 | 3.065 | 20.412 | 59.712 | 1.00 | 33.47 |
| 13868 | O | HOH | X | 637 | 1.195 | 19.586 | 62.191 | 1.00 | 25.83 |
| 13871 | O | HOH | X | 638 | 1.698 | 28.875 | 62.058 | 1.00 | 18.53 |
| 13874 | O | HOH | X | 639 | 4.594 | 27.854 | 67.016 | 1.00 | 19.97 |
| 13877 | O | HOH | X | 640 | 6.041 | 32.000 | 69.643 | 1.00 | 27.84 |
| 13880 | O | HOH | X | 641 | 4.971 | 30.281 | 64.365 | 1.00 | 22.85 |
| 13883 | O | HOH | X | 642 | 7.125 | 28.763 | 62.307 | 1.00 | 18.59 |
| 13886 | O | HOH | X | 643 | 7.927 | 34.300 | 70.775 | 1.00 | 29.37 |
| 13889 | O | HOH | X | 644 | 9.249 | 31.986 | 71.543 | 1.00 | 27.57 |
| 13892 | O | HOH | X | 645 | 8.546 | 25.258 | 69.680 | 1.00 | 27.16 |
| 13895 | O | HOH | X | 646 | 12.146 | 22.503 | 71.668 | 1.00 | 32.07 |
| 13898 | O | HOH | X | 647 | 9.146 | 34.991 | 74.540 | 1.00 | 27.62 |
| 13901 | O | HOH | X | 648 | 9.953 | 35.653 | 71.853 | 1.00 | 24.14 |
| 13904 | O | HOH | X | 649 | 9.609 | 38.252 | 71.188 | 1.00 | 30.75 |
| 13907 | O | HOH | X | 650 | 38.747 | 42.766 | 31.630 | 1.00 | 27.43 |
| 13910 | O | HOH | X | 651 | 38.261 | 30.763 | 30.474 | 1.00 | 21.93 |
| 13913 | O | HOH | X | 652 | 40.417 | 29.047 | 26.700 | 1.00 | 27.80 |
| 13916 | O | HOH | X | 653 | 33.205 | 37.721 | 30.596 | 1.00 | 19.64 |
| 13919 | O | HOH | X | 654 | 39.315 | 16.517 | 46.960 | 1.00 | 20.58 |
| 13922 | O | HOH | X | 655 | 31.094 | 15.403 | 48.156 | 1.00 | 26.65 |
| 13925 | O | HOH | X | 656 | 62.244 | 31.953 | 43.253 | 1.00 | 33.03 |
| 13928 | O | HOH | X | 657 | 55.933 | 30.432 | 44.302 | 1.00 | 27.59 |
| 13931 | O | HOH | X | 658 | 51.696 | 42.268 | 36.364 | 1.00 | 31.06 |
| 13934 | O | HOH | X | 659 | 54.520 | 40.328 | 37.482 | 1.00 | 23.46 |

FIGURE 3 (Cont.)

| A | B | C | D | E | F | G | H | I | J |
|---|---|---|---|---|---|---|---|---|---|
| 13937 | O | HOH | X | 660 | 57.994 | 44.251 | 42.595 | 1.00 | 25.41 |
| 13940 | O | HOH | X | 661 | 49.544 | 47.984 | 42.942 | 1.00 | 23.39 |
| 13943 | O | HOH | X | 662 | 50.468 | 49.348 | 54.674 | 1.00 | 25.64 |
| 13946 | O | HOH | X | 663 | 50.136 | 51.103 | 52.859 | 1.00 | 29.50 |
| 13949 | O | HOH | X | 664 | 46.746 | 50.419 | 48.438 | 1.00 | 33.94 |
| 13952 | O | HOH | X | 665 | 54.059 | 47.230 | 66.336 | 1.00 | 27.46 |
| 13955 | O | HOH | X | 666 | 53.067 | 46.049 | 68.726 | 1.00 | 24.62 |
| 13958 | O | HOH | X | 667 | 52.319 | 46.733 | 71.415 | 1.00 | 32.92 |
| 13961 | O | HOH | X | 668 | 53.046 | 50.988 | 68.283 | 1.00 | 24.57 |
| 13964 | O | HOH | X | 669 | 52.702 | 50.769 | 71.661 | 1.00 | 32.67 |
| 13967 | O | HOH | X | 670 | 52.186 | 48.197 | 74.166 | 1.00 | 32.28 |
| 13970 | O | HOH | X | 671 | 40.276 | 61.922 | 82.481 | 1.00 | 28.96 |
| 13973 | O | HOH | X | 672 | 39.652 | 62.892 | 80.064 | 1.00 | 26.46 |
| 13976 | O | HOH | X | 673 | 36.438 | 63.075 | 79.978 | 1.00 | 24.55 |
| 13979 | O | HOH | X | 674 | 40.207 | 65.449 | 80.010 | 1.00 | 28.93 |
| 13982 | O | HOH | X | 675 | 37.672 | 61.328 | 75.799 | 1.00 | 26.02 |
| 13985 | O | HOH | X | 676 | 38.693 | 62.994 | 73.933 | 1.00 | 28.49 |
| 13988 | O | HOH | X | 678 | 39.320 | 51.075 | 80.234 | 1.00 | 30.67 |
| 13991 | O | HOH | X | 679 | 34.469 | 56.370 | 76.494 | 1.00 | 20.87 |
| 13994 | O | HOH | X | 680 | 41.562 | 52.320 | 79.258 | 1.00 | 15.43 |
| 13997 | O | HOH | X | 681 | 36.864 | 59.010 | 74.830 | 1.00 | 15.02 |
| 14000 | O | HOH | X | 682 | 53.562 | 50.436 | 74.303 | 1.00 | 34.55 |
| 14003 | O | HOH | X | 683 | 49.771 | 37.993 | 57.541 | 1.00 | 32.56 |
| 14006 | O | HOH | X | 684 | 50.355 | 40.291 | 55.802 | 1.00 | 24.54 |
| 14009 | O | HOH | X | 685 | 50.411 | 42.319 | 57.395 | 1.00 | 23.82 |
| 14012 | O | HOH | X | 686 | 61.136 | 24.224 | 40.064 | 1.00 | 33.36 |
| 14015 | O | HOH | X | 687 | 33.190 | 13.832 | 33.496 | 1.00 | 26.28 |
| 14018 | O | HOH | X | 688 | 5.961 | 30.693 | 46.914 | 1.00 | 31.94 |
| 14021 | O | HOH | X | 689 | 11.315 | 35.053 | 41.801 | 1.00 | 30.15 |
| 14024 | O | HOH | X | 690 | 8.236 | 31.564 | 38.823 | 1.00 | 25.45 |
| 14027 | O | HOH | X | 691 | 5.342 | 26.000 | 36.581 | 1.00 | 27.81 |
| 14030 | O | HOH | X | 692 | 7.539 | 22.499 | 38.947 | 1.00 | 28.57 |
| 14033 | O | HOH | X | 693 | 5.708 | 28.951 | 53.613 | 1.00 | 30.35 |
| 14036 | O | HOH | X | 694 | 3.538 | 35.162 | 57.952 | 1.00 | 27.69 |
| 14039 | O | HOH | X | 695 | 6.983 | 34.404 | 64.765 | 1.00 | 25.04 |
| 14042 | O | HOH | X | 696 | 44.250 | 28.266 | 74.329 | 1.00 | 27.75 |
| 14045 | O | HOH | X | 697 | 42.789 | 24.603 | 71.575 | 1.00 | 24.65 |
| 14048 | O | HOH | X | 698 | 42.238 | 24.769 | 80.149 | 1.00 | 26.59 |
| 14051 | O | HOH | X | 699 | 40.080 | 23.509 | 95.230 | 1.00 | 26.29 |
| 14054 | O | HOH | X | 700 | 36.752 | 24.588 | 96.325 | 1.00 | 30.75 |
| 14057 | O | HOH | X | 701 | 38.811 | 24.977 | 98.597 | 1.00 | 25.57 |
| 14060 | O | HOH | X | 702 | 35.139 | 25.477 | 101.545 | 1.00 | 27.69 |
| 14063 | O | HOH | X | 703 | 35.612 | 42.931 | 99.544 | 1.00 | 34.22 |
| 14066 | O | HOH | X | 704 | 34.532 | 40.965 | 100.992 | 1.00 | 28.88 |
| 14069 | O | HOH | X | 705 | 33.627 | 46.599 | 97.466 | 1.00 | 20.68 |
| 14072 | O | HOH | X | 706 | 31.060 | 47.669 | 94.106 | 1.00 | 21.86 |
| 14075 | O | HOH | X | 707 | 32.419 | 49.680 | 93.309 | 1.00 | 25.11 |
| 14078 | O | HOH | X | 708 | 35.153 | 49.751 | 94.813 | 1.00 | 22.18 |
| 14081 | O | HOH | X | 709 | 26.931 | 50.680 | 91.231 | 1.00 | 26.22 |
| 14084 | O | HOH | X | 710 | 24.281 | 41.785 | 91.987 | 1.00 | 28.84 |
| 14087 | O | HOH | X | 711 | 20.179 | 42.551 | 95.164 | 1.00 | 38.86 |
| 14090 | O | HOH | X | 712 | 20.460 | 45.310 | 92.860 | 1.00 | 26.19 |

FIGURE 3 (Cont.)

| A | B | C | D | E | F | G | H | I | J |
|---|---|---|---|---|---|---|---|---|---|
| 14093 | O | HOH | X | 713 | 24.023 | 19.802 | 74.920 | 1.00 | 38.27 |
| 14096 | O | HOH | X | 714 | 17.796 | 22.177 | 69.106 | 1.00 | 25.34 |
| 14099 | O | HOH | X | 715 | 14.208 | 23.066 | 75.382 | 1.00 | 28.32 |
| 14102 | O | HOH | X | 716 | 47.210 | 53.297 | 75.938 | 1.00 | 15.17 |
| 14105 | O | HOH | X | 717 | 56.258 | 36.855 | 61.432 | 1.00 | 28.50 |
| 14108 | O | HOH | X | 718 | 56.576 | 34.814 | 66.232 | 1.00 | 28.42 |
| 14111 | O | HOH | X | 719 | 54.879 | 35.855 | 69.799 | 1.00 | 21.85 |
| 14114 | O | HOH | X | 720 | 56.413 | 23.670 | 58.012 | 1.00 | 27.55 |
| 14117 | O | HOH | X | 721 | 57.014 | 21.427 | 58.803 | 1.00 | 25.17 |
| 14120 | O | HOH | X | 722 | 54.156 | 24.860 | 60.547 | 1.00 | 28.00 |
| 14123 | O | HOH | X | 723 | 48.569 | 15.495 | 65.677 | 1.00 | 26.17 |
| 14126 | O | HOH | X | 724 | 46.492 | 15.892 | 60.886 | 1.00 | 26.08 |
| 14129 | O | HOH | X | 725 | 29.775 | 27.682 | 49.207 | 1.00 | 18.56 |
| 14132 | O | HOH | X | 726 | 20.983 | 28.860 | 42.426 | 1.00 | 22.49 |
| 14135 | O | HOH | X | 727 | 17.069 | 17.850 | 67.700 | 1.00 | 31.25 |
| 14138 | O | HOH | X | 728 | 18.500 | 19.887 | 68.571 | 1.00 | 28.04 |
| 14141 | O | HOH | X | 729 | 28.606 | 11.264 | 64.668 | 1.00 | 26.44 |
| 14144 | O | HOH | X | 730 | 32.650 | 13.611 | 68.868 | 1.00 | 28.32 |
| 14147 | O | HOH | X | 731 | 39.538 | 18.167 | 71.076 | 1.00 | 24.46 |
| 14150 | O | HOH | X | 732 | 44.301 | 17.465 | 71.869 | 1.00 | 27.20 |
| 14153 | O | HOH | X | 733 | 35.443 | 16.334 | 74.420 | 1.00 | 23.20 |
| 14156 | O | HOH | X | 734 | 13.153 | 15.522 | 46.958 | 1.00 | 20.02 |
| 14159 | O | HOH | X | 735 | 12.470 | 19.150 | 45.655 | 1.00 | 30.24 |
| 14162 | O | HOH | X | 736 | 10.966 | 21.917 | 44.866 | 1.00 | 24.07 |
| 14165 | O | HOH | X | 737 | 33.369 | 54.110 | 40.895 | 1.00 | 34.94 |
| 14168 | O | HOH | X | 738 | 31.455 | 54.135 | 42.718 | 1.00 | 39.58 |
| 14171 | O | HOH | X | 739 | 47.576 | 49.203 | 46.362 | 1.00 | 23.31 |
| 14174 | O | HOH | X | 740 | 51.726 | 50.187 | 47.580 | 1.00 | 27.66 |
| 14177 | O | HOH | X | 741 | 52.870 | 46.396 | 53.036 | 1.00 | 26.52 |
| 14180 | O | HOH | X | 742 | 58.284 | 44.707 | 51.125 | 1.00 | 28.41 |
| 14183 | O | HOH | X | 743 | 57.821 | 51.105 | 49.694 | 1.00 | 29.49 |
| 14186 | O | HOH | X | 744 | 42.311 | 33.784 | 75.196 | 1.00 | 22.66 |
| 14189 | O | HOH | X | 745 | 43.030 | 33.840 | 77.638 | 1.00 | 20.77 |
| 14192 | O | HOH | X | 746 | 42.653 | 29.458 | 71.470 | 1.00 | 22.38 |
| 14195 | O | HOH | X | 747 | 7.357 | 39.493 | 72.501 | 1.00 | 26.00 |
| 14198 | O | HOH | X | 748 | 8.168 | 40.692 | 68.191 | 1.00 | 24.98 |
| 14201 | O | HOH | X | 749 | 4.964 | 40.635 | 69.073 | 1.00 | 28.88 |
| 14204 | O | HOH | X | 750 | 13.772 | 33.482 | 45.348 | 1.00 | 27.82 |
| 14207 | O | HOH | X | 751 | 25.374 | 31.261 | 19.992 | 1.00 | 23.73 |
| 14210 | O | HOH | X | 752 | 21.226 | 29.765 | 18.764 | 1.00 | 26.07 |
| 14213 | O | HOH | X | 753 | 15.986 | 32.135 | 22.076 | 1.00 | 24.78 |
| 14216 | O | HOH | X | 754 | 19.263 | 29.936 | 20.408 | 1.00 | 26.06 |
| 14219 | O | HOH | X | 755 | 23.451 | 19.849 | 30.360 | 1.00 | 21.78 |
| 14222 | O | HOH | X | 756 | 34.200 | 29.874 | 27.826 | 1.00 | 28.13 |
| 14225 | O | HOH | X | 757 | 21.809 | 42.208 | 57.845 | 1.00 | 23.79 |
| 14228 | O | HOH | X | 758 | 17.448 | 40.187 | 55.912 | 1.00 | 20.20 |
| 14231 | O | HOH | X | 759 | 13.716 | 42.895 | 60.189 | 1.00 | 24.66 |
| 14234 | O | HOH | X | 760 | 14.045 | 49.867 | 60.803 | 1.00 | 25.65 |
| 14237 | O | HOH | X | 761 | 9.095 | 55.322 | 61.639 | 1.00 | 25.93 |
| 14240 | O | HOH | X | 762 | 37.080 | 13.569 | 34.728 | 1.00 | 34.70 |
| 14243 | O | HOH | X | 763 | 39.415 | 14.029 | 32.179 | 1.00 | 38.98 |
| 14246 | O | HOH | X | 764 | 40.689 | 12.113 | 33.046 | 1.00 | 22.53 |

FIGURE 3 (Cont.)

| A | B | C | D | E | F | G | H | I | J |
|---|---|---|---|---|---|---|---|---|---|
| 14249 | O | HOH | X | 765 | 42.772 | 13.616 | 33.119 | 1.00 | 28.19 |
| 14252 | O | HOH | X | 766 | 44.040 | 12.976 | 35.371 | 1.00 | 25.74 |
| 14255 | O | HOH | X | 767 | 42.129 | 16.316 | 32.636 | 1.00 | 26.13 |
| 14258 | O | HOH | X | 768 | 38.491 | 36.919 | 28.582 | 1.00 | 23.63 |
| 14261 | O | HOH | X | 769 | 39.039 | 35.217 | 26.639 | 1.00 | 25.31 |
| 14264 | O | HOH | X | 770 | 33.881 | 38.944 | 24.308 | 1.00 | 29.37 |
| 14267 | O | HOH | X | 771 | 30.539 | 38.266 | 20.965 | 1.00 | 28.70 |
| 14270 | O | HOH | X | 772 | 33.227 | 36.312 | 24.509 | 1.00 | 25.82 |
| 14273 | O | HOH | X | 773 | 28.650 | 46.001 | 72.027 | 1.00 | 21.58 |
| 14276 | O | HOH | X | 774 | 46.881 | 54.312 | 55.770 | 1.00 | 26.26 |
| 14279 | O | HOH | X | 775 | 53.975 | 49.841 | 65.628 | 1.00 | 25.28 |
| 14282 | O | HOH | X | 776 | 54.851 | 45.263 | 60.605 | 1.00 | 32.37 |
| 14285 | O | HOH | X | 777 | 53.307 | 38.908 | 53.561 | 1.00 | 26.80 |
| 14288 | O | HOH | X | 778 | 60.481 | 28.976 | 41.467 | 1.00 | 26.94 |
| 14291 | O | HOH | X | 779 | 61.565 | 31.643 | 38.500 | 1.00 | 28.55 |
| 14294 | O | HOH | X | 780 | 57.399 | 26.810 | 38.424 | 1.00 | 29.20 |
| 14297 | O | HOH | X | 781 | 36.840 | 33.219 | 37.951 | 1.00 | 25.66 |
| 14300 | O | HOH | X | 782 | 10.305 | 34.123 | 56.170 | 1.00 | 27.61 |
| 14303 | O | HOH | X | 783 | 17.162 | 33.648 | 55.200 | 1.00 | 21.59 |

CRYSTAL STRUCTURE OF MVAS

FIELD OF THE INVENTION

The present invention relates to a mevalonate pathway enzyme responsible for the synthesis of 3-Hydroxy-3-methylglutaryl-CoA (HMG-CoA) and more specifically to MvaS also known as HMG-CoA Synthase. Provided is MvaS in crystalline form, methods of forming crystals comprising MVAS, methods of using crystals comprising MvaS, a crystal structure of MvaS, and methods of using the crystal structure.

BACKGROUND OF THE INVENTION

A general approach to designing inhibitors that are selective for a given protein is to determine how a putative inhibitor interacts with a three-dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising MvaS and particularly crystals comprising MvaS that have sufficient size and quality to obtain useful information about the structural properties of MvaS and molecules or complexes that may associate with MvaS.

In one embodiment, a composition is provided that comprises a protein in crystalline form wherein at least a portion of the protein has 55%, 65%, 75%, 85%, 90%, 95%, 97%, 99% or greater identity with residues 2–384 of SEQ. ID No. 1.

In one variation, the protein has activity characteristic of MvaS. For example, the protein may optionally be inhibited by inhibitors of wild type MvaS. The protein crystal may also diffract X-rays for a determination of structure coordinates to a resolution of 4 Å, 3.5 Å, 3.0 Å or less.

In one variation, the protein crystal has a crystal lattice in a $P2_12_12_1$ space group. The protein crystal may also have a crystal lattice having unit cell dimensions, +/−5%, of a=68.7 b=79.6 c=150.2, $\alpha=\beta=\gamma=90$.

The present invention is also directed to crystallizing MvaS. The present invention is also directed to the conditions useful for crystallizing MvaS. It should be recognized that a wide variety of crystallization methods can be used in combination with the crystallization conditions to form crystals comprising MvaS including, but not limited to, vapor diffusion, batch, dialysis, and other methods of contacting the protein solution for the purpose of crystallization.

The present invention is also directed to crystallizing MvaS. The present invention is also directed to the conditions useful for crystallizing MvaS. It should be recognized that a wide variety of crystallization methods can be used in combination with the crystallization conditions to form crystals comprising MvaS including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 2–384 of SEQ. ID No. 1; and storing the crystallization volume under conditions suitable for crystal formation.

In one embodiment, a method is provided for forming crystals of a protein comprising: forming a crystallization volume comprising: a protein that has at least 55% identity with residues 2–384 of SEQ. ID No.1 in a concentration between 1 mg/ml and 100 mg/ml; 5–50% w/v of precipitant wherein the precipitant comprises one or more members of the group consisting of PEG or PEG MME having a molecular weight between 200 and 10000; optionally 0.05 to 2.5M additives wherein the additives comprise a monovalent and/or divalent salt (for example, sodium, lithium, magnesium, calcium, and the like); and storing the crystallization volume under conditions suitable for crystal formation. The method also optionally further includes performing the crystallization at a temperature between 1° C.–37° C.

The method may optionally further comprise forming a protein crystal that has a crystal lattice in a $P2_12_12_1$, space group. The method also optionally further comprises forming a protein crystal that has a crystal lattice having unit cell dimensions, +/−5%, a=68.7 b=79.6 c=150.2, $\alpha=\beta=\gamma=90$. The invention also relates to protein crystals formed by these methods.

The present invention is also directed to a composition comprising an isolated protein that comprises or consists of one or more of the protein sequence(s) of MvaS taught herein for crystallizing MvaS. The present invention is also directed to a composition comprising an isolated nucleic acid molecule that comprises or consists of the nucleotides for expressing the protein sequence of MvaS taught herein for crystallizing MvaS.

The present invention is also directed to an expression vector that may be used to express the isolated proteins taught herein for crystallizing MvaS.

The present invention is also directed to an expression vector that may be used to express the isolated proteins taught herein for crystallizing MvaS. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for MvaS as well as structure coordinates that are comparatively similar to these structure coordinates. It is noted that these comparatively similar structure coordinates may encompass proteins with similar sequences and/or structures, such as ketoacyl-ACP synthases. For example, machine-readable data storage media is provided having data storage material encoded with machine-readable data that comprises structure coordinates that are comparatively similar to the structure coordinates of MvaS. The present invention is also directed to a machine readable data storage medium having data storage material encoded with machine readable data, which, when read by an appropriate machine, can display a three dimensional representation of all or a portion of a structure of MvaS or a model that is comparatively similar to the structure of all or a portion of MvaS.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.98 Å, 0.65 Å, or 0.49 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.98 | 0.65 | 0.49 |
| (4 Angstrom set) | main-chain atoms[1] | 0.91 | 0.61 | 0.45 |
| | all non-hydrogen[2] | 1.10 | 0.71 | 0.54 |
| Table 3 | alpha-carbon atoms[1] | 0.89 | 0.60 | 0.45 |
| (7 Angstrom set) | main-chain atoms[1] | 0.84 | 0.56 | 0.42 |
| | all non-hydrogen[2] | 0.99 | 0.66 | 0.49 |
| Table 4 | alpha-carbon atoms[1] | 0.98 | 0.65 | 0.49 |
| (10 Angstrom set) | main-chain atoms[1] | 0.95 | 0.64 | 0.48 |
| | all non-hydrogen[2] | 1.11 | 0.74 | 0.56 |
| 2-384 of | alpha-carbon atoms[1] | 1.30 | 0.86 | 0.65 |
| SEQ. ID No. 1 | main-chain atoms[1] | 1.31 | 0.87 | 0.65 |
| | all non-hydrogen[2] | 1.42 | 0.94 | 0.71 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

The present invention is also directed to a three-dimensional structure of all or a portion of MvaS. This three-dimensional structure may be used to identify binding sites, to provide mutants having desirable binding properties, and ultimately, to design, characterize, or identify ligands capable of interacting with MvaS. Ligands that interact with MvaS may be any type of atom, compound, protein or chemical group that binds to or otherwise associates with the protein. Examples of types of ligands include natural substrates for MvaS, inhibitors of MvaS, and heavy atoms. The inhibitors of MvaS may optionally be used as drugs to treat therapeutic indications by modifying the in vivo activity of MvaS.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of MvaS.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of MvaS, in particular the structure coordinates of MvaS and the surface contour defined by them, in methods for screening, designing, or optimizing molecules or other chemical entities that interact with and preferably inhibit MvaS.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of MvaS and/or its structure coordinates to evaluate the ability of entities to associate with MvaS. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising: generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 2–384 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 2–384 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for MvaS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for MvaS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of MvaS. For example, the protein may optionally be inhibited by inhibitors of wild type MvaS.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 2–384 of SEQ. ID No. 1; and performing rational drug design using a three dimensional structure that is based on the obtained structure coordinates.

The protein crystals may optionally have a crystal lattice with a $P2_1 2_1 2_1$ space group and unit cell dimensions, +/−5%, of a=68.7 b=79.6 c=150.2, $\alpha=\beta=\gamma=90$.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1 and 2 referred to in this application.

FIG. 3 lists a set of atomic structure coordinates for MvaS as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
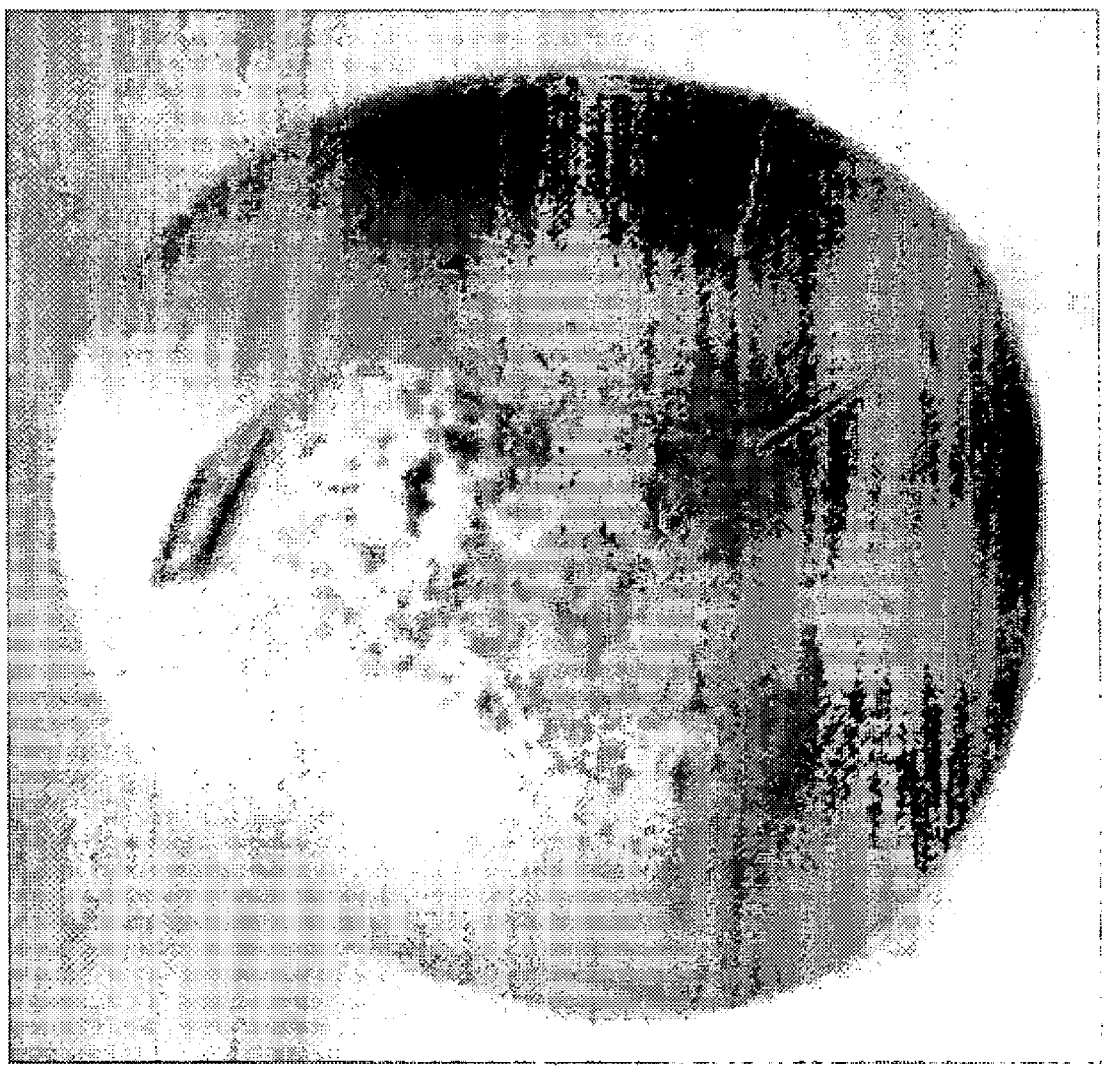
FIG. 2 illustrates crystal of MvaS corresponding to SEQ. ID No. 1, having a crystal lattice in a $P2_1 2_1 2_1$ space group and unit cell dimensions, +/−5%, of a=68.7 b=79.6 c=150.2, $\alpha=\beta=\gamma=90$.

The present invention relates to 3-Hydroxy-3-methylglutaryl-CoA (HMG-CoA) and more specifically to MvaS also known as HMG-CoA Synthase. Provided is MvaS in crystalline form, methods of forming crystals comprising MvaS, methods of using crystals comprising MvaS, a crystal structure of MvaS, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=MSE=Selenomethionine; K=Lys=Lysine; G=Gly=Glycine; R=Arg=Arginine; S=Ser=Serine; and H=His=Histidine.

1. MvaS

The protein MvaS is an acyl-keto synthase that condenses acetyl-CoA and acetoacetyl-CoA to from HMG-CoA. In humans, the enzyme catalyzes a committed step in the pathways for isoprenoid, cholesterol, and ketone body production. The importance of the enzyme is underscored by the observed regulation of various isozymes (Quaint P. A. (1994) Essays Biochem, 28, 13–25) as well the role the enzyme in fasting hypoketotic coma (N Engl J Med. 1997 Oct. 23;337(17):1203–7)

MvaS is also found in gram-positive pathogenic bacteria such and *Enterococcus facaelis*. As such knowledge of the 3-dimensional structure of a bacterial MvaS enzyme will facilitate the development of compounds that inhibit the growth of pathogens dependent on the mevalonate pathway for the synthesis of isoprenoids.

In one embodiment, MvaS comprises the wild-type form of full length MvaS, set forth herein as SEQ. ID No. 1 (GenBank Accession Number AF290092).

In another embodiment, MvaS comprises residues 2–384 of SEQ. ID No. 1 which comprises the active site domain of wild-type MvaS that is represented in the set of structural coordinates shown in FIG. 3.

It should be recognized that the invention may be readily extended to various variants of wild-type MvaS and variants of fragments thereof. In another embodiment, MvaS comprises a sequence wherein at least a portion of the sequence has 55%, 65%, 75%, 85%, 90%, 95%, 97%, 99% or greater identity with SEQ. ID No. 1.

It is also noted that the above sequences of MvaS are also intended to encompass isoforms, mutants and fusion proteins of these sequences. An example of a fusion protein is provided by SEQ. ID No. 1, which includes a 6 residue C-terminal tag (6 residues are histidine) that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the MvaS amino acids shown in Table 2 encompass a 4-Angstrom radius around the MvaS active site and thus likely to interact with any active site inhibitor of MvaS. Applicants have also determined that the amino acids of Table 3 encompass a 7-Angstrom radius around the MvaS active site. Further it has been determined that the amino acids of Table 4 encompass a 10-Angstrom radius around the MvaS active site. It is noted that there is one MvaS molecule in the asymmetric unit, referred to as chain A. Structural coordinates appear in FIG. 3. It is noted that the sequence and structure of the residues in the active site may also be conserved and hence pertinent to other MvaS and homologs.

One or more of the sets of amino acids set forth in the tables is preferably conserved in a variant of MvaS. Hence, MvaS may optionally comprise a sequence wherein at least a portion of the sequence has 55%, 65%, 75%, 85%, 90%, 95%, 97%, 99% or greater identity with any one of the above sequences (e.g., all of SEQ. ID No. 1 or residues 2–384 of SEQ. ID No. 1) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the MvaS active site.

| ASP 29 | GLY 31 | LYS 32 |
|---|---|---|
| GLY 36 | GLU 79 | ALA 110 |
| CYS 111 | TYR 143 | GLY 148 |
| GLY 149 | THR 152 | PHE 185 |
| VAL 196 | GLY 198 | SER 201 |
| ASN 202 | TYR 205 | HIS 233 |
| PRO 235 | TYR 236 | MSE 239 |
| LYS 242 | ASN 275 | TYR 306 |
| GLY 307 | SER 308 | |

TABLE 3

Amino Acids encompassed by a 7-Angstrom radius around the MvaS active site.

| VAL 28 | ASP 29 | PRO 30 |
|---|---|---|
| GLY 31 | LYS 32 | PHE 33 |
| HIS 34 | ILE 35 | GLY 36 |
| ILE 37 | GLU 79 | GLU 109 |
| ALA 110 | CYS 111 | TYR 112 |
| ASP 139 | TYR 143 | SER 147 |
| GLY 148 | GLY 149 | GLU 150 |
| PRO 151 | THR 152 | ASP 184 |
| PHE 185 | TRP 186 | PRO 194 |
| VAL 196 | ASP 197 | GLY 198 |
| PRO 199 | LEU 200 | SER 201 |
| ASN 202 | GLU 203 | THR 204 |
| TYR 205 | ILE 206 | HIS 233 |
| ILE 234 | PRO 235 | TYR 236 |
| LYS 238 | MSE 239 | LYS 242 |
| ASN 275 | TYR 277 | THR 278 |
| SER 280 | TYR 306 | GLY 307 |
| SER 308 | GLY 309 | |

TABLE 4

Amino Acids encompassed by a 10-Angstrom radius around the MvaS active site.

| MSE 19 | ALA 23 | ASN 27 |
|---|---|---|
| VAL 28 | ASP 29 | PRO 30 |
| GLY 31 | LYS 32 | PHE 33 |
| HIS 34 | ILE 35 | GLY 36 |
| ILE 37 | GLY 38 | GLN 39 |
| MSE 42 | THR 78 | GLU 79 |
| SER 80 | LYS 108 | GLU 109 |
| ALA 110 | CYS 111 | TYR 112 |
| GLY 113 | ALA 114 | ASP 139 |
| ILE 140 | ALA 141 | LYS 142 |
| TYR 143 | GLY 144 | ASN 146 |
| SER 147 | GLY 148 | GLY 149 |
| GLU 150 | PRO 151 | THR 152 |
| GLN 153 | GLY 154 | ILE 182 |
| TYR 183 | ASP 184 | PHE 185 |
| TRP 186 | ARG 187 | PRO 194 |
| MSE 195 | VAL 196 | ASP 197 |
| GLY 198 | PRO 199 | LEU 200 |
| SER 201 | ASN 202 | GLU 203 |
| THR 204 | TYR 205 | ILE 206 |
| GLN 207 | SER 208 | PHE 232 |
| HIS 233 | ILE 234 | PRO 235 |
| TYR 236 | THR 237 | LYS 238 |
| MSE 239 | GLY 240 | LYS 241 |
| LYS 242 | ALA 243 | LEU 245 |
| TYR 263 | GLY 274 | ASN 275 |
| LEU 276 | TYR 277 | THR 278 |
| GLY 279 | SER 280 | LEU 281 |
| PHE 304 | SER 305 | TYR 306 |
| GLY 307 | SER 308 | GLY 309 |
| ALA 310 | VAL 311 | ALA 312 |

With the benefit of the crystal structure and guidance provided by Tables 2, 3 and 4, a wide variety of MvaS variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of MvaS.

Variants of MvaS may be insertional variants in which one or more amino acid residues are introduced into a predetermined site in the MvaS sequence. For instance, insertional variants can be fusions of heterologous proteins or polypeptides to the amino or carboxyl terminus of the subunits.

Variants of MvaS also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Asp→Glu, Ser→Cys, and Cys→Ser for example.

Another class of variants is deletional variants, which are characterized by the removal of one or more amino acid residues from the MvaS sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminaseN catalyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79–86, 1983), acetylation of the N-terminal amine and amidation of any C-terminal carboxyl group.

As can be seen, modifications of the nucleic sequence encoding MvaS may be accomplished by a variety of well-known techniques, such as site-directed mutagenesis (see, Gillman and Smith, *Gene* 8:81–97 (1979) and Roberts, S. et al., *Nature* 328:731–734 (1987)). When modifications are made, these modifications may optionally be evaluated for there affect on a variety of different properties including, for example, solubility, crystallizability and a modification to the protein's structure and activity.

In one variation, the variant and/or fragment of wild-type MvaS is functional in the sense that the resulting protein is capable of associating with at least one same chemical entity that is also capable of selectively associating with a protein comprising the wild-type MvaS (e.g., residues 2–384 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of MvaS, and the atomic structure coordinates obtained there from, can be used to identify compounds that bind to the native domain. These compounds may affect the activity of the native domain.

Amino acid substitutions, deletions and additions that do not significantly interfere with the three-dimensional structure of MvaS will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of MvaS will be apparent to those having skills in the art, particularly in view of the three dimensional structure of MvaS provided herein.

2. Cloning, Expression and Purification of MvaS

The gene encoding MvaS can be isolated from RNA, cDNA or cDNA libraries. In this case, the portion of the gene encoding amino acid residues 2–384 (SEQ. ID No. 1) was isolated and is shown as SEQ. ID No. 2. It is noted that the gene was modified to include a C-terminal 6 residue polyhistidine tag.

Construction of expression vectors and recombinant proteins from the DNA sequence encoding MvaS may be performed by various methods well known in the art. For example, these techniques may be performed according to Sambrook et al., Molecular Cloning—A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of MvaS. Example 1 provides one such expression system.

Once expressed, purification steps are employed to produce MvaS in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

MvaS may optionally be affinity labeled during cloning, preferably with a N-terminal six-histidine tag and rTev cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising MvaS

One aspect of the present invention relates to methods for forming crystals comprising MvaS as well as crystals comprising MvaS.

In one embodiment, a method for forming crystals comprising MvaS is provided comprising forming a crystallization volume comprising MvaS, one or more precipitants, optionally a buffer, optionally a monovalent and/or divalent salt and optionally an organic solvent; and storing the crystallization volume under conditions suitable for crystal formation.

In yet another embodiment, a method for forming crystals comprising MvaS is provided comprising forming a crystallization volume comprising MvaS in solution comprising the components shown in Table 5; and storing the crystallization volume under conditions suitable for crystal formation.

TABLE 5

| Precipitant |
| --- |
| 5–50% w/v of precipitant wherein the precipitant comprises one or more members of the group consisting of PEG MME having a molecular weight range between 1000–10000, PEG having a molecular weight range between 100–10000. 0.3–2.0 M Sodium, potassium or ammonium phosphate. |
| pH |
| pH 4–10. Buffers that may be used include, but are not limited to tris, bicine, phosphate, cacodylate, acetate, citrate, HEPES, PIPES, MES and combinations thereof. |
| Additives |
| Optionally 0.05 to 2.5 M additives wherein the additives comprise a monovalent and/or divalent salt (for example, sodium, lithium, magnesium, calcium, and the like) |
| Protein Concentration |
| 1 mg/ml–50 mg/ml |
| Temperature |
| 1° C.–25° C. |

In yet another embodiment, a method for forming crystals comprising MvaS is provided comprising forming a crystallization volume comprising MvaS; introducing crystals comprising MvaS as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising MvaS and crystals comprising MvaS according to the invention are not intended to be limited to the wild type, full length MvaS shown in SEQ. ID No. 1, fragments comprising residues 2–384 of SEQ. ID No. 1 and fragments comprising residues 2–384 of SEQ. ID No. 1. Rather, it should be recognized that the invention may be extended to various other fragments and variants of wild-type MvaS as described above.

It should also be understood that forming crystals comprising MvaS and crystals comprising MvaS according to the invention may be such that MvaS is optionally complexed with one or more ligands and one or more copies of the same ligand. The ligand used to form the complex may be any ligand capable of binding to MvaS. In one variation, the ligand is a natural substrate. In another variation, the ligand is an inhibitor.

In one particular embodiment, MvaS crystals have a crystal lattice in the $P2_12_12_1$, space group. MvaS crystals may also optionally have unit cell dimensions, +/−5%, of a=68.7 b=79.6 c=150.2, $\alpha=\beta=\gamma=90$. MvaS crystals also preferably are capable of diffracting X-rays for determination of atomic coordinates to a resolution of 4 Å, 3.5 Å, 3.0 Å or better.

Crystals comprising MvaS may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens, et al. (2000) *Curr. Opin. Struct. Biol.*: 10(5):558–63, and U.S. Pat. Nos. 6,296,673, 5,419,278, and 5,096,676.

In one variation, crystals comprising MvaS are formed by mixing substantially pure MvaS with an aqueous buffer containing a precipitant at a concentration just below a concentration necessary to precipitate the protein. One suitable precipitant for crystallizing MvaS is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a MvaS complex were obtained. In order to accomplish this, systematic broad screen crystallization trials were performed on an MvaS complex using the sitting drop technique. In each experiment, a 100 nL mixture of MvaS complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect MvaS crystallization was obtained. Based on this understanding, a series of crystallization conditions were identified that may be used to form crystals comprising MvaS. These conditions are summarized in Table 5. A particular example of crystallization conditions that may be used to form diffraction quality crystals of the MvaS complex is detailed in Example 2. FIG. 2 illustrates crystals of the MvaS complex formed using the crystallization conditions provided in Table 5.

One skilled in the art will recognize that the crystallization conditions provided in Table 5 and Example 2 can be varied and still yield protein crystals comprising MvaS. For example, it is noted that variations on the crystallization conditions described herein can be readily determined by taking the conditions provided in Table 5 and performing fine screens around those conditions by varying the type and concentration of the components in order to determine additional suitable conditions for crystallizing MvaS, variants of MvaS, and ligand complexes thereof.

Crystals comprising MvaS have a wide range of uses. For example, now that crystals comprising MvaS have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising MvaS according to the present invention, the crystals so formed can be used by this crystallization technique to initiate crystal growth of other MvaS comprising crystals, including MvaS complexed to other ligands.

As will be described herein in greater detail, crystals may also be used to perform X-ray or neutron diffraction analysis in order to determine the three-dimensional structure of MvaS and, in particular, to assist in the identification of its active site. Knowledge of the binding site region allows rational design and construction of ligands including inhibitors. Crystallization and structural determination of MvaS mutants having altered bioactivity allows the evaluation of whether such changes are caused by general structure deformation or by side chain alterations at the substitution site.

4. X-Ray Data Collection and Structure Determination

Crystals comprising MvaS may be obtained as described above in Section 3. As described herein, these crystals may then be used to perform X-ray data collection and for structure determination.

In one embodiment, described in Example 2, crystals of MvaS were obtained where MvaS has the sequence of residues shown in SEQ. ID No. 1. These particular crystals were used to determine the three dimensional structure of MvaS. However, it is noted that other crystals comprising MvaS including different MvaS variants, fragments, and complexes thereof may also be used.

Diffraction data was collected from cryocooled crystals (100K) of MvaS at the Advanced Light Source (ALS) beam line 5.0.3 using an ADSC Quantum CCD detector. The diffraction pattern of the MvaS crystals displayed symmetry consistent with space group $P2_12_12_1$, with unit cell dimensions of a=68.7 b=79.6 c=150.2, $\alpha=\beta=\gamma=90$ (+/−5%). Data were collected and integrated to 2.0 Å with the HKL2000 program package (Otwinowski, Z. and Minor, W., *Meth. Enzymol.* 276:307 (1997).

The structure solution for MvaS in the space group $P2_12_12_1$, with unit cell dimensions of a=68.7 b=79.6 c=150.2, $\alpha=\beta=\gamma=90$ (+/−5%) was obtained by rigid body refinement method using the program REFMAC (Collaborative Computational Project, N. The CCP4 Suite: Programs for Protein Crystallography. *Acta Crystallogr.* D50, 760–763 (1994)), with the coordinates of unliganded MvaS (unpublished results, (2002) Syrrx Inc.) used as a search model. All subsequent crystallographic calculations were performed using the CCP4 program package (Collaborative Computational Project, N. The CCP4 Suite: Programs for Protein Crystallography. *Acta Crystallogr.* D50, 760–763 (1994)). The rigid body solution was subjected to restrained least-squares refinement using the maximum likelihood method as implemented in REFMAC (Murshudov, G. N., Vagin, A. A. and Dodson E. J. *Acta Crystallogr* D53:240 (1997)). Multiple rounds of manual fitting of the MvaS sequence were performed with Xfit (McRee, D. E., *J. Struct. Biol.* 125:156 (1999)). Manual fitting was interspersed with restrained least-squares refinement in REFMAC against data from 10.0 to 2.0 Å. All stages of refinement were carried with bulk solvent corrections and anisotropic scaling, and excluded 5% of $R_{free}$ reflections for cross-validation. The data collection and data refinement statistics are given in Table 6.

TABLE 6

Crystal data

| | |
|---|---|
| Space group | $P2_12_12_1$ |
| Unit cell dimensions | a = 68.70 Å |
| | b = 79.60 Å |
| | c = 150.20 Å |

Data collection

| | | |
|---|---|---|
| X-ray source | | ALS BL 5.0.3 |
| Wavelength [Å] | | 1.00 |
| Resolution [Å] | | 2.00 |
| Observations (unique) | | 52889 |
| Redundancy | | 4.7 |
| Completeness | overall (outer shell) | 93.6 (59)% |
| I/σ(I) | overall (outer shell) | 24.4 (6.0) |
| $R_{symm}^1$ | overall (outer shell) | 0.070 (.116) |

Refinement

| | |
|---|---|
| Reflections used | 50122 |
| R-factor | 15.7% |
| $R_{free}$ | 19.6% |
| r.m.s bonds | 0.007 Å |
| r.m.s angles | 1.33° |

During structure determination, where the unit cell dimensions were a=68.7 b=79.6 c=150.2, α=β=γ=90, it was realized that the asymmetric unit comprised two MvaS molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 1. Structure coordinates are not reported for residues 1 and 384–391 in molecule A and residues 1 and 388–391 in molecule B because the electron density obtained was insufficient to identify their position. Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the MvaS structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of MvaS would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442–453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for MvaS, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1HND was identified as having the smallest RMSD values relative to the structure coordinates provided herein. Table 7 below provides a series of RMSD values that were calculated by the above described process using the structure coordinates in FIG. 3 as the reference protein and the structure coordinates from PDB code: 1HND (3-oxoacyl-[acyl-carrier protein] synthase) as the target protein.

TABLE 7

| AA RESIDUES USED TO PERFORM RMSD COMPARISON WITH PDB:1VR2 | PORTION OF EACH AA RESIDUE USED TO PERFORM RMSD COMPARISON WITH PDB:1HND | RMSD [Å] |
|---|---|---|
| Table 2 | alpha-carbon atoms[1] | 1.96 |
| (4 Angstrom set) | main-chain atoms[1] | 1.82 |
| | all non-hydrogen[2] | 2.15 |
| Table 3 | alpha-carbon atoms[1] | 1.78 |
| (7 Angstrom set) | main-chain atoms[1] | 1.67 |
| | all non-hydrogen[2] | 1.98 |
| Table 4 | alpha-carbon atoms[1] | 1.96 |
| (10 Angstrom set) | main-chain atoms[1] | 1.91 |
| | all non-hydrogen[2] | 2.23 |
| 2-384 of | alpha-carbon atoms[1] | 2.60 |
| SEQ. ID No. 1 | main-chain atoms[1] | 2.62 |
| | all non-hydrogen[2] | 2.84 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

It is noted that mutants and variants of MvaS are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the MvaS structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. MvaS Structure

The present invention is also directed to a three-dimensional crystal structure of MvaS. This crystal structure may be used to identify binding sites, to provide mutants having desirable binding properties, and ultimately, to design, characterize, or identify ligands that interact with MvaS as well as other structurally similar proteins.

The three-dimensional crystal structure of MvaS may be generated, as is known in the art, from the structure coordinates shown in FIG. 3 and similar such coordinates.

During the course of structure solution it became evident that the crystals of MvaS of the present invention contained two MvaS molecules in the asymmetric unit. It is noted that the sequence of the structure coordinates presented in FIG. 3 differ in some regards from the sequence shown in SEQ. ID No. 1. The final refined coordinates do not include amino acid residues 1 and 384–391 in molecule A and residues 1 and 388–391 in molecule B because the electron density obtained was insufficient to identify their position. The final coordinate set additionally includes 747 solvent molecules modeled as water and two molecules of HMG-CoA.

Figure 4:
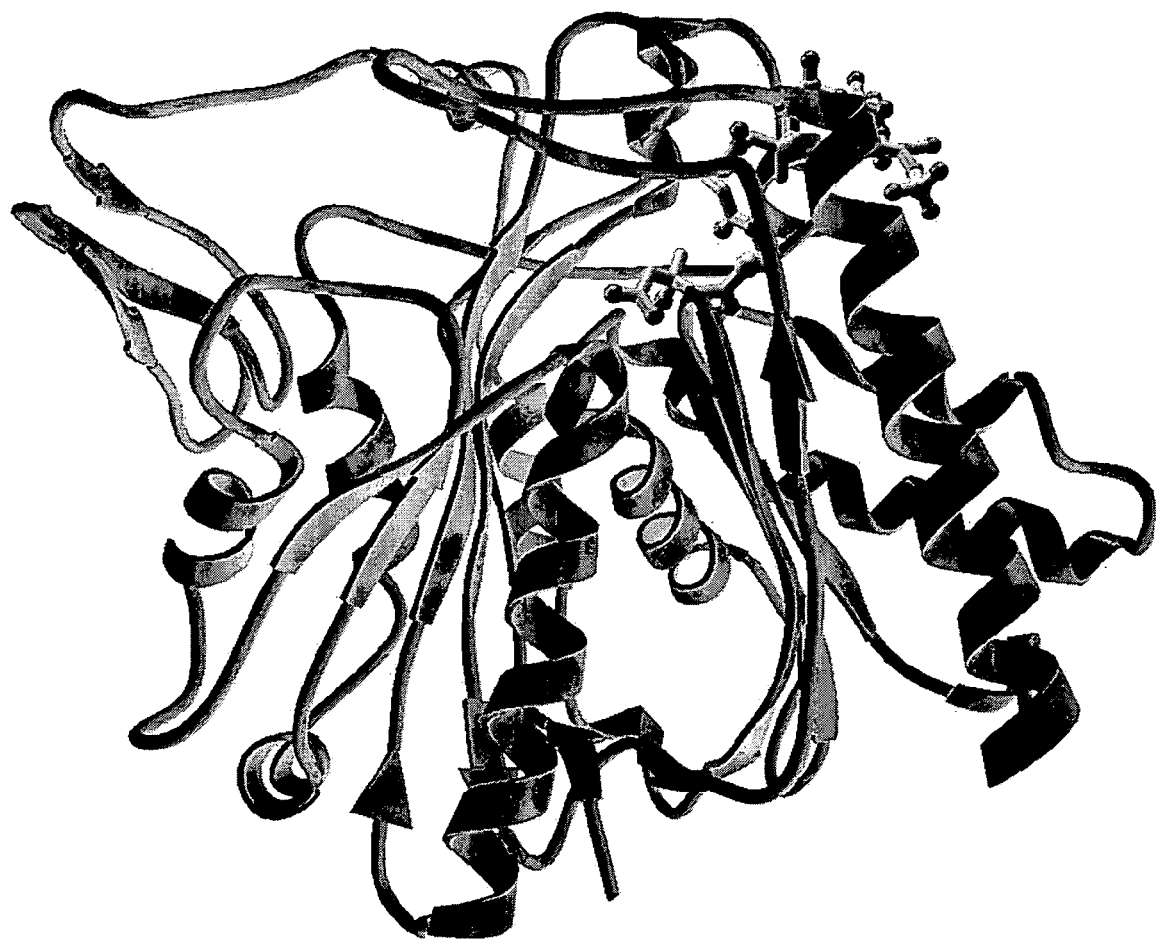
FIG. 4 illustrates a ribbon diagram overview of the structure of MvaS, highlighting secondary structural elements of the protein.

FIG. 4 illustrates a ribbon diagram overview of the structure of MvaS, highlighting the secondary structural elements of the protein. As can be seen, the monomer exhibits a five-layered core structure, $\alpha$-$\beta$-$\alpha$-$\beta$-$\alpha$, where each $\alpha$ comprises two $\alpha$-helices and each $\beta$ is made of a five-stranded, mixed $\beta$-sheet. The active site of MvaS is occupied by its reaction product HMG-CoA, which binds in a deep tunnel that is lined with conserved aromatic and hydrophobic residues. Catalytic Cys111, which biochemical studies have implicated as forming an enzyme-S-acetyl intermediate, is located at the base of the tunnel and is unmodified in this product bound structure.

The MvaS dimer is large and primarily hydrophobic with the interface spanning several secondary structure region. Complementary interactions between $\alpha 5$, $\beta 6$, and $\alpha 6$ link the catalytic site at Cys111 and form a continuous 10-stranded $\beta$ sheet in the dimer. Additional interactions, including those between the $\beta 9$-$\alpha 7$ loop of one monomer, with the $\alpha 5$-$\beta 5$ loop and a 3-stranded antiparallel $\beta$-sheet containing domain of the other complete the dimer interface.

6. MvaS Active Site and Ligand Interaction

The term "binding site" or "binding pocket", as the terms are used herein, refers to a region of a protein that, as a result of its shape, favorably associates with a ligand or substrate. The term "MvaS-like binding pocket" refers to a portion of a molecule or molecular complex whose shape is sufficiently similar to the MvaS binding pockets as to bind common ligands. This commonality of shape may be quantitatively defined based on a comparison to a reference point, that reference point being the structure coordinates provided herein. For example the commonality of shape may be quantitatively defined based on a root mean square deviation (RMSD) from the structure coordinates of the backbone atoms of the amino acids that make up the binding pockets in MvaS (as set forth in FIG. 3).

The "active site binding pockets" or "active site" of MvaS refers to the area on the surface of MvaS where the substrate binds.

Figure 5:
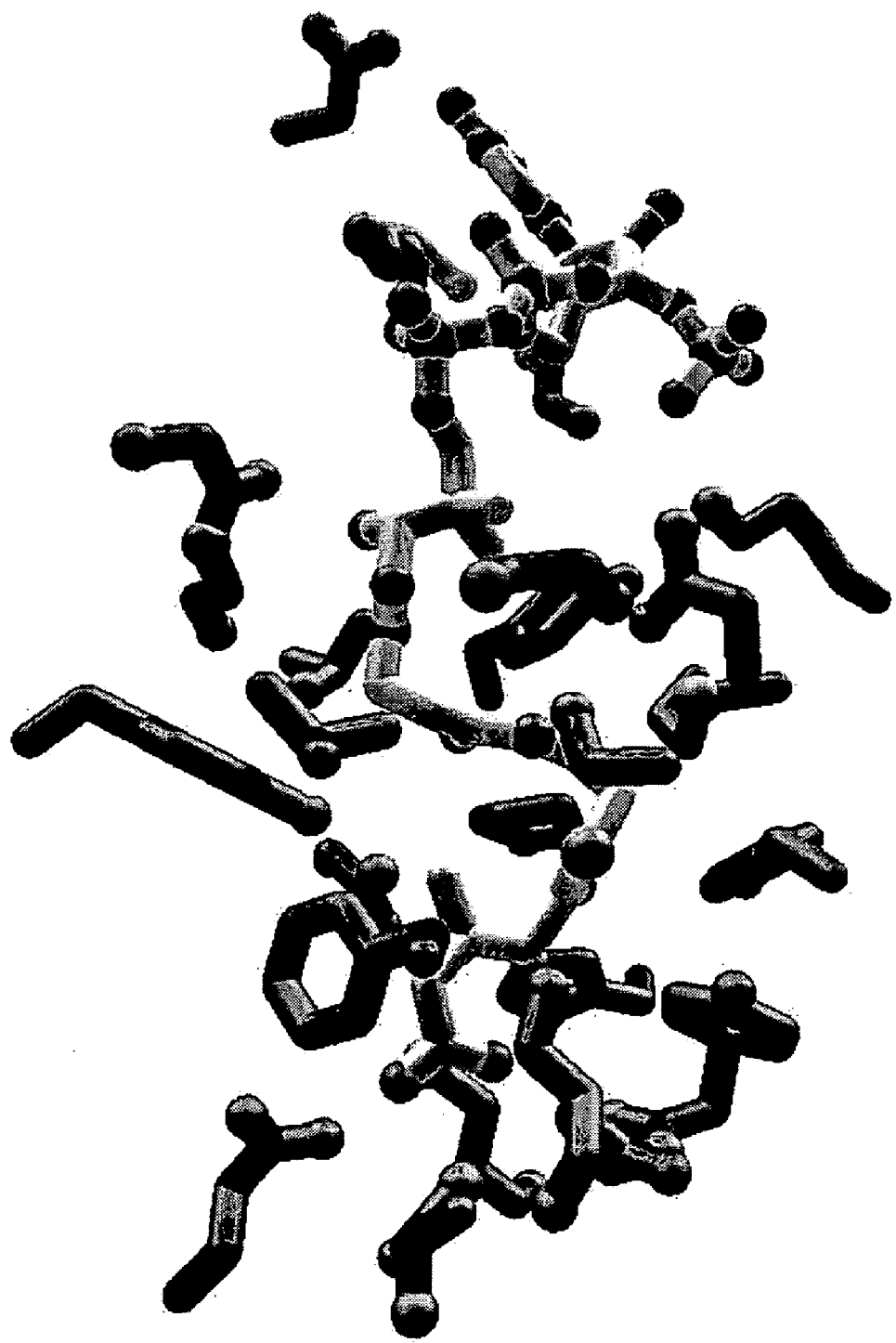
FIG. 5 illustrates the MvaS binding site of MvaS based on the determined crystal structure for the molecule in the asymmetric unit corresponding to the coordinates shown in FIG. 3.
Figure 6:
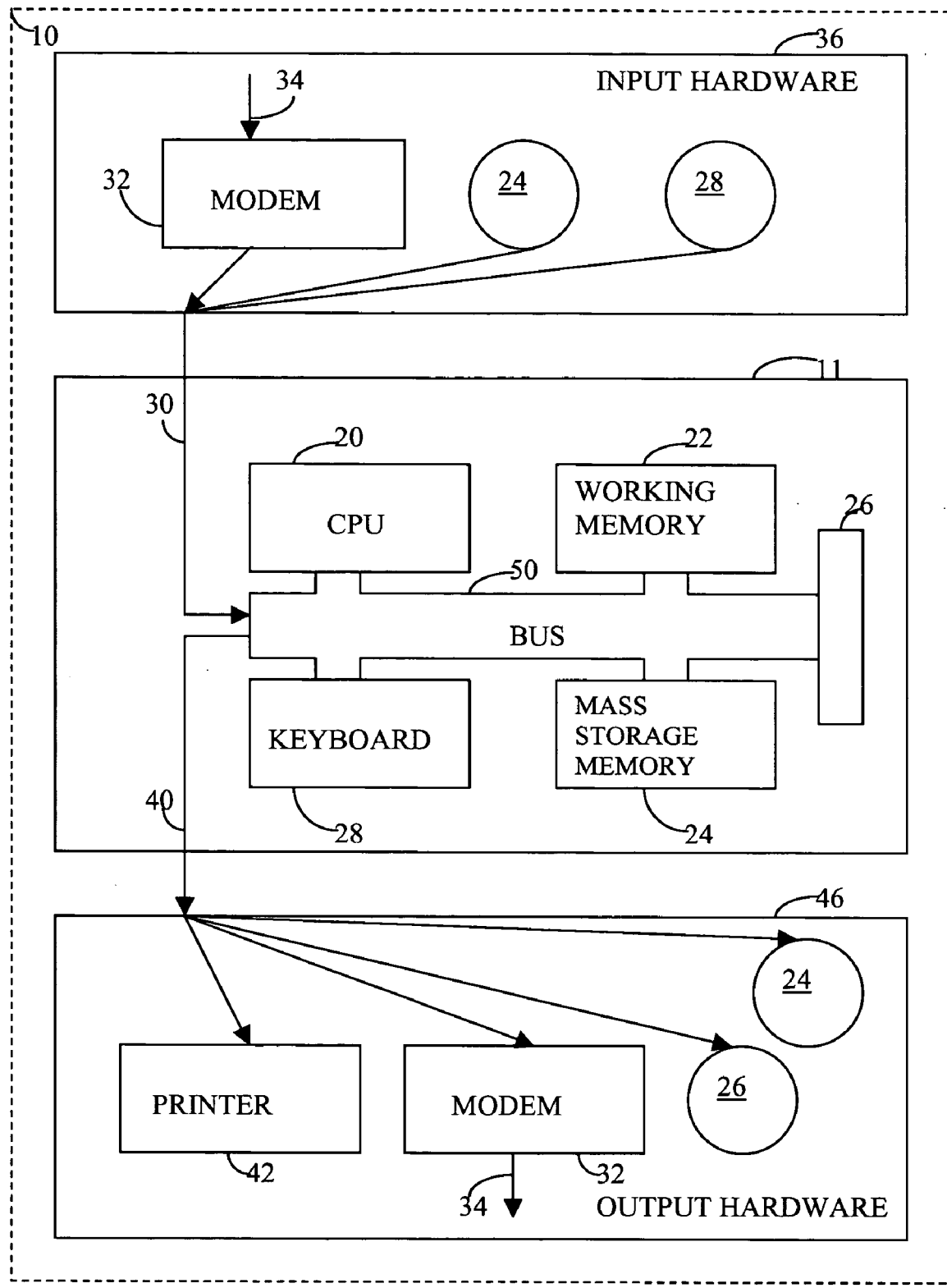
FIG. 6 illustrates a system that may be used to carry out instructions for displaying a crystal structure of MvaS encoded on a storage medium.

FIG. 5 illustrates the HMG-CoA binding site of MvaS based on the determined crystal structure for the molecule in the asymmetric unit corresponding to the structure coordinates shown in FIG. 3. The catalytic site for HMG-CoA is located in the long hydrophobic tunnel constructed from conserved residues that emanate from α7, as well as several loop regions. These regions include residues from the β9-α7 loop, the β11-β12 loop, the β6-α6 loop, the β5-α5 loop, the β7-β8 loop, α10-α11 loop, and the β10-α9 loop (FIG. 4). All the residues within 4 Å of the HMG-CoA binding pocket as described in table 2 are illustrated in FIG. 5.

In resolving the crystal structure of MvaS, applicants determined that MvaS amino acids shown in Table 2 (above) are encompassed within a 4-Angstrom radius around the MvaS active site and therefore are likely close enough to interact with an active site inhibitor of MvaS. Applicants have also determined that the amino acids shown in Table 3 (above) are encompassed within a 7-Angstrom radius around the MvaS active site. Further, the amino acids shown in Table 4 (above) are encompassed within a 10-Angstrom radius around the MvaS active site. Due to their proximity to the active site, the amino acids in the 4, 7, and/or 10 Angstroms sets are preferably conserved in variants of MvaS. While it is desirable to largely conserve these residues, it should be recognized however that variants may also involve varying 1, 2, 3, 4 or more of the residues set forth in Tables 2, 3 and 4 in order to evaluate the roles these amino acids play in the binding pocket.

With the knowledge of the MvaS crystal structure provided herein, Applicants are able to know the contour of an MvaS binding pocket based on the relative positioning of the 4, 7, and/or 10 Angstroms sets of amino acids. Again, it is noted that it may be desirable to form variants where 1, 2, 3, 4 or more of the residues set forth in Tables 2, 3 and 4 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted above, there are many different ways to express the surface contours of the MvaS structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of MvaS may be different than that set forth for MvaS. Corresponding amino acids in other isoforms of MvaS are easily identified by visual inspection of the amino acid sequences or by using commercially available homology software programs, as further described below.

7. System for Displaying the Three Dimensional Structure of MvaS

The present invention is also directed to machine-readable data storage media having data storage material encoded with machine-readable data that comprises structure coordinates for MvaS. The present invention is also directed to a machine readable data storage media having data storage material encoded with machine readable data, which, when read by an appropriate machine, can display a three dimensional representation of a structure of MvaS.

All or a portion of the MvaS coordinate data shown in FIG. 3, when used in conjunction with a computer programmed with software to translate those coordinates into the three-dimensional structure of MvaS may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of MvaS and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an MvaS-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising MvaS or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other MvaS-like enzymes, and isoforms of MvaS.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of MvaS described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of MvaS

The three-dimensional crystal structure of the present invention may be used to identify MvaS binding sites, be used as a molecular replacement model to solve the structure of unknown crystallized proteins, to design mutants having desirable binding properties, and ultimately, to design, characterize, identify entities capable of interacting with MvaS and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The MvaS structure coordinates provided herein are useful for screening and identifying drugs that inhibit MvaS and other structurally similar proteins. For example, the structure encoded by the data may be computationally evaluated for its ability to associate with putative substrates or ligands. Such compounds that associate with MvaS may inhibit MvaS, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with MvaS or a fragment or variant thereof by using all or a portion of the structure coordinates provided in FIG. 3 or functional equivalents thereof. A method is also provided for evaluating the potential of an entity to associate with MvaS or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an MvaS-like binding pocket. One embodiment of the method comprises: using all or a portion of the structure coordinates provided herein to generate a three-dimensional structure of an MvaS-like binding pocket; employing the three-dimensional structure to design or select a potential ligand; synthesizing the potential ligand; and contacting the synthesized potential ligand with a protein comprising an MvaS-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an MvaS-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an MvaS-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for MvaS, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an MvaS-like binding pocket with the synthesized entity.

With the structure provided herein, the present invention for the first time permits the use of molecular design techniques to identify, select or design potential inhibitors of MvaS, based on the structure of an MvaS-like binding pocket. Such a predictive model is valuable in light of the high costs associated with the preparation and testing of the many diverse compounds that may possibly bind to the MvaS protein.

According to this invention, a potential MvaS inhibitor may now be evaluated for its ability to bind an MvaS-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an MvaS-like binding pocket may be computationally evaluated using a series of steps in which chemical entities or fragments are screened and selected for their ability to associate with the MvaS-like binding pockets.

One skilled in the art may use one of several methods to screen entities (whether chemical or protein) for their ability to associate with an MvaS-like binding pocket. This process may begin by visual inspection of, for example, an MvaS-like binding pocket on a computer screen based on the MvaS structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849–857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29–34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195–202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269–288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of MvaS. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182–196 (1989); G. Lauri and P. A. Bartlett, "CAVEAT: a Program to Facilitate the Design of Organic Molecules", J. Comput. Aided Mol. Des., 8, pp. 51–66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145–2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199–221 (1994). HOOK is available from Molecular Simulations, San Diego, Calif.

Instead of proceeding to build an inhibitor of an MvaS-like binding pocket in a step-wise fashion one fragment or entity at a time as described above, inhibitory or other MvaS binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61–78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127–153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883–894 (1990); see also, M. A. Navia and M. A. Murcko, "The Use of Structural Information in Drug Design", Current Opinions in Structural Biology, 2, pp. 202–210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337–380 (1994); see also, W. C. Guida, "Software For Structure-Based Drug Design", Curr. Opin. Struct. Biology, 4, pp. 777–781 (1994)).

Once an entity has been designed or selected, for example, by the above methods, the efficiency with which that entity may bind to an MvaS binding pocket may be tested and optimized by computational evaluation. For example, an effective MvaS binding pocket inhibitor preferably demonstrates a relatively small difference in energy between its bound and free states (i.e., a small deformation energy of binding). Thus, the most efficient MvaS binding pocket inhibitors should preferably be designed with deformation energy of binding of not greater than about 10 kcal/mole, more preferably, not greater than 7 kcal/mole. MvaS binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an MvaS binding pocket may be further computationally optimized so that in its bound state it would preferably lack repulsive electrostatic interaction with the target enzyme and with the surrounding water molecules. Such non-complementary electrostatic interactions include repulsive charge—charge, dipole—dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT. 1995); AMBER, version 4.1 (P. A. Kollman, University of California at San Francisco, COPYRGT 1995); QUANTA/CHARMM (Molecular Simulations, Inc., San Diego, Calif. COPYRGT. 1995); Insight II/Discover (Molecular Simulations, Inc., San Diego, Calif. COPYRGT. 1995); DelPhi (Molecular Simulations, Inc., San Diego, Calif. COPYRGT. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an MvaS binding pocket. In this screening, the quality of fit of such entities to the binding site may be judged either by shape complementarities or by estimated interaction energy [E. C. Meng et al., J. Comp. Chem., 13, 505–524 (1992)].

According to another embodiment, the invention provides compounds that associate with an MvaS-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the MvaS provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of MvaS according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55–77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of MvaS can be resolved by this method.

In one embodiment, the method of molecular replacement is utilized to obtain structural information about the present invention and any other MvaS-like molecule. The structure coordinates of MvaS, as provided by this invention, are particularly useful in solving the structure of other isoforms of MvaS or MvaS complexes.

The structure coordinates of MvaS as provided by this invention are useful in solving the structure of MvaS variants that have amino acid substitutions, additions and/or deletions (referred to collectively as "MvaS mutants", as compared to naturally occurring MvaS). These MvaS mutants may optionally be crystallized in co-complex with a ligand, such as an inhibitor, substrate analogue or a suicide substrate. The crystal structures of a series of such complexes may then be solved by molecular replacement and compared with that of MvaS. Potential sites for modification within the various binding sites of the enzyme may thus be identified. This information provides an additional tool for determining the most efficient binding interactions such as, for example, increased hydrophobic interactions, between MvaS and a ligand. It is noted that the ligand may be the protein's natural ligand or may be a potential agonist or antagonist of a protein.

All of the complexes referred to above may be studied using well-known X-ray diffraction techniques and may be refined versus 1.5–3 Å resolution X-ray data to an R value of about 0.22 or less using computer software, such as X-PLOR [Yale University, COPYRIGHT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known MvaS inhibitors, and more importantly, to design new MvaS inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of MvaS

Crystals, crystallization conditions and the diffraction pattern of MvaS that can be generated from the crystals also have a range of uses. One particular use relates to screening entities that are not known ligands of MvaS for their ability to bind to MvaS. For example, with the availability of crystallization conditions, crystals and diffraction patterns of MvaS provided according to the present invention, it is possible to take a crystal of MvaS; expose the crystal to one or more entities that may be a ligand of MvaS; and determine whether a ligand/MvaS complex is formed. The crystals of MvaS may be exposed to potential ligands by various methods, including but not limited to, soaking a crystal in a solution of one or more potential ligands or co-crystallizing MvaS in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/MvaS complex(es) may be used to design new ligands that bind tighter, bind more specifically, have better biological activity or have better safety profile than known ligands.

In one embodiment, a method is provided for identifying a ligand that binds to MvaS comprising: (a) attempting to crystallize a protein that comprises a sequence wherein at least a portion of the sequence has 55%, 65%, 75%, 85%, 90%, 95%, 97%, 99% or greater identity with SEQ. ID No. 1 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to MvaS comprising: soaking a crystal of a protein wherein at least a portion of the protein has 55%, 65%, 75%, 85%, 90%, 95%, 97%, 99% or greater identity with SEQ. ID No. 1 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-MvaS complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of MvaS Ef

This example describes the expression of MvaS_Ef. It should be noted that a variety of other expression systems and hosts are also suitable for the expression of MvaS_Ef, as would be readily appreciated by one of skill in the art.

The gene encoding residues 1–383 (from SEQ. ID No. 1), which corresponds to the full-length MvaS from *E. faecalis*, was isolated by PCR from *E. faecalis* genomic DNA (ATCC700800D) and cloned into the TOPO-activated cloning site of pSX26 vector. This DNA sequence is presented in SEQ. ID No. 2. Expression in this vector generated a fusion of the full-length MvaS with non-cleavable carboxy-terminal six histidine tag, the amino acid sequence of which is shown, underlined, in FIG. 1 (SEQ. ID No. 1). For production of seleno methionine labeled protein, the expression plasmid encoding for MvaS_Ef fused with carboxy-terminal histidine tag was transformed into methionine auxotroph DL41 (Hendrickson, W. 1990, *EMBO J.* 9:1655–0).

Biomass for purification of recombinant seleno-methionine labeled MvaS_Ef was generated using minimal media supplemented with seleno-methionine (Sigma, MO) using 96-well fermentor. It should be noted that a variety of other protocols and expression strains are also suitable for the expression of selenomethionine derivative of MvaS website: cbr.med.harvard.edu/investigators/springer/lab/protocols/sara_SeMet Doublie, S. (1997). *Methods in Enzymology* 276, 523–530; website: novagen.com/docs/ndis/INNO10005.pdf as would be readily appreciated by one of skill in the art. Cells from a single 70 ml fermentor tubes was thawed by addition of 21 ml of lysis buffer (50 mM Tris/HCl pH 7.9, 50 mM NaCl, 1 mM $MgCl_2$) containing hen egg white lysozyme (0.6 mg/ml) and Benzonase (2.5 U/ml) and sonicated using Sonic Hedgehog robot. The sonicate was allowed to stand for 30 minutes at ~4° C. Total lysate was clarified by centrifugation and 2 mL of 5M NaCl were added to the cleared lysate. The cleared lysate from four fermentor tubes was applied to 3 ml bed ProBond column that had been equilibrated to 50 mM Potassium Phosphate pH 7.8, 0.4 M NaCl, 0.1 M KCl, 20 mM imidazole, 10% glycerol, 0.25 mM TCEP. The solution was passed through the column using gravity flow and the column was washed with 6 bed volumes of 50 mM Potassium Phosphate pH 7.8, 0.4 M NaCl, 0.1 M KCl, 40 mM imidazole, 10% glycerol, 0.25 mM TCEP. The product was eluted with 12 ml of 50 mM Potassium Phosphate pH 7.4, 0.4 M NaCl, 0.1 M KCl, 200 mM imidazole, 10% glycerol, 0.25 mM TCEP. The eluted protein was concentrated and buffer-exchanged into 25 mM Tris pH 7.9, 150 mM NaCl by using Vivaspin centrifugal concentrators. Following three five-fold dilution buffer-exchanges, the IMAC purified MvaS_Ef was concentrated to 10 mg/ml with a total volume of 0.47 ml. The molecular weight of the purified protein corresponded to the 100% incorporation of seleno-methionine as determined by Mass Spectrograph (MS) analysis (43,443 observed and 43,436 expected without N-terminal methionine). Purified MvaS_Ef exhibited a major band by both isoelectric focusing (IEF) and by sodium-dodecyl-sulfate polyacrylamide gel electrophoresis (SDS-PAGE) analyses.

Example 2

Crystallization of MvaS

This example describes the crystallization of MvaS. It is noted that the precise crystallization conditions used may be further varied, for example by performing a fine screen based on these crystallization conditions.

MvaS protein samples (corresponding to SEQ. ID No. 1) were incubated with 5 mM HMG-CoA and 5 mM $MgCl_2$ before setting crystallization trials. Crystals were obtained after an extensive and broad screen of conditions, followed by optimization. Diffraction quality crystals were grown in 100 nL sitting droplets using the vapor diffusion method. 50 nL comprising the MvaS-HMG-CoA complex (10 mg/ml) was mixed with 50 nL from a reservoir solution (100 µL) comprising: 24% PEG MME 2000; and 0.1M Citrate buffer pH-5.0. The resulting solution was incubated over a period of two weeks at 4° C. These crystals could also be obtained from PEG MME 550, PEG 3350, PEG 4000 and PEG 6000, PEG 800 at 4° C. and 20° C. Crystals typically appeared after 1 days and grew to a maximum size within 3–7 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of the MvaS-HMG-CoA complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A method for displaying a three dimensional representation of a structure of a protein comprising:

taking machine readable data comprising structure coordinates that have a root mean square deviation equal to or less than 0.98 Angstrom when compared to the structure coordinates of FIG. 3, the root mean square deviation being calculated such that the alpha-carbon atom positions of each set of structure coordinates are superimposed and the root mean square deviation is based only on those amino acid residues in the structure coordinates that are also present in the portion of the protein specified in Table 2;

computing a three dimensional representation of a structure based on the structure coordinates; and displaying the three dimensional representation.

2. A method according to claim 1, wherein the root mean square deviation is less than or equal to 0.65 Angstrom.

3. A method according to claim 1, wherein the root mean square deviation is less than or equal to 0.49 Angstrom.

4. A method according to claim 1, wherein the root mean square deviation comparison is also based on main-chain atoms positions of the amino acid residues and the root mean square deviation is equal to or less than 0.98 Angstrom.

5. A method according to claim 1, wherein the root mean square deviation comparison is also based on non-hydrogen atoms positions of the amino acid residues and the root mean square deviation is equal to or less than 0.89 Angstrom.

* * * * *

SEQUENCE LISTING

<160> NUMBER OF SEQ ID NOS: 2

<210> SEQ ID NO 1
<211> LENGTH: 391
<212> TYPE: PRT
<213> ORGANISM: Enterococcus faecalis
<220> FEATURE:
<221> NAME/KEY: Full-length E. faecalis MvaS
<222> LOCATION: (1)..(391)
<223> OTHER INFORMATION:
<220> FEATURE:
<221> NAME/KEY: Full-length E. faecalis MvaS
<222> LOCATION: (1)..(385)
<223> OTHER INFORMATION:
<220> FEATURE:
<221> NAME/KEY: 6 residue polyhistidine C-terminal tag
<222> LOCATION: (386)..(391)
<223> OTHER INFORMATION:

<400> SEQUENCE: 1

```
Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Val Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
```

```
              290              295              300
Ser Tyr Gly Ser Gly Ala Val Ala Glu Phe Phe Thr Gly Glu Leu Val
305                      310                      315                      320

Ala Gly Tyr Gln Asn His Leu Gln Lys Glu Thr His Leu Ala Leu Leu
                325                      330                      335

Asp Asn Arg Thr Glu Leu Ser Ile Ala Glu Tyr Glu Ala Met Phe Ala
                340                      345                      350

Glu Thr Leu Asp Thr Asp Ile Asp Gln Thr Leu Glu Asp Glu Leu Lys
                355                      360                      365

Tyr Ser Ile Ser Ala Ile Asn Asn Thr Val Arg Ser Tyr Arg Asn Lys
370                      375                      380

Gly His His His His His His
385                      390

<210> SEQ ID NO 2
<211> LENGTH: 1176
<212> TYPE: DNA
<213> ORGANISM: Enterococcus faecalis
<220> FEATURE:
<221> NAME/KEY: cDNA sequence encoding MvaS
<222> LOCATION: (1)..(1175)
<223> OTHER INFORMATION:
<220> FEATURE:
<221> NAME/KEY: 6 residue polyhistidine C-terminal tag
<222> LOCATION: (1156)..(1173)
<223> OTHER INFORMATION:

<400> SEQUENCE: 2
atgacaattg ggattgataa aattagtttt tttgtgcccc cttattatat tgatatgacg      60
gcactggctg aagccagaaa tgtagaccct ggaaaatttc atattggtat tgggcaagac     120
caaatggcgg tgaacccaat cagccaagat attgtgacat ttgcagccaa tgccgcagaa     180
gcgatcttga ccaaagaaga taagaggcc attgatatgg tgattgtcgg gactgagtcc     240
agtatcgatg agtcaaaagc ggccgcagtt gtcttacatc gtttaatggg gattcaacct     300
ttcgctcgct ctttcgaaat caaggaagct tgttacggag caacagcagg cttacagtta     360
gctaagaatc acgtagcctt acatccagat aaaaaagtct tggtcgtagc ggcagatatt     420
gcaaaatatg gcttaaattc tggcggtgag cctacacaag gagctggggc ggttgcaatg     480
ttagttgcta gtgaaccgcg catttttggct ttaaaagagg ataatgtgat gctgacgcaa     540 gatatctat acttttggcg tccaacaggc acccgtatc ctatggtcga tggtccttg       600 tcaaacgaaa cctacatcca atcttttgcc caagtctggg atgaacataa aaaacgaacc     660
ggtcttgatt ttgcagatta tgatgcttta gcgttccata ttccttacac aaaaatgggc     720
aaaaaagcct attagcaaa atctccgac caaactgaag cagaacagga acgaattta      780 gcccgttatg aagaaagtat cgtctatagt cgtcgcgtag gaaacttgta tacgggttca     840
ctttatctgg gactcatttc ccttttagaa aatgcaacga ctttaaccgc aggcaatcaa     900
attggtttat tcagttatgg ttctggtgct gtcgctgaat tttcactgg tgaattagta     960 gctggttatc aaaatcattt acaaaaagaa actcatttag cactgctgga taatcggaca    1020
gaactttcta tcgctgaata tgaagccatg tttgcagaaa ctttagacac agacattgat    1080
caaacgttag aagatgaatt aaaatatagt atttctgcta ttaataatac cgttcgttct    1140
tatcgaaaca aagggcacca ccaccaccac cactag                             1176
```